US011549121B2

United States Patent
(12) United States Patent
Lenaghan et al.

(10) Patent No.: US 11,549,121 B2
(45) Date of Patent: Jan. 10, 2023

(54) EPISOMAL DNA VECTORS FOR PLANT GENETIC ENGINEERING

(71) Applicant: UNIVERSITY OF TENNESSEE RESEARCH FOUNDATION, Knoxville, TN (US)

(72) Inventors: Scott C. Lenaghan, Knoxville, TN (US); Alessandro Occhialini, Knoxville, TN (US); Alexander C. Pfotenhauer, Knoxville, TN (US); Agnieszka Piatek, Klucze (PL); C. Neal Stewart, Jr., Knoxville, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 66 days.

(21) Appl. No.: 16/595,887

(22) Filed: Oct. 8, 2019

(65) Prior Publication Data

US 2020/0109409 A1 Apr. 9, 2020

Related U.S. Application Data

(60) Provisional application No. 62/742,640, filed on Oct. 8, 2018.

(51) Int. Cl.
*C12N 15/82* (2006.01)

(52) U.S. Cl.
CPC .... *C12N 15/8214* (2013.01); *C12N 2800/108* (2013.01); *C12N 2820/55* (2013.01)

(58) Field of Classification Search
None
See application file for complete search history.

(56) References Cited

U.S. PATENT DOCUMENTS 5,693,507 A * 12/1997 Daniell .............. C12N 15/8214 435/320.1

OTHER PUBLICATIONS

Scharff et al. (Plant molecular biology 62.4 (2006): 611-621). (Year: 2006).*

Min et al. (Plant Biotechnology Reports 9.6 (2015): 443-449). (Year: 2015).*

PGEM®-T and pGEM®-T Easy Vector Systems technical manual, dated Dec. 2018. (Year: 2018).*

Bock, Ralph. "Transgenic plastids in basic research and plant biotechnology." Journal of molecular biology 312.3 (2001): 425-438. (Year: 2001).*

Karas, et al. (Nat Commun 6: 6925. (2015)). (Year: 2015).*

Barbrook, A.C. et al. "Polyuridylylation and processing of transcripts from multiple gene minicircles in chloroplasts of the dinoflagellate *Amphidinium carterae*" *Plant Mol Biol*, 2012, pp. 347-357, vol. 79.

Barbrook, A.C. et al. "Minicircular plastid DNA in the dinoflagellate *Amphidinium operculatum*" *Mol Gen Genet*, 2000, pp. 152-158, vol. 263.

Bock, R. "Strategies for metabolic pathway engineering with multiple transgenes" *Plant Mol Biol*, 2013, pp. 21-31, vol. 83.

Daniell, H. et al. "Chloroplast genomes: diversity, evolution, and applications in genetic engineering" *Genome Biology*, 2016, pp. 1-29, vol. 17, No. 134.

Howe, C.J. et al. "Evolution of the chloroplast genome" *Phil. Trans. R. Soc. Lond.* B, Dec. 12, 2002, pp. 99-107, vol. 358.

Howe, C.J. et al. "The remarkable chloroplast genome of dinoflagellates" *Journal of Experimental Botany*, 2008, pp. 1035-1045, vol. 59, No. 5.

Jin, S. et al. "Engineered Chloroplast Genome just got Smarter" *Trends Plant Sci.*, Oct. 2015, pp. 1-31, vol. 20, No. 10.

Koressaar, T. et al. "Enhancements and modifications of primer design program Primer3" *Bioinformatics Applications Note*, 2007, pp. 1289-1291, vol. 23, No. 10.

Kota, M. et al. "Overexpression of the *Bacillus thuringiensis* (Bt) Cry2Aa2 protein in chloroplasts confers resistance to plants against susceptible and Bt-resistant insects" *Proc. Natl. Acad. Sci. USA*, Mar. 1999, pp. 1840-1845, vol. 96.

Koumandou, V.L. et al. "The Copy Number of Chloroplast Gene Minicircles Changes Dramatically with Growth Phase in the Dinoflagellate *Amphidinium operculatum*" *Protist*, Jan. 2007, pp. 89-103, vol. 158.

Krishnan, N.M. et al. "A comparative approach to elucidate chloroplast genome replication" *BMC Genomics*, May 2009, pp. 1-17, vol. 10, No. 237.

Kunnimalaiyaan, M. et al. "Fine mapping of replication origins (oriA and oriB) in *Nicotiana tabacum* chloroplast DNA" *Nucleic Acids Research*, 1997, pp. 3681-3686, vol. 25, No. 18.

Lin, M.T. et al. "A faster Rubisco with potential to increase photosynthesis in crops" *Nature*, Sep. 25, 2014, pp. 1-19, vol. 513, No. 7519.

Meeker, R. et al. "Localization of Replication Origins in Pea Chloroplast DNA" *Molecular and Cellular Biology*, Mar. 1988, pp. 1216-1223, vol. 8, No. 3.

(Continued)

*Primary Examiner* — Charles Logsdon
(74) *Attorney, Agent, or Firm* — Saliwanchik, Lloyd & Eisenschenk

(57) ABSTRACT

This disclosure pertains to a novel platform for genetic engineering of chloroplasts. The disclosure provides episomal DNA vectors containing a chloroplast origin of replication. These vectors remain extra-plastomic and sustainably and autonomously replicate in chloroplasts of the plant cells transformed with the vectors and in the plants regenerated from the transformed plant cells. The episomal DNA vectors do not contain any sequence that shares sequence homology with the plastome DNA and, thus, do not get integrated into the plastome DNA. The vectors can also comprise one or more genes of interest that confer desirable characteristics to the transformed plant cells. The disclosure also provides methods of transforming plant cells with the episomal DNA vectors and regenerating from the transformed plant cells plants having desirable characteristics. The vectors and methods disclosed herein provide a significant advancement in speed, flexibility, and prospects of introducing genes into plant cells for effective metabolic engineering.

17 Claims, 21 Drawing Sheets
(14 of 21 Drawing Sheet(s) Filed in Color)

Specification includes a Sequence Listing.

(56) References Cited

OTHER PUBLICATIONS

Min, S.R. et al. "An episomal vector system for plastid transformation in higher plants" *Plant Biotechnol Rep*, 2015, pp. 443-449, vol. 9.
Nisbet, R.E.R. et al. "Novel plastid gene minicircles in the dinoflagellate *Amphidinium operculatum*" *Gene*, 2004, pp. 141-147, vol. 331.
Occhialini, A. et al. "MoChlo: A Versatile, Modular Cloning Toolbox for Chloroplast Biotechnology" *Plant Physiology*, Mar. 2019, pp. 943-957, vol. 179.
Pasoreck, E.K. et al. "Terpene metabolic engineering via nuclear or chloroplast genomes profoundly and globally impacts off-target pathways through metabolite signaling" *Plant Biotechnology Journal*, 2016, pp. 1862-1875, vol. 14.
Schindel, H.S. et al. "The plastid genome as a chassis for synthetic biology-enabled metabolic engineering: players in gene expression" *Plant Cell Reports*, 2018, pp. 1419-1429, vol. 37.
Shinozaki, K. et al. "The complete nucleotide sequence of the tobacco chloroplast genome: its gene organization and expression" *The EMBO Journal*, 1986, pp. 2043-2049, vol. 5, No. 9.
Sidorov, V.A. et al. "Stable chloroplast transformation in potato: use of green fluorescent protein as a plastid marker" *The Plant Journal*, 1999, pp. 209-216, vol. 19, No. 2.
Svab, Z. et al. "High-frequency plastid transformation in tobacco by selection for a chimeric aadA gene" *Proc. Natl. Acad. Sci. USA*, Feb. 1993, pp. 913-917, vol. 90.
Svab, Z. et al. "Stable transformation of plastids in higher plants" *Proc. Natl. Acad. Sci. USA*, Nov. 1990, pp. 8526-8530, vol. 87.
Untergasser, A. et al. "Primer3—new capabilities and interfaces" *Nucleic Acids Research*, Jun. 2012, pp. 1-12, vol. 40, No. 15, e115.
Valkov, V.T. et al. "High efficiency plastid transformation in potato and regulation of transgene expression in leaves and tubers by alternative 5' and 3' regulatory sequences" *Transgenic Res*, 2011, pp. 137-151, vol. 20.
Verma, D. et al. "Chloroplast Vector Systems for Biotechnology Applications" *Plant Physiology*, Dec. 2007, pp. 1129-1143, vol. 145.
Waddell, J. et al. "Electron microscopic localization of the chloroplast DNA replicative origins in *Chlamydomonas reinhardii*" *Nucleic Acids Research*, 1984, pp. 3843-3856, vol. 12, No. 9.
Wurbs, D. et al. "Contained metabolic engineering in tomatoes by expression of carotenoid biosynthesis genes from the plastid genome" *The Plant Journal*, 2007, pp. 276-288, vol. 49.
Yu, Q. et al. "Efficient Plastid Transformation in *Arabidopsis*" *Plant Physiology*, Sep. 2017, pp. 186-193, vol. 175.

* cited by examiner

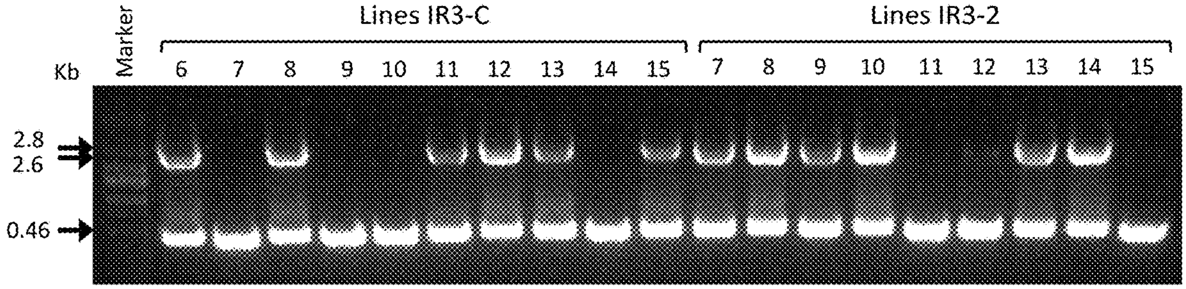
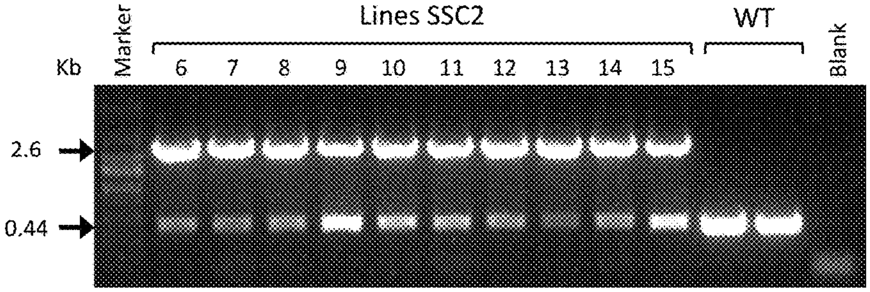
Figure 5A
| Name | Tot. (n) | Trans. (n) | Tot. Int. (n) | Int. (%) |
|---|---|---|---|---|
| IR3-C | 15 | 15 | 10 | 67 |
| IR3-2 | 15 | 15 | 12 | 80 |
| SSC2 | 15 | 15 | 15 | 100 |
Figure 5B mGFP Chlorophyll Bright-field Merge

| Line | Epi. IR3-2 [1] | Epi. IR3-2 [2] | Epi. IR3-C [1] | Epi. IR3-C [2] | Epi. IR3-C [3] | Epi. Ir3-C [4] |
|---|---|---|---|---|---|---|
| | pSmart | pSmart | pMagic | pMagic | pMagic | pMagic |
| Plastome/Epi. DNA | 4.8 | 6.2 | 0.5 | 1.2 | 1.2 | 1.1 |
| SD | ± 0.8 | ± 1.1 | ± 0.1 | ± 0.1 | ± 0.1 | ± 0.1 |

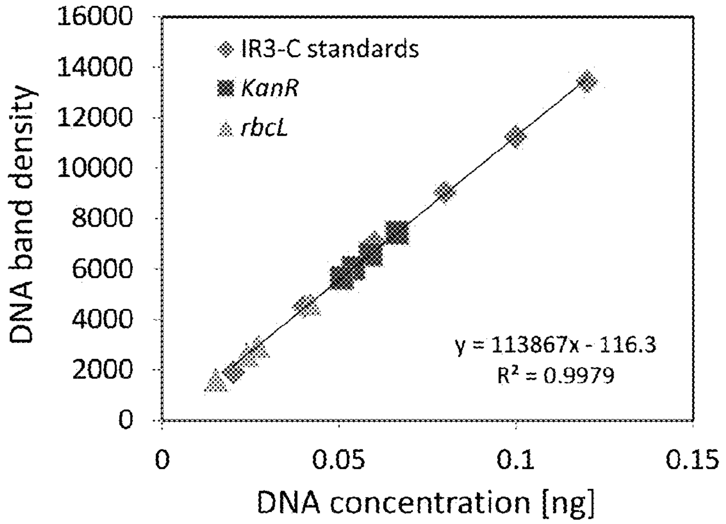
Figure 13A
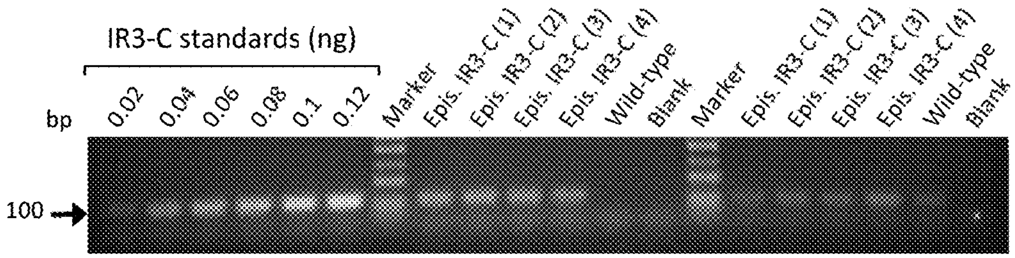
Figure 13B
| | **Episomal plasmid** (*KanR* copy n.) | | **Plastome** (*rbcL* copy n.) | | **Molar ratio** E. plasmid/Plastome | |
|---|---|---|---|---|---|---|
| Samples | mean ($x10^6$) | ± sd ($x10^6$) | mean ($x10^6$) | ± sd ($x10^6$) | mean | ± sd |
| Epis. IR3-C (1) | 4.11 | 0.37 | 1.17 | 0.38 | 3.8 | 1.08 |
| Epis. IR3-C (2) | 4.01 | 0.41 | 1.78 | 0.35 | 2.3 | 0.36 |
| Epis. IR3-C (3) | 3.40 | 0.33 | 1.60 | 0.41 | 2.3 | 0.64 |
| Epis. IR3-C (4) | 3.04 | 0.41 | 2.84 | 0.39 | 1.1 | 0.15 |
Figure 13C

N. callus/transformation

| | IR3-C | IR3-2 | SSC2 |
|---|---|---|---|
| Mean | 9.4 | 9.6 | 8.5 |
| SD | 6.0 | 13.5 | 4.6 |

% callus originating plantlets

| | IR3-C | IR3-2 | SSC2 |
|---|---|---|---|
| Mean | 42.9 | 26.6 | 31.5 |
| SD | 13.9 | 19.5 | 14.8 |

EPISOMAL DNA VECTORS FOR PLANT GENETIC ENGINEERING

CROSS-REFERENCE TO RELATED APPLICATION

This application claims the benefit of U.S. Provisional Application Ser. No. 62/742,640, filed Oct. 8, 2018, the disclosure of which is hereby incorporated by reference in its entirety, including all figures, tables and amino acid or nucleic acid sequences.

The Sequence Listing for this application is labeled "Seq-List.txt" which was created on Oct. 8, 2019, and is 599 KB. The Sequence Listing is incorporated herein by reference in its entirety.

This invention was made with government support under grant number DE-AR0000660 awarded by the Department of Energy (DOE) and under DARPA award D17AC00016 awarded by the Department of Defense (DOD)/Defense Advanced Research Projects Agency (DARPA). The government has certain rights in the invention.

FIELD OF THE INVENTION

This disclosure relates to plant genetic engineering. Episomal DNA vectors are provided for advanced genetic engineering of chloroplasts. These vectors remain in the chloroplasts as extra-plastomic DNA and sustainably and autonomously replicate in the chloroplasts of the plant cells and in the plants regenerated from the transformed plant cells. The disclosure also provides methods of transforming chloroplasts in the plant cells with the vectors and regenerating from the transformed plant cells plants having desirable characteristics.

BACKGROUND OF THE INVENTION

Traditional plastid genome (plastome) engineering is performed using homologous recombination to integrate transgenes into the endogenous plastome of plants. For species with the most efficient tissue culture systems, the complete replacement of the native plastomes with engineered plastomes (homoplasmy) is laborious and lengthy. Therefore, quick and efficient methods are desirable for transforming chloroplasts with nucleic acid constructs containing genes that confer desirable characteristics to the plant cells.

SUMMARY OF THE INVENTION

A novel approach is disclosed for expressing one or more genes of interest in chloroplasts. Episomal DNA vectors are designed to function as extra-plastomic DNA that replicate sustainably and autonomously in the chloroplasts of the transformed plant cells and in the plants regenerated from the transformed plant cells. The episomal DNA vectors contain a chloroplast origin of replication (Ori) that facilitates autonomous and sustainable extra-plastomic replication of these vectors even in the absence of selection pressure, such as spectinomycin selection. In addition to Ori, the episomal DNA vectors can also contain: one or more genes of interest, optionally, flanked by DNA sequences that do not have any sequence homology with the plastomic sequence of the transformed plant cell, a selection marker for bacteria, a bacterial origin of replication and/or a selection marker for plant cells.

The episomal DNA vectors can be used for transforming chloroplasts of a plant cell with one or more genes of interest that confer desirable characteristics to the transformed plant cell. The episomal DNA vectors autonomously and sustainably replicate in the transformed plant cell, the plants regenerated from the transformed plant cell, and in the progeny plants thereby conferring stable expression of the one or more genes of interest. Therefore, methods are also provided for transforming chloroplasts in a plant cell with one or more episomal DNA vectors that carry one or more genes of interest, wherein the one or more episomal DNA vectors autonomously and sustainably replicate in the chloroplasts of the transformed plant cell and its progeny plants.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5A-5B. Screening for putative episomal lines. (A) Vector integration in the plastome of IR3-C, IR3-2 and SCC2 transplastomic lines. PCRs using primers for IR (trnI/trnA) or SSC (ndhG/ndhI) regions were used to check vector integration in IR3 and SCC2 lines, respectively. Lines 6-15 per construct are shown. PCR bands of 2.8 and 2.6 kb indicate correct integration of IR3-C and IR3-2 (or SSC2) vectors, respectively. Lower-molecular weight bands of 0.46 and 0.44 kb indicate wild-type IR and SSC regions of plastome, respectively. The negative controls, wild-type samples and blanks are shown in the gels. DNA markers (Kb) are also indicated. (B) Table indicating the % of vector integration. Name: Name of constructs; Tot. (n): total number of transplastomic lines analyzed; Trans. (n): total number of positive lines for the presence of the two transgenes aadA and mGFP; Tot. int. (n): total number of lines with correct vector integration; Int. (%): percentage of plants with correct vector integration.

FIGS. 13A-13C. Determination of the molar ratio episomal vector/plastome in the episomal IR3-C plants. (A, B) Primers design on KanR and rbcL have been used to detect the episomal vector backbone and the plastome, respectively. Known concentrations of the IR3-C plasmid (0.02-0.12 ng) have been used as standards. 10 ng of total leaf genomic DNA were used in each PCR. Primary heteroplasmic plant (Epis. IR3-C 1); plants obtained from two consecutive clonal propagation (Epis. IR3-C 2 and 3); second generation of transplastomic plants (Epis. IR3-C 4). Wild-type samples were used as negative control. The PCR-band intensities were obtained using ImageJ software (NIH, USA) and the standard curves (X axis: DNA band density vs Y axis: DNA concentration) using Microsoft Excel. An example of standard curve and DNA gel are shown in panel A and B, respectively. (C) Table summarizing the copy number of episomal plasmid (KanR copy n) and plastome (rbcL copy n), along with the molar ratio (E. plasmid/plastome) in episomal IR3-C line at different stages (Epis. IR3-C 1-4). Results are expressed as mean± standard deviation (sd) of 13 independent experiment of semi-quantitate PCR (n=13).

BRIEF DESCRIPTION OF THE SEQUENCES

Figure 1:
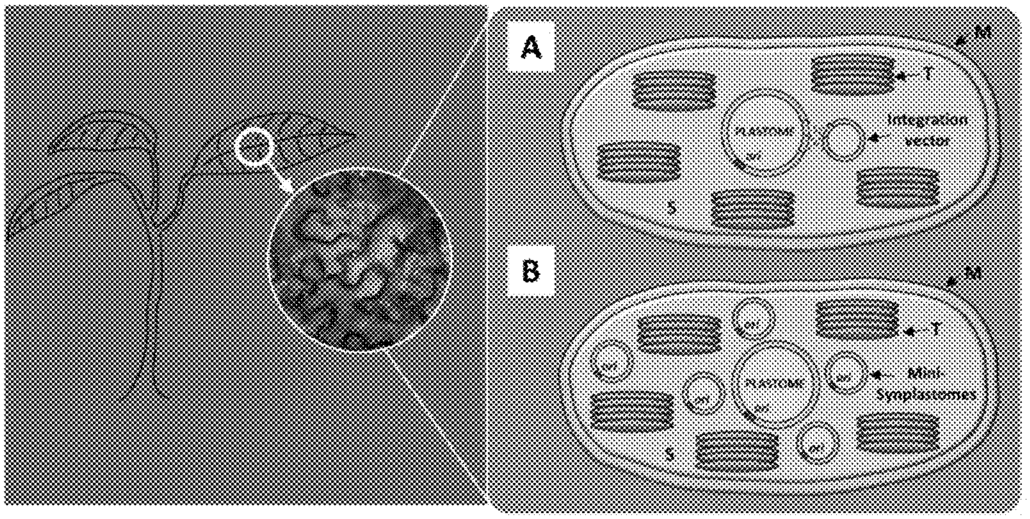
FIG. 1. Different methods of chloroplast transformation. Panel A shows the classical method of chloroplast transformation based on the vectors able to integrate into the plastome in a site-specific manner by homologous recombination. Panel B shows the novel method disclosed herein for chloroplast transformation based non-integrating episomal DNA vectors equipped with a chloroplast Ori. The non-integrating episomal DNA vectors are able to replicate autonomously and sustainably to persist as independent extra-plastomic DNA, also referenced herein as synthetic plastomes (Synplastomes) or Mini-Synplastomes. The chloroplast genome (plastome), integration vector and Mini-Synplastomes are indicated into the stroma (S) of chloroplasts. The chloroplast Ori (in red), thylakoids (T) and chloroplast membranes (M) are also indicated.

SEQ ID NOs: 1 to 30: Sequences of exemplary chloroplast Ori.

SEQ ID NOs: 31 to 89: Sequences of exemplary episomal DNA vectors.

SEQ ID NO: 90: Sequence of trnI used as a part of the promoter for driving the expression of the gene of interest.

SEQ ID NO: 91: Sequence of trnA used as a part of the promoter portion for driving the expression of the gene of interest.

SEQ ID NOs: 92 to 121: Sequences of the primers used in analysis of the transformed plant cells.

DETAILED DESCRIPTION OF THE INVENTION

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", include the phrases "consisting essentially of", "consists essentially of", "consisting", and "consists".

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" covers values within ±10% of the stated value.

In the present disclosure, ranges are stated in shorthand to avoid having to set out at length and describe each and every value within the range. Any appropriate value within the range can be selected, where appropriate, as the upper value, lower value, or the terminus of the range. For example, a range of 1-10 represents the terminal values of 1 and 10, as well as the intermediate values of 2, 3, 4, 5, 6, 7, 8, 9, and all intermediate ranges encompassed within 1-10, such as 2-5, 2-8, and 7-10. Values having at least two significant digits within a range are envisioned, for example, a range of 5-10 indicates all the values between 5.0 and 10.0 as well as between 5.00 and 10.00 including the terminal values. Also, when ranges are used herein, combinations and sub-combinations of ranges (e.g., subranges within the disclosed range) and specific embodiments therein are intended to be explicitly included.

As used herein, the term "expressing a gene of interest" or grammatical variations thereof refer to a condition in a genetically modified plant cell or a genetically modified plant wherein the gene of interest encodes for a protein or a regulatory RNA at a level higher than the parent plant cell or the plant without the genetic modification. Thus, a parent plant cell or a parent plant is genetically modified to produce a modified plant cell or modified plant that expresses a gene to produce a protein or a regulatory RNA at a higher level compared to the parent plant cell or the parent plant.

Typically, expressing a gene in a plant cell or a plant part comprises introducing into the chloroplast of the plant cell an episomal DNA vector comprising a gene of interest. The nucleic acid construct is designed to induce the expression of the protein or the regulatory RNA encoded by the gene. Methods of producing and introducing various nucleic acid constructs comprising genes of interest into the chloroplast of a plant cell to overexpress the gene of interest are well known to a person of ordinary skill in the art and such embodiments are within the purview of the invention.

As used herein, the term "plant" includes reference to whole plants, plant organs (e.g., leaves, stems, roots, etc.), seeds, plant cells, and progeny of same. Parts of transgenic plants are to be understood within the scope of the invention comprise, for example, plant cells, protoplasts, tissues, callus, embryos as well as flowers, stems, fruits, ovules, leaves, or roots originating in transgenic plants or their progeny previously transformed with an episomal DNA vectors of the invention, and therefore comprises at least in part of transgenic cells. As used herein, the term "plant cell" includes, without limitation, seeds, suspension cultures, embryos, meristematic regions, callus tissue, leaves, roots, crown, buds, apex, stems, shoots, gametophytes, sporophytes, pollen, and microspores. Monocotyledonous plants, dicotyledonous plants and ferns can be transformed with the episomal DNA vectors disclosed herein.

As used herein, "vector" refers to a DNA molecule such as a plasmid for introducing a nucleotide construct, for example, a DNA construct, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide a selectable characteristic, such as tetracycline resistance, hygromycin resistance or ampicillin resistance.

The term "minicircle" as used herein refers to a circular double stranded DNA vector having the size of between about 2 kb to about 15 kb.

As used in herein, the terms "identical" or "percent identity", in the context of describing two or more polynucleotide sequences, refer to two or more sequences or subsequences that are the same or have a specified percentage of nucleotides that are the same over the compared region. For example, a homologous nucleotide sequence used in the method of this invention has at least 80% sequence identity, preferably 85%, 90%, 91%, 92%, 93, 94%, 95%, 96%, 97%, 98%, 99%, or 100% identity, to a reference sequence, when compared and aligned for maximum correspondence over a comparison window, or over a designated region as measured using a comparison algorithms or by manual alignment and visual inspection. With regard to polynucleotide sequences, this definition also refers to the complement of a test sequence.

The prospects of engineering new metabolic pathways into plastid genome, for example, chloroplast genome, may enable crop improvement not readily attainable by engineering the nuclear genome. Like the plant model *Nicotiana tabacum* (tobacco), the genetic engineering of plastid genome (plastome) in *Solanum tuberosum* (potato) is performed using homologous recombination to integrate transgenes into the native plastome. However, this method is hampered by the need for homoplasmy and potential size limitations inherent to the native plastome.

The plastome in higher plant chloroplasts is typically composed of a single circular molecule ranging from 107 to 218 kb in size, which encodes 120 to 130 genes. In some marine dinoflagellates, such as Heterocapsa triquetra the plastome size is significantly smaller and is composed of multiple minicircles of 2-3 kb. Each minicircle contains a core sequence with an Ori and encodes up to a few genes. Plastid gene expression is partially regulated by the copy-number of each minicircle as the dinoflagellate responds to its environment.

This disclosure shows that dinoflagellate plastome organization may be translated to angiosperms to enable a versatile platform for plastid engineering that complements, rather than replaces, the endogenous plant genome (FIG. 1). Indeed, in an earlier attempt the episomal vectors were not maintained in plants when spectinomycin selection was removed (Min et al.). To address this and other drawbacks of conventional episomal vector transformation, certain embodiments of the invention provide episomal DNA vectors that remain as extra-plastomic DNA and replicate sustainably and autonomously in the chloroplasts of the transformed plant cells and in the plants regenerated from the transformed plant cells. The episomal DNA vectors disclosed herein contain a chloroplast Ori, which facilitates autonomous and sustainable extra-plastomic replication even in the absence of selection pressure, such as spectinomycin selection. The episomal DNA vectors disclosed herein do not contain any stretch of DNA sequence that shares sequence homology with the plastomic sequence of the transformed plant cell and, thus, does not integrate into the plastome of the chloroplasts of plant cells transformed with the episomal DNA vectors.

Accordingly, certain embodiments of the invention provide an episomal DNA vector comprising a chloroplast Ori and, optionally, one or more genes of interest. To avoid integration into the plastomic DNA of the host chloroplast, the episomal DNA vectors disclosed herein do not contain any sequence that engages in homologous recombination with the plastomic DNA of the host chloroplast. Therefore, the episomal DNA vectors are free from any stretch of more than 10 consecutive bp, preferably, more than 20 consecutive bp, even more preferably, more than 40 consecutive bp, and most preferably, more than 50 consecutive bp, that has a sequence identity of more than 70%, preferably, more than 75%, more preferably, more than 80%, and even more preferably, more than 90%, with a sequence of the plastomic DNA of the host chloroplast.

In addition to the chloroplast Ori, the episomal DNA vectors can further contain: one or more genes of interest, a selection marker for bacteria, a bacterial origin of replication and/or a selection marker for plant cells.

An "episomal DNA vectors" as used herein refers to a DNA construct that remains outside the plastome of the host chloroplast and replicates independent of the plastome of the host chloroplast.

A "plastome" refers to the genomic DNA of a chloroplast. "Extra-plastomic DNA" refers to DNA in a transformed chloroplast and replicates independent of the genomic DNA of the transformed chloroplast.

The phrase "a transformed plant cell" as used herein refers to a plant cell in which the chloroplasts are transformed with an episomal DNA vector disclosed herein.

The phrase "sustainable replication" as it relates to the replication of an episomal DNA vector within a chloroplast refers to the replication of the episomal DNA vector independent of the presence of any selection pressure for the replication of the episomal DNA vector. Typically, selection pressure, for example, presence of an antibiotic, induces replication of an episomal DNA vector that contains a gene that confers resistance to the antibiotic. A sustainable replication of an episomal DNA vector containing an antibiotic resistance gene refers to replication of the episomal DNA vector in the absence of the antibiotic.

The phrase "autonomous replication" as it relates to the replication of an episomal DNA vector within a chloroplast refers to the replication of the episomal DNA vector independent of the replication of the plastomic DNA. Autonomous replication is driven by a chloroplast Ori. A chloroplast Ori sequence used in the episomal DNA vectors can be a naturally occurring Ori sequence or a synthetic Ori sequence.

For transforming chloroplasts of a plant cell, naturally occurring chloroplast Ori from a different species, for example, a plant species or a Chlamydomonas species, is selected. This selection avoids the possibility of any homology between the chloroplast Ori sequence of the host chloroplast plastomic DNA and the chloroplast Ori sequence present in the episomal DNA vector. For example, episomal DNA vectors designed to transform a potato plant cell can contain a chloroplast Ori sequence from a tobacco plant cell and vice versa. A person of ordinary skill in the art can select and utilize appropriate chloroplast Ori sequence.

Non-limiting examples of the Ori sequences are provided by SEQ ID NOs: 1 to 30. Therefore, in certain embodiments, the Ori sequence comprises the sequence of any of SEQ ID NOs: 1 to 30 or a sequence having at least about 80%, preferably, at least 85%, more preferably, at least about 90%, and most preferably, at least about 95%, sequence identity to any of SEQ ID NOs: 1 to 30. In certain embodiments, naturally occurring chloroplast Ori sequences can be optimized for use in golden gate cloning, for example, using native BsaI or BbsI site SNPs.

In certain embodiments, each of the one or more genes of interest or a cassette containing the one or more genes of interest is flanked by sequences that do not share sequence homology to the plastome of the chloroplasts of the plant cells into which the episomal DNA vector is designed to be transformed.

Alternatively, the sequences flanking the one or more genes of interest can be designed based on the sequence of the plastome of the plant cells into which the episomal DNA vector is designed to be transformed. Particularly, the sequences flanking the one or more genes of interest are designed such that these sequences do not share sequence homology to the plastome of the plant cells. This lack of sequence homology ensures that the sequences flanking the one or more genes of interest cannot induce homologous recombination of the one or more genes of interest into the plastome of the transformed plant cells. Therefore, the one or more genes of interest are expressed from the extra-plastomic genetic material and provide to the transformed plant cells the desirable characteristics conferred by the one or more genes of interest.

The sequences flanking the one or more genes of interest are references herein as "non-homologous sequences". The non-homologous sequences, when present flaking the one or genes of interest, can be between 10 bp to 2,000 bp, preferably, between 50 bp to 1,800 bp, more preferably, between 200 bp to 1,500 bp, and even more preferably, between 500 bp to 1,000 bp.

To avoid homologous recombination with the plastomic DNA, the non-homologous sequence does not contain any region of more than 10 consecutive bp, preferably, more than 20 consecutive bp, even more preferably, more than 40 consecutive bp, and most preferably, more than 50 consecutive bp, that has a sequence identity of more than 70%, preferably, more than 75%, more preferably, more than 80%, and even more preferably, more than 90%, with a sequence of the plastome.

The non-homologous sequences can also be absent and the sequences flanking the one or more genes of interest can be the sequences of the Ori, a selection marker for bacteria, a bacterial origin of replication or a selection marker for plant cells.

Chloroplast plastomic sequences from several plants are known in the art. Exemplary chloroplast plastomic sequences and their GenBank accession numbers are provided in Table 1. The sequences of each of the chloroplast plastomic provided in Table 1 are incorporated herein by reference in their entireties.

TABLE 1

Sequence information for exemplary chloroplast plastome sequences.

| Organism | GenBank accession number for the chloroplast genome | Organism | GenBank accession number for the chloroplast genome |
|---|---|---|---|
| *Cucumis sativus* | NC_007144.1 | *Chenopodium quinoa* | NC_034949.1 |
| *Arabidopsis thaliana* | NC_000932.1 | *Cicer arietinum* | NC_011163.1 |
| *Bathycoccus prasinos* | NC_024811.1 | *Citrus sinensis* | NC_008334.1 |
| *Betula pendula* | LT855378.1 | *Coffea arabica* | NC_008535.1 |
| *Brassica napus* | NC_016734.1 | *Cucumis melo* | NC_015983.1 |
| *Capsicum annuum* | NC_024624.1 | *Cucurbita argyrosperma* | CM014103.1 |
| *Carica papaya* | NC_010323.1 | *Dendrobium catenatum* | NC_037361.1 |
| *Chlamydomonas reinhardtii* | NC_005353.1 | *Elaeis guineensis* | NC_017602.1 |
| *Daucus carota* | NC_017855.1 | *Eucalyptus grandis* | NC_014570.1 |
| *Glycine max* | NC_020455.1 | *Fragaria vesca* | NC_015206.1 |
| *Glycine soja* | NC_022868.1 | *Gossypium arboreum* | NC_016712.1 |
| *Gossypium hirsutum* | NC_007944.1 | *Gossypium raimondii* | NC_016668.1 |
| *Helianthus annuus* | NC_023337.1 | *Hevea brasiliensis* | NC_015308.1 |
| *Ipomoea nil* | NC_031159.1 | *Jatropha curcas* | NC_012224.1 |
| *Klebsormidium nitens* | DF238762.1 | *Lactuca sativa* | NC_007578.1 |
| *Micractinium conductrix* | CM009644.1 | *Manihot esculenta* | NC_010433.1 |
| *Micromonas commoda* | NC_012575.1 | *Medicago truncatula* | NC_003119.6 |
| *Monoraphidium neglectum* | NW_ 014013626.1 | *Nelumbo nucifera* | NC_025339.1 |
| *Nicotiana tabacum* | NC_001879.2 | *Nicotiana sylvestris* | NC_007500.1 |
| *Ostreococcus tauri* | NC_008289.1 | *Nicotiana tomentosiformis* | NC_007602.1 |
| *Phoenix dactylifera* | NC_013991.2 | *Olea europaea* | NC_015401.1 |
| *Physcomitrella patens* | NC_005087.1 | *Papaver somniferum* | NC_029434.1 |
| *Prototheca wickerhamii* | CM009949.1 | *Phalaenopsis equestris* | NC_017609.1 |
| *Raphanus sativus* | NC_024469.1 | *Picea glauca* | KT634228.1 |
| *Rosa chinensis* | CM009590.1 | *Populus euphratica* | NC_024747.1 |
| *Solanum lycopersicum* | NC_007898.3 | *Populus trichocarpa* | NC_009143.1 |
| *Sorghum bicolor* | NC_008602.1 | *Prunus mume* | NC_023798.1 |
| *Vigna angularis* | NC_021091.1 | *Prunus persica* | NC_014697.1 |
| *Vigna radiata* | NC_013843.1 | *Quercus lobata* | CM012305.1 |
| *Vitis vinifera* | NC_007957.1 | *Ricinus communis* | NC_016736.1 |
| *Zea mays* | NC_001666.2 | *Sequoia sempervirens* | CM017438.1 |
| *Aegilops tauschii* | NC_022133.1 | *Sequoiadendron giganteum* | CM017437.1 |
| *Alloteropsis semialata* | CM014279.1 | *Sesamum indicum* | NC_016433.2 |
| *Amborella trichopoda* | NC_005086.1 | *Setaria italica* | NC_022850.1 |
| *Ananas comosus* | NC_026220.1 | *Solanum pennellii* | HG975452.1 |
| *Arabidopsis lyrata* | NC_034379.1 | *Solanum tuberosum* | NC_008096.2 |
| *Arachis hypogaea* | NC_037358.1 | *Spinacia oleracea* | NC_002202.1 |
| *Brachypodium distachyon* | NC_011032.1 | *Theobroma cacao* | NC_014676.2 |
| *Cajanus cajan* | NC_031429.1 | *Vigna unguiculata* | NC_018051.1 |
| *Camellia sinensis* | NC_020019.1 | | |

Based on the sequence of a chloroplast plastome of interest, a person of ordinary skill in the art can design non-homologous sequences for inclusion in the episomal DNA vectors.

One can also compare a sequence against within an episomal DNA vector to the known chloroplast plastome sequences to check whether the searched sequence has sequence homology with the plastome sequence that can facilitate homologous recombination between the plastome and the episomal DNA vector. If sequence homology is observed, the sequence can be modified to avoid the homology.

A bacterial origin of replication facilitates cloning and characterization of the episomal DNA vectors of the invention in bacteria.

A selection marker for bacteria can be used in the episomal DNA vectors to facilitate cloning and production of the episomal DNA vectors in bacteria. Typical selection markers for bacteria include genes that confer resistance to bacterial anti-biotics, such as carbenicillin, ampicillin, actinomycin D, kanamycin, streptomycin, neomycin, polymyxin, zeocin, chloramphenicol, hygromycin B, tetracycline, spectinomycin, bleomycin, and erythromycin. Additional bacterial selection markers are known in the art and such embodiments are within the purview of the invention.

A selection marker for plant cells can be used in the episomal DNA vectors to facilitate selection of plant cells transformed with the episomal DNA vectors of the invention. Typical selection markers for plant cells include genes that confer resistance to an antibiotic that inhibits the growth of a plant cell. Such antibiotics include kanamycin, hygromycin, phosphinothricin and glyphosate. For example, the genes neomycin phosphotransferase II (NPT II), hygromycin B phosphotransferase (HPT), phosphinothricin N-acetyltransferase (NPT), and 5-enolpyruvilshikimate-3-phosphate (EPSP) synthase confer resistance to kanamycin, hygromycin, phosphinothricin tripeptide, and glyphosate, respectively.

Choice of an appropriate plant selection marker for use in the episomal DNA vector depends on, among other parameters, the type of host plant cell used. For example, if the host plant cell is from a monocotyledonous plant, the preferred selection antibiotic is hygromycin and the preferred antibiotic resistance gene is hpt; whereas, if the host plant cell is from a dicotyledonous plant, preferred selection antibiotic is kanamycin and the preferred antibiotic resistance gene is NPT II.

Additional plant selection markers are known in the art and such embodiments are within the purview of the invention.

The episomal DNA vectors can be used for transforming chloroplasts of a plant cell with one or more genes of interest that confer desirable characteristics to the transformed plant cell. Any gene that confers a desirable characteristic to a plant cell can be used in the episomal DNA vectors of the invention.

An episomal DNA construct can contain only one gene of interest or more than one gene of interest. When more than one gene of interest are present, these genes are typically involved in a common metabolic pathway and confer a desirable characteristic to the host plant cell. Multiple genes of interest can also be present on multiple episomal DNA vectors so that a combination of episomal DNA vectors, when transformed into chloroplasts of a plant cell, confers a desirable characteristic to the plant cell or a plant regenerated from the transformed plant cell.

A gene of interest refers to a transcribable DNA molecule that, when expressed in a plant cell or a plant, confers to the plant cell or the plant a desirable characteristic. A gene of interest can affect the plant's morphology, physiology, growth, development, yield, grain composition, nutritional profile, disease or pest resistance, and/or environmental or chemical tolerance or may act as a pesticide for a pest that feeds on the plant.

A desirable characteristic conferred to a plant by one or more genes of interest include herbicide tolerance, insect resistance, increased yield of a product of interest, disease resistance, pathogen resistance, modified plant growth and development, modified starch content, modified oil content, modified fatty acid content, modified protein content, modified fruit ripening, enhanced animal and human nutrition, biopolymer productions, environmental stress resistance, expression of a pharmaceutical peptide, improved processing quality, improved flavor, improved fiber production, biofuel production, and a combination thereof.

Examples of genes of interest that are known to confer herbicide resistance are described in the U.S. Pat. Nos. 6,803,501; 6,448,476; 6,248,876; 6,225,114; 6,107,549; 5,866,775; 5,804,425; 5,633,435; and 5,463,175. Examples of genes of interest that are known to confer increased yield are described in the U.S. Pat. Nos. RE38,446; 6,716,474; 6,663,906; 6,476,295; 6,441,277; 6,423,828; 6,399,330; 6,372,211; 6,235,971; 6,222,098; and 5,716,837. Examples of genes of interest that confer insect control are described in the U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241. Examples of genes of interest that confer fungal disease resistance are described in the U.S. Pat. Nos. 6,653,280; 6,573,361; 6,506,962; 6,316, 407; 6,215,048; 5,516,671; 5,773,696; 6,121,436; 6,316, 407; and 6,506,962. Examples of genes of interest that confer resistance to viral infection are disclosed in the U.S. Pat. Nos. 6,617,496; 6,608,241; 6,015,940; 6,013,864; 5,850,023; and 5,304,730. Examples of genes of interest that confer nematode resistance are described in the U.S. Pat. No. 6,228,992. Examples of genes of interest that confer resistance to bacterial diseases are described in the U.S. Pat. No. 5,516,671. Examples of genes of interest that confer improved plant growth and development are described in the U.S. Pat. Nos. 6,723,897 and 6,518,488. Examples of genes of interest that confer improved starch production are disclosed in the U.S. Pat. Nos. 6,538,181; 6,538,179; 6,538, 178; 5,750,876; and 6,476,295. Examples of genes of interest that confer modified oils production are disclosed in the U.S. Pat. Nos. 6,444,876; 6,426,447; and 6,380,462. Examples of genes of interest that confer high oil production are disclosed in the U.S. Pat. Nos. 6,495,739; 5,608,149; 6,483,008; and 6,476,295. Examples of genes of interest that confer modified fatty acid content are disclosed in the U.S. Pat. Nos. 6,828,475; 6,822,141; 6,770,465; 6,706,950; 6,660,849; 6,596,538; 6,589,767; 6,537,750; 6,489,461; and 6,459,018. Examples of genes of interest that confer high protein production are disclosed in the U.S. Pat. No. 6,380, 466. Examples of genes of interest that confer improved fruit ripening are disclosed in the U.S. Pat. No. 5,512,466. Examples of genes of interest that confer enhanced animal and human nutrition are disclosed in the U.S. Pat. Nos. 6,723,837; 6,653,530; 6,541,259; 5,985,605; and 6,171,640. Examples of genes of interest that confer the ability to synthesize biopolymers are disclosed in the U.S. Pat. Nos. RE37,543; 6,228,623; 5,958,745; and 6,946,588. Examples of genes of interest that confer environmental stress resistance are described in the U.S. Pat. No. 6,072,103. Examples of genes of interest that confer the ability to synthesize pharmaceutical peptides and secretable peptides are disclosed in the U.S. Pat. Nos. 6,812,379; 6,774,283; 6,140, 075; and 6,080,560. Examples of the genes of interest that confer improved processing traits are described in the U.S. Pat. No. 6,476,295. Examples of genes of interest that confer improved digestibility are disclosed in the U.S. Pat. No. 6,531,648. Examples of the genes of interest that confer low raffinose content are disclosed in the U.S. Pat. No. 6,166, 292. Examples of genes of interest that make the plant cells suitable for industrial enzyme production are disclosed in the U.S. Pat. No. 5,543,576. Examples of genes of interest that confer improved flavor, nitrogen fixation, hybrid seed production, and biofuel production are described in the U.S. Pat. Nos. 6,011,199; 5,229,114; 5,689,041; and 5,998,700, respectively. Examples of genes of interest that confer improved fiber production are described in the U.S. Pat. Nos. 6,576,818; 6,271,443; 5,981,834; and 5,869,720. Each of the U.S. patents and the U.S. patent application publications listed in this paragraph is incorporated herein by reference in its entirety.

A gene of interest can also encode for a regulatory RNA molecule that alters the expression of a target gene and the altered expression of the target gene in turn confers a desirable characteristic to the plant cell. Examples of genes of interest that encode regulatory RNA molecules include antisense nucleic acid molecules (described in the U.S. Pat. No. 5,107,065); inhibitory RNA (such as miRNA-, siRNA-, trans-acting siRNA-, and phased sRNA-mediated mechanisms, as described in the U.S. patent application publication Nos. 2006/0200878, 2008/0066206 and 2009-0070898. Each of the U.S. patents and the U.S. patent application publications listed in this paragraph is incorporated herein by reference in its entirety.

A gene of interest can also encode a catalytic RNA molecule, e.g., a ribozyme or a riboswitch as described in the U.S. patent application publication No. 2006/0200878, which is incorporated herein by reference in its entirety. A catalytic RNA molecule can be engineered to cleave a desired endogenous mRNA product.

Expression of a gene of interest in a plant cell can also be used to suppress or prevent plant pests from feeding on the plant cell. Typically, the gene of interest encodes a peptide or a protein that is toxic to a pest. The plant pests include arthropod pests, nematode pests, and fungal or microbial pests.

Additional examples of one or more genes of interest that confer one or more desirable characteristics to a plant cell or a plant are known in the art and such embodiments are within the purview of the invention.

In the episomal DNA vectors of the invention, a gene of interest can be operably linked to a regulatory element, i.e., a DNA sequence that facilitates and preferably, increases, the expression of the gene of interest. Many suitable chloroplast specific regulatory elements, such as promoters, that are useful for expressing a gene of interest in chloroplasts of plant cells are known in the art. Exemplary promoters that can be used in the episomal DNA vectors of the invention include: bacterial $\sigma^{70}$ type promoter with or without −10 and −35 consensus elements, psbA promoter, psbB promoter, psbT promoter, psbH promoter, psbD light-responsive promoter, plastid rRNA operon (prrn) promoter, rpoB promoter, rpoA promoter, accD promoter, or a combination thereof. A person of ordinary skill in the art can select and use an appropriate chloroplast specific promoter from the promoters known in the art and such embodiments are within the purview of the invention.

The episomal DNA vectors autonomously and sustainably replicate in the transformed plant cell, the plants regenerated from the transformed plant cell, and in the progeny plants thereby conferring stable expression of the one or more genes of interest. Therefore, methods are also provided for transforming plant plastids in a plant cell with one or more episomal DNA vectors that carry one or more genes of interest, wherein the one or more episomal DNA vectors autonomously and sustainably replicate in the plastids of the transformed plant cell and its progeny plants.

Figure 16:
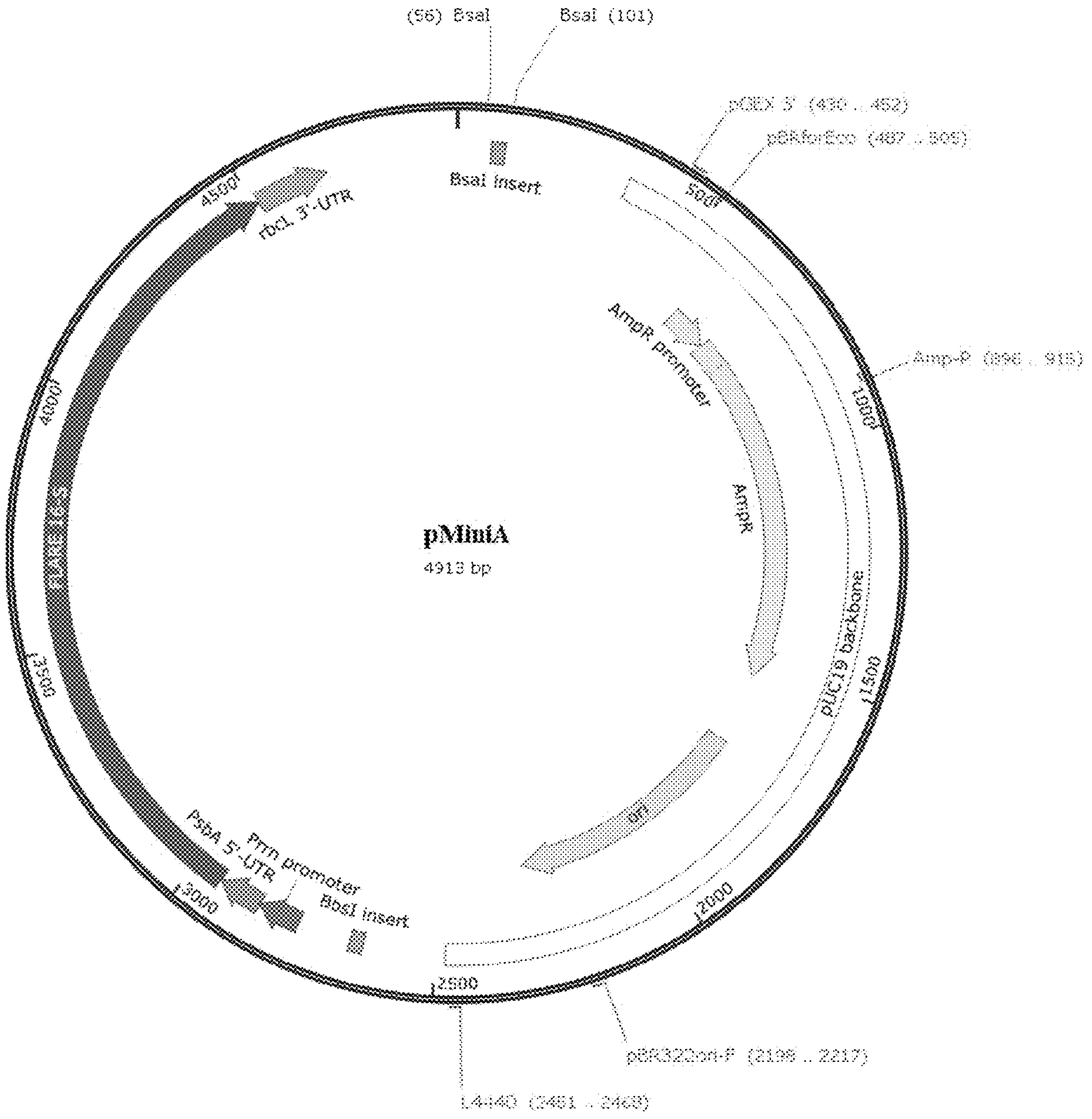
FIG. 16. Vector map of pMiniA, which is an example of an episomal DNA vector. A chloroplast Ori of interest, for example, from SEQ ID NOs: 1 to 30, can be cloned, for example, in the BsaI insert site. One or more genes of interest can be cloned, for example, in the BbsI insert site. The "ori" highlighted in yellow indicates a bacterial origin of replication and is different from chloroplast Ori.
Figure 17:
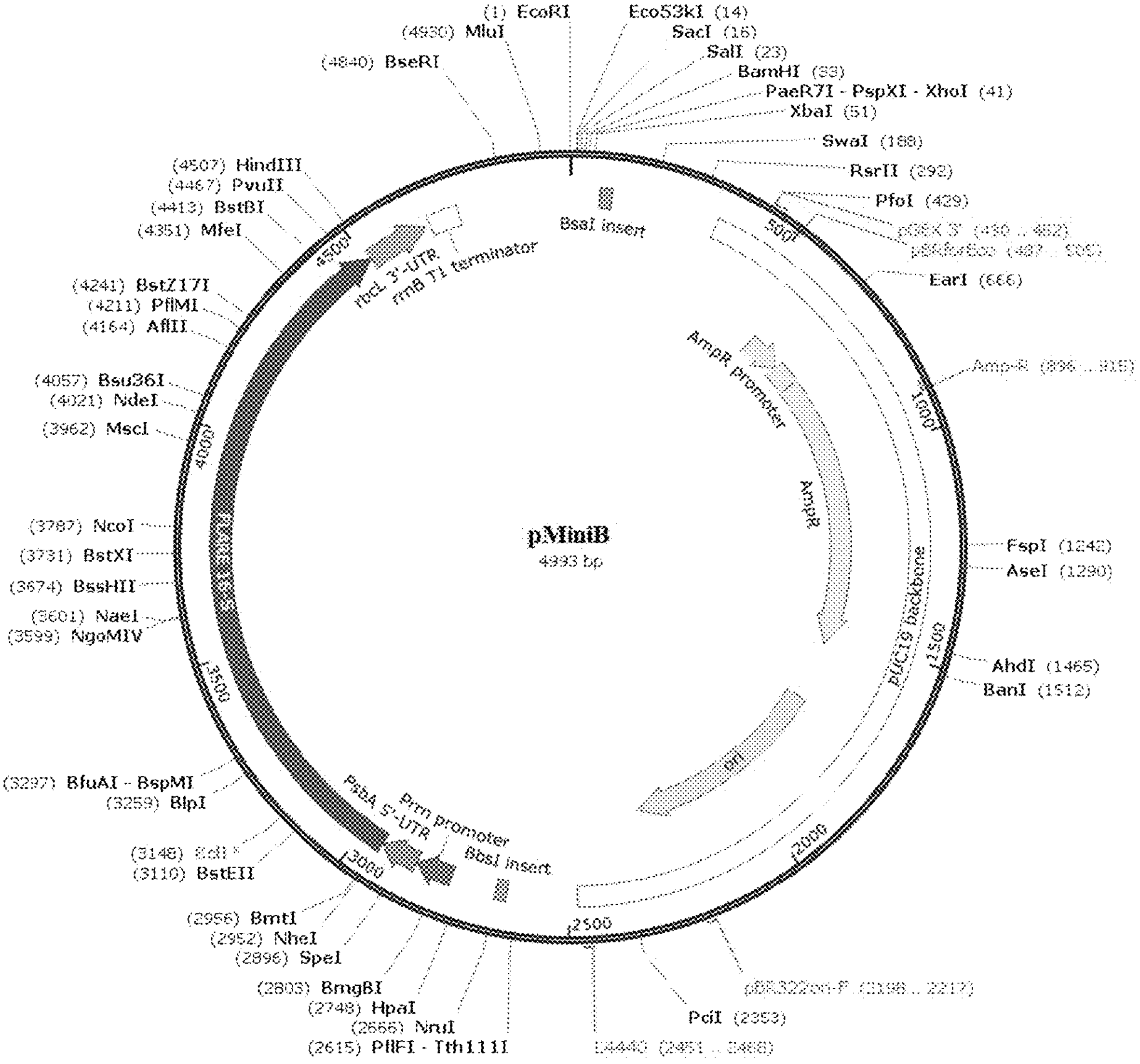
FIG. 17. Vector map of pMiniB, which is an example of an episomal DNA vector. A chloroplast Ori of interest, for example, from SEQ ID NOs: 1 to 30, can be cloned, for example, in the BsaI or the BbsI insert site. One or more genes of interest can be cloned, for example, in the BsaI or the BbsI insert site. The "ori" highlighted in yellow indicates a bacterial origin of replication and is different from chloroplast Ori.

Certain examples of the episomal DNA vectors of the invention include pMagic (SEQ ID NO: 85), pSmart (SEQ ID NO: 86), pMini-synplastome-1 (SEQ ID NO: 87), pMiniA (SEQ ID NO: 88), optionally, with further addition of a chloroplast Ori and pMiniB (SEQ ID NO: 89), optionally, with further addition of a chloroplast Ori.

pSmart, pMagic, or pMini-synplastome-1 can be used to include one or more genes of interest and transformed into chloroplasts of plant cells to confer desirable characteristics to the plant cells and to the plants regenerated from the transformed plant cells. pMiniA or pMiniB can be modified to include a chloroplast Ori and further modified to include one or more genes of interest and transformed into chloroplasts of plant cells to confer desirable characteristics to the plant cells and to the plants regenerated from the transformed plant cells. For example, a chloroplast Ori can be cloned into the BsaI insert site and, optionally, further one or more genes of interest can be cloned in the BbsI insert site (FIGS. 16-17). Alternatively, a chloroplast Ori can be cloned into the BbsI insert site and, optionally, further one or more genes of interest can be cloned in the BsaI insert site (FIGS. 16-17). Certain examples of pMiniA or pMiniB modified to contain an Ori are provided by SEQ ID NOs: 31 to 84.

Accordingly, certain embodiments of the invention provide episomal DNA vectors comprising the sequences of SEQ ID NOs: 31 to 89 or vectors having at least about 80%, preferably, at least 85%, more preferably, at least about 90%, and most preferably, at least about 95%, sequence identity to any of SEQ ID NOs: 31 to 89. In certain embodiments, the sequence identity of at least about 85% to at least about 99% is measured when compared to at least over 90% of the length of the sequence of SEQ ID NO: 31 to 89; preferably, at least over 95% of the length of the sequence of SEQ ID NO: 31 to 89; and more preferably, over the entirety of the sequence of SEQ ID NO: 31 to 89. Therefore, DNA vectors having the lengths of up to ±10% compared to the sequence of SEQ ID NO: 31 to 89 and having at least about 95% sequence identity to any of SEQ ID NOs: 31 to 89 are envisioned.

Plant species suitable for transformation with the episomal DNA vectors disclosed herein include, but are not limited to, corn (*Zea cans*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Other plants suitable for transformation with the episomal DNA vectors disclosed herein include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Additionally, ferns and monocots, such as maize, rice, barley, oats, wheat, sorghum, rye, sugarcane, ferns, mosses, grasses, switchgrass, pineapple, yams, onion, banana, coconut, Miscanthus (grass), *Brachypodium distachyon* (grass), cowpea, poplar, *Physcomitrella patens* (moss), *Pteris vittata* (fern), *Arabidopsis thaliana*, and dates can be transformed with the episomal DNA vectors disclosed herein.

Numerous methods of transforming chloroplasts are known. Certain methods include delivering the episomal DNA vectors into the leaf cells using a particle delivery system. In these methods, the episomal DNA vectors are coated on the surface of the gold or tungsten microparticles and shot on to the abaxial surface of four to six weeks old sterile leaves using a gene gun. The leaves so treated are incubated for 48 h in the dark, cut into small discs and the placed on regeneration medium supplemented with the appropriate antibiotic and hormones. Primary shoots containing transformed plastids typically arise within 2 to 3 months.

Additional methods of transforming chloroplasts are known in the art, some of which are described by Yu et al. (2017), *Plant Physiology*, Vo. 175, pp. 186-193. The Yu et al. reference is incorporated herein by reference in its entirety.

The calluses or shoots generated from the transformed plant cells can be tested for the presence of the episomal DNA vectors and the shoots that are identified to contain the episomal DNA vectors can be further regenerated into plant parts of plants.

Accordingly, certain embodiments of the invention provide a method of transforming a chloroplast in a plant cell by an episomal DNA vector of the invention; producing the calluses or shoots from the transformed plant cell, and regenerating a plant from the calluses or shoots produced from the transformed plant cells.

A variety of methods for the regeneration of plants from plant tissue are known. The particular method of regeneration depends on the starting plant tissue and the particular plant species to be regenerated. The regeneration, development, and cultivation of plants from single plant chloroplast transformants typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. The regenerated plants can be self-pollinated to provide homozygous transgenic plants. Alternatively, pollen obtained from the regenerated plants can be crossed to seed-grown plants of agronomically important lines. Conversely, pollen from plants of these important lines is used to pollinate regenerated plants.

In certain instances, an episomal DNA vector designed according to this disclosure, despite being designed to avoid integration into the plastomic DNA, undergoes homologous recombination with the plastomic DNA, which results in the incorporation of one or more genes of interest into the plastomic DNA. According to certain embodiments, plant cells containing the plastomic integration of the one or more genes of interest can be used to design and synthesize episomal DNA vectors that can sustainably and autonomously replicate in the chloroplasts of the transformed plant cells.

Thus, certain embodiments of the invention provide a method for designing an improved episomal DNA vector that sustainably and autonomously replicates in the chloroplasts of the transformed plant cells. The methods comprise the steps of:

a) designing an episomal DNA vector that does not contain any sequence that could engage in an homologous recombination with the plastomic DNA of the chloroplast of a plant cell, b) transforming the episomal DNA vector into the chloroplast of the plant cell and culturing the plant cell to produce progeny plant cells, c) testing the progeny plant cells for the integration of the episomal DNA vector or a fragment thereof into the plastome of the chloroplast of the progeny plant cells, d) isolating from the progeny plant cells that exhibit integration of the episomal DNA vector or a fragment thereof into the plastome of the chloroplast the episomal DNA vector that resulted from the homologous recombination and that is autonomously replicating in the chloroplasts of the progeny plant cells; and e) repeating the steps b) to d) with the episomal DNA vectors isolated in step d) until an improved episomal DNA vector is obtained, wherein the improved episomal DNA vector sustainably and autonomously replicates in the chloroplasts and does not integrate into the plastome of the chloroplasts of plant cells transformed with the improved episomal DNA vector.

An episomal DNA vector that does not contain any sequence that could engage in homologous recombination with the plastomic DNA of the chloroplast of a plant cell is free from any stretch of more than 10 consecutive bp, preferably, more than 20 consecutive bp, even more preferably, more than 40 consecutive bp, and most preferably, more than 50 consecutive bp, that has a sequence identity of more than 70%, preferably, more than 75%, more preferably, more than 80%, and even more preferably, more than 90%, with a sequence of the plastomic DNA of the host chloroplast.

In step c), the plastomic DNA of the transformed plant cells is tested, for example, with PCR, for the presence of the DNA from the episomal DNA vector. Presence in the plastomic DNA of the sequences from the episomal DNA vector indicates homologous recombination between the episomal DNA vector and the plastomic DNA. Such homologous recombination causes integration of the sequences from the episomal DNA vector into the plastomic DNA, which is undesirable.

If integration of the sequences from the episomal DNA vector into the plastomic DNA is observed, extra-plastomic DNA is isolated from the transformed plant cells and tested for the presence of the episomal DNA vectors that are produced as a result of the homologous recombination of the episomal DNA vectors used to transform the plant cells. These episomal DNA vectors typically do not contain sequences that are homologous to the plastomic DNA because the homologous sequences are already used for the recombination and integration process. These isolated episomal DNA vectors can be used as episomal DNA vectors to further test and use for plastid transformation of the plant cells.

This cycle of testing and rebuilding episomal DNA vectors ultimately provides episomal DNA vectors that can sustainably and autonomously replicate in chloroplasts of plant cells without getting integrated into the plastome of the chloroplasts. Certain examples of the episomal DNA vectors produced according to the methods of the invention include pSmart (SEQ ID NO: 86), pMagic (SEQ ID NO: 85), pMini-synplastome-1 (SEQ ID NO: 87), pMiniA (SEQ ID NO: 88) with further addition of an Ori and pMiniB (SEQ ID NO: 89) with further addition of an Ori.

In certain embodiments, the episomal DNA vectors disclosed herein can be transfected into isolated chloroplasts. The chloroplasts transformed with the episomal DNA vectors can be cultured to increase the copy number of the transformed episomal DNA vectors and/or to produce progeny chloroplasts. The chloroplasts containing the episomal DNA vectors that sustainably and autonomously replicate can then be introduced into a plant cell of interest using, for example, microinjection of the transformed chloroplasts into the plant cell. The plant cell containing the transformed chloroplasts can be cultured to produce the progeny plant cells. The progeny plant cells can then be further cultured to produce plant parts or the plants.

Materials and Methods

Plant Growth Conditions

*Solanum tuberosum* (potato) var. Desirée were grown in sterile conditions in Magenta boxes (W×L×H=77 mm×77 mm×97 mm) containing MS Reg. media (4.33 g/l Murashige and Skoog (MS) basal salt mixture; 25 g/l sucrose; 100 mg/l myo-inositol; 170 mg/l sodium phosphate monobasic monohydrate; 440 mg/l calcium chloride dihydrate; 0.9 mg/l thiamine-HC1; 2 mg/l glycine; 0.5 mg/l nicotinic acid; 0.5 mg/l pyridoxine-HCl; 1×MS vitamins; 3 g/l phytagel; pH 5.8). Transplastomic lines were grown in selective MS rooting media (4.33 g/l MS basal salt mixture; 1× Gamborg B5 vitamins; 30 g/l sucrose; 200 mg/l spectinomycin; 3 g/l phytagel; pH 5.8). Both wild-type and transgenic plants were kept in a controlled environment at 16 hours of light and 8 hours of dark. The temperature was kept at 24° C. during light/dark cycles. Tissue culture/selection/regeneration steps for generation of transplastomic lines were performed in the same controlled environment.

Generation of Transformation Vectors

Construction of IR3-2, IR3-C and SSC2 plasmids. IR and SSC homologous regions of tobacco (*Nicotiana tabacum*) chloroplast genome were synthesized by GeneArt at Thermo Fisher Scientific and cloned into the pMK vectors. Compared to wild-type sequences, IR3 and SSC2 were designed to contain additional restriction enzyme recognition sites for ease of cloning. The chloroplast-specific dual selection cassette (Prrn-SD::aadA::5'UTR::mGFP::psbA3'UTR) of PLD-PTD-GFP plasmid was PCR amplified and blunt-cloned into the PmeI site of either IR (trnI/trnA) or SCC (ndhG/ndhI) homologous sequences generating the IR (IR3-2 and IR3-C) or SSC2 plasmids, respectively. The pair of primers 1Fw/1Rv and 2Fw/2Rv was used to amplify the selection cassette for IR3-2 and SSC2 or IR3-C plasmids, respectively.

Construction of pMagic-aadA-mGFP (Mini-Synplastome). The dual selection cassette of IR3-2 plasmid was amplified using the pair of primers 3Fw/3Rv equipped with PsiI restriction sites at both 5' and 3' ends. The pMagic-aadA-mGFP was then generated by cloning the aforementioned DNA fragment into the PsiI site located in the backbone of pMagic. The sequences of primers used in this disclosure are shown in Table 2.

TABLE 2

Sequences of primers used in this disclosure.

| Abbreviation | Full name | Sequence | SEQ ID NO: |
|---|---|---|---|
| Forward Primers | | | |
| 1 Fw | Selectio-Cassette-1-Fw | CAATGTGAGTTTTTGTAGTTGGATTTGCTCC | 92 |
| 2 Fw | Selectio-Cassette-2-Fw | CAGTAGAGTCTTTCAGTGGCACGTT | 93 |
| 3 Fw | Cloning-Magic-PsiI-Fw | GACTCATTATAAAAACTGCCGAATTCGGATCC | 94 |
| 4 Fw | trnA-Fw | CAGTAGAGTCTTTCAGTGGCACGTT | 95 |
| 5 Fw | SSC2-Fw | CCCCCTAATATAAGACCCGACCC | 96 |
| 6 Fw | mGFP-full-Fw | ATGAGTAAAGGAGAAGAACTTT | 97 |
| 7 Fw | SmR-full-Fw | ATGGCAGAAGCGGTGATC | 98 |
| 8 Fw | KanR-full-Fw | ATGATTGAACAGGATGGCCTG | 99 |
| 9 Fw | SpcR-full-Fw | ATGCGTAGCCGTAATTGGA | 100 |
| 10 Fw | rbcL-P-Fw | GCTGCCGAATCTTCTACTGG | 101 |
| 11 Fw | IR3-full-left-Fw | TCTCCACTGGATCTGTTCCCGG | 102 |
| 12 Fw | IR3-full-right-Fw | CAAACCTGCTCCCATTTCGAG | 103 |
| 13 Fw | IR3-5'-ext-cas-Fw | GAAGGCGTCCTTGGGGTGAT | 104 |
| 14 Fw | KanR-q-Fw | CGGCAGAAAAAGTGAGCATT | 105 |
| 15 Fw | rbcL-q-Fw | AGATCTGCGAATCCCTGTTG | 106 |
| Reverse primers | | | |
| 1 Rv | Selectio-Cassette-1-RV | CTGCAGCCCAAACAAATACAAAATCAAAATAGA | 107 |
| 2 Rv | Selectio-Cassette-2-RV | GCCAGGGTAAGGAAGAAGGGG | 108 |
| 3 Rv | Cloning-Magic-PsiI-Rv | GACTCATTATAACATGTGCATCCTCTAGTAGCG | 109 |
| 4 Rv | trnI-Rv | GCCAGGGTAAGGAAGAAGGGG | 110 |
| 5 Rv | SSC2-Rv | CCGAATTACGAAGGCTTAGTTCGG | 111 |
| 6 Rv | mGFP-full-Rv | TTATTTGTATAGTTCATCCATGCC | 112 |
| 7 Rv | SmR-full-Rv | TTATTTGCCGACTACCTTGGT | 113 |
| 8 Rv | KanR-full-Rv | TTAGAAAAATTCATCCAGCAGAC | 114 |
| 9 Rv | SpcR-full-Rv | TTATTTACCCACCACTTTGGTAA | 115 |
| 10 Rv | rbcL-P-Rv | CAGGGCTTTGAACCCAAATA | 116 |
| 11 Rv | IR3-full-left-Rv | CATGGACGGTAGTTGGAGTCG | 117 |
| 12 Rv | IR3-full-right-Rv | GTGGAACAGAATTGACTGGGTGGT | 118 |

TABLE 2-continued

| Sequences of primers used in this disclosure. | | | |
|---|---|---|---|
| Abbreviation | Full name | Sequence | SEQ ID NO: |
| 13 Rv | IR3-3'-ext-cas-Rv | TCTCTCGAGCACAGGTTTAGCA | 119 |
| 14 Rv | KanR-q-Rv | CGCACGTTCAATACGATGTT | 120 |
| 15 Rv | rbcL-q-Rv | CAGGGGACGACCATACTTGT | 121 |

Generation of Transplastomic Lines and Propagation

The Gene-Gun PDS-1000/He delivery system (Bio-Rad) was used to transform chloroplasts. Transplastomic plants were obtained from transformed leaf material by applying a tissue culture/selection/regeneration protocol as described by Valcov et al. About 6 $cm^2$ of leaf tissue collected from one month-old potato plants grown in sterile condition were placed in the center of a petri dish containing M6M media (4.33 g/l MS basal salt mixture; 1× Gamborg B5 vitamins; 30 g/l sucrose; 18.2 g/l mannitol; 18.2 g/l sorbitol; 0.8 mg/l zeatin riboside (ZR); 2 mg/l 2,4-dichlorophenoxyacetic acid (2,4-D); 3 g/l phytagel; pH 5.8). The tissue was kept overnight in the dark at room temperature before transformation. Experiments of Gene-Gun particle delivery using BY2 cells and pMDC45 vector were performed to optimize transformation parameters (DNA concentration; rupture disk pressure, psi; and sample distance). The DNA binding capacity of gold particles at different sonication and mixing conditions was also determined (optimization of transformation parameters are shown in FIG. 13). Based on these results, 0.3 mg of 0.6 μm gold-particles were used to bind 1 μg of plasmid following the manufacture protocol (Seashell Technology). The gold-DNA complexes were subjected to two steps of sonication (1 minute each at amplitude 50) to avoid particles aggregation. The samples was placed at 6 cm from the gun and transformed under vacuum using 1,100 psi rupture disks. After two days of incubation in the dark at room temperature, leaf material was cut in small pieces (5 $mm^2$) and placed in selective M6 media (4.33 g/l MS basal salt mixture; 1× Gamborg B5 vitamins; 30 g/l sucrose; 0.8 mg/l zeatin riboside (ZR); 2 mg/l 2,4-dichlorophenoxyacetic acid (2,4-D); 400 mg/l spectinomycin; 3 g/l phytagel; pH 5.8) at the growth condition described before. After one month-incubation in controlled environment, the plant material was transferred in selective Ti media (4.33 g/l MS basal salt mixture; 1× Gamborg B5 vitamins; 16 g/l glucose; 3 mg/l zeatin riboside (ZR); 2 mg/l indole acetic acid (IAA); 1 mg/l gibberellic acid ($GA_3$); 400 mg/l spectinomycin; 3 g/l phytagel; pH 5.8). 4-8 weeks later, transplastomic green callus was obtained from transformed leaves. Green callus was transferred in selective DH media (2.16 g/l MS basal salt mixture $NH_4NO_3^-$ free; 268 mg/l $NH_4Cl$; 1×Nitsch vitamin mixture; 2.5 g/l sucrose; 36.4 g/l mannitol; 100 mg/l casein hydrolysate; 80 mg adenine hemisulfate; 2.5 mg/l zeatin riboside (ZR); 0.1 mg/l indole acetic acid (IAA); 400 mg/l spectinomycin; 3 g/l phytagel; pH 5.8) for another month of growth, and after that placed in selective MON media (4.33 g/l MS basal salt mixture; 1× Gamborg B5 vitamins; 30 g/l sucrose; 0.1 mg/l naphthaleneacetic acid (NAA); 5 mg/l zeatin riboside (ZR); 400 mg/l spectinomycin; 3 g/l phytagel; pH 5.8) for shoots regeneration. Primary transplastomic shoots were transferred in Magenta boxes containing selective MS rooting media for roots regeneration. Graphs summarizing the number of green callus obtained per event of transformation (x plate) and graphs showing the number of calluses able to produce primary plantlets are shown in FIG. 14.

Primary transplastomic plants were clonal propagated in new Magenta boxes containing selective MS rooting media each 4-6 weeks. For clonal propagation, a single steam was cut in several pieces at the level of internodes and then placed in new boxes. For the second generation of transplastomic plants another cycle of tissue culture/selection/regeneration (as described before) was performed starting from leaves of heteroplasmic plant material.

Total DNA Extraction and PCR Analysis

Two different total DNA extraction procedures were used for different purposes. For the screen of primary transplastomic lines we used the DNA extraction buffer method. For the genetic characterization of the second generation of transplastomic lines, episomal IR3 lines, semi-quantitative PCRs and qPCRs were used in the CTAB-based procedure. For the DNA extraction buffer procedure, about 25 mg of leaf tissue was frozen in liquid nitrogen and finely ground in an Eppendorf tube. The grinding was protracted in 400 μl of extraction buffer (200 mM Tris-HCl pH 7.5; 250 mM NaCl; 25 mM EDTA; 0.5% SDS; 0.1 mg/ml RNaseA) and then, the sample was mixed for 5 minutes using a vortex. Cell debris was eliminated by centrifugation for 5 minutes at 15,000 g in a benchtop centrifuge. 300 μl of clarified supernatant were mixed with an equal volume of ice-cold dry isopropanol. The sample was incubated at room temperature for 10 minutes and then centrifuged for 30 minutes at 15,000 g. The DNA pellet was washed using 500 μl of 75% (v/v) ethanol. After removal of the supernatant, the air-dried DNA pellet was resuspended in 50-100 μl of sterile water and quantified using a Nano-Drop spectrophotometer.

For more pure DNA preparations a classical CTAB-based procedure was used. About 50 mg of leaf tissue frozen in liquid nitrogen was finely ground in an Eppendorf tube. The ground leaf material was resuspended in 500 μl of CTAB extraction buffer (2% hexadecyltrimethyl ammonium bromide; 1% (w/v) polyvinyl pyrrolidone; 100 mM Tris-HCl; 1.4 M NaCl; 20 mM EDTA; 0.1 mg/ml RNaseA), thoroughly vortexed and incubated for 10 minutes at room temperature. The incubation was protracted for 30 minutes at 60° C., and then the cellular debris was eliminated by centrifugation at 15,000 g for 5 minutes. An equal volume of a solution containing chloroform/isoamyl alcohol (24:1) was added to the clarified supernatant. The sample was vortexed for 5 seconds and centrifuged at 4° C. for 1 minute at 15,000 g. The upper aqueous phase was transferred in a new tube, and the DNA was precipitated by adding an equal volume of ice-cold dry isopropanol. The samples was incubated for 30 minutes on ice and then centrifuged at 4° C. for 30 minutes at 15,000 g. The DNA precipitated in the tube was washed in 500 μl of ice-cold 75% (v/v) ethanol. The air-dried pellet was resuspended in 50-100 μl of sterile $H_2O$ and quantified using a Nano-Drop spectrophotometer.

Two pairs of primers 4Fw/4Rv and 5Fw/5Rv were used to check the integration in the IR (trnI/trnA) and SSC (ndhG/ndhI) sites of plastome, respectively. Two pairs of primers 6Fw/6Rv and 7Fw/7Rv were used to check the presence of full-length mGFP (encoding monomeric green fluorescent protein, NCBI ID: AEX93343.1) and aadA (encoding the streptomycin 3'-adenylyltransferase, NCBI ID: AAR14532.1) genes, respectively. Two pairs of primers 8Fw/8Rv and 9Fw/9Rv were used to check the presence of KanR (encoding aminoglycoside 3'-phosphotransferase, NCBI ID: WP_004614937.1) and SpcR (encoding aminoglycoside nucleotidyltransferase AadA1, NCBI ID: WP_010891332.1) selective genes of the backbone, respectively. The primer pair 10Fw/10Rv was used to amplify an internal fragment of rbcL (*Solanum tuberosum* plastome, NCBI ID: 4099985) as a loading control. The sequences of primers used in this study are shown in Table 2.

*Escherichia coli* Transformation with Episomal Vector Extracted from Leaf Tissue 25 μl chemically competent *E. coli* TOP10 (Thermo Fisher Scientific) were transformed using 500 ng of pure genomic DNA preparations (CTAB procedure) from leaves of episomal IR3 lines using the heat-shock method. Transformed cells were grown in Luria-Bertani (LB) agar media (10 g/l of bacto-tryptone; 5 g/l of yeast extract; 10 g/l NaCl; 15 g/l bacto agar; pH 7) containing 50 μg/ml kanamycin. Pure preparations of extra-plastomic DNA (pMagic, pSmart and pMagic-aadA-mGFP) were extracted from bacterial cells using QIAprep Spin Miniprep Kit (QIAGEN). The presence of left and right homologous arms along with the internal cassette was tested by PCRs using the pairs of primers 11Fw/11Rv, 12Fw/12Rv and 13Fw/13Rv, respectively. The sequences of primers are shown in Table 2. The entire sequences of different extra-plastomic DNA units extracted from plant tissue were obtained by Sanger DNA sequencing (Massachusetts General Hospital MGH, Center for Computational & Integrative Biology CCIB, DNA Core, Boston, Mass.).

Real-Time PCR and Copy Number Determination

The Real-Time PCRs were performed in a total volume of 15 μl in 1× PowerUp™ SYBR™ Green Master Mix (Thermo Fisher Scientific), using 5 ng of pure genomic DNA (CTAB procedure) from the second generation of episomal IR3 lines, and 0.5 μM of both forward and reverse primers. 0.1, 1, 20, 40, 60, 80 and 100 pg of purified pMagic (molecular weight: 9965 bp) were used as standards of copy number. The pairs of primers 14Fw/14Rv and 15Fw/15Rv were used to detect the backbone KanR of extra-plastomic DNA (encoding aminoglycoside 3'-phosphotransferase, NCBI ID: WP_004614937.1) and the plastome internal control rbcL (*Solanum tuberosum* plastome, NCBI ID: 4099985), respectively. All primers were designed to amplify a fragment of about 100 bp at a compatible annealing temperature of 57° C. using the online software Primer3 input v. 0.4.0 (Howard Hughes Medical Institute and by the National Institutes of Health). The sequences of primers are shown in Table 2. The Real-Time PCR was performed using a QuantStudio™ 6 Flex Real-Time PCR System (Thermo Fisher Scientific), whereas data were acquired using the QuantStudio™ Real-Time PCR Software v1.1 (Thermo Fisher Scientific). The Microsoft Excel software was used to process and for the graphical representation of the data. Linear regression graphs of delta Rn (normalized SYBR fluorescent signal) data of standards at exponential phase (Y axis) vs copy number of standards (X axis) were used to calculate the copy number of both endogenous plastome and extra-plastomic plasmids (pSmart or pMagic) in the second generation of episomal IR3-2 (1 and 2) and IR3-C (1-4) lines, respectively. The ratios of plastome copy number to extra-plastomic DNA copy number were calculated in each sample using the aforementioned data. Wild-type plants and blanks were used as negative controls. The data are mean± standard deviation (SD) of 9 independent experiments (n=9), using three technical replicates per sample in each experiment.

Confocal Microscopy

Healthy leaves from 3-4 weeks-old wild-type potato and transplastomic lines grown in sterile conditions were imaged using an Olympus Fv1000 confocal microscope (Olympus). Green fluorescent protein (GFP) was excited using a 488 nm-argon laser and detected at 509 nm of wavelength emission. The chlorophyll auto-fluorescent was excited using a 543 nm HeNe laser and detected at 667 nm of wavelength emission. Digital images were acquired using Olympus FV10-ASW Viewer software Ver.4.2a (Olympus). Confocal images were processed using ImageJ 1.41o (National Institute of Health, Bethesda, Md., USA).

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Episomal DNA Vecors and Methods of Synthesizing Them

Figure 2A:
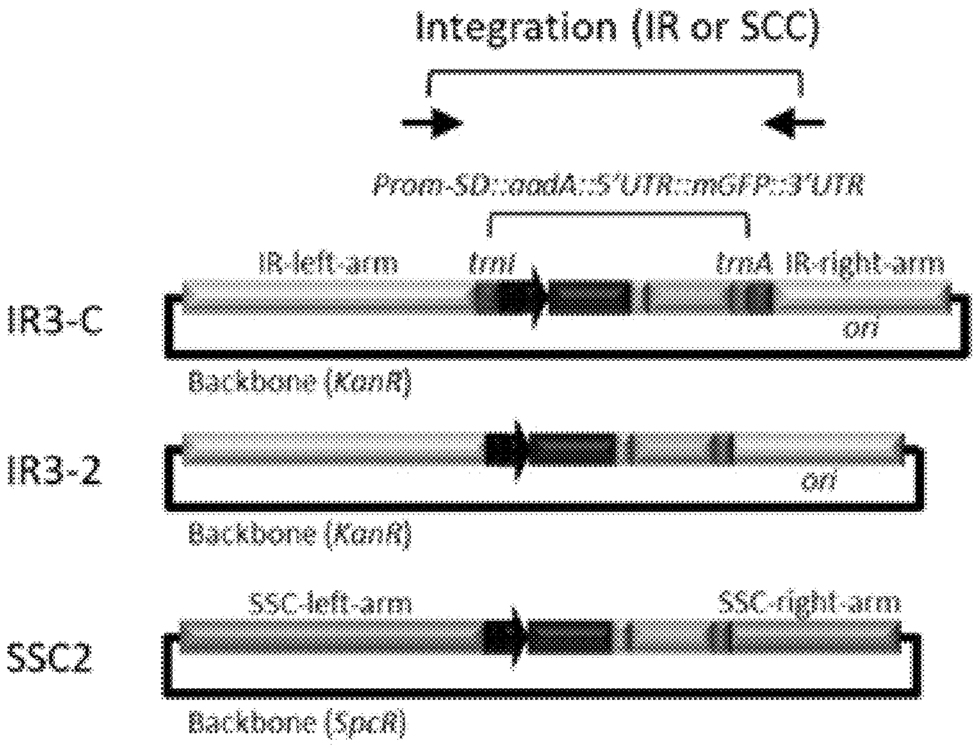
FIGS. 2A-2G. Screening for putative episomal lines. (A) Schematic representation of three DNA constructs: IR3-C, IR3-2 and SSC2. IR left (~4.7 kb) and right (~2.9 kb; including OriA) homologous arms (orange), and SCC left (~5 kb) and right (~1.8 kb) homologous arms (cyan) are indicated. A selection cassette located between arms is indicated: Prom-SD: rrn promoter along with a Shine-Dalgarno sequence (black); aadA: spectinomycin resistance gene (blue); 5 'UTR: 5' untranslated region (gray); mGFP: gene encoding monomeric green fluorescent protein (green); and 3 'UTR: 3' untranslated region (deep gray). trnI (191 bp) (SEQ ID NO: 90) and trnA (173 bp) (SEQ ID NO: 91) sequences (red) are located at 5' and 3' ends of the selection cassette in IR3-C, respectively. Backbone vectors containing kanamycin (KanR) or streptomycin (SpcR) resistance gene are indicated in IR3s and SSC2 constructs, respectively. (B) Vector integration in the plastome of transplastomic IR3-C, IR3-2 and SSC2 lines. Polymerase Chain Reactions (PCRs) using primers for IR (trnI/trnA) or SSC (ndhG/ndhI) regions were used to check vector integration in IR3s and SCC2 lines, respectively (Black arrows; A). 15 lines per construct were tested (lines 1-5 panel B and 6-15 in FIG. 5A). PCR bands of 2.8 and 2.6 kb indicate correct integration of IR3-C and IR3-2 (or SSC2) vectors, respectively. Lower-molecular weight bands of 0.46 and 0.44 kb indicate wild-type IR and SSC regions of plastome, respectively. (C-E) PCRs using primers specific for mGFP (0.72 kb), aadA (0.79 kb) and the loading control rbcL gene (0.22 kb) are shown in C, D and E, respectively. (F, G) Presence of backbone vector in different transplastomic lines. PCRs using primers specific for the KanR gene (0.8 kb) indicate the presence of backbone vector in one IR3-C (line 2) and one IR3-2 (line 11) plants. PCRs using primers specific for SpcR confirm the absence of backbone in all SCC2 lines. Positive (IR3-C vector) and negative (non-episomal IR3 lines) controls along with wild-type samples and blanks are shown in the gels. Kb of DNA molecular markers are also indicated in the gels.

This example describes design-build-test cycles to produce exemplary episomal DNA vectors, referred to in this Example as "Mini-Synplastome engineering platform". The first design-build-test cycle for engineering synthetic extra-chromosomal DNA into potato plastids was performed with tobacco transplastome engineering vectors (IR3-C and IR3-2) engineered to include long arms (~4.7 and ~2.9 kb, respectively) homologous to the intergenic region (IR) (FIG. 2A). Tobacco sequences were used to decrease the chances of vector integration into potato plastomes thereby increasing the chances of intact episomal replication. These vectors contained Ori-A from tobacco in the 2.9 kb arm and a dual selection cassette containing an aadA spectinomycin selection gene and a GFP gene between the arms. Of the two vectors, IR3-C contains two extra sequences homologous to trnI (191 bp) and trnA (173 bp) at the 5' and 3' ends of the selection cassette, respectively. These two sequences were added to monitor and verify the effect of a short event of recombination in possible vector recircularization and propagation as autonomous unit. A third vector with long arms (~5 and ~1.8 kb) homologous to the small single copy region (SSC) has been used as a negative control without an Ori (FIG. 2A).

Figure 2B:
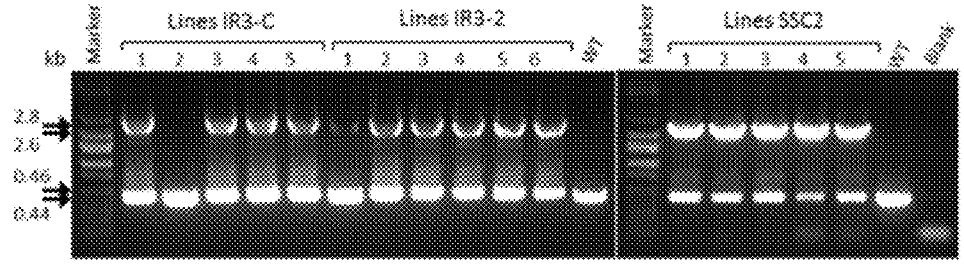
Figure 2C:
Figure 2D:
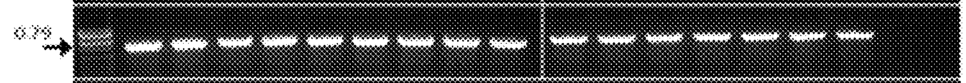
Figure 2E:
Figure 2F:
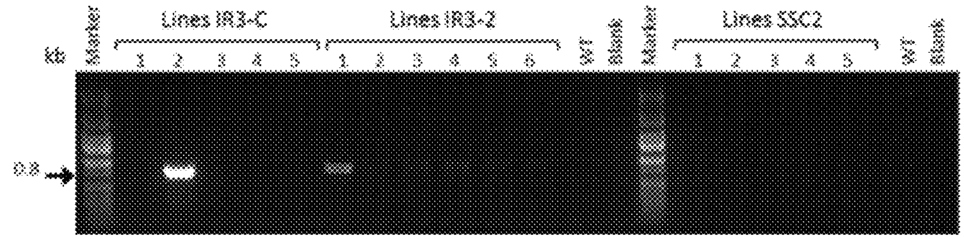
Figure 2G:
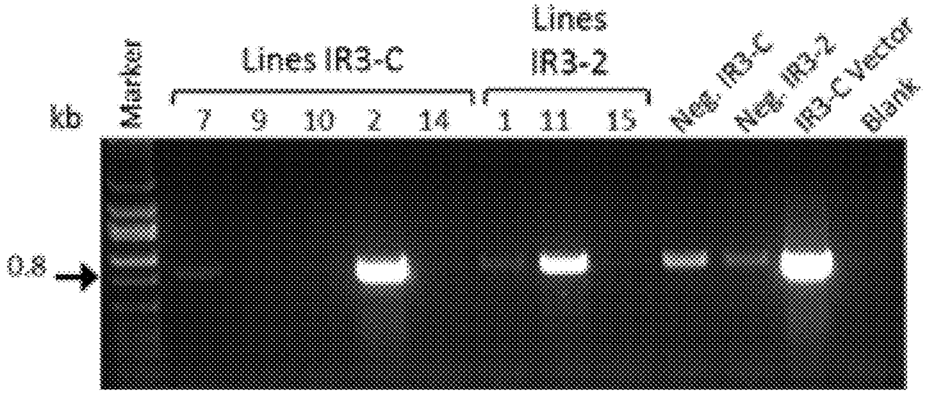

Genetically engineered potato calluses recovered during spectinomycin selection of tissue cultures contained plastids with a mixture of recombined episomal DNA as well as recombined plastome DNA (FIGS. 2B-2D). Despite clear transgene detection in all analyzed plants, the presence of specific PCR products at ~2.8 for IR3-C and ~2.6 kb for IR3-2, indicate correct integration in only 67 and 80% of IR3-C and IR3-2 lines, respectively (FIGS. 2B-2E and FIGS. 5A-5B). To the contrary, the negative control vector SSC2 correctly integrated in all analyzed plants (~2.6 kb band; FIGS. 2B-2E and FIGS. 5A-5B). DNA bands of 464 and 443 bp indicate the presence of wild-type IR3 and SSC2 integration sites, respectively. All transplastomic lines show normal growth in vitro and the detection of strong GFP signal localized into chloroplasts confirms protein expression and correct localization (FIGS. 6A-6B and 7A-7B, respectively). Despite extensive recombination between vectors and the native plastome, a few lines had less integration (FIGS. 2F-2G). The stably-maintained intact recombined plasmids were extracted from the top performing lines. These plasmids were transformed into *E. coli* to characterize the episomal DNA vectors. Two new vectors, pMagic and pSmart, were recovered from IR3-C and IR3-2 lines, respectively.

Figure 3A:
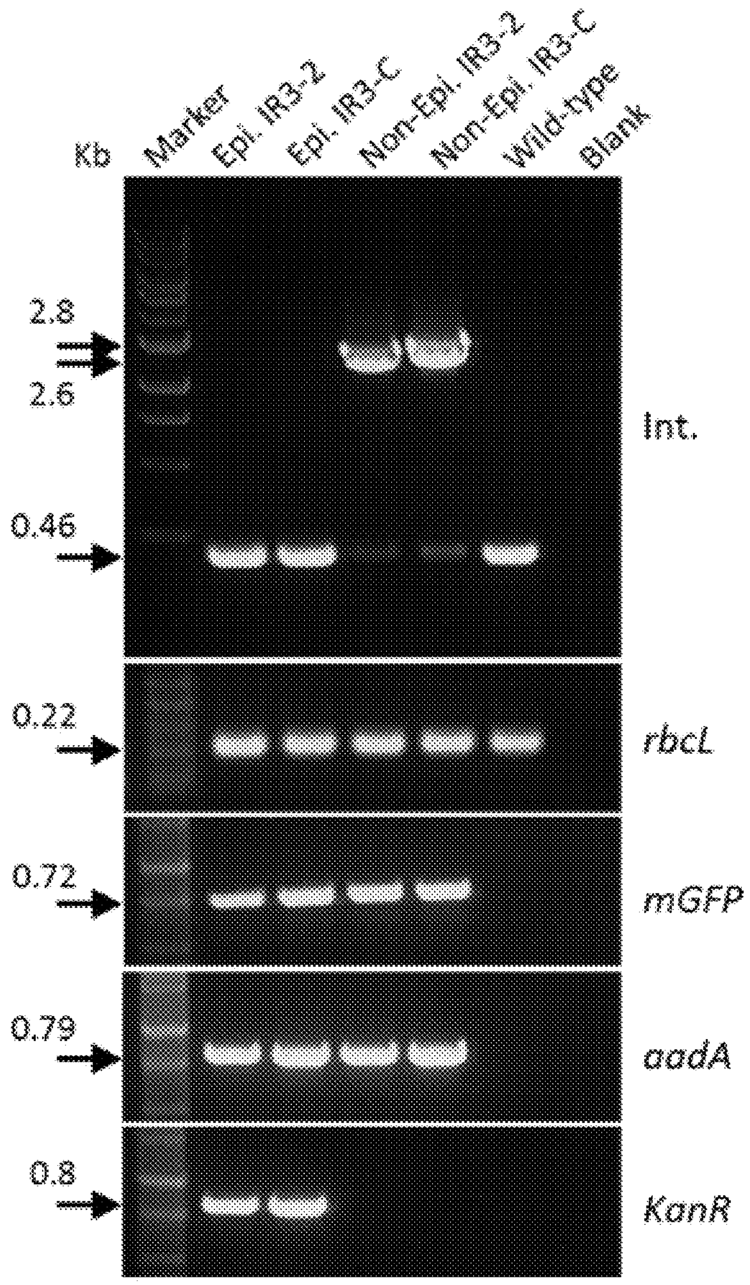
FIGS. 3A-3F. Characterization of the second generation of episomal lines. (A) Vector integration in the plastome of the second generation of episomal and non-episomal lines. PCRs using primers for IR (trnI/trnA) were used to check vector integration (Int) in episomal (Epi) and non-episomal (Non-Epi) IR3-C and IR3-2 lines, respectively. DNA-bands of 2.8 and 2.6 kb indicate integration of IR3-C and IR3-2 vectors, respectively. Lower-molecular weight bands of 0.46 kb indicate wild-type IR regions of plastome. PCRs using primers specific for rbcL fragment (0.22 kb), mGFP (0.72 kb), aadA (0.79 kb) and KanR (0.8 kb) are also indicated. A wild-type sample and blank are shown in the gels. Kb: DNA molecular markers. (B) Schematic representation of pMagic and pSmart extracted from IR3-C and IR3-2 episomal lines, respectively. IR left (~4.7 kb) and right (~2.9 kb; including OriA) homologous arms (orange) linked together (black arrow). The backbone vectors containing kanamycin resistance gene (KanR) is indicated. (C, D) Two weeks-old IR3-C and IR3-2 lines are shown in C and D, respectively (FIG. 6). Inserts showing bacterial colonies transformed with pMagic and pSmart extracted from leaf tissue. (E, F) Confocal images showing mGFP localization into the chloroplast stroma of episomal IR3-C and IR3-2 lines (E and F, respectively; also FIG. 7). Merge images of bright field (gray), mGFP (green) and chlorophyll (red) are shown. Scale bars: 10 mm (C, D and inserts); 20 μm (E, F).
Figure 3B:
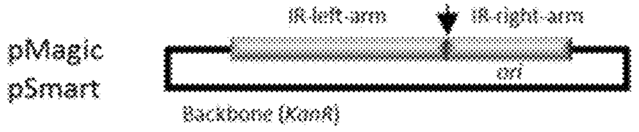
Figure 3C:
Figure 3D:
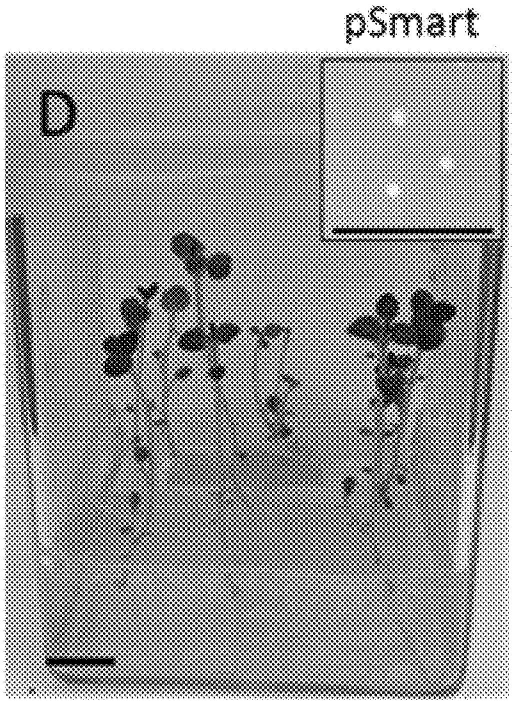
Figure 3E:
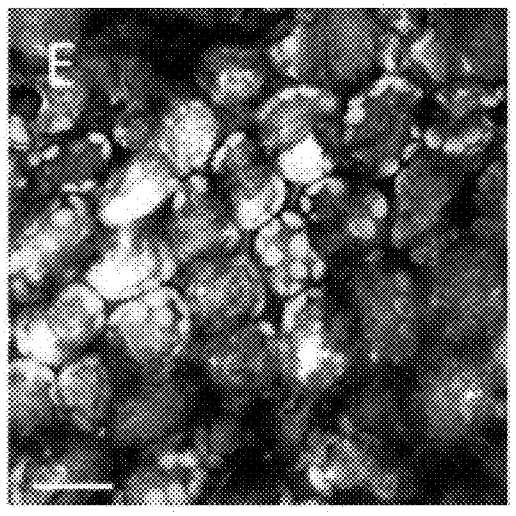
Figure 3F:
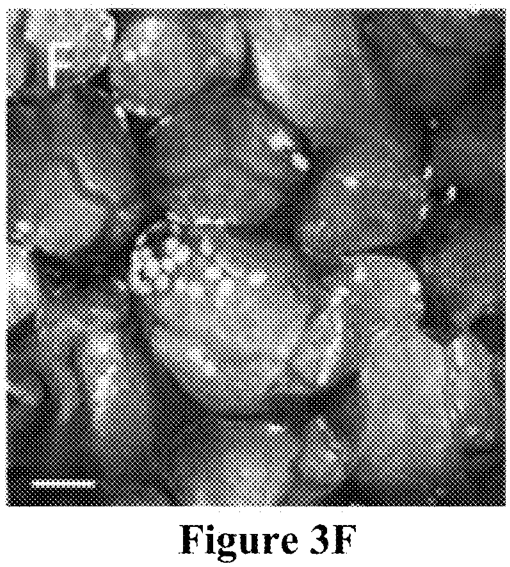

Both pMagic and pSmart were used in a second design-build-test cycle to produced mini-synplastomic plants (FIGS. 3A-3B). The presence of episomal plasmids in IR lines without integration has been verified by amplifying genes of the backbone. In two independent lines, episomal IR3-C and IR3-2, the backbone gene KanR is easily detectable in leaf tissue of the first and second generations of the transgenic plants (FIGS. 2F-2G and FIG. 3A, respectively). To the contrary, the SpcR gene located in the backbone of the SCC2 vector is not detectable in control lines (FIG. 2F). Two plasmids pMagic and pSmart contained in total genomic DNA preparations of episomal IR3-C and IR3-2 lines, respectively, have been recovered by back-transformation to *E. coli*, demonstrating the ability of both units to replicate efficiently as extra plastomic DNA (FIG. 3B-3F).

Figure 8A:
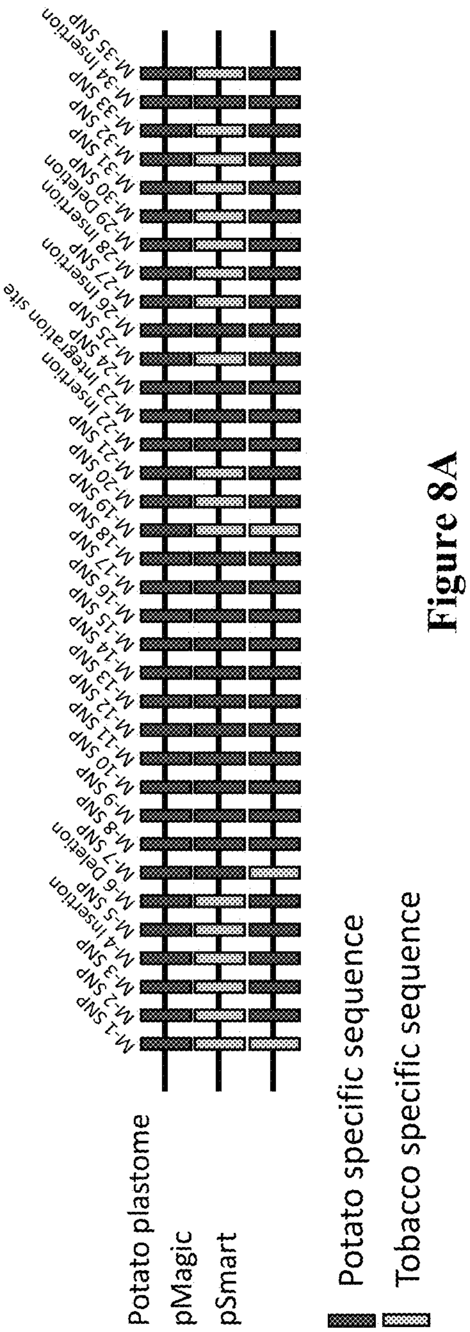
FIGS. 8A-8B. Sequence alignment of potato plastome versus homologous arms of pMagic and pSmart. (A) There were 35 mutations between the trnI/trnA region of potato plastome (red) and the tobacco IR homologous arms used to design the original IR3 vectors (yellow). Mutations 1 to 35 (M-1 to M-35) are indicated. These mutations include: SNP, single nucleotide polymorphism; bases insertion and deletion; the position of the integration site is also indicated. These mutations can be used as markers for homologous recombination between the endogenous plastome and the extra-plastomic DNA. The episomal constructs have different potato plastome-specific sequences, demonstrating multiple events of homologous recombination. (B) Image showing homologous recombination between the endogenous potato plastome and episomal plasmids (pMagic or pSmart).
Figure 8B:
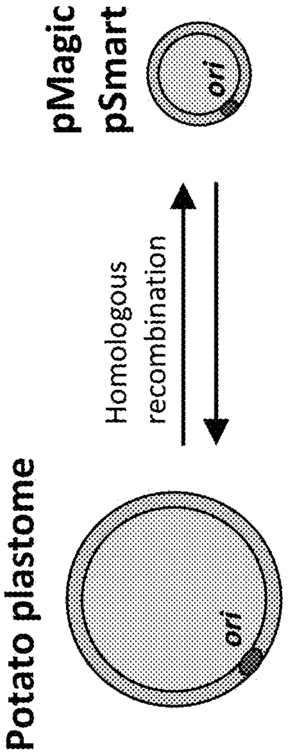
Figure 9A:
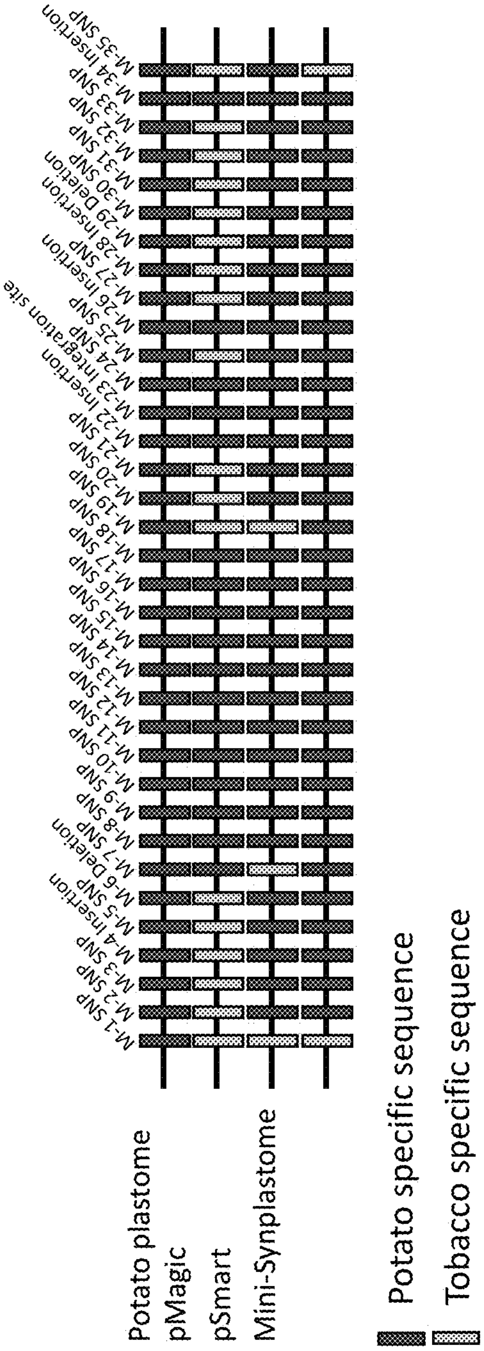
FIGS. 9A-9B. Sequence alignment of potato plastome versus homologous arms of the Mini-Synplastome. (A) There were 35 mutations between the trnI/trnA region of potato plastome (red) and the tobacco IR homologous arms used to design the original IR3 vectors (yellow). Mutations 1 to 35 (M-1 to M-35) are indicated. These mutations include: SNP, single nucleotide polymorphism; bases insertion and deletion; the position of the integration site is also indicated. These mutations can be used as markers for homologous recombination between the endogenous plastome and the extra-plastomic DNA. Comparing to the original pMagic, the Mini-Synplastome got almost all potato plastome-specific sequences except for two SNPs at both sites (M-1 and M35 respectively). Homologous arms of pMagic and pSmart have been included as comparisons. (B) Image showing homologous recombination between the endogenous potato plastome and the Mini-Synplastome.
Figure 9B:
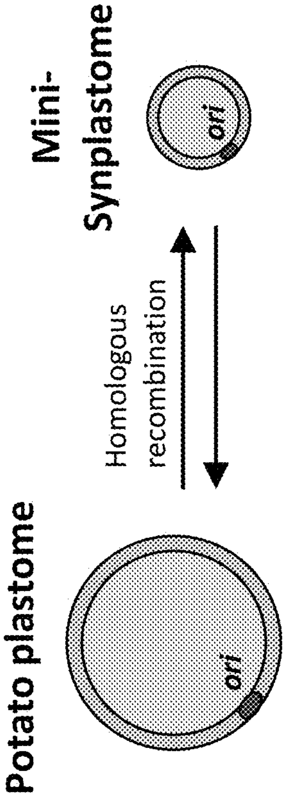
Figure 10A:
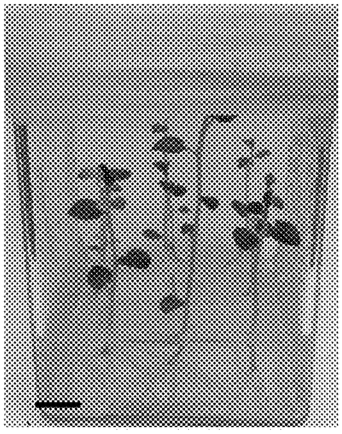
FIGS. 10A-10F. Phenotype of non-episomal and episomal IR3 lines along with SSC2 and wild-type potato. Images showing two weeks-old plants. Wild-type potato (A); SSC2 line (B); non-episomal IR3-2 line (C); non-episomal IR3-C line (D); episomal IR3-2 line harboring pSmart (E); and episomal IR3-C line harboring pMagic (F). Scale bars: 10 mm.
Figure 10B:
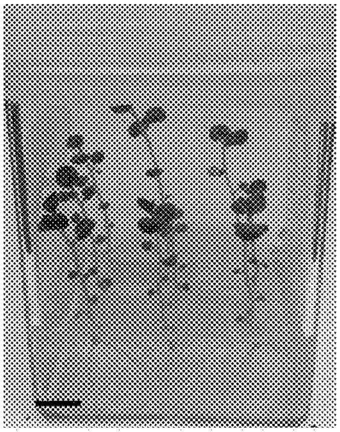
Figure 10C:
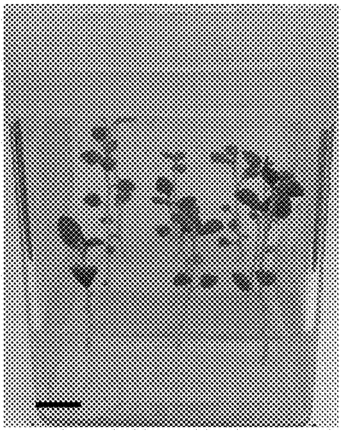
Figure 10D:
Figure 10E:
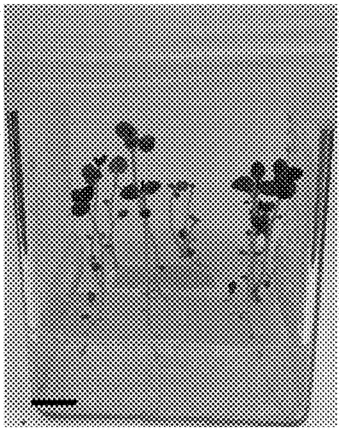
Figure 10F:
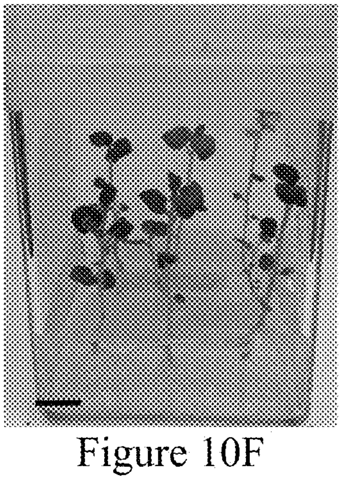
Figures 11A, 11B, 11C, 11D:
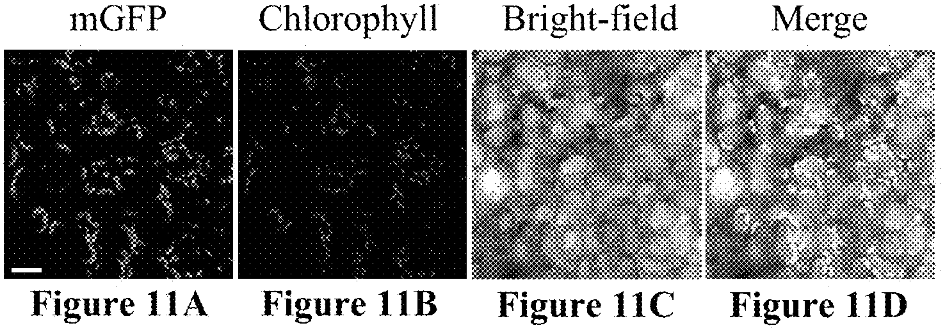
FIGS. 11A-11T. Confocal images showing mGFP localization in non-episomal and episomal IR3 lines along with SSC2 and wild-type potato. Confocal images showing correct mGFP localization into the chloroplast stroma of the indicated lines: SSC2 line (A-D); non-episomal IR3-2 line (E-H); non-episomal IR3-C line (I-L); episomal IR3-2 line harboring pSmart (M-P); and episomal IR3-C line harboring pMagic (Q-T). GFP (green), chlorophyll (red), bright-field (gray) and merge images (GFP/chlorophyll/bright-field) are shown. Scale bars: 20 μm.
Figures 11E, 11F, 11G, 11H:
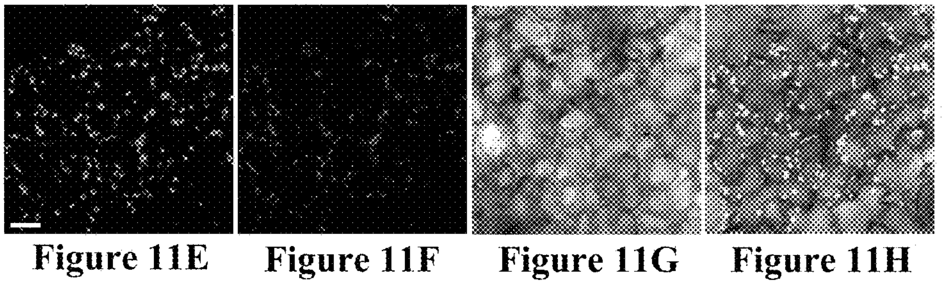
Figures 11I, 11J, 11K, 11L:
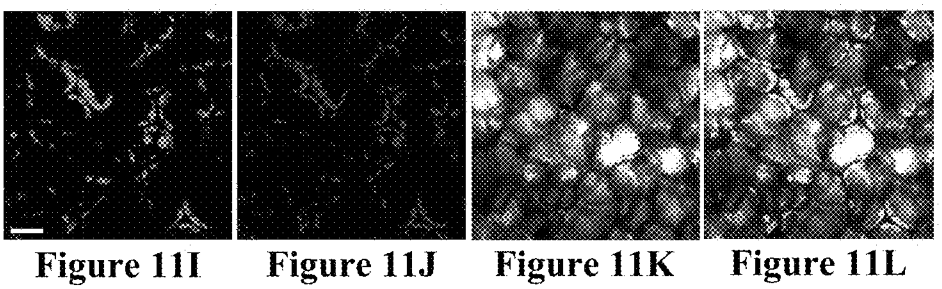
Figures 11M, 11N, 11O, 11P:
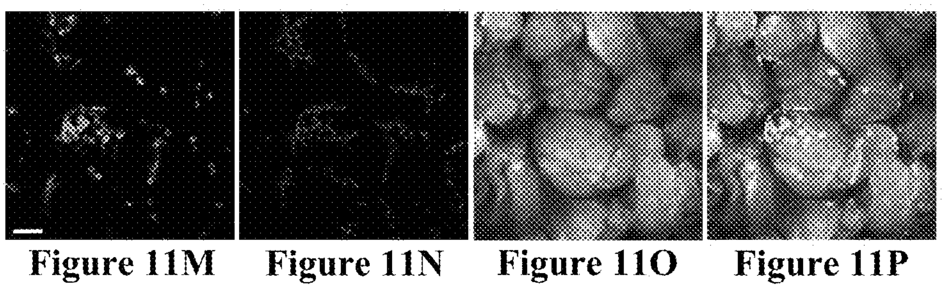
Figures 11Q, 11R, 11S, 11T:
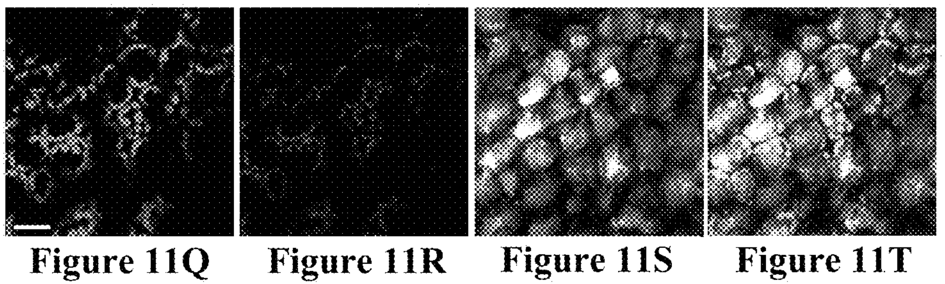

PCR and sequence analysis performed on pMagic and pSmart extracted from leaf tissue demonstrated that these extra-plastomic units contain the backbone vector along with full-length 4.7 and 2.9 kb arms devoid of the transgene cassettes. The selection cassette is removed, integrating in an unpredicted site of plastome by a secondary event of homologous recombination (FIG. 3B and FIGS. 8A-8B). There are 35 sequence-differences between the potato plastome and the tobacco IR homologous arms of episomal plasmids. Comparing with the original IR3 constructs, the homologous arms of pMagic and pSmart contain a different set of potato plastome-specific sequences, demonstrating multiple events of homologous recombination with the endogenous plastome (FIGS. 9A-9B). These recombination events between the plasmid and the plastome don't prevent the pMagic and pSmart from being stably maintained episomally. Moreover, no mutations have been found in the backbone of these plasmids indicating that OriA is necessary and sufficient for reliable replication.

Figure 4A:
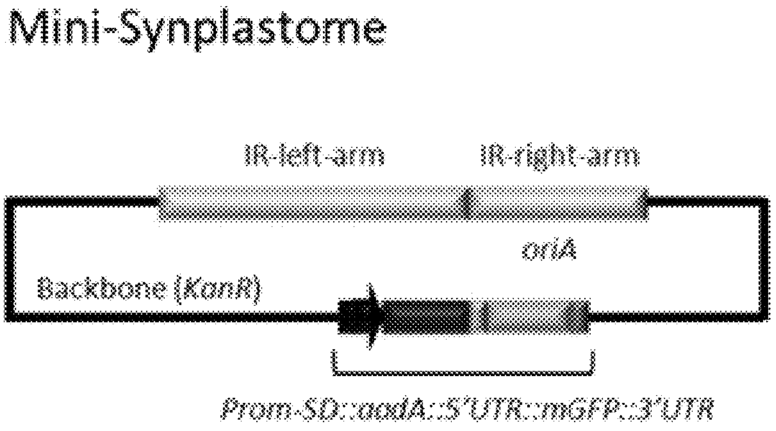
FIGS. 4A-4C. Characterization of transplastomic green callus transformed with the Mini-Synplastome. (A) Schematic representation of the Mini-Synplastome. IR left (~4.7 kb) and right (~2.9 kb; including OriA) homologous arms (orange) linked together. The dual selection cassette (Prom-SD::aadA::5'UTR::mGFP::3'UTR) has been cloned in the backbone vectors. Prom-SD: rrn promoter along with a Shine-Dalgarno sequence (black); aadA: spectinomycin resistance gene (blue); 5 'UTR: 5' untranslated region (gray); mGFP: gene encoding monomeric green fluorescent protein (green); and 3 'UTR: 3' untranslated region (deep gray) are indicated. (B) Confocal image showing mGFP localization into the chloroplast of transplastomic green callus transformed with the Mini-Synplastome. Bright field, mGFP (green), chlorophyll (red) and merge signals are indicated. Insert (bright field) showing bacterial colonies transformed with the Mini-Synplastome extracted from green callus. Scale bars: 20 μm (B); 10 mm (inserts). (C) Molecular characterization of green callus transformed with the Mini-Synplastome. PCRs using primers for IR (trnI/trnA) were used to check vector integration (Int). DNA-bands of 2.8 kb indicate integration of IR3-C vector. Lower-molecular weight bands of 0.46 kb indicate wild-type IR regions of plastome. PCRs using primers specific for rbcL fragment (0.22 kb), mGFP (0.72 kb), aadA (0.79 kb) and KanR (0.8 kb) are also indicated. Transplastomic green callus transformed with the Mini-Synplastome along with two controls episomal (Epi) and non-episomal (Non-Epi) IR3-C lines are shown. Wild-type samples and blanks are also shown in the gels. Kb: DNA molecular markers.
Figure 4B:
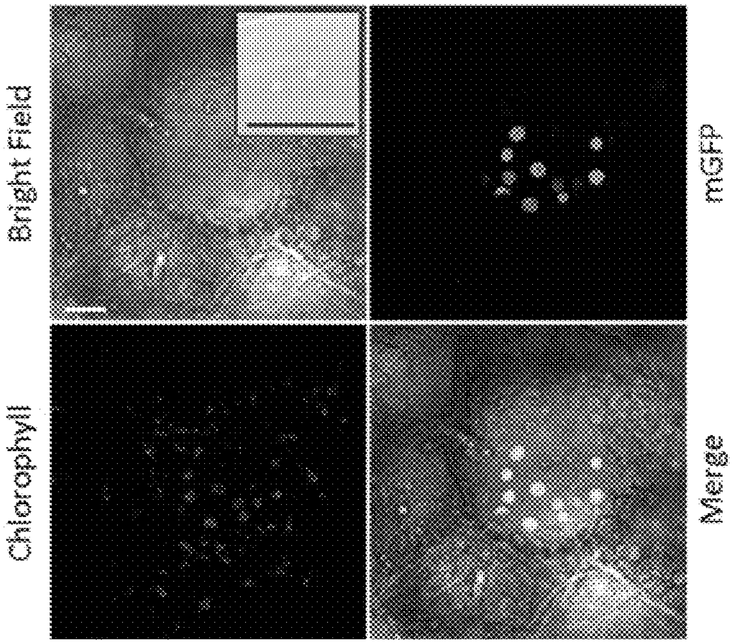
Figure 4C:
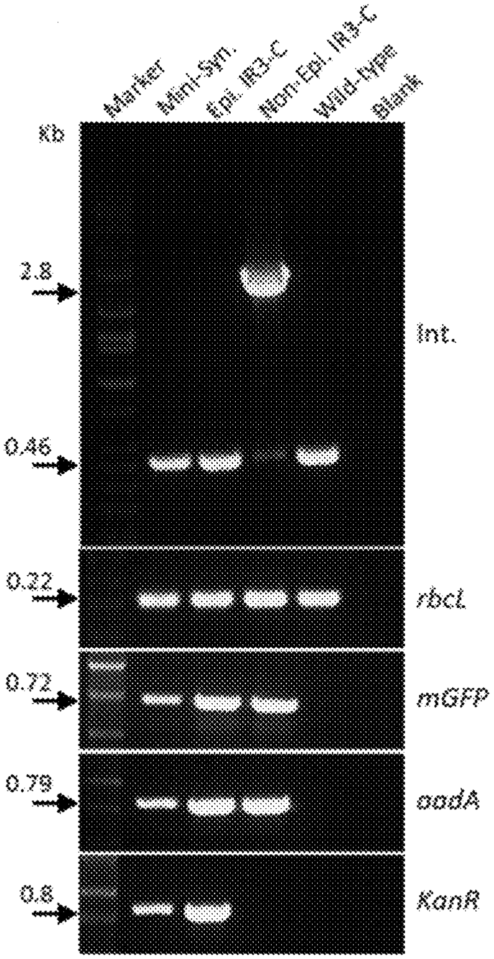
Figure 6A:
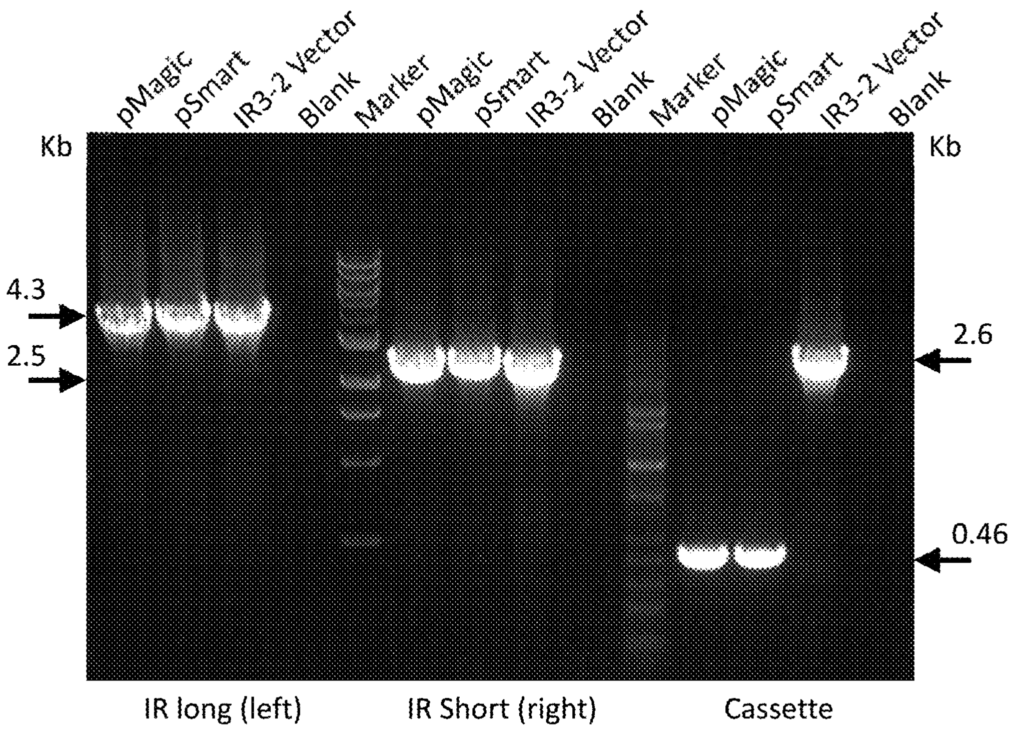
FIGS. 6A-6B. PCR characterization of pMagic and pSmart extracted from episomal lines. (A) PCRs using primers for the long (left) and short (right) IR (trnI/trnA) homologous arms along with primers external of the dual-selection cassette were used to characterize pMagic and pSmart. PCR bands of 4.3 and 2.5 kb at the same molecular weight of the positive control IR3-2 vector indicate the presence of long and short arms in both pMagic and pSmart. The presence of lower-molecular weight bands of 0.46 kb rather than 2.6 kb (positive control IR3-2 vector) indicate removal of the dual selection cassette in pMagic and pSmart. (B) PCRs using primers specific for mGFP (0.72 kb), aadA (0.79 kb) and KanR gene (0.8 kb) confirmed the absence of the selection cassette and the presence of backbone vector in pMagic and pSmart. The original IR3-2 vector has been used as positive control for comparison of the molecular weight of the DNA bands. The negative controls (blanks) and DNA molecular markers (kb) are also indicated in the gels. These PCR results have been confirmed by sequencing the entire pMagic and pSmart.
Figure 6B:
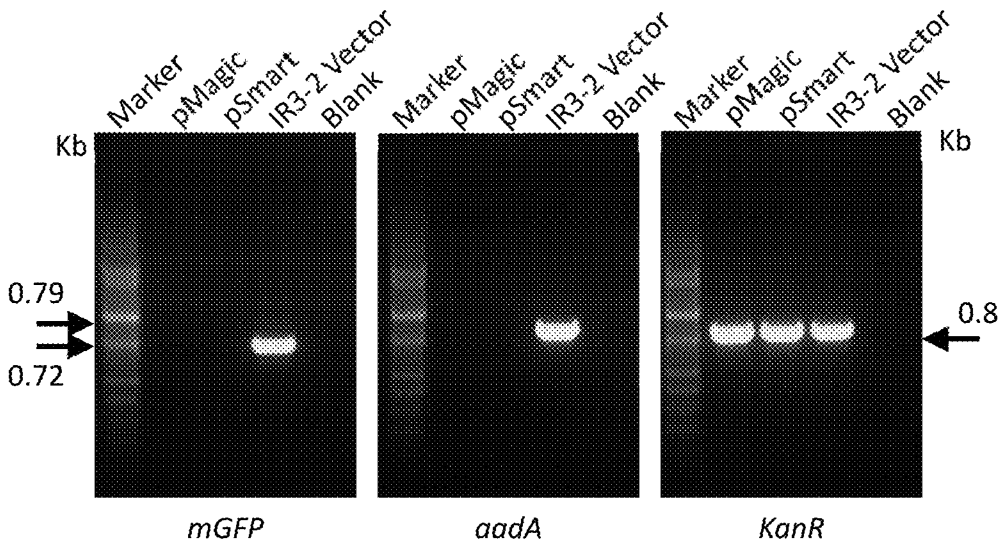
Figure 7A:
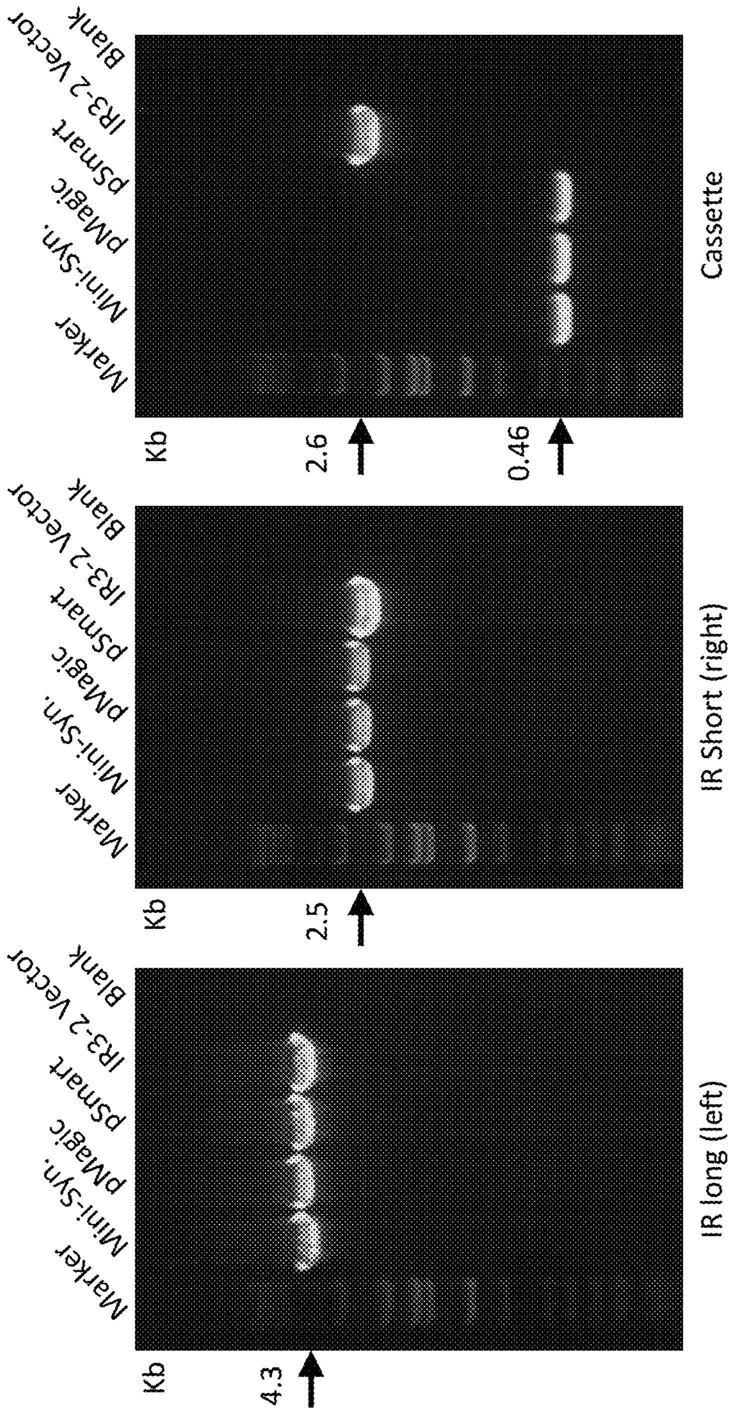
FIGS. 7A-7B. PCR characterization of Mini-Synplastome extracted from transplastomic green callus. (A) PCRs using primers for the long (left) and short (right) IR (trnI/trnA) homologous arms along with primers external of the dual-selection cassette were used to characterize the Mini-Synplastome purified from transplastomic callus. pMagic, pSmart and the original IR3-2 vector were used as comparison. PCR bands of 4.3 and 2.5 kb at the same molecular weight of the positive control IR3-2 vector indicate the presence of long and short arms in the Mini-Synplastome. The presence of lower-molecular weight bands of 0.46 kb rather than 2.6 kb (IR3-2 vector) suggests correct location of the cassette integrated in the backbone. (B) PCRs using primers specific for mGFP (0.72 kb), aadA (0.79 kb) and KanR gene (0.8 kb) confirmed the presence of both transgenes (dual-selection cassette) located in the backbone. The negative controls (blanks) and DNA molecular markers (kb) are also indicate in the gels. These PCR results have been confirmed by sequencing of the entire Mini-Synplastome.
Figure 7B:
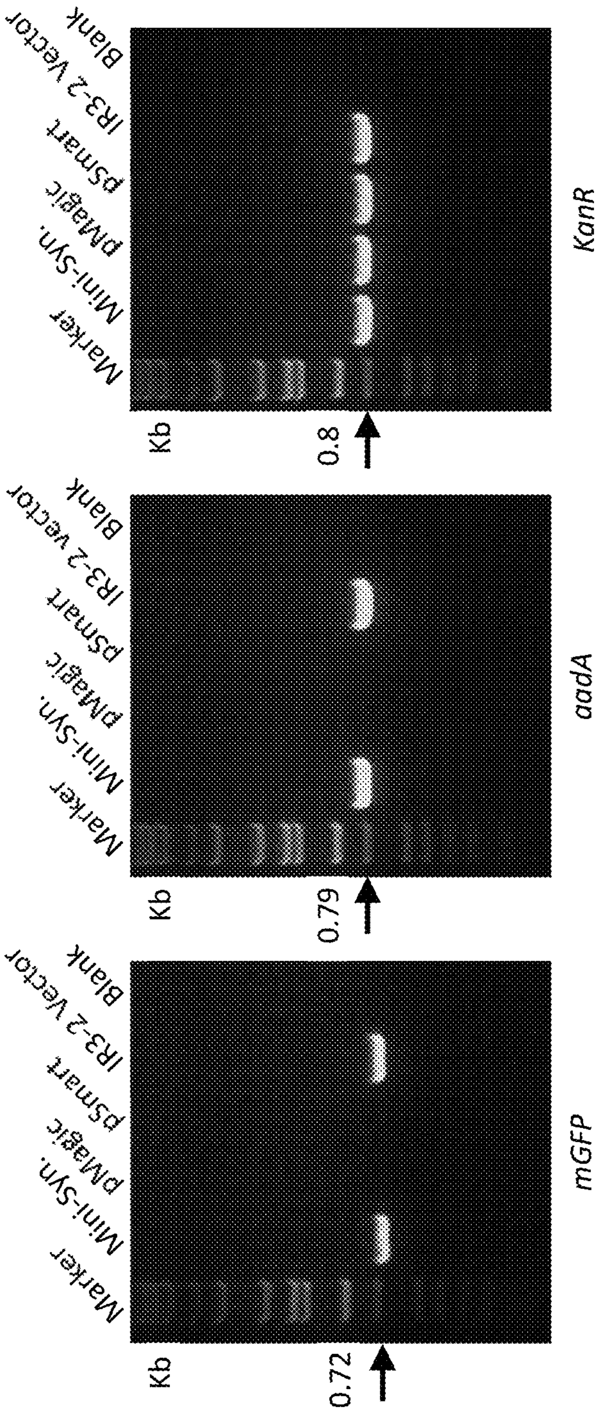

Both pMagic and pSmart represent Mini-Synplastome platforms. Since all sequences involved in plasmid instability have already recombined with the endogenous genome, these plasmids are able to be maintained episomally at high copy number even after the second generation of transplastomic plants (FIGS. 10A-10F). pMagic was modified to stably express transgenes directly from a stable episomal vector by including a dual marker aadA-GFP cassette: Mini-Synplastome-1 (pMinS1) (FIG. 4A). Engineered callus with plastid-localized GFP was obtained from leaf tissue (FIG. 4B). In back-transformation experiments to *E. coli*, the intact pMinS1 vector was recovered from engineered plastids (FIG. 4C and FIG. 11). These results demonstrate that pMinS1 is a stable Mini-Synplastome platform and can be used for metabolic engineering.

Figures 12A, 12B:
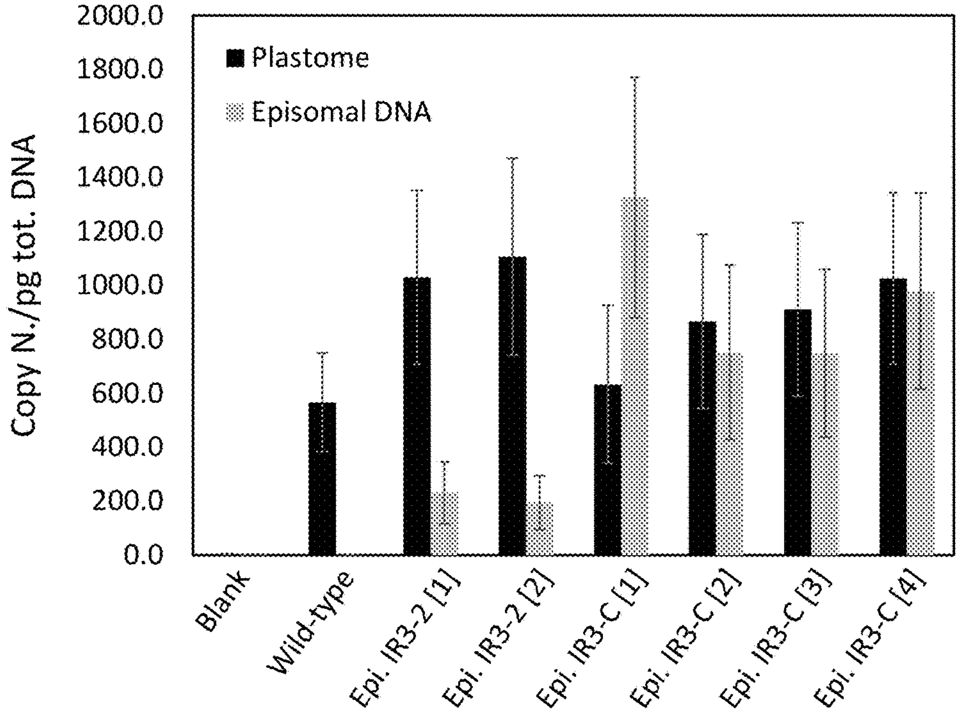
FIGS. 12A-12B. Determination of the molar ratio Plastome/Episomal DNA in the second generation of episomal IR3 lines. (A) Graph summarizing the copy number (Copy N) of plastome and episomal DNA per pg of total genomic DNA extracted from different IR3-2 (1 and 2) and IR3-C (1-4) episomal lines. (B) Table summarizing the molar ratio Plastome/Episomal DNA in the indicated second generation of episomal IR3 lines. Results are expressed as mean± standard deviation (SD) of 9 independent experiments of Real-Time PCR (n=9). One experiment includes 3 technical replicates for each sample.
Figure 14A:
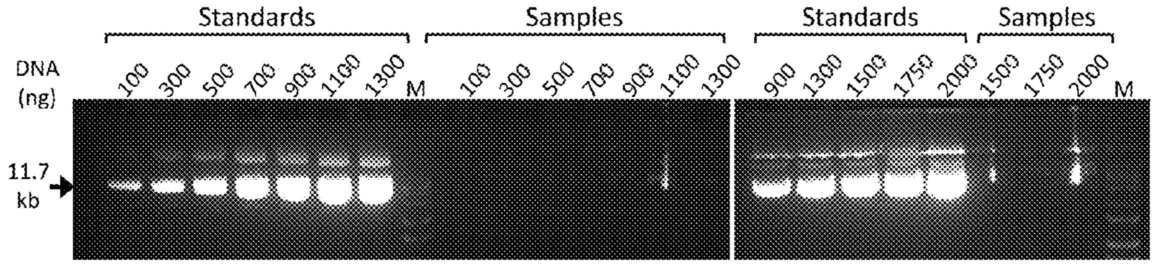
FIGS. 14A-14D. (A) DNA binding capacity of gold particles. For each sample, 0.3 mg of 0.6 μm diameter gold particles was used to bind the indicated ng of pMDC45 (from 100 to 2000 ng). DNA unable to be bound by gold-particles is separated in the gel. 0.3 mg of gold-particles can bind up to 1750-2000 ng of DNA. Known amount of pure pMDC45 have been used as standards (100-2000 ng). (B) Effect of mixing and sonication on DNA binding capacity. 0.3 mg of 0.6 μm gold particles binding 800 ng of pMDC45 have been used for each treatment. NT: non-treated sample; Mixed: sample mixed by vortexing; Son 25×1-2 and Son 50×1-2: samples sonicated 1 or 2 times for 1 minute each at the amplitude of 25 or 50, respectively. For all condition the samples have been separated into gold pellet and supernatant. NT and samples have a similar gel profile indicating stability of DNA-gold complexes after each treatment. 50 to 800 ng of purified pMDC45 have been used as standards. DNA markers (M) and the molecular weight of bands (11.7 kb) are indicated. (C-D) Graphs representing transformed BY2 cells per plate (500 μl of cellular pellet) using the Gene-Gun particle delivery. (C) 0.3 mg of 0.6 μm gold-particles binding a different amount of DNA (1.4, 1, 0.7 and 0.4 μg) were used. All samples were placed at 6 cm-distance from the gun and shot at 1,100 psi of rupture disk pressure. (D) 0.3 mg of 0.6 μm gold particles binding 1 μg of DNA have been used. Samples have been shot at a variable distance (6-9 cm) and rupture disk pressure (900, 1,000 and 1,350 psi). Results are expressed as mean± standard deviation (sd) of two plates per each condition, repeated in two independent experiments (n=2).
Figure 14B:
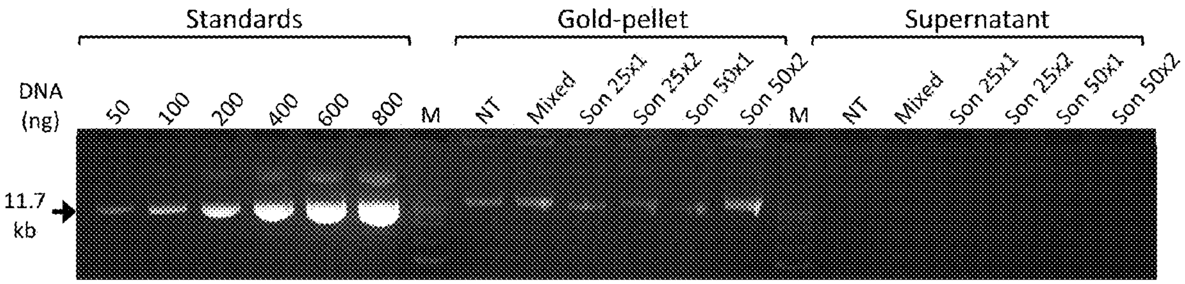
Figure 14C:
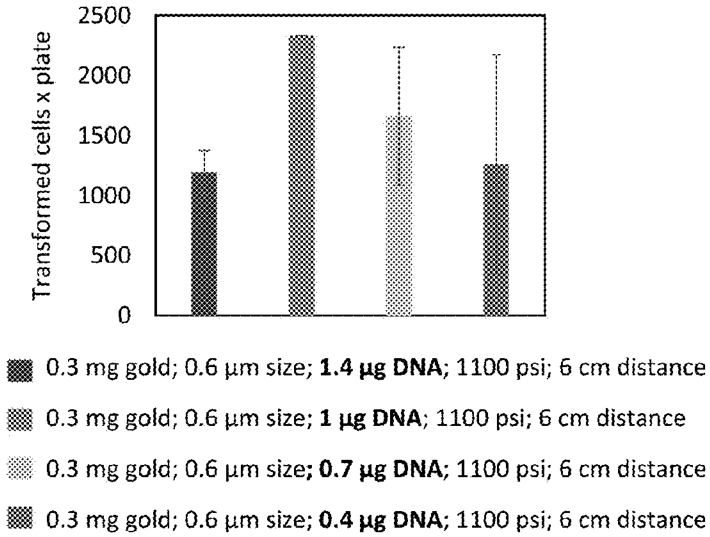
Figure 14D:
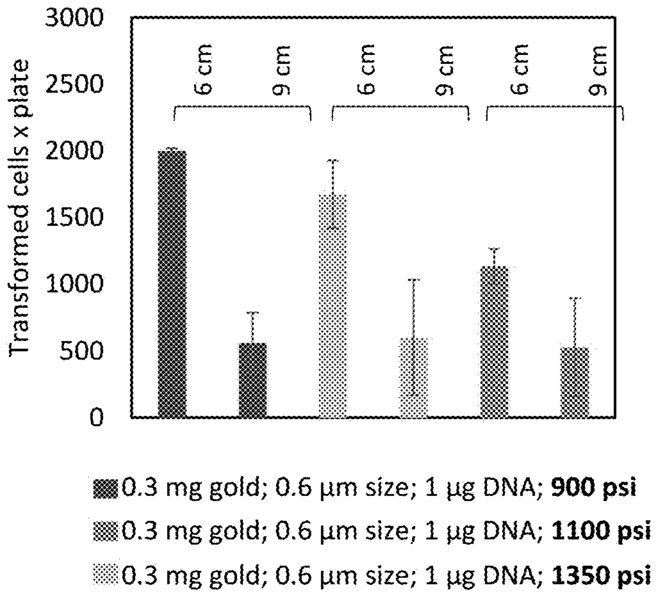
Figure 15A:
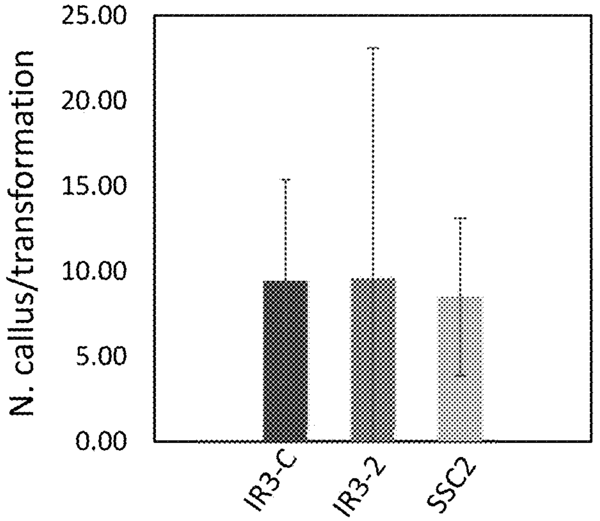
FIGS. 15A-15B. (A) Graphs showing the number of green callus obtained per transformation (plate containing about 6 $cm^2$ of leaf tissue). Per transformation, 0.3 mg of 0.6 μm gold binding 1 μg of DNA were shot at 6 cm of target distance and 1,100 psi. (B) Graphs showing the number of calluses able to originate primary plantlets. Three different constructs, IR3-C, IR3-2 and SSC2 were transformed. The results of the two graphs are summarized in the corresponding tables below the graphs. Results are expressed as mean± standard deviation (sd) of 5 plates (transformations) per each condition, repeated in four independent experiments (n=4).
Figure 15B:
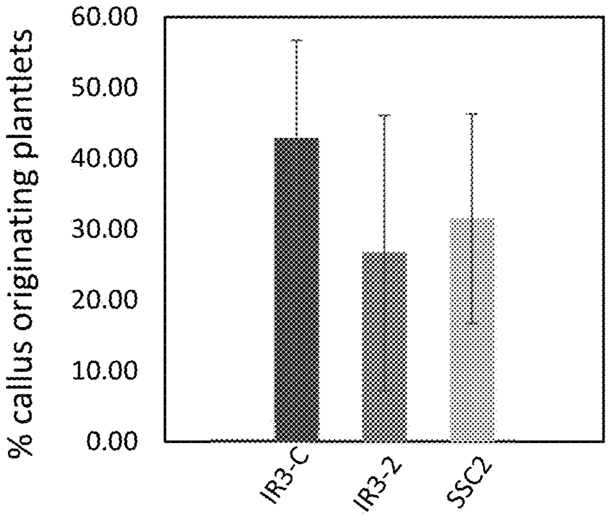

The correct sequences of the Mini-Synplastome extracted from transplastomic green callus were confirmed by PCR analysis and sequencing of the entire plasmid, demonstrating that transgenes (mGFP and aadA) can be expressed from an extra-plastomic DNA (FIG. 11). In this case, the presence of the selection cassette at the opposite site of the homologous sequence prevents its recombination with the plastome and removal. Compared with the original plasmid pMagic, the homology arms of pMagic-aadA-mGFP contained all potato specific sequences with the exception of two SNPs (FIGS. 12A-12B).

The ability of the episomal DNA vectors disclosed herein to autonomously replicate and to stably persist in high copy number makes them a valuable tool for chloroplast metabolic engineering and other biotechnological applications. In fact, the ability to regenerate transplastomic green calluses from transformed leaf tissue makes it an excellent material for early screening of synthetic operons. Moreover, the possibility to express genes without the interference of surrounding sequences of the plastome makes the Mini-Synplastomes particularly suited for the study of chloroplast regulatory elements (promoters together with 5' and 3' UTRs). For this purpose, dozens of chloroplast constructs can be assembled in relatively short time by using a modular cloning kit (MoChlo kit) based on Golden-Gate assembly.

The Mini-Synplastome platform has the potential to introduce an entire metabolic pathway, organized in one or multiple synthetic operons that can be installed in chloroplasts without the requirement of multiple events of homologous recombination. This will significantly reduce the time necessary to install a multigene pathway and at the same time, the possibility to split genes in different constructs will simplify the cloning process. Mini-Synplastomes will also allow a fine regulation of gene expression, providing the possibility to modulate expression at both the regulatory level and through different origins of replication. In fact, many chloroplast-specific Ori have been characterized from different organisms, including higher plants and algae. The use of single or multiple Ori with different activities could provide another level of regulation of gene expression by modulating the gene copy number.

Thus, the episomal DNA vectors disclosed herein can be used to insert and organize transgenes into chloroplasts. Their ability to autonomously replicate allows flexibility in plant genetic engineering similar to flexibility of engineering bacterial cells.

REFERENCES

1. Wurbs, D., Ruf, S. & Bock, R. Contained metabolic engineering in tomatoes by expression of carotenoid biosynthesis genes from the plastid genome. *The Plant journal: for cell and molecular biology* 49, 276-288, doi:10.1111/j.1365-313X.2006.02960.x (2007).

2. Pasoreck, E. K. et al. Terpene metabolic engineering via nuclear or chloroplast genomes profoundly and globally impacts off-target pathways through metabolite signalling. *Plant biotechnology journal* 14, 1862-1875, doi:10.1111/pbi.12548 (2016).

3. Lin, M. T., Occhialini, A., Andralojc, P. J., Parry, M. A. & Hanson, M. R. A faster Rubisco with potential to increase photosynthesis in crops. *Nature* 513, 547-550, doi:10.1038/nature13776 (2014).

4. Svab, Z. & Maliga, P. High-frequency plastid transformation in tobacco by selection for a chimeric aadA gene. *Proceedings of the National Academy of Sciences of the United States of America* 90, 913-917 (1993).

5. Kota, M. et al. Overexpression of the Bacillus thuringiensis (Bt) Cry2Aa2 protein in chloroplasts confers resistance to plants against susceptible and Bt-resistant insects. *Proceedings of the National Academy of Sciences of the United States of America* 96, 1840-1845 (1999).

6. Svab, Z., Hajdukiewicz, P. & Maliga, P. Stable transformation of plastids in higher plants. *Proceedings of the National Academy of Sciences of the United States of America* 87, 8526-8530 (1990).

7. Valkov, V. T. et al. High efficiency plastid transformation in potato and regulation of transgene expression in leaves and tubers by alternative 5' and 3' regulatory sequences. *Transgenic research* 20, 137-151, doi:10.1007/s11248-010-9402-9 (2011).

8. Sidorov, V. A. et al. Technical Advance: Stable chloroplast transformation in potato: use of green fluorescent protein as a plastid marker. *The Plant journal: for cell and molecular biology* 19, 209-216 (1999).

9. Jin, S. & Daniell, H. The Engineered Chloroplast Genome Just Got Smarter. *Trends in plant science* 20, 622-640, doi:10.1016/j.tplants.2015.07.004 (2015).

10. Bock, R. Strategies for metabolic pathway engineering with multiple transgenes. *Plant molecular biology* 83, 21-31, doi:10.1007/s11103-013-0045-0 (2013).

11. Daniell, H., Lin, C. S., Yu, M. & Chang, W. J. Chloroplast genomes: diversity, evolution, and applications in genetic engineering. *Genome biology* 17, 134, doi:10.1186/s13059-016-1004-2 (2016).

12. Shinozaki, K. et al. The complete nucleotide sequence of the tobacco chloroplast genome: its gene organization and expression. *The EMBO journal* 5, 2043-2049 (1986).

13. Howe, C. J., Nisbet, R. E. & Barbrook, A. C. The remarkable chloroplast genome of dinoflagellates. *Journal of experimental botany* 59, 1035-1045, doi:10.1093/jxb/erm292 (2008).

14. Howe, C. J. et al. Evolution of the chloroplast genome. *Philosophical transactions of the Royal Society of London. Series B, Biological sciences* 358, 99-106; discussion 106-107, doi:10.1098/rstb.2002.1176 (2003).

15. Koumandou, V. L. & Howe, C. J. The copy number of chloroplast gene minicircles changes dramatically with growth phase in the dinoflagellate Amphidinium operculatum. *Protist* 158, 89-103, doi:10.1016/j.protis.2006.08.003 (2007).

16. Barbrook, A. C. et al. Polyuridylylation and processing of transcripts from multiple gene minicircles in chloroplasts of the dinoflagellate Amphidinium carterae. *Plant molecular biology* 79, 347-357, doi:10.1007/s11103-012-9916-z (2012).

17. Barbrook, A. C. & Howe, C. J. Minicircular plastid DNA in the dinoflagellate Amphidinium operculatum. *Molecular & general genetics: MGG* 263, 152-158 (2000).

18. Min, S. R. et al. An episomal vector system for plastid transformation in higher plants. *Plant Biotechnology Reports* 9, 443-449, doi:10.1007/s11816-015-0381-4 (2015).

19. Verma, D. & Daniell, H. Chloroplast vector systems for biotechnology applications. *Plant physiology* 145, 1129-1143, doi:10.1104/pp. 107.106690 (2007).

20. Kunnimalaiyaan, M. & Nielsen, B. L. Fine mapping of replication origins (ori A and ori B) in *Nicotiana tabacum* chloroplast DNA. *Nucleic acids research* 25, 3681-3686 (1997).

21. Krishnan, N. M. & Rao, B. J. A comparative approach to elucidate chloroplast genome replication. *BMC genomics* 10, 237, doi:10.1186/1471-2164-10-237 (2009).

22. Schindel, H. S., Piatek, A. A., Stewart, C. N., Jr. & Lenaghan, S. C. The plastid genome as a chassis for synthetic biology-enabled metabolic engineering: players in gene expression. *Plant cell reports* 37, 1419-1429, doi:10.1007/s00299-018-2323-4 (2018).

23. Occhialini, A. et al. MoChlo: A versatile modular cloning toolbox for chloroplast biotechnology. *Plant physiology, doi:*10.1104/pp. 18.01220 (2019).

24. Waddell, J., Wang, X. M. & Wu, M. Electron microscopic localization of the chloroplast DNA replicative origins in Chlamydomonas reinhardii. *Nucleic acids research* 12, 3843-3856 (1984).

25. Meeker, R., Nielsen, B. & Tewari, K. K. Localization of replication origins in pea chloroplast DNA. *Molecular and cellular biology* 8, 1216-1223 (1988).

26. Nisbet, R. E., Koumandou, L., Barbrook, A. C. & Howe, C. J. Novel plastid gene minicircles in the dinoflagellate Amphidinium operculatum. *Gene* 331, 141-147, doi:10.1016/j.gene.2004.02.008 (2004).

27. Untergasser, A. et al. Primer3—new capabilities and interfaces. *Nucleic acids research* 40, e115, doi:10.1093/nar/gks596 (2012).

28. Koressaar, T. & Remm, M. Enhancements and modifications of primer design program Primer3. *Bioinformatics* (*Oxford, England*) 23, 1289-1291, doi:10.1093/bioinformatics/btm091 (2007).

What is claimed is:

1. An episomal DNA vector comprising a chloroplast origin of replication (Ori) and, optionally, one or more genes of interest, wherein the episomal DNA vector does not contain any sequence that engages in homologous recombination with the plastomic DNA of a host chloroplast, wherein the Ori comprises the sequence of any of SEQ ID NOs: 1 to 30 or a sequence having at least 90% sequence identity to the sequence of any of SEQ ID NOs: 1 to 30, and the episomal DNA vector comprises the sequence of any of SEQ ID NOs: 31 to 89 or a sequence having at least 90% sequence identity to the sequence of any of SEQ ID NOs: 31 to 89 and the chloroplast Ori is from a species different from the species of the host chloroplast.

2. The episomal DNA vector of claim 1, comprising the one or more genes of interest and wherein the one or more genes of interest are flanked at one or both ends by a non-homologous sequence, wherein the non-homologous sequence does not contain any sequence that engages in homologous recombination with the plastomic DNA of the host chloroplast.

3. The episomal DNA vector of claim 1, wherein the episomal DNA vector is free from a stretch of more than 50 consecutive base pairs that has a sequence identity of more than 90% with a sequence of the plastomic DNA of the host chloroplast.

4. The episomal DNA vector of claim 1, further comprising a selection marker for a bacterium, a bacterial origin of replication and/or a selection marker for a plant cell.

5. The episomal DNA vector of claim 4, wherein the selection marker for the bacterium comprises a gene that confers resistance to an anti-bacterial antibiotic.

6. The episomal DNA vector of claim 5, wherein the anti-bacterial antibiotic is carbenicillin, ampicillin, actinomycin D, kanamycin, streptomycin, neomycin, polymyxin, zeocin, chloramphenicol, hygromycin B, tetracycline, spectinomycin, bleomycin or erythromycin.

7. The episomal DNA vector of claim 4, wherein the selection marker for the plant cell comprises a gene that confers resistance to an antibiotic that inhibits the growth of the plant cell.

8. The episomal DNA vector of claim 7, wherein the antibiotic that inhibits the growth of the plant cell is kanamycin, hygromycin, phosphinothricin or glyphosate.

9. The episomal DNA vector of claim 1, wherein the Ori comprises the sequence of SEQ ID NO: 30 or a sequence having at least 90% sequence identity to the sequence of SEQ ID NO: 30.

10. The episomal DNA vector of claim 1, wherein the one or more genes of interest confer to the plant cell one or more of: herbicide tolerance, insect resistance, increased yield of a product of interest, disease resistance, pathogen resistance, modified growth and development, modified starch content, modified oil content, modified fatty acid content, modified protein content, enhanced animal or human nutrition, biopolymer production, environmental stress resistance, expression of a pharmaceutical peptide, improved processing quality, improved flavor, improved fiber production, biofuel production or a combination thereof.

11. The episomal DNA vector of claim 1, comprising the sequence of SEQ ID NO: 87 or a sequence having at least 90% sequence identity to the sequence of SEQ ID NO: 87.

12. A method of producing a plant cell having a desirable characteristic, the method comprising introducing into the chloroplast of the plant cell, the episomal DNA vector of claim 1 and culturing the plant cell to sustainably and autonomously replicate the episomal DNA vector thereby producing the plant cell having the desirable characteristic.

13. The method of claim 12, wherein the plant cell is from a dicotyledonous plant.

14. The method of claim 12, wherein the plant cell is from a monocotyledonous plant.

15. The method of claim 12, further comprising producing a callus from the plant cell comprising the episomal DNA vector that sustainably and autonomously replicates in the chloroplasts of the plant cell.

16. The method of claim 15, further comprising regenerating a plant part or a plant from the callus.

17. A plant cell comprising a chloroplast containing an episomal DNA vector of claim 1 comprising a chloroplast origin of replication (Ori) and, optionally, one or more genes of interest, wherein the episomal DNA does not contain any sequence that engages in homologous recombination with the plastomic DNA of the chloroplast.

* * * * *

SEQUENCE LISTING

```
<160> NUMBER OF SEQ ID NOS: 121

<210> SEQ ID NO 1
<211> LENGTH: 1055
<212> TYPE: DNA
<213> ORGANISM: Artificial Sequence
<220> FEATURE:
<223> OTHER INFORMATION: An example of chloroplast origin of replication

<400> SEQUENCE: 1

atcgatagta ttgttcattg tataaagtgt acgtacccgt taagggtacg tacactttaa     60
```

-continued

```
tgcaagataa acaaaaatca atacatatta ctagttacta gtataaagta caattgattt    120
ctgtgtattt gtagctttta aattaaattt ttaattaact gttacataaa aatttaaaat    180
tataaataaa aacatgttaa gtccaaaaag aacaaaattc cgtaaaccac accgtggtca    240
tttaagagga aaagcaacac gtggtaataa aattgtattt ggtgattttg cattacaagc    300
acaagaacct tgttggatta catcacgtca aattgaagcc ggacgtcgtg ttttaacacg    360
ttatgttcgt cgtggtggta aattatggat tcgtattttc ccagataaag ctgttactat    420
gcgtcctgct ggtactcgta tgggttctgg taaaggtgca cctgattatt gggtagctgt    480
tgtacatcct ggtaaaattt tatatgaaat gcaaggtgta tctgaaacaa ttgctagaca    540
agcaatgcgc attgcagctt ataaaatgcc agtaaaaaca aaatttttaa caaaaacagt    600
gtaattattg ttattaaaaa tgttgtttag aaagaattaa tgatttaact tacttaaaaa    660
gcataatctc aaattagagc acaagtataa tttaaaaaat atttaagaaa attaagagca    720
taagtattgt ttcgctttgg ctcaaaagcc aatactaaag ataatattac tttttgtaag    780
tttttactta ctcggtttgt accaggcaac cctataaata tagtaaaatg gaattaaact    840
agatatatct ctttaagaaa gattttctca tcaaggctgc cctttaactt taacctagaa    900
tgactaaaag gagtaagcaa ataccgagaa atttattttt tcacttaatg aaaaaataaa    960
ttttatctct ttctctttta agcatataaa tatgaaggta agtaaactct actagggaaa   1020
agcatagtgt tgaaggatat actttcttgg gatcc                              1055
```

```
<210> SEQ ID NO 2
<211> LENGTH: 5246
<212> TYPE: DNA
<213> ORGANISM: Artificial Sequence
<220> FEATURE:
<223> OTHER INFORMATION: An example of chloroplast origin of replication

<400> SEQUENCE: 2
```

```
aattccaacc aggctcaggt ggtcaattag cacgttcagc tggtgccatg gttgaaattt     60
tagcaaaaga aggcaatttt gtaacaatcc gtttaccttc taaagaaatt cgtttagttt    120
caaaaaattg ttgggcaact gtgggtcaag ttggtaacat tgaagcatac aacttaacta    180
ttggtaaagc aggtcgtaca cgttggttag gtaaacgtcc tacagtacgt ggttcggtga    240
tgaaccctgt ggatcaccca catggtggtg gtgagggtcg tgcaccgatt ggtcgtagcc    300
gtccagttac accatggggt cgcccagctt taggtcaatt aactagaaaa cctaaaaaat    360
atagtaatac tttaattgtt aaaaaaagaa aaaaataact aattaaagat aggtcaatta    420
aaacaagtgg cctcttttgg ctatttattt acccccttc cccttacggg acaataaata    480
aatttgttgg caggcaactg cctccctctc ctcgggcaag taaacttaga ataaaattta    540
tttgctgcgc tagcaggttt acatactcct aagtttactt gcccgaaggg gaaggagggc    600
gtccccttac gggaatataa atattagtgg cagtggtaca ataaataaat agtatataaa    660
tatcggcagt tggcaggcaa ctgccactga cgtccactaa aatttattct ttctcgggga    720
caataaataa atttgtcctg taaagggacg taaaatagca gtaagcataa gtatggccac    780
ttgcttaaat tttacaatat taaaaaaatt ctagaaataa taaagttttg gttgataaat    840
ttttaacgtt aattgtttgt ttaaacttta tagatatcgg gacttagtaa gtctaaagtc    900
gctaaaaaca accagtttca gataaacatt tgtttcaact gattggttcg ttttgtttat    960
ccttagagtt tatatatctt aactctatat tgggtaaacc actataatgg tcatatgttg   1020
```

-continued

```
gaaaaattcc aataaatttc aatttaatgt ggaatttaaa aagctcatat gtacttaaaa   1080
tagacaattg ttaaacatga atagaaaata ttacctactt ttatttttat aaatacagct   1140
ttagccatta ttataaaatt caaaagtcat tttaaaaaat caaatgtcac gttctcttaa   1200
aaaaggtcct tttgtagcag atcatttact taaaaaaatt gagaaattaa atgctaaagg   1260
taaaaaagtt gttattaaaa cttggtcacg ttcatcaatg attgttccac ctatgattgg   1320
tcatactatt ggtgtttata atgggcgtga acatattccc gtatttgtaa gtgatcaaat   1380
ggtaggtcat agattaggtg aattttcacc tacacgtaca tatcgtggcc atgctaaaaa   1440
agataaaaaa gcaaaacgtt aattttttgt tatttactgc tatttggtac accttagttt   1500
cctaaactaa tttctataaa ctactattct ttgcagttaa ccggaatata aacatcgact   1560
ttgggaaacc agttggtaag aacttgttgt cttgcagctc tttgcgcgct gccagacggc   1620
aagttctttt cccttcggaa ggcagctaat tatgtttata gtctatttgc aatgccactc   1680
tgagtaaata aatttcccct ttgtgatatt aatatgagct gccactacca tcctcttaga   1740
agtatataaa tatgcactgg catcctagag aaattaatta cttttatagc tatagaatgc   1800
ttgttaaggg atttactact ataaaattaa tgtgctcctt ggggtaaata cacttaataa   1860
atccctttag gtatttaaat agctatttgg gtaaaggctt tttaaatatg taataaatta   1920
tatatattag ttttatgtgg ttttttatat ctatgggaac tttacttttt tatactgtta   1980
aattcctagt taagagtaat aagagccata tttttaaagt tgcttgtttt ataaagatta   2040
aactaatttt accataagta ttctgtttta ataaatttat gcccatgaac gctgccaaag   2100
gacgagtggc tcgccactgc cccttacggg tacataaatg tcctaacttg atatttattt   2160
acctgtaagg gttagcctat aggcgaggta aataaattta agtcagccat agctattcta   2220
gagtataacg tgtacgtatc cttacgggta cgtacacgtt atactcagtt agcagggact   2280
tgttagccta taagcgagat aagtacactt ggccaacggt ttatattaat atactccagc   2340
agaagaacaa ttaaagtaaa atctaaaaat atctatcttt ttgctgaaga attgcggaaa   2400
aatcgatagt attgttcatt gtataaagtg tacgtacccg ttaagggtac gtacacttta   2460
atgcaagata aacaaaaatc aatacatatt actagttact agtataaagt acaattgatt   2520
tctgtgtatt tgtagctttt aaattaaatt tttaattaac tgttacataa aaatttaaaa   2580
ttataaataa aaacatgtta agtccaaaaa gaacaaaatt ccgtaaacca caccgtggtc   2640
atttaagagg aaaagcaaca cgtggtaata aaattgtatt tggtgatttt gcattacaag   2700
cacaagaacc ttgttggatt acatcacgtc aaattgaagc cggacgtcgt gttttaacac   2760
gttatgttcg tcgtggtggt aaattatgga ttcgtatttt cccagataaa gctgttacta   2820
tgcgtcctgc tggtactcgt atgggttctg gtaaaggtgc acctgattat tgggtagctg   2880
ttgtacatcc tggtaaaatt ttatatgaaa tgcaaggtgt atctgaaaca attgctagac   2940
aagcaatgcg cattgcagct tataaaatgc cagtaaaaac aaaattttta acaaaaacag   3000
tgtaattatt gttattaaaa atgttgttta gaaagaatta atgatttaac ttacttaaaa   3060
agcataatct caaattagag cacaagtata atttaaaaaa tatttaagaa aattaagagc   3120
ataagtattg tttcgctttg gctcaaaagc caatactaaa gataatatta ctttttgtaa   3180
gtttttactt actcggtttg taccaggcaa ccctataaat atagtaaaat ggaattaaac   3240
tagatatatc tctttaagaa agattttctc atcaaggctg ccctttaact ttaacctaga   3300
atgactaaaa ggagtaagca aataccgaga aatttatttt ttcacttaat gaaaaaataa   3360
attttatctc tttctctttt aagcatataa atatgaaggt aagtaaactc tactagggaa   3420
```

-continued

```
aagcatagtg ttgaaggata tactttcttg ggatccaaaa aagtaaacct aaacaagata   3480
tacttaatta atgataataa tataaaactt ttttttaaac ttatgattaa acctttatct   3540
tatttaaatg tagcagataa tagtggtgct cgtgaattaa tgtgtattcg tgctcttggt   3600
ggcagttatc gtgaatcggc aaatattggt gatgttatta ttgcagttgt taaagatgca   3660
ttaccaaata tgcctgtaaa acgttcagat attgtacgag ctgttattgt acgtacacgt   3720
aaaggtatcc gtcgtgaaaa tggtatggca attcgttttg atgataacgc tgcagttatt   3780
attaacaaag aaggaaatcc tcgtggtaca cgtgtttttg gtccaattgc acgtgaatta   3840
cgtgataaaa attttacaaa aattgtttct ttagcacctg aagttttata aaaactactt   3900
tttaaatttt tttacaatag taaaatcgat agttatatgc ccgttagaag attaacgccg   3960
tcgtattcac atagacaatt aattactcga ggtttacttg cctaggattt taatactccg   4020
aaggaggcag ttggcaggca actgcctcct tccccttcgg gcaagtaaac ttagcatgtt   4080
tacatactcc gaaggaggac gtccccttac gggaatataa atattagtgg cagtggtacc   4140
gccactgcct agtatataaa tatcggcagt tggcaggcaa caataaataa atttgtccac   4200
taaaatttat ttacccgaag gaccgtcctt cggagtatat aaatatagga ttttaatact   4260
ccgaagaggc agttggcagg caactgcaac tgacgtcccg aaggaaggac ggcaggggac   4320
gtctccttac ggggacattt atgtcccctg ccttttaatt cgggggatat gctttgcaat   4380
tagtagaaaa ttgcgaatag gatttccata taaaattaaa ataattctat cttctttaaa   4440
atttgatatg agtaatatta taataaaatg cttattaagt taaatctttt tataaccagt   4500
tgatttggat aaaaagaaca cataatgcaa agccaaaatg atagctctca taaaagcagt   4560
aggcggtgta actttcatta aaatttattt actttaaggt gacgtcccct tacggatatc   4620
taaatattta ctgtatcctc gctaaataaa ttgctatatt gtattgtata gcgcattacc   4680
ttttggctta acattatcta tatgtgcatt ttattttttt ttaatatgac acaacgttta   4740
aaaaatttat atactaaaac tattgttcct aaattaacta caaattttaa ttacagtaat   4800
atgcatgaag tgccaaaaat tgaaaaaatt gtaattaacc gtggtattgg tgatgcatca   4860
caaaaccaaa aaattgtgga atctagttta aaagaattag ctatgattgc aggtcaaaaa   4920
ggtgttgtta cacgttcaaa aaaagctatt gctggcttta aattaagaca acaaatgccc   4980
gtaggtgtaa ctgttacatt acgtggtgat cgtatgtatg gttttctaga tcgtttaatt   5040
catttagcat taccgcgtgt acgcgatttc caaggtatta gctcaaaaag ttttgataaa   5100
aaaggtaatt atagtttagg tttagaagaa caattaatgt tcccagaaat tgaatatgat   5160
aaaattgatc aagtacgtgg tatggatatt tcaattgtaa caacagcaaa aacacaagaa   5220
gaaggtcttg cattattaaa agaatt                                        5246
```

<210> SEQ ID NO 3
<211> LENGTH: 1001
<212> TYPE: DNA
<213> ORGANISM: Artificial Sequence
<220> FEATURE:
<223> OTHER INFORMATION: An example of chloroplast origin of replication

<400> SEQUENCE: 3

```
accacctgcc ggtgcggggt gtggtggtta tgttgtaggt gaaacggtaa aacttttaaa     60
agagttaaat gctttttttcg aatacgatgt tattttattt gatgttttag gtgatgttgt    120
ttgtggtggc tttgctgctc cattaaacta cgctgattat tgtattattg taactgataa    180
```

-continued

```
tggttttgat gctttatttg ctgcaaatcg tattgcagct tcagttcgtg aaaaagcacg    240

tacacatcca ttgcgtttag cgggtttaat cggaaatcgt acatcaaaac gtgatttaat    300

tgataaatat gtagaagctt gtcctatgcc agtattagaa gttttaccat taattgaaga    360

aattcgtatt tcacgtgtta aaggcaaaac tttatttgaa atgtcaaata aaaataatat    420

gacttcggct catatggatg gctctaaagg tgacaattct acagtaggag tgtcagaaac    480

tccatcggaa gattatattt gtaattttta tttaaatatt gctgatcaat tattaacaga    540

accagaagga gttattccac gtgaattagc agataaagaa ctttttactc ttttatcaga    600

tttctatctt aaaatttaat aagaataaag cagctttaaa tactttcctg tttataattt    660

aggaaattaa atggatattt gttgaaacta atccccagtt ggatacccat tggtagttaa    720

ttgccactgc ctgcttcacc ttacaaaatg tatggacaca aaacggctaa taaatacaga    780

ctcccggtgg catttgttgg ctgcttcgcc ctgaaaggag aaagtgattt ctttccttat    840

tagctaatct attctttttc ctgttttggt aaataatagc gtcctcatat ccatatctat    900

aacaaaaagt taaatgtttt aattttaaaa gtctttttta cattaataaa cacttttaat    960

tgatgggaca tctttagttt ttaaaataaa taaagatgca c                       1001
```

<210> SEQ ID NO 4
<211> LENGTH: 454
<212> TYPE: DNA
<213> ORGANISM: Artificial Sequence
<220> FEATURE:
<223> OTHER INFORMATION: An example of chloroplast origin of replication

<400> SEQUENCE: 4

```
cgtgtacgta caattacagc tcgaattact tcggatcttt ctagaggcat ttggggcact     60

gcgtctttga ttacagcaat aataacatca ccaatacgag catatcgctg attaccagcg    120

gctcctatga ctcgaataca catcaatttt cgagctccac tgttatctgc tacatttaaa    180

agggtctgag gttgaatcat attatttgga tttccatttg ttatttcaat gcaaaaggat    240

gaaagaaata ttgtctttcc agaaagaaaa accaggggtt ttttatcttc aatattcctt    300

tttggggttc tatatctcta atcgaagaaa ttgacttcgt atgggcattt tactggcagc    360

tatagagata gctgctctag ctacagtttc ggatactccg ctcatttcat aaagtattcg    420

acctggttta acaacggcta cccaatattc gggg                                454
```

<210> SEQ ID NO 5
<211> LENGTH: 515
<212> TYPE: DNA
<213> ORGANISM: Artificial Sequence
<220> FEATURE:
<223> OTHER INFORMATION: An example of chloroplast origin of replication

<400> SEQUENCE: 5

```
gtaataatat taagaagaac gatgaagaaa ggttaaggaa acgtacgaag gataacgaag     60

gctgttgaag tcacaatcga caggagtgat taactgagga caaatgttgt cagacaaccc    120

ctcgtcctgg tcatgtgata ggcttctcga tgaaactgtt ccatctctac cccagtagag    180

aaaaatccag gtcatatcat aggagataga aatgaatgac gagaacgaag acagaatgac    240

gttgaagaga acgattaggt aatatgtaga aacgacaatg aaagtcctcg aaggaggcag    300

gtaataaaga tgacaaagga gcgcgctacc acgcgaaaca agccattagg cagttctcct    360

atcccctccg aacgaatacc ttttagtaag agggtgaaac agtgacacaa agccggtgag    420

gccgtcacgc gtacttcaga acatgagtga tgagtactgt taaacatacc caggcgtgag    480
```

ccaacaatgc aaagaaccct gagaagggag tgaaa 515

<210> SEQ ID NO 6
<211> LENGTH: 398
<212> TYPE: DNA
<213> ORGANISM: Artificial Sequence
<220> FEATURE:
<223> OTHER INFORMATION: An example of chloroplast origin of replication

<400> SEQUENCE: 6
tgaactggag aacaacgctg aataatgttg acgaaggata acgaacccta tgtcgatacg 60
tctctctaac tgaggacaaa tgttgtcaga caacccctcg tcctggtcat gtgataggct 120
tctcgatgaa actgttccat ctctacccca gtagagaaaa atacgatgac accataggga 180
catgaatgag tgatcgagag aatcaaatga caaacctttc taaggacgat tagacacatg 240
tagaaacgac aacttatagg tgccgaaagg caaacaatat ggaataggcc tagttacggc 300
tggtcatgat taacttaacc ctacctggag agggtgttgg ctccagggta acctcgatgt 360
gcctccgtgc acgtttgctg ctggttacta ttggccgt 398

<210> SEQ ID NO 7
<211> LENGTH: 572
<212> TYPE: DNA
<213> ORGANISM: Artificial Sequence
<220> FEATURE:
<223> OTHER INFORMATION: An example of chloroplast origin of replication

<400> SEQUENCE: 7
cttaacgact aggcgatcaa aactaatgta ggtgtaaaga atgatgtctt aaacgtacga 60
aggataacga aggctgttga agtcacaatc gacaggagtg attaactgag gacaaatgtt 120
gtcagacaac ccctcgtcct ggtcatgtga taggcttctc gatgaaactg ttccatctct 180
accccagtag agaaaaatcc aggtcatatc ataggagata gaaatgaatg acgagaacga 240
agacagaatg acgttgaaga gaacgattag gtaatatgta gaaacgacaa caatatgagt 300
aataaagatg aaataggcct aactgcggtt ggtcatgatt aaacgaacct cctggttggg 360
tagaaacacc agttagccga agttgcctaa gtgcaatggt atctagaatt cagtgcctgg 420
ctattaagga accctcgtag gagggagaat atgaactact gcctcgatgt aacatcagat 480
gcaagaactc taatgtgagt taagatgcct attcagcatc aggtgcctat gtgtaccatc 540
aaagtcatgg gattactctt ctctattatt ga 572

<210> SEQ ID NO 8
<211> LENGTH: 526
<212> TYPE: DNA
<213> ORGANISM: Artificial Sequence
<220> FEATURE:
<223> OTHER INFORMATION: An example of chloroplast origin of replication

<400> SEQUENCE: 8
ctgtttcact gccgcaagac ttgtgcctaa cttcgttata cggtgaacag acttgcgata 60
ggctgcccgt ttcgactcta aataagtcta ttttagctaa tttagtcagt ttttccctct 120
caaagggggg tctggtgact tttgggggtt ttttgaaagt tccatgtttt gactttccag 180
aataagtaga ggggttagtt tttcaagaat gttttgaaaa gttaagaaat ctttgatggg 240
tttgcaatat tttgacccac atttactcat ttttccctct caaagggggg tctggtgact 300
tttgggggtt tttcgaaagt tccatgtttt gactttccag aataagtaga ggggttagtt 360
ttttaagaca attgaaatgg gtgtttaaga aatcttagtt tttccctctc aaagggggt 420 ctggtgactt ttgggggttt tttgaaagtt ccatgttttg actttagcaa ataagtagag 480
gggttagttt tttagaaaag tttaagaaag tttagccaat tgttat 526

<210> SEQ ID NO 9
<211> LENGTH: 752
<212> TYPE: DNA
<213> ORGANISM: Artificial Sequence
<220> FEATURE:
<223> OTHER INFORMATION: An example of chloroplast origin of replication

<400> SEQUENCE: 9
cgaaagggtg gggtgaaact cctcagtttt aattattatt cgatgttttt ctcactttcc 60
tagattttac caaatcctga taaatttcac ttttctcagt acttttcccc ggtaaaaggg 120
ggggggtgtc tgcgatttca aagtggagtc ccaaacgcat gtctggaata tatgaggaga 180
agttattttc tcagatattc tcagatattc tcagatattt gaagatattc tcagatattc 240
tcagatattc tcagattcca tgtaattttg cttgcatttc acttattttc ctaaaagtgc 300
atttttgcac gattttaaga aaacacatgc aatttgcctt ggattttggc caagccgcaa 360
gtcctttaaa aaaaaacacc tcgtgaaatg ttttctatct atctatcata ccaccaaagg 420
tggtattata gatagattgc taggattcac gagttgaata aaaaagggga aaataattct 480
tgaaatctgg gttttgatga ttttgaaatc tcaaattccg caagtcggcg atttctgggg 540
ctcagatttg ggttttggg tatttttctg gatgttgcta aatcctgata aatttcactt 600
ttctcagtac ttttccccgg taaaaggggg ggggtgtctg cgatttcaaa gtggagtccc 660
aaacgcatgt ctggaatata tgaggagggg taaaattctg gtaagtttta gaaagttagt 720
taaaattgta gaaatgttgg tgatggtgat gg 752

<210> SEQ ID NO 10
<211> LENGTH: 595
<212> TYPE: DNA
<213> ORGANISM: Artificial Sequence
<220> FEATURE:
<223> OTHER INFORMATION: An example of chloroplast origin of replication

<400> SEQUENCE: 10
aaatcctgat aaatttcact tttctcagta cttttccccg gtaaaagggg gggggtgtct 60
gcgatttcaa agtggagtcc caaacgcatg tctggaatat atgaggagaa gttattttct 120
cagatattct cagacatgta attttgcttg catttcactt attttataaa aagtgcattt 180
ttgcacgatt ttaagaaaac acatgcaatt tgccttggat tttggccaag ccgcaagtcc 240
tttaaaaaaa aacacctcgt gaaatgtttt ctatctatct atcataccac ctttggtggt 300
attatagata gattgctagg attcacgagt tgaataaaaa aggggaaaat aattttgcag 360
aaatctgggt tttgatttt atgaaattcc gcaagtcggc gattttagaa atctttttaa 420
gatttgtgga tcagaaattg ggggttttgt ggattttgct aaatcctgat aaatttcact 480
tttctcagta cttttccccg gtaaaagggg gggggtgtct gcgatttcaa agtggagtcc 540
caaacgcatg tctggaatat atgaggagga gtaaaattct gggaagtttt agaaa 595

<210> SEQ ID NO 11
<211> LENGTH: 1474
<212> TYPE: DNA
<213> ORGANISM: Artificial Sequence
<220> FEATURE:
<223> OTHER INFORMATION: An example of chloroplast origin of replication

<400> SEQUENCE: 11
accaaaaata tatgcctctg cattataaat aagattcaag ccacttctaa tctcacacaa 60
gttaaaatgg gaattcattt atctaacatt attgttttgg gaatttagtg gatatagcat 120
ctcatcttgg atctaattta cctaacatca tgtaattcgc tattttctaa ctttagcgga 180
atctgggctt ttatcggaat ttaatactag ctttacacat aagacactcg caaaatagcc 240
gtatttcggc atctgcaggg tattggtagc cttgtggaca caatgaagca atttaaggga 300
aatcatgtaa ttaacggaaa ttaatggtat taggatttgg attatttaca atatcttcaa 360
tttacacaat gtggttggac agctctgctg ttggtgttgg caacacaacc aaccacgaat 420
aattaatggc acacaatcca ctcaacaggc atctacaagc aaattcacga atctcacgat 480
tctcgcgatt tctcgcaaat tccctcacgt acgagcgcat aatgcacacg cgcatcaaaa 540
ctaaaagaca aaaattaaag ccctacaaat gtaatgggtt cgtgggtatt tataaataac 600
cctacgggtt atttagaaat gcccccgagg gaatataacc ccctaaaggg ggttattatt 660
cccgagtcgg cttaacacgt gtacacgtac acgaggaacc gaaggttccg acacacacac 720
aatcataccc acgatgaatc ttcgattcca gctgatactc tcgccaacca accaagagca 780
gctttgctgc gaatgagcgt agcgaataac ctgccgcagg cagaatattg cgaagcaata 840
ccatgagcga agcgaataat aatgcgaagc attacctgcc gaaggcagaa tagccgaagg 900
ctacctaata gcgaagctat tgtcaaaaag cttgaaacct catgcagcta acagctgcac 960
aatctaattc acttgggatt attgattctt caaaccattc aacacacacc atgagcgaag 1020
ggaataatag agcgaagctc taccctgccg caggcagaat attgcgaagc aataccatga 1080
gcgaagcgaa taacagaacg aagttctgcc tggctttagc cagaacaatg cgaagcattg 1140
aaataaaaag aaaatgttaa acagaatgca tcttatcaca atctactcaa ccacaacagg 1200
aatcgagttt cattaactgt ttatcaattt caatgaaagt aattttggtt ggctgtaacg 1260
ttacaagcac ataacagaac acagttggtt atcgattatg gacattcatt aaatggtgta 1320
atgttaagtc gagatatggc ttcatcacat aaactctggt tgtaattaaa tggatgttaa 1380
gagttgtaaa ggtaaaatgg atctacaatt ggttagccta atcatttatg gctggttggt 1440
tgtgagacaa aaaggtgatg aaactataac gtgg 1474

<210> SEQ ID NO 12
<211> LENGTH: 2071
<212> TYPE: DNA
<213> ORGANISM: Artificial Sequence
<220> FEATURE:
<223> OTHER INFORMATION: An example of chloroplast origin of replication

<400> SEQUENCE: 12
agcttctccc cccctttatc cgcccgactc tttgctctta agaatgtagg tttgaagtta 60
agaatgagta attgcacttc tccgaccctt aactgttcaa cctaagatac ggagaactaa 120
ggcgttttca ggttgaacag ggttctatgg tcggtccgcg acccctggat gccaaagggt 180
ccttggggtg atctcgtagt tcctacgggg tggagacgat ggggtcggtc catggatttt 240
ctttcctttt gttttcccgc atttcgctca aagggttgaa gggagatagt gcatcaagct 300
gttcgcaagg gccagcttga tcctcttccc caggatttca gatgaggaaa ccctaggaga 360
gccaccgact ctaactaccg tccatgtatg atccatacta gatctgacca acttcccatc 420
ctacctcctc tacggacagc ccatccttgt ctcagtagag tctttcagtg gcatgtttcg 480

```
gtcctctttc ccattactta gaaaaagtga gccaccggtt caggtacaag atactatcat    540

taccgcctgg acaattagac atccaacccg taatcgcaac gacccaattg caagagcgga    600

gctctaccaa ctgagctata tccccccgag ccaagttgga gcatgcatga aggagtcaaa    660

tccgtctttt agtcttttcc ttggcgcagc tgggccatcc tggacttgaa ccagtgacct    720

cgcccgtgaa gtaaatcatc gcacctacgg tccatccaat tgggagagaa tcaatagatt    780

ccttttcggg agcgattcat ccttcccgaa cgcagcatac aactatccat tgtactgcgc    840

tctccaagtg tgcttgtttc cccttctttc ttatcatgac aagtctttgt ggaataactc    900

tgatgagaag aaaaaagaaa acgttaaggg acactctaag atcctttttc aaacctgctc    960

ccatttcgag tcaagagaat ggtacgatcc cgccgtcacc tcagaataaa aggggtgatc   1020

tcgtagttct tggtctgtga agatacgttg ttaggtgctc cgtttttctt tttccattga   1080

ggccaaacct aaacctgtgc tcgagagata gttatccata tactgataag ggatgtatga   1140

attctcgaga ggagaggagc catgatggtc ccccctggac cgcccggatc ccacgagtga   1200

atagaaagtt ggatctacat tggatctcac ctgaatcgcc ccatctatct tcctgaggag   1260

gagtttggtt tcaaaccccg gttcaaacag gagaagtacg ccatgctaat gtgccttgga   1320

tggtccacat ctcagggtca ggcgctgatg aacacattga actatctatg tggctgatag   1380

ccctcacagt ccaggcacaa cgacgcaatt atcaggggcg cgctctacca ctgagctaat   1440

agcccgttgt gtgggccccc cgaaggggcc cactatgtca aaagtgagag aaaccccatc   1500

tctctctttc ccctttgttt gcctcatgtc gcccacgggg cgacatgggt caaaaaagag   1560

gagctcctat caagttgttc cgacctagga taataagctc atgagattag tgtcactgac   1620

attctcatca cccacaggaa acgaaaggag acttccacct actaactttg cctcgataac   1680

cccttcgctt cagcggtgtg aaacagtgta aaacccaatc acccaaaaag cgttctctgt   1740

tctccctgaa taggttaata agctagctcc tgagctaggt gtgacttcac cgtcgagaaa   1800

cgaaacataa cggaaatcta cctactagtg cgatgtagct tttctttact ttaacggggt   1860

gtgagtgacg cagtgtaaaa cctaattaca caaaaagcat tagttctccc tgaaaaggag   1920

gtgatccagt cgcaccttcc agtacggcta ccttgttacg acttcactcc agtcactagc   1980

cctgccttcg gcatccccct ccttgcggtt aaggtaatga cttcgggcat ggccagctcc   2040

catagtgtga cgggcggtgt gtacaaggcc c                                   2071
```

```
<210> SEQ ID NO 13
<211> LENGTH: 4213
<212> TYPE: DNA
<213> ORGANISM: Artificial Sequence
<220> FEATURE:
<223> OTHER INFORMATION: An example of chloroplast origin of replication

<400> SEQUENCE: 13

gggcctagtc actgcgaccc cctttgtgag gaggcacccc ttctcccgaa gttacggggc     60

tattttgccg agttccttag agagagttgt ctcgcgcccc taggtattct ctacctaccc    120

acctgtgtcg gtttccggta caggtaccct cttgttgtag gtcgttcgaa cttttcctgg    180

gagtatggca tcaattactt tagcgccaga gtgcgcgcct cgtactcgta ctcgaatttt    240

ggctcgaggg catttctct acccccttact taccctgaaa aaaacaggga gtcaccttat    300

gttcttgaac cgataaccat ctttcggcta acctagcctc ctccgtccct cgggaccaac    360

aaggggcagt acaggaatat taacctgttg tccatcgact acgcctttcg gcctgatctt    420

aggtcctgac ttaccctccg tggacgaacc ttgcggagga atccttaggt tttcggggca    480
```

-continued

```
ttggattctc accaatgttt tcgttactca agccgacatt ctcgcttccg cttcgtccaa    540
ccctgctcgc gcgggtactt ctttctaagg cggaacgctc ccctaccgat tcatttttac    600
atcccacagc ttcggcaaat cgcttagccc cgttcatctt cggcgcaaga gcgctcgatc    660
agtgagctat tacgcactct ttgaagggtg gctgcttcta ggcaaacctc ctggctgtct    720
ctgcactcct acctccttta tcactgagcg atcatttagg ggccttagct ggtgatctgg    780
gctgtttccc tctcgacaga tgaagcttat cccccatcgt ctcactggcc gaccttgacc    840
cgtcggggtc atatctagta ttcagagttt gcctcgattt ggtaccgctc tcgcggcccg    900
cgccgaaaca gtgctttacc cctagatgtc cagtcaactg ctgcgcctca acgcatttcg    960
gggagaacca gctagctctg ggttcgattg gcatttcacc gctaaccaca actcatccgc   1020
tgatttttca acatcagtcg gttcggacct ccacttagtt tcacctaaac ttcatcctgg   1080
tcatggatag atcacccagg ttcgggtcca taagcagtga caatagccct atgaagactc   1140
gctttcgcta cggctccggt ggtttccctt aaccaagcca ctgcctatga gtcgccggct   1200
cattcttcaa caggcacgcg gtcagagccc cagctcctcc cactgttggg agcttacggt   1260
ttcatgttct atttcactcc ccgccagggg ttcttttcac ctttccctca cggtactact   1320
tcactatcgg tcacccagga gtatttagcc ttgcaaggtg gtccttgctg attcacacgg   1380
gatttcacgt gccccatgtt actcgggtca gagcataagc tagtgatgct ttcggctact   1440
ggactttcac catctagggt gcaacattcg actgcttcgc ctagcagcac gacgcttgta   1500
ttgctctccc acaaccccgt tttcacggtt taggctgctc ccatttcgct cgccgctact   1560
acgggaatcg cttttgcttt cttttcctct ggctactaag atgtttcagt tcgccaggtt   1620
gtctcttgcc tgctcgtgaa ttcagcagca gttcgaaagg ttgacctatt cgggaatcct   1680
cggatctatg cttattttca actccccgaa gcatttcgtc gcttactacg cccttcctcg   1740
tctctgggtg cctaggtatc caccataagc ctttcctcgt ttgaacctcg cccttcaact   1800
ctatgccatc ctaaggtgct gctagatgga aggatcttat caacgtccat aaataataaa   1860
tcataacata gctaaaacaa aaaaatgaac gagttggaga taagcggact cgaaccgctg   1920
acatccgcca cagggtaaat caccgcctct caagccccaa ctgattctac catagaggcc   1980
aacgatagac aataaccctc cgaacacagc ttacaacttt catcgtactg tgctctccaa   2040
agagcaactc ttctcaaaat atcaaagggt gctgagttgg aatcccattc aaacaaggat   2100
tcttgtggtt gcggaagatc cagctacagg ccgagaacga aaagcttctc ccccccttta   2160
tccgcccgac tctttgctct taagaatgta ggtttgaagt taagaatgag taattgcact   2220
tctccgaccc ttaactgttc aacctaagat acggagaact aaggcgtttt caggttgaac   2280
agggttctat ggtcggtccg cgacccctgg atgccaaagg gtccttgggg tgatctcgta   2340
gttcctacgg ggtggagacg atggggtcgg tccatggatt ttctttcctt ttgttttccc   2400
gcatttcgct caaagggttg aagggagata gtgcatcaag ctgttcgcaa gggccagctt   2460
gatcctcttc cccaggattt cagatgagga aaccctagga gagccaccga ctctaactac   2520
cgtccatgta tgatccatac tagatctgac caacttccca tcctacctcc tctacggaca   2580
gcccatcctt gtctcagtag agtctttcag tggcatgttt cggtcctctt tcccattact   2640
tagaaaaagt gagccaccgg ttcaggtaca agatactatc attaccgcct ggacaattag   2700
acatccaacc cgtaatcgca acgacccaat tgcaagagcg gagctctacc aactgagcta   2760
tatcccccg agccaagttg gagcatgcat gaaggagtca aatccgtctt ttagtctttt   2820
```

-continued

```
ccttggcgca gctgggccat cctggacttg aaccagagtc ctcgcccgtg aagtaaatca   2880
tcgcacctac ggtccatcca attgggagag aatcaataga ttccttttcg ggagcgattc   2940
atccttcccg aacgcagcat acaactatcc attgtactgc gctctccaag tgtgcttgtt   3000
tccccttctt tcttatcatg acaagtcttt gtggaataac tctgatgaga agaaaaaaga   3060
aaacgttaag ggacactcta agatcctttt tcaaacctgc tcccatttcg agtcaagaga   3120
atggtacgat cccgccgtca cctcagaata aaaggggtga tctcgtagtt cttggtctgt   3180
gaagatacgt tgttaggtgc tccgtttttc tttttccatt gaggccaaac ctaaacctgt   3240
gctcgagaga tagttatcca tatactgata agggatgtat gaattctcga gaggagagga   3300
gccatgatgg tccccctgg accgcccgga tcccacgagt gaatagaaag ttggatctac   3360
attggatctc acctgaatcg ccccatctat cttcctgagg aggagtttgg tttcaaaccc   3420
cggttcaaac aggagaagta cgccatgcta atgtgccttg gatggtccac atctcagggt   3480
caggcgctga tgaacacatt gaactatcta tgtggctgat agccctcaca gtccaggcac   3540
aacgacgcaa ttatcagggg cgcgctctac cactgagcta atagcccgtt gtgtgggccc   3600
cccgaagggg cccactatgt caaaagtgag agaaacccca tctctctctt tcccctttgt   3660
ttgcctcatg tcgcccacgg ggcgacatgg gtcaaaaaag aggagctcct atcaagttgt   3720
tccgacctag gataataagc tcatgagatt agtgtcactg acattctcat cacccacagg   3780
aaacgaaagg agacttccac ctactaactt tgcctcgata accccttcgc ttcagcggtg   3840
tgaaacagtg taaaacccaa tcacccaaaa agcgttctct gttctccctg aataggttaa   3900
taagctagct cctgagctag gtgtgacttc accgtcgaga aacgaaacat aacggaaatc   3960
tacctactag tgcgatgtag cttttcttta ctttaacggg gtgtgagtga cgcagtgtaa   4020
aacctaatta cacaaaaagc attagttctc cctgaaaagg aggtgatcca gtcgcacctt   4080
ccagtacggc taccttgtta cgacttcact ccagtcacta gccctgcctt cggcatcccc   4140
ctccttgcgg ttaaggtaat gacttcgggc atggccagct cccatagtgt gacgggcggt   4200
gtgtacaagg ccc                                                       4213
```

<210> SEQ ID NO 14
<211> LENGTH: 1118
<212> TYPE: DNA
<213> ORGANISM: Artificial Sequence
<220> FEATURE:
<223> OTHER INFORMATION: An example of chloroplast origin of replication

<400> SEQUENCE: 14

```
agatccaatg tagatccaac tttcgattca ctcgtgggat ccgggcggtc cggggggac     60
caccacggct cctctcttct cgtcacatcg acaattcaat aaggtatccg acattaacaa    120
tgatttaaat tgtgttcatt gtgtttttta tggtacataa ccttcataga tttatagatt    180
ataaactgaa agaagcctca aaaacagaag aaagggtgga aagtgaggaa gaaagagatg    240
tagaaataga aactgcttcc gaaatgaagg ggactaaaca ggaacaagag ggatccactg    300
aagaagatcc ttatccttct ccttcccttt tttcggaaga agggtgggat ccggacaaaa    360
tcgatgaaac ggaagaaatc cgagtgaatg gaaaggacaa aataaaggat aaattccact    420
ctcacttcct atatgaggaa gtatccttcc ccgcagtcaa gaccaaggtt agtattctct    480
gctaggaagt ttacttaggt tactctagca tgtgcctgga taaccctcta ggcaaaggtg    540
gattgacttt gtactgtcct cagatcgacg ttggatgaac tgtcgcgcca cgaggggctg    600
tggagcgcat tgcgacacat tggtgcgctg ctaacccatc ctttccagta cggctactga    660
```

```
tgtccacgct cccagcctgc tacgctccgc ccggtgagag tggaatttat cctttatttt    720

gtcctttcca ttcactcgga tttcttccgt ttcatcgatt ttgtccggat cccacccttc    780

ttccgaaaaa agggaaggag aaggataagg atcttcttca gtggatccct cttgttcctg    840

tttagtcccc ttcatttcgg aagcagtttc tatttctaca tctctttctt cctcactttc    900

caccctttct tctgtttttg aggcttcttt cagttttgct agaaagttat tcttttcgtc    960

ttaatgatta tatgtaaatc gccctctata tattaactct acttatatgg aaaaactatg   1020

attaagtagt tacagtcgag aagagaggag ccgtggtggt cccccccgga ccgcccggat   1080

cccacgagtg aatcgaaagt tggatctaca ttggatct                           1118
```

<210> SEQ ID NO 15
<211> LENGTH: 857
<212> TYPE: DNA
<213> ORGANISM: Artificial Sequence
<220> FEATURE:
<223> OTHER INFORMATION: An example of chloroplast origin of replication

<400> SEQUENCE: 15

```
tcagggagag ctaatgcttg ttgggtattt tggtctgact cttccttttc acccaaaacg     60

aggccagcta catctgagtg aaacttggag atggtagtct tctttcgttt ctcgacggtg    120

aagtaagacc aagctcatga gcttattatc ctaggtcgga acaagtcggt aggatcccct    180

tttggacgtc cccatgccct ttccgcgcgg ggtagcatgt ccccgcgccc tttccgcgct    240

ggggggcatg gggcgaaaa aaggaaggag ggggatgggg tttctctcgc ttttgacata    300

gcagcgggcc ccggtgggag gcccgcacga cgacgacgat tagctcattg gtaggatccc    360

cttttggacg tccccatgcc ctttccgcgc ggggtagcat gggggcgaaa aaaggaagta    420

aaataaggag gctttgacat agcagcgggc cccggtggga ggcccgcacg acacgacgat    480

tagattagct cattggtagg acgacgatta gctcattggt aggacgacga ttagctcatt    540

ggtaggacga cgattagctc gttggtattg gtaggatccc cttttggacg ttgacatagg    600

agcggatgac ataggagcgg gccccagcgg gagtcccgca cgacgacgac acgacgacga    660

cgattagctc gttggtattg gtaggatccc cttttggacg ttgggagcgg atgacatagg    720

agcgggcccc agcgggagtc ccgcacgacg acgacacgac gacgacgatt agctcattgg    780

taggacgacg attagctcat tggtaggatt agctcagtgt tagagttaga gcgggcccca    840

gtgggaggcc cgcacaa                                                   857
```

<210> SEQ ID NO 16
<211> LENGTH: 2859
<212> TYPE: DNA
<213> ORGANISM: Artificial Sequence
<220> FEATURE:
<223> OTHER INFORMATION: An example of chloroplast origin of replication

<400> SEQUENCE: 16

```
agaacatgct gagccaaatc ttcttcatgg aaaacctgct tgatttagat cgggagaatc     60

gtacggtttt atgaaaccat gtgctatggc tcgaatccgt attcaatcct atttccgata    120

ggagcagttg acaatggaat ccaatttttc cattattttc gtatccgtaa tagtgcgaaa    180

cgaaggcccg tctccaagtt gttcaagaat aaatagtggc gttgagtttc ttgacccttt    240

gtcttaggat tagtcagttc catttcttga tgggagcagg gaagggatat aactcagcgg    300

tagagtgtca ccttgacgtg gtggaagtca tcagttcgag cctgattatc cctaaaacca    360
```

-continued

```
atgcgagttt ttctattttg acttactccc ccgccgtgat cgaatgaaaa tggataagag    420
gctcgtggga ttgacgtgag ggataggta tgcctattcc gaatccgctt tgtctacgaa    480
caaggaagct ataagtaatg caactatgaa tctcatggag agttcgatcc tggctcagga    540
tgaacgctgg cggcatgctt aacacatgcg agtcggacgg gaagtggtgt ttccagtggc    600
ggacgggtga gtaacgcgta agaacctgcc cttgggaggg gaacaacagc tggaaacggc    660
tgctaatacc ccgtaggctg aggagcaaaa ggaggaatcc gcccgaggag gggctcgcgt    720
ctgattagct agttggtgag gcaatagctt accaaggcga tgatcagtag ctggtccgag    780
aggatgatca gccacactgg gactgagaca cggcccagac tcctacggga ggcagcagtg    840
gggaattttc cgcaatgggc gaaagcctga cggagcaatg ccgcgtggag gtagaaggcc    900
cacgggtcgt gaacttcttt tcccggagaa gaagcaatga cggtatccgg ggaataagca    960
tcggctaact ctgtgccagc agccgcggta agacagagga tgcaagcgtt atccggaatg   1020
attgggcgta aagcgtctgt aggtggcttt ttaagtccgc cgtcaaatcc cagggctcaa   1080
ccctggacag gcggtggaaa ctaccaagct ggagtacggt aggggcagag ggaatttccg   1140
gtggagcgat gaaatgcgtt gagatcggaa agaacaccaa cggcgaaagc actctgctgg   1200
gccgacactg acactgagag acgaaagcta ggggagcgaa tgggattagt gaccccagta   1260
gtcctagccg taaacgatgg atactaggcg ctgtgcgtat cgacccgtgc agtgctgtag   1320
ctaacgcgtt aagtatcccg cctggggagt acgttcgcaa gaatgaaact caaaggaatt   1380
gacgggggcc cgcacaagcg gtggagcatg tggtttaatt cgatgcaaag cgaagaacct   1440
taccagggct tgacatgccg cgaacccttt tgaaagagag gtgtgccttc gggaacgcgg   1500
acacaggtgg tgcatggctg tcgtcagctc gtgccgtaag gtgttgggtt aagtcccgca   1560
acgagcgcaa ccctcgtgtt tagttgccaa tgttgagttt ggaaccctga acagactgcc   1620
ggtgctaagc cggaggaagg cgaggatgac gtcaagtcat catgcccctt acgccctggg   1680
cgacacacgt gctacaatgg ccgggacaaa gggtcgcgat cccgcgaggg tgagctaact   1740
ccaaaaaccc gtcctcagtt cggattgcag gctgcaactc gcctgcatga agtaggaatc   1800
gctagtaatc gccggtcagc catacggcgg tgaattcgtt cccgggcctt gtacacaccg   1860
cccgtcacac tatgggagct ggccatgcct gaagtcgtta ccttaaccac aaggaggggg   1920
atgccgaagg caaggcttgg tgactggagt gaagtcgtaa caaggtagcc gtactggaag   1980
gtgcggctgg atcacctcct tttcagggag agctaatgct tgttgggtat tttggtctga   2040
ctcttccttt tcacccaaaa cgaggccagc tacatctgag tgaaacttgg agatggtagt   2100
cttctttcgt ttctcgacgg tgaagtaaga ccaagctcat gagcttatta tcctaggtcg   2160
gaacaagtcg gtaggatccc cttttggacg tccccatgcc ctttccgcgc ggggtagcat   2220
gtccccgcgc cctttccgcg ctggggggca tgggggcgaa aaaaggaagg agggggatgg   2280
ggtttctctc gcttttgaca tagcagcggg ccccggtggg aggcccgcac gacgacgacg   2340
attagctcat tggtaggatc cccttttgga cgtccccatg ccctttccgc gcggggtagc   2400
atgggggcga aaaaaggaag taaaataagg aggctttgac atagcagcgg gccccggtgg   2460
gaggcccgca cgacacgacg attagattag ctcattggta ggacgacgat tagctcattg   2520
gtaggacgac gattagctca ttggtaggac gacgattagc tcgttggtat tggtaggatc   2580
cccttttgga cgttgacata ggagcggatg acataggagc gggccccagc gggagtcccg   2640
cacgacgacg acacgacgac gacgattagc tcgttggtat tggtaggatc cccttttgga   2700
cgttgggagc ggatgacata ggagcgggcc ccagcgggag tcccgcacga cgacgacacg   2760
```

acgacgacga ttagctcatt ggtaggacga cgattagctc attggtagga ttagctcagt 2820
gttagagtta gagcgggccc cagtgggagg cccgcacaa 2859

<210> SEQ ID NO 17
<211> LENGTH: 1958
<212> TYPE: DNA
<213> ORGANISM: Artificial Sequence
<220> FEATURE:
<223> OTHER INFORMATION: An example of chloroplast origin of replication

<400> SEQUENCE: 17
agaacatgct gagccaaatc ttcttcatgg aaaacctgct tgatttagat cgggagaatc 60
gtacggtttt atgaaaccat gtgctatggc tcgaatccgt attcaatcct atttccgata 120
ggagcagttg acaatggaat ccaatttttc cattattttc gtatccgtaa tagtgcgaaa 180
cgaaggcccg tctccaagtt gttcaagaat aaatagtggc gttgagtttc ttgacccttt 240
gtcttaggat tagtcagttc catttcttga tgggagcagg gaagggatat aactcagcgg 300
tagagtgtca ccttgacgtg gtggaagtca tcagttcgag cctgattatc cctaaaacca 360
atgcgagttt ttctattttg acttactccc ccgccgtgat cgaatgaaaa tggataagag 420
gctcgtggga ttgacgtgag ggataggta tgcctattcc gaatccgctt tgtctacgaa 480
caaggaagct ataagtaatg caactatgaa tctcatggag agttcgatcc tggctcagga 540
tgaacgctgg cggcatgctt aacacatgcg agtcggacgg gaagtggtgt ttccagtggc 600
ggacgggtga gtaacgcgta agaacctgcc cttgggaggg gaacaacagc tggaaacggc 660
tgctaatacc ccgtaggctg aggagcaaaa ggaggaatcc gcccgaggag gggctcgcgt 720
ctgattagct agttggtgag gcaatagctt accaaggcga tgatcagtag ctggtccgag 780
aggatgatca gccacactgg gactgagaca cggcccagac tcctacggga ggcagcagtg 840
gggaattttc cgcaatgggc gaaagcctga cggagcaatg ccgcgtggag gtagaaggcc 900
cacgggtcgt gaacttcttt tcccggagaa gaagcaatga cggtatccgg ggaataagca 960
tcggctaact ctgtgccagc agccgcggta agacagagga ttcacatcga caattcaata 1020
aggtatccga cattaacaat gatttaaatt gtgttcattg tgttttttat ggtacataac 1080
cttcatagat ttatagatta ttcagggaga gctaatgctt gttgggtatt ttggtctgac 1140
tcttcctttt cacccaaaac gaggccagct acatctgagt gaaacttgga gatggtagtc 1200
ttctttcgtt tctcgacggt gaagtaagac caagctcatg agcttattat cctaggtcgg 1260
aacaagtcgg taggatcccc ttttggacgt ccccatgccc tttccgcgcg gggtagcatg 1320
tccccgcgcc ctttccgcgc tggggggcat gggggcgaaa aaaggaagga gggggatggg 1380
gtttctctcg cttttgacat agcagcgggc cccggtggga ggcccgcacg acgacgacga 1440
ttagctcatt ggtaggatcc ccttttggac gtccccatgc cctttccgcg cggggtagca 1500
tgggggcgaa aaaaggaagt aaaataagga ggctttgaca tagcagcggg ccccggtggg 1560
aggcccgcac gacacgacga ttagattagc tcattggtag gacgacgatt agctcattgg 1620
taggacgacg attagctcat tggtaggacg acgattagct cgttggtatt ggtaggatcc 1680
ccttttggac gttgacatag gagcggatga cataggagcg ggccccagcg ggagtcccgc 1740
acgacgacga cacgacgacg acgattagct cgttggtatt ggtaggatcc ccttttggac 1800
gttgggagcg gatgacatag gagcgggccc cagcgggagt cccgcacgac gacgacacga 1860
cgacgacgat tagctcattg gtaggacgac gattagctca ttggtaggat tagctcagtg 1920

-continued ttagagttag agcgggcccc agtgggaggc ccgcacaa 1958

<210> SEQ ID NO 18
<211> LENGTH: 4792
<212> TYPE: DNA
<213> ORGANISM: Artificial Sequence
<220> FEATURE:
<223> OTHER INFORMATION: An example of chloroplast origin of replication

<400> SEQUENCE: 18
gagctcggat tctaaccttg tgtcagaccc gcgggccaag ggacagtctc aggtagacag 60
tttctatggg gcgtaggcct cccaaaaggt aacggaggcg tgcaaaggtt tcctcgggcc 120
agacggacat tggtcctcga gtgcaaaggc agaagggagc ttgactgcaa gactcacccg 180
tcgagcagag acgaaagtcg gccttagtga tccgacggtg ccgagtggaa gggccgtcgc 240
tcaacggata aaagttactc tagggataac aggctgatct tccccaagag tccacatcga 300
cgggaaggtt tggcacctcg atgtcggctc ttcgccacct ggagctgtag gtggttccaa 360
gggttgggct gttcgcccat taatgcggta cgtgagctgg gttcagaacg tcgtgagaca 420
gttcggtcca tatccggtgt gggcgttaga gcattgagag gacctttccc tagtacgaga 480
ggaccgggaa ggacgcacct ctggtgtacc agttatcgtg cctacggtaa acgctgggta 540
gccaagtgcg gagaggataa ctgctgaaag catataagta gtaagcccac cccaagatga 600
gtgctctctc ctccgacttc cctagagcct ccggtagcac agccgagaca gcgacgggtt 660
ctccacccat acggggatgg agcgacagaa gcatggaaat aggataaggt agcggcgaga 720
cgagccgttt aaataggtgt caagtggaag tgcagtgatg tatgcagctg aggcatccta 780
acgaacgaac gatttgaacc ttgttcctac acgacctgat caaatcgatc aggcacttgc 840
catctatctt cattgttcaa ctctttgatg aaaagatgaa aaaaccaaaa aaaagctctg 900
cccttccatc tcttggatag atagagaggg agggcagagg cctttggtgt cccttccagt 960
caagaattgg ggcttcacaa ttactagcca atatttctct catgcctttc ctcgttcatg 1020
gttcgatatt ctggtgtcct aggcgtagag gaaccacacc aatccatccc gaatttggtg 1080
gttaaactct actgcggtga cgatactgta ggggaggtcc tgcggcaaaa tagctcgatg 1140
ccagaatgat aaaaagctta acacctctta tttgactttt tcactatttt gaaatacgaa 1200
aaagatccaa atccaaaatg caaaggtcgt cttattcaaa acctcaatca tcacatcccc 1260
tctctcccac ttcacacctc ggaacgcact gttcttatag agagaaaggg gctttcccat 1320
cttcttaacc cgaaatgaaa tggctgagga gagggaggtt ccttttgggg ggtacccccg 1380
ggaagagatc cagtggagac ggggtgggcc tgtagctcag aggattagag cacgtggcta 1440
cgaaccacgg tgtcgggggt tcgaatccct cctcgcccac agccttccaa aggggaaggg 1500
cctttacttt ccccctgagg gtaggaaaac catgatcggg atagcggacg taaagctatt 1560
gaacttgggt atgctctttc cttttgtcga agtggaatcg tagaacagaa tgtgatacga 1620
tgagataaaa tgcaatagaa acaaggatag cgaacgggtt acctactcct aagggtcaaa 1680
gcaagccctt taattcaatt ctttattctt acattaaaga atgaatcaaa tctccccaag 1740
taggattcga acctacgacc agtcagttaa cagccgaccg ctctaccact gagctactga 1800
ggaacaaggg ggattcgacc tcctagagtt caactcccgc tctcaaccca tgaacaatat 1860
gagtccgaag cttctttcgt aactcccgga atttcttcgt agtggctccg ttccatgcct 1920
catttcatag gtaagcccag agtggctcta tttcattcta tttcacttcc tagcacttcc 1980
tatcatttaa tatccatccc tttggtctta ttgacataag agatgtcatt tatagtctat 2040

```
ctctttctat atatggaaag tcaagaaatt ctcatcgaaa catcgagaaa ttgtgcatat   2100
agaaaactct aaagaaagaa aaaaagcaca cccatgccat gattttcaaa tcttttctac   2160
ttagtagtct aagtttctcg atgaggataa ttaattcggt cgttgcggtc ggactctatt   2220
atgggtttct gaccacattc tccatgggtc cctcttagat ctttcctata tgaggaagta   2280
tccttccccg cagtcaagac caaggttagt attctctgct aggaagttta cttaggttac   2340
tctagcatgt gcctggataa ccctctaggc aaaggtggat tgactttgta ctgtcctcag   2400
atcgacgttg gatgaactgt cgcgccacga ggggctgtgg agcgcattgc gacacattgg   2460
tgcgctgcta acccatcctt tccagtacgg ctactgatgt ccacgctccc agcctgctac   2520
gctccgcccg agatctaaga gggacccatg gagaatgtgg tcagaaaccc ataatagagt   2580
ccgaccgcaa cgaccgaatt aattatcctc atcgagaaac ttagactact aagtagaaaa   2640
gatttgaaaa tcatggcatg ggtgtgcttt ttttctttct ttagagtttt ctatatgcac   2700
aatttctcga tgtttcgatg agaatttctt gactttccat atatagaaag agatagacta   2760
taaatgacat ctcttatgtc aataagacca aagggatgga tattaaatga taggaagtgc   2820
taggaagtga aatagaatga aatagagcca ctctgggctt acctatgaaa tgaggcatgg   2880
aacggagcca ctacgaagaa attccgggag ttacgaaaga agcttcggac tcatattgtt   2940
catgggttga gagcgggagt tgaactctag gaggtcgaat ccccccttgtt cctcagtagc   3000
tcagtggtag agcggtcggc tgttaactga ctggtcgtag gttcgaatcc tacttgggga   3060
gatttgattc attctttaat gtaagaataa agaattgaat taaagggctt gctttgaccc   3120
ttaggagtag gtaacccgtt cgctatcctt gtttctattg cattttatct catcgtatca   3180
cattctgttc tacgattcca cttcgacaaa aggaaagagc atacccaagt tcaatagctt   3240
tacgtccgct atcccgatca tggttttcct accctcaggg ggaaagtaaa ggcccttccc   3300
ctttggaagg ctgtgggcga ggagggattc gaacccccga caccgtggtt cgtagccacg   3360
tgctctaatc ctctgagcta caggcccacc ccgtctccac tggatctctt cccgggggta   3420
ccccccaaaa ggaacctccc tctcctcagc catttcattt cgggttaaga agatgggaaa   3480
gcccctttct ctctataaga acagtgcgtt ccgaggtgtg aagtgggaga gaggggatgt   3540
gatgattgag gttttgaata agacgacctt tgcattttgg atttggatct ttttcgtatt   3600
tcaaaatagt gaaaaagtca aataagaggt gttaagcttt ttatcattct ggcatcgagc   3660
tattttgccg caggacctcc cctacagtat cgtcaccgca gtagagttta accaccaaat   3720
tcgggatgga ttggtgtggt tcctctacgc ctaggacacc agaatatcga accatgaacg   3780
aggaaaggca tgagagaaat attggctagt aattgtgaag ccccaattct tgactggaag   3840
ggacaccaaa ggcctctgcc ctccctctct atctatccaa gagatggaag ggcagagctt   3900
ttttttggtt ttttcatctt ttcatcaaag agttgaacaa tgaagataga tggcaagtgc   3960
ctgatcgatt tgatcaggtc gtgtaggaac aaggttcaaa tcgttcgttc gttaggatgc   4020
ctcagctgca tacatcactg cacttccact tgacacctat ttaaacggct cgtctcgccg   4080
ctaccttatc ctatttccat gcttctgtcg ctccatcccc gtatgggtgg agaacccgtc   4140
gctgtctcgg ctgtgctacc ggaggctcta gggaagtcgg aggagagagc actcatcttg   4200
gggtgggctt actacttata tgctttcagc agttatcctc tccgcacttg gctacccagc   4260
gtttaccgta ggcacgataa ctggtacacc agaggtgcgt ccttcccggt cctctcgtac   4320
tagggaaagg tcctctcaat gctctaacgc ccacaccgga tatggaccga actgtctcac   4380
```

-continued

```
gacgttctga acccagctca cgtaccgcat taatgggcga acagcccaac ccttggaacc   4440

acctacagct ccaggtggcg aagagccgac atcgaggtgc caaaccttcc cgtcgatgtg   4500

gactcttggg gaagatcagc ctgttatccc tagagtaact tttatccgtt gagcgacggc   4560

ccttccactc ggcaccgtcg gatcactaag gccgactttc gtctctgctc gacgggtgag   4620

tcttgcagtc aagctccctt ctgcctttgc actcgaggac caatgtccgt ctggcccgag   4680

gaaacctttg cacgcctccg ttaccttttg ggaggcctac gccccataga aactgtctac   4740

ctgagactgt cccttggccc gcgggtctga cacaaggtta gaatccgagc tc           4792
```

```
<210> SEQ ID NO 19
<211> LENGTH: 2262
<212> TYPE: DNA
<213> ORGANISM: Artificial Sequence
<220> FEATURE:
<223> OTHER INFORMATION: An example of chloroplast origin of replication

<400> SEQUENCE: 19

gagctcggat tctaaccttg tgtcagaccc gcgggccaag ggacagtctc aggtagacag     60

tttctatggg gcgtaggcct cccaaaaggt aacggaggcg tgcaaaggtt tcctcgggcc    120

agacggacat tggtcctcga gtgcaaaggc agaagggagc ttgactgcaa gactcacccg    180

tcgagcagag acgaaagtcg gccttagtga tccgacggtg ccgagtggaa gggccgtcgc    240

tcaacggata aaagttactc tagggataac aggctgatct tccccaagag tccacatcga    300

cgggaaggtt tggcacctcg atgtcggctc ttcgccacct ggagctgtag gtggttccaa    360

gggttgggct gttcgcccat taatgcggta cgtgagctgg gttcagaacg tcgtgagaca    420

gttcggtcca tatccggtgt gggcgttaga gcattgagag gacctttccc tagtacgaga    480

ggaccgggaa ggacgcacct ctggtgtacc agttatcgtg cctacggtaa acgctgggta    540

gccaagtgcg gagaggataa ctgctgaaag catataagta gtaagcccac cccaagatga    600

gtgctctctc ctccgacttc cctagagcct ccggtagcac agccgagaca gcgacgggtt    660

ctccacccat acggggatgg agcgacagaa gcatggaaat aggataaggt agcggcgaga    720

cgagccgttt aaataggtgt caagtggaag tgcagtgatg tatgcagctg aggcatccta    780

acgaacgaac gatttgaacc ttgttcctac acgacctgat caaatcgatc aggcacttgc    840

catctatctt cattgttcaa ctctttgatg aaaagatgaa aaaaccaaaa aaaagctctg    900

cccttccatc tcttggatag atagagaggg agggcagagg cctttggtgt cccttccagt    960

caagaattgg ggcttcacaa ttactagcca atatttctct catgcctttc ctcgttcatg   1020

gttcgatatt ctggtgtcct aggcgtagag gaaccacacc aatccatccc gaatttggtg   1080

gttaaactct actgcggtga cgatactgta ggggaggtcc tgcggcaaaa tagctcgatg   1140

ccagaatgat aaaaagctta acacctctta tttgactttt tcactatttt gaaatacgaa   1200

aaagatccaa atccaaaatg caaaggtcgt cttattcaaa acctcaatca tcacatcccc   1260

tctctcccac ttcacacctc ggaacgcact gttcttatag agagaaaggg gctttcccat   1320

cttcttaacc cgaaatgaaa tggctgagga gagggaggtt ccttttgggg ggtacccccg   1380

ggaagagatc cagtggagac ggggtgggcc tgtagctcag aggattagag cacgtggcta   1440

cgaaccacgg tgtcgggggt tcgaatccct cctcgcccac agccttccaa aggggaaggg   1500

cctttacttt ccccctgagg gtaggaaaac catgatcggg atagcggacg taaagctatt   1560

gaacttgggt atgctctttc cttttgtcga agtggaatcg tagaacagaa tgtgatacga   1620

tgagataaaa tgcaatagaa acaaggatag cgaacgggtt acctactcct aagggtcaaa   1680
```

gcaagccctt taattcaatt ctttattctt acattaaaga atgaatcaaa tctccccaag 1740
taggattcga acctacgacc agtcagttaa cagccgaccg ctctaccact gagctactga 1800
ggaacaaggg ggattcgacc tcctagagtt caactcccgc tctcaaccca tgaacaatat 1860
gagtccgaag cttctttcgt aactcccgga atttcttcgt agtggctccg ttccatgcct 1920
catttcatag gtaagcccag agtggctcta tttcattcta tttcacttcc tagcacttcc 1980
tatcatttaa tatccatccc tttggtctta ttgacataag agatgtcatt tatagtctat 2040
ctctttctat atatggaaag tcaagaaatt ctcatcgaaa catcgagaaa ttgtgcatat 2100
agaaaactct aaagaaagaa aaaaagcaca cccatgccat gattttcaaa tcttttctac 2160
ttagtagtct aagtttctcg atgaggataa ttaattcggt cgttgcggtc ggactctatt 2220
atgggtttct gaccacattc tccatgggtc cctcttagat ct 2262

<210> SEQ ID NO 20
<211> LENGTH: 1118
<212> TYPE: DNA
<213> ORGANISM: Artificial Sequence
<220> FEATURE:
<223> OTHER INFORMATION: An example of chloroplast origin of replication

<400> SEQUENCE: 20
cgagaagaga ggagccgtgg tggtcccccc cggaccgccc ggatcccacg agtgaatcga 60
aagttggatc tacattggat cttcacatcg acaattcaat aaggtatccg acattaacaa 120
tgatttaaat tgtgttcatt gtgtttttta tggtacataa ccttcataga tttatagatt 180
atcctgtctc tgtaaggtga gagtggaatt tatcctttat tttgtccttt ccattcactc 240
ggatttcttc cgtttcatcg attttgtccg gatcccacct ttcttccgaa aaaagggaag 300
gagaaggata aggatcttct tcagtggatc cctcttgttc ctgtttagtc cccttcattt 360
cggaagctgt ttctatttct acatctcttt cttcctcact ttccaccctt tcttctgttt 420
ttgagttcct atatgaggaa gtatccttcc ccgcagtcaa gaccaaggtt agtattctct 480
gctaggaagt ttacttaggt tactctagca tgtgcctgga taaccctcta ggcaaaggtg 540
gattgacttt gtactgtcct cagatcgacg ttggatgaac tgtcgcgcca cgaggggctg 600
tggagcgcat tgcgacacat tggtgcgctg ctaacccatc ctttccagta cggctactga 660
tgtccacgct cccagcctgc tacgctccgc ccgctcaaaa acagaagaaa gggtggaaag 720
tgaggaagaa agagatgtag aaatagaaac agcttccgaa atgaagggga ctaaacagga 780
acaagaggga tccactgaag aagatcctta tccttctcct tcccttttt cggaagaaag 840 gtgggatccg gacaaaatcg atgaaacgga agaaatccga gtgaatggaa aggacaaaat 900
aaaggataaa ttccactctc accttacaga gacaggtgct agaaagttat tcttttcgtc 960
ttaatgatta tatgtaaatc gccctctata tattaactct acttatatgg aaaaactatg 1020
attaagtagt tacagtagat ccaatgtaga tccaactttc gattcactcg tgggatccgg 1080
gcggtccggg ggggaccacc acggctcctc tcttctcg 1118

<210> SEQ ID NO 21
<211> LENGTH: 825
<212> TYPE: DNA
<213> ORGANISM: Artificial Sequence
<220> FEATURE:
<223> OTHER INFORMATION: An example of chloroplast origin of replication

<400> SEQUENCE: 21

-continued cctaaggtgc tgctaaatgg atggatctta tcaacgtcca tgaatgataa atcatagatc 60
gaaccgccga atcggaaaaa ttgggtgcta tcataaagct ttgtatcggc taagttcacg 120
agttggagat aagcggactc gaaccgctga catccgccgc agggtaaacc accgcctctc 180
aggtcccccg actgattcta ccatagaggc caacgataga caataactcc cccccgaaca 240
cagcttacaa ctttcatcgt actgtgctct ccaaagagca actcttctca aaatctcact 300
caaaaggtgc tgagttggaa tcccattcta actaagaatg agtcattgcc cttctccgac 360
cctgactgcc caacctgaga gcggacagct aatgcgttcc acttattgaa cagggttcta 420
tggtcggtcc gtgacccctg gatgccgaag gcgtccttgg ggtgatctcg tagttcctac 480
ggggtggaga tgatggggtc ggtccatgga ttttccttcc ttttcttttg ccgcatttcg 540
ctcaaagggt tgaagggaga tagtgcatca agctgttcgc aagggccaac ttgatcctct 600
tccccagaga tctcagatga gggaaccctg ggagagccgc cgactccaac taccgtccat 660
gtacgatcca tactagatct gaccaactgc ccatcctacc tcctctacgt tcttgacagc 720
ccatctttgt ctcagtagag tctttcagtg gcacgtttcg gtcctcttcc ccattactta 780
gaaaaagtga gccaccggtt caggtacaag atactatcat taccg 825

<210> SEQ ID NO 22
<211> LENGTH: 1118
<212> TYPE: DNA
<213> ORGANISM: Artificial Sequence
<220> FEATURE:
<223> OTHER INFORMATION: An example of chloroplast origin of replication

<400> SEQUENCE: 22
cgagaagaga ggagccgtgg tggtcccccc cggaccgccc ggatcccacg agtgaatcga 60
aagttggatc tacattggat cttcacatcg acaattcaat aaggtatccg acattaacaa 120
tgatttaaat tgtgttcatt gtgtttttta tggtacataa ccttcataga tttatagatt 180
atctcaaaaa cagaagaaag ggtggaaagt gaggaagaaa gagatgtaga aatagaaaca 240
gcttccgaaa tgaaggggac taaacaggaa caagagggat ccactgaaga agatccttat 300
ccttctcctt cccttttttc ggaagaaagg tgggatccgg acaaaatcga tgaaacggaa 360
gaaatccgag tgaatggaaa ggacaaaata aaggataaat tccactctca ccttacagag 420
acaggttcct atatgaggaa gtatccttcc ccgcagtcaa gaccaaggtt agtattctct 480
gctaggaagt ttacttaggt tactctagca tgtgcctgga taaccctcta ggcaaaggtg 540
gattgacttt gtactgtcct cagatcgacg ttggatgaac tgtcgcgcca cgaggggctg 600
tggagcgcat tgcgacacat tggtgcgctg ctaacccatc ctttccagta cggctactga 660
tgtccacgct cccagcctgc tacgctccgc ccgcctgtct ctgtaaggtg agagtggaat 720
ttatccttta ttttgtcctt tccattcact cggatttctt ccgtttcatc gattttgtcc 780
ggatcccacc tttcttccga aaaaagggaa ggagaaggat aaggatcttc ttcagtggat 840
ccctcttgtt cctgtttagt ccccttcatt tcggaagctg tttctatttc tacatctctt 900
tcttcctcac tttccaccct ttcttctgtt tttgagtgct agaaagttat tcttttcgtc 960
ttaatgatta tatgtaaatc gccctctata tattaactct acttatatgg aaaaactatg 1020
attaagtagt tacagtagat ccaatgtaga tccaactttc gattcactcg tgggatccgg 1080
gcggtccggg ggggaccacc acggctcctc tcttctcg 1118

<210> SEQ ID NO 23
<211> LENGTH: 1118

-continued

<212> TYPE: DNA
<213> ORGANISM: Artificial Sequence
<220> FEATURE:
<223> OTHER INFORMATION: An example of chloroplast origin of replication

<400> SEQUENCE: 23
caccatagcg cgccggttgc ctgcggttac tggaccaagc tcgtcaactc ggagcaggct 60
ttatgggcct cgcttcctta agtcacatcg acaattcaat aaggtatccg acattaacaa 120
tgatttaaat tgtgttcatt gtgtttttta tggtacataa ccttcataga tttatagatt 180
atctcaaaaa cagaagaaag ggtggaaagt gaggaagaaa gagatgtaga aatagaaaca 240
gcttccgaaa tgaaggggac taaacaggaa caagagggat ccactgaaga agatccttat 300
ccttctcctt cccttttttc ggaagaaagg tgggatccgg acaaaatcga tgaaacggaa 360
gaaatccgag tgaatggaaa ggacaaaata aaggataaat tccactctca ccttacagag 420
acaggttcct atatgaggaa gtatccttcc ccgcagtcaa gaccaaggtt agtattctct 480
gctaggaagt ttacttaggt tactctagca tgtgcctgga taaccctcta ggcaaaggtg 540
gattgacttt gtactgtcct cagatcgacg ttggatgaac tgtcgcgcca cgaggggctg 600
tggagcgcat tgcgacacat tggtgcgctg ctaacccatc ctttccagta cggctactga 660
tgtccacgct cccagcctgc tacgctccgc ccggcgtggt ctgctgtcct acttccctgt 720
gttcccgtcg aatctttttt tgctttgcct tctccccatt ccaatctttg cgactgaaac 780
gtacgtacac tgtgctttgc attattagtt tttgaaattg tggcctattt tttgtcctta 840
aaccgctcat ctttacacca tcgttctttg tggacattct tttccttgct aattggtatt 900
ctacaaactg gcactagctg tagtcaatct gactgttgct agaaagttat tcttttcgtc 960
ttaatgatta tatgtaaatc gccctctata tattaactct acttatatgg aaaaactatg 1020
attaagtagt tacagtcgac gcgcgggtga cacccctacg ccgactcgat aaacaggatg 1080
ggtcatgggc ctggcacgtg ttattcaaag gtacagcg 1118

<210> SEQ ID NO 24
<211> LENGTH: 1118
<212> TYPE: DNA
<213> ORGANISM: Artificial Sequence
<220> FEATURE:
<223> OTHER INFORMATION: An example of chloroplast origin of replication

<400> SEQUENCE: 24
caccatagcg cgccggttgc ctgcggttac tggaccaagc tcgtcaactc ggagcaggct 60
ttatgggcct cgcttcctta agtcacatcg acaattcaat aaggtatccg acattaacaa 120
tgatttaaat tgtgttcatt gtgtttttta tggtacataa ccttcataga tttatagatt 180
atctcaaaaa cagaagaaag ggtggaaagt gaggaagaaa gagatgtaga aatagaaaca 240
gcttccgaaa tgaaggggac taaacaggaa caagagggat ccactgaaga agatccttat 300
ccttctcctt cccttttttc ggaagaaagg tgggatccgg acaaaatcga tgaaacggaa 360
gaaatccgag tgaatggaaa ggacaaaata aaggataaat tccactctca ccttacagag 420
acaggttcct atatgaggaa gtatccttcc ccgcagtcaa gaccaaggtt agtattctct 480
gctaggaagt ttacttaggt tactctagca tgtgcctgga taaccctcta ggcaaaggtg 540
gattgacttt gtactgtcct cagatcgacg ttggatgaac tgtcgcgcca cgaggggctg 600
tggagcgcat tgcgacacat tggtgcgctg ctaacccatc ctttccagta cggctactga 660
tgtccacgct cccagcctgc tacgctccgc ccgcctgtct ctgtaaggtg agagtggaat 720

```
ttatccttta ttttgtcctt tccattcact cggatttctt ccgtttcatc gattttgtcc    780

ggatcccacc tttcttccga aaaaagggaa ggagaaggat aaggatcttc ttcagtggat    840

ccctcttgtt cctgtttagt ccccttcatt tcggaagctg tttctatttc tacatctctt    900

tcttcctcac tttccaccct ttcttctgtt tttgagtgct agaaagttat tcttttcgtc    960

ttaatgatta tatgtaaatc gccctctata tattaactct acttatatgg aaaaactatg   1020

attaagtagt tacagtcgag aagagaggag ccgtggtggt cccccccgga ccgcccggat   1080

cccacgagtg aatcgaaagt tggatctaca ttggatct                          1118
```

<210> SEQ ID NO 25
<211> LENGTH: 1118
<212> TYPE: DNA
<213> ORGANISM: Artificial Sequence
<220> FEATURE:
<223> OTHER INFORMATION: An example of chloroplast origin of replication

<400> SEQUENCE: 25

```
caccatagcg cgccggttgc ctgcggttac tggaccaagc tcgtcaactc ggagcaggct     60

ttatgggcct cgcttcctta agtcacatcg acaattcaat aaggtatccg acattaacaa    120

tgatttaaat tgtgttcatt gtgtttttta tggtacataa ccttcataga tttatagatt    180

atctcaaaaa cagaagaaag ggtggaaagt gaggaagaaa gagatgtaga aatagaaaca    240

gcttccgaaa tgaaggggac taaacaggaa caagagggat ccactgaaga agatccttat    300

ccttctcctt cccttttttc ggaagaaagg tgggatccgg acaaaatcga tgaaacggaa    360

gaaatccgag tgaatggaaa ggacaaaata aaggataaat tccactctca ccttacagag    420

acaggttcct atatgaggaa gtatccttcc ccgcagtcaa gaccaaggtt agtattctct    480

gctaggaagt ttacttaggt tactctagca tgtgcctgga taaccctcta ggcaaaggtg    540

gattgacttt gtactgtcct cagatcgacg ttggatgaac tgtcgcgcca cgaggggctg    600

tggagcgcat tgcgacacat tggtgcgctg ctaacccatc ctttccagta cggctactga    660

tgtccacgct cccagcctgc tacgctccgc ccgcctgtct ctgtaaggtg agagtggaat    720

ttatccttta ttttgtcctt tccattcact cggatttctt ccgtttcatc gattttgtcc    780

ggatcccacc tttcttccga aaaaagggaa ggagaaggat aaggatcttc ttcagtggat    840

ccctcttgtt cctgtttagt ccccttcatt tcggaagctg tttctatttc tacatctctt    900

tcttcctcac tttccaccct ttcttctgtt tttgagtgct agaaagttat tcttttcgtc    960

ttaatgatta tatgtaaatc gccctctata tattaactct acttatatgg aaaaactatg   1020

attaagtagt tacagtcgac gcgcgggtga cacccctacg ccgactcgat aaacaggatg   1080

ggtcatgggc ctggcacgtg ttattcaaag gtacagcg                          1118
```

<210> SEQ ID NO 26
<211> LENGTH: 1118
<212> TYPE: DNA
<213> ORGANISM: Artificial Sequence
<220> FEATURE:
<223> OTHER INFORMATION: An example of chloroplast origin of replication

<400> SEQUENCE: 26

```
agatccaatg tagatccaac tttcgattca ctcgtgggat ccgggcggtc cggggggggac     60

caccacggct cctctcttct cgtcacatcg acaattcaat aaggtatccg acattaacaa    120

tgatttaaat tgtgttcatt gtgtttttta tggtacataa ccttcataga tttatagatt    180

atctcaaaaa cagaagaaag ggtggaaagt gaggaagaaa gagatgtaga aatagaaaca    240
```

gcttccgaaa tgaaggggac taaacaggaa caagagggat ccactgaaga agatccttat 300
ccttctcctt cccttttttc ggaagaaagg tgggatccgg acaaaatcga tgaaacggaa 360
gaaatccgag tgaatggaaa ggacaaaata aaggataaat tccactctca ccttacagag 420
acaggttcct atatgaggaa gtatccttcc ccgcagtcaa gaccaaggtt agtattctct 480
gctaggaagt ttacttaggt tactctagca tgtgcctgga taaccctcta ggcaaaggtg 540
gattgacttt gtactgtcct cagatcgacg ttggatgaac tgtcgcgcca cgaggggctg 600
tggagcgcat tgcgacacat tggtgcgctg ctaacccatc ctttccagta cggctactga 660
tgtccacgct cccagcctgc tacgctccgc ccgctcaaaa acagaagaaa gggtggaaag 720
tgaggaagaa agagatgtag aaatagaaac agcttccgaa atgaagggga ctaaacagga 780
acaagaggga tccactgaag aagatcctta tccttctcct tccctttttt cggaagaaag 840
gtgggatccg gacaaaatcg atgaaacgga agaaatccga gtgaatggaa aggacaaaat 900
aaaggataaa ttccactctc accttacaga gacaggtgct agaaagttat tcttttcgtc 960
ttaatgatta tatgtaaatc gccctctata tattaactct acttatatgg aaaaactatg 1020
attaagtagt tacagtagat ccaatgtaga tccaactttc gattcactcg tgggatccgg 1080
gcggtccggg ggggaccacc acggctcctc tcttctcg 1118

<210> SEQ ID NO 27
<211> LENGTH: 1118
<212> TYPE: DNA
<213> ORGANISM: Artificial Sequence
<220> FEATURE:
<223> OTHER INFORMATION: An example of chloroplast origin of replication

<400> SEQUENCE: 27
agatccaatg tagatccaac tttcgattca ctcgtgggat ccgggcggtc cgggggggac 60
caccacggct cctctcttct cgtcacatcg acaattcaat aaggtatccg acattaacaa 120
tgatttaaat tgtgttcatt gtgtttttta tggtacataa ccttcataga tttatagatt 180
atctcaaaaa cagaagaaag ggtggaaagt gaggaagaaa gagatgtaga aatagaaaca 240
gcttccgaaa tgaaggggac taaacaggaa caagagggat ccactgaaga agatccttat 300
ccttctcctt cccttttttc ggaagaaagg tgggatccgg acaaaatcga tgaaacggaa 360
gaaatccgag tgaatggaaa ggacaaaata aaggataaat tccactctca ccttacagag 420
acaggttcct atatgaggaa gtatccttcc ccgcagtcaa gaccaaggtt agtattctct 480
gctaggaagt ttacttaggt tactctagca tgtgcctgga taaccctcta ggcaaaggtg 540
gattgacttt gtactgtcct cagatcgacg ttggatgaac tgtcgcgcca cgaggggctg 600
tggagcgcat tgcgacacat tggtgcgctg ctaacccatc ctttccagta cggctactga 660
tgtccacgct cccagcctgc tacgctccgc ccgcctgtct ctgtaaggtg agagtggaat 720
ttatccttta ttttgtcctt tccattcact cggatttctt ccgtttcatc gattttgtcc 780
ggatcccacc tttcttccga aaaaagggaa ggagaaggat aaggatcttc ttcagtggat 840
ccctcttgtt cctgtttagt ccccttcatt tcggaagctg tttctatttc tacatctctt 900
tcttcctcac tttccaccct ttcttctgtt tttgagtgct agaaagttat tcttttcgtc 960
ttaatgatta tatgtaaatc gccctctata tattaactct acttatatgg aaaaactatg 1020
attaagtagt tacagtcgag aagagaggag ccgtggtggt cccccccgga ccgcccggat 1080
cccacgagtg aatcgaaagt tggatctaca ttggatct 1118

<210> SEQ ID NO 28
<211> LENGTH: 7687
<212> TYPE: DNA
<213> ORGANISM: Artificial Sequence
<220> FEATURE:
<223> OTHER INFORMATION: An example of chloroplast origin of replication

<400> SEQUENCE: 28
ggccattatg gccgttcgac acaattggga tttttttgg aaattggaag cagttactaa 60
ttccaccccc tctccactgg atctgttccc gggagtaccc tcaaaaaaag gaacctttcc 120
tctccccagc catttcgggt taagaagatg tgaaggcgcg tttatctcta taagaagggt 180
gcgttccgag gtgtgaagtg ggagagaagg gatgtcacaa ttggggtttt gaataaaacg 240
accttttgat ttttcatttt ttttttttc gttttcatat tgaaaaagta ataagaatga 300
gaggtgttaa gctttttatc atcctggcgt cgagctattt ttccgcagga cctcccctac 360
agtatcgtca ccgcagtaga gtttaaccac caagttcggg atggattggt gtggttcctc 420
tacgcctagg acaccagaat atcgaaccat gaacgaagaa aggcatgaga gaaaagcata 480
ttggctagtg attgtgaggc cccaattctt gactggaggg gacaccaaag gcctctgccc 540
ttccatccct tggatagata gagagggagg gcagagcttt tggtttttc atgttgtcaa 600
agagttgaac aatggttttt tcgtgttgtc aaagatttga acaatgaaaa tagatggcga 660
gtgcctgatc gaattgatca ggtcatgtag gaacaaggtt caagtctacc ggtctgttag 720
gatgcctcag ctgcatacat cactgcactt ccacttgaca cctatcgtaa tgataaacgg 780
ctcgtctcgc cgtgaccttc tcttgaattc tcaaaaaaac ttctgtcgct ccatccccgc 840
aggggcagag aacccgtcgc tgtctcggct gtgctaccgg aagctctggg gaagtcggaa 900
taggagagca ctcatcttgg ggtgggctta ctacttagat gctttcagca gttatccgct 960
ccgcacttgg ctacccagcg tttaccgtgg gcacgataac tggtacacca gaggtgcgtc 1020
cttcccggtc ctctcgtact agggaaaggt cctctcaatg ctctaacgcc cacaccggat 1080
atggaccgaa ctgtctcacg acgttctgaa cccagctcac gtaccgcttt aatgggcgaa 1140
cagcccaacc cttggaacat actacagccc caggtggcga agagccgaca tcgaggtgcc 1200
aaaccttccc gtcgatgtga gctcttgggg aagatcagcc tgttatccct agagtaactt 1260
ttatccgttg agcgacggcc cttccactcg gcaccgtcgg atcactaagg ccgactttcg 1320
tccctgctcg acgggtgggt cttgcagtca agctcccttc tgcctttgca ctcgagggcc 1380
aatctccgtc cggcccgagg aaacctttgc acgcctccgt taccttttgg gaggcctacg 1440
ccccatagaa actgtctacc tgagactgtc ccttggcccg taggtcctga cacaaggtta 1500
gaattctagc ccttccagag tggtatctca ctgatggctc gggccccccc ggaaggaggc 1560
cttcttcgcc ttccacctaa gctgcgcagg aaaggcccaa agccaatccc agggaacagt 1620
gaagcttcat agggtctttc tgtccaggtg caggtagtcc gcatcttcac agacatgtct 1680
atttcaccga gcctctctcc gagacagtgc ccagatcgtt acgcctttcg tgcgggtcgg 1740
aacttacccg acaaggaatt tcgctacctt aggaccgtta tagttacggc cgccgttcac 1800
cggggcttcg gtcgccggct cccctgtcat caggtcacca acttccttga ccttccggca 1860
ctgggcaggc gtcagccccc atacatggtc ttacgacttt gcggagacct gtgtttttgg 1920
taaacagtcg cccgggcctg gtcactgcga cccccttgt gaggaggcac cccttctccc 1980
gaagttacgg ggctattttg ccgagttcct tagagagagt tgtctcgcgc ccctaggtat 2040
tctctaccta cccacctgtg tcggtttcgg gtacaggtac cctcttgctt aacgtcgttc 2100

```
gagcttttcc tgggagtatg gcatgggtta cttcagcgcc gtagcgcctg gtattcgaac   2160
attggctcga ggcattttct ctaccccttc ttaccctgaa aaagcaggga caccttacgt   2220
tcttgaaccg ataaccatct ttcggctaac ctagcctcct ccgtccctcg ggactaacaa   2280
ggggtagtac aggaatattc acctgttgtc catcgactac gcctttcggc ctgatcttag   2340
gccctgactc accctccgtg gacgaacctt gcggaggaac ccttaggttt tcggggcatt   2400
ggattctcac caatgtttgc gttactcaag ccgacattct cgcttccgct tcgtccacca   2460
ccgctcgcgc ggaggcttct ctctaaggcg gaacgctccc ctaccgatgt atttttacat   2520
cccacagctt cggcagaccg cttagccccg ttcatcttcg gcgcaagagc gctcgatcag   2580
tgagctatta cgcactcttt caagggtggc tgcttctagg caaacctcct ggctgtctct   2640
gcacccctac ctcctttatc actgagcggt catttagggg ccttagctgg tgatccgggc   2700
tgtttccctc tcgacgatga agcttatccc ccatcgtctc actagccgac cttgacccct   2760
gttattttga ggtcatatct agtattcaga gtttgcctcg atttggtacc gctctcgcgg   2820
cccgcaccga aacagtgctt taccccctaga tgtccagtca actgctgcgc ctcaacgcat   2880
ttcggggaga accagctagc tctgggttcg agtggcattt cacccctaac cacaactcat   2940
ccgctgattc ttcaacatca gtcggttcgg acctccactt agtttcaccc aagcttcatc   3000
ctggtcatgg atagatcacc caggttcggg tccataagca gtgacaattg ccctatgaag   3060
actcgctttc gctacggctc cggtgggttc ccttaaccaa gccactgcct atgagtcgcc   3120
ggctcattct tcaacaggca cgcggtcaga gccctggctc ctcccactgc ttgggagctt   3180
acggtttcat gttctatttc actccccgat gggggttctt ttcacccttc cctcacggta   3240
ctacttcgct atcggtcacc caggagtatt tagccttgca aggtggtcct tgctgattca   3300
cacgggattc cacgtgcccc atgctactcg ggtcagagca taagctagtg atgctttcgg   3360
ctactggact ttcgccatct agggtgcagc attcgggctg cttcgcctag cagcacgacg   3420
cttgtattgc tctcccacaa ccccgttttc acggtttagg ctgctcccat ttcgctcgcc   3480
gctactacgg gaatcgcttt tgctttcttt tcctctggct actaagatgt ttcagttcgc   3540
caggttgtct cttgcctgcc catggattca gcagcagttc gaaaggttgc cctattcggg   3600
aatctccgga tctatgctta ttttcaactc cccgaagcat ttcgtcgatt actacgccct   3660
tcctagtctc tgggtgccta ggtatccacc gtaagccttt cctcgtttga acctcgccct   3720
tcacttttaa ggctatgcca tcctaaggtg ctgctaaatg gatggatctt atcaacgtcc   3780
atgaatgata aatcatagat cgaaccgccg aatcggaaaa attgggtgct atcataaagc   3840
tttgtatcgg ctaagttcac gagttggaga taagcggact cgaaccgctg acatccgccg   3900
cagggtaaac caccgcctct caggtccccc gactgattct accatagagg ccaacgatag   3960
acaataactc ccccccgaac acagcttaca actttcatcg tactgtgctc tccaaagagc   4020
aactcttctc aaaatctcac tcaaaaggtg ctgagttgga atcccattct aactaaggat   4080
tcttgtggtt ccggaggatc caactacagg agaaccagga acggagggct ttccccccct   4140
tccgcccgac tctttggtct taagaacgct ggttttaaga atgagtcatt gcccttctcc   4200
gaccctgact gcccaacctg agagcggaca gctaatgcgt tccacttatt gaacagggtt   4260
ctatggtcgg tccgtgaccc ctggatgccg aaggcgtcct tggggtgatc tcgtagttcc   4320
tacggggtgg agatgatggg gtcggtccat ggattttcct tccttttctt ttgccgcatt   4380
tcgctcaaag ggttgaaggg agatagtgca tcaagctgtt cgcaagggcc aacttgatcc   4440
```

-continued

```
tcttccccag agatctcaga tgagggaacc ctgggagagc cgccgactcc aactaccgtc   4500
catgtacgat ccatactaga tctgaccaac tgcccatcct acctcctcta cgttcttgac   4560
agcccatctt tgtctcagta gagtctttca gtggcacgtt tcggtcctct tccccattac   4620
ttagaaaaag tgagccaccg gttcaggtac aagatactat cattaccgcc tggacaatta   4680
gacatccaac ccgtaatcgc aacgacccaa ttgcaagagc ggagctctac caactgagct   4740
atatcccccc gagccaagtg gagcatgcat gaagtagtca gatgcttctt ctattctttt   4800
ccctggcgca gctgggccat cctggacttg aaccagagac ctcgcccgtg aagtaaatca   4860
tcgcacctac ggtccaacca attgggagag aatcaataga ttccttttcg ggagcgattc   4920
atccttcccg aacgcagcat acaactctcc gttgtactgc gctctccaag tgtgcttgtt   4980
ccccccttct tccttaccct ggcaagtctt tgtgaaataa ctccgatgag aagaaaaaag   5040
aaggcgttaa gagagcctcc tggcccaacc ctagacactc taagatcctt tttcaaacct   5100
gctcccattt cgatttcgag tcaagaaaaa aacggctcga atggtacgat ccctccgtca   5160
ccccagaatg aaaggggcga tctcgtagtt cttggtctgt gaagatgcgt tgttaggtgc   5220
tccattttat tttcccattg ctaaacctgt gctcgagaga tagctgtcca tacactgata   5280
agggatgtat ggattctcga gaagagagga gccgtggtgg tccccccccgg accgcccgga   5340
tcccacgagt gaatcgaaag ttggatctac attggatctc acccgaatcg ccccatctat   5400
cctcctgagg aggagtttgg tttcaaaccc cggttcgaac aggaggagta cgccatgcta   5460
atgtgccttg gatgatccac atctcagggt caggcgccga tgagcacatt gaactatcca   5520
tgtggctgag agccctcaca gcccaggcac aacgacgcaa ttatcagggg cgcgctctac   5580
cactgagcta atagcccgtc gtgcgagcct cccactgggg gcccgctatg ccaaaagcga   5640
gagaaacccc atccctctct ttcctttttt cgcccccatg tcgccacacg gggggaacat   5700
ggggacgtaa aaaagggggt cctatcaact tgttccgacc taggataata agctcatgag   5760
cttggtctta cttcaccgtc gagaaaggaa agatgacttc catctccaag tttaactcag   5820
acgtagctcc cttctttttt ttgggggtgt gaagcagtgt caaaccaaaa tacccaacaa   5880
gcattagctc tccctgaaaa ggaggtgatc cagccgcacc ttccagtacg gctaccttgt   5940
tacgacttca ctccagtcac tagccctgcc ttcggcatcc ccctccttgc ggttaaggta   6000
acgacttcgg gcatggccag ctcccatagt gtgacgggcg gtgtgtacaa ggcccgggaa   6060
cgaattcacc gccgtatggc tgaccggcga ttactagcga ttccggcttc atgcaggcga   6120
gttgcagcct gcaatccgaa ctgaggacgg gtttttgggg ttagctcacc ctcgcgggat   6180
cgcgaccctt tgtcccggcc attgtagcac gtgtgtcgcc cagggcataa ggggcatgat   6240
gacttgacgt catcctcacc ttcctccggc ttatcaccgg cagtctgttc agggttccaa   6300
actcaacgat ggcaactaaa cacgagggtt gcgctcgttg cgggacttaa cccaacacct   6360
tacggcacga gctgacgaca gccatgcacc acctgtgtcc gcgttcccga aggcacccct   6420
ctctttcaag aggattcgcg gcatgtcaag ccctggtaag gttcttcgct ttgcatcgaa   6480
ttaaaccaca tgctccaccg cttgtgcggg cccccgtcaa ttcctttgag tttcattctt   6540
gcgaacgtac tccccaggcg ggatacttaa cgcgttagct acagcactgc acgggtcgat   6600
acgcacagcg cctagtatcc atcgtttacg gctaggacta ctggggtatc taatcccatt   6660
cgctccccta gctttcgtgt ctcagtgtca gtgtcggccc agcagagtgc tttcgccgtt   6720
ggtgttcttt ccgatctcta cgcatttcac cgctccaccg gaaattccct ctgcccctac   6780
cgtactccag cttggtagtt tccaccgcct gtccagggtt gagccctggg atttgacggc   6840
```

ggacttaaaa agccacctac agacgcttta cgcccaatca ttccggataa cgcttgcatc 6900
ctctgtatta ccgcggctgc tggcacagag ttagccgatg cttattcccc agataccgtc 6960
attgcttctt ctccgggaaa agaagttcac gacccgtggg ccttctacct ccacgcggca 7020
ttgctccgtc aggctttcgc ccattgcgga aaattcccca ctgctgcctc ccgtaggagt 7080
ctgggccgtg tctcagtccc agtgtggctg atcatcctct cggaccagct actgatcatc 7140
gccttggtaa gctattgcct caccaactag ctaatcagac gcgagcccct cctcgggcgg 7200
attcctcctt ttgctcctca gcctacgggg tattagcagc cgtttccagc tgttgttccc 7260
ctcccaaggg caggttctta cgcgttactc acccgtccgc cactggaaac accgtttccc 7320
gtgtttcccg tccgacttgc atgtgttaag catgccgcca gcgttcatcc tgagccagga 7380
tcgaactctc catgagattc atagttgcat tacttatagc ttccttgttc gtagacaaag 7440
cggattcgga attgtctttc attccaaggc ataacttgta tccatgcgct tcatattcgc 7500
ccggagttcg ctcccagaaa tatagccatc cctgcccccct cacgtcaatc ccacgagcct 7560
cttatccatt ctcattgaac gacggcgggg gagcaaatcc aactagaaaa actcacattg 7620
ggctgactct accacccagt caattctgtt ccacttaatc cctctttcat ggccggccat 7680
tatggcc 7687

<210> SEQ ID NO 29
<211> LENGTH: 7701
<212> TYPE: DNA
<213> ORGANISM: Artificial Sequence
<220> FEATURE:
<223> OTHER INFORMATION: An example of chloroplast origin of replication

<400> SEQUENCE: 29
ggccattatg gccgttcgac acaattggga ttttttttgg aaattggaag cagttactaa 60
ttccaccccc tctccactgg atctgttccg gggagtaccc tcaaaaaaag gaacctttcc 120
tctccccagc catttcgggt taagaagatg tgaaagcgcg tttatctcta taagtctata 180
agaagggtgc gttccgaggt gtgaagtggg agagaaggga tgtcacaatt ggggttttga 240
ataaaacgac ctttttattt ttcatttttt tttttcgttt tcatattgaa aaagtaataa 300
gaatgagagg tgttaagctt tttatcatcc tggcgtcgag ctatttttcc gcaggacctc 360
ccctacagta tcgtcaccgc agtagagttt aaccaccaag ttcgggatgg attggtgtgg 420
ttcctctacg cctaggacac cagaatatcg aaccatgaac gaagaaaggc atgagagaaa 480
agcatattgg ctagtgattg tgaggcccca attcttgact ggaggggaca ccaaaggcct 540
ctgcccttcc atcccttgga tagatagaga gggagggcag agcttttggt tttttcatgt 600
tgtcaaagag ttgaacaatg gttttttcgt gttgtcaaag atttgaacaa tgaaaataga 660
tggcgagtgc ctgatcgaat tgatcaggtc atgtaggaac aaggttcaag tctaccggtc 720
tgttaggatg cctcagctgc atacatcact gcacttccac ttgacaccta tcgtaatgat 780
aaacggctcg tctcgccgtg accttctctt gaattctcaa aaaaacttct gtcgctccat 840
ccccgcaggg gcagagaacc cgtcgctgtc tcggctgtgc taccggaagc tctggggaag 900
tcggaatagg agagcactca tcttggggtg ggcttactac ttagatgctt tcagcagtta 960
tccgctccgc acttggctac ccagcgttta ccgtgggcac gataactggt acaccagagg 1020
tgcgtccttc ccggtcctct cgtactaggg aaaggtcctc tcaatgctct aacgcccaca 1080
ccggatatgg accgaactgt ctcacgacgt tctgaaccca gctcacgtac cgctttaatg 1140

-continued

```
ggcgaacagc ccaacccttg gaacatacta cagccccagg tggcgaagag ccgacatcga   1200
ggtgccaaac cttcccgtcg atgtgagctc ttggggaaga tcagcctgtt atccctagag   1260
taacttttat ccgttgagcg acggcccttc cactcggcac cgtcggatca ctaaggccga   1320
ctttcgtccc tgctcgacgg gtgggtcttg cagtcaagct cccttctgcc tttgcactcg   1380
agggccaatc tccgtccggc ccgaggaaac ctttgcacgc ctccgttacc ttttgggagg   1440
cctacgcccc atagaaactg tctacctgag actgtccctt ggcccgtagg tcctgacaca   1500
aggttagaat tctagccctt ccagagtggt atctcactga tggctcgggc ccccccggaa   1560
ggaggccttc ttcgccttcc acctaagctg cgcaggaaag gcccaaagcc aatcccaggg   1620
aacagtgaag cttcataggg tctttctgtc caggtgcagg tagtccgcat cttcacagac   1680
atgtctattt caccgagcct ctctccgaga cagtgcccag atcgttacgc ctttcgtgcg   1740
ggtcggaact tacccgacaa ggaatttcgc taccttagga ccgttatagt tacggccgcc   1800
gttcaccggg gcttcggtcg ccggctcccc tgtcatcagg tcaccaactt ccttgacctt   1860
ccggcactgg gcaggcgtca gcccccatac atggtcttac gactttgcgg agacctgtgt   1920
ttttggtaaa cagtcgcccg ggcctggtca ctgcgacccc ctttgtgagg aggcacccct   1980
tctcccgaag ttacggggct attttgccga gttccttaga gagagttgtc tcgcgcccct   2040
aggtattctc tacctaccca cctgtgtcgg tttcgggtac aggtaccctc ttgcttaacg   2100
tcgttcgagc ttttcctggg agtatggcat gggttacttc agcgccgtag cgcctggtat   2160
tcgaacattg gctcgaggca ttttctctac cccttcttac cctgaaaaag cagggacacc   2220
ttacgttctt gaaccgataa ccatctttcg gctaacctag cctcctccgt ccctcgggac   2280
taacaagggg tagtacagga atattcacct gttgtccatc gactacgcct ttcggcctga   2340
tcttaggccc tgactcaccc tccgtggacg aaccttgcgg aggaaccctt aggttttcgg   2400
ggcattggat tctcaccaat gtttgcgtta ctcaagccga cattctcgct tccgcttcgt   2460
ccaccaccgc tcgcgcggag gcttctctct aaggcggaac gctcccctac cgatgtattt   2520
ttacatccca cagcttcggc agaccgctta gccccgttca tcttcggcgc aagagcgctc   2580
gatcagtgag ctattacgca ctctttcaag ggtggctgct tctaggcaaa cctcctggct   2640
gtctctgcac ccctacctcc tttatcactg agcggtcatt taggggcctt agctggtgat   2700
ccgggctgtt tccctctcga cgatgaagct tatcccccat cgtctcacta gccgaccttg   2760
acccctgtta ttttgaggtc atatctagta ttcagagttt gcctcgattt ggtaccgctc   2820
tcgcggcccg caccgaaaca gtgctttacc cctagatgtc cagtcaactg ctgcgcctca   2880
acgcatttcg gggagaacca gctagctctg ggttcgagtg gcatttcacc cctaaccaca   2940
actcatccgc tgattcttca acatcagtcg gttcggacct ccacttagtt tcacccaagc   3000
ttcatcctgg tcatggatag atcacccagg ttcgggtcca taagcagtga caattgccct   3060
atgaagactc gctttcgcta cggctccggt gggttccctt aaccaagcca ctgcctatga   3120
gtcgccggct cattcttcaa caggcacgcg gtcagagccc tggctcctcc cactgcttgg   3180
gagcttacgg tttcatgttc tatttcactc cccgatgggg gttcttttca cccttccctc   3240
acggtactac ttcgctatcg gtcacccagg agtatttagc cttgcaaggt ggtccttgct   3300
gattcacacg ggattccacg tgccccatgc tactcgggtc agagcgtaag ctagtgatgc   3360
tttcggctac tggactttcg ccatctaggg tgcagcattc aggctgcttc gcctagcagc   3420
acgacgcttg tattgctctc ccacaacccc gttttcacgg tttaggctgc tcccatttcg   3480
ctcgccgcta ctacgggaat cgcttttgct ttcttttcct ctggctacta agatgtttca   3540
```

-continued

```
gttcgccagg ttgtctcttg cctgcccatg gattcagcag cagttcgaaa ggttgcccta   3600
ttcgggaatc tccggatcta tgcttatttt caactccccg aagcatttcg tcgattacta   3660
cgcccttcct cgtctctggg tgcctaggta tccaccgtaa gcctttcctc gtttgaacct   3720
cgcccttcac ttttaaggct atgccatcct aaggtgctgc taaatggatg gatcttatca   3780
acgtccatga atgataaatc atagatcgaa ccgccgaatc ggaaaaattg ggtgctatca   3840
taaagctttg tatcggctaa gttcacgagt tggagataag cggactcgaa ccgctgacat   3900
ccgccgcagg gtaaaccacc gcctctcagg tcccccgact gattctacca tagaggccaa   3960
cgatagacaa taactccccc ccgaacacag cttacaactt tcatcgtact gtgctctcca   4020
aagagcaact cttctcaaaa tctcactcaa aaggtgctga gttggaatcc cattctaact   4080
aaggattctt gtggttccgg aggatccaac tacaggagaa ccaggaacgg agggctttcc   4140
ccccttccg cccgactctt tggtcttaag aacgctggtt ttaagaatga gtcattgccc   4200
ttctccgacc ctgactgccc aacctgagag cggacagcta atgcgttcca cttattgaac   4260
agggttctat ggtcggtccg tgacccctgg atgccgaagg cgtccttggg gtgatctcgt   4320
agttcctacg gggtggagat gatggggtcg gtccatggat tttccttcct tttcttttgc   4380
cgcatttcgc tcaaagggtt gaagggagat agtgcatcaa gctgttcgca agggccaact   4440
tgatcctctt ccccagagat ctcagatgag ggaaccctgg gagagccgcc gactccaact   4500
accgtccatg tacgatccat actagatctg accaactgcc catcctacct cctctacgtt   4560
cttgacagcc catctttgtc tcagtagagt ctttcagtgg cacgtttcgg tcctcttccc   4620
cattacttag aaaaagtgag ccaccggttc aggtacaaga tactatcatt accgcctgga   4680
caattagaca tccaacccgt aatcgcaacg acccaattgc aagagcggag ctctaccaac   4740
tgagctatat ccccccgagc caagtggagc atgcatgaag tagtcagatg cttcttctat   4800
tcttttccct ggcgcagctg ggccatcctg gacttgaacc agagacctcg cccgtgaagt   4860
aaatcatcgc acctacggtc caaccaattg ggagagaatc aatagattcc ttttcgggag   4920
cgattcatcc ttcccgaacg cagcatacaa ctctccgttg tactgcgctc tccaagtgtg   4980
cttgttcccc ccttcttcct taccctggca agtctttgtg aaataactcc gatgagaaga   5040
aaaaagaagg cgttaagaga ccctcctggc ccaaccctag acactctaag atccttttc   5100
aaacctgctc ccatttcgat ttcgagtcaa gaaaaaaacg gctcgaatgg tacgatccct   5160
ccgtcacccc agaatgaaag gggtgatctc gtagttcttg gtctgtgaag atgcgttgtt   5220
aggtgctcca ttttattttc ccattgaggc cgaacctaaa cctgtgctcg agagatagct   5280
gtccatacac tgataaggga tgtatggatt ctcgagaaga gaggagccgt ggtggtcccc   5340
cccggaccgc ccggatccca cgagtgaatc gaaagttgga tctacattgg atctcacccg   5400
aatcgcccca tctatcctcc tgaggaggag tttggtttca aaccccggtt cgaacaggag   5460
gagtacgcca tgctaatgtg ccttggatga tccacatctc agggtcaggc gccgatgagc   5520
acattgaact atccatgtgg ctgagagccc tcacagccca ggcacaacga cgcaattatc   5580
aggggcgcgc tctaccactg agctaatagc ccgtcgtgcg agcctcccac tgggggcccg   5640
ctatgccaaa agcgagagaa accccatccc tctctttcct tttttcgccc ccatgtcgcc   5700
acacggggga acatagggac gtaaaaaagg ggatcctatc aacttgttcc gacctaggat   5760
aataagctca tgagcttggt cttacttcac cgtcgagaaa ggaaagaaga cttccatctc   5820
caagtttaac tcagacgtag ctcccttctt ttttttgggg gtgtgaagca gtgtcaaacc   5880
```

-continued aaaataccca acaagcatta gctctccctg aaaaggaggt gatccagccg caccttccag 5940
tacggctacc ttgttacgac ttcactccag tcactagccc tgccttcggc atccccctcc 6000
ttgcggttaa ggtaacgact tcgggcatgg ccagctccca tagtgtgacg ggcggtgtgt 6060
acaaggcccg ggaacgaatt caccgccgta tggctgaccg gcgattacta gcgattccgg 6120
cttcatgcag gcgagttgca gcctgcaatc cgaactgagg acgggttttt ggggttagct 6180
caccctcgcg ggatcgcgac cctttgtccc ggccattgta gcacgtgtgt cgcccagggc 6240
ataaggggca tgatgacttg acgtcatcct caccttcctc cggcttatca ccggcagtct 6300
gttcagggtt ccaaactcaa cgatggcaac taaacacgag ggttgcgctc gttgcgggac 6360
ttaacccaac accttacggc acgagctgac gacagccatg caccacctgt gtccgcgttc 6420
ccgaaggcac ccctctcttt caagaggatt cgcggcatgt caagccctgg taaggttctt 6480
cgctttgcat cgaattaaac cacatgctcc accgcttgtg cgggcccccg tcaattcctt 6540
tgagtttcat tcttgcgaac gtactcccca ggcgggatac ttaacgcgtt agctacagca 6600
ctgcacgggt cgatacgcac agcgcctagt atccatcgtt tacggctagg actactgggg 6660
tatctaatcc cattcgctcc cctagctttc gtctctcagt gtcagtgtcg gcccagcaga 6720
gtgctttcgc cgttggtgtt ctttccgatc tctacgcatt tcaccgctcc accggaaatt 6780
ccctctgccc ctaccgtact ccagcttggt agtttccacc gcctgtccag ggttgagccc 6840
tgggatttga cggcggactt aaaaagccac ctacagacgc tttacgccca atcattccgg 6900
ataacgcttg catcctctgt attaccgcgg ctgctggcac agagttagcc gatgcttatt 6960
ccccagatac cgtcattgct tcttctccgg gaaaagaagt tcacgacccg tgggccttct 7020
acctccacgc ggcattgctc cgtcaggctt tcgcccattg cggaaaattc cccactgctg 7080
cctcccgtag gagtctgggc cgtgtctcag tcccagtgtg gctgatcatc ctctcggacc 7140
agctactgat catcgccttg gtaagctatt gcctcaccaa ctagctaatc agacgcgagc 7200
ccctcctcgg gcggattcct ccttttgctc ctcagcctac ggggtattag cagccgtttc 7260
cagctgttgt tcccctccca agggcaggtt cttacgcgtt actcacccgt ccgccactgg 7320
aaacaccgtt tcccgtgttt cccgtccgac ttgcatgtgt taagcatgcc gccagcgttc 7380
atcctgagcc aggatcgaac tctccatgag attcatagtt gcattactta tagcttcctt 7440
gttcgtagac aaagcggatt cggaattgtc tttcattcca aggcataact tgtatccatg 7500
cgcttcatat tcgcccggag ttcgctccca gaaatatagt catccctgcc ccctcacgtc 7560
aatcccacga gcctcttatc cattctcatt gaacgacggc gggggagcaa atccaactag 7620
aaaaactcac attgggctga ctctaccacc cagtcaattc tgttccactt aatccctctt 7680
tcatggccgg ccattatggc c 7701

<210> SEQ ID NO 30
<211> LENGTH: 7701
<212> TYPE: DNA
<213> ORGANISM: Artificial Sequence
<220> FEATURE:
<223> OTHER INFORMATION: An example of chloroplast origin of replication

<400> SEQUENCE: 30
ggccattatg gccgttcgac acaattggga ttttttttgg aaattggaag cagttactaa 60
ttccaccccc tctccactgg atctgttccg gggagtaccc tcaaaaaaag gaacctttcc 120
tctccccagc catttcgggt taagaagatg tgaaagcgcg tttatctcta taagtctata 180
agaagggtgc gttccgaggt gtgaagtggg agagaaggga tgtcacaatt ggggttttga 240

-continued

```
ataaaacgac ctttttattt ttcatttttt tttttcgttt tcatattgaa aaagtaataa    300
gaatgagagg tgttaagctt tttatcatcc tggcgtcgag ctatttttcc gcaggacctc    360
ccctacagta tcgtcaccgc agtagagttt aaccaccaag ttcgggatgg attggtgtgg    420
ttcctctacg cctaggacac cagaatatcg aaccatgaac gaagaaaggc atgagagaaa    480
agcatattgg ctagtgattg tgaggcccca attcttgact ggaggggaca ccaaaggcct    540
ctgcccttcc atcccttgga tagatagaga gggagggcag agcttttggt tttttcatgt    600
tgtcaaagag ttgaacaatg gtttttttcgt gttgtcaaag atttgaacaa tgaaaataga    660
tggcgagtgc ctgatcgaat tgatcaggtc atgtaggaac aaggttcaag tctaccggtc    720
tgttaggatg cctcagctgc atacatcact gcacttccac ttgacaccta tcgtaatgat    780
aaacggctcg tctcgccgtg accttctctt gaattctcaa aaaaacttct gtcgctccat    840
ccccgcaggg gcagagaacc cgtcgctgtc tcggctgtgc taccggaagc tctggggaag    900
tcggaatagg agagcactca tcttggggtg ggcttactac ttagatgctt tcagcagtta    960
tccgctccgc acttggctac ccagcgttta ccgtgggcac gataactggt acaccagagg   1020
tgcgtccttc ccggtcctct cgtactaggg aaaggtcctc tcaatgctct aacgcccaca   1080
ccggatatgg accgaactgt ctcacgacgt tctgaaccca gctcacgtac cgctttaatg   1140
ggcgaacagc ccaacccttg gaacatacta cagccccagg tggcgaagag ccgacatcga   1200
ggtgccaaac cttcccgtcg atgtgagctc ttggggaaga tcagcctgtt atccctagag   1260
taacttttat ccgttgagcg acggcccttc cactcggcac cgtcggatca ctaaggccga   1320
ctttcgtccc tgctcgacgg gtgggtcttg cagtcaagct cccttctgcc tttgcactcg   1380
agggccaatc tccgtccggc ccgaggaaac ctttgcacgc ctccgttacc ttttgggagg   1440
cctacgcccc atagaaactg tctacctgag actgtccctt ggcccgtagg tcctgacaca   1500
aggttagaat tctagccctt ccagagtggt atctcactga tggctcgggc ccccccggaa   1560
ggaggccttc ttcgccttcc acctaagctg cgcaggaaag gcccaaagcc aatcccaggg   1620
aacagtgaag cttcataggg tctttctgtc caggtgcagg tagtccgcat cttcacagac   1680
atgtctattt caccgagcct ctctccgaga cagtgcccag atcgttacgc ctttcgtgcg   1740
ggtcggaact tacccgacaa ggaatttcgc taccttagga ccgttatagt tacggccgcc   1800
gttcaccggg gcttcggtcg ccggctcccc tgtcatcagg tcaccaactt ccttgacctt   1860
ccggcactgg gcaggcgtca gcccccatac atggtcttac gactttgcgg agacctgtgt   1920
ttttggtaaa cagtcgcccg ggcctggtca ctgcgacccc ctttgtgagg aggcacccct   1980
tctcccgaag ttacggggct attttgccga gttccttaga gagagttgtc tcgcgcccct   2040
aggtattctc tacctaccca cctgtgtcgg tttcgggtac aggtaccctc ttgcttaacg   2100
tcgttcgagc ttttcctggg agtatggcat gggttacttc agcgccgtag cgcctggtat   2160
tcgaacattg gctcgaggca ttttctctac cccttcttac cctgaaaaag cagggacacc   2220
ttacgttctt gaaccgataa ccatctttcg gctaacctag cctcctccgt ccctcgggac   2280
taacaagggg tagtacagga atattcacct gttgtccatc gactacgcct ttcggcctga   2340
tcttaggccc tgactcaccc tccgtggacg aaccttgcgg aggaaccctt aggttttcgg   2400
ggcattggat tctcaccaat gtttgcgtta ctcaagccga cattctcgct tccgcttcgt   2460
ccaccaccgc tcgcgcggag gcttctctct aaggcggaac gctcccctac cgatgtattt   2520
ttacatccca cagcttcggc agaccgctta gccccgttca tcttcggcgc aagagcgctc   2580
```

-continued

```
gatcagtgag ctattacgca ctctttcaag ggtggctgct tctaggcaaa cctcctggct   2640
gtctctgcac ccctacctcc tttatcactg agcggtcatt taggggcctt agctggtgat   2700
ccgggctgtt tccctctcga cgatgaagct tatcccccat cgtctcacta gccgaccttg   2760
acccctgtta ttttgaggtc atatctagta ttcagagttt gcctcgattt ggtaccgctc   2820
tcgcggcccg caccgaaaca gtgctttacc cctagatgtc cagtcaactg ctgcgcctca   2880
acgcatttcg gggagaacca gctagctctg ggttcgagtg gcatttcacc cctaaccaca   2940
actcatccgc tgattcttca acatcagtcg gttcggacct ccacttagtt tcacccaagc   3000
ttcatcctgg tcatggatag atcacccagg ttcgggtcca taagcagtga caattgccct   3060
atgaagactc gctttcgcta cggctccggt gggttccctt aaccaagcca ctgcctatga   3120
gtcgccggct cattcttcaa caggcacgcg gtcagagccc tggctcctcc cactgcttgg   3180
gagcttacgg tttcatgttc tatttcactc cccgatgggg gttcttttca cccttccctc   3240
acggtactac ttcgctatcg gtcacccagg agtatttagc cttgcaaggt ggtccttgct   3300
gattcacacg ggattccacg tgccccatgc tactcgggtc agagcgtaag ctagtgatgc   3360
tttcggctac tggactttcg ccatctaggg tgcagcattc aggctgcttc gcctagcagc   3420
acgacgcttg tattgctctc ccacaacccc gttttcacgg tttaggctgc tcccatttcg   3480
ctcgccgcta ctacgggaat cgcttttgct ttcttttcct ctggctacta agatgtttca   3540
gttcgccagg ttgtctcttg cctgcccatg gattcagcag cagttcgaaa ggttgcccta   3600
ttcgggaatc tccggatcta tgcttatttt caactccccg aagcatttcg tcgattacta   3660
cgcccttcct cgtctctggg tgcctaggta tccaccgtaa gcctttcctc gtttgaacct   3720
cgcccttcac ttttaaggct atgccatcct aaggtgctgc taaatggatg gatcttatca   3780
acgtccatga atgataaatc atagatcgaa ccgccgaatc ggaaaaattg ggtgctatca   3840
taaagctttg tatcggctaa gttcacgagt tggagataag cggactcgaa ccgctgacat   3900
ccgccgcagg gtaaaccacc gcctctcagg tcccccgact gattctacca tagaggccaa   3960
cgatagacaa taactccccc ccgaacacag cttacaactt tcatcgtact gtgctctcca   4020
aagagcaact cttctcaaaa tctcactcaa aaggtgctga gttggaatcc cattctaact   4080
aaggattctt gtggttccgg aggatccaac tacaggagaa ccaggaacgg agggctttcc   4140
ccccttccg cccgactctt tggtcttaag aacgctggtt ttaagaatga gtcattgccc   4200
ttctccgacc ctgactgccc aacctgagag cggacagcta atgcgttcca cttattgaac   4260
agggttctat ggtcggtccg tgacccctgg atgccgaagg cgtccttggg gtgatctcgt   4320
agttcctacg gggtggagat gatggggtcg gtccatggat tttccttcct tttcttttgc   4380
cgcatttcgc tcaaagggtt gaagggagat agtgcatcaa gctgttcgca agggccaact   4440
tgatcctctt ccccagagat ctcagatgag ggaaccctgg gagagccgcc gactccaact   4500
accgtccatg tacgatccat actagatctg accaactgcc catcctacct cctctacgtt   4560
cttgacagcc catctttgtc tcagtagagt ctttcagtgg cacgtttcgg tcctcttccc   4620
cattacttag aaaaagtgag ccaccggttc aggtacaaga tactatcatt accgcctgga   4680
caattagaca tccaacccgt aatcgcaacg acccaattgc aagagcggag ctctaccaac   4740
tgagctatat ccccccgagc caagtggagc atgcatgaag tagtcagatg cttcttctat   4800
tcttttccct ggcgcagctg ggccatcctg gacttgaacc agagacctcg cccgtgaagt   4860
aaatcatcgc acctacggtc caaccaattg ggagagaatc aatagattcc ttttcgggag   4920
cgattcatcc ttcccgaacg cagcatacaa ctctccgttg tactgcgctc tccaagtgtg   4980
```

```
cttgttcccc ccttcttcct taccctggca agtctttgtg aaataactcc gatgagaaga   5040
aaaaagaagg cgttaagaga ccctcctggc ccaaccctag acactctaag atcctttttc   5100
aaacctgctc ccatttcgat ttcgagtcaa gaaaaaaacg gctcgaatgg tacgatccct   5160
ccgtcacccc agaatgaaag gggtgatctc gtagttcttg gtctgtgaag atgcgttgtt   5220
aggtgctcca ttttattttc ccattgaggc cgaacctaaa cctgtgctcg agagatagct   5280
gtccatacac tgataaggga tgtatggatt ctcgagaaga gaggagccgt ggtggtcccc   5340
cccggaccgc ccggatccca cgagtgaatc gaaagttgga tctacattgg atctcacccg   5400
aatcgcccca tctatcctcc tgaggaggag tttggtttca aaccccggtt cgaacaggag   5460
gagtacgcca tgctaatgtg ccttggatga tccacatctc agggtcaggc gccgatgagc   5520
acattgaact atccatgtgg ctgagagccc tcacagccca ggcacaacga cgcaattatc   5580
aggggcgcgc tctaccactg agctaatagc ccgtcgtgcg agcctcccac tgggggcccg   5640
ctatgccaaa agcgagagaa accccatccc tctctttcct tttttcgccc ccatgtcgcc   5700
acacgggggga acatagggac gtaaaaaagg ggatcctatc aacttgttcc gacctaggat   5760
aataagctca tgagcttggt cttacttcac cgtcgagaaa ggaaagaaga cttccatctc   5820
caagtttaac tcagacgtag ctcccttctt ttttttgggg gtgtgaagca gtgtcaaacc   5880
aaaataccca acaagcatta gctctccctg aaaaggaggt gatccagccg caccttccag   5940
tacggctacc ttgttacgac ttcactccag tcactagccc tgccttcggc atcccctcc   6000
ttgcggttaa ggtaacgact tcgggcatgg ccagctccca tagtgtgacg ggcggtgtgt   6060
acaaggcccg ggaacgaatt caccgccgta tggctgaccg gcgattacta gcgattccgg   6120
cttcatgcag gcgagttgca gcctgcaatc cgaactgagg acgggttttt ggggttagct   6180
caccctcgcg ggatcgcgac cctttgtccc ggccattgta gcacgtgtgt cgcccagggc   6240
ataaggggca tgatgacttg acgtcatcct caccttcctc cggcttatca ccggcagtct   6300
gttcagggtt ccaaactcaa cgatggcaac taaacacgag ggttgcgctc gttgcgggac   6360
ttaacccaac accttacggc acgagctgac gacagccatg caccacctgt gtccgcgttc   6420
ccgaaggcac ccctctcttt caagaggatt cgcggcatgt caagccctgg taaggttctt   6480
cgctttgcat cgaattaaac cacatgctcc accgcttgtg cgggcccccg tcaattcctt   6540
tgagtttcat tcttgcgaac gtactcccca ggcgggatac ttaacgcgtt agctacagca   6600
ctgcacgggt cgatacgcac agcgcctagt atccatcgtt tacggctagg actactgggg   6660
tatctaatcc cattcgctcc cctagctttc gtctctcagt gtcagtgtcg gcccagcaga   6720
gtgctttcgc cgttggtgtt ctttccgatc tctacgcatt tcaccgctcc accggaaatt   6780
ccctctgccc ctaccgtact ccagcttggt agtttccacc gcctgtccag ggttgagccc   6840
tgggatttga cggcggactt aaaaagccac ctacagacgc tttacgccca atcattccgg   6900
ataacgcttg catcctctgt attaccgcgg ctgctggcac agagttagcc gatgcttatt   6960
ccccagatac cgtcattgct tcttctccgg gaaaagaagt tcacgacccg tgggccttct   7020
acctccacgc ggcattgctc cgtcaggctt tcgcccattg cggaaaattc cccactgctg   7080
cctcccgtag gagtctgggc cgtgtctcag tcccagtgtg gctgatcatc ctctcggacc   7140
agctactgat catcgccttg gtaagctatt gcctcaccaa ctagctaatc agacgcgagc   7200
ccctcctcgg gcggattcct ccttttgctc ctcagcctac ggggtattag cagccgtttc   7260
cagctgttgt tcccctccca agggcaggtt cttacgcgtt actcacccgt ccgccactgg   7320
```

```
aaacaccgtt tcccgtgttt cccgtccgac ttgcatgtgt taagcatgcc gccagcgttc   7380

atcctgagcc aggatcgaac tctccatgag attcatagtt gcattactta tagcttcctt   7440

gttcgtagac aaagcggatt cggaattgtc tttcattcca aggcataact tgtatccatg   7500

cgcttcatat tcgcccggag ttcgctccca gaaatatagc catccctgcc ccctcacgtc   7560

aatcccacga gcctcttatc cattctcatt gaacgacggc gggggagcaa atccaactag   7620

aaaaactcac attgggctga ctctaccacc cagtcaattc tgttccactt aatccctctt   7680

tcatggccgg ccattatggc c                                             7701
```

<210> SEQ ID NO 31
<211> LENGTH: 6007
<212> TYPE: DNA
<213> ORGANISM: Artificial Sequence
<220> FEATURE:
<223> OTHER INFORMATION: An example of an episomal DNA vector

<400> SEQUENCE: 31

```
tgccatcgat agtattgttc attgtataaa gtgtacgtac ccgttaaggg tacgtacact     60

ttaatgcaag ataaacaaaa atcaatacat attactagtt actagtataa agtacaattg    120

atttctgtgt atttgtagct tttaaattaa atttttaatt aactgttaca taaaaattta    180

aaattataaa taaaaacatg ttaagtccaa aaagaacaaa attccgtaaa ccacaccgtg    240

gtcatttaag aggaaaagca acacgtggta ataaaattgt atttggtgat tttgcattac    300

aagcacaaga accttgttgg attacatcac gtcaaattga agccggacgt cgtgttttaa    360

cacgttatgt tcgtcgtggt ggtaaattat ggattcgtat tttcccagat aaagctgtta    420

ctatgcgtcc tgctggtact cgtatgggtt ctggtaaagg tgcacctgat tattgggtag    480

ctgttgtaca tcctggtaaa attttatatg aaatgcaagg tgtatctgaa acaattgcta    540

gacaagcaat gcgcattgca gcttataaaa tgccagtaaa aacaaaattt ttaacaaaaa    600

cagtgtaatt attgttatta aaaatgttgt ttagaaagaa ttaatgattt aacttactta    660

aaaagcataa tctcaaatta gagcacaagt ataatttaaa aaatatttaa gaaaattaag    720

agcataagta ttgtttcgct ttggctcaaa agccaatact aaagataata ttactttttg    780

taagttttta cttactcggt ttgtaccagg caaccctata aatatagtaa aatggaatta    840

aactagatat atctctttaa gaaagatttt ctcatcaagg ctgcccttta actttaacct    900

agaatgacta aaaggagtaa gcaaataccg agaaatttat tttttcactt aatgaaaaaa    960

taaattttat ctctttctct tttaagcata taaatatgaa ggtaagtaaa ctctactagg   1020

gaaaagcata gtgttgaagg atatactttc ttgggatccg ggagcgcacg cgcaaggtcg   1080

caactacccg agaatcgatg tggcggaatg ggttacgtga gctattatcc ggcgggccct   1140

caatttaaat cgttacagtt gctcgtaacg gcaaccggct cggtcctttt tccctagaac   1200

agtatcttat acttgctgct ctcgttactt cggcgatcct ggtgcagtcg gtccgtaaat   1260

cggcgcacac ttttacgtcg taccagacag gctcgcataa gccagccccg acacccgcca   1320

acacccgctg acgcgccctg acgggcttgt ctgctcccgg catccgctta cagacaagct   1380

gtgacctccg ggagctgcat gtgtcagagg ttttcaccgt catcaccgaa acgcgcacga   1440

aagggcctcg tgatacgcct atttttatag gttaatgtca tgataataat ggtttcttag   1500

acgtcaggtg gcacttttcg gggaaatgtg cgcggaaccc ctatttgttt atttttctaa   1560

atacattcaa atatgtatcc gctcatgaga caataaccct gataaatgct tcaataatat   1620

tgaaaaagga agagtatgag tattcaacat ttccgtgtcg cccttattcc cttttttgcg   1680
```

-continued

```
gcattttgcc ttcctgtttt tgctcaccca gaaacgctgg tgaaagtaaa agatgctgaa   1740
gatcagttgg gtgcacgagt gggttacatc gaactggatc tcaacagcgg taagatcctt   1800
gagagttttc gccccgaaga acgttttcca atgatgagca cttttaaagt tctgctatgt   1860
ggcgcggtat tatcccgtat tgacgccggg caagagcaac tcggtcgccg catacactat   1920
tctcagaatg acttggttga gtactcacca gtcacagaaa agcatcttac ggatggcatg   1980
acagtaagag aattatgcag tgctgccata accatgagtg ataacactgc ggccaactta   2040
cttctgacaa cgatcggagg accgaaggag ctaaccgctt ttttgcacaa catgggggat   2100
catgtaactc gccttgatcg ttgggaaccg gagctgaatg aagccatacc aaacgacgag   2160
cgtgacacca cgatgcctgt agcaatggca acaacgttgc gcaaactatt aactggcgaa   2220
ctacttactc tagcttcccg gcaacaatta atagactgga tggaggcgga taaagttgca   2280
ggaccacttc tgcgctcggc ccttccggct ggctggttta ttgctgataa atctggagcc   2340
ggtgagcgtg gctcacgcgg tatcattgca gcactggggc cagatggtaa gccctcccgt   2400
atcgtagtta tctacacgac ggggagtcag gcaactatgg atgaacgaaa tagacagatc   2460
gctgagatag gtgcctcact gattaagcat tggtaactgt cagaccaagt ttactcatat   2520
atactttaga ttgatttaaa acttcatttt taatttaaaa ggatctaggt gaagatcctt   2580
tttgataatc tcatgaccaa aatcccttaa cgtgagtttt cgttccactg agcgtcagac   2640
cccgtagaaa agatcaaagg atcttcttga gatccttttt ttctgcgcgt aatctgctgc   2700
ttgcaaacaa aaaaaccacc gctaccagcg gtggtttgtt tgccggatca agagctacca   2760
actctttttc cgaaggtaac tggcttcagc agagcgcaga taccaaatac tgttcttcta   2820
gtgtagccgt agttaggcca ccacttcaag aactctgtag caccgcctac atacctcgct   2880
ctgctaatcc tgttaccagt ggctgctgcc agtggcgata agtcgtgtct taccgggttg   2940
gactcaagac gatagttacc ggataaggcg cagcggtcgg gctgaacggg gggttcgtgc   3000
acacagccca gcttggagcg aacgacctac accgaactga gatacctaca gcgtgagcta   3060
tgagaaagcg ccacgcttcc cgaagggaga aaggcggaca ggtatccggt aagcggcagg   3120
gtcggaacag gagagcgcac gagggagctt ccagggggaa acgcctggta tctttatagt   3180
cctgtcgggt ttcgccacct ctgacttgag cgtcgatttt tgtgatgctc gtcagggggg   3240
cggagcctat ggaaaaacgc cagcaacgcg gcctttttac ggttcctggc cttttgctgg   3300
ccttttgctc acatgttctt tcctgcgtta tcccctgatt ctgtggataa ccgtattacc   3360
gcctttgagt gagctgatac cgctcgccgc agccgaacga ccgagcgcag cgagtcagtg   3420
agcgaggaag cggaagaacg cggacaccca gcgtaacaat ctaatattgt ttctcaaatc   3480
gggctgttat cgcatggtgc tcatgatgag gttactgacc aaattcgcca cgcatcggtg   3540
ctggtagaat gttcacttcg aggtgggtag acggcgtcac gtgcaatgcc ttgtcttccc   3600
ctatctgcgg ccccgactgc ctcgcgaaga caagggatcg gacgtcgaac gtattctgtt   3660
tgctaccggc acgggagtag gatcgttgat atacaccatg cgcgttaact ctgaccccct   3720
tcctcttaaa tgagaatgga taagaggctc gtgggattga cgtgaggggg cagggatggc   3780
tatatttctg ggagcgaact ccgggcgaat tactaataaa aagccttcca ttttctattt   3840
tgatttgtag aaaactagtg tgcttgggag tccctgatga ttaaataaac caagatttta   3900
ccaatggggg ctagcgaagc ggtgatcgcc gaagtatcga ctcaactatc agaggtagtt   3960
ggcgtcatcg agcgccatct cgaaccgacg ttgctggccg tacatttgta cggctccgca   4020
```

-continued

```
gtggatggcg gcctgaagcc acacagtgat attgatttgc tggttacggt gaccgtaagg   4080
cttgatgaaa caacgcggcg agctttgatc aacgaccttt tggaaacttc ggcttcccct   4140
ggagagagcg agattctccg cgctgtagaa gtcaccattg ttgtgcacga cgacatcatt   4200
ccgtggcgtt atccagctaa gcgcgaactg caatttggag aatggcagcg caatgacatt   4260
cttgcaggta tcttcgagcc agccacgatc gacattgatc tggctatctt gctgacaaaa   4320
gcaagagaac atagcgttgc cttggtaggt ccagcggcgg aggaactctt tgatccggtt   4380
cctgaacagg atctatttga ggcgctaaat gaaaccttaa cgctatggaa ctcgccgccc   4440
gactgggctg gcgatgagcg aaatgtagtg cttacgttgt cccgcatttg gtacagcgca   4500
gtaaccggca aaatcgcgcc gaaggatgtc gctgccgact gggcaatgga gcgcctgccg   4560
gcccagtatc agcccgtcat acttgaagct agacaggctt atcttggaca agaagaagat   4620
cgcttggcct cgcgcgcaga tcagttggaa gaatttgtcc actacgtgaa aggcgagatc   4680
accaaggtag tgggcaaaga acttgttgaa ggaaaattgg agctagtaga aggtcttaaa   4740
gtcgccatgg ctagtaaagg agaagaactt ttcactggag ttgtcccaat tcttgttgaa   4800
ttagatggtg atgttaatgg gcacaaattt tctgtcagtg gagagggtga aggtgatgca   4860
acatacggaa aacttaccct taaatttatt tgcactactg gaaaactacc tgttccttgg   4920
ccaacacttg tcactacttt ctcttatggt gttcaatgct tttcaagata cccagatcat   4980
atgaagcggc acgacttctt caagagcgcc atgcctgagg gatacgtgca ggagaggacc   5040
atctctttca aggacgacgg gaactacaag acacgtgctg aagtcaagtt tgagggagac   5100
accctcgtca acaggatcga gcttaaggga atcgatttca aggaggacgg aaacatcctc   5160
ggccacaagt tggaatacaa ctacaactcc cacaacgtat acatcacggc agacaaacaa   5220
aagaatggaa tcaaagctaa cttcaaaatt agacacaaca ttgaagatgg aagcgttcaa   5280
ctagcagacc attatcaaca aaatactcca attggcgatg gccctgtcct tttaccagac   5340
aaccattacc tgtccacaca atctgccctt tcgaaagatc ccaacgaaaa gagagatcac   5400
atggtccttc ttgagtttgt aacagctgct gggattacac atggcatgga tgaactatac   5460
aaataagctt aaacagtaga cattagcaga taaattagca ggaaataaag aaggataagg   5520
agaaagaact caagtaatta tccttcgttc tcttaattga attgcaatta aactcggccc   5580
aatcttttac taaaaggatt gagccgaata ccgctccagg catcaaataa aacgaaaggc   5640
tcagtcgaaa gactgggcct ttcgttttat ctgttgtttg tcggtgaacg ctctcacaac   5700
agctccctgg aacaccagga gaacacactt atctcgcgtc ttgaggtgat accacgcctg   5760
acacgtgagg gcagtacggt taattcggtt tagccggaca tcagcgctcc tcattgagcg   5820
ctgggccctt cacatgaaga tcgcactgag gattggtcct agccaggctt ctcagtactg   5880
atacagtacg cgtcgcttct cgtattgttt gagtcttgga attagtttgt atccttccgc   5940
cgctgcccta agaattctaa ttgagctcga acagtcgacc gccggatcct gctcgagtgc   6000
ctctaga                                                             6007
```

<210> SEQ ID NO 32
<211> LENGTH: 5927
<212> TYPE: DNA
<213> ORGANISM: Artificial Sequence
<220> FEATURE:
<223> OTHER INFORMATION: An example of an episomal DNA vector

<400> SEQUENCE: 32

```
tgccatcgat agtattgttc attgtataaa gtgtacgtac ccgttaaggg tacgtacact     60
```

-continued

```
ttaatgcaag ataaacaaaa atcaatacat attactagtt actagtataa agtacaattg    120
atttctgtgt atttgtagct tttaaattaa atttttaatt aactgttaca taaaaattta    180
aaattataaa taaaaacatg ttaagtccaa aaagaacaaa attccgtaaa ccacaccgtg    240
gtcatttaag aggaaaagca acacgtggta ataaaattgt atttggtgat tttgcattac    300
aagcacaaga accttgttgg attacatcac gtcaaattga agccggacgt cgtgttttaa    360
cacgttatgt tcgtcgtggt ggtaaattat ggattcgtat tttcccagat aaagctgtta    420
ctatgcgtcc tgctggtact cgtatgggtt ctggtaaagg tgcacctgat tattgggtag    480
ctgttgtaca tcctggtaaa attttatatg aaatgcaagg tgtatctgaa acaattgcta    540
gacaagcaat gcgcattgca gcttataaaa tgccagtaaa aacaaaattt ttaacaaaaa    600
cagtgtaatt attgttatta aaaatgttgt ttagaaagaa ttaatgattt aacttactta    660
aaaagcataa tctcaaatta gagcacaagt ataatttaaa aaatatttaa gaaaattaag    720
agcataagta ttgtttcgct ttggctcaaa agccaatact aaagataata ttactttttg    780
taagttttta cttactcggt ttgtaccagg caaccctata aatatagtaa aatggaatta    840
aactagatat atctctttaa gaaagatttt ctcatcaagg ctgcccttta actttaacct    900
agaatgacta aaaggagtaa gcaaataccg agaaatttat tttttcactt aatgaaaaaa    960
taaattttat ctctttctct tttaagcata taaatatgaa ggtaagtaaa ctctactagg   1020
gaaaagcata gtgttgaagg atatactttc ttgggatccg ggagcgcacg cgcaaggtcg   1080
caactacccg agaatcgatg tggcggaatg ggttacgtga gctattatcc ggcgggccct   1140
caatttaaat cgttacagtt gctcgtaacg gcaaccggct cggtcctttt tccctagaac   1200
agtatcttat acttgctgct ctcgttactt cggcgatcct ggtgcagtcg gtccgtaaat   1260
cggcgcacac ttttacgtcg taccagacag gctcgcataa gccagccccg acacccgcca   1320
acacccgctg acgcgccctg acgggcttgt ctgctcccgg catccgctta cagacaagct   1380
gtgacctccg ggagctgcat gtgtcagagg ttttcaccgt catcaccgaa acgcgcacga   1440
aagggcctcg tgatacgcct atttttatag gttaatgtca tgataataat ggtttcttag   1500
acgtcaggtg gcacttttcg gggaaatgtg cgcggaaccc ctatttgttt atttttctaa   1560
atacattcaa atatgtatcc gctcatgaga caataaccct gataaatgct tcaataatat   1620
tgaaaaagga agagtatgag tattcaacat ttccgtgtcg cccttattcc cttttttgcg   1680
gcattttgcc ttcctgtttt tgctcaccca gaaacgctgg tgaaagtaaa agatgctgaa   1740
gatcagttgg gtgcacgagt gggttacatc gaactggatc tcaacagcgg taagatcctt   1800
gagagttttc gccccgaaga acgttttcca atgatgagca cttttaaagt tctgctatgt   1860
ggcgcggtat tatcccgtat tgacgccggg caagagcaac tcggtcgccg catacactat   1920
tctcagaatg acttggttga gtactcacca gtcacagaaa agcatcttac ggatggcatg   1980
acagtaagag aattatgcag tgctgccata accatgagtg ataacactgc ggccaactta   2040
cttctgacaa cgatcggagg accgaaggag ctaaccgctt ttttgcacaa catgggggat   2100
catgtaactc gccttgatcg ttgggaaccg gagctgaatg aagccatacc aaacgacgag   2160
cgtgacacca cgatgcctgt agcaatggca acaacgttgc gcaaactatt aactggcgaa   2220
ctacttactc tagcttcccg gcaacaatta atagactgga tggaggcgga taaagttgca   2280
ggaccacttc tgcgctcggc ccttccggct ggctggttta ttgctgataa atctggagcc   2340
ggtgagcgtg gctcacgcgg tatcattgca gcactggggc cagatggtaa gccctcccgt   2400
```

```
atcgtagtta tctacacgac ggggagtcag gcaactatgg atgaacgaaa tagacagatc   2460
gctgagatag gtgcctcact gattaagcat tggtaactgt cagaccaagt ttactcatat   2520
atactttaga ttgatttaaa acttcatttt taatttaaaa ggatctaggt gaagatcctt   2580
tttgataatc tcatgaccaa aatcccttaa cgtgagtttt cgttccactg agcgtcagac   2640
cccgtagaaa agatcaaagg atcttcttga gatccttttt ttctgcgcgt aatctgctgc   2700
ttgcaaacaa aaaaaccacc gctaccagcg gtggtttgtt tgccggatca agagctacca   2760
actctttttc cgaaggtaac tggcttcagc agagcgcaga taccaaatac tgttcttcta   2820
gtgtagccgt agttaggcca ccacttcaag aactctgtag caccgcctac atacctcgct   2880
ctgctaatcc tgttaccagt ggctgctgcc agtggcgata agtcgtgtct taccgggttg   2940
gactcaagac gatagttacc ggataaggcg cagcggtcgg gctgaacggg gggttcgtgc   3000
acacagccca gcttggagcg aacgacctac accgaactga gatacctaca gcgtgagcta   3060
tgagaaagcg ccacgcttcc cgaagggaga aaggcggaca ggtatccggt aagcggcagg   3120
gtcggaacag gagagcgcac gagggagctt ccagggggaa acgcctggta tctttatagt   3180
cctgtcgggt ttcgccacct ctgacttgag cgtcgatttt tgtgatgctc gtcagggggg   3240
cggagcctat ggaaaaacgc cagcaacgcg gcctttttac ggttcctggc cttttgctgg   3300
ccttttgctc acatgttctt tcctgcgtta tcccctgatt ctgtggataa ccgtattacc   3360
gcctttgagt gagctgatac cgctcgccgc agccgaacga ccgagcgcag cgagtcagtg   3420
agcgaggaag cggaagaacg cggacaccca gcgtaacaat ctaatattgt ttctcaaatc   3480
gggctgttat cgcatggtgc tcatgatgag gttactgacc aaattcgcca cgcatcggtg   3540
ctggtagaat gttcacttcg aggtgggtag acggcgtcac gtgcaatgcc ttgtcttccc   3600
ctatctgcgg ccccgactgc ctcgcgaaga caagggatcg gacgtcgaac gtattctgtt   3660
tgctaccggc acgggagtag gatcgttgat atacaccatg cgcgttaact ctgacccccct   3720
tcctcttaaa tgagaatgga taagaggctc gtgggattga cgtgaggggg cagggatggc   3780
tatatttctg ggagcgaact ccgggcgaat tactaataaa aagccttcca ttttctattt   3840
tgatttgtag aaaactagtg tgcttgggag tccctgatga ttaaataaac caagatttta   3900
ccaatggggg ctagcgaagc ggtgatcgcc gaagtatcga ctcaactatc agaggtagtt   3960
ggcgtcatcg agcgccatct cgaaccgacg ttgctggccg tacatttgta cggctccgca   4020
gtggatggcg gcctgaagcc acacagtgat attgatttgc tggttacggt gaccgtaagg   4080
cttgatgaaa caacgcggcg agctttgatc aacgaccttt tggaaacttc ggcttcccct   4140
ggagagagcg agattctccg cgctgtagaa gtcaccattg ttgtgcacga cgacatcatt   4200
ccgtggcgtt atccagctaa gcgcgaactg caatttggag aatggcagcg caatgacatt   4260
cttgcaggta tcttcgagcc agccacgatc gacattgatc tggctatctt gctgacaaaa   4320
gcaagagaac atagcgttgc cttggtaggt ccagcggcgg aggaactctt tgatccggtt   4380
cctgaacagg atctatttga ggcgctaaat gaaaccttaa cgctatggaa ctcgccgccc   4440
gactgggctg gcgatgagcg aaatgtagtg cttacgttgt cccgcatttg gtacagcgca   4500
gtaaccggca aaatcgcgcc gaaggatgtc gctgccgact gggcaatgga gcgcctgccg   4560
gcccagtatc agcccgtcat acttgaagct agacaggctt atcttggaca agaagaagat   4620
cgcttggcct cgcgcgcaga tcagttggaa gaatttgtcc actacgtgaa aggcgagatc   4680
accaaggtag tgggcaaaga acttgttgaa ggaaaattgg agctagtaga aggtcttaaa   4740
gtcgccatgg ctagtaaagg agaagaactt ttcactggag ttgtcccaat tcttgttgaa   4800
```

```
ttagatggtg atgttaatgg gcacaaattt tctgtcagtg gagagggtga aggtgatgca   4860

acatacggaa aacttaccct taaatttatt tgcactactg gaaaactacc tgttccttgg   4920

ccaacacttg tcactacttt ctcttatggt gttcaatgct tttcaagata cccagatcat   4980

atgaagcggc acgacttctt caagagcgcc atgcctgagg gatacgtgca ggagaggacc   5040

atctctttca aggacgacgg gaactacaag acacgtgctg aagtcaagtt tgagggagac   5100

accctcgtca acaggatcga gcttaaggga atcgatttca aggaggacgg aaacatcctc   5160

ggccacaagt tggaatacaa ctacaactcc cacaacgtat acatcacggc agacaaacaa   5220

aagaatggaa tcaaagctaa cttcaaaatt agacacaaca ttgaagatgg aagcgttcaa   5280

ctagcagacc attatcaaca aaatactcca attggcgatg gccctgtcct tttaccagac   5340

aaccattacc tgtccacaca atctgccctt tcgaaagatc ccaacgaaaa gagagatcac   5400

atggtccttc ttgagtttgt aacagctgct gggattacac atggcatgga tgaactatac   5460

aaataagctt aaacagtaga cattagcaga taaattagca ggaaataaag aaggataagg   5520

agaaagaact caagtaatta tccttcgttc tcttaattga attgcaatta aactcggccc   5580

aatcttttac taaaaggatt gagccgaata ccgctacaac agctccctgg aacaccagga   5640

gaacacactt atctcgcgtc ttgaggtgat accacgcctg acacgtgagg gcagtacggt   5700

taattcggtt tagccggaca tcagcgctcc tcattgagcg ctgggccctt cacatgaaga   5760

tcgcactgag gattggtcct agccaggctt ctcagtactg atacagtacg cgtcgcttct   5820

cgtattgttt gagtcttgga attagtttgt atccttccgc cgctgcccta agaattctaa   5880

ttgagctcga acagtcgacc gccggatcct gctcgagtgc ctctaga                 5927
```

<210> SEQ ID NO 33
<211> LENGTH: 10118
<212> TYPE: DNA
<213> ORGANISM: Artificial Sequence
<220> FEATURE:
<223> OTHER INFORMATION: An example of an episomal DNA vector

<400> SEQUENCE: 33

```
tgccaattcc aaccaggctc aggtggtcaa ttagcacgtt cagctggtgc catggttgaa     60

attttagcaa aagaaggcaa ttttgtaaca atccgtttac cttctaaaga aattcgttta    120

gtttcaaaaa attgttgggc aactgtgggt caagttggta acattgaagc atacaactta    180

actattggta aagcaggtcg tacacgttgg ttaggtaaac gtcctacagt acgtggttcg    240

gtgatgaacc ctgtggatca cccacatggt ggtggtgagg gtcgtgcacc gattggtcgt    300

agccgtccag ttacaccatg ggtcgcccca gctttaggtc aattaactag aaaacctaaa    360

aaatatagta atactttaat tgttaaaaaa agaaaaaaat aactaattaa agataggtca    420

attaaaacaa gtggcctctt ttggctattt atttaccccc cttcccctta cgggacaata    480

aataaatttg ttggcaggca actgcctccc tctcctcggg caagtaaact tagaataaaa    540

tttatttgct gcgctagcag gtttacatac tcctaagttt acttgcccga aggggaagga    600

gggcgtcccc ttacgggaat ataaatatta gtggcagtgg tacaataaat aaatagtata    660

taaatatcgg cagttggcag gcaactgcca ctgacgtcca ctaaaattta ttctttctcg    720

gggacaataa ataaatttgt cctgtaaagg gacgtaaaat agcagtaagc ataagtatgg    780

ccacttgctt aaattttaca atattaaaaa aattctagaa ataataaagt tttggttgat    840

aaatttttaa cgttaattgt ttgtttaaac tttatagata tcgggactta gtaagtctaa    900
```

-continued

```
agtcgctaaa aacaaccagt ttcagataaa catttgtttc aactgattgg ttcgttttgt    960
ttatccttag agtttatata tcttaactct atattgggta aaccactata atggtcatat   1020
gttggaaaaa ttccaataaa tttcaattta atgtggaatt taaaaagctc atatgtactt   1080
aaaatagaca attgttaaac atgaatagaa aatattacct acttttattt ttataaatac   1140
agctttagcc attattataa aattcaaaag tcattttaaa aaatcaaatg tcacgttctc   1200
ttaaaaaagg tccttttgta gcagatcatt tacttaaaaa aattgagaaa ttaaatgcta   1260
aaggtaaaaa agttgttatt aaaacttggt cacgttcatc aatgattgtt ccacctatga   1320
ttggtcatac tattggtgtt tataatgggc gtgaacatat tcccgtattt gtaagtgatc   1380
aaatggtagg tcatagatta ggtgaatttt cacctacacg tacatatcgt ggccatgcta   1440
aaaaagataa aaaagcaaaa cgttaatttt ttgttattta ctgctatttg gtacacctta   1500
gtttcctaaa ctaatttcta taaactacta ttctttgcag ttaaccggaa tataaacatc   1560
gactttggga aaccagttgg taagaacttg ttgtcttgca gctctttgcg cgctgccaga   1620
cggcaagttc ttttcccttc ggaaggcagc taattatgtt tatagtctat ttgcaatgcc   1680
actctgagta aataaatttc ccctttgtga tattaatatg agctgccact accatcctct   1740
tagaagtata taaatatgca ctggcatcct agagaaatta attactttta tagctataga   1800
atgcttgtta agggatttac tactataaaa ttaatgtgct ccttggggta aatacactta   1860
ataaatccct ttaggtattt aaatagctat ttgggtaaag gctttttaaa tatgtaataa   1920
attatatata ttagttttat gtggtttttt atatctatgg gaactttact tttttatact   1980
gttaaattcc tagttaagag taataagagc catattttta aagttgcttg ttttataaag   2040
attaaactaa ttttaccata agtattctgt tttaataaat ttatgcccat gaacgctgcc   2100
aaaggacgag tggctcgcca ctgcccctta cgggtacata aatgtcctaa cttgatattt   2160
atttacctgt aagggttagc ctataggcga ggtaaataaa tttaagtcag ccatagctat   2220
tctagagtat aacgtgtacg tatccttacg ggtacgtaca cgttatactc agttagcagg   2280
gacttgttag cctataagcg agataagtac acttggccaa cggtttatat taatatactc   2340
cagcagaaga acaattaaag taaaatctaa aaatatctat ctttttgctg aagaattgcg   2400
gaaaaatcga tagtattgtt cattgtataa agtgtacgta cccgttaagg gtacgtacac   2460
tttaatgcaa gataaacaaa aatcaataca tattactagt tactagtata aagtacaatt   2520
gatttctgtg tatttgtagc ttttaaatta aatttttaat taactgttac ataaaaattt   2580
aaaattataa ataaaaacat gttaagtcca aaaagaacaa aattccgtaa accacaccgt   2640
ggtcatttaa gaggaaaagc aacacgtggt aataaaattg tatttggtga ttttgcatta   2700
caagcacaag aaccttgttg gattacatca cgtcaaattg aagccggacg tcgtgtttta   2760
acacgttatg ttcgtcgtgg tggtaaatta tggattcgta ttttcccaga taaagctgtt   2820
actatgcgtc ctgctggtac tcgtatgggt tctggtaaag gtgcacctga ttattgggta   2880
gctgttgtac atcctggtaa aattttatat gaaatgcaag gtgtatctga aacaattgct   2940
agacaagcaa tgcgcattgc agcttataaa atgccagtaa aaacaaaatt tttaacaaaa   3000
acagtgtaat tattgttatt aaaaatgttg tttagaaaga attaatgatt taacttactt   3060
aaaaagcata atctcaaatt agagcacaag tataatttaa aaaatattta agaaaattaa   3120
gagcataagt attgtttcgc tttggctcaa aagccaatac taaagataat attacttttt   3180
gtaagttttt acttactcgg tttgtaccag gcaaccctat aaatatagta aaatggaatt   3240
aaactagata tatctcttta agaaagattt tctcatcaag gctgcccttt aactttaacc   3300
```

tagaatgact aaaaggagta agcaaatacc gagaaattta ttttttcact taatgaaaaa 3360
ataaatttta tctctttctc ttttaagcat ataaatatga aggtaagtaa actctactag 3420
ggaaaagcat agtgttgaag gatatacttt cttgggatcc aaaaaagtaa acctaaacaa 3480
gatatactta attaatgata ataatataaa actttttttt aaacttatga ttaaaccttt 3540
atcttattta aatgtagcag ataatagtgg tgctcgtgaa ttaatgtgta ttcgtgctct 3600
tggtggcagt tatcgtgaat cggcaaatat tggtgatgtt attattgcag ttgttaaaga 3660
tgcattacca aatatgcctg taaaacgttc agatattgta cgagctgtta ttgtacgtac 3720
acgtaaaggt atccgtcgtg aaaatggtat ggcaattcgt tttgatgata acgctgcagt 3780
tattattaac aaagaaggaa atcctcgtgg tacacgtgtt tttggtccaa ttgcacgtga 3840
attacgtgat aaaaatttta caaaaattgt ttctttagca cctgaagttt tataaaaact 3900
actttttaaa tttttttaca atagtaaaat cgatagttat atgcccgtta gaagattaac 3960
gccgtcgtat tcacatagac aattaattac tcgaggttta cttgcctagg attttaatac 4020
tccgaaggag gcagttggca ggcaactgcc tccttcccct tcgggcaagt aaacttagca 4080
tgtttacata ctccgaagga ggacgtcccc ttacgggaat ataaatatta gtggcagtgg 4140
taccgccact gcctagtata taaatatcgg cagttggcag gcaacaataa ataaatttgt 4200
ccactaaaat ttatttaccc gaaggaccgt ccttcggagt atataaatat aggattttaa 4260
tactccgaag aggcagttgg caggcaactg caactgacgt cccgaaggaa ggacggcagg 4320
ggacgtctcc ttacggggac atttatgtcc cctgcctttt aattcggggg atatgctttg 4380
caattagtag aaaattgcga ataggatttc catataaaat taaaataatt ctatcttctt 4440
taaaatttga tatgagtaat attataataa aatgcttatt aagttaaatc tttttataac 4500
cagttgattt ggataaaaag aacacataat gcaaagccaa aatgatagct ctcataaaag 4560
cagtaggcgg tgtaactttc attaaaattt atttacttta aggtgacgtc cccttacgga 4620
tatctaaata tttactgtat cctcgctaaa taaattgcta tattgtattg tatagcgcat 4680
taccttttgg cttaacatta tctatatgtg cattttattt ttttttaata tgacacaacg 4740
tttaaaaaat ttatatacta aaactattgt tcctaaatta actacaaatt ttaattacag 4800
taatatgcat gaagtgccaa aaattgaaaa aattgtaatt aaccgtggta ttggtgatgc 4860
atcacaaaac caaaaaattg tggaatctag tttaaaagaa ttagctatga ttgcaggtca 4920
aaaaggtgtt gttacacgtt caaaaaaagc tattgctggc tttaaattaa gacaacaaat 4980
gcccgtaggt gtaactgtta cattacgtgg tgatcgtatg tatggttttc tagatcgttt 5040
aattcattta gcattaccgc gtgtacgcga tttccaaggt attagctcaa aaagttttga 5100
taaaaaaggt aattatagtt taggtttaga agaacaatta atgttcccag aaattgaata 5160
tgataaaatt gatcaagtac gtggtatgga tatttcaatt gtaacaacag caaaaacaca 5220
agaagaaggt cttgcattat taaaagaatt gggagcgcac gcgcaaggtc gcaactaccc 5280
gagaatcgat gtggcggaat gggttacgtg agctattatc cggcgggccc tcaatttaaa 5340
tcgttacagt tgctcgtaac ggcaaccggc tcggtccttt ttccctagaa cagtatctta 5400
tacttgctgc tctcgttact tcggcgatcc tggtgcagtc ggtccgtaaa tcggcgcaca 5460
cttttacgtc gtaccagaca ggctcgcata agccagcccc gacacccgcc aacacccgct 5520
gacgcgccct gacgggcttg tctgctcccg gcatccgctt acagacaagc tgtgacctcc 5580
gggagctgca tgtgtcagag gttttcaccg tcatcaccga aacgcgcacg aaagggcctc 5640

-continued

```
gtgatacgcc tatttttata ggttaatgtc atgataataa tggtttctta gacgtcaggt   5700
ggcacttttc ggggaaatgt gcgcggaacc cctatttgtt tatttttcta aatacattca   5760
aatatgtatc cgctcatgag acaataaccc tgataaatgc ttcaataata ttgaaaaagg   5820
aagagtatga gtattcaaca tttccgtgtc gcccttattc ccttttttgc ggcattttgc   5880
cttcctgttt ttgctcaccc agaaacgctg gtgaaagtaa aagatgctga agatcagttg   5940
ggtgcacgag tgggttacat cgaactggat ctcaacagcg gtaagatcct tgagagtttt   6000
cgccccgaag aacgttttcc aatgatgagc acttttaaag ttctgctatg tggcgcggta   6060
ttatcccgta ttgacgccgg gcaagagcaa ctcggtcgcc gcatacacta ttctcagaat   6120
gacttggttg agtactcacc agtcacagaa aagcatctta cggatggcat gacagtaaga   6180
gaattatgca gtgctgccat aaccatgagt gataacactg cggccaactt acttctgaca   6240
acgatcggag gaccgaagga gctaaccgct tttttgcaca acatggggga tcatgtaact   6300
cgccttgatc gttgggaacc ggagctgaat gaagccatac caaacgacga gcgtgacacc   6360
acgatgcctg tagcaatggc aacaacgttg cgcaaactat taactggcga actacttact   6420
ctagcttccc ggcaacaatt aatagactgg atggaggcgg ataaagttgc aggaccactt   6480
ctgcgctcgg cccttccggc tggctggttt attgctgata aatctggagc cggtgagcgt   6540
ggctcacgcg gtatcattgc agcactgggg ccagatggta agccctcccg tatcgtagtt   6600
atctacacga cggggagtca ggcaactatg gatgaacgaa atagacagat cgctgagata   6660
ggtgcctcac tgattaagca ttggtaactg tcagaccaag tttactcata tatactttag   6720
attgatttaa aacttcattt ttaatttaaa aggatctagg tgaagatcct ttttgataat   6780
ctcatgacca aaatccctta acgtgagttt tcgttccact gagcgtcaga ccccgtagaa   6840
aagatcaaag gatcttcttg agatcctttt tttctgcgcg taatctgctg cttgcaaaca   6900
aaaaaaccac cgctaccagc ggtggtttgt ttgccggatc aagagctacc aactcttttt   6960
ccgaaggtaa ctggcttcag cagagcgcag ataccaaata ctgttcttct agtgtagccg   7020
tagttaggcc accacttcaa gaactctgta gcaccgccta catacctcgc tctgctaatc   7080
ctgttaccag tggctgctgc cagtggcgat aagtcgtgtc ttaccgggtt ggactcaaga   7140
cgatagttac cggataaggc gcagcggtcg ggctgaacgg ggggttcgtg cacacagccc   7200
agcttggagc gaacgaccta caccgaactg agatacctac agcgtgagct atgagaaagc   7260
gccacgcttc ccgaagggag aaaggcggac aggtatccgg taagcggcag ggtcggaaca   7320
ggagagcgca cgagggagct tccaggggga aacgcctggt atctttatag tcctgtcggg   7380
tttcgccacc tctgacttga gcgtcgattt ttgtgatgct cgtcaggggg gcggagccta   7440
tggaaaaacg ccagcaacgc ggccttttta cggttcctgg ccttttgctg gccttttgct   7500
cacatgttct ttcctgcgtt atcccctgat tctgtggata accgtattac cgcctttgag   7560
tgagctgata ccgctcgccg cagccgaacg accgagcgca gcgagtcagt gagcgaggaa   7620
gcggaagaac gcggacaccc agcgtaacaa tctaatattg tttctcaaat cgggctgtta   7680
tcgcatggtg ctcatgatga ggttactgac caaattcgcc acgcatcggt gctggtagaa   7740
tgttcacttc gaggtgggta gacggcgtca cgtgcaatgc cttgtcttcc cctatctgcg   7800
gccccgactg cctcgcgaag acaagggatc ggacgtcgaa cgtattctgt ttgctaccgg   7860
cacgggagta ggatcgttga tatacaccat gcgcgttaac tctgaccccc ttcctcttaa   7920
atgagaatgg ataagaggct cgtgggattg acgtgagggg gcagggatgg ctatatttct   7980
gggagcgaac tccgggcgaa ttactaataa aagccttcc atttctatt ttgatttgta     8040
```

gaaaactagt gtgcttggga gtccctgatg attaaataaa ccaagatttt accaatgggg 8100
gctagcgaag cggtgatcgc cgaagtatcg actcaactat cagaggtagt tggcgtcatc 8160
gagcgccatc tcgaaccgac gttgctggcc gtacatttgt acggctccgc agtggatggc 8220
ggcctgaagc cacacagtga tattgatttg ctggttacgg tgaccgtaag gcttgatgaa 8280
acaacgcggc gagctttgat caacgacctt ttggaaactt cggcttcccc tggagagagc 8340
gagattctcc gcgctgtaga agtcaccatt gttgtgcacg acgacatcat tccgtggcgt 8400
tatccagcta agcgcgaact gcaatttgga gaatggcagc gcaatgacat tcttgcaggt 8460
atcttcgagc cagccacgat cgacattgat ctggctatct tgctgacaaa agcaagagaa 8520
catagcgttg ccttggtagg tccagcggcg gaggaactct ttgatccggt tcctgaacag 8580
gatctatttg aggcgctaaa tgaaacctta acgctatgga actcgccgcc cgactgggct 8640
ggcgatgagc gaaatgtagt gcttacgttg tcccgcattt ggtacagcgc agtaaccggc 8700
aaaatcgcgc cgaaggatgt cgctgccgac tgggcaatgg agcgcctgcc ggcccagtat 8760
cagcccgtca tacttgaagc tagacaggct tatcttggac aagaagaaga tcgcttggcc 8820
tcgcgcgcag atcagttgga agaatttgtc cactacgtga aaggcgagat caccaaggta 8880
gtgggcaaag aacttgttga aggaaaattg gagctagtag aaggtcttaa agtcgccatg 8940
gctagtaaag gagaagaact tttcactgga gttgtcccaa ttcttgttga attagatggt 9000
gatgttaatg ggcacaaatt ttctgtcagt ggagagggtg aaggtgatgc aacatacgga 9060
aaacttaccc ttaaatttat ttgcactact ggaaaactac ctgttccttg gccaacactt 9120
gtcactactt tctcttatgg tgttcaatgc ttttcaagat acccagatca tatgaagcgg 9180
cacgacttct tcaagagcgc catgcctgag ggatacgtgc aggagaggac catctctttc 9240
aaggacgacg ggaactacaa gacacgtgct gaagtcaagt ttgagggaga caccctcgtc 9300
aacaggatcg agcttaaggg aatcgatttc aaggaggacg gaaacatcct cggccacaag 9360
ttggaataca actacaactc ccacaacgta tacatcacgg cagacaaaca aaagaatgga 9420
atcaaagcta acttcaaaat tagacacaac attgaagatg gaagcgttca actagcagac 9480
cattatcaac aaaatactcc aattggcgat ggccctgtcc ttttaccaga caaccattac 9540
ctgtccacac aatctgccct ttcgaaagat cccaacgaaa agagagatca catggtcctt 9600
cttgagtttg taacagctgc tgggattaca catggcatgg atgaactata caaataagct 9660
taaacagtag acattagcag ataaattagc aggaaataaa gaaggataag gagaaagaac 9720
tcaagtaatt atccttcgtt ctcttaattg aattgcaatt aaactcggcc caatctttta 9780
ctaaaaggat tgagccgaat accgctacaa cagctccctg gaacaccagg agaacacact 9840
tatctcgcgt cttgaggtga taccacgcct gacacgtgag ggcagtacgg ttaattcggt 9900
ttagccggac atcagcgctc ctcattgagc gctgggccct tcacatgaag atcgcactga 9960
ggattggtcc tagccaggct tctcagtact gatacagtac gcgtcgcttc tcgtattgtt 10020
tgagtcttgg aattagtttg tatccttccg ccgctgccct aagaattcta attgagctcg 10080
aacagtcgac cgccggatcc tgctcgagtg cctctaga 10118

<210> SEQ ID NO 34
<211> LENGTH: 10198
<212> TYPE: DNA
<213> ORGANISM: Artificial Sequence
<220> FEATURE:
<223> OTHER INFORMATION: An example of an episomal DNA vector

<400> SEQUENCE: 34

```
tgccaattcc aaccaggctc aggtggtcaa ttagcacgtt cagctggtgc catggttgaa     60
attttagcaa aagaaggcaa ttttgtaaca atccgtttac cttctaaaga aattcgttta    120
gtttcaaaaa attgttgggc aactgtgggt caagttggta acattgaagc atacaactta    180
actattggta aagcaggtcg tacacgttgg ttaggtaaac gtcctacagt acgtggttcg    240
gtgatgaacc ctgtggatca cccacatggt ggtggtgagg gtcgtgcacc gattggtcgt    300
agccgtccag ttacaccatg gggtcgccca gctttaggtc aattaactag aaaacctaaa    360
aaatatagta atactttaat tgttaaaaaa agaaaaaaat aactaattaa agataggtca    420
attaaaacaa gtggcctctt ttggctattt atttaccccc cttcccctta cgggacaata    480
aataaatttg ttggcaggca actgcctccc tctcctcggg caagtaaact tagaataaaa    540
tttatttgct gcgctagcag gtttacatac tcctaagttt acttgcccga aggggaagga    600
gggcgtcccc ttacgggaat ataaatatta gtggcagtgg tacaataaat aaatagtata    660
taaatatcgg cagttggcag gcaactgcca ctgacgtcca ctaaaattta ttctttctcg    720
gggacaataa ataaatttgt cctgtaaagg gacgtaaaat agcagtaagc ataagtatgg    780
ccacttgctt aaattttaca atattaaaaa aattctagaa ataataaagt tttggttgat    840
aaatttttaa cgttaattgt ttgtttaaac tttatagata tcgggactta gtaagtctaa    900
agtcgctaaa aacaaccagt ttcagataaa catttgtttc aactgattgg ttcgttttgt    960
ttatccttag agtttatata tcttaactct atattgggta aaccactata atggtcatat   1020
gttggaaaaa ttccaataaa tttcaattta atgtggaatt taaaaagctc atatgtactt   1080
aaaatagaca attgttaaac atgaatagaa aatattacct acttttattt ttataaatac   1140
agctttagcc attattataa aattcaaaag tcattttaaa aaatcaaatg tcacgttctc   1200
ttaaaaaagg tccttttgta gcagatcatt tacttaaaaa aattgagaaa ttaaatgcta   1260
aaggtaaaaa agttgttatt aaaacttggt cacgttcatc aatgattgtt ccacctatga   1320
ttggtcatac tattggtgtt tataatgggc gtgaacatat tcccgtattt gtaagtgatc   1380
aaatggtagg tcatagatta ggtgaatttt cacctacacg tacatatcgt ggccatgcta   1440
aaaaagataa aaaagcaaaa cgttaatttt ttgttattta ctgctatttg gtacacctta   1500
gtttcctaaa ctaatttcta taaactacta ttctttgcag ttaaccggaa tataaacatc   1560
gactttggga aaccagttgg taagaacttg ttgtcttgca gctctttgcg cgctgccaga   1620
cggcaagttc ttttcccttc ggaaggcagc taattatgtt tatagtctat ttgcaatgcc   1680
actctgagta aataaatttc ccctttgtga tattaatatg agctgccact accatcctct   1740
tagaagtata taaatatgca ctggcatcct agagaaatta attactttta tagctataga   1800
atgcttgtta agggatttac tactataaaa ttaatgtgct ccttggggta aatacactta   1860
ataaatccct ttaggtattt aaatagctat ttgggtaaag gctttttaaa tatgtaataa   1920
attatatata ttagttttat gtggtttttt atatctatgg gaactttact tttttatact   1980
gttaaattcc tagttaagag taataagagc catattttta aagttgcttg ttttataaag   2040
attaaactaa ttttaccata agtattctgt tttaataaat ttatgcccat gaacgctgcc   2100
aaaggacgag tggctcgcca ctgcccctta cgggtacata aatgtcctaa cttgatattt   2160
atttacctgt aagggttagc ctataggcga ggtaaataaa tttaagtcag ccatagctat   2220
tctagagtat aacgtgtacg tatccttacg ggtacgtaca cgttatactc agttagcagg   2280
gacttgttag cctataagcg agataagtac acttggccaa cggtttatat taatatactc   2340
```

cagcagaaga acaattaaag taaaatctaa aaatatctat ctttttgctg aagaattgcg 2400
gaaaaatcga tagtattgtt cattgtataa agtgtacgta cccgttaagg gtacgtacac 2460
tttaatgcaa gataaacaaa aatcaataca tattactagt tactagtata aagtacaatt 2520
gatttctgtg tatttgtagc ttttaaatta aatttttaat taactgttac ataaaaattt 2580
aaaattataa ataaaaacat gttaagtcca aaaagaacaa aattccgtaa accacaccgt 2640
ggtcatttaa gaggaaaagc aacacgtggt aataaaattg tatttggtga ttttgcatta 2700
caagcacaag aaccttgttg gattacatca cgtcaaattg aagccggacg tcgtgtttta 2760
acacgttatg ttcgtcgtgg tggtaaatta tggattcgta ttttcccaga taaagctgtt 2820
actatgcgtc ctgctggtac tcgtatgggt tctggtaaag gtgcacctga ttattgggta 2880
gctgttgtac atcctggtaa aattttatat gaaatgcaag gtgtatctga aacaattgct 2940
agacaagcaa tgcgcattgc agcttataaa atgccagtaa aaacaaaatt tttaacaaaa 3000
acagtgtaat tattgttatt aaaaatgttg tttagaaaga attaatgatt taacttactt 3060
aaaaagcata atctcaaatt agagcacaag tataatttaa aaaatattta agaaaattaa 3120
gagcataagt attgtttcgc tttggctcaa aagccaatac taaagataat attacttttt 3180
gtaagttttt acttactcgg tttgtaccag gcaaccctat aaatatagta aaatggaatt 3240
aaactagata tatctcttta agaaagattt tctcatcaag gctgcccttt aactttaacc 3300
tagaatgact aaaaggagta agcaaatacc gagaaattta ttttttcact taatgaaaaa 3360
ataaatttta tctctttctc ttttaagcat ataaatatga aggtaagtaa actctactag 3420
ggaaaagcat agtgttgaag gatatacttt cttgggatcc aaaaaagtaa acctaaacaa 3480
gatatactta attaatgata ataatataaa actttttttt aaacttatga ttaaaccttt 3540
atcttattta aatgtagcag ataatagtgg tgctcgtgaa ttaatgtgta ttcgtgctct 3600
tggtggcagt tatcgtgaat cggcaaatat tggtgatgtt attattgcag ttgttaaaga 3660
tgcattacca aatatgcctg taaaacgttc agatattgta cgagctgtta ttgtacgtac 3720
acgtaaaggt atccgtcgtg aaaatggtat ggcaattcgt tttgatgata acgctgcagt 3780
tattattaac aaagaaggaa atcctcgtgg tacacgtgtt tttggtccaa ttgcacgtga 3840
attacgtgat aaaaatttta caaaaattgt ttctttagca cctgaagttt tataaaaact 3900
actttttaaa ttttttttaca atagtaaaat cgatagttat atgcccgtta gaagattaac 3960
gccgtcgtat tcacatagac aattaattac tcgaggttta cttgcctagg attttaatac 4020
tccgaaggag gcagttggca ggcaactgcc tccttcccct tcgggcaagt aaacttagca 4080
tgtttacata ctccgaagga ggacgtcccc ttacgggaat ataaatatta gtggcagtgg 4140
taccgccact gcctagtata taaatatcgg cagttggcag gcaacaataa ataaatttgt 4200
ccactaaaat ttatttaccc gaaggaccgt ccttcggagt atataaatat aggattttaa 4260
tactccgaag aggcagttgg caggcaactg caactgacgt cccgaaggaa ggacggcagg 4320
ggacgtctcc ttacggggac atttatgtcc cctgcctttt aattcggggg atatgctttg 4380
caattagtag aaaattgcga ataggatttc catataaaat taaaataatt ctatcttctt 4440
taaaatttga tatgagtaat attataataa aatgcttatt aagttaaatc tttttataac 4500
cagttgattt ggataaaaag aacacataat gcaaagccaa aatgatagct ctcataaaag 4560
cagtaggcgg tgtaactttc attaaaattt atttacttta aggtgacgtc cccttacgga 4620
tatctaaata tttactgtat cctcgctaaa taaattgcta tattgtattg tatagcgcat 4680

-continued

```
taccttttgg cttaacatta tctatatgtg cattttattt tttttaata tgacacaacg   4740
tttaaaaaat ttatatacta aaactattgt tcctaaatta actacaaatt ttaattacag   4800
taatatgcat gaagtgccaa aaattgaaaa aattgtaatt aaccgtggta ttggtgatgc   4860
atcacaaaac caaaaaattg tggaatctag tttaaaagaa ttagctatga ttgcaggtca   4920
aaaaggtgtt gttacacgtt caaaaaaagc tattgctggc tttaaattaa gacaacaaat   4980
gcccgtaggt gtaactgtta cattacgtgg tgatcgtatg tatggttttc tagatcgttt   5040
aattcattta gcattaccgc gtgtacgcga tttccaaggt attagctcaa aaagttttga   5100
taaaaaaggt aattatagtt taggtttaga agaacaatta atgttcccag aaattgaata   5160
tgataaaatt gatcaagtac gtggtatgga tatttcaatt gtaacaacag caaaaacaca   5220
agaagaaggt cttgcattat taaaagaatt gggagcgcac gcgcaaggtc gcaactaccc   5280
gagaatcgat gtggcggaat gggttacgtg agctattatc cggcgggccc tcaatttaaa   5340
tcgttacagt tgctcgtaac ggcaaccggc tcggtccttt ttccctagaa cagtatctta   5400
tacttgctgc tctcgttact tcggcgatcc tggtgcagtc ggtccgtaaa tcggcgcaca   5460
cttttacgtc gtaccagaca ggctcgcata agccagcccc gacacccgcc aacacccgct   5520
gacgcgccct gacgggcttg tctgctcccg gcatccgctt acagacaagc tgtgacctcc   5580
gggagctgca tgtgtcagag gttttcaccg tcatcaccga aacgcgcacg aaagggcctc   5640
gtgatacgcc tatttttata ggttaatgtc atgataataa tggtttctta gacgtcaggt   5700
ggcacttttc ggggaaatgt gcgcggaacc cctatttgtt tatttttcta aatacattca   5760
aatatgtatc cgctcatgag acaataaccc tgataaatgc ttcaataata ttgaaaaagg   5820
aagagtatga gtattcaaca tttccgtgtc gcccttattc ccttttttgc ggcattttgc   5880
cttcctgttt ttgctcaccc agaaacgctg gtgaaagtaa aagatgctga agatcagttg   5940
ggtgcacgag tgggttacat cgaactggat ctcaacagcg gtaagatcct tgagagtttt   6000
cgccccgaag aacgttttcc aatgatgagc acttttaaag ttctgctatg tggcgcggta   6060
ttatcccgta ttgacgccgg gcaagagcaa ctcggtcgcc gcatacacta ttctcagaat   6120
gacttggttg agtactcacc agtcacagaa aagcatctta cggatggcat gacagtaaga   6180
gaattatgca gtgctgccat aaccatgagt gataacactg cggccaactt acttctgaca   6240
acgatcggag gaccgaagga gctaaccgct tttttgcaca acatgggga tcatgtaact   6300
cgccttgatc gttgggaacc ggagctgaat gaagccatac caaacgacga gcgtgacacc   6360
acgatgcctg tagcaatggc aacaacgttg cgcaaactat taactggcga actacttact   6420
ctagcttccc ggcaacaatt aatagactgg atggaggcgg ataaagttgc aggaccactt   6480
ctgcgctcgg cccttccggc tggctggttt attgctgata aatctggagc cggtgagcgt   6540
ggctcacgcg gtatcattgc agcactgggg ccagatggta agccctcccg tatcgtagtt   6600
atctacacga cggggagtca ggcaactatg gatgaacgaa atagacagat cgctgagata   6660
ggtgcctcac tgattaagca ttggtaactg tcagaccaag tttactcata tatactttag   6720
attgatttaa aacttcattt ttaatttaaa aggatctagg tgaagatcct ttttgataat   6780
ctcatgacca aaatccctta acgtgagttt tcgttccact gagcgtcaga ccccgtagaa   6840
aagatcaaag gatcttcttg agatcctttt tttctgcgcg taatctgctg cttgcaaaca   6900
aaaaaaccac cgctaccagc ggtggtttgt ttgccggatc aagagctacc aactcttttt   6960
ccgaaggtaa ctggcttcag cagagcgcag ataccaaata ctgttcttct agtgtagccg   7020
tagttaggcc accacttcaa gaactctgta gcaccgccta catacctcgc tctgctaatc   7080
```

ctgttaccag tggctgctgc cagtggcgat aagtcgtgtc ttaccgggtt ggactcaaga 7140
cgatagttac cggataaggc gcagcggtcg ggctgaacgg ggggttcgtg cacacagccc 7200
agcttggagc gaacgaccta caccgaactg agatacctac agcgtgagct atgagaaagc 7260
gccacgcttc ccgaagggag aaaggcggac aggtatccgg taagcggcag ggtcggaaca 7320
ggagagcgca cgagggagct tccaggggga aacgcctggt atctttatag tcctgtcggg 7380
tttcgccacc tctgacttga gcgtcgattt ttgtgatgct cgtcaggggg gcggagccta 7440
tggaaaaacg ccagcaacgc ggccttttta cggttcctgg ccttttgctg gccttttgct 7500
cacatgttct ttcctgcgtt atcccctgat tctgtggata accgtattac cgcctttgag 7560
tgagctgata ccgctcgccg cagccgaacg accgagcgca gcgagtcagt gagcgaggaa 7620
gcggaagaac gcggacaccc agcgtaacaa tctaatattg tttctcaaat cgggctgtta 7680
tcgcatggtg ctcatgatga ggttactgac caaattcgcc acgcatcggt gctggtagaa 7740
tgttcacttc gaggtgggta gacggcgtca cgtgcaatgc cttgtcttcc cctatctgcg 7800
gccccgactg cctcgcgaag acaagggatc ggacgtcgaa cgtattctgt ttgctaccgg 7860
cacgggagta ggatcgttga tatacaccat gcgcgttaac tctgaccccc ttcctcttaa 7920
atgagaatgg ataagaggct cgtgggattg acgtgagggg gcagggatgg ctatatttct 7980
gggagcgaac tccgggcgaa ttactaataa aaagccttcc attttctatt ttgatttgta 8040
gaaaactagt gtgcttggga gtccctgatg attaaataaa ccaagatttt accaatgggg 8100
gctagcgaag cggtgatcgc cgaagtatcg actcaactat cagaggtagt tggcgtcatc 8160
gagcgccatc tcgaaccgac gttgctggcc gtacatttgt acggctccgc agtggatggc 8220
ggcctgaagc cacacagtga tattgatttg ctggttacgg tgaccgtaag gcttgatgaa 8280
acaacgcggc gagctttgat caacgacctt ttggaaactt cggcttcccc tggagagagc 8340
gagattctcc gcgctgtaga agtcaccatt gttgtgcacg acgacatcat tccgtggcgt 8400
tatccagcta agcgcgaact gcaatttgga gaatggcagc gcaatgacat tcttgcaggt 8460
atcttcgagc cagccacgat cgacattgat ctggctatct tgctgacaaa agcaagagaa 8520
catagcgttg ccttggtagg tccagcggcg gaggaactct ttgatccggt tcctgaacag 8580
gatctatttg aggcgctaaa tgaaacctta acgctatgga actcgccgcc cgactgggct 8640
ggcgatgagc gaaatgtagt gcttacgttg tcccgcattt ggtacagcgc agtaaccggc 8700
aaaatcgcgc cgaaggatgt cgctgccgac tgggcaatgg agcgcctgcc ggcccagtat 8760
cagcccgtca tacttgaagc tagacaggct tatcttggac aagaagaaga tcgcttggcc 8820
tcgcgcgcag atcagttgga agaatttgtc cactacgtga aaggcgagat caccaaggta 8880
gtgggcaaag aacttgttga aggaaaattg gagctagtag aaggtcttaa agtcgccatg 8940
gctagtaaag gagaagaact tttcactgga gttgtcccaa ttcttgttga attagatggt 9000
gatgttaatg ggcacaaatt ttctgtcagt ggagagggtg aaggtgatgc aacatacgga 9060
aaacttaccc ttaaatttat ttgcactact ggaaaactac ctgttccttg gccaacactt 9120
gtcactactt tctcttatgg tgttcaatgc ttttcaagat acccagatca tatgaagcgg 9180
cacgacttct tcaagagcgc catgcctgag ggatacgtgc aggagaggac catctctttc 9240
aaggacgacg ggaactacaa gacacgtgct gaagtcaagt ttgagggaga caccctcgtc 9300
aacaggatcg agcttaaggg aatcgatttc aaggaggacg gaaacatcct cggccacaag 9360
ttggaataca actacaactc ccacaacgta tacatcacgg cagacaaaca aaagaatgga 9420

-continued

```
atcaaagcta acttcaaaat tagacacaac attgaagatg gaagcgttca actagcagac   9480
cattatcaac aaaatactcc aattggcgat ggccctgtcc ttttaccaga caaccattac   9540
ctgtccacac aatctgccct ttcgaaagat cccaacgaaa agagagatca catggtcctt   9600
cttgagtttg taacagctgc tgggattaca catggcatgg atgaactata caaataagct   9660
taaacagtag acattagcag ataaattagc aggaaataaa gaaggataag gagaaagaac   9720
tcaagtaatt atccttcgtt ctcttaattg aattgcaatt aaactcggcc caatctttta   9780
ctaaaaggat tgagccgaat accgctccag gcatcaaata aaacgaaagg ctcagtcgaa   9840
agactgggcc tttcgtttta tctgttgttt gtcggtgaac gctctcacaa cagctccctg   9900
gaacaccagg agaacacact tatctcgcgt cttgaggtga taccacgcct gacacgtgag   9960
ggcagtacgg ttaattcggt ttagccggac atcagcgctc ctcattgagc gctgggccct  10020
tcacatgaag atcgcactga ggattggtcc tagccaggct tctcagtact gatacagtac  10080
gcgtcgcttc tcgtattgtt tgagtcttgg aattagtttg tatccttccg ccgctgccct  10140
aagaattcta attgagctcg aacagtcgac cgccggatcc tgctcgagtg cctctaga    10198
```

```
<210> SEQ ID NO 35
<211> LENGTH: 5873
<212> TYPE: DNA
<213> ORGANISM: Artificial Sequence
<220> FEATURE:
<223> OTHER INFORMATION: An example of an episomal DNA vector

<400> SEQUENCE: 35
```

```
tgccaccacc tgccggtgcg gggtgtggtg gttatgttgt aggtgaaacg gtaaaacttt     60
taaaagagtt aaatgctttt ttcgaatacg atgttatttt atttgatgtt ttaggtgatg    120
ttgtttgtgg tggctttgct gctccattaa actacgctga ttattgtatt attgtaactg    180
ataatggttt tgatgcttta tttgctgcaa atcgtattgc agcttcagtt cgtgaaaaag    240
cacgtacaca tccattgcgt ttagcgggtt taatcggaaa tcgtacatca aaacgtgatt    300
taattgataa atatgtagaa gcttgtccta tgccagtatt agaagtttta ccattaattg    360
aagaaattcg tatttcacgt gttaaaggca aaactttatt tgaaatgtca aataaaaata    420
atatgacttc ggctcatatg gatggctcta aaggtgacaa ttctacagta ggagtgtcag    480
aaactccatc ggaagattat atttgtaatt tttatttaaa tattgctgat caattattaa    540
cagaaccaga aggagttatt ccacgtgaat tagcagataa agaacttttt actcttttat    600
cagatttcta tcttaaaatt taataagaat aaagcagctt taaatacttt cctgtttata    660
atttaggaaa ttaaatggat atttgttgaa actaatcccc agttggatac ccattggtag    720
ttaattgcca ctgcctgctt caccttacaa aatgtatgga cacaaaacgg ctaataaata    780
cagactcccg gtggcatttg ttggctgctt cgccctgaaa ggagaaagtg atttctttcc    840
ttattagcta atctattctt tttcctgttt tggtaaataa tagcgtcctc atatccatat    900
ctataacaaa aagttaaatg ttttaatttt aaaagtcttt tttacattaa taaacacttt    960
taattgatgg gacatcttta gtttttaaaa taaataaaga tgcacgggag cgcacgcgca   1020
aggtcgcaac tacccgagaa tcgatgtggc ggaatgggtt acgtgagcta ttatccggcg   1080
ggccctcaat ttaaatcgtt acagttgctc gtaacggcaa ccggctcggt ccttttttccc  1140
tagaacagta tcttatactt gctgctctcg ttacttcggc gatcctggtg cagtcggtcc   1200
gtaaatcggc gcacactttt acgtcgtacc agacaggctc gcataagcca gccccgacac   1260
ccgccaacac ccgctgacgc gccctgacgg gcttgtctgc tcccggcatc cgcttacaga   1320
```

-continued

```
caagctgtga cctccgggag ctgcatgtgt cagaggtttt caccgtcatc accgaaacgc   1380
gcacgaaagg gcctcgtgat acgcctattt ttataggtta atgtcatgat aataatggtt   1440
tcttagacgt caggtggcac ttttcgggga aatgtgcgcg gaacccctat ttgtttattt   1500
ttctaaatac attcaaatat gtatccgctc atgagacaat aaccctgata aatgcttcaa   1560
taatattgaa aaaggaagag tatgagtatt caacatttcc gtgtcgccct tattcccttt   1620
tttgcggcat tttgccttcc tgtttttgct cacccagaaa cgctggtgaa agtaaaagat   1680
gctgaagatc agttgggtgc acgagtgggt tacatcgaac tggatctcaa cagcggtaag   1740
atccttgaga gttttcgccc cgaagaacgt tttccaatga tgagcacttt taaagttctg   1800
ctatgtggcg cggtattatc ccgtattgac gccgggcaag agcaactcgg tcgccgcata   1860
cactattctc agaatgactt ggttgagtac tcaccagtca cagaaaagca tcttacggat   1920
ggcatgacag taagagaatt atgcagtgct gccataacca tgagtgataa cactgcggcc   1980
aacttacttc tgacaacgat cggaggaccg aaggagctaa ccgctttttt gcacaacatg   2040
ggggatcatg taactcgcct tgatcgttgg gaaccggagc tgaatgaagc cataccaaac   2100
gacgagcgtg acaccacgat gcctgtagca atggcaacaa cgttgcgcaa actattaact   2160
ggcgaactac ttactctagc ttcccggcaa caattaatag actggatgga ggcggataaa   2220
gttgcaggac cacttctgcg ctcggccctt ccggctggct ggtttattgc tgataaatct   2280
ggagccggtg agcgtggctc acgcggtatc attgcagcac tggggccaga tggtaagccc   2340
tcccgtatcg tagttatcta cacgacgggg agtcaggcaa ctatggatga acgaaataga   2400
cagatcgctg agataggtgc ctcactgatt aagcattggt aactgtcaga ccaagtttac   2460
tcatatatac tttagattga tttaaaactt catttttaat ttaaaaggat ctaggtgaag   2520
atcctttttg ataatctcat gaccaaaatc ccttaacgtg agttttcgtt ccactgagcg   2580
tcagaccccg tagaaaagat caaaggatct tcttgagatc ctttttttct gcgcgtaatc   2640
tgctgcttgc aaacaaaaaa accaccgcta ccagcggtgg tttgtttgcc ggatcaagag   2700
ctaccaactc tttttccgaa ggtaactggc ttcagcagag cgcagatacc aaatactgtt   2760
cttctagtgt agccgtagtt aggccaccac ttcaagaact ctgtagcacc gcctacatac   2820
ctcgctctgc taatcctgtt accagtggct gctgccagtg gcgataagtc gtgtcttacc   2880
gggttggact caagacgata gttaccggat aaggcgcagc ggtcgggctg aacggggggt   2940
tcgtgcacac agcccagctt ggagcgaacg acctacaccg aactgagata cctacagcgt   3000
gagctatgag aaagcgccac gcttcccgaa gggagaaagg cggacaggta tccggtaagc   3060
ggcagggtcg gaacaggaga gcgcacgagg gagcttccag ggggaaacgc ctggtatctt   3120
tatagtcctg tcgggtttcg ccacctctga cttgagcgtc gatttttgtg atgctcgtca   3180
ggggggcgga gcctatggaa aaacgccagc aacgcggcct ttttacggtt cctggccttt   3240
tgctggcctt ttgctcacat gttctttcct gcgttatccc ctgattctgt ggataaccgt   3300
attaccgcct ttgagtgagc tgataccgct cgccgcagcc gaacgaccga gcgcagcgag   3360
tcagtgagcg aggaagcgga agaacgcgga cacccagcgt aacaatctaa tattgtttct   3420
caaatcgggc tgttatcgca tggtgctcat gatgaggtta ctgaccaaat tcgccacgca   3480
tcggtgctgg tagaatgttc acttcgaggt gggtagacgg cgtcacgtgc aatgccttgt   3540
cttcccctat ctgcggcccc gactgcctcg cgaagacaag ggatcggacg tcgaacgtat   3600
tctgtttgct accggcacgg gagtaggatc gttgatatac accatgcgcg ttaactctga   3660
```

```
ccccccttcct cttaaatgag aatggataag aggctcgtgg gattgacgtg agggggcagg   3720
gatggctata tttctgggag cgaactccgg gcgaattact aataaaaagc cttccatttt   3780
ctattttgat ttgtagaaaa ctagtgtgct tgggagtccc tgatgattaa ataaaccaag   3840
attttaccaa tgggggctag cgaagcggtg atcgccgaag tatcgactca actatcagag   3900
gtagttggcg tcatcgagcg ccatctcgaa ccgacgttgc tggccgtaca tttgtacggc   3960
tccgcagtgg atggcggcct gaagccacac agtgatattg atttgctggt tacggtgacc   4020
gtaaggcttg atgaaacaac gcggcgagct ttgatcaacg accttttgga aacttcggct   4080
tcccctggag agagcgagat tctccgcgct gtagaagtca ccattgttgt gcacgacgac   4140
atcattccgt ggcgttatcc agctaagcgc gaactgcaat ttggagaatg gcagcgcaat   4200
gacattcttg caggtatctt cgagccagcc acgatcgaca ttgatctggc tatcttgctg   4260
acaaaagcaa gagaacatag cgttgccttg gtaggtccag cggcggagga actctttgat   4320
ccggttcctg aacaggatct atttgaggcg ctaaatgaaa ccttaacgct atggaactcg   4380
ccgcccgact gggctggcga tgagcgaaat gtagtgctta cgttgtcccg catttggtac   4440
agcgcagtaa ccggcaaaat cgcgccgaag gatgtcgctg ccgactgggc aatggagcgc   4500
ctgccggccc agtatcagcc cgtcatactt gaagctagac aggcttatct tggacaagaa   4560
gaagatcgct tggcctcgcg cgcagatcag ttggaagaat ttgtccacta cgtgaaaggc   4620
gagatcacca aggtagtggg caaagaactt gttgaaggaa aattggagct agtagaaggt   4680
cttaaagtcg ccatggctag taaaggagaa gaacttttca ctggagttgt cccaattctt   4740
gttgaattag atggtgatgt taatgggcac aaattttctg tcagtggaga gggtgaaggt   4800
gatgcaacat acggaaaact tacccttaaa tttatttgca ctactggaaa actacctgtt   4860
ccttggccaa cacttgtcac tactttctct tatggtgttc aatgcttttc aagataccca   4920
gatcatatga agcggcacga cttcttcaag agcgccatgc ctgagggata cgtgcaggag   4980
aggaccatct ctttcaagga cgacgggaac tacaagacac gtgctgaagt caagtttgag   5040
ggagacaccc tcgtcaacag gatcgagctt aagggaatcg atttcaagga ggacggaaac   5100
atcctcggcc acaagttgga atacaactac aactcccaca acgtatacat cacggcagac   5160
aaacaaaaga atggaatcaa agctaacttc aaaattagac acaacattga agatggaagc   5220
gttcaactag cagaccatta tcaacaaaat actccaattg gcgatggccc tgtcctttta   5280
ccagacaacc attacctgtc cacacaatct gccctttcga aagatcccaa cgaaaagaga   5340
gatcacatgg tccttcttga gtttgtaaca gctgctggga ttacacatgg catggatgaa   5400
ctatacaaat aagcttaaac agtagacatt agcagataaa ttagcaggaa ataaagaagg   5460
ataaggagaa agaactcaag taattatcct tcgttctctt aattgaattg caattaaact   5520
cggcccaatc ttttactaaa aggattgagc cgaataccgc tacaacagct ccctggaaca   5580
ccaggagaac acacttatct cgcgtcttga ggtgatacca cgcctgacac gtgagggcag   5640
tacggttaat tcggtttagc cggacatcag cgctcctcat tgagcgctgg gcccttcaca   5700
tgaagatcgc actgaggatt ggtcctagcc aggcttctca gtactgatac agtacgcgtc   5760
gcttctcgta ttgtttgagt cttggaatta gtttgtatcc ttccgccgct gccctaagaa   5820
ttctaattga gctcgaacag tcgaccgccg gatcctgctc gagtgcctct aga          5873
```

<210> SEQ ID NO 36
<211> LENGTH: 5953
<212> TYPE: DNA
<213> ORGANISM: Artificial Sequence
<220> FEATURE:
<223> OTHER INFORMATION: An example of an episomal DNA vector

<400> SEQUENCE: 36

```
tgccaccacc tgccggtgcg gggtgtggtg gttatgttgt aggtgaaacg gtaaaacttt     60
taaaagagtt aaatgctttt ttcgaatacg atgttatttt atttgatgtt ttaggtgatg    120
ttgtttgtgg tggctttgct gctccattaa actacgctga ttattgtatt attgtaactg    180
ataatggttt tgatgcttta tttgctgcaa atcgtattgc agcttcagtt cgtgaaaaag    240
cacgtacaca tccattgcgt ttagcgggtt taatcggaaa tcgtacatca aaacgtgatt    300
taattgataa atatgtagaa gcttgtccta tgccagtatt agaagtttta ccattaattg    360
aagaaattcg tatttcacgt gttaaaggca aaactttatt tgaaatgtca aataaaaata    420
atatgacttc ggctcatatg gatggctcta aaggtgacaa ttctacagta ggagtgtcag    480
aaactccatc ggaagattat atttgtaatt tttatttaaa tattgctgat caattattaa    540
cagaaccaga aggagttatt ccacgtgaat tagcagataa agaacttttt actcttttat    600
cagatttcta tcttaaaatt taataagaat aaagcagctt taaatacttt cctgtttata    660
atttaggaaa ttaaatggat atttgttgaa actaatcccc agttggatac ccattggtag    720
ttaattgcca ctgcctgctt caccttacaa aatgtatgga cacaaaacgg ctaataaata    780
cagactcccg gtggcatttg ttggctgctt cgccctgaaa ggagaaagtg atttctttcc    840
ttattagcta atctattctt tttcctgttt tggtaaataa tagcgtcctc atatccatat    900
ctataacaaa aagttaaatg ttttaatttt aaaagtcttt tttacattaa taaacacttt    960
taattgatgg gacatcttta gtttttaaaa taaataaaga tgcacgggag cgcacgcgca   1020
aggtcgcaac tacccgagaa tcgatgtggc ggaatgggtt acgtgagcta ttatccggcg   1080
ggccctcaat ttaaatcgtt acagttgctc gtaacggcaa ccggctcggt ccttttttccc  1140
tagaacagta tcttatactt gctgctctcg ttacttcggc gatcctggtg cagtcggtcc   1200
gtaaatcggc gcacactttt acgtcgtacc agacaggctc gcataagcca gccccgacac   1260
ccgccaacac ccgctgacgc gccctgacgg gcttgtctgc tcccggcatc cgcttacaga   1320
caagctgtga cctccgggag ctgcatgtgt cagaggtttt caccgtcatc accgaaacgc   1380
gcacgaaagg gcctcgtgat acgcctattt ttataggtta atgtcatgat aataatggtt   1440
tcttagacgt caggtggcac ttttcgggga aatgtgcgcg gaacccctat ttgtttattt   1500
ttctaaatac attcaaatat gtatccgctc atgagacaat aaccctgata aatgcttcaa   1560
taatattgaa aaaggaagag tatgagtatt caacatttcc gtgtcgccct tattcccttt   1620
tttgcggcat tttgccttcc tgtttttgct cacccagaaa cgctggtgaa agtaaaagat   1680
gctgaagatc agttgggtgc acgagtgggt tacatcgaac tggatctcaa cagcggtaag   1740
atccttgaga gttttcgccc cgaagaacgt tttccaatga tgagcacttt taaagttctg   1800
ctatgtggcg cggtattatc ccgtattgac gccgggcaag agcaactcgg tcgccgcata   1860
cactattctc agaatgactt ggttgagtac tcaccagtca cagaaaagca tcttacggat   1920
ggcatgacag taagagaatt atgcagtgct gccataacca tgagtgataa cactgcggcc   1980
aacttacttc tgacaacgat cggaggaccg aaggagctaa ccgctttttt gcacaacatg   2040
ggggatcatg taactcgcct tgatcgttgg gaaccggagc tgaatgaagc cataccaaac   2100
gacgagcgtg acaccacgat gcctgtagca atggcaacaa cgttgcgcaa actattaact   2160
ggcgaactac ttactctagc ttcccggcaa caattaatag actggatgga ggcggataaa   2220
```

-continued

```
gttgcaggac cacttctgcg ctcggccctt ccggctggct ggtttattgc tgataaatct   2280
ggagccggtg agcgtggctc acgcggtatc attgcagcac tggggccaga tggtaagccc   2340
tcccgtatcg tagttatcta cacgacgggg agtcaggcaa ctatggatga acgaaataga   2400
cagatcgctg agataggtgc ctcactgatt aagcattggt aactgtcaga ccaagtttac   2460
tcatatatac tttagattga tttaaaactt catttttaat ttaaaaggat ctaggtgaag   2520
atcctttttg ataatctcat gaccaaaatc ccttaacgtg agttttcgtt ccactgagcg   2580
tcagaccccg tagaaaagat caaaggatct tcttgagatc cttttttct gcgcgtaatc   2640
tgctgcttgc aaacaaaaaa accaccgcta ccagcggtgg tttgtttgcc ggatcaagag   2700
ctaccaactc tttttccgaa ggtaactggc ttcagcagag cgcagatacc aaatactgtt   2760
cttctagtgt agccgtagtt aggccaccac ttcaagaact ctgtagcacc gcctacatac   2820
ctcgctctgc taatcctgtt accagtggct gctgccagtg gcgataagtc gtgtcttacc   2880
gggttggact caagacgata gttaccggat aaggcgcagc ggtcgggctg aacggggggt   2940
tcgtgcacac agcccagctt ggagcgaacg acctacaccg aactgagata cctacagcgt   3000
gagctatgag aaagcgccac gcttcccgaa gggagaaagg cggacaggta tccggtaagc   3060
ggcagggtcg gaacaggaga gcgcacgagg gagcttccag ggggaaacgc ctggtatctt   3120
tatagtcctg tcgggtttcg ccacctctga cttgagcgtc gatttttgtg atgctcgtca   3180
ggggggcgga gcctatggaa aaacgccagc aacgcggcct ttttacggtt cctggccttt   3240
tgctggcctt ttgctcacat gttctttcct gcgttatccc ctgattctgt ggataaccgt   3300
attaccgcct ttgagtgagc tgataccgct cgccgcagcc gaacgaccga gcgcagcgag   3360
tcagtgagcg aggaagcgga agaacgcgga cacccagcgt aacaatctaa tattgtttct   3420
caaatcgggc tgttatcgca tggtgctcat gatgaggtta ctgaccaaat tcgccacgca   3480
tcggtgctgg tagaatgttc acttcgaggt gggtagacgg cgtcacgtgc aatgccttgt   3540
cttcccctat ctgcggcccc gactgcctcg cgaagacaag ggatcggacg tcgaacgtat   3600
tctgtttgct accggcacgg gagtaggatc gttgatatac accatgcgcg ttaactctga   3660
ccccccttcct cttaaatgag aatggataag aggctcgtgg gattgacgtg agggggcagg   3720
gatggctata tttctgggag cgaactccgg gcgaattact aataaaaagc cttccatttt   3780
ctattttgat ttgtagaaaa ctagtgtgct tgggagtccc tgatgattaa ataaaccaag   3840
attttaccaa tgggggctag cgaagcggtg atcgccgaag tatcgactca actatcagag   3900
gtagttggcg tcatcgagcg ccatctcgaa ccgacgttgc tggccgtaca tttgtacggc   3960
tccgcagtgg atggcggcct gaagccacac agtgatattg atttgctggt tacggtgacc   4020
gtaaggcttg atgaaacaac gcggcgagct ttgatcaacg acctttttgga aacttcggct   4080
tcccctggag agagcgagat tctccgcgct gtagaagtca ccattgttgt gcacgacgac   4140
atcattccgt ggcgttatcc agctaagcgc gaactgcaat ttggagaatg gcagcgcaat   4200
gacattcttg caggtatctt cgagccagcc acgatcgaca ttgatctggc tatcttgctg   4260
acaaaagcaa gagaacatag cgttgccttg gtaggtccag cggcggagga actctttgat   4320
ccggttcctg aacaggatct atttgaggcg ctaaatgaaa ccttaacgct atggaactcg   4380
ccgcccgact gggctggcga tgagcgaaat gtagtgctta cgttgtcccg catttggtac   4440
agcgcagtaa ccggcaaaat cgcgccgaag gatgtcgctg ccgactgggc aatggagcgc   4500
ctgccggccc agtatcagcc cgtcatactt gaagctagac aggcttatct tggacaagaa   4560
gaagatcgct tggcctcgcg cgcagatcag ttggaagaat ttgtccacta cgtgaaaggc   4620
```

gagatcacca aggtagtggg caaagaactt gttgaaggaa aattggagct agtagaaggt 4680
cttaaagtcg ccatggctag taaaggagaa gaacttttca ctggagttgt cccaattctt 4740
gttgaattag atggtgatgt taatgggcac aaattttctg tcagtggaga gggtgaaggt 4800
gatgcaacat acggaaaact tacccttaaa tttatttgca ctactggaaa actacctgtt 4860
ccttggccaa cacttgtcac tactttctct tatggtgttc aatgcttttc aagataccca 4920
gatcatatga agcggcacga cttcttcaag agcgccatgc ctgagggata cgtgcaggag 4980
aggaccatct ctttcaagga cgacgggaac tacaagacac gtgctgaagt caagtttgag 5040
ggagacaccc tcgtcaacag gatcgagctt aagggaatcg atttcaagga ggacggaaac 5100
atcctcggcc acaagttgga atacaactac aactcccaca acgtatacat cacggcagac 5160
aaacaaaaga atggaatcaa agctaacttc aaaattagac acaacattga agatggaagc 5220
gttcaactag cagaccatta tcaacaaaat actccaattg gcgatggccc tgtcctttta 5280
ccagacaacc attacctgtc cacacaatct gccctttcga aagatcccaa cgaaaagaga 5340
gatcacatgg tccttcttga gtttgtaaca gctgctggga ttacacatgg catggatgaa 5400
ctatacaaat aagcttaaac agtagacatt agcagataaa ttagcaggaa ataaagaagg 5460
ataaggagaa agaactcaag taattatcct tcgttctctt aattgaattg caattaaact 5520
cggcccaatc ttttactaaa aggattgagc cgaataccgc tccaggcatc aaataaaacg 5580
aaaggctcag tcgaaagact gggcctttcg ttttatctgt tgtttgtcgg tgaacgctct 5640
cacaacagct ccctggaaca ccaggagaac acacttatct cgcgtcttga ggtgatacca 5700
cgcctgacac gtgagggcag tacggttaat tcggtttagc cggacatcag cgctcctcat 5760
tgagcgctgg gcccttcaca tgaagatcgc actgaggatt ggtcctagcc aggcttctca 5820
gtactgatac agtacgcgtc gcttctcgta ttgtttgagt cttggaatta gtttgtatcc 5880
ttccgccgct gccctaagaa ttctaattga gctcgaacag tcgaccgccg gatcctgctc 5940
gagtgcctct aga 5953

<210> SEQ ID NO 37
<211> LENGTH: 5326
<212> TYPE: DNA
<213> ORGANISM: Artificial Sequence
<220> FEATURE:
<223> OTHER INFORMATION: An example of an episomal DNA vector

<400> SEQUENCE: 37
tgcccgtgta cgtacaatta cagctcgaat tacttcggat ctttctagag gcatttgggg 60
cactgcgtct ttgattacag caataataac atcaccaata cgagcatatc gctgattacc 120
agcggctcct atgactcgaa tacacatcaa ttttcgagct ccactgttat ctgctacatt 180
taaaagggtc tgaggttgaa tcatattatt tggatttcca tttgttattt caatgcaaaa 240
ggatgaaaga aatattgtct ttccagaaag aaaaaccagg ggtttttat cttcaatatt 300 cctttttggg gttctatatc tctaatcgaa gaaattgact tcgtatgggc attttactgg 360
cagctataga gatagctgct ctagctacag tttcggatac tccgctcatt tcataaagta 420
ttcgacctgg tttaacaacg gctacccaat attcgggggg gagcgcacgc gcaaggtcgc 480
aactacccga gaatcgatgt ggcggaatgg gttacgtgag ctattatccg gcgggccctc 540
aatttaaatc gttacagttg ctcgtaacgg caaccggctc ggtccttttt ccctagaaca 600
gtatcttata cttgctgctc tcgttacttc ggcgatcctg gtgcagtcgg tccgtaaatc 660

-continued

```
ggcgcacact tttacgtcgt accagacagg ctcgcataag ccagccccga cacccgccaa    720
cacccgctga cgcgccctga cgggcttgtc tgctcccggc atccgcttac agacaagctg    780
tgacctccgg gagctgcatg tgtcagaggt tttcaccgtc atcaccgaaa cgcgcacgaa    840
agggcctcgt gatacgccta tttttatagg ttaatgtcat gataataatg gtttcttaga    900
cgtcaggtgg cacttttcgg ggaaatgtgc gcggaacccc tatttgttta tttttctaaa    960
tacattcaaa tatgtatccg ctcatgagac aataaccctg ataaatgctt caataatatt   1020
gaaaaaggaa gagtatgagt attcaacatt tccgtgtcgc ccttattccc ttttttgcgg   1080
cattttgcct tcctgttttt gctcacccag aaacgctggt gaaagtaaaa gatgctgaag   1140
atcagttggg tgcacgagtg ggttacatcg aactggatct caacagcggt aagatccttg   1200
agagttttcg ccccgaagaa cgttttccaa tgatgagcac ttttaaagtt ctgctatgtg   1260
gcgcggtatt atcccgtatt gacgccgggc aagagcaact cggtcgccgc atacactatt   1320
ctcagaatga cttggttgag tactcaccag tcacagaaaa gcatcttacg gatggcatga   1380
cagtaagaga attatgcagt gctgccataa ccatgagtga taacactgcg gccaacttac   1440
ttctgacaac gatcggagga ccgaaggagc taaccgcttt tttgcacaac atgggggatc   1500
atgtaactcg ccttgatcgt tgggaaccgg agctgaatga agccatacca aacgacgagc   1560
gtgacaccac gatgcctgta gcaatggcaa caacgttgcg caaactatta actggcgaac   1620
tacttactct agcttcccgg caacaattaa tagactggat ggaggcggat aaagttgcag   1680
gaccacttct gcgctcggcc cttccggctg gctggtttat tgctgataaa tctggagccg   1740
gtgagcgtgg ctcacgcggt atcattgcag cactggggcc agatggtaag ccctcccgta   1800
tcgtagttat ctacacgacg gggagtcagg caactatgga tgaacgaaat agacagatcg   1860
ctgagatagg tgcctcactg attaagcatt ggtaactgtc agaccaagtt tactcatata   1920
tactttagat tgatttaaaa cttcattttt aatttaaaag gatctaggtg aagatccttt   1980
ttgataatct catgaccaaa atcccttaac gtgagttttc gttccactga gcgtcagacc   2040
ccgtagaaaa gatcaaagga tcttcttgag atcctttttt tctgcgcgta atctgctgct   2100
tgcaaacaaa aaaaccaccg ctaccagcgg tggtttgttt gccggatcaa gagctaccaa   2160
ctctttttcc gaaggtaact ggcttcagca gagcgcagat accaaatact gttcttctag   2220
tgtagccgta gttaggccac cacttcaaga actctgtagc accgcctaca tacctcgctc   2280
tgctaatcct gttaccagtg gctgctgcca gtggcgataa gtcgtgtctt accgggttgg   2340
actcaagacg atagttaccg gataaggcgc agcggtcggg ctgaacgggg ggttcgtgca   2400
cacagcccag cttggagcga acgacctaca ccgaactgag atacctacag cgtgagctat   2460
gagaaagcgc cacgcttccc gaagggagaa aggcggacag gtatccggta agcggcaggg   2520
tcggaacagg agagcgcacg agggagcttc cagggggaaa cgcctggtat ctttatagtc   2580
ctgtcgggtt tcgccacctc tgacttgagc gtcgattttt gtgatgctcg tcaggggggc   2640
ggagcctatg gaaaaacgcc agcaacgcgg cctttttacg gttcctggcc ttttgctggc   2700
cttttgctca catgttcttt cctgcgttat cccctgattc tgtggataac cgtattaccg   2760
cctttgagtg agctgatacc gctcgccgca gccgaacgac cgagcgcagc gagtcagtga   2820
gcgaggaagc ggaagaacgc ggacacccag cgtaacaatc taatattgtt tctcaaatcg   2880
ggctgttatc gcatggtgct catgatgagg ttactgacca aattcgccac gcatcggtgc   2940
tggtagaatg ttcacttcga ggtgggtaga cggcgtcacg tgcaatgcct tgtcttcccc   3000
tatctgcggc cccgactgcc tcgcgaagac aagggatcgg acgtcgaacg tattctgttt   3060
```

```
gctaccggca cgggagtagg atcgttgata tacaccatgc gcgttaactc tgacccccct   3120
cctcttaaat gagaatggat aagaggctcg tgggattgac gtgagggggc agggatggct   3180
atatttctgg gagcgaactc cgggcgaatt actaataaaa agccttccat tttctatttt   3240
gatttgtaga aaactagtgt gcttgggagt ccctgatgat taaataaacc aagattttac   3300
caatgggggc tagcgaagcg gtgatcgccg aagtatcgac tcaactatca gaggtagttg   3360
gcgtcatcga gcgccatctc gaaccgacgt tgctggccgt acatttgtac ggctccgcag   3420
tggatggcgg cctgaagcca cacagtgata ttgatttgct ggttacggtg accgtaaggc   3480
ttgatgaaac aacgcggcga gctttgatca acgacctttt ggaaacttcg gcttcccctg   3540
gagagagcga gattctccgc gctgtagaag tcaccattgt tgtgcacgac gacatcattc   3600
cgtggcgtta tccagctaag cgcgaactgc aatttggaga atggcagcgc aatgacattc   3660
ttgcaggtat cttcgagcca gccacgatcg acattgatct ggctatcttg ctgacaaaag   3720
caagagaaca tagcgttgcc ttggtaggtc cagcggcgga ggaactcttt gatccggttc   3780
ctgaacagga tctatttgag gcgctaaatg aaaccttaac gctatggaac tcgccgcccg   3840
actgggctgg cgatgagcga aatgtagtgc ttacgttgtc ccgcatttgg tacagcgcag   3900
taaccggcaa aatcgcgccg aaggatgtcg ctgccgactg ggcaatggag cgcctgccgg   3960
cccagtatca gcccgtcata cttgaagcta gacaggctta tcttggacaa gaagaagatc   4020
gcttggcctc gcgcgcagat cagttggaag aatttgtcca ctacgtgaaa ggcgagatca   4080
ccaaggtagt gggcaaagaa cttgttgaag gaaaattgga gctagtagaa ggtcttaaag   4140
tcgccatggc tagtaaagga gaagaacttt tcactggagt tgtcccaatt cttgttgaat   4200
tagatggtga tgttaatggg cacaaatttt ctgtcagtgg agagggtgaa ggtgatgcaa   4260
catacggaaa acttaccctt aaatttattt gcactactgg aaaactacct gttccttggc   4320
caacacttgt cactactttc tcttatggtg ttcaatgctt ttcaagatac ccagatcata   4380
tgaagcggca cgacttcttc aagagcgcca tgcctgaggg atacgtgcag gagaggacca   4440
tctctttcaa ggacgacggg aactacaaga cacgtgctga agtcaagttt gagggagaca   4500
ccctcgtcaa caggatcgag cttaagggaa tcgatttcaa ggaggacgga aacatcctcg   4560
gccacaagtt ggaatacaac tacaactccc acaacgtata catcacggca gacaaacaaa   4620
agaatggaat caaagctaac ttcaaaatta gacacaacat tgaagatgga agcgttcaac   4680
tagcagacca ttatcaacaa aatactccaa ttggcgatgg ccctgtcctt ttaccagaca   4740
accattacct gtccacacaa tctgcccttt cgaaagatcc caacgaaaag agagatcaca   4800
tggtccttct tgagtttgta acagctgctg ggattacaca tggcatggat gaactataca   4860
aataagctta aacagtagac attagcagat aaattagcag gaaataaaga aggataagga   4920
gaaagaactc aagtaattat ccttcgttct cttaattgaa ttgcaattaa actcggccca   4980
atcttttact aaaaggattg agccgaatac cgctacaaca gctccctgga acaccaggag   5040
aacacactta tctcgcgtct tgaggtgata ccacgcctga cacgtgaggg cagtacggtt   5100
aattcggttt agccggacat cagcgctcct cattgagcgc tgggcccttc acatgaagat   5160
cgcactgagg attggtccta gccaggcttc tcagtactga tacagtacgc gtcgcttctc   5220
gtattgtttg agtcttggaa ttagtttgta tccttccgcc gctgccctaa gaattctaat   5280
tgagctcgaa cagtcgaccg ccggatcctg ctcgagtgcc tctaga                  5326
```

<210> SEQ ID NO 38

<211> LENGTH: 5406
<212> TYPE: DNA
<213> ORGANISM: Artificial Sequence
<220> FEATURE:
<223> OTHER INFORMATION: An example of an episomal DNA vector

<400> SEQUENCE: 38
tgcccgtgta cgtacaatta cagctcgaat tacttcggat ctttctagag gcatttgggg 60
cactgcgtct ttgattacag caataataac atcaccaata cgagcatatc gctgattacc 120
agcggctcct atgactcgaa tacacatcaa ttttcgagct ccactgttat ctgctacatt 180
taaaagggtc tgaggttgaa tcatattatt tggatttcca tttgttattt caatgcaaaa 240
ggatgaaaga aatattgtct ttccagaaag aaaaaccagg ggtttttat cttcaatatt 300 ccttttggg gttctatatc tctaatcgaa gaaattgact tcgtatgggc attttactgg 360
cagctataga gatagctgct ctagctacag tttcggatac tccgctcatt tcataaagta 420
ttcgacctgg tttaacaacg gctacccaat attcgggggg gagcgcacgc gcaaggtcgc 480
aactacccga gaatcgatgt ggcggaatgg gttacgtgag ctattatccg gcgggccctc 540
aatttaaatc gttacagttg ctcgtaacgg caaccggctc ggtccttttt ccctagaaca 600
gtatcttata cttgctgctc tcgttacttc ggcgatcctg gtgcagtcgg tccgtaaatc 660
ggcgcacact tttacgtcgt accagacagg ctcgcataag ccagccccga cacccgccaa 720
cacccgctga cgcgccctga cgggcttgtc tgctcccggc atccgcttac agacaagctg 780
tgacctccgg gagctgcatg tgtcagaggt tttcaccgtc atcaccgaaa cgcgcacgaa 840
agggcctcgt gatacgccta tttttatagg ttaatgtcat gataataatg gtttcttaga 900
cgtcaggtgg cacttttcgg ggaaatgtgc gcggaacccc tatttgttta tttttctaaa 960
tacattcaaa tatgtatccg ctcatgagac aataaccctg ataaatgctt caataatatt 1020
gaaaaaggaa gagtatgagt attcaacatt tccgtgtcgc ccttattccc ttttttgcgg 1080
cattttgcct tcctgttttt gctcacccag aaacgctggt gaaagtaaaa gatgctgaag 1140
atcagttggg tgcacgagtg ggttacatcg aactggatct caacagcggt aagatccttg 1200
agagttttcg ccccgaagaa cgttttccaa tgatgagcac ttttaaagtt ctgctatgtg 1260
gcgcggtatt atcccgtatt gacgccgggc aagagcaact cggtcgccgc atacactatt 1320
ctcagaatga cttggttgag tactcaccag tcacagaaaa gcatcttacg gatggcatga 1380
cagtaagaga attatgcagt gctgccataa ccatgagtga taacactgcg gccaacttac 1440
ttctgacaac gatcggagga ccgaaggagc taaccgcttt tttgcacaac atgggggatc 1500
atgtaactcg ccttgatcgt tgggaaccgg agctgaatga agccatacca aacgacgagc 1560
gtgacaccac gatgcctgta gcaatggcaa caacgttgcg caaactatta actggcgaac 1620
tacttactct agcttcccgg caacaattaa tagactggat ggaggcggat aaagttgcag 1680
gaccacttct gcgctcggcc cttccggctg gctggtttat tgctgataaa tctggagccg 1740
gtgagcgtgg ctcacgcggt atcattgcag cactggggcc agatggtaag ccctcccgta 1800
tcgtagttat ctacacgacg gggagtcagg caactatgga tgaacgaaat agacagatcg 1860
ctgagatagg tgcctcactg attaagcatt ggtaactgtc agaccaagtt tactcatata 1920
tactttagat tgatttaaaa cttcattttt aatttaaaag gatctaggtg aagatccttt 1980
ttgataatct catgaccaaa atcccttaac gtgagttttc gttccactga gcgtcagacc 2040
ccgtagaaaa gatcaaagga tcttcttgag atcctttttt tctgcgcgta atctgctgct 2100
tgcaaacaaa aaaaccaccg ctaccagcgg tggtttgttt gccggatcaa gagctaccaa 2160

```
ctctttttcc gaaggtaact ggcttcagca gagcgcagat accaaatact gttcttctag   2220
tgtagccgta gttaggccac cacttcaaga actctgtagc accgcctaca tacctcgctc   2280
tgctaatcct gttaccagtg gctgctgcca gtggcgataa gtcgtgtctt accgggttgg   2340
actcaagacg atagttaccg gataaggcgc agcggtcggg ctgaacgggg ggttcgtgca   2400
cacagcccag cttggagcga acgacctaca ccgaactgag atacctacag cgtgagctat   2460
gagaaagcgc cacgcttccc gaagggagaa aggcggacag gtatccggta agcggcaggg   2520
tcggaacagg agagcgcacg agggagcttc caggggggaaa cgcctggtat ctttatagtc   2580
ctgtcgggtt tcgccacctc tgacttgagc gtcgattttt gtgatgctcg tcaggggggc   2640
ggagcctatg gaaaaacgcc agcaacgcgg cctttttacg gttcctggcc ttttgctggc   2700
cttttgctca catgttcttt cctgcgttat cccctgattc tgtggataac cgtattaccg   2760
cctttgagtg agctgatacc gctcgccgca gccgaacgac cgagcgcagc gagtcagtga   2820
gcgaggaagc ggaagaacgc ggacacccag cgtaacaatc taatattgtt tctcaaatcg   2880
ggctgttatc gcatggtgct catgatgagg ttactgacca aattcgccac gcatcggtgc   2940
tggtagaatg ttcacttcga ggtgggtaga cggcgtcacg tgcaatgcct tgtcttcccc   3000
tatctgcggc cccgactgcc tcgcgaagac aagggatcgg acgtcgaacg tattctgttt   3060
gctaccggca cgggagtagg atcgttgata tacaccatgc gcgttaactc tgacccccctt   3120
cctcttaaat gagaatggat aagaggctcg tgggattgac gtgagggggc agggatggct   3180
atatttctgg gagcgaactc cgggcgaatt actaataaaa agccttccat tttctatttt   3240
gatttgtaga aaactagtgt gcttgggagt ccctgatgat taaataaacc aagattttac   3300
caatgggggc tagcgaagcg gtgatcgccg aagtatcgac tcaactatca gaggtagttg   3360
gcgtcatcga gcgccatctc gaaccgacgt tgctggccgt acatttgtac ggctccgcag   3420
tggatggcgg cctgaagcca cacagtgata ttgatttgct ggttacggtg accgtaaggc   3480
ttgatgaaac aacgcggcga gctttgatca acgacctttt ggaaacttcg gcttcccctg   3540
gagagagcga gattctccgc gctgtagaag tcaccattgt tgtgcacgac gacatcattc   3600
cgtggcgtta tccagctaag cgcgaactgc aatttggaga atggcagcgc aatgacattc   3660
ttgcaggtat cttcgagcca gccacgatcg acattgatct ggctatcttg ctgacaaaag   3720
caagagaaca tagcgttgcc ttggtaggtc cagcggcgga ggaactcttt gatccggttc   3780
ctgaacagga tctatttgag gcgctaaatg aaaccttaac gctatggaac tcgccgcccg   3840
actgggctgg cgatgagcga aatgtagtgc ttacgttgtc ccgcatttgg tacagcgcag   3900
taaccggcaa aatcgcgccg aaggatgtcg ctgccgactg ggcaatggag cgcctgccgg   3960
cccagtatca gcccgtcata cttgaagcta gacaggctta tcttggacaa gaagaagatc   4020
gcttggcctc gcgcgcagat cagttggaag aatttgtcca ctacgtgaaa ggcgagatca   4080
ccaaggtagt gggcaaagaa cttgttgaag gaaaattgga gctagtagaa ggtcttaaag   4140
tcgccatggc tagtaaagga gaagaacttt tcactggagt tgtcccaatt cttgttgaat   4200
tagatggtga tgttaatggg cacaaatttt ctgtcagtgg agagggtgaa ggtgatgcaa   4260
catacggaaa acttaccctt aaatttattt gcactactgg aaaactacct gttccttggc   4320
caacacttgt cactactttc tcttatggtg ttcaatgctt ttcaagatac ccagatcata   4380
tgaagcggca cgacttcttc aagagcgcca tgcctgaggg atacgtgcag gagaggacca   4440
tctctttcaa ggacgacggg aactacaaga cacgtgctga agtcaagttt gagggagaca   4500
```

-continued

```
ccctcgtcaa caggatcgag cttaagggaa tcgatttcaa ggaggacgga aacatcctcg   4560
gccacaagtt ggaatacaac tacaactccc acaacgtata catcacggca gacaaacaaa   4620
agaatggaat caaagctaac ttcaaaatta gacacaacat tgaagatgga agcgttcaac   4680
tagcagacca ttatcaacaa aatactccaa ttggcgatgg ccctgtcctt ttaccagaca   4740
accattacct gtccacacaa tctgcccttt cgaaagatcc caacgaaaag agagatcaca   4800
tggtccttct tgagtttgta acagctgctg ggattacaca tggcatggat gaactataca   4860
aataagctta aacagtagac attagcagat aaattagcag gaaataaaga aggataagga   4920
gaaagaactc aagtaattat ccttcgttct cttaattgaa ttgcaattaa actcggccca   4980
atcttttact aaaaggattg agccgaatac cgctccaggc atcaaataaa acgaaaggct   5040
cagtcgaaag actgggcctt tcgttttatc tgttgtttgt cggtgaacgc tctcacaaca   5100
gctccctgga acaccaggag aacacactta tctcgcgtct tgaggtgata ccacgcctga   5160
cacgtgaggg cagtacggtt aattcggttt agccggacat cagcgctcct cattgagcgc   5220
tgggcccttc acatgaagat cgcactgagg attggtccta gccaggcttc tcagtactga   5280
tacagtacgc gtcgcttctc gtattgtttg agtcttggaa ttagtttgta tccttccgcc   5340
gctgccctaa gaattctaat tgagctcgaa cagtcgaccg ccggatcctg ctcgagtgcc   5400
tctaga                                                              5406
```

<210> SEQ ID NO 39
<211> LENGTH: 5387
<212> TYPE: DNA
<213> ORGANISM: Artificial Sequence
<220> FEATURE:
<223> OTHER INFORMATION: An example of an episomal DNA vector

<400> SEQUENCE: 39

```
tgccgtaata atattaagaa gaacgatgaa gaaaggttaa ggaaacgtac gaaggataac     60
gaaggctgtt gaagtcacaa tcgacaggag tgattaactg aggacaaatg ttgtcagaca    120
acccctcgtc ctggtcatgt gataggcttc tcgatgaaac tgttccatct ctaccccagt    180
agagaaaaat ccaggtcata tcataggaga tagaaatgaa tgacgagaac gaagacagaa    240
tgacgttgaa gagaacgatt aggtaatatg tagaaacgac aatgaaagtc ctcgaaggag    300
gcaggtaata aagatgacaa aggagcgcgc taccacgcga aacaagccat taggcagttc    360
tcctatcccc tccgaacgaa taccttttag taagagggtg aaacagtgac acaaagccgg    420
tgaggccgtc acgcgtactt cagaacatga gtgatgagta ctgttaaaca tacccaggcg    480
tgagccaaca atgcaaagaa ccctgagaag ggagtgaaag ggagcgcacg cgcaaggtcg    540
caactacccg agaatcgatg tggcggaatg ggttacgtga gctattatcc ggcgggccct    600
caatttaaat cgttacagtt gctcgtaacg gcaaccggct cggtcctttt tccctagaac    660
agtatcttat acttgctgct ctcgttactt cggcgatcct ggtgcagtcg gtccgtaaat    720
cggcgcacac ttttacgtcg taccagacag gctcgcataa gccagccccg acacccgcca    780
acacccgctg acgcgccctg acgggcttgt ctgctcccgg catccgctta cagacaagct    840
gtgacctccg ggagctgcat gtgtcagagg ttttcaccgt catcaccgaa acgcgcacga    900
aagggcctcg tgatacgcct atttttatag gttaatgtca tgataataat ggtttcttag    960
acgtcaggtg gcacttttcg gggaaatgtg cgcggaaccc ctatttgttt atttttctaa   1020
atacattcaa atatgtatcc gctcatgaga caataaccct gataaatgct tcaataatat   1080
tgaaaaagga agagtatgag tattcaacat ttccgtgtcg cccttattcc cttttttgcg   1140
```

-continued

```
gcattttgcc ttcctgtttt tgctcaccca gaaacgctgg tgaaagtaaa agatgctgaa   1200
gatcagttgg gtgcacgagt gggttacatc gaactggatc tcaacagcgg taagatcctt   1260
gagagttttc gccccgaaga acgttttcca atgatgagca cttttaaagt tctgctatgt   1320
ggcgcggtat tatcccgtat tgacgccggg caagagcaac tcggtcgccg catacactat   1380
tctcagaatg acttggttga gtactcacca gtcacagaaa agcatcttac ggatggcatg   1440
acagtaagag aattatgcag tgctgccata accatgagtg ataacactgc ggccaactta   1500
cttctgacaa cgatcggagg accgaaggag ctaaccgctt ttttgcacaa catgggggat   1560
catgtaactc gccttgatcg ttgggaaccg gagctgaatg aagccatacc aaacgacgag   1620
cgtgacacca cgatgcctgt agcaatggca acaacgttgc gcaaactatt aactggcgaa   1680
ctacttactc tagcttcccg gcaacaatta atagactgga tggaggcgga taaagttgca   1740
ggaccacttc tgcgctcggc ccttccggct ggctggttta ttgctgataa atctggagcc   1800
ggtgagcgtg gctcacgcgg tatcattgca gcactggggc cagatggtaa gccctcccgt   1860
atcgtagtta tctacacgac ggggagtcag gcaactatgg atgaacgaaa tagacagatc   1920
gctgagatag gtgcctcact gattaagcat tggtaactgt cagaccaagt ttactcatat   1980
atactttaga ttgatttaaa acttcatttt taatttaaaa ggatctaggt gaagatcctt   2040
tttgataatc tcatgaccaa aatcccttaa cgtgagtttt cgttccactg agcgtcagac   2100
cccgtagaaa agatcaaagg atcttcttga gatccttttt ttctgcgcgt aatctgctgc   2160
ttgcaaacaa aaaaaccacc gctaccagcg gtggtttgtt tgccggatca agagctacca   2220
actctttttc cgaaggtaac tggcttcagc agagcgcaga taccaaatac tgttcttcta   2280
gtgtagccgt agttaggcca ccacttcaag aactctgtag caccgcctac atacctcgct   2340
ctgctaatcc tgttaccagt ggctgctgcc agtggcgata agtcgtgtct taccgggttg   2400
gactcaagac gatagttacc ggataaggcg cagcggtcgg gctgaacggg gggttcgtgc   2460
acacagccca gcttggagcg aacgacctac accgaactga gatacctaca gcgtgagcta   2520
tgagaaagcg ccacgcttcc cgaagggaga aaggcggaca ggtatccggt aagcggcagg   2580
gtcggaacag gagagcgcac gagggagctt ccagggggaa acgcctggta tctttatagt   2640
cctgtcgggt ttcgccacct ctgacttgag cgtcgatttt tgtgatgctc gtcagggggg   2700
cggagcctat ggaaaaacgc cagcaacgcg gcctttttac ggttcctggc cttttgctgg   2760
ccttttgctc acatgttctt tcctgcgtta tcccctgatt ctgtggataa ccgtattacc   2820
gcctttgagt gagctgatac cgctcgccgc agccgaacga ccgagcgcag cgagtcagtg   2880
agcgaggaag cggaagaacg cggacaccca gcgtaacaat ctaatattgt ttctcaaatc   2940
gggctgttat cgcatggtgc tcatgatgag gttactgacc aaattcgcca cgcatcggtg   3000
ctggtagaat gttcacttcg aggtgggtag acggcgtcac gtgcaatgcc ttgtcttccc   3060
ctatctgcgg ccccgactgc ctcgcgaaga caagggatcg gacgtcgaac gtattctgtt   3120
tgctaccggc acgggagtag gatcgttgat atacaccatg cgcgttaact ctgacccccct   3180
tcctcttaaa tgagaatgga taagaggctc gtgggattga cgtgaggggg cagggatggc   3240
tatatttctg ggagcgaact ccgggcgaat tactaataaa aagccttcca ttttctattt   3300
tgatttgtag aaaactagtg tgcttgggag tccctgatga ttaaataaac caagatttta   3360
ccaatggggg ctagcgaagc ggtgatcgcc gaagtatcga ctcaactatc agaggtagtt   3420
ggcgtcatcg agcgccatct cgaaccgacg ttgctggccg tacatttgta cggctccgca   3480
```

```
gtggatggcg gcctgaagcc acacagtgat attgatttgc tggttacggt gaccgtaagg   3540

cttgatgaaa caacgcggcg agctttgatc aacgaccttt tggaaacttc ggcttcccct   3600

ggagagagcg agattctccg cgctgtagaa gtcaccattg ttgtgcacga cgacatcatt   3660

ccgtggcgtt atccagctaa gcgcgaactg caatttggag aatggcagcg caatgacatt   3720

cttgcaggta tcttcgagcc agccacgatc gacattgatc tggctatctt gctgacaaaa   3780

gcaagagaac atagcgttgc cttggtaggt ccagcggcgg aggaactctt tgatccggtt   3840

cctgaacagg atctatttga ggcgctaaat gaaaccttaa cgctatggaa ctcgccgccc   3900

gactgggctg gcgatgagcg aaatgtagtg cttacgttgt cccgcatttg gtacagcgca   3960

gtaaccggca aaatcgcgcc gaaggatgtc gctgccgact gggcaatgga gcgcctgccg   4020

gcccagtatc agcccgtcat acttgaagct agacaggctt atcttggaca agaagaagat   4080

cgcttggcct cgcgcgcaga tcagttggaa gaatttgtcc actacgtgaa aggcgagatc   4140

accaaggtag tgggcaaaga acttgttgaa ggaaaattgg agctagtaga aggtcttaaa   4200

gtcgccatgg ctagtaaagg agaagaactt ttcactggag ttgtcccaat tcttgttgaa   4260

ttagatggtg atgttaatgg gcacaaattt tctgtcagtg gagagggtga aggtgatgca   4320

acatacggaa aacttaccct taaatttatt tgcactactg gaaaactacc tgttccttgg   4380

ccaacacttg tcactacttt ctcttatggt gttcaatgct tttcaagata cccagatcat   4440

atgaagcggc acgacttctt caagagcgcc atgcctgagg gatacgtgca ggagaggacc   4500

atctctttca aggacgacgg gaactacaag acacgtgctg aagtcaagtt tgagggagac   4560

accctcgtca acaggatcga gcttaaggga atcgatttca aggaggacgg aaacatcctc   4620

ggccacaagt tggaatacaa ctacaactcc cacaacgtat acatcacggc agacaaacaa   4680

aagaatggaa tcaaagctaa cttcaaaatt agacacaaca ttgaagatgg aagcgttcaa   4740

ctagcagacc attatcaaca aaatactcca attggcgatg gccctgtcct tttaccagac   4800

aaccattacc tgtccacaca atctgccctt tcgaaagatc ccaacgaaaa gagagatcac   4860

atggtccttc ttgagtttgt aacagctgct gggattacac atggcatgga tgaactatac   4920

aaataagctt aaacagtaga cattagcaga taaattagca ggaaataaag aaggataagg   4980

agaaagaact caagtaatta tccttcgttc tcttaattga attgcaatta aactcggccc   5040

aatcttttac taaaaggatt gagccgaata ccgctacaac agctccctgg aacaccagga   5100

gaacacactt atctcgcgtc ttgaggtgat accacgcctg acacgtgagg gcagtacggt   5160

taattcggtt tagccggaca tcagcgctcc tcattgagcg ctgggccctt cacatgaaga   5220

tcgcactgag gattggtcct agccaggctt ctcagtactg atacagtacg cgtcgcttct   5280

cgtattgttt gagtcttgga attagtttgt atccttccgc cgctgcccta agaattctaa   5340

ttgagctcga acagtcgacc gccggatcct gctcgagtgc ctctaga                 5387
```

<210> SEQ ID NO 40
<211> LENGTH: 5387
<212> TYPE: DNA
<213> ORGANISM: Artificial Sequence
<220> FEATURE:
<223> OTHER INFORMATION: An example of an episomal DNA vector

<400> SEQUENCE: 40

```
tgccgtaata atattaagaa gaacgatgaa gaaaggttaa ggaaacgtac gaaggataac     60

gaaggctgtt gaagtcacaa tcgacaggag tgattaactg aggacaaatg ttgtcagaca    120

acccctcgtc ctggtcatgt gataggcttc tcgatgaaac tgttccatct ctaccccagt    180
```

-continued

```
agagaaaaat ccaggtcata tcataggaga tagaaatgaa tgacgagaac gaagacagaa    240
tgacgttgaa gagaacgatt aggtaatatg tagaaacgac aatgaaagtc ctcgaaggag    300
gcaggtaata aagatgacaa aggagcgcgc taccacgcga aacaagccat taggcagttc    360
tcctatcccc tccgaacgaa taccttttag taagagggtg aaacagtgac acaaagccgg    420
tgaggccgtc acgcgtactt cagaacatga gtgatgagta ctgttaaaca tacccaggcg    480
tgagccaaca atgcaaagaa ccctgagaag ggagtgaaag ggagcgcacg cgcaaggtcg    540
caactacccg agaatcgatg tggcggaatg ggttacgtga gctattatcc ggcgggccct    600
caatttaaat cgttacagtt gctcgtaacg gcaaccggct cggtcctttt tccctagaac    660
agtatcttat acttgctgct ctcgttactt cggcgatcct ggtgcagtcg gtccgtaaat    720
cggcgcacac ttttacgtcg taccagacag gctcgcataa gccagccccg acacccgcca    780
acacccgctg acgcgccctg acgggcttgt ctgctcccgg catccgctta cagacaagct    840
gtgacctccg ggagctgcat gtgtcagagg ttttcaccgt catcaccgaa acgcgcacga    900
aagggcctcg tgatacgcct atttttatag gttaatgtca tgataataat ggtttcttag    960
acgtcaggtg gcacttttcg gggaaatgtg cgcggaaccc ctatttgttt atttttctaa   1020
atacattcaa atatgtatcc gctcatgaga caataaccct gataaatgct tcaataatat   1080
tgaaaaagga agagtatgag tattcaacat ttccgtgtcg cccttattcc cttttttgcg   1140
gcattttgcc ttcctgtttt tgctcaccca gaaacgctgg tgaaagtaaa agatgctgaa   1200
gatcagttgg gtgcacgagt gggttacatc gaactggatc tcaacagcgg taagatcctt   1260
gagagttttc gccccgaaga acgttttcca atgatgagca cttttaaagt tctgctatgt   1320
ggcgcggtat tatcccgtat tgacgccggg caagagcaac tcggtcgccg catacactat   1380
tctcagaatg acttggttga gtactcacca gtcacagaaa agcatcttac ggatggcatg   1440
acagtaagag aattatgcag tgctgccata accatgagtg ataacactgc ggccaactta   1500
cttctgacaa cgatcggagg accgaaggag ctaaccgctt ttttgcacaa catgggggat   1560
catgtaactc gccttgatcg ttgggaaccg gagctgaatg aagccatacc aaacgacgag   1620
cgtgacacca cgatgcctgt agcaatggca acaacgttgc gcaaactatt aactggcgaa   1680
ctacttactc tagcttcccg gcaacaatta atagactgga tggaggcgga taaagttgca   1740
ggaccacttc tgcgctcggc ccttccggct ggctggttta ttgctgataa atctggagcc   1800
ggtgagcgtg gctcacgcgg tatcattgca gcactggggc cagatggtaa gccctcccgt   1860
atcgtagtta tctacacgac ggggagtcag gcaactatgg atgaacgaaa tagacagatc   1920
gctgagatag gtgcctcact gattaagcat tggtaactgt cagaccaagt ttactcatat   1980
atactttaga ttgatttaaa acttcatttt taatttaaaa ggatctaggt gaagatcctt   2040
tttgataatc tcatgaccaa aatcccttaa cgtgagtttt cgttccactg agcgtcagac   2100
cccgtagaaa agatcaaagg atcttcttga gatccttttt ttctgcgcgt aatctgctgc   2160
ttgcaaacaa aaaaaccacc gctaccagcg gtggtttgtt tgccggatca agagctacca   2220
actctttttc cgaaggtaac tggcttcagc agagcgcaga taccaaatac tgttcttcta   2280
gtgtagccgt agttaggcca ccacttcaag aactctgtag caccgcctac atacctcgct   2340
ctgctaatcc tgttaccagt ggctgctgcc agtggcgata agtcgtgtct taccgggttg   2400
gactcaagac gatagttacc ggataaggcg cagcggtcgg gctgaacggg gggttcgtgc   2460
acacagccca gcttggagcg aacgacctac accgaactga gatacctaca gcgtgagcta   2520
```

-continued

```
tgagaaagcg ccacgcttcc cgaagggaga aaggcggaca ggtatccggt aagcggcagg   2580
gtcggaacag gagagcgcac gagggagctt ccagggggaa acgcctggta tctttatagt   2640
cctgtcgggt ttcgccacct ctgacttgag cgtcgatttt tgtgatgctc gtcagggggg   2700
cggagcctat ggaaaaacgc cagcaacgcg gcctttttac ggttcctggc cttttgctgg   2760
ccttttgctc acatgttctt tcctgcgtta tcccctgatt ctgtggataa ccgtattacc   2820
gcctttgagt gagctgatac cgctcgccgc agccgaacga ccgagcgcag cgagtcagtg   2880
agcgaggaag cggaagaacg cggacaccca gcgtaacaat ctaatattgt ttctcaaatc   2940
gggctgttat cgcatggtgc tcatgatgag gttactgacc aaattcgcca cgcatcggtg   3000
ctggtagaat gttcacttcg aggtgggtag acggcgtcac gtgcaatgcc ttgtcttccc   3060
ctatctgcgg ccccgactgc ctcgcgaaga caagggatcg gacgtcgaac gtattctgtt   3120
tgctaccggc acgggagtag gatcgttgat atacaccatg cgcgttaact ctgaccccct   3180
tcctcttaaa tgagaatgga taagaggctc gtgggattga cgtgaggggg cagggatggc   3240
tatatttctg ggagcgaact ccgggcgaat tactaataaa aagccttcca ttttctattt   3300
tgatttgtag aaaactagtg tgcttgggag tccctgatga ttaaataaac caagatttta   3360
ccaatggggg ctagcgaagc ggtgatcgcc gaagtatcga ctcaactatc agaggtagtt   3420
ggcgtcatcg agcgccatct cgaaccgacg ttgctggccg tacatttgta cggctccgca   3480
gtggatggcg gcctgaagcc acacagtgat attgatttgc tggttacggt gaccgtaagg   3540
cttgatgaaa caacgcggcg agctttgatc aacgaccttt tggaaacttc ggcttcccct   3600
ggagagagcg agattctccg cgctgtagaa gtcaccattg ttgtgcacga cgacatcatt   3660
ccgtggcgtt atccagctaa gcgcgaactg caatttggag aatggcagcg caatgacatt   3720
cttgcaggta tcttcgagcc agccacgatc gacattgatc tggctatctt gctgacaaaa   3780
gcaagagaac atagcgttgc cttggtaggt ccagcggcgg aggaactctt tgatccggtt   3840
cctgaacagg atctatttga ggcgctaaat gaaaccttaa cgctatggaa ctcgccgccc   3900
gactgggctg gcgatgagcg aaatgtagtg cttacgttgt cccgcatttg gtacagcgca   3960
gtaaccggca aaatcgcgcc gaaggatgtc gctgccgact gggcaatgga gcgcctgccg   4020
gcccagtatc agcccgtcat acttgaagct agacaggctt atcttggaca agaagaagat   4080
cgcttggcct cgcgcgcaga tcagttggaa gaatttgtcc actacgtgaa aggcgagatc   4140
accaaggtag tgggcaaaga acttgttgaa ggaaaattgg agctagtaga aggtcttaaa   4200
gtcgccatgg ctagtaaagg agaagaactt ttcactggag ttgtcccaat tcttgttgaa   4260
ttagatggtg atgttaatgg gcacaaattt tctgtcagtg gagagggtga aggtgatgca   4320
acatacggaa aacttaccct taaatttatt tgcactactg gaaaactacc tgttccttgg   4380
ccaacacttg tcactacttt ctcttatggt gttcaatgct tttcaagata cccagatcat   4440
atgaagcggc acgacttctt caagagcgcc atgcctgagg gatacgtgca ggagaggacc   4500
atctctttca aggacgacgg gaactacaag acacgtgctg aagtcaagtt tgagggagac   4560
accctcgtca acaggatcga gcttaaggga atcgatttca aggaggacgg aaacatcctc   4620
ggccacaagt tggaatacaa ctacaactcc cacaacgtat acatcacggc agacaaacaa   4680
aagaatggaa tcaaagctaa cttcaaaatt agacacaaca ttgaagatgg aagcgttcaa   4740
ctagcagacc attatcaaca aaatactcca attggcgatg gccctgtcct tttaccagac   4800
aaccattacc tgtccacaca atctgccctt tcgaaagatc ccaacgaaaa gagagatcac   4860
atggtccttc ttgagtttgt aacagctgct gggattacac atggcatgga tgaactatac   4920
```

```
aaataagctt aaacagtaga cattagcaga taaattagca ggaaataaag aaggataagg   4980

agaaagaact caagtaatta tccttcgttc tcttaattga attgcaatta aactcggccc   5040

aatcttttac taaaaggatt gagccgaata ccgctacaac agctccctgg aacaccagga   5100

gaacacactt atctcgcgtc ttgaggtgat accacgcctg acacgtgagg gcagtacggt   5160

taattcggtt tagccggaca tcagcgctcc tcattgagcg ctgggccctt cacatgaaga   5220

tcgcactgag gattggtcct agccaggctt ctcagtactg atacagtacg cgtcgcttct   5280

cgtattgttt gagtcttgga attagtttgt atccttccgc cgctgcccta agaattctaa   5340

ttgagctcga acagtcgacc gccggatcct gctcgagtgc ctctaga                 5387


<210> SEQ ID NO 41
<211> LENGTH: 5270
<212> TYPE: DNA
<213> ORGANISM: Artificial Sequence
<220> FEATURE:
<223> OTHER INFORMATION: An example of an episomal DNA vector

<400> SEQUENCE: 41

tgcctgaact ggagaacaac gctgaataat gttgacgaag gataacgaac cctatgtcga     60

tacgtctctc taactgagga caaatgttgt cagacaaccc ctcgtcctgg tcatgtgata    120

ggcttctcga tgaaactgtt ccatctctac cccagtagag aaaaatacga tgacaccata    180

gggacatgaa tgagtgatcg agagaatcaa atgacaaacc tttctaagga cgattagaca    240

catgtagaaa cgacaactta taggtgccga aaggcaaaca atatggaata ggcctagtta    300

cggctggtca tgattaactt aaccctacct ggagagggtg ttggctccag ggtaacctcg    360

atgtgcctcc gtgcacgttt gctgctggtt actattggcc gtgggagcgc acgcgcaagg    420

tcgcaactac ccgagaatcg atgtggcgga atgggttacg tgagctatta tccggcgggc    480

cctcaattta aatcgttaca gttgctcgta acggcaaccg gctcggtcct tttccctag     540

aacagtatct tatacttgct gctctcgtta cttcggcgat cctggtgcag tcggtccgta    600

aatcggcgca cacttttacg tcgtaccaga caggctcgca taagccagcc ccgacacccg    660

ccaacacccg ctgacgcgcc ctgacgggct tgtctgctcc cggcatccgc ttacagacaa    720

gctgtgacct ccgggagctg catgtgtcag aggttttcac cgtcatcacc gaaacgcgca    780

cgaaagggcc tcgtgatacg cctattttta taggttaatg tcatgataat aatggtttct    840

tagacgtcag gtggcacttt tcggggaaat gtgcgcggaa cccctatttg tttatttttc    900

taaatacatt caaatatgta tccgctcatg agacaataac cctgataaat gcttcaataa    960

tattgaaaaa ggaagagtat gagtattcaa catttccgtg tcgcccttat tccctttttt   1020

gcggcatttt gccttcctgt ttttgctcac ccagaaacgc tggtgaaagt aaaagatgct   1080

gaagatcagt tgggtgcacg agtgggttac atcgaactgg atctcaacag cggtaagatc   1140

cttgagagtt ttcgccccga agaacgtttt ccaatgatga gcacttttaa agttctgcta   1200

tgtggcgcgg tattatcccg tattgacgcc gggcaagagc aactcggtcg ccgcatacac   1260

tattctcaga atgacttggt tgagtactca ccagtcacag aaaagcatct tacggatggc   1320

atgacagtaa gagaattatg cagtgctgcc ataaccatga gtgataacac tgcggccaac   1380

ttacttctga caacgatcgg aggaccgaag gagctaaccg cttttttgca caacatgggg   1440

gatcatgtaa ctcgccttga tcgttgggaa ccggagctga atgaagccat accaaacgac   1500

gagcgtgaca ccacgatgcc tgtagcaatg gcaacaacgt tgcgcaaact attaactggc   1560
```

gaactactta ctctagcttc ccggcaacaa ttaatagact ggatggaggc ggataaagtt 1620
gcaggaccac ttctgcgctc ggcccttccg gctggctggt ttattgctga taaatctgga 1680
gccggtgagc gtggctcacg cggtatcatt gcagcactgg ggccagatgg taagccctcc 1740
cgtatcgtag ttatctacac gacggggagt caggcaacta tggatgaacg aaatagacag 1800
atcgctgaga taggtgcctc actgattaag cattggtaac tgtcagacca agtttactca 1860
tatatacttt agattgattt aaaacttcat ttttaattta aaaggatcta ggtgaagatc 1920
ctttttgata atctcatgac caaaatccct taacgtgagt tttcgttcca ctgagcgtca 1980
gaccccgtag aaaagatcaa aggatcttct tgagatcctt tttttctgcg cgtaatctgc 2040
tgcttgcaaa caaaaaaacc accgctacca gcggtggttt gtttgccgga tcaagagcta 2100
ccaactcttt ttccgaaggt aactggcttc agcagagcgc agataccaaa tactgttctt 2160
ctagtgtagc cgtagttagg ccaccacttc aagaactctg tagcaccgcc tacatacctc 2220
gctctgctaa tcctgttacc agtggctgct gccagtggcg ataagtcgtg tcttaccggg 2280
ttggactcaa gacgatagtt accggataag gcgcagcggt cgggctgaac ggggggttcg 2340
tgcacacagc ccagcttgga gcgaacgacc tacaccgaac tgagatacct acagcgtgag 2400
ctatgagaaa gcgccacgct tcccgaaggg agaaaggcgg acaggtatcc ggtaagcggc 2460
agggtcggaa caggagagcg cacgagggag cttccagggg gaaacgcctg gtatctttat 2520
agtcctgtcg ggtttcgcca cctctgactt gagcgtcgat ttttgtgatg ctcgtcaggg 2580
gggcggagcc tatggaaaaa cgccagcaac gcggcctttt tacggttcct ggccttttgc 2640
tggccttttg ctcacatgtt ctttcctgcg ttatcccctg attctgtgga taaccgtatt 2700
accgcctttg agtgagctga taccgctcgc cgcagccgaa cgaccgagcg cagcgagtca 2760
gtgagcgagg aagcggaaga acgcggacac ccagcgtaac aatctaatat tgtttctcaa 2820
atcgggctgt tatcgcatgg tgctcatgat gaggttactg accaaattcg ccacgcatcg 2880
gtgctggtag aatgttcact tcgaggtggg tagacggcgt cacgtgcaat gccttgtctt 2940
cccctatctg cggccccgac tgcctcgcga agacaaggga tcggacgtcg aacgtattct 3000
gtttgctacc ggcacgggag taggatcgtt gatatacacc atgcgcgtta actctgaccc 3060
ccttcctctt aaatgagaat ggataagagg ctcgtgggat tgacgtgagg gggcagggat 3120
ggctatattt ctgggagcga actccgggcg aattactaat aaaaagcctt ccattttcta 3180
ttttgatttg tagaaaacta gtgtgcttgg gagtccctga tgattaaata aaccaagatt 3240
ttaccaatgg gggctagcga agcggtgatc gccgaagtat cgactcaact atcagaggta 3300
gttggcgtca tcgagcgcca tctcgaaccg acgttgctgg ccgtacattt gtacggctcc 3360
gcagtggatg gcggcctgaa gccacacagt gatattgatt tgctggttac ggtgaccgta 3420
aggcttgatg aaacaacgcg gcgagctttg atcaacgacc ttttggaaac ttcggcttcc 3480
cctggagaga gcgagattct ccgcgctgta gaagtcacca ttgttgtgca cgacgacatc 3540
attccgtggc gttatccagc taagcgcgaa ctgcaatttg gagaatggca gcgcaatgac 3600
attcttgcag gtatcttcga gccagccacg atcgacattg atctggctat cttgctgaca 3660
aaagcaagag aacatagcgt tgccttggta ggtccagcgg cggaggaact ctttgatccg 3720
gttcctgaac aggatctatt tgaggcgcta aatgaaacct taacgctatg gaactcgccg 3780
cccgactggg ctggcgatga gcgaaatgta gtgcttacgt tgtcccgcat ttggtacagc 3840
gcagtaaccg gcaaaatcgc gccgaaggat gtcgctgccg actgggcaat ggagcgcctg 3900
ccggcccagt atcagcccgt catacttgaa gctagacagg cttatcttgg acaagaagaa 3960

```
gatcgcttgg cctcgcgcgc agatcagttg gaagaatttg tccactacgt gaaaggcgag   4020
atcaccaagg tagtgggcaa agaacttgtt gaaggaaaat tggagctagt agaaggtctt   4080
aaagtcgcca tggctagtaa aggagaagaa cttttcactg gagttgtccc aattcttgtt   4140
gaattagatg gtgatgttaa tgggcacaaa ttttctgtca gtggagaggg tgaaggtgat   4200
gcaacatacg gaaaacttac ccttaaattt atttgcacta ctggaaaact acctgttcct   4260
tggccaacac ttgtcactac tttctcttat ggtgttcaat gcttttcaag atacccagat   4320
catatgaagc ggcacgactt cttcaagagc gccatgcctg agggatacgt gcaggagagg   4380
accatctctt tcaaggacga cgggaactac aagacacgtg ctgaagtcaa gtttgaggga   4440
gacaccctcg tcaacaggat cgagcttaag ggaatcgatt tcaaggagga cggaaacatc   4500
ctcggccaca agttggaata caactacaac tcccacaacg tatacatcac ggcagacaaa   4560
caaaagaatg gaatcaaagc taacttcaaa attagacaca acattgaaga tggaagcgtt   4620
caactagcag accattatca acaaaatact ccaattggcg atggccctgt ccttttacca   4680
gacaaccatt acctgtccac acaatctgcc ctttcgaaag atcccaacga aaagagagat   4740
cacatggtcc ttcttgagtt tgtaacagct gctgggatta cacatggcat ggatgaacta   4800
tacaaataag cttaaacagt agacattagc agataaatta gcaggaaata aagaaggata   4860
aggagaaaga actcaagtaa ttatccttcg ttctcttaat tgaattgcaa ttaaactcgg   4920
cccaatcttt tactaaaagg attgagccga ataccgctac aacagctccc tggaacacca   4980
ggagaacaca cttatctcgc gtcttgaggt gataccacgc ctgacacgtg agggcagtac   5040
ggttaattcg gtttagccgg acatcagcgc tcctcattga gcgctgggcc cttcacatga   5100
agatcgcact gaggattggt cctagccagg cttctcagta ctgatacagt acgcgtcgct   5160
tctcgtattg tttgagtctt ggaattagtt tgtatccttc cgccgctgcc ctaagaattc   5220
taattgagct cgaacagtcg accgccggat cctgctcgag tgcctctaga              5270
```

<210> SEQ ID NO 42
<211> LENGTH: 5350
<212> TYPE: DNA
<213> ORGANISM: Artificial Sequence
<220> FEATURE:
<223> OTHER INFORMATION: An example of an episomal DNA vector

<400> SEQUENCE: 42

```
tgcctgaact ggagaacaac gctgaataat gttgacgaag gataacgaac cctatgtcga     60
tacgtctctc taactgagga caaatgttgt cagacaaccc ctcgtcctgg tcatgtgata    120
ggcttctcga tgaaactgtt ccatctctac cccagtagag aaaaatacga tgacaccata    180
gggacatgaa tgagtgatcg agagaatcaa atgacaaacc tttctaagga cgattagaca    240
catgtagaaa cgacaactta taggtgccga aaggcaaaca atatggaata ggcctagtta    300
cggctggtca tgattaactt aaccctacct ggagagggtg ttggctccag ggtaacctcg    360
atgtgcctcc gtgcacgttt gctgctggtt actattggcc gtgggagcgc acgcgcaagg    420
tcgcaactac ccgagaatcg atgtggcgga atgggttacg tgagctatta tccggcgggc    480
cctcaattta aatcgttaca gttgctcgta acggcaaccg gctcggtcct tttccctag     540
aacagtatct tatacttgct gctctcgtta cttcggcgat cctggtgcag tcggtccgta    600
aatcggcgca cacttttacg tcgtaccaga caggctcgca taagccagcc ccgacacccg    660
ccaacacccg ctgacgcgcc ctgacgggct tgtctgctcc cggcatccgc ttacagacaa    720
```

-continued

```
gctgtgacct ccgggagctg catgtgtcag aggttttcac cgtcatcacc gaaacgcgca    780
cgaaagggcc tcgtgatacg cctattttta taggttaatg tcatgataat aatggtttct    840
tagacgtcag gtggcacttt tcggggaaat gtgcgcggaa cccctatttg tttatttttc    900
taaatacatt caaatatgta tccgctcatg agacaataac cctgataaat gcttcaataa    960
tattgaaaaa ggaagagtat gagtattcaa catttccgtg tcgcccttat tccctttttt   1020
gcggcatttt gccttcctgt ttttgctcac ccagaaacgc tggtgaaagt aaaagatgct   1080
gaagatcagt tgggtgcacg agtgggttac atcgaactgg atctcaacag cggtaagatc   1140
cttgagagtt ttcgccccga agaacgtttt ccaatgatga gcacttttaa agttctgcta   1200
tgtggcgcgg tattatcccg tattgacgcc gggcaagagc aactcggtcg ccgcatacac   1260
tattctcaga atgacttggt tgagtactca ccagtcacag aaaagcatct tacggatggc   1320
atgacagtaa gagaattatg cagtgctgcc ataaccatga gtgataacac tgcggccaac   1380
ttacttctga caacgatcgg aggaccgaag gagctaaccg cttttttgca caacatgggg   1440
gatcatgtaa ctcgccttga tcgttgggaa ccggagctga atgaagccat accaaacgac   1500
gagcgtgaca ccacgatgcc tgtagcaatg gcaacaacgt tgcgcaaact attaactggc   1560
gaactactta ctctagcttc ccggcaacaa ttaatagact ggatggaggc ggataaagtt   1620
gcaggaccac ttctgcgctc ggcccttccg gctggctggt ttattgctga taaatctgga   1680
gccggtgagc gtggctcacg cggtatcatt gcagcactgg ggccagatgg taagccctcc   1740
cgtatcgtag ttatctacac gacggggagt caggcaacta tggatgaacg aaatagacag   1800
atcgctgaga taggtgcctc actgattaag cattggtaac tgtcagacca agtttactca   1860
tatatacttt agattgattt aaaacttcat ttttaattta aaaggatcta ggtgaagatc   1920
ctttttgata atctcatgac caaaatccct taacgtgagt tttcgttcca ctgagcgtca   1980
gaccccgtag aaaagatcaa aggatcttct tgagatcctt tttttctgcg cgtaatctgc   2040
tgcttgcaaa caaaaaaacc accgctacca gcggtggttt gtttgccgga tcaagagcta   2100
ccaactcttt ttccgaaggt aactggcttc agcagagcgc agataccaaa tactgttctt   2160
ctagtgtagc cgtagttagg ccaccacttc aagaactctg tagcaccgcc tacatacctc   2220
gctctgctaa tcctgttacc agtggctgct gccagtggcg ataagtcgtg tcttaccggg   2280
ttggactcaa gacgatagtt accggataag gcgcagcggt cgggctgaac ggggggttcg   2340
tgcacacagc ccagcttgga gcgaacgacc tacaccgaac tgagatacct acagcgtgag   2400
ctatgagaaa gcgccacgct tcccgaaggg agaaaggcgg acaggtatcc ggtaagcggc   2460
agggtcggaa caggagagcg cacgagggag cttccagggg gaaacgcctg gtatctttat   2520
agtcctgtcg ggtttcgcca cctctgactt gagcgtcgat ttttgtgatg ctcgtcaggg   2580
gggcggagcc tatggaaaaa cgccagcaac gcggcctttt tacggttcct ggccttttgc   2640
tggccttttg ctcacatgtt ctttcctgcg ttatcccctg attctgtgga taaccgtatt   2700
accgcctttg agtgagctga taccgctcgc cgcagccgaa cgaccgagcg cagcgagtca   2760
gtgagcgagg aagcggaaga acgcggacac ccagcgtaac aatctaatat tgtttctcaa   2820
atcgggctgt tatcgcatgg tgctcatgat gaggttactg accaaattcg ccacgcatcg   2880
gtgctggtag aatgttcact tcgaggtggg tagacggcgt cacgtgcaat gccttgtctt   2940
cccctatctg cggccccgac tgcctcgcga agacaaggga tcggacgtcg aacgtattct   3000
gtttgctacc ggcacgggag taggatcgtt gatatacacc atgcgcgtta actctgaccc   3060
ccttcctctt aaatgagaat ggataagagg ctcgtgggat tgacgtgagg gggcagggat   3120
```

```
ggctatattt ctgggagcga actccgggcg aattactaat aaaaagcctt ccattttcta   3180
ttttgatttg tagaaaacta gtgtgcttgg gagtccctga tgattaaata aaccaagatt   3240
ttaccaatgg gggctagcga agcggtgatc gccgaagtat cgactcaact atcagaggta   3300
gttggcgtca tcgagcgcca tctcgaaccg acgttgctgg ccgtacattt gtacggctcc   3360
gcagtggatg gcggcctgaa gccacacagt gatattgatt tgctggttac ggtgaccgta   3420
aggcttgatg aaacaacgcg gcgagctttg atcaacgacc ttttggaaac ttcggcttcc   3480
cctggagaga gcgagattct ccgcgctgta gaagtcacca ttgttgtgca cgacgacatc   3540
attccgtggc gttatccagc taagcgcgaa ctgcaatttg gagaatggca gcgcaatgac   3600
attcttgcag gtatcttcga gccagccacg atcgacattg atctggctat cttgctgaca   3660
aaagcaagag aacatagcgt tgccttggta ggtccagcgg cggaggaact ctttgatccg   3720
gttcctgaac aggatctatt tgaggcgcta aatgaaacct taacgctatg gaactcgccg   3780
cccgactggg ctggcgatga gcgaaatgta gtgcttacgt tgtcccgcat ttggtacagc   3840
gcagtaaccg gcaaaatcgc gccgaaggat gtcgctgccg actgggcaat ggagcgcctg   3900
ccggcccagt atcagcccgt catacttgaa gctagacagg cttatcttgg acaagaagaa   3960
gatcgcttgg cctcgcgcgc agatcagttg gaagaatttg tccactacgt gaaaggcgag   4020
atcaccaagg tagtgggcaa agaacttgtt gaaggaaaat tggagctagt agaaggtctt   4080
aaagtcgcca tggctagtaa aggagaagaa cttttcactg gagttgtccc aattcttgtt   4140
gaattagatg gtgatgttaa tgggcacaaa ttttctgtca gtggagaggg tgaaggtgat   4200
gcaacatacg gaaaacttac ccttaaattt atttgcacta ctggaaaact acctgttcct   4260
tggccaacac ttgtcactac tttctcttat ggtgttcaat gcttttcaag atacccagat   4320
catatgaagc ggcacgactt cttcaagagc gccatgcctg agggatacgt gcaggagagg   4380
accatctctt tcaaggacga cgggaactac aagacacgtg ctgaagtcaa gtttgaggga   4440
gacaccctcg tcaacaggat cgagcttaag ggaatcgatt tcaaggagga cggaaacatc   4500
ctcggccaca agttggaata caactacaac tcccacaacg tatacatcac ggcagacaaa   4560
caaaagaatg gaatcaaagc taacttcaaa attagacaca acattgaaga tggaagcgtt   4620
caactagcag accattatca acaaaatact ccaattggcg atggccctgt ccttttacca   4680
gacaaccatt acctgtccac acaatctgcc ctttcgaaag atcccaacga aaagagagat   4740
cacatggtcc ttcttgagtt tgtaacagct gctgggatta cacatggcat ggatgaacta   4800
tacaaataag cttaaacagt agacattagc agataaatta gcaggaaata aagaaggata   4860
aggagaaaga actcaagtaa ttatccttcg ttctcttaat tgaattgcaa ttaaactcgg   4920
cccaatcttt tactaaaagg attgagccga ataccgctcc aggcatcaaa taaaacgaaa   4980
ggctcagtcg aaagactggg cctttcgttt tatctgttgt ttgtcggtga acgctctcac   5040
aacagctccc tggaacacca ggagaacaca cttatctcgc gtcttgaggt gataccacgc   5100
ctgacacgtg agggcagtac ggttaattcg gtttagccgg acatcagcgc tcctcattga   5160
gcgctgggcc cttcacatga agatcgcact gaggattggt cctagccagg cttctcagta   5220
ctgatacagt acgcgtcgct tctcgtattg tttgagtctt ggaattagtt tgtatccttc   5280
cgccgctgcc ctaagaattc taattgagct cgaacagtcg accgccggat cctgctcgag   5340
tgcctctaga                                                          5350
```

<210> SEQ ID NO 43

<211> LENGTH: 5444
<212> TYPE: DNA
<213> ORGANISM: Artificial Sequence
<220> FEATURE:
<223> OTHER INFORMATION: An example of an episomal DNA vector

<400> SEQUENCE: 43

```
tgcccttaac gactaggcga tcaaaactaa tgtaggtgta aagaatgatg tcttaaacgt     60
acgaaggata acgaaggctg ttgaagtcac aatcgacagg agtgattaac tgaggacaaa    120
tgttgtcaga caacccctcg tcctggtcat gtgataggct tctcgatgaa actgttccat    180
ctctacccca gtagagaaaa atccaggtca tatcatagga gatagaaatg aatgacgaga    240
acgaagacag aatgacgttg aagagaacga ttaggtaata tgtagaaacg acaacaatat    300
gagtaataaa gatgaaatag gcctaactgc ggttggtcat gattaaacga acctcctggt    360
tgggtagaaa caccagttag ccgaagttgc ctaagtgcaa tggtatctag aattcagtgc    420
ctggctatta aggaaccctc gtaggaggga gaatatgaac tactgcctcg atgtaacatc    480
agatgcaaga actctaatgt gagttaagat gcctattcag catcaggtgc ctatgtgtac    540
catcaaagtc atgggattac tcttctctat tattgaggga gcgcacgcgc aaggtcgcaa    600
ctacccgaga atcgatgtgg cggaatgggt tacgtgagct attatccggc gggccctcaa    660
tttaaatcgt tacagttgct cgtaacggca accggctcgg tccttttttcc ctagaacagt    720
atcttatact tgctgctctc gttacttcgg cgatcctggt gcagtcggtc cgtaaatcgg    780
cgcacacttt tacgtcgtac cagacaggct cgcataagcc agccccgaca cccgccaaca    840
cccgctgacg cgccctgacg ggcttgtctg ctcccggcat ccgcttacag acaagctgtg    900
acctccggga gctgcatgtg tcagaggttt tcaccgtcat caccgaaacg cgcacgaaag    960
ggcctcgtga tacgcctatt tttataggtt aatgtcatga taataatggt ttcttagacg   1020
tcaggtggca cttttcgggg aaatgtgcgc ggaaccccta tttgtttatt tttctaaata   1080
cattcaaata tgtatccgct catgagacaa taaccctgat aaatgcttca ataatattga   1140
aaaaggaaga gtatgagtat tcaacatttc cgtgtcgccc ttattccctt ttttgcggca   1200
ttttgccttc ctgtttttgc tcacccagaa acgctggtga aagtaaaaga tgctgaagat   1260
cagttgggtg cacgagtggg ttacatcgaa ctggatctca acagcggtaa gatccttgag   1320
agttttcgcc ccgaagaacg ttttccaatg atgagcactt ttaaagttct gctatgtggc   1380
gcggtattat cccgtattga cgccgggcaa gagcaactcg gtcgccgcat acactattct   1440
cagaatgact tggttgagta ctcaccagtc acagaaaagc atcttacgga tggcatgaca   1500
gtaagagaat tatgcagtgc tgccataacc atgagtgata acactgcggc caacttactt   1560
ctgacaacga tcggaggacc gaaggagcta accgcttttt tgcacaacat gggggatcat   1620
gtaactcgcc ttgatcgttg ggaaccggag ctgaatgaag ccataccaaa cgacgagcgt   1680
gacaccacga tgcctgtagc aatggcaaca acgttgcgca aactattaac tggcgaacta   1740
cttactctag cttcccggca acaattaata gactggatgg aggcggataa agttgcagga   1800
ccacttctgc gctcggccct tccggctggc tggtttattg ctgataaatc tggagccggt   1860
gagcgtggct cacgcggtat cattgcagca ctggggccag atggtaagcc ctcccgtatc   1920
gtagttatct acacgacggg gagtcaggca actatggatg aacgaaatag acagatcgct   1980
gagataggtg cctcactgat taagcattgg taactgtcag accaagttta ctcatatata   2040
ctttagattg atttaaaact tcatttttaa tttaaaagga tctaggtgaa gatccttttt   2100
gataatctca tgaccaaaat cccttaacgt gagttttcgt tccactgagc gtcagacccc   2160
```

gtagaaaaga tcaaaggatc ttcttgagat cctttttttc tgcgcgtaat ctgctgcttg 2220
caaacaaaaa aaccaccgct accagcggtg gtttgtttgc cggatcaaga gctaccaact 2280
ctttttccga aggtaactgg cttcagcaga gcgcagatac caaatactgt tcttctagtg 2340
tagccgtagt taggccacca cttcaagaac tctgtagcac cgcctacata cctcgctctg 2400
ctaatcctgt taccagtggc tgctgccagt ggcgataagt cgtgtcttac cgggttggac 2460
tcaagacgat agttaccgga taaggcgcag cggtcgggct gaacgggggg ttcgtgcaca 2520
cagcccagct tggagcgaac gacctacacc gaactgagat acctacagcg tgagctatga 2580
gaaagcgcca cgcttcccga agggagaaag gcggacaggt atccggtaag cggcagggtc 2640
ggaacaggag agcgcacgag ggagcttcca gggggaaacg cctggtatct ttatagtcct 2700
gtcgggtttc gccacctctg acttgagcgt cgatttttgt gatgctcgtc aggggggcgg 2760
agcctatgga aaaacgccag caacgcggcc tttttacggt tcctggcctt ttgctggcct 2820
tttgctcaca tgttctttcc tgcgttatcc cctgattctg tggataaccg tattaccgcc 2880
tttgagtgag ctgataccgc tcgccgcagc cgaacgaccg agcgcagcga gtcagtgagc 2940
gaggaagcgg aagaacgcgg acacccagcg taacaatcta atattgtttc tcaaatcggg 3000
ctgttatcgc atggtgctca tgatgaggtt actgaccaaa ttcgccacgc atcggtgctg 3060
gtagaatgtt cacttcgagg tgggtagacg gcgtcacgtg caatgccttg tcttccccta 3120
tctgcggccc cgactgcctc gcgaagacaa gggatcggac gtcgaacgta ttctgtttgc 3180
taccggcacg ggagtaggat cgttgatata caccatgcgc gttaactctg accccccttcc 3240 tcttaaatga gaatggataa gaggctcgtg ggattgacgt gagggggcag ggatggctat 3300
atttctggga gcgaactccg ggcgaattac taataaaaag ccttccattt tctattttga 3360
tttgtagaaa actagtgtgc ttgggagtcc ctgatgatta aataaaccaa gattttacca 3420
atgggggcta gcgaagcggt gatcgccgaa gtatcgactc aactatcaga ggtagttggc 3480
gtcatcgagc gccatctcga accgacgttg ctggccgtac atttgtacgg ctccgcagtg 3540
gatggcggcc tgaagccaca cagtgatatt gatttgctgg ttacggtgac cgtaaggctt 3600
gatgaaacaa cgcggcgagc tttgatcaac gaccttttgg aaacttcggc ttcccctgga 3660
gagagcgaga ttctccgcgc tgtagaagtc accattgttg tgcacgacga catcattccg 3720
tggcgttatc cagctaagcg cgaactgcaa tttggagaat ggcagcgcaa tgacattctt 3780
gcaggtatct tcgagccagc cacgatcgac attgatctgg ctatcttgct gacaaaagca 3840
agagaacata gcgttgcctt ggtaggtcca gcggcggagg aactctttga tccggttcct 3900
gaacaggatc tatttgaggc gctaaatgaa accttaacgc tatggaactc gccgcccgac 3960
tgggctggcg atgagcgaaa tgtagtgctt acgttgtccc gcatttggta cagcgcagta 4020
accggcaaaa tcgcgccgaa ggatgtcgct gccgactggg caatggagcg cctgccggcc 4080
cagtatcagc ccgtcatact tgaagctaga caggcttatc ttggacaaga agaagatcgc 4140
ttggcctcgc gcgcagatca gttggaagaa tttgtccact acgtgaaagg cgagatcacc 4200
aaggtagtgg gcaaagaact tgttgaagga aaattggagc tagtagaagg tcttaaagtc 4260
gccatggcta gtaaaggaga agaacttttc actggagttg tcccaattct tgttgaatta 4320
gatggtgatg ttaatgggca caaattttct gtcagtggag agggtgaagg tgatgcaaca 4380
tacggaaaac ttacccttaa atttatttgc actactggaa aactacctgt tccttggcca 4440
acacttgtca ctactttctc ttatggtgtt caatgctttt caagataccc agatcatatg 4500

```
aagcggcacg acttcttcaa gagcgccatg cctgagggat acgtgcagga gaggaccatc   4560
tctttcaagg acgacgggaa ctacaagaca cgtgctgaag tcaagtttga gggagacacc   4620
ctcgtcaaca ggatcgagct taagggaatc gatttcaagg aggacggaaa catcctcggc   4680
cacaagttgg aatacaacta caactcccac aacgtataca tcacggcaga caaacaaaag   4740
aatggaatca aagctaactt caaaattaga cacaacattg aagatggaag cgttcaacta   4800
gcagaccatt atcaacaaaa tactccaatt ggcgatggcc ctgtcctttt accagacaac   4860
cattacctgt ccacacaatc tgccctttcg aaagatccca acgaaaagag agatcacatg   4920
gtccttcttg agtttgtaac agctgctggg attacacatg gcatggatga actatacaaa   4980
taagcttaaa cagtagacat tagcagataa attagcagga aataaagaag gataaggaga   5040
aagaactcaa gtaattatcc ttcgttctct taattgaatt gcaattaaac tcggcccaat   5100
cttttactaa aaggattgag ccgaataccg ctacaacagc tccctggaac accaggagaa   5160
cacacttatc tcgcgtcttg aggtgatacc acgcctgaca cgtgagggca gtacggttaa   5220
ttcggtttag ccggacatca gcgctcctca ttgagcgctg ggcccttcac atgaagatcg   5280
cactgaggat tggtcctagc caggcttctc agtactgata cagtacgcgt cgcttctcgt   5340
attgtttgag tcttggaatt agtttgtatc cttccgccgc tgccctaaga attctaattg   5400
agctcgaaca gtcgaccgcc ggatcctgct cgagtgcctc taga                    5444
```

<210> SEQ ID NO 44
<211> LENGTH: 5524
<212> TYPE: DNA
<213> ORGANISM: Artificial Sequence
<220> FEATURE:
<223> OTHER INFORMATION: An example of an episomal DNA vector

<400> SEQUENCE: 44

```
tgcccttaac gactaggcga tcaaaactaa tgtaggtgta aagaatgatg tcttaaacgt     60
acgaaggata acgaaggctg ttgaagtcac aatcgacagg agtgattaac tgaggacaaa    120
tgttgtcaga caacccctcg tcctggtcat gtgataggct tctcgatgaa actgttccat    180
ctctacccca gtagagaaaa atccaggtca tatcatagga gatagaaatg aatgacgaga    240
acgaagacag aatgacgttg aagagaacga ttaggtaata tgtagaaacg acaacaatat    300
gagtaataaa gatgaaatag gcctaactgc ggttggtcat gattaaacga acctcctggt    360
tgggtagaaa caccagttag ccgaagttgc ctaagtgcaa tggtatctag aattcagtgc    420
ctggctatta aggaaccctc gtaggaggga gaatatgaac tactgcctcg atgtaacatc    480
agatgcaaga actctaatgt gagttaagat gcctattcag catcaggtgc ctatgtgtac    540
catcaaagtc atgggattac tcttctctat tattgaggga gcgcacgcgc aaggtcgcaa    600
ctacccgaga atcgatgtgg cggaatgggt tacgtgagct attatccggc gggccctcaa    660
tttaaatcgt tacagttgct cgtaacggca accggctcgg tcctttttcc ctagaacagt    720
atcttatact tgctgctctc gttacttcgg cgatcctggt gcagtcggtc cgtaaatcgg    780
cgcacacttt tacgtcgtac cagacaggct cgcataagcc agccccgaca cccgccaaca    840
cccgctgacg cgccctgacg ggcttgtctg ctcccggcat ccgcttacag acaagctgtg    900
acctccggga gctgcatgtg tcagaggttt tcaccgtcat caccgaaacg cgcacgaaag    960
ggcctcgtga tacgcctatt tttataggtt aatgtcatga taataatggt ttcttagacg   1020
tcaggtggca cttttcgggg aaatgtgcgc ggaacccta tttgtttatt tttctaaata   1080
cattcaaata tgtatccgct catgagacaa taaccctgat aaatgcttca ataatattga   1140
```

```
aaaaggaaga gtatgagtat tcaacatttc cgtgtcgccc ttattccctt ttttgcggca   1200
ttttgccttc ctgtttttgc tcacccagaa acgctggtga aagtaaaaga tgctgaagat   1260
cagttgggtg cacgagtggg ttacatcgaa ctggatctca acagcggtaa gatccttgag   1320
agttttcgcc ccgaagaacg ttttccaatg atgagcactt ttaaagttct gctatgtggc   1380
gcggtattat cccgtattga cgccgggcaa gagcaactcg gtcgccgcat acactattct   1440
cagaatgact tggttgagta ctcaccagtc acagaaaagc atcttacgga tggcatgaca   1500
gtaagagaat tatgcagtgc tgccataacc atgagtgata acactgcggc caacttactt   1560
ctgacaacga tcggaggacc gaaggagcta accgcttttt tgcacaacat gggggatcat   1620
gtaactcgcc ttgatcgttg ggaaccggag ctgaatgaag ccataccaaa cgacgagcgt   1680
gacaccacga tgcctgtagc aatggcaaca acgttgcgca aactattaac tggcgaacta   1740
cttactctag cttcccggca acaattaata gactggatgg aggcggataa agttgcagga   1800
ccacttctgc gctcggccct tccggctggc tggtttattg ctgataaatc tggagccggt   1860
gagcgtggct cacgcggtat cattgcagca ctggggccag atggtaagcc ctcccgtatc   1920
gtagttatct acacgacggg gagtcaggca actatggatg aacgaaatag acagatcgct   1980
gagataggtg cctcactgat taagcattgg taactgtcag accaagttta ctcatatata   2040
ctttagattg atttaaaact tcatttttaa tttaaaagga tctaggtgaa gatccttttt   2100
gataatctca tgaccaaaat cccttaacgt gagttttcgt tccactgagc gtcagacccc   2160
gtagaaaaga tcaaaggatc ttcttgagat cctttttttc tgcgcgtaat ctgctgcttg   2220
caaacaaaaa aaccaccgct accagcggtg gtttgtttgc cggatcaaga gctaccaact   2280
ctttttccga aggtaactgg cttcagcaga gcgcagatac caaatactgt tcttctagtg   2340
tagccgtagt taggccacca cttcaagaac tctgtagcac cgcctacata cctcgctctg   2400
ctaatcctgt taccagtggc tgctgccagt ggcgataagt cgtgtcttac cgggttggac   2460
tcaagacgat agttaccgga taaggcgcag cggtcgggct gaacgggggg ttcgtgcaca   2520
cagcccagct tggagcgaac gacctacacc gaactgagat acctacagcg tgagctatga   2580
gaaagcgcca cgcttcccga agggagaaag gcggacaggt atccggtaag cggcagggtc   2640
ggaacaggag agcgcacgag ggagcttcca gggggaaacg cctggtatct ttatagtcct   2700
gtcgggtttc gccacctctg acttgagcgt cgatttttgt gatgctcgtc aggggggcgg   2760
agcctatgga aaaacgccag caacgcggcc tttttacggt tcctggcctt ttgctggcct   2820
tttgctcaca tgttctttcc tgcgttatcc cctgattctg tggataaccg tattaccgcc   2880
tttgagtgag ctgataccgc tcgccgcagc cgaacgaccg agcgcagcga gtcagtgagc   2940
gaggaagcgg aagaacgcgg acacccagcg taacaatcta atattgtttc tcaaatcggg   3000
ctgttatcgc atggtgctca tgatgaggtt actgaccaaa ttcgccacgc atcggtgctg   3060
gtagaatgtt cacttcgagg tgggtagacg gcgtcacgtg caatgccttg tcttccccta   3120
tctgcggccc cgactgcctc gcgaagacaa gggatcggac gtcgaacgta ttctgtttgc   3180
taccggcacg ggagtaggat cgttgatata caccatgcgc gttaactctg accccccttcc   3240
tcttaaatga gaatggataa gaggctcgtg ggattgacgt gagggggcag ggatggctat   3300
atttctggga gcgaactccg ggcgaattac taataaaaag ccttccattt tctattttga   3360
tttgtagaaa actagtgtgc ttgggagtcc ctgatgatta aataaaccaa gatttaccca   3420
atgggggcta gcgaagcggt gatcgccgaa gtatcgactc aactatcaga ggtagttggc   3480
```

-continued

```
gtcatcgagc gccatctcga accgacgttg ctggccgtac atttgtacgg ctccgcagtg   3540
gatggcggcc tgaagccaca cagtgatatt gatttgctgg ttacggtgac cgtaaggctt   3600
gatgaaacaa cgcggcgagc tttgatcaac gaccttttgg aaacttcggc ttcccctgga   3660
gagagcgaga ttctccgcgc tgtagaagtc accattgttg tgcacgacga catcattccg   3720
tggcgttatc cagctaagcg cgaactgcaa tttggagaat ggcagcgcaa tgacattctt   3780
gcaggtatct tcgagccagc cacgatcgac attgatctgg ctatcttgct gacaaaagca   3840
agagaacata gcgttgcctt ggtaggtcca gcggcggagg aactctttga tccggttcct   3900
gaacaggatc tatttgaggc gctaaatgaa accttaacgc tatggaactc gccgcccgac   3960
tgggctggcg atgagcgaaa tgtagtgctt acgttgtccc gcatttggta cagcgcagta   4020
accggcaaaa tcgcgccgaa ggatgtcgct gccgactggg caatggagcg cctgccggcc   4080
cagtatcagc ccgtcatact tgaagctaga caggcttatc ttggacaaga agaagatcgc   4140
ttggcctcgc gcgcagatca gttggaagaa tttgtccact acgtgaaagg cgagatcacc   4200
aaggtagtgg gcaaagaact tgttgaagga aaattggagc tagtagaagg tcttaaagtc   4260
gccatggcta gtaaaggaga agaacttttc actggagttg tcccaattct tgttgaatta   4320
gatggtgatg ttaatgggca caaattttct gtcagtggag agggtgaagg tgatgcaaca   4380
tacggaaaac ttacccttaa atttatttgc actactggaa aactacctgt tccttggcca   4440
acacttgtca ctactttctc ttatggtgtt caatgctttt caagataccc agatcatatg   4500
aagcggcacg acttcttcaa gagcgccatg cctgagggat acgtgcagga gaggaccatc   4560
tctttcaagg acgacgggaa ctacaagaca cgtgctgaag tcaagtttga gggagacacc   4620
ctcgtcaaca ggatcgagct taagggaatc gatttcaagg aggacggaaa catcctcggc   4680
cacaagttgg aatacaacta caactcccac aacgtataca tcacggcaga caaacaaaag   4740
aatggaatca aagctaactt caaaattaga cacaacattg aagatggaag cgttcaacta   4800
gcagaccatt atcaacaaaa tactccaatt ggcgatggcc ctgtcctttt accagacaac   4860
cattacctgt ccacacaatc tgccctttcg aaagatccca acgaaaagag agatcacatg   4920
gtccttcttg agtttgtaac agctgctggg attacacatg gcatggatga actatacaaa   4980
taagcttaaa cagtagacat tagcagataa attagcagga aataaagaag gataaggaga   5040
aagaactcaa gtaattatcc ttcgttctct taattgaatt gcaattaaac tcggcccaat   5100
cttttactaa aaggattgag ccgaataccg ctccaggcat caaataaaac gaaaggctca   5160
gtcgaaagac tgggcctttc gttttatctg ttgtttgtcg gtgaacgctc tcacaacagc   5220
tccctggaac accaggagaa cacacttatc tcgcgtcttg aggtgatacc acgcctgaca   5280
cgtgagggca gtacggttaa ttcggtttag ccggacatca gcgctcctca ttgagcgctg   5340
ggcccttcac atgaagatcg cactgaggat tggtcctagc caggcttctc agtactgata   5400
cagtacgcgt cgcttctcgt attgtttgag tcttggaatt agtttgtatc cttccgccgc   5460
tgccctaaga attctaattg agctcgaaca gtcgaccgcc ggatcctgct cgagtgcctc   5520
taga                                                                 5524
```

<210> SEQ ID NO 45
<211> LENGTH: 5398
<212> TYPE: DNA
<213> ORGANISM: Artificial Sequence
<220> FEATURE:
<223> OTHER INFORMATION: An example of an episomal DNA vector

<400> SEQUENCE: 45

```
tgccctgttt cactgccgca agacttgtgc ctaacttcgt tatacggtga acagacttgc      60
gataggctgc ccgtttcgac tctaaataag tctattttag ctaatttagt cagtttttcc     120
ctctcaaagg ggggtctggt gacttttggg ggttttttga aagttccatg ttttgacttt     180
ccagaataag tagaggggtt agtttttcaa gaatgttttg aaaagttaag aaatctttga     240
tgggtttgca atattttgac ccacatttac tcatttttcc ctctcaaagg ggggtctggt     300
gacttttggg ggtttttcga aagttccatg ttttgacttt ccagaataag tagaggggtt     360
agtttttaa gacaattgaa atgggtgttt aagaaatctt agtttttccc tctcaaaggg     420
gggtctggtg acttttgggg gttttttgaa agttccatgt tttgacttta gcaaataagt     480
agaggggtta gtttttaga aaagtttaag aaagtttagc caattgttat gggagcgcac     540
gcgcaaggtc gcaactaccc gagaatcgat gtggcggaat gggttacgtg agctattatc     600
cggcgggccc tcaatttaaa tcgttacagt tgctcgtaac ggcaaccggc tcggtccttt     660
ttccctagaa cagtatctta tacttgctgc tctcgttact tcggcgatcc tggtgcagtc     720
ggtccgtaaa tcggcgcaca cttttacgtc gtaccagaca ggctcgcata agccagcccc     780
gacacccgcc aacacccgct gacgcgccct gacgggcttg tctgctcccg gcatccgctt     840
acagacaagc tgtgacctcc gggagctgca tgtgtcagag gttttcaccg tcatcaccga     900
aacgcgcacg aaagggcctc gtgatacgcc tatttttata ggttaatgtc atgataataa     960
tggtttctta gacgtcaggt ggcacttttc ggggaaatgt gcgcggaacc cctatttgtt    1020
tatttttcta aatacattca aatatgtatc cgctcatgag acaataaccc tgataaatgc    1080
ttcaataata ttgaaaaagg aagagtatga gtattcaaca tttccgtgtc gcccttattc    1140
ccttttttgc ggcattttgc cttcctgttt ttgctcaccc agaaacgctg gtgaaagtaa    1200
aagatgctga agatcagttg ggtgcacgag tgggttacat cgaactggat ctcaacagcg    1260
gtaagatcct tgagagtttt cgccccgaag aacgttttcc aatgatgagc acttttaaag    1320
ttctgctatg tggcgcggta ttatcccgta ttgacgccgg gcaagagcaa ctcggtcgcc    1380
gcatacacta ttctcagaat gacttggttg agtactcacc agtcacagaa aagcatctta    1440
cggatggcat gacagtaaga gaattatgca gtgctgccat aaccatgagt gataacactg    1500
cggccaactt acttctgaca acgatcggag gaccgaagga gctaaccgct tttttgcaca    1560
acatggggga tcatgtaact cgccttgatc gttgggaacc ggagctgaat gaagccatac    1620
caaacgacga gcgtgacacc acgatgcctg tagcaatggc aacaacgttg cgcaaactat    1680
taactggcga actacttact ctagcttccc ggcaacaatt aatagactgg atggaggcgg    1740
ataaagttgc aggaccactt ctgcgctcgg cccttccggc tggctggttt attgctgata    1800
aatctggagc cggtgagcgt ggctcacgcg gtatcattgc agcactgggg ccagatggta    1860
agccctcccg tatcgtagtt atctacacga cggggagtca ggcaactatg gatgaacgaa    1920
atagacagat cgctgagata ggtgcctcac tgattaagca ttggtaactg tcagaccaag    1980
tttactcata tatactttag attgatttaa aacttcattt ttaatttaaa aggatctagg    2040
tgaagatcct ttttgataat ctcatgacca aaatccctta acgtgagttt tcgttccact    2100
gagcgtcaga ccccgtagaa aagatcaaag gatcttcttg agatcctttt tttctgcgcg    2160
taatctgctg cttgcaaaca aaaaaaccac cgctaccagc ggtggtttgt ttgccggatc    2220
aagagctacc aactcttttt ccgaaggtaa ctggcttcag cagagcgcag ataccaaata    2280
ctgttcttct agtgtagccg tagttaggcc accacttcaa gaactctgta gcaccgccta    2340
```

-continued

```
catacctcgc tctgctaatc ctgttaccag tggctgctgc cagtggcgat aagtcgtgtc   2400
ttaccgggtt ggactcaaga cgatagttac cggataaggc gcagcggtcg ggctgaacgg   2460
ggggttcgtg cacacagccc agcttggagc gaacgaccta caccgaactg agatacctac   2520
agcgtgagct atgagaaagc gccacgcttc ccgaagggag aaaggcggac aggtatccgg   2580
taagcggcag ggtcggaaca ggagagcgca cgagggagct tccaggggga aacgcctggt   2640
atctttatag tcctgtcggg tttcgccacc tctgacttga gcgtcgattt ttgtgatgct   2700
cgtcaggggg gcggagccta tggaaaaacg ccagcaacgc ggccttttta cggttcctgg   2760
ccttttgctg gccttttgct cacatgttct ttcctgcgtt atcccctgat tctgtggata   2820
accgtattac cgcctttgag tgagctgata ccgctcgccg cagccgaacg accgagcgca   2880
gcgagtcagt gagcgaggaa gcggaagaac gcggacaccc agcgtaacaa tctaatattg   2940
tttctcaaat cgggctgtta tcgcatggtg ctcatgatga ggttactgac caaattcgcc   3000
acgcatcggt gctggtagaa tgttcacttc gaggtgggta gacggcgtca cgtgcaatgc   3060
cttgtcttcc cctatctgcg gccccgactg cctcgcgaag acaagggatc ggacgtcgaa   3120
cgtattctgt ttgctaccgg cacgggagta ggatcgttga tatacaccat gcgcgttaac   3180
tctgaccccc ttcctcttaa atgagaatgg ataagaggct cgtgggattg acgtgagggg   3240
gcagggatgg ctatatttct gggagcgaac tccgggcgaa ttactaataa aaagccttcc   3300
attttctatt ttgatttgta gaaaactagt gtgcttggga gtccctgatg attaaataaa   3360
ccaagatttt accaatgggg gctagcgaag cggtgatcgc cgaagtatcg actcaactat   3420
cagaggtagt tggcgtcatc gagcgccatc tcgaaccgac gttgctggcc gtacatttgt   3480
acggctccgc agtggatggc ggcctgaagc cacacagtga tattgatttg ctggttacgg   3540
tgaccgtaag gcttgatgaa acaacgcggc gagctttgat caacgacctt ttggaaactt   3600
cggcttcccc tggagagagc gagattctcc gcgctgtaga agtcaccatt gttgtgcacg   3660
acgacatcat tccgtggcgt tatccagcta agcgcgaact gcaatttgga gaatggcagc   3720
gcaatgacat tcttgcaggt atcttcgagc cagccacgat cgacattgat ctggctatct   3780
tgctgacaaa agcaagagaa catagcgttg ccttggtagg tccagcggcg gaggaactct   3840
ttgatccggt tcctgaacag gatctatttg aggcgctaaa tgaaacctta acgctatgga   3900
actcgccgcc cgactgggct ggcgatgagc gaaatgtagt gcttacgttg tcccgcattt   3960
ggtacagcgc agtaaccggc aaaatcgcgc cgaaggatgt cgctgccgac tgggcaatgg   4020
agcgcctgcc ggcccagtat cagcccgtca tacttgaagc tagacaggct tatcttggac   4080
aagaagaaga tcgcttggcc tcgcgcgcag atcagttgga agaatttgtc cactacgtga   4140
aaggcgagat caccaaggta gtgggcaaag aacttgttga aggaaaattg gagctagtag   4200
aaggtcttaa agtcgccatg gctagtaaag gagaagaact tttcactgga gttgtcccaa   4260
ttcttgttga attagatggt gatgttaatg ggcacaaatt ttctgtcagt ggagagggtg   4320
aaggtgatgc aacatacgga aaacttaccc ttaaatttat ttgcactact ggaaaactac   4380
ctgttccttg gccaacactt gtcactactt tctcttatgg tgttcaatgc ttttcaagat   4440
acccagatca tatgaagcgg cacgacttct tcaagagcgc catgcctgag ggatacgtgc   4500
aggagaggac catctctttc aaggacgacg ggaactacaa gacacgtgct gaagtcaagt   4560
ttgagggaga caccctcgtc aacaggatcg agcttaaggg aatcgatttc aaggaggacg   4620
gaaacatcct cggccacaag ttggaataca actacaactc ccacaacgta tacatcacgg   4680
cagacaaaca aaagaatgga atcaaagcta acttcaaaat tagacacaac attgaagatg   4740
```

```
gaagcgttca actagcagac cattatcaac aaaatactcc aattggcgat ggccctgtcc   4800

ttttaccaga caaccattac ctgtccacac aatctgccct ttcgaaagat cccaacgaaa   4860

agagagatca catggtcctt cttgagtttg taacagctgc tgggattaca catggcatgg   4920

atgaactata caaataagct taaacagtag acattagcag ataaattagc aggaaataaa   4980

gaaggataag gagaaagaac tcaagtaatt atccttcgtt ctcttaattg aattgcaatt   5040

aaactcggcc caatctttta ctaaaaggat tgagccgaat accgctacaa cagctccctg   5100

gaacaccagg agaacacact tatctcgcgt cttgaggtga taccacgcct gacacgtgag   5160

ggcagtacgg ttaattcggt ttagccggac atcagcgctc ctcattgagc gctgggccct   5220

tcacatgaag atcgcactga ggattggtcc tagccaggct tctcagtact gatacagtac   5280

gcgtcgcttc tcgtattgtt tgagtcttgg aattagtttg tatccttccg ccgctgccct   5340

aagaattcta attgagctcg aacagtcgac cgccggatcc tgctcgagtg cctctaga     5398
```

<210> SEQ ID NO 46
<211> LENGTH: 5478
<212> TYPE: DNA
<213> ORGANISM: Artificial Sequence
<220> FEATURE:
<223> OTHER INFORMATION: An example of an episomal DNA vector

<400> SEQUENCE: 46

```
tgccctgttt cactgccgca agacttgtgc ctaacttcgt tatacggtga acagacttgc     60

gataggctgc ccgtttcgac tctaaataag tctattttag ctaatttagt cagtttttcc    120

ctctcaaagg ggggtctggt gacttttggg ggtttttga aagttccatg ttttgacttt    180

ccagaataag tagaggggtt agtttttcaa gaatgttttg aaaagttaag aaatctttga    240

tgggtttgca atattttgac ccacatttac tcatttttcc ctctcaaagg ggggtctggt    300

gacttttggg ggtttttcga aagttccatg ttttgacttt ccagaataag tagaggggtt    360

agttttttaa gacaattgaa atgggtgttt aagaaatctt agtttttccc tctcaaaggg    420

gggtctggtg actttttgggg gtttttgaa agttccatgt tttgacttta gcaaataagt    480

agaggggtta gtttttaga aaagtttaag aaagtttagc caattgttat gggagcgcac    540

gcgcaaggtc gcaactaccc gagaatcgat gtggcggaat gggttacgtg agctattatc    600

cggcgggccc tcaatttaaa tcgttacagt tgctcgtaac ggcaaccggc tcggtccttt    660

ttccctagaa cagtatctta tacttgctgc tctcgttact tcggcgatcc tggtgcagtc    720

ggtccgtaaa tcggcgcaca cttttacgtc gtaccagaca ggctcgcata agccagcccc    780

gacacccgcc aacacccgct gacgcgccct gacgggcttg tctgctcccg gcatccgctt    840

acagacaagc tgtgacctcc gggagctgca tgtgtcagag gttttcaccg tcatcaccga    900

aacgcgcacg aaagggcctc gtgatacgcc tatttttata ggttaatgtc atgataataa    960

tggtttctta gacgtcaggt ggcacttttc ggggaaatgt gcgcggaacc cctatttgtt   1020

tatttttcta aatacattca aatatgtatc cgctcatgag acaataaccc tgataaatgc   1080

ttcaataata ttgaaaaagg aagagtatga gtattcaaca tttccgtgtc gcccttattc   1140

cctttttgc ggcattttgc cttcctgttt ttgctcaccc agaaacgctg gtgaaagtaa   1200

aagatgctga agatcagttg ggtgcacgag tgggttacat cgaactggat ctcaacagcg   1260

gtaagatcct tgagagtttt cgccccgaag aacgttttcc aatgatgagc acttttaaag   1320

ttctgctatg tggcgcggta ttatcccgta ttgacgccgg gcaagagcaa ctcggtcgcc   1380
```

-continued gcatacacta ttctcagaat gacttggttg agtactcacc agtcacagaa aagcatctta 1440
cggatggcat gacagtaaga gaattatgca gtgctgccat aaccatgagt gataacactg 1500
cggccaactt acttctgaca acgatcggag gaccgaagga gctaaccgct tttttgcaca 1560
acatggggga tcatgtaact cgccttgatc gttgggaacc ggagctgaat gaagccatac 1620
caaacgacga gcgtgacacc acgatgcctg tagcaatggc aacaacgttg cgcaaactat 1680
taactggcga actacttact ctagcttccc ggcaacaatt aatagactgg atggaggcgg 1740
ataaagttgc aggaccactt ctgcgctcgg cccttccggc tggctggttt attgctgata 1800
aatctggagc cggtgagcgt ggctcacgcg gtatcattgc agcactgggg ccagatggta 1860
agccctcccg tatcgtagtt atctacacga cggggagtca ggcaactatg gatgaacgaa 1920
atagacagat cgctgagata ggtgcctcac tgattaagca ttggtaactg tcagaccaag 1980
tttactcata tatactttag attgatttaa aacttcattt ttaatttaaa aggatctagg 2040
tgaagatcct ttttgataat ctcatgacca aaatccctta acgtgagttt tcgttccact 2100
gagcgtcaga ccccgtagaa aagatcaaag gatcttcttg agatcctttt tttctgcgcg 2160
taatctgctg cttgcaaaca aaaaaaccac cgctaccagc ggtggtttgt ttgccggatc 2220
aagagctacc aactcttttt ccgaaggtaa ctggcttcag cagagcgcag ataccaaata 2280
ctgttcttct agtgtagccg tagttaggcc accacttcaa gaactctgta gcaccgccta 2340
catacctcgc tctgctaatc ctgttaccag tggctgctgc cagtggcgat aagtcgtgtc 2400
ttaccgggtt ggactcaaga cgatagttac cggataaggc gcagcggtcg ggctgaacgg 2460
ggggttcgtg cacacagccc agcttggagc gaacgaccta caccgaactg agatacctac 2520
agcgtgagct atgagaaagc gccacgcttc ccgaagggag aaaggcggac aggtatccgg 2580
taagcggcag ggtcggaaca ggagagcgca cgagggagct tccaggggga aacgcctggt 2640
atctttatag tcctgtcggg tttcgccacc tctgacttga gcgtcgattt ttgtgatgct 2700
cgtcaggggg gcggagccta tggaaaaacg ccagcaacgc ggccttttta cggttcctgg 2760
ccttttgctg gccttttgct cacatgttct ttcctgcgtt atcccctgat tctgtggata 2820
accgtattac cgcctttgag tgagctgata ccgctcgccg cagccgaacg accgagcgca 2880
gcgagtcagt gagcgaggaa gcggaagaac gcggacaccc agcgtaacaa tctaatattg 2940
tttctcaaat cgggctgtta tcgcatggtg ctcatgatga ggttactgac caaattcgcc 3000
acgcatcggt gctggtagaa tgttcacttc gaggtgggta gacggcgtca cgtgcaatgc 3060
cttgtcttcc cctatctgcg gccccgactg cctcgcgaag acaagggatc ggacgtcgaa 3120
cgtattctgt ttgctaccgg cacgggagta ggatcgttga tatacaccat gcgcgttaac 3180
tctgaccccc ttcctcttaa atgagaatgg ataagaggct cgtgggattg acgtgagggg 3240
gcagggatgg ctatatttct gggagcgaac tccgggcgaa ttactaataa aaagccttcc 3300
attttctatt ttgatttgta gaaaactagt gtgcttggga gtccctgatg attaaataaa 3360
ccaagatttt accaatgggg gctagcgaag cggtgatcgc cgaagtatcg actcaactat 3420
cagaggtagt tggcgtcatc gagcgccatc tcgaaccgac gttgctggcc gtacatttgt 3480
acggctccgc agtggatggc ggcctgaagc cacacagtga tattgatttg ctggttacgg 3540
tgaccgtaag gcttgatgaa acaacgcggc gagctttgat caacgacctt ttggaaactt 3600
cggcttcccc tggagagagc gagattctcc gcgctgtaga agtcaccatt gttgtgcacg 3660
acgacatcat tccgtggcgt tatccagcta agcgcgaact gcaatttgga gaatggcagc 3720
gcaatgacat tcttgcaggt atcttcgagc cagccacgat cgacattgat ctggctatct 3780
tgctgacaaa agcaagagaa catagcgttg ccttggtagg tccagcggcg gaggaactct 3840
ttgatccggt tcctgaacag gatctatttg aggcgctaaa tgaaacctta acgctatgga 3900
actcgccgcc cgactgggct ggcgatgagc gaaatgtagt gcttacgttg tcccgcattt 3960
ggtacagcgc agtaaccggc aaaatcgcgc cgaaggatgt cgctgccgac tgggcaatgg 4020
agcgcctgcc ggcccagtat cagcccgtca tacttgaagc tagacaggct tatcttggac 4080
aagaagaaga tcgcttggcc tcgcgcgcag atcagttgga agaatttgtc cactacgtga 4140
aaggcgagat caccaaggta gtgggcaaag aacttgttga aggaaaattg gagctagtag 4200
aaggtcttaa agtcgccatg gctagtaaag gagaagaact tttcactgga gttgtcccaa 4260
ttcttgttga attagatggt gatgttaatg ggcacaaatt ttctgtcagt ggagagggtg 4320
aaggtgatgc aacatacgga aaacttaccc ttaaatttat ttgcactact ggaaaactac 4380
ctgttccttg gccaacactt gtcactactt tctcttatgg tgttcaatgc ttttcaagat 4440
acccagatca tatgaagcgg cacgacttct tcaagagcgc catgcctgag ggatacgtgc 4500
aggagaggac catctctttc aaggacgacg ggaactacaa gacacgtgct gaagtcaagt 4560
ttgagggaga caccctcgtc aacaggatcg agcttaaggg aatcgatttc aaggaggacg 4620
gaaacatcct cggccacaag ttggaataca actacaactc ccacaacgta tacatcacgg 4680
cagacaaaca aaagaatgga atcaaagcta acttcaaaat tagacacaac attgaagatg 4740
gaagcgttca actagcagac cattatcaac aaaatactcc aattggcgat ggccctgtcc 4800
ttttaccaga caaccattac ctgtccacac aatctgccct ttcgaaagat cccaacgaaa 4860
agagagatca catggtcctt cttgagtttg taacagctgc tgggattaca catggcatgg 4920
atgaactata caaataagct taaacagtag acattagcag ataaattagc aggaaataaa 4980
gaaggataag gagaaagaac tcaagtaatt atccttcgtt ctcttaattg aattgcaatt 5040
aaactcggcc caatctttta ctaaaaggat tgagccgaat accgctccag gcatcaaata 5100
aaacgaaagg ctcagtcgaa agactgggcc tttcgtttta tctgttgttt gtcggtgaac 5160
gctctcacaa cagctccctg gaacaccagg agaacacact tatctcgcgt cttgaggtga 5220
taccacgcct gacacgtgag ggcagtacgg ttaattcggt ttagccggac atcagcgctc 5280
ctcattgagc gctgggccct tcacatgaag atcgcactga ggattggtcc tagccaggct 5340
tctcagtact gatacagtac gcgtcgcttc tcgtattgtt tgagtcttgg aattagtttg 5400
tatccttccg ccgctgccct aagaattcta attgagctcg aacagtcgac cgccggatcc 5460
tgctcgagtg cctctaga 5478

<210> SEQ ID NO 47
<211> LENGTH: 5624
<212> TYPE: DNA
<213> ORGANISM: Artificial Sequence
<220> FEATURE:
<223> OTHER INFORMATION: An example of an episomal DNA vector

<400> SEQUENCE: 47
tgcccgaaag ggtggggtga aactcctcag ttttaattat tattcgatgt ttttctcact 60
ttcctagatt ttaccaaatc ctgataaatt tcacttttct cagtactttt ccccggtaaa 120
aggggggggg tgtctgcgat ttcaaagtgg agtcccaaac gcatgtctgg aatatatgag 180
gagaagttat tttctcagat attctcagat attctcagat atttgaagat attctcagat 240
attctcagat attctcagat tccatgtaat tttgcttgca tttcacttat tttcctaaaa 300

-continued

```
gtgcattttt gcacgatttt aagaaaacac atgcaatttg ccttggattt tggccaagcc    360
gcaagtcctt taaaaaaaaa cacctcgtga aatgttttct atctatctat cataccacca    420
aaggtggtat tatagataga ttgctaggat tcacgagttg aataaaaaag ggaaaaataa    480
ttcttgaaat ctgggttttg atgattttga aatctcaaat tccgcaagtc ggcgatttct    540
ggggctcaga tttggggttt tggtattttt tctggatgtt gctaaatcct gataaatttc    600
acttttctca gtacttttcc ccggtaaaag gggggggtg tctgcgattt caaagtggag     660
tcccaaacgc atgtctggaa tatatgagga ggggtaaaat tctggtaagt tttagaaagt    720
tagttaaaat tgtagaaatg ttggtgatgg tgatgggga gcgcacgcgc aaggtcgcaa     780
ctacccgaga atcgatgtgg cggaatgggt tacgtgagct attatccggc gggccctcaa    840
tttaaatcgt tacagttgct cgtaacggca accggctcgg tcctttttcc ctagaacagt    900
atcttatact tgctgctctc gttacttcgg cgatcctggt gcagtcggtc cgtaaatcgg    960
cgcacacttt tacgtcgtac cagacaggct cgcataagcc agccccgaca cccgccaaca   1020
cccgctgacg cgccctgacg ggcttgtctg ctcccggcat ccgcttacag acaagctgtg   1080
acctccggga gctgcatgtg tcagaggttt tcaccgtcat caccgaaacg cgcacgaaag   1140
ggcctcgtga tacgcctatt tttataggtt aatgtcatga taataatggt ttcttagacg   1200
tcaggtggca cttttcgggg aaatgtgcgc ggaaccccta tttgtttatt tttctaaata   1260
cattcaaata tgtatccgct catgagacaa taaccctgat aaatgcttca ataatattga   1320
aaaaggaaga gtatgagtat tcaacatttc cgtgtcgccc ttattccctt ttttgcggca   1380
ttttgccttc ctgtttttgc tcacccagaa acgctggtga aagtaaaaga tgctgaagat   1440
cagttgggtg cacgagtggg ttacatcgaa ctggatctca acagcggtaa gatccttgag   1500
agttttcgcc ccgaagaacg ttttccaatg atgagcactt ttaaagttct gctatgtggc   1560
gcggtattat cccgtattga cgccgggcaa gagcaactcg gtcgccgcat acactattct   1620
cagaatgact tggttgagta ctcaccagtc acagaaaagc atcttacgga tggcatgaca   1680
gtaagagaat tatgcagtgc tgccataacc atgagtgata acactgcggc caacttactt   1740
ctgacaacga tcggaggacc gaaggagcta accgcttttt tgcacaacat gggggatcat   1800
gtaactcgcc ttgatcgttg ggaaccggag ctgaatgaag ccataccaaa cgacgagcgt   1860
gacaccacga tgcctgtagc aatggcaaca acgttgcgca aactattaac tggcgaacta   1920
cttactctag cttcccggca acaattaata gactggatgg aggcggataa agttgcagga   1980
ccacttctgc gctcggccct tccggctggc tggtttattg ctgataaatc tggagccggt   2040
gagcgtggct cacgcggtat cattgcagca ctggggccag atggtaagcc ctcccgtatc   2100
gtagttatct acacgacggg gagtcaggca actatggatg aacgaaatag acagatcgct   2160
gagataggtg cctcactgat taagcattgg taactgtcag accaagttta ctcatatata   2220
ctttagattg atttaaaact tcatttttaa tttaaaagga tctaggtgaa gatccttttt   2280
gataatctca tgaccaaaat cccttaacgt gagttttcgt tccactgagc gtcagacccc   2340
gtagaaaaga tcaaaggatc ttcttgagat cctttttttc tgcgcgtaat ctgctgcttg   2400
caaacaaaaa aaccaccgct accagcggtg gtttgtttgc cggatcaaga gctaccaact   2460
ctttttccga aggtaactgg cttcagcaga gcgcagatac caaatactgt tcttctagtg   2520
tagccgtagt taggccacca cttcaagaac tctgtagcac cgcctacata cctcgctctg   2580
ctaatcctgt taccagtggc tgctgccagt ggcgataagt cgtgtcttac cgggttggac   2640
tcaagacgat agttaccgga taaggcgcag cggtcgggct gaacgggggg ttcgtgcaca   2700
```

```
cagcccagct tggagcgaac gacctacacc gaactgagat acctacagcg tgagctatga   2760
gaaagcgcca cgcttcccga agggagaaag gcggacaggt atccggtaag cggcagggtc   2820
ggaacaggag agcgcacgag ggagcttcca gggggaaacg cctggtatct ttatagtcct   2880
gtcgggtttc gccacctctg acttgagcgt cgatttttgt gatgctcgtc aggggggcgg   2940
agcctatgga aaaacgccag caacgcggcc tttttacggt tcctggcctt ttgctggcct   3000
tttgctcaca tgttctttcc tgcgttatcc cctgattctg tggataaccg tattaccgcc   3060
tttgagtgag ctgataccgc tcgccgcagc cgaacgaccg agcgcagcga gtcagtgagc   3120
gaggaagcgg aagaacgcgg acacccagcg taacaatcta atattgtttc tcaaatcggg   3180
ctgttatcgc atggtgctca tgatgaggtt actgaccaaa ttcgccacgc atcggtgctg   3240
gtagaatgtt cacttcgagg tgggtagacg gcgtcacgtg caatgccttg tcttccccta   3300
tctgcggccc cgactgcctc gcgaagacaa gggatcggac gtcgaacgta ttctgtttgc   3360
taccggcacg ggagtaggat cgttgatata caccatgcgc gttaactctg accccccttcc   3420
tcttaaatga gaatggataa gaggctcgtg ggattgacgt gagggggcag ggatggctat   3480
atttctggga gcgaactccg ggcgaattac taataaaaag ccttccattt tctattttga   3540
tttgtagaaa actagtgtgc ttgggagtcc ctgatgatta aataaaccaa gattttacca   3600
atgggggcta gcgaagcggt gatcgccgaa gtatcgactc aactatcaga ggtagttggc   3660
gtcatcgagc gccatctcga accgacgttg ctggccgtac atttgtacgg ctccgcagtg   3720
gatggcggcc tgaagccaca cagtgatatt gatttgctgg ttacggtgac cgtaaggctt   3780
gatgaaacaa cgcggcgagc tttgatcaac gaccttttgg aaacttcggc ttcccctgga   3840
gagagcgaga ttctccgcgc tgtagaagtc accattgttg tgcacgacga catcattccg   3900
tggcgttatc cagctaagcg cgaactgcaa tttggagaat ggcagcgcaa tgacattctt   3960
gcaggtatct tcgagccagc cacgatcgac attgatctgg ctatcttgct gacaaaagca   4020
agagaacata gcgttgcctt ggtaggtcca gcggcggagg aactctttga tccggttcct   4080
gaacaggatc tatttgaggc gctaaatgaa accttaacgc tatggaactc gccgcccgac   4140
tgggctggcg atgagcgaaa tgtagtgctt acgttgtccc gcatttggta cagcgcagta   4200
accggcaaaa tcgcgccgaa ggatgtcgct gccgactggg caatggagcg cctgccggcc   4260
cagtatcagc ccgtcatact tgaagctaga caggcttatc ttggacaaga agaagatcgc   4320
ttggcctcgc gcgcagatca gttggaagaa tttgtccact acgtgaaagg cgagatcacc   4380
aaggtagtgg gcaaagaact tgttgaagga aaattggagc tagtagaagg tcttaaagtc   4440
gccatggcta gtaaaggaga agaacttttc actggagttg tcccaattct tgttgaatta   4500
gatggtgatg ttaatgggca caaattttct gtcagtggag agggtgaagg tgatgcaaca   4560
tacggaaaac ttacccttaa atttatttgc actactggaa aactacctgt tccttggcca   4620
acacttgtca ctactttctc ttatggtgtt caatgctttt caagataccc agatcatatg   4680
aagcggcacg acttcttcaa gagcgccatg cctgagggat acgtgcagga gaggaccatc   4740
tctttcaagg acgacgggaa ctacaagaca cgtgctgaag tcaagtttga gggagacacc   4800
ctcgtcaaca ggatcgagct taagggaatc gatttcaagg aggacggaaa catcctcggc   4860
cacaagttgg aatacaacta caactcccac aacgtataca tcacggcaga caaacaaaag   4920
aatggaatca aagctaactt caaaattaga cacaacattg aagatggaag cgttcaacta   4980
gcagaccatt atcaacaaaa tactccaatt ggcgatggcc ctgtcctttt accagacaac   5040
```

```
cattacctgt ccacacaatc tgccctttcg aaagatccca acgaaaagag agatcacatg   5100
gtccttcttg agtttgtaac agctgctggg attacacatg gcatggatga actatacaaa   5160
taagcttaaa cagtagacat tagcagataa attagcagga aataaagaag gataaggaga   5220
aagaactcaa gtaattatcc ttcgttctct taattgaatt gcaattaaac tcggcccaat   5280
cttttactaa aaggattgag ccgaataccg ctacaacagc tccctggaac accaggagaa   5340
cacacttatc tcgcgtcttg aggtgatacc acgcctgaca cgtgagggca gtacggttaa   5400
ttcggtttag ccggacatca gcgctcctca ttgagcgctg ggcccttcac atgaagatcg   5460
cactgaggat tggtcctagc caggcttctc agtactgata cagtacgcgt cgcttctcgt   5520
attgtttgag tcttggaatt agtttgtatc cttccgccgc tgccctaaga attctaattg   5580
agctcgaaca gtcgaccgcc ggatcctgct cgagtgcctc taga                     5624
```

<210> SEQ ID NO 48
<211> LENGTH: 5704
<212> TYPE: DNA
<213> ORGANISM: Artificial Sequence
<220> FEATURE:
<223> OTHER INFORMATION: An example of an episomal DNA vector

<400> SEQUENCE: 48

```
tgcccgaaag ggtggggtga aactcctcag ttttaattat tattcgatgt ttttctcact     60
ttcctagatt ttaccaaatc ctgataaatt tcacttttct cagtactttt ccccggtaaa    120
aggggggggg tgtctgcgat ttcaaagtgg agtcccaaac gcatgtctgg aatatatgag    180
gagaagttat tttctcagat attctcagat attctcagat atttgaagat attctcagat    240
attctcagat attctcagat tccatgtaat tttgcttgca tttcacttat tttcctaaaa    300
gtgcattttt gcacgatttt aagaaaacac atgcaatttg ccttggattt tggccaagcc    360
gcaagtcctt taaaaaaaaa cacctcgtga aatgttttct atctatctat cataccacca    420
aaggtggtat tatagataga ttgctaggat tcacgagttg aataaaaaag gggaaaataa    480
ttcttgaaat ctgggttttg atgattttga aatctcaaat tccgcaagtc ggcgatttct    540
ggggctcaga tttggggttt tgggtatttt tctggatgtt gctaaatcct gataaatttc    600
acttttctca gtacttttcc ccggtaaaag gggggggtg tctgcgattt caaagtggag     660
tcccaaacgc atgtctggaa tatatgagga ggggtaaaat tctggtaagt tttagaaagt    720
tagttaaaat tgtagaaatg ttggtgatgg tgatggggga gcgcacgcgc aaggtcgcaa    780
ctacccgaga atcgatgtgg cggaatgggt tacgtgagct attatccggc gggccctcaa    840
tttaaatcgt tacagttgct cgtaacggca accggctcgg tcctttttcc ctagaacagt    900
atcttatact tgctgctctc gttacttcgg cgatcctggt gcagtcggtc cgtaaatcgg    960
cgcacacttt tacgtcgtac cagacaggct cgcataagcc agccccgaca cccgccaaca   1020
cccgctgacg cgccctgacg ggcttgtctg ctcccggcat ccgcttacag acaagctgtg   1080
acctccggga gctgcatgtg tcagaggttt tcaccgtcat caccgaaacg cgcacgaaag   1140
ggcctcgtga tacgcctatt tttataggtt aatgtcatga taataatggt ttcttagacg   1200
tcaggtggca cttttcgggg aaatgtgcgc ggaaccccta tttgtttatt tttctaaata   1260
cattcaaata tgtatccgct catgagacaa taaccctgat aaatgcttca ataatattga   1320
aaaaggaaga gtatgagtat tcaacatttc cgtgtcgccc ttattccctt ttttgcggca   1380
ttttgccttc ctgtttttgc tcacccagaa acgctggtga aagtaaaaga tgctgaagat   1440
cagttgggtg cacgagtggg ttacatcgaa ctggatctca acagcggtaa gatccttgag   1500
```

```
agttttcgcc ccgaagaacg ttttccaatg atgagcactt ttaaagttct gctatgtggc   1560
gcggtattat cccgtattga cgccgggcaa gagcaactcg gtcgccgcat acactattct   1620
cagaatgact tggttgagta ctcaccagtc acagaaaagc atcttacgga tggcatgaca   1680
gtaagagaat tatgcagtgc tgccataacc atgagtgata acactgcggc caacttactt   1740
ctgacaacga tcggaggacc gaaggagcta accgcttttt tgcacaacat gggggatcat   1800
gtaactcgcc ttgatcgttg ggaaccggag ctgaatgaag ccataccaaa cgacgagcgt   1860
gacaccacga tgcctgtagc aatggcaaca acgttgcgca aactattaac tggcgaacta   1920
cttactctag cttcccggca acaattaata gactggatgg aggcggataa agttgcagga   1980
ccacttctgc gctcggccct tccggctggc tggtttattg ctgataaatc tggagccggt   2040
gagcgtggct cacgcggtat cattgcagca ctggggccag atggtaagcc ctcccgtatc   2100
gtagttatct acacgacggg gagtcaggca actatggatg aacgaaatag acagatcgct   2160
gagataggtg cctcactgat taagcattgg taactgtcag accaagttta ctcatatata   2220
ctttagattg atttaaaact tcatttttaa tttaaaagga tctaggtgaa gatccttttt   2280
gataatctca tgaccaaaat cccttaacgt gagttttcgt tccactgagc gtcagacccc   2340
gtagaaaaga tcaaaggatc ttcttgagat cctttttttc tgcgcgtaat ctgctgcttg   2400
caaacaaaaa aaccaccgct accagcggtg gtttgtttgc cggatcaaga gctaccaact   2460
ctttttccga aggtaactgg cttcagcaga gcgcagatac caaatactgt tcttctagtg   2520
tagccgtagt taggccacca cttcaagaac tctgtagcac cgcctacata cctcgctctg   2580
ctaatcctgt taccagtggc tgctgccagt ggcgataagt cgtgtcttac cgggttggac   2640
tcaagacgat agttaccgga taaggcgcag cggtcgggct gaacgggggg ttcgtgcaca   2700
cagcccagct tggagcgaac gacctacacc gaactgagat acctacagcg tgagctatga   2760
gaaagcgcca cgcttcccga agggagaaag gcggacaggt atccggtaag cggcagggtc   2820
ggaacaggag agcgcacgag ggagcttcca gggggaaacg cctggtatct ttatagtcct   2880
gtcgggtttc gccacctctg acttgagcgt cgatttttgt gatgctcgtc aggggggcgg   2940
agcctatgga aaaacgccag caacgcggcc tttttacggt tcctggcctt ttgctggcct   3000
tttgctcaca tgttctttcc tgcgttatcc cctgattctg tggataaccg tattaccgcc   3060
tttgagtgag ctgataccgc tcgccgcagc cgaacgaccg agcgcagcga gtcagtgagc   3120
gaggaagcgg aagaacgcgg acacccagcg taacaatcta atattgtttc tcaaatcggg   3180
ctgttatcgc atggtgctca tgatgaggtt actgaccaaa ttcgccacgc atcggtgctg   3240
gtagaatgtt cacttcgagg tgggtagacg gcgtcacgtg caatgccttg tcttccccta   3300
tctgcggccc cgactgcctc gcgaagacaa gggatcggac gtcgaacgta ttctgtttgc   3360
taccggcacg ggagtaggat cgttgatata caccatgcgc gttaactctg accccccttcc   3420
tcttaaatga gaatggataa gaggctcgtg ggattgacgt gagggggcag ggatggctat   3480
atttctggga gcgaactccg ggcgaattac taataaaaag ccttccattt tctattttga   3540
tttgtagaaa actagtgtgc ttgggagtcc ctgatgatta aataaaccaa gattttacca   3600
atgggggcta gcgaagcggt gatcgccgaa gtatcgactc aactatcaga ggtagttggc   3660
gtcatcgagc gccatctcga accgacgttg ctggccgtac atttgtacgg ctccgcagtg   3720
gatggcggcc tgaagccaca cagtgatatt gatttgctgg ttacggtgac cgtaaggctt   3780
gatgaaacaa cgcggcgagc tttgatcaac gaccttttgg aaacttcggc ttcccctgga   3840
```

gagagcgaga ttctccgcgc tgtagaagtc accattgttg tgcacgacga catcattccg 3900
tggcgttatc cagctaagcg cgaactgcaa tttggagaat ggcagcgcaa tgacattctt 3960
gcaggtatct tcgagccagc cacgatcgac attgatctgg ctatcttgct gacaaaagca 4020
agagaacata gcgttgcctt ggtaggtcca gcggcggagg aactctttga tccggttcct 4080
gaacaggatc tatttgaggc gctaaatgaa accttaacgc tatggaactc gccgcccgac 4140
tgggctggcg atgagcgaaa tgtagtgctt acgttgtccc gcatttggta cagcgcagta 4200
accggcaaaa tcgcgccgaa ggatgtcgct gccgactggg caatggagcg cctgccggcc 4260
cagtatcagc ccgtcatact tgaagctaga caggcttatc ttggacaaga agaagatcgc 4320
ttggcctcgc gcgcagatca gttggaagaa tttgtccact acgtgaaagg cgagatcacc 4380
aaggtagtgg gcaaagaact tgttgaagga aaattggagc tagtagaagg tcttaaagtc 4440
gccatggcta gtaaaggaga agaacttttc actggagttg tcccaattct tgttgaatta 4500
gatggtgatg ttaatgggca caaattttct gtcagtggag agggtgaagg tgatgcaaca 4560
tacggaaaac ttacccttaa atttatttgc actactggaa aactacctgt tccttggcca 4620
acacttgtca ctactttctc ttatggtgtt caatgctttt caagataccc agatcatatg 4680
aagcggcacg acttcttcaa gagcgccatg cctgagggat acgtgcagga gaggaccatc 4740
tctttcaagg acgacgggaa ctacaagaca cgtgctgaag tcaagtttga gggagacacc 4800
ctcgtcaaca ggatcgagct taagggaatc gatttcaagg aggacggaaa catcctcggc 4860
cacaagttgg aatacaacta caactcccac aacgtataca tcacggcaga caaacaaaag 4920
aatggaatca aagctaactt caaaattaga cacaacattg aagatggaag cgttcaacta 4980
gcagaccatt atcaacaaaa tactccaatt ggcgatggcc ctgtcctttt accagacaac 5040
cattacctgt ccacacaatc tgccctttcg aaagatccca acgaaaagag agatcacatg 5100
gtccttcttg agtttgtaac agctgctggg attacacatg gcatggatga actatacaaa 5160
taagcttaaa cagtagacat tagcagataa attagcagga aataaagaag gataaggaga 5220
aagaactcaa gtaattatcc ttcgttctct taattgaatt gcaattaaac tcggcccaat 5280
cttttactaa aaggattgag ccgaataccg ctccaggcat caaataaaac gaaaggctca 5340
gtcgaaagac tgggcctttc gttttatctg ttgtttgtcg gtgaacgctc tcacaacagc 5400
tccctggaac accaggagaa cacacttatc tcgcgtcttg aggtgatacc acgcctgaca 5460
cgtgagggca gtacggttaa ttcggtttag ccggacatca gcgctcctca ttgagcgctg 5520
ggcccttcac atgaagatcg cactgaggat tggtcctagc caggcttctc agtactgata 5580
cagtacgcgt cgcttctcgt attgtttgag tcttggaatt agtttgtatc cttccgccgc 5640
tgccctaaga attctaattg agctcgaaca gtcgaccgcc ggatcctgct cgagtgcctc 5700
taga 5704

<210> SEQ ID NO 49
<211> LENGTH: 5467
<212> TYPE: DNA
<213> ORGANISM: Artificial Sequence
<220> FEATURE:
<223> OTHER INFORMATION: An example of an episomal DNA vector

<400> SEQUENCE: 49
tgccaaatcc tgataaattt cacttttctc agtacttttc cccggtaaaa gggggggggt 60
gtctgcgatt tcaaagtgga gtcccaaacg catgtctgga atatatgagg agaagttatt 120
ttctcagata ttctcagaca tgtaattttg cttgcatttc acttatttta taaaaagtgc 180

```
atttttgcac gattttaaga aaacacatgc aatttgcctt ggattttggc caagccgcaa    240
gtcctttaaa aaaaaacacc tcgtgaaatg ttttctatct atctatcata ccacctttgg    300
tggtattata gatagattgc taggattcac gagttgaata aaaaagggga aaataatttt    360
gcagaaatct gggtttttga ttttatgaaa ttccgcaagt cggcgatttt agaaatcttt    420
ttaagatttg tggatcagaa attgggggtt ttgtggattt tgctaaatcc tgataaattt    480
cacttttctc agtacttttc cccggtaaaa gggggggggt gtctgcgatt tcaaagtgga    540
gtcccaaacg catgtctgga atatatgagg aggagtaaaa ttctgggaag ttttagaaag    600
ggagcgcacg cgcaaggtcg caactacccg agaatcgatg tggcggaatg ggttacgtga    660
gctattatcc ggcgggccct caatttaaat cgttacagtt gctcgtaacg gcaaccggct    720
cggtcctttt tccctagaac agtatcttat acttgctgct ctcgttactt cggcgatcct    780
ggtgcagtcg gtccgtaaat cggcgcacac ttttacgtcg taccagacag gctcgcataa    840
gccagccccg acacccgcca acacccgctg acgcgccctg acgggcttgt ctgctcccgg    900
catccgctta cagacaagct gtgacctccg ggagctgcat gtgtcagagg ttttcaccgt    960
catcaccgaa acgcgcacga aagggcctcg tgatacgcct atttttatag gttaatgtca   1020
tgataataat ggtttcttag acgtcaggtg gcacttttcg gggaaatgtg cgcggaaccc   1080
ctatttgttt atttttctaa atacattcaa atatgtatcc gctcatgaga caataaccct   1140
gataaatgct tcaataatat tgaaaaagga agagtatgag tattcaacat ttccgtgtcg   1200
cccttattcc cttttttgcg gcattttgcc ttcctgtttt tgctcaccca gaaacgctgg   1260
tgaaagtaaa agatgctgaa gatcagttgg gtgcacgagt gggttacatc gaactggatc   1320
tcaacagcgg taagatcctt gagagttttc gccccgaaga acgttttcca atgatgagca   1380
cttttaaagt tctgctatgt ggcgcggtat tatcccgtat tgacgccggg caagagcaac   1440
tcggtcgccg catacactat tctcagaatg acttggttga gtactcacca gtcacagaaa   1500
agcatcttac ggatggcatg acagtaagag aattatgcag tgctgccata accatgagtg   1560
ataacactgc ggccaactta cttctgacaa cgatcggagg accgaaggag ctaaccgctt   1620
ttttgcacaa catgggggat catgtaactc gccttgatcg ttgggaaccg gagctgaatg   1680
aagccatacc aaacgacgag cgtgacacca cgatgcctgt agcaatggca acaacgttgc   1740
gcaaactatt aactggcgaa ctacttactc tagcttcccg gcaacaatta atagactgga   1800
tggaggcgga taaagttgca ggaccacttc tgcgctcggc ccttccggct ggctggttta   1860
ttgctgataa atctggagcc ggtgagcgtg gctcacgcgg tatcattgca gcactggggc   1920
cagatggtaa gccctcccgt atcgtagtta tctacacgac ggggagtcag gcaactatgg   1980
atgaacgaaa tagacagatc gctgagatag gtgcctcact gattaagcat tggtaactgt   2040
cagaccaagt ttactcatat atactttaga ttgatttaaa acttcatttt taatttaaaa   2100
ggatctaggt gaagatcctt tttgataatc tcatgaccaa aatcccttaa cgtgagtttt   2160
cgttccactg agcgtcagac cccgtagaaa agatcaaagg atcttcttga gatccttttt   2220
ttctgcgcgt aatctgctgc ttgcaaacaa aaaaaccacc gctaccagcg gtggtttgtt   2280
tgccggatca agagctacca actctttttc cgaaggtaac tggcttcagc agagcgcaga   2340
taccaaatac tgttcttcta gtgtagccgt agttaggcca ccacttcaag aactctgtag   2400
caccgcctac atacctcgct ctgctaatcc tgttaccagt ggctgctgcc agtggcgata   2460
agtcgtgtct taccgggttg gactcaagac gatagttacc ggataaggcg cagcggtcgg   2520
```

-continued

```
gctgaacggg gggttcgtgc acacagccca gcttggagcg aacgacctac accgaactga   2580
gatacctaca gcgtgagcta tgagaaagcg ccacgcttcc cgaagggaga aaggcggaca   2640
ggtatccggt aagcggcagg gtcggaacag gagagcgcac gagggagctt ccagggggaa   2700
acgcctggta tctttatagt cctgtcgggt ttcgccacct ctgacttgag cgtcgatttt   2760
tgtgatgctc gtcagggggg cggagcctat ggaaaaacgc cagcaacgcg gcctttttac   2820
ggttcctggc cttttgctgg ccttttgctc acatgttctt tcctgcgtta tcccctgatt   2880
ctgtggataa ccgtattacc gcctttgagt gagctgatac cgctcgccgc agccgaacga   2940
ccgagcgcag cgagtcagtg agcgaggaag cggaagaacg cggacaccca gcgtaacaat   3000
ctaatattgt ttctcaaatc gggctgttat cgcatggtgc tcatgatgag gttactgacc   3060
aaattcgcca cgcatcggtg ctggtagaat gttcacttcg aggtgggtag acggcgtcac   3120
gtgcaatgcc ttgtcttccc ctatctgcgg ccccgactgc ctcgcgaaga caagggatcg   3180
gacgtcgaac gtattctgtt tgctaccggc acgggagtag gatcgttgat atacaccatg   3240
cgcgttaact ctgacccccct tcctcttaaa tgagaatgga taagaggctc gtgggattga   3300
cgtgaggggg cagggatggc tatatttctg ggagcgaact ccgggcgaat tactaataaa   3360
aagccttcca ttttctattt tgatttgtag aaaactagtg tgcttgggag tccctgatga   3420
ttaaataaac caagatttta ccaatggggg ctagcgaagc ggtgatcgcc gaagtatcga   3480
ctcaactatc agaggtagtt ggcgtcatcg agcgccatct cgaaccgacg ttgctggccg   3540
tacatttgta cggctccgca gtggatggcg gcctgaagcc acacagtgat attgatttgc   3600
tggttacggt gaccgtaagg cttgatgaaa caacgcggcg agctttgatc aacgaccttt   3660
tggaaacttc ggcttcccct ggagagagcg agattctccg cgctgtagaa gtcaccattg   3720
ttgtgcacga cgacatcatt ccgtggcgtt atccagctaa gcgcgaactg caatttggag   3780
aatggcagcg caatgacatt cttgcaggta tcttcgagcc agccacgatc gacattgatc   3840
tggctatctt gctgacaaaa gcaagagaac atagcgttgc cttggtaggt ccagcggcgg   3900
aggaactctt tgatccggtt cctgaacagg atctatttga ggcgctaaat gaaaccttaa   3960
cgctatggaa ctcgccgccc gactgggctg gcgatgagcg aaatgtagtg cttacgttgt   4020
cccgcatttg gtacagcgca gtaaccggca aaatcgcgcc gaaggatgtc gctgccgact   4080
gggcaatgga gcgcctgccg gcccagtatc agcccgtcat acttgaagct agacaggctt   4140
atcttggaca agaagaagat cgcttggcct cgcgcgcaga tcagttggaa gaatttgtcc   4200
actacgtgaa aggcgagatc accaaggtag tgggcaaaga acttgttgaa ggaaaattgg   4260
agctagtaga aggtcttaaa gtcgccatgg ctagtaaagg agaagaactt ttcactggag   4320
ttgtcccaat tcttgttgaa ttagatggtg atgttaatgg gcacaaattt tctgtcagtg   4380
gagagggtga aggtgatgca acatacggaa aacttaccct taaatttatt tgcactactg   4440
gaaaactacc tgttccttgg ccaacacttg tcactacttt ctcttatggt gttcaatgct   4500
tttcaagata cccagatcat atgaagcggc acgacttctt caagagcgcc atgcctgagg   4560
gatacgtgca ggagaggacc atctctttca aggacgacgg gaactacaag acacgtgctg   4620
aagtcaagtt tgagggagac accctcgtca acaggatcga gcttaaggga atcgatttca   4680
aggaggacgg aaacatcctc ggccacaagt tggaatacaa ctacaactcc cacaacgtat   4740
acatcacggc agacaaacaa aagaatggaa tcaaagctaa cttcaaaatt agacacaaca   4800
ttgaagatgg aagcgttcaa ctagcagacc attatcaaca aaatactcca attggcgatg   4860
gccctgtcct tttaccagac aaccattacc tgtccacaca atctgccctt tcgaaagatc   4920
```

ccaacgaaaa gagagatcac atggtccttc ttgagtttgt aacagctgct gggattacac 4980
atggcatgga tgaactatac aaataagctt aaacagtaga cattagcaga taaattagca 5040
ggaaataaag aaggataagg agaaagaact caagtaatta tccttcgttc tcttaattga 5100
attgcaatta aactcggccc aatcttttac taaaaggatt gagccgaata ccgctacaac 5160
agctccctgg aacaccagga gaacacactt atctcgcgtc ttgaggtgat accacgcctg 5220
acacgtgagg gcagtacggt taattcggtt tagccggaca tcagcgctcc tcattgagcg 5280
ctgggccctt cacatgaaga tcgcactgag gattggtcct agccaggctt ctcagtactg 5340
atacagtacg cgtcgcttct cgtattgttt gagtcttgga attagtttgt atccttccgc 5400
cgctgcccta agaattctaa ttgagctcga acagtcgacc gccggatcct gctcgagtgc 5460
ctctaga 5467

<210> SEQ ID NO 50
<211> LENGTH: 5547
<212> TYPE: DNA
<213> ORGANISM: Artificial Sequence
<220> FEATURE:
<223> OTHER INFORMATION: An example of an episomal DNA vector

<400> SEQUENCE: 50
tgccaaatcc tgataaattt cacttttctc agtacttttc cccggtaaaa gggggggggt 60
gtctgcgatt tcaaagtgga gtcccaaacg catgtctgga atatatgagg agaagttatt 120
ttctcagata ttctcagaca tgtaattttg cttgcatttc acttatttta taaaaagtgc 180
atttttgcac gattttaaga aaacacatgc aatttgcctt ggattttggc caagccgcaa 240
gtcctttaaa aaaaaacacc tcgtgaaatg ttttctatct atctatcata ccacctttgg 300
tggtattata gatagattgc taggattcac gagttgaata aaaaagggga aaataatttt 360
gcagaaatct gggtttttga ttttatgaaa ttccgcaagt cggcgatttt agaaatcttt 420
ttaagatttg tggatcagaa attgggggtt ttgtggattt tgctaaatcc tgataaattt 480
cacttttctc agtacttttc cccggtaaaa gggggggggt gtctgcgatt tcaaagtgga 540
gtcccaaacg catgtctgga atatatgagg aggagtaaaa ttctgggaag ttttagaaag 600
ggagcgcacg cgcaaggtcg caactacccg agaatcgatg tggcggaatg ggttacgtga 660
gctattatcc ggcgggccct caatttaaat cgttacagtt gctcgtaacg gcaaccggct 720
cggtcctttt tccctagaac agtatcttat acttgctgct ctcgttactt cggcgatcct 780
ggtgcagtcg gtccgtaaat cggcgcacac ttttacgtcg taccagacag gctcgcataa 840
gccagccccg acacccgcca acacccgctg acgcgccctg acgggcttgt ctgctcccgg 900
catccgctta cagacaagct gtgacctccg ggagctgcat gtgtcagagg ttttcaccgt 960
catcaccgaa acgcgcacga aagggcctcg tgatacgcct atttttatag gttaatgtca 1020
tgataataat ggtttcttag acgtcaggtg gcacttttcg gggaaatgtg cgcggaaccc 1080
ctatttgttt atttttctaa atacattcaa atatgtatcc gctcatgaga caataaccct 1140
gataaatgct tcaataatat tgaaaaagga agagtatgag tattcaacat ttccgtgtcg 1200
cccttattcc cttttttgcg gcattttgcc ttcctgtttt tgctcaccca gaaacgctgg 1260
tgaaagtaaa agatgctgaa gatcagttgg gtgcacgagt gggttacatc gaactggatc 1320
tcaacagcgg taagatcctt gagagttttc gccccgaaga acgttttcca atgatgagca 1380
cttttaaagt tctgctatgt ggcgcggtat tatcccgtat tgacgccggg caagagcaac 1440

-continued

```
tcggtcgccg catacactat tctcagaatg acttggttga gtactcacca gtcacagaaa   1500
agcatcttac ggatggcatg acagtaagag aattatgcag tgctgccata accatgagtg   1560
ataacactgc ggccaactta cttctgacaa cgatcggagg accgaaggag ctaaccgctt   1620
ttttgcacaa catgggggat catgtaactc gccttgatcg ttgggaaccg gagctgaatg   1680
aagccatacc aaacgacgag cgtgacacca cgatgcctgt agcaatggca acaacgttgc   1740
gcaaactatt aactggcgaa ctacttactc tagcttcccg gcaacaatta atagactgga   1800
tggaggcgga taaagttgca ggaccacttc tgcgctcggc ccttccggct ggctggttta   1860
ttgctgataa atctggagcc ggtgagcgtg gctcacgcgg tatcattgca gcactggggc   1920
cagatggtaa gccctcccgt atcgtagtta tctacacgac ggggagtcag gcaactatgg   1980
atgaacgaaa tagacagatc gctgagatag gtgcctcact gattaagcat tggtaactgt   2040
cagaccaagt ttactcatat atactttaga ttgatttaaa acttcatttt taatttaaaa   2100
ggatctaggt gaagatcctt tttgataatc tcatgaccaa aatcccttaa cgtgagtttt   2160
cgttccactg agcgtcagac cccgtagaaa agatcaaagg atcttcttga gatccttttt   2220
ttctgcgcgt aatctgctgc ttgcaaacaa aaaaaccacc gctaccagcg gtggtttgtt   2280
tgccggatca agagctacca actctttttc cgaaggtaac tggcttcagc agagcgcaga   2340
taccaaatac tgttcttcta gtgtagccgt agttaggcca ccacttcaag aactctgtag   2400
caccgcctac atacctcgct ctgctaatcc tgttaccagt ggctgctgcc agtggcgata   2460
agtcgtgtct taccgggttg gactcaagac gatagttacc ggataaggcg cagcggtcgg   2520
gctgaacggg gggttcgtgc acacagccca gcttggagcg aacgacctac accgaactga   2580
gatacctaca gcgtgagcta tgagaaagcg ccacgcttcc cgaagggaga aaggcggaca   2640
ggtatccggt aagcggcagg gtcggaacag gagagcgcac gagggagctt ccagggggaa   2700
acgcctggta tctttatagt cctgtcgggt ttcgccacct ctgacttgag cgtcgatttt   2760
tgtgatgctc gtcagggggg cggagcctat ggaaaaacgc cagcaacgcg gcctttttac   2820
ggttcctggc cttttgctgg ccttttgctc acatgttctt tcctgcgtta tcccctgatt   2880
ctgtggataa ccgtattacc gcctttgagt gagctgatac cgctcgccgc agccgaacga   2940
ccgagcgcag cgagtcagtg agcgaggaag cggaagaacg cggacaccca gcgtaacaat   3000
ctaatattgt ttctcaaatc gggctgttat cgcatggtgc tcatgatgag gttactgacc   3060
aaattcgcca cgcatcggtg ctggtagaat gttcacttcg aggtgggtag acggcgtcac   3120
gtgcaatgcc ttgtcttccc ctatctgcgg ccccgactgc ctcgcgaaga caagggatcg   3180
gacgtcgaac gtattctgtt tgctaccggc acgggagtag gatcgttgat atacaccatg   3240
cgcgttaact ctgacccccct tcctcttaaa tgagaatgga taagaggctc gtgggattga   3300
cgtgaggggg cagggatggc tatatttctg ggagcgaact ccgggcgaat tactaataaa   3360
aagccttcca ttttctattt tgatttgtag aaaactagtg tgcttgggag tccctgatga   3420
ttaaataaac caagatttta ccaatggggg ctagcgaagc ggtgatcgcc gaagtatcga   3480
ctcaactatc agaggtagtt ggcgtcatcg agcgccatct cgaaccgacg ttgctggccg   3540
tacatttgta cggctccgca gtggatggcg gcctgaagcc acacagtgat attgatttgc   3600
tggttacggt gaccgtaagg cttgatgaaa caacgcggcg agctttgatc aacgaccttt   3660
tggaaacttc ggcttcccct ggagagagcg agattctccg cgctgtagaa gtcaccattg   3720
ttgtgcacga cgacatcatt ccgtggcgtt atccagctaa gcgcgaactg caatttggag   3780
aatggcagcg caatgacatt cttgcaggta tcttcgagcc agccacgatc gacattgatc   3840
```

```
tggctatctt gctgacaaaa gcaagagaac atagcgttgc cttggtaggt ccagcggcgg   3900

aggaactctt tgatccggtt cctgaacagg atctatttga ggcgctaaat gaaaccttaa   3960

cgctatggaa ctcgccgccc gactgggctg gcgatgagcg aaatgtagtg cttacgttgt   4020

cccgcatttg gtacagcgca gtaaccggca aaatcgcgcc gaaggatgtc gctgccgact   4080

gggcaatgga gcgcctgccg gcccagtatc agcccgtcat acttgaagct agacaggctt   4140

atcttggaca agaagaagat cgcttggcct cgcgcgcaga tcagttggaa gaatttgtcc   4200

actacgtgaa aggcgagatc accaaggtag tgggcaaaga acttgttgaa ggaaaattgg   4260

agctagtaga aggtcttaaa gtcgccatgg ctagtaaagg agaagaactt ttcactggag   4320

ttgtcccaat tcttgttgaa ttagatggtg atgttaatgg gcacaaattt tctgtcagtg   4380

gagagggtga aggtgatgca acatacggaa aacttaccct taaatttatt tgcactactg   4440

gaaaactacc tgttccttgg ccaacacttg tcactacttt ctcttatggt gttcaatgct   4500

tttcaagata cccagatcat atgaagcggc acgacttctt caagagcgcc atgcctgagg   4560

gatacgtgca ggagaggacc atctctttca aggacgacgg gaactacaag acacgtgctg   4620

aagtcaagtt tgagggagac accctcgtca acaggatcga gcttaaggga atcgatttca   4680

aggaggacgg aaacatcctc ggccacaagt tggaatacaa ctacaactcc cacaacgtat   4740

acatcacggc agacaaacaa aagaatggaa tcaaagctaa cttcaaaatt agacacaaca   4800

ttgaagatgg aagcgttcaa ctagcagacc attatcaaca aaatactcca attggcgatg   4860

gccctgtcct tttaccagac aaccattacc tgtccacaca atctgccctt tcgaaagatc   4920

ccaacgaaaa gagagatcac atggtccttc ttgagtttgt aacagctgct gggattacac   4980

atggcatgga tgaactatac aaataagctt aaacagtaga cattagcaga taaattagca   5040

ggaaataaag aaggataagg agaaagaact caagtaatta tccttcgttc tcttaattga   5100

attgcaatta aactcggccc aatcttttac taaaaggatt gagccgaata ccgctccagg   5160

catcaaataa aacgaaaggc tcagtcgaaa gactgggcct ttcgttttat ctgttgtttg   5220

tcggtgaacg ctctcacaac agctccctgg aacaccagga gaacacactt atctcgcgtc   5280

ttgaggtgat accacgcctg acacgtgagg gcagtacggt taattcggtt tagccggaca   5340

tcagcgctcc tcattgagcg ctgggccctt cacatgaaga tcgcactgag gattggtcct   5400

agccaggctt ctcagtactg atacagtacg cgtcgcttct cgtattgttt gagtcttgga   5460

attagtttgt atccttccgc cgctgcccta agaattctaa ttgagctcga acagtcgacc   5520

gccggatcct gctcgagtgc ctctaga                                       5547
```

<210> SEQ ID NO 51
<211> LENGTH: 6346
<212> TYPE: DNA
<213> ORGANISM: Artificial Sequence
<220> FEATURE:
<223> OTHER INFORMATION: An example of an episomal DNA vector

<400> SEQUENCE: 51

```
tgccaccaaa aatatatgcc tctgcattat aaataagatt caagccactt ctaatctcac     60

acaagttaaa atgggaattc atttatctaa cattattgtt ttgggaattt agtggatata    120

gcatctcatc ttggatctaa tttacctaac atcatgtaat tcgctatttt ctaactttag    180

cggaatctgg gcttttatcg gaatttaata ctagctttac acataagaca ctcgcaaaat    240

agccgtattt cggcatctgc agggtattgg tagccttgtg gacacaatga agcaatttaa    300
```

-continued

```
gggaaatcat gtaattaacg gaaattaatg gtattaggat ttggattatt tacaatatct    360
tcaatttaca caatgtggtt ggacagctct gctgttggtg ttggcaacac aaccaaccac    420
gaataattaa tggcacacaa tccactcaac aggcatctac aagcaaattc acgaatctca    480
cgattctcgc gatttctcgc aaattccctc acgtacgagc gcataatgca cacgcgcatc    540
aaaactaaaa gacaaaaatt aaagccctac aaatgtaatg ggttcgtggg tatttataaa    600
taaccctacg ggttatttag aaatgccccc gagggaatat aaccccctaa agggggttat    660
tattcccgag tcggcttaac acgtgtacac gtacacgagg aaccgaaggt tccgacacac    720
acacaatcat acccacgatg aatcttcgat tccagctgat actctcgcca accaaccaag    780
agcagctttg ctgcgaatga gcgtagcgaa taacctgccg caggcagaat attgcgaagc    840
aataccatga gcgaagcgaa taataatgcg aagcattacc tgccgaaggc agaatagccg    900
aaggctacct aatagcgaag ctattgtcaa aaagcttgaa acctcatgca gctaacagct    960
gcacaatcta attcacttgg gattattgat tcttcaaacc attcaacaca caccatgagc   1020
gaagggaata atagagcgaa gctctaccct gccgcaggca gaatattgcg aagcaatacc   1080
atgagcgaag cgaataacag aacgaagttc tgcctggctt tagccagaac aatgcgaagc   1140
attgaaataa aaagaaaatg ttaaacagaa tgcatcttat cacaatctac tcaaccacaa   1200
caggaatcga gtttcattaa ctgtttatca atttcaatga aagtaatttt ggttggctgt   1260
aacgttacaa gcacataaca gaacacagtt ggttatcgat tatggacatt cattaaatgg   1320
tgtaatgtta agtcgagata tggcttcatc acataaactc tggttgtaat taaatggatg   1380
ttaagagttg taaaggtaaa atggatctac aattggttag cctaatcatt tatggctggt   1440
tggttgtgag acaaaaaggt gatgaaacta taacgtgggg gagcgcacgc gcaaggtcgc   1500
aactacccga gaatcgatgt ggcggaatgg gttacgtgag ctattatccg gcgggccctc   1560
aatttaaatc gttacagttg ctcgtaacgg caaccggctc ggtccttttt ccctagaaca   1620
gtatcttata cttgctgctc tcgttacttc ggcgatcctg gtgcagtcgg tccgtaaatc   1680
ggcgcacact tttacgtcgt accagacagg ctcgcataag ccagccccga cacccgccaa   1740
cacccgctga cgcgccctga cgggcttgtc tgctcccggc atccgcttac agacaagctg   1800
tgacctccgg gagctgcatg tgtcagaggt tttcaccgtc atcaccgaaa cgcgcacgaa   1860
agggcctcgt gatacgccta tttttatagg ttaatgtcat gataataatg gtttcttaga   1920
cgtcaggtgg cacttttcgg ggaaatgtgc gcggaacccc tatttgttta tttttctaaa   1980
tacattcaaa tatgtatccg ctcatgagac aataaccctg ataaatgctt caataatatt   2040
gaaaaaggaa gagtatgagt attcaacatt tccgtgtcgc ccttattccc ttttttgcgg   2100
cattttgcct tcctgttttt gctcacccag aaacgctggt gaaagtaaaa gatgctgaag   2160
atcagttggg tgcacgagtg ggttacatcg aactggatct caacagcggt aagatccttg   2220
agagttttcg ccccgaagaa cgttttccaa tgatgagcac ttttaaagtt ctgctatgtg   2280
gcgcggtatt atcccgtatt gacgccgggc aagagcaact cggtcgccgc atacactatt   2340
ctcagaatga cttggttgag tactcaccag tcacagaaaa gcatcttacg gatggcatga   2400
cagtaagaga attatgcagt gctgccataa ccatgagtga taacactgcg gccaacttac   2460
ttctgacaac gatcggagga ccgaaggagc taaccgcttt tttgcacaac atgggggatc   2520
atgtaactcg ccttgatcgt tgggaaccgg agctgaatga agccatacca aacgacgagc   2580
gtgacaccac gatgcctgta gcaatggcaa caacgttgcg caaactatta actggcgaac   2640
tacttactct agcttcccgg caacaattaa tagactggat ggaggcggat aaagttgcag   2700
```

-continued

```
gaccacttct gcgctcggcc cttccggctg gctggtttat tgctgataaa tctggagccg   2760
gtgagcgtgg ctcacgcggt atcattgcag cactggggcc agatggtaag ccctcccgta   2820
tcgtagttat ctacacgacg gggagtcagg caactatgga tgaacgaaat agacagatcg   2880
ctgagatagg tgcctcactg attaagcatt ggtaactgtc agaccaagtt tactcatata   2940
tactttagat tgatttaaaa cttcattttt aatttaaaag gatctaggtg aagatccttt   3000
ttgataatct catgaccaaa atcccttaac gtgagttttc gttccactga gcgtcagacc   3060
ccgtagaaaa gatcaaagga tcttcttgag atcctttttt tctgcgcgta atctgctgct   3120
tgcaaacaaa aaaaccaccg ctaccagcgg tggtttgttt gccggatcaa gagctaccaa   3180
ctctttttcc gaaggtaact ggcttcagca gagcgcagat accaaatact gttcttctag   3240
tgtagccgta gttaggccac cacttcaaga actctgtagc accgcctaca tacctcgctc   3300
tgctaatcct gttaccagtg gctgctgcca gtggcgataa gtcgtgtctt accgggttgg   3360
actcaagacg atagttaccg gataaggcgc agcggtcggg ctgaacgggg ggttcgtgca   3420
cacagcccag cttggagcga acgacctaca ccgaactgag atacctacag cgtgagctat   3480
gagaaagcgc cacgcttccc gaagggagaa aggcggacag gtatccggta agcggcaggg   3540
tcggaacagg agagcgcacg agggagcttc cagggggaaa cgcctggtat ctttatagtc   3600
ctgtcgggtt tcgccacctc tgacttgagc gtcgattttt gtgatgctcg tcaggggggc   3660
ggagcctatg gaaaaacgcc agcaacgcgg cctttttacg gttcctggcc ttttgctggc   3720
cttttgctca catgttcttt cctgcgttat cccctgattc tgtggataac cgtattaccg   3780
cctttgagtg agctgatacc gctcgccgca gccgaacgac cgagcgcagc gagtcagtga   3840
gcgaggaagc ggaagaacgc ggacacccag cgtaacaatc taatattgtt tctcaaatcg   3900
ggctgttatc gcatggtgct catgatgagg ttactgacca aattcgccac gcatcggtgc   3960
tggtagaatg ttcacttcga ggtgggtaga cggcgtcacg tgcaatgcct tgtcttcccc   4020
tatctgcggc cccgactgcc tcgcgaagac aagggatcgg acgtcgaacg tattctgttt   4080
gctaccggca cgggagtagg atcgttgata tacaccatgc gcgttaactc tgacccccct   4140
cctcttaaat gagaatggat aagaggctcg tgggattgac gtgagggggc agggatggct   4200
atatttctgg gagcgaactc cgggcgaatt actaataaaa agccttccat ttctatttt   4260
gatttgtaga aaactagtgt gcttgggagt ccctgatgat taaataaacc aagattttac   4320
caatgggggc tagcgaagcg gtgatcgccg aagtatcgac tcaactatca gaggtagttg   4380
gcgtcatcga gcgccatctc gaaccgacgt tgctggccgt acatttgtac ggctccgcag   4440
tggatggcgg cctgaagcca cacagtgata ttgatttgct ggttacggtg accgtaaggc   4500
ttgatgaaac aacgcggcga gctttgatca acgacctttt ggaaacttcg gcttcccctg   4560
gagagagcga gattctccgc gctgtagaag tcaccattgt tgtgcacgac gacatcattc   4620
cgtggcgtta tccagctaag cgcgaactgc aatttggaga atggcagcgc aatgacattc   4680
ttgcaggtat cttcgagcca gccacgatcg acattgatct ggctatcttg ctgacaaaag   4740
caagagaaca tagcgttgcc ttggtaggtc cagcggcgga ggaactcttt gatccggttc   4800
ctgaacagga tctatttgag gcgctaaatg aaaccttaac gctatggaac tcgccgcccg   4860
actgggctgg cgatgagcga aatgtagtgc ttacgttgtc ccgcatttgg tacagcgcag   4920
taaccggcaa aatcgcgccg aaggatgtcg ctgccgactg ggcaatggag cgcctgccgg   4980
cccagtatca gcccgtcata cttgaagcta gacaggctta tcttggacaa gaagaagatc   5040
```

gcttggcctc gcgcgcagat cagttggaag aatttgtcca ctacgtgaaa ggcgagatca 5100
ccaaggtagt gggcaaagaa cttgttgaag gaaaattgga gctagtagaa ggtcttaaag 5160
tcgccatggc tagtaaagga gaagaacttt tcactggagt tgtcccaatt cttgttgaat 5220
tagatggtga tgttaatggg cacaaatttt ctgtcagtgg agagggtgaa ggtgatgcaa 5280
catacggaaa acttaccctt aaatttattt gcactactgg aaaactacct gttccttggc 5340
caacacttgt cactactttc tcttatggtg ttcaatgctt ttcaagatac ccagatcata 5400
tgaagcggca cgacttcttc aagagcgcca tgcctgaggg atacgtgcag gagaggacca 5460
tctctttcaa ggacgacggg aactacaaga cacgtgctga agtcaagttt gagggagaca 5520
ccctcgtcaa caggatcgag cttaagggaa tcgatttcaa ggaggacgga aacatcctcg 5580
gccacaagtt ggaatacaac tacaactccc acaacgtata catcacggca gacaaacaaa 5640
agaatggaat caaagctaac ttcaaaatta gacacaacat tgaagatgga agcgttcaac 5700
tagcagacca ttatcaacaa aatactccaa ttggcgatgg ccctgtcctt ttaccagaca 5760
accattacct gtccacacaa tctgcccttt cgaaagatcc caacgaaaag agagatcaca 5820
tggtccttct tgagtttgta acagctgctg ggattacaca tggcatggat gaactataca 5880
aataagctta aacagtagac attagcagat aaattagcag gaaataaaga aggataagga 5940
gaaagaactc aagtaattat ccttcgttct cttaattgaa ttgcaattaa actcggccca 6000
atcttttact aaaaggattg agccgaatac cgctacaaca gctccctgga acaccaggag 6060
aacacactta tctcgcgtct tgaggtgata ccacgcctga cacgtgaggg cagtacggtt 6120
aattcggttt agccggacat cagcgctcct cattgagcgc tgggcccttc acatgaagat 6180
cgcactgagg attggtccta gccaggcttc tcagtactga tacagtacgc gtcgcttctc 6240
gtattgtttg agtcttggaa ttagtttgta tccttccgcc gctgccctaa gaattctaat 6300
tgagctcgaa cagtcgaccg ccggatcctg ctcgagtgcc tctaga 6346

<210> SEQ ID NO 52
<211> LENGTH: 6426
<212> TYPE: DNA
<213> ORGANISM: Artificial Sequence
<220> FEATURE:
<223> OTHER INFORMATION: An example of an episomal DNA vector

<400> SEQUENCE: 52
tgccaccaaa aatatatgcc tctgcattat aaataagatt caagccactt ctaatctcac 60
acaagttaaa atgggaattc atttatctaa cattattgtt ttgggaattt agtggatata 120
gcatctcatc ttggatctaa tttacctaac atcatgtaat tcgctatttt ctaactttag 180
cggaatctgg gcttttatcg gaatttaata ctagctttac acataagaca ctcgcaaaat 240
agccgtattt cggcatctgc agggtattgg tagccttgtg gacacaatga agcaatttaa 300
gggaaatcat gtaattaacg gaaattaatg gtattaggat ttggattatt tacaatatct 360
tcaatttaca caatgtggtt ggacagctct gctgttggtg ttggcaacac aaccaaccac 420
gaataattaa tggcacacaa tccactcaac aggcatctac aagcaaattc acgaatctca 480
cgattctcgc gatttctcgc aaattccctc acgtacgagc gcataatgca cacgcgcatc 540
aaaactaaaa gacaaaaatt aaagccctac aaatgtaatg ggttcgtggg tatttataaa 600
taaccctacg ggttatttag aaatgccccc gagggaatat aaccccctaa agggggttat 660
tattcccgag tcggcttaac acgtgtacac gtacacgagg aaccgaaggt tccgacacac 720
acacaatcat acccacgatg aatcttcgat tccagctgat actctcgcca accaaccaag 780

-continued

```
agcagctttg ctgcgaatga gcgtagcgaa taacctgccg caggcagaat attgcgaagc    840
aataccatga gcgaagcgaa taataatgcg aagcattacc tgccgaaggc agaatagccg    900
aaggctacct aatagcgaag ctattgtcaa aaagcttgaa acctcatgca gctaacagct    960
gcacaatcta attcacttgg gattattgat tcttcaaacc attcaacaca caccatgagc   1020
gaagggaata atagagcgaa gctctaccct gccgcaggca gaatattgcg aagcaatacc   1080
atgagcgaag cgaataacag aacgaagttc tgcctggctt tagccagaac aatgcgaagc   1140
attgaaataa aaagaaaatg ttaaacagaa tgcatcttat cacaatctac tcaaccacaa   1200
caggaatcga gtttcattaa ctgtttatca atttcaatga aagtaatttt ggttggctgt   1260
aacgttacaa gcacataaca gaacacagtt ggttatcgat tatggacatt cattaaatgg   1320
tgtaatgtta agtcgagata tggcttcatc acataaactc tggttgtaat taaatggatg   1380
ttaagagttg taaaggtaaa atggatctac aattggttag cctaatcatt tatggctggt   1440
tggttgtgag acaaaaaggt gatgaaacta taacgtgggg gagcgcacgc gcaaggtcgc   1500
aactacccga gaatcgatgt ggcggaatgg gttacgtgag ctattatccg gcgggccctc   1560
aatttaaatc gttacagttg ctcgtaacgg caaccggctc ggtccttttt ccctagaaca   1620
gtatcttata cttgctgctc tcgttacttc ggcgatcctg gtgcagtcgg tccgtaaatc   1680
ggcgcacact tttacgtcgt accagacagg ctcgcataag ccagccccga cacccgccaa   1740
cacccgctga cgcgccctga cgggcttgtc tgctcccggc atccgcttac agacaagctg   1800
tgacctccgg gagctgcatg tgtcagaggt tttcaccgtc atcaccgaaa cgcgcacgaa   1860
agggcctcgt gatacgccta tttttatagg ttaatgtcat gataataatg gtttcttaga   1920
cgtcaggtgg cacttttcgg ggaaatgtgc gcggaacccc tatttgttta tttttctaaa   1980
tacattcaaa tatgtatccg ctcatgagac aataaccctg ataaatgctt caataatatt   2040
gaaaaaggaa gagtatgagt attcaacatt tccgtgtcgc ccttattccc ttttttgcgg   2100
cattttgcct tcctgttttt gctcacccag aaacgctggt gaaagtaaaa gatgctgaag   2160
atcagttggg tgcacgagtg ggttacatcg aactggatct caacagcggt aagatccttg   2220
agagttttcg ccccgaagaa cgttttccaa tgatgagcac ttttaaagtt ctgctatgtg   2280
gcgcggtatt atcccgtatt gacgccgggc aagagcaact cggtcgccgc atacactatt   2340
ctcagaatga cttggttgag tactcaccag tcacagaaaa gcatcttacg gatggcatga   2400
cagtaagaga attatgcagt gctgccataa ccatgagtga taacactgcg gccaacttac   2460
ttctgacaac gatcggagga ccgaaggagc taaccgcttt tttgcacaac atgggggatc   2520
atgtaactcg ccttgatcgt tgggaaccgg agctgaatga agccatacca aacgacgagc   2580
gtgacaccac gatgcctgta gcaatggcaa caacgttgcg caaactatta actggcgaac   2640
tacttactct agcttcccgg caacaattaa tagactggat ggaggcggat aaagttgcag   2700
gaccacttct gcgctcggcc cttccggctg gctggtttat tgctgataaa tctggagccg   2760
gtgagcgtgg ctcacgcggt atcattgcag cactggggcc agatggtaag ccctcccgta   2820
tcgtagttat ctacacgacg gggagtcagg caactatgga tgaacgaaat agacagatcg   2880
ctgagatagg tgcctcactg attaagcatt ggtaactgtc agaccaagtt tactcatata   2940
tactttagat tgatttaaaa cttcattttt aatttaaaag gatctaggtg aagatccttt   3000
ttgataatct catgaccaaa atcccttaac gtgagttttc gttccactga gcgtcagacc   3060
ccgtagaaaa gatcaaagga tcttcttgag atcctttttt tctgcgcgta atctgctgct   3120
```

-continued

```
tgcaaacaaa aaaaccaccg ctaccagcgg tggtttgttt gccggatcaa gagctaccaa   3180
ctctttttcc gaaggtaact ggcttcagca gagcgcagat accaaatact gttcttctag   3240
tgtagccgta gttaggccac cacttcaaga actctgtagc accgcctaca tacctcgctc   3300
tgctaatcct gttaccagtg gctgctgcca gtggcgataa gtcgtgtctt accgggttgg   3360
actcaagacg atagttaccg gataaggcgc agcggtcggg ctgaacgggg ggttcgtgca   3420
cacagcccag cttggagcga acgacctaca ccgaactgag atacctacag cgtgagctat   3480
gagaaagcgc cacgcttccc gaagggagaa aggcggacag gtatccggta agcggcaggg   3540
tcggaacagg agagcgcacg agggagcttc caggggggaaa cgcctggtat ctttatagtc   3600
ctgtcgggtt tcgccacctc tgacttgagc gtcgattttt gtgatgctcg tcaggggggc   3660
ggagcctatg gaaaaacgcc agcaacgcgg cctttttacg gttcctggcc ttttgctggc   3720
cttttgctca catgttcttt cctgcgttat cccctgattc tgtggataac cgtattaccg   3780
cctttgagtg agctgatacc gctcgccgca gccgaacgac cgagcgcagc gagtcagtga   3840
gcgaggaagc ggaagaacgc ggacacccag cgtaacaatc taatattgtt tctcaaatcg   3900
ggctgttatc gcatggtgct catgatgagg ttactgacca aattcgccac gcatcggtgc   3960
tggtagaatg ttcacttcga ggtgggtaga cggcgtcacg tgcaatgcct tgtcttcccc   4020
tatctgcggc cccgactgcc tcgcgaagac aagggatcgg acgtcgaacg tattctgttt   4080
gctaccggca cgggagtagg atcgttgata tacaccatgc gcgttaactc tgaccccctt   4140
cctcttaaat gagaatggat aagaggctcg tgggattgac gtgagggggc agggatggct   4200
atatttctgg gagcgaactc cgggcgaatt actaataaaa agccttccat ttctatttt   4260
gatttgtaga aaactagtgt gcttgggagt ccctgatgat taaataaacc aagattttac   4320
caatgggggc tagcgaagcg gtgatcgccg aagtatcgac tcaactatca gaggtagttg   4380
gcgtcatcga gcgccatctc gaaccgacgt tgctggccgt acatttgtac ggctccgcag   4440
tggatggcgg cctgaagcca cacagtgata ttgatttgct ggttacggtg accgtaaggc   4500
ttgatgaaac aacgcggcga gctttgatca acgacctttt ggaaacttcg gcttcccctg   4560
gagagagcga gattctccgc gctgtagaag tcaccattgt tgtgcacgac gacatcattc   4620
cgtggcgtta tccagctaag cgcgaactgc aatttggaga atggcagcgc aatgacattc   4680
ttgcaggtat cttcgagcca gccacgatcg acattgatct ggctatcttg ctgacaaaag   4740
caagagaaca tagcgttgcc ttggtaggtc cagcggcgga ggaactcttt gatccggttc   4800
ctgaacagga tctatttgag gcgctaaatg aaaccttaac gctatggaac tcgccgcccg   4860
actgggctgg cgatgagcga aatgtagtgc ttacgttgtc ccgcatttgg tacagcgcag   4920
taaccggcaa aatcgcgccg aaggatgtcg ctgccgactg ggcaatggag cgcctgccgg   4980
cccagtatca gcccgtcata cttgaagcta gacaggctta tcttggacaa gaagaagatc   5040
gcttggcctc gcgcgcagat cagttggaag aatttgtcca ctacgtgaaa ggcgagatca   5100
ccaaggtagt gggcaaagaa cttgttgaag gaaaattgga gctagtagaa ggtcttaaag   5160
tcgccatggc tagtaaagga gaagaacttt tcactggagt tgtcccaatt cttgttgaat   5220
tagatggtga tgttaatggg cacaaatttt ctgtcagtgg agagggtgaa ggtgatgcaa   5280
catacggaaa acttaccctt aaatttattt gcactactgg aaaactacct gttccttggc   5340
caacacttgt cactactttc tcttatggtg ttcaatgctt ttcaagatac ccagatcata   5400
tgaagcggca cgacttcttc aagagcgcca tgcctgaggg atacgtgcag gagaggacca   5460
tctctttcaa ggacgacggg aactacaaga cacgtgctga agtcaagttt gagggagaca   5520
```

```
ccctcgtcaa caggatcgag cttaagggaa tcgatttcaa ggaggacgga aacatcctcg   5580

gccacaagtt ggaatacaac tacaactccc acaacgtata catcacggca gacaaacaaa   5640

agaatggaat caaagctaac ttcaaaatta gacacaacat tgaagatgga agcgttcaac   5700

tagcagacca ttatcaacaa aatactccaa ttggcgatgg ccctgtcctt ttaccagaca   5760

accattacct gtccacacaa tctgcccttt cgaaagatcc caacgaaaag agagatcaca   5820

tggtccttct tgagtttgta acagctgctg ggattacaca tggcatggat gaactataca   5880

aataagctta aacagtagac attagcagat aaattagcag gaaataaaga aggataagga   5940

gaaagaactc aagtaattat ccttcgttct cttaattgaa ttgcaattaa actcggccca   6000

atcttttact aaaaggattg agccgaatac cgctccaggc atcaaataaa acgaaaggct   6060

cagtcgaaag actgggcctt tcgttttatc tgttgtttgt cggtgaacgc tctcacaaca   6120

gctccctgga acaccaggag aacacactta tctcgcgtct tgaggtgata ccacgcctga   6180

cacgtgaggg cagtacggtt aattcggttt agccggacat cagcgctcct cattgagcgc   6240

tgggcccttc acatgaagat cgcactgagg attggtccta gccaggcttc tcagtactga   6300

tacagtacgc gtcgcttctc gtattgtttg agtcttggaa ttagtttgta tccttccgcc   6360

gctgccctaa gaattctaat tgagctcgaa cagtcgaccg ccggatcctg ctcgagtgcc   6420

tctaga                                                              6426
```

<210> SEQ ID NO 53
<211> LENGTH: 6943
<212> TYPE: DNA
<213> ORGANISM: Artificial Sequence
<220> FEATURE:
<223> OTHER INFORMATION: An example of an episomal DNA vector

<400> SEQUENCE: 53

```
tgccagcttc tccccccctt tatccgcccg actctttgct cttaagaatg taggtttgaa     60

gttaagaatg agtaattgca cttctccgac ccttaactgt tcaacctaag atacggagaa    120

ctaaggcgtt ttcaggttga acagggttct atggtcggtc cgcgacccct ggatgccaaa    180

gggtccttgg ggtgatctcg tagttcctac ggggtggaga cgatggggtc ggtccatgga    240

ttttctttcc ttttgttttc ccgcatttcg ctcaaagggt tgaagggaga tagtgcatca    300

agctgttcgc aagggccagc ttgatcctct tccccaggat ttcagatgag gaaaccctag    360

gagagccacc gactctaact accgtccatg tatgatccat actagatctg accaacttcc    420

catcctacct cctctacgga cagcccatcc ttgtctcagt agagtctttc agtggcatgt    480

ttcggtcctc tttcccatta cttagaaaaa gtgagccacc ggttcaggta caagatacta    540

tcattaccgc ctggacaatt agacatccaa cccgtaatcg caacgaccca attgcaagag    600

cggagctcta ccaactgagc tatatccccc cgagccaagt tggagcatgc atgaaggagt    660

caaatccgtc ttttagtctt ttccttggcg cagctgggcc atcctggact tgaaccagtg    720

acctcgcccg tgaagtaaat catcgcacct acggtccatc caattgggag agaatcaata    780

gattcctttt cgggagcgat tcatccttcc cgaacgcagc atacaactat ccattgtact    840

gcgctctcca agtgtgcttg tttccccttc tttcttatca tgacaagtct ttgtggaata    900

actctgatga gaagaaaaaa gaaaacgtta agggacactc taagatcctt tttcaaacct    960

gctcccattt cgagtcaaga gaatggtacg atcccgccgt cacctcagaa taaaaggggt   1020

gatctcgtag ttcttggtct gtgaagatac gttgttaggt gctccgtttt tctttttcca   1080
```

-continued

```
ttgaggccaa acctaaacct gtgctcgaga gatagttatc catatactga taagggatgt   1140
atgaattctc gagaggagag gagccatgat ggtcccccct ggaccgcccg gatcccacga   1200
gtgaatagaa agttggatct acattggatc tcacctgaat cgccccatct atcttcctga   1260
ggaggagttt ggtttcaaac ccggttcaa acaggagaag tacgccatgc taatgtgcct    1320
tggatggtcc acatctcagg gtcaggcgct gatgaacaca ttgaactatc tatgtggctg   1380
atagccctca cagtccaggc acaacgacgc aattatcagg ggcgcgctct accactgagc   1440
taatagcccg ttgtgtgggc cccccgaagg ggcccactat gtcaaaagtg agagaaaccc   1500
catctctctc tttccccttt gtttgcctca tgtcgcccac ggggcgacat gggtcaaaaa   1560
agaggagctc ctatcaagtt gttccgacct aggataataa gctcatgaga ttagtgtcac   1620
tgacattctc atcacccaca ggaaacgaaa ggagacttcc acctactaac tttgcctcga   1680
taacccottc gcttcagcgg tgtgaaacag tgtaaaaccc aatcacccaa aaagcgttct   1740
ctgttctccc tgaataggtt aataagctag ctcctgagct aggtgtgact tcaccgtcga   1800
gaaacgaaac ataacggaaa tctacctact agtgcgatgt agcttttctt tactttaacg   1860
gggtgtgagt gacgcagtgt aaaacctaat tacacaaaaa gcattagttc tccctgaaaa   1920
ggaggtgatc cagtcgcacc ttccagtacg gctaccttgt tacgacttca ctccagtcac   1980
tagccctgcc ttcggcatcc ccctccttgc ggttaaggta atgacttcgg gcatggccag   2040
ctcccatagt gtgacgggcg gtgtgtacaa ggcccgggag cgcacgcgca aggtcgcaac   2100
tacccgagaa tcgatgtggc ggaatgggtt acgtgagcta ttatccggcg ggccctcaat   2160
ttaaatcgtt acagttgctc gtaacggcaa ccggctcggt ccttttttccc tagaacagta  2220
tcttatactt gctgctctcg ttacttcggc gatcctggtg cagtcggtcc gtaaatcggc   2280
gcacactttt acgtcgtacc agacaggctc gcataagcca gccccgacac ccgccaacac   2340
ccgctgacgc gccctgacgg gcttgtctgc tcccggcatc cgcttacaga caagctgtga   2400
cctccgggag ctgcatgtgt cagaggtttt caccgtcatc accgaaacgc gcacgaaagg   2460
gcctcgtgat acgcctattt ttataggtta atgtcatgat aataatggtt tcttagacgt   2520
caggtggcac ttttcgggga aatgtgcgcg gaacccctat ttgtttattt ttctaaatac   2580
attcaaatat gtatccgctc atgagacaat aaccctgata aatgcttcaa taatattgaa   2640
aaaggaagag tatgagtatt caacatttcc gtgtcgccct tattcccttt tttgcggcat   2700
tttgccttcc tgtttttgct cacccagaaa cgctggtgaa agtaaaagat gctgaagatc   2760
agttgggtgc acgagtgggt tacatcgaac tggatctcaa cagcggtaag atccttgaga   2820
gttttcgccc cgaagaacgt tttccaatga tgagcacttt taaagttctg ctatgtggcg   2880
cggtattatc ccgtattgac gccgggcaag agcaactcgg tcgccgcata cactattctc   2940
agaatgactt ggttgagtac tcaccagtca cagaaaagca tcttacggat ggcatgacag   3000
taagagaatt atgcagtgct gccataacca tgagtgataa cactgcggcc aacttacttc   3060
tgacaacgat cggaggaccg aaggagctaa ccgctttttt gcacaacatg ggggatcatg   3120
taactcgcct tgatcgttgg gaaccggagc tgaatgaagc cataccaaac gacgagcgtg   3180
acaccacgat gcctgtagca atggcaacaa cgttgcgcaa actattaact ggcgaactac   3240
ttactctagc ttcccggcaa caattaatag actggatgga ggcggataaa gttgcaggac   3300
cacttctgcg ctcggccctt ccggctggct ggtttattgc tgataaatct ggagccggtg   3360
agcgtggctc acgcggtatc attgcagcac tggggccaga tggtaagccc tcccgtatcg   3420
tagttatcta cacgacgggg agtcaggcaa ctatggatga acgaaataga cagatcgctg   3480
```

agataggtgc ctcactgatt aagcattggt aactgtcaga ccaagtttac tcatatatac 3540
tttagattga tttaaaactt catttttaat ttaaaaggat ctaggtgaag atcctttttg 3600
ataatctcat gaccaaaatc ccttaacgtg agttttcgtt ccactgagcg tcagaccccg 3660
tagaaaagat caaaggatct tcttgagatc cttttttct gcgcgtaatc tgctgcttgc 3720
aaacaaaaaa accaccgcta ccagcggtgg tttgtttgcc ggatcaagag ctaccaactc 3780
tttttccgaa ggtaactggc ttcagcagag cgcagatacc aaatactgtt cttctagtgt 3840
agccgtagtt aggccaccac ttcaagaact ctgtagcacc gcctacatac ctcgctctgc 3900
taatcctgtt accagtggct gctgccagtg gcgataagtc gtgtcttacc gggttggact 3960
caagacgata gttaccggat aaggcgcagc ggtcgggctg aacggggggt tcgtgcacac 4020
agcccagctt ggagcgaacg acctacaccg aactgagata cctacagcgt gagctatgag 4080
aaagcgccac gcttcccgaa gggagaaagg cggacaggta tccggtaagc ggcagggtcg 4140
gaacaggaga gcgcacgagg gagcttccag ggggaaacgc ctggtatctt tatagtcctg 4200
tcgggtttcg ccacctctga cttgagcgtc gatttttgtg atgctcgtca ggggggcgga 4260
gcctatggaa aaacgccagc aacgcggcct ttttacggtt cctggccttt tgctggcctt 4320
ttgctcacat gttctttcct gcgttatccc ctgattctgt ggataaccgt attaccgcct 4380
ttgagtgagc tgataccgct cgccgcagcc gaacgaccga gcgcagcgag tcagtgagcg 4440
aggaagcgga agaacgcgga cacccagcgt aacaatctaa tattgtttct caaatcgggc 4500
tgttatcgca tggtgctcat gatgaggtta ctgaccaaat tcgccacgca tcggtgctgg 4560
tagaatgttc acttcgaggt gggtagacgg cgtcacgtgc aatgccttgt cttcccctat 4620
ctgcggcccc gactgcctcg cgaagacaag ggatcggacg tcgaacgtat tctgtttgct 4680
accggcacgg gagtaggatc gttgatatac accatgcgcg ttaactctga ccccccttcct 4740
cttaaatgag aatggataag aggctcgtgg gattgacgtg agggggcagg gatggctata 4800
tttctgggag cgaactccgg gcgaattact aataaaaagc cttccatttt ctattttgat 4860
ttgtagaaaa ctagtgtgct tgggagtccc tgatgattaa ataaaccaag attttaccaa 4920
tgggggctag cgaagcggtg atcgccgaag tatcgactca actatcagag gtagttggcg 4980
tcatcgagcg ccatctcgaa ccgacgttgc tggccgtaca tttgtacggc tccgcagtgg 5040
atggcggcct gaagccacac agtgatattg atttgctggt tacggtgacc gtaaggcttg 5100
atgaaacaac gcggcgagct ttgatcaacg accttttgga aacttcggct tcccctggag 5160
agagcgagat tctccgcgct gtagaagtca ccattgttgt gcacgacgac atcattccgt 5220
ggcgttatcc agctaagcgc gaactgcaat ttggagaatg gcagcgcaat gacattcttg 5280
caggtatctt cgagccagcc acgatcgaca ttgatctggc tatcttgctg acaaaagcaa 5340
gagaacatag cgttgccttg gtaggtccag cggcggagga actctttgat ccggttcctg 5400
aacaggatct atttgaggcg ctaaatgaaa ccttaacgct atggaactcg ccgcccgact 5460
gggctggcga tgagcgaaat gtagtgctta cgttgtcccg catttggtac agcgcagtaa 5520
ccggcaaaat cgcgccgaag gatgtcgctg ccgactgggc aatggagcgc ctgccggccc 5580
agtatcagcc cgtcatactt gaagctagac aggcttatct tggacaagaa gaagatcgct 5640
tggcctcgcg cgcagatcag ttggaagaat ttgtccacta cgtgaaaggc gagatcacca 5700
aggtagtggg caaagaactt gttgaaggaa aattggagct agtagaaggt cttaaagtcg 5760
ccatggctag taaaggagaa gaacttttca ctggagttgt cccaattctt gttgaattag 5820

-continued

```
atggtgatgt taatgggcac aaattttctg tcagtggaga gggtgaaggt gatgcaacat   5880
acggaaaact tacccttaaa tttatttgca ctactggaaa actacctgtt ccttggccaa   5940
cacttgtcac tactttctct tatggtgttc aatgcttttc aagataccca gatcatatga   6000
agcggcacga cttcttcaag agcgccatgc ctgagggata cgtgcaggag aggaccatct   6060
ctttcaagga cgacgggaac tacaagacac gtgctgaagt caagtttgag ggagacaccc   6120
tcgtcaacag gatcgagctt aagggaatcg atttcaagga ggacggaaac atcctcggcc   6180
acaagttgga atacaactac aactcccaca acgtatacat cacggcagac aaacaaaaga   6240
atggaatcaa agctaacttc aaaattagac acaacattga agatggaagc gttcaactag   6300
cagaccatta tcaacaaaat actccaattg gcgatggccc tgtcctttta ccagacaacc   6360
attacctgtc cacacaatct gccctttcga aagatcccaa cgaaaagaga gatcacatgg   6420
tccttcttga gtttgtaaca gctgctggga ttacacatgg catggatgaa ctatacaaat   6480
aagcttaaac agtagacatt agcagataaa ttagcaggaa ataaagaagg ataaggagaa   6540
agaactcaag taattatcct tcgttctctt aattgaattg caattaaact cggcccaatc   6600
ttttactaaa aggattgagc cgaataccgc tacaacagct ccctggaaca ccaggagaac   6660
acacttatct cgcgtcttga ggtgatacca cgcctgacac gtgagggcag tacggttaat   6720
tcggtttagc cggacatcag cgctcctcat tgagcgctgg gcccttcaca tgaagatcgc   6780
actgaggatt ggtcctagcc aggcttctca gtactgatac agtacgcgtc gcttctcgta   6840
ttgtttgagt cttggaatta gtttgtatcc ttccgccgct gccctaagaa ttctaattga   6900
gctcgaacag tcgaccgccg gatcctgctc gagtgcctct aga                     6943
```

<210> SEQ ID NO 54
<211> LENGTH: 7023
<212> TYPE: DNA
<213> ORGANISM: Artificial Sequence
<220> FEATURE:
<223> OTHER INFORMATION: An example of an episomal DNA vector

<400> SEQUENCE: 54

```
tgccagcttc tccccccctt tatccgcccg actctttgct cttaagaatg taggtttgaa     60
gttaagaatg agtaattgca cttctccgac ccttaactgt tcaacctaag atacggagaa    120
ctaaggcgtt ttcaggttga acagggttct atggtcggtc cgcgacccct ggatgccaaa    180
gggtccttgg ggtgatctcg tagttcctac ggggtggaga cgatggggtc ggtccatgga    240
ttttctttcc ttttgttttc ccgcatttcg ctcaaagggt tgaagggaga tagtgcatca    300
agctgttcgc aagggccagc ttgatcctct tccccaggat ttcagatgag gaaaccctag    360
gagagccacc gactctaact accgtccatg tatgatccat actagatctg accaacttcc    420
catcctacct cctctacgga cagcccatcc ttgtctcagt agagtctttc agtggcatgt    480
ttcggtcctc tttcccatta cttagaaaaa gtgagccacc ggttcaggta caagatacta    540
tcattaccgc ctggacaatt agacatccaa cccgtaatcg caacgaccca attgcaagag    600
cggagctcta ccaactgagc tatatccccc cgagccaagt tggagcatgc atgaaggagt    660
caaatccgtc ttttagtctt ttccttggcg cagctgggcc atcctggact tgaaccagtg    720
acctcgcccg tgaagtaaat catcgcacct acggtccatc caattgggag agaatcaata    780
gattcctttt cgggagcgat tcatccttcc cgaacgcagc atacaactat ccattgtact    840
gcgctctcca agtgtgcttg tttccccttc tttcttatca tgacaagtct ttgtggaata    900
actctgatga gaagaaaaaa gaaaacgtta agggacactc taagatcctt tttcaaacct    960
```

gctcccattt cgagtcaaga gaatggtacg atcccgccgt cacctcagaa taaaaggggt 1020
gatctcgtag ttcttggtct gtgaagatac gttgttaggt gctccgtttt tctttttcca 1080
ttgaggccaa acctaaacct gtgctcgaga gatagttatc catatactga taagggatgt 1140
atgaattctc gagaggagag gagccatgat ggtcccccct ggaccgcccg gatcccacga 1200
gtgaatagaa agttggatct acattggatc tcacctgaat cgccccatct atcttcctga 1260
ggaggagttt ggtttcaaac cccggttcaa acaggagaag tacgccatgc taatgtgcct 1320
tggatggtcc acatctcagg gtcaggcgct gatgaacaca ttgaactatc tatgtggctg 1380
atagccctca cagtccaggc acaacgacgc aattatcagg ggcgcgctct accactgagc 1440
taatagcccg ttgtgtgggc cccccgaagg ggcccactat gtcaaaagtg agagaaaccc 1500
catctctctc tttccccttt gtttgcctca tgtcgcccac ggggcgacat gggtcaaaaa 1560
agaggagctc ctatcaagtt gttccgacct aggataataa gctcatgaga ttagtgtcac 1620
tgacattctc atcacccaca ggaaacgaaa ggagacttcc acctactaac tttgcctcga 1680
taaccccttc gcttcagcgg tgtgaaacag tgtaaaaccc aatcacccaa aaagcgttct 1740
ctgttctccc tgaataggtt aataagctag ctcctgagct aggtgtgact tcaccgtcga 1800
gaaacgaaac ataacggaaa tctacctact agtgcgatgt agcttttctt tactttaacg 1860
gggtgtgagt gacgcagtgt aaaacctaat tacacaaaaa gcattagttc tccctgaaaa 1920
ggaggtgatc cagtcgcacc ttccagtacg gctaccttgt tacgacttca ctccagtcac 1980
tagccctgcc ttcggcatcc ccctccttgc ggttaaggta atgacttcgg gcatggccag 2040
ctcccatagt gtgacgggcg gtgtgtacaa ggcccgggag cgcacgcgca aggtcgcaac 2100
tacccgagaa tcgatgtggc ggaatgggtt acgtgagcta ttatccggcg ggccctcaat 2160
ttaaatcgtt acagttgctc gtaacggcaa ccggctcggt ccttttttccc tagaacagta 2220
tcttatactt gctgctctcg ttacttcggc gatcctggtg cagtcggtcc gtaaatcggc 2280
gcacactttt acgtcgtacc agacaggctc gcataagcca gccccgacac ccgccaacac 2340
ccgctgacgc gccctgacgg gcttgtctgc tcccggcatc cgcttacaga caagctgtga 2400
cctccgggag ctgcatgtgt cagaggtttt caccgtcatc accgaaacgc gcacgaaagg 2460
gcctcgtgat acgcctattt ttataggtta atgtcatgat aataatggtt tcttagacgt 2520
caggtggcac ttttcgggga aatgtgcgcg gaacccctat ttgtttattt ttctaaatac 2580
attcaaatat gtatccgctc atgagacaat aaccctgata aatgcttcaa taatattgaa 2640
aaaggaagag tatgagtatt caacatttcc gtgtcgccct tattcccttt tttgcggcat 2700
tttgccttcc tgtttttgct cacccagaaa cgctggtgaa agtaaaagat gctgaagatc 2760
agttgggtgc acgagtgggt tacatcgaac tggatctcaa cagcggtaag atccttgaga 2820
gttttcgccc cgaagaacgt tttccaatga tgagcacttt taaagttctg ctatgtggcg 2880
cggtattatc ccgtattgac gccgggcaag agcaactcgg tcgccgcata cactattctc 2940
agaatgactt ggttgagtac tcaccagtca cagaaaagca tcttacggat ggcatgacag 3000
taagagaatt atgcagtgct gccataacca tgagtgataa cactgcggcc aacttacttc 3060
tgacaacgat cggaggaccg aaggagctaa ccgctttttt gcacaacatg ggggatcatg 3120
taactcgcct tgatcgttgg gaaccggagc tgaatgaagc cataccaaac gacgagcgtg 3180
acaccacgat gcctgtagca atggcaacaa cgttgcgcaa actattaact ggcgaactac 3240
ttactctagc ttcccggcaa caattaatag actggatgga ggcggataaa gttgcaggac 3300

-continued

```
cacttctgcg ctcggccctt ccggctggct ggtttattgc tgataaatct ggagccggtg   3360
agcgtggctc acgcggtatc attgcagcac tggggccaga tggtaagccc tcccgtatcg   3420
tagttatcta cacgacgggg agtcaggcaa ctatggatga acgaaataga cagatcgctg   3480
agataggtgc ctcactgatt aagcattggt aactgtcaga ccaagtttac tcatatatac   3540
tttagattga tttaaaactt catttttaat ttaaaaggat ctaggtgaag atcctttttg   3600
ataatctcat gaccaaaatc ccttaacgtg agttttcgtt ccactgagcg tcagaccccg   3660
tagaaaagat caaaggatct tcttgagatc ctttttttct gcgcgtaatc tgctgcttgc   3720
aaacaaaaaa accaccgcta ccagcggtgg tttgtttgcc ggatcaagag ctaccaactc   3780
tttttccgaa ggtaactggc ttcagcagag cgcagatacc aaatactgtt cttctagtgt   3840
agccgtagtt aggccaccac ttcaagaact ctgtagcacc gcctacatac ctcgctctgc   3900
taatcctgtt accagtggct gctgccagtg gcgataagtc gtgtcttacc gggttggact   3960
caagacgata gttaccggat aaggcgcagc ggtcgggctg aacggggggt tcgtgcacac   4020
agcccagctt ggagcgaacg acctacaccg aactgagata cctacagcgt gagctatgag   4080
aaagcgccac gcttcccgaa gggagaaagg cggacaggta tccggtaagc ggcagggtcg   4140
gaacaggaga gcgcacgagg gagcttccag ggggaaacgc ctggtatctt tatagtcctg   4200
tcgggtttcg ccacctctga cttgagcgtc gatttttgtg atgctcgtca ggggggcgga   4260
gcctatggaa aaacgccagc aacgcggcct ttttacggtt cctggccttt tgctggcctt   4320
ttgctcacat gttctttcct gcgttatccc ctgattctgt ggataaccgt attaccgcct   4380
ttgagtgagc tgataccgct cgccgcagcc gaacgaccga gcgcagcgag tcagtgagcg   4440
aggaagcgga agaacgcgga cacccagcgt aacaatctaa tattgtttct caaatcgggc   4500
tgttatcgca tggtgctcat gatgaggtta ctgaccaaat tcgccacgca tcggtgctgg   4560
tagaatgttc acttcgaggt gggtagacgg cgtcacgtgc aatgccttgt cttcccctat   4620
ctgcggcccc gactgcctcg cgaagacaag ggatcggacg tcgaacgtat tctgtttgct   4680
accggcacgg gagtaggatc gttgatatac accatgcgcg ttaactctga ccccccttcct   4740
cttaaatgag aatggataag aggctcgtgg gattgacgtg agggggcagg gatggctata   4800
tttctgggag cgaactccgg gcgaattact aataaaaagc cttccatttt ctattttgat   4860
ttgtagaaaa ctagtgtgct tgggagtccc tgatgattaa ataaaccaag attttaccaa   4920
tgggggctag cgaagcggtg atcgccgaag tatcgactca actatcagag gtagttggcg   4980
tcatcgagcg ccatctcgaa ccgacgttgc tggccgtaca tttgtacggc tccgcagtgg   5040
atggcggcct gaagccacac agtgatattg atttgctggt tacggtgacc gtaaggcttg   5100
atgaaacaac gcggcgagct ttgatcaacg accttttgga aacttcggct tcccctggag   5160
agagcgagat tctccgcgct gtagaagtca ccattgttgt gcacgacgac atcattccgt   5220
ggcgttatcc agctaagcgc gaactgcaat ttggagaatg gcagcgcaat gacattcttg   5280
caggtatctt cgagccagcc acgatcgaca ttgatctggc tatcttgctg acaaaagcaa   5340
gagaacatag cgttgccttg gtaggtccag cggcggagga actctttgat ccggttcctg   5400
aacaggatct atttgaggcg ctaaatgaaa ccttaacgct atggaactcg ccgcccgact   5460
gggctggcga tgagcgaaat gtagtgctta cgttgtcccg catttggtac agcgcagtaa   5520
ccggcaaaat cgcgccgaag gatgtcgctg ccgactgggc aatggagcgc ctgccggccc   5580
agtatcagcc cgtcatactt gaagctagac aggcttatct tggacaagaa gaagatcgct   5640
tggcctcgcg cgcagatcag ttggaagaat ttgtccacta cgtgaaaggc gagatcacca   5700
```

aggtagtggg caaagaactt gttgaaggaa aattggagct agtagaaggt cttaaagtcg 5760
ccatggctag taaaggagaa gaacttttca ctggagttgt cccaattctt gttgaattag 5820
atggtgatgt taatgggcac aaattttctg tcagtggaga gggtgaaggt gatgcaacat 5880
acggaaaact tacccttaaa tttatttgca ctactggaaa actacctgtt ccttggccaa 5940
cacttgtcac tactttctct tatggtgttc aatgcttttc aagataccca gatcatatga 6000
agcggcacga cttcttcaag agcgccatgc ctgagggata cgtgcaggag aggaccatct 6060
ctttcaagga cgacgggaac tacaagacac gtgctgaagt caagtttgag ggagacaccc 6120
tcgtcaacag gatcgagctt aagggaatcg atttcaagga ggacggaaac atcctcggcc 6180
acaagttgga atacaactac aactcccaca acgtatacat cacggcagac aaacaaaaga 6240
atggaatcaa agctaacttc aaaattagac acaacattga agatggaagc gttcaactag 6300
cagaccatta tcaacaaaat actccaattg gcgatggccc tgtcctttta ccagacaacc 6360
attacctgtc cacacaatct gccctttcga aagatcccaa cgaaaagaga gatcacatgg 6420
tccttcttga gtttgtaaca gctgctggga ttacacatgg catggatgaa ctatacaaat 6480
aagcttaaac agtagacatt agcagataaa ttagcaggaa ataaagaagg ataaggagaa 6540
agaactcaag taattatcct tcgttctctt aattgaattg caattaaact cggcccaatc 6600
ttttactaaa aggattgagc cgaataccgc tccaggcatc aaataaaacg aaaggctcag 6660
tcgaaagact gggcctttcg ttttatctgt tgtttgtcgg tgaacgctct cacaacagct 6720
ccctggaaca ccaggagaac acacttatct cgcgtcttga ggtgatacca cgcctgacac 6780
gtgagggcag tacggttaat tcggtttagc cggacatcag cgctcctcat tgagcgctgg 6840
gcccttcaca tgaagatcgc actgaggatt ggtcctagcc aggcttctca gtactgatac 6900
agtacgcgtc gcttctcgta ttgtttgagt cttggaatta gtttgtatcc ttccgccgct 6960
gccctaagaa ttctaattga gctcgaacag tcgaccgccg gatcctgctc gagtgcctct 7020
aga 7023

<210> SEQ ID NO 55
<211> LENGTH: 9085
<212> TYPE: DNA
<213> ORGANISM: Artificial Sequence
<220> FEATURE:
<223> OTHER INFORMATION: An example of an episomal DNA vector

<400> SEQUENCE: 55
tgccgggcct agtcactgcg accccctttg tgaggaggca ccccttctcc cgaagttacg 60
gggctatttt gccgagttcc ttagagagag ttgtctcgcg cccctaggta ttctctacct 120
acccacctgt gtcggtttcc ggtacaggta ccctcttgtt gtaggtcgtt cgaacttttc 180
ctgggagtat ggcatcaatt actttagcgc cagagtgcgc gcctcgtact cgtactcgaa 240
ttttggctcg agggcatttt ctctacccct tacttaccct gaaaaaaaca gggagtcacc 300
ttatgttctt gaaccgataa ccatctttcg gctaacctag cctcctccgt ccctcgggac 360
caacaagggg cagtacagga atattaacct gttgtccatc gactacgcct ttcggcctga 420
tcttaggtcc tgacttaccc tccgtggacg aaccttgcgg aggaatcctt aggttttcgg 480
ggcattggat tctcaccaat gttttcgtta ctcaagccga cattctcgct tccgcttcgt 540
ccaaccctgc tcgcgcgggt acttctttct aaggcggaac gctcccctac cgattcattt 600
ttacatccca cagcttcggc aaatcgctta gccccgttca tcttcggcgc aagagcgctc 660

-continued

```
gatcagtgag ctattacgca ctctttgaag ggtggctgct tctaggcaaa cctcctggct    720
gtctctgcac tcctacctcc tttatcactg agcgatcatt taggggcctt agctggtgat    780
ctgggctgtt tccctctcga cagatgaagc ttatccccca tcgtctcact ggccgacctt    840
gacccgtcgg ggtcatatct agtattcaga gtttgcctcg atttggtacc gctctcgcgg    900
cccgcgccga aacagtgctt taccccctaga tgtccagtca actgctgcgc ctcaacgcat    960
ttcggggaga accagctagc tctgggttcg attggcattt caccgctaac cacaactcat   1020
ccgctgattt ttcaacatca gtcggttcgg acctccactt agtttcacct aaacttcatc   1080
ctggtcatgg atagatcacc caggttcggg tccataagca gtgacaatag ccctatgaag   1140
actcgctttc gctacggctc cggtggtttc ccttaaccaa gccactgcct atgagtcgcc   1200
ggctcattct tcaacaggca cgcggtcaga gccccagctc ctcccactgt tgggagctta   1260
cggtttcatg ttctatttca ctccccgcca ggggttcttt tcacctttcc ctcacggtac   1320
tacttcacta tcggtcaccc aggagtattt agccttgcaa ggtggtcctt gctgattcac   1380
acgggatttc acgtgcccca tgttactcgg gtcagagcat aagctagtga tgctttcggc   1440
tactggactt tcaccatcta gggtgcaaca ttcgactgct tcgcctagca gcacgacgct   1500
tgtattgctc tcccacaacc ccgttttcac ggtttaggct gctcccattt cgctcgccgc   1560
tactacggga atcgcttttg ctttcttttc ctctggctac taagatgttt cagttcgcca   1620
ggttgtctct tgcctgctcg tgaattcagc agcagttcga aaggttgacc tattcgggaa   1680
tcctcggatc tatgcttatt ttcaactccc cgaagcattt cgtcgcttac tacgcccttc   1740
ctcgtctctg ggtgcctagg tatccaccat aagcctttcc tcgtttgaac ctcgcccttc   1800
aactctatgc catcctaagg tgctgctaga tggaaggatc ttatcaacgt ccataaataa   1860
taaatcataa catagctaaa acaaaaaaat gaacgagttg gagataagcg gactcgaacc   1920
gctgacatcc gccacagggt aaatcaccgc ctctcaagcc ccaactgatt ctaccataga   1980
ggccaacgat agacaataac cctccgaaca cagcttacaa ctttcatcgt actgtgctct   2040
ccaaagagca actcttctca aaatatcaaa gggtgctgag ttggaatccc attcaaacaa   2100
ggattcttgt ggttgcggaa gatccagcta caggccgaga acgaaaagct tctccccccc   2160
tttatccgcc cgactctttg ctcttaagaa tgtaggtttg aagttaagaa tgagtaattg   2220
cacttctccg acccttaact gttcaaccta agatacggag aactaaggcg ttttcaggtt   2280
gaacagggtt ctatggtcgg tccgcgaccc ctggatgcca aagggtcctt ggggtgatct   2340
cgtagttcct acggggtgga gacgatgggg tcggtccatg gattttcttt ccttttgttt   2400
tcccgcattt cgctcaaagg gttgaaggga gatagtgcat caagctgttc gcaagggcca   2460
gcttgatcct cttccccagg atttcagatg aggaaaccct aggagagcca ccgactctaa   2520
ctaccgtcca tgtatgatcc atactagatc tgaccaactt cccatcctac ctcctctacg   2580
gacagcccat ccttgtctca gtagagtctt tcagtggcat gtttcggtcc tctttcccat   2640
tacttagaaa aagtgagcca ccggttcagg tacaagatac tatcattacc gcctggacaa   2700
ttagacatcc aacccgtaat cgcaacgacc caattgcaag agcggagctc taccaactga   2760
gctatatccc cccgagccaa gttggagcat gcatgaagga gtcaaatccg tcttttagtc   2820
ttttccttgg cgcagctggg ccatcctgga cttgaaccag agtcctcgcc cgtgaagtaa   2880
atcatcgcac ctacggtcca tccaattggg agagaatcaa tagattcctt ttcgggagcg   2940
attcatcctt cccgaacgca gcatacaact atccattgta ctgcgctctc caagtgtgct   3000
tgtttcccct tctttcttat catgacaagt ctttgtggaa taactctgat gagaagaaaa   3060
```

-continued aagaaaacgt taagggacac tctaagatcc tttttcaaac ctgctcccat ttcgagtcaa 3120
gagaatggta cgatcccgcc gtcacctcag aataaaaggg gtgatctcgt agttcttggt 3180
ctgtgaagat acgttgttag gtgctccgtt tttcttttc cattgaggcc aaacctaaac 3240
ctgtgctcga gagatagtta tccatatact gataagggat gtatgaattc tcgagaggag 3300
aggagccatg atggtccccc ctggaccgcc cggatcccac gagtgaatag aaagttggat 3360
ctacattgga tctcacctga atcgccccat ctatcttcct gaggaggagt ttggtttcaa 3420
accccggttc aaacaggaga agtacgccat gctaatgtgc cttggatggt ccacatctca 3480
gggtcaggcg ctgatgaaca cattgaacta tctatgtggc tgatagccct cacagtccag 3540
gcacaacgac gcaattatca ggggcgcgct ctaccactga gctaatagcc cgttgtgtgg 3600
gccccccgaa ggggcccact atgtcaaaag tgagagaaac cccatctctc tctttcccct 3660
ttgtttgcct catgtcgccc acggggcgac atgggtcaaa aaagaggagc tcctatcaag 3720
ttgttccgac ctaggataat aagctcatga gattagtgtc actgacattc tcatcaccca 3780
caggaaacga aaggagactt ccacctacta actttgcctc gataacccct tcgcttcagc 3840
ggtgtgaaac agtgtaaaac ccaatcaccc aaaaagcgtt ctctgttctc cctgaatagg 3900
ttaataagct agctcctgag ctaggtgtga cttcaccgtc gagaaacgaa acataacgga 3960
aatctaccta ctagtgcgat gtagcttttc tttactttaa cggggtgtga gtgacgcagt 4020
gtaaaaccta attacacaaa aagcattagt tctccctgaa aaggaggtga tccagtcgca 4080
ccttccagta cggctacctt gttacgactt cactccagtc actagccctg ccttcggcat 4140
ccccctcctt gcggttaagg taatgacttc gggcatggcc agctcccata gtgtgacggg 4200
cggtgtgtac aaggcccggg agcgcacgcg caaggtcgca actacccgag aatcgatgtg 4260
gcggaatggg ttacgtgagc tattatccgg cgggccctca atttaaatcg ttacagttgc 4320
tcgtaacggc aaccggctcg gtccttttc cctagaacag tatcttatac ttgctgctct 4380
cgttacttcg gcgatcctgg tgcagtcggt ccgtaaatcg gcgcacactt ttacgtcgta 4440
ccagacaggc tcgcataagc cagccccgac acccgccaac acccgctgac gcgccctgac 4500
gggcttgtct gctcccggca tccgcttaca gacaagctgt gacctccggg agctgcatgt 4560
gtcagaggtt ttcaccgtca tcaccgaaac gcgcacgaaa gggcctcgtg atacgcctat 4620
ttttataggt taatgtcatg ataataatgg tttcttagac gtcaggtggc acttttcggg 4680
gaaatgtgcg cggaacccct atttgtttat ttttctaaat acattcaaat atgtatccgc 4740
tcatgagaca ataaccctga taaatgcttc aataatattg aaaaaggaag agtatgagta 4800
ttcaacattt ccgtgtcgcc cttattccct tttttgcggc attttgcctt cctgtttttg 4860
ctcacccaga aacgctggtg aaagtaaaag atgctgaaga tcagttgggt gcacgagtgg 4920
gttacatcga actggatctc aacagcggta agatccttga gagttttcgc cccgaagaac 4980
gttttccaat gatgagcact tttaaagttc tgctatgtgg cgcggtatta tcccgtattg 5040
acgccgggca agagcaactc ggtcgccgca tacactattc tcagaatgac ttggttgagt 5100
actcaccagt cacagaaaag catcttacgg atggcatgac agtaagagaa ttatgcagtg 5160
ctgccataac catgagtgat aacactgcgg ccaacttact tctgacaacg atcggaggac 5220
cgaaggagct aaccgctttt ttgcacaaca tgggggatca tgtaactcgc cttgatcgtt 5280
gggaaccgga gctgaatgaa gccataccaa acgacgagcg tgacaccacg atgcctgtag 5340
caatggcaac aacgttgcgc aaactattaa ctggcgaact acttactcta gcttcccggc 5400

-continued aacaattaat agactggatg gaggcggata aagttgcagg accacttctg cgctcggccc 5460
ttccggctgg ctggtttatt gctgataaat ctggagccgg tgagcgtggc tcacgcggta 5520
tcattgcagc actggggcca gatggtaagc cctcccgtat cgtagttatc tacacgacgg 5580
ggagtcaggc aactatggat gaacgaaata gacagatcgc tgagataggt gcctcactga 5640
ttaagcattg gtaactgtca gaccaagttt actcatatat actttagatt gatttaaaac 5700
ttcattttta atttaaaagg atctaggtga agatcctttt tgataatctc atgaccaaaa 5760
tcccttaacg tgagttttcg ttccactgag cgtcagaccc cgtagaaaag atcaaaggat 5820
cttcttgaga tccttttttt ctgcgcgtaa tctgctgctt gcaaacaaaa aaaccaccgc 5880
taccagcggt ggtttgtttg ccggatcaag agctaccaac tctttttccg aaggtaactg 5940
gcttcagcag agcgcagata ccaaatactg ttcttctagt gtagccgtag ttaggccacc 6000
acttcaagaa ctctgtagca ccgcctacat acctcgctct gctaatcctg ttaccagtgg 6060
ctgctgccag tggcgataag tcgtgtctta ccgggttgga ctcaagacga tagttaccgg 6120
ataaggcgca gcggtcgggc tgaacggggg gttcgtgcac acagcccagc ttggagcgaa 6180
cgacctacac cgaactgaga tacctacagc gtgagctatg agaaagcgcc acgcttcccg 6240
aagggagaaa ggcggacagg tatccggtaa gcggcagggt cggaacagga gagcgcacga 6300
gggagcttcc agggggaaac gcctggtatc tttatagtcc tgtcgggttt cgccacctct 6360
gacttgagcg tcgatttttg tgatgctcgt caggggggcg gagcctatgg aaaaacgcca 6420
gcaacgcggc ctttttacgg ttcctggcct tttgctggcc ttttgctcac atgttctttc 6480
ctgcgttatc ccctgattct gtggataacc gtattaccgc ctttgagtga gctgataccg 6540
ctcgccgcag ccgaacgacc gagcgcagcg agtcagtgag cgaggaagcg gaagaacgcg 6600
gacacccagc gtaacaatct aatattgttt ctcaaatcgg gctgttatcg catggtgctc 6660
atgatgaggt tactgaccaa attcgccacg catcggtgct ggtagaatgt tcacttcgag 6720
gtgggtagac ggcgtcacgt gcaatgcctt gtcttcccct atctgcggcc ccgactgcct 6780
cgcgaagaca agggatcgga cgtcgaacgt attctgtttg ctaccggcac gggagtagga 6840
tcgttgatat acaccatgcg cgttaactct gacccccttc ctcttaaatg agaatggata 6900
agaggctcgt gggattgacg tgagggggca gggatggcta tatttctggg agcgaactcc 6960
gggcgaatta ctaataaaaa gccttccatt ttctattttg atttgtagaa aactagtgtg 7020
cttgggagtc cctgatgatt aaataaacca agattttacc aatgggggct agcgaagcgg 7080
tgatcgccga agtatcgact caactatcag aggtagttgg cgtcatcgag cgccatctcg 7140
aaccgacgtt gctggccgta catttgtacg gctccgcagt ggatggcggc ctgaagccac 7200
acagtgatat tgatttgctg gttacggtga ccgtaaggct tgatgaaaca acgcggcgag 7260
ctttgatcaa cgaccttttg gaaacttcgg cttcccctgg agagagcgag attctccgcg 7320
ctgtagaagt caccattgtt gtgcacgacg acatcattcc gtggcgttat ccagctaagc 7380
gcgaactgca atttggagaa tggcagcgca atgacattct tgcaggtatc ttcgagccag 7440
ccacgatcga cattgatctg gctatcttgc tgacaaaagc aagagaacat agcgttgcct 7500
tggtaggtcc agcggcggag gaactctttg atccggttcc tgaacaggat ctatttgagg 7560
cgctaaatga aaccttaacg ctatggaact cgccgcccga ctgggctggc gatgagcgaa 7620
atgtagtgct tacgttgtcc cgcatttggt acagcgcagt aaccggcaaa atcgcgccga 7680
aggatgtcgc tgccgactgg gcaatggagc gcctgccggc ccagtatcag cccgtcatac 7740
ttgaagctag acaggcttat cttggacaag aagaagatcg cttggcctcg cgcgcagatc 7800

```
agttggaaga atttgtccac tacgtgaaag gcgagatcac caaggtagtg ggcaaagaac   7860
ttgttgaagg aaaattggag ctagtagaag gtcttaaagt cgccatggct agtaaaggag   7920
aagaactttt cactggagtt gtcccaattc ttgttgaatt agatggtgat gttaatgggc   7980
acaaattttc tgtcagtgga gagggtgaag gtgatgcaac atacggaaaa cttaccctta   8040
aatttatttg cactactgga aaactacctg ttccttggcc aacacttgtc actactttct   8100
cttatggtgt tcaatgcttt tcaagatacc cagatcatat gaagcggcac gacttcttca   8160
agagcgccat gcctgaggga tacgtgcagg agaggaccat ctctttcaag gacgacggga   8220
actacaagac acgtgctgaa gtcaagtttg agggagacac cctcgtcaac aggatcgagc   8280
ttaagggaat cgatttcaag gaggacggaa acatcctcgg ccacaagttg gaatacaact   8340
acaactccca caacgtatac atcacggcag acaaacaaaa gaatggaatc aaagctaact   8400
tcaaaattag acacaacatt gaagatggaa gcgttcaact agcagaccat tatcaacaaa   8460
atactccaat tggcgatggc cctgtccttt taccagacaa ccattacctg tccacacaat   8520
ctgccctttc gaaagatccc aacgaaaaga gagatcacat ggtccttctt gagtttgtaa   8580
cagctgctgg gattacacat ggcatggatg aactatacaa ataagcttaa acagtagaca   8640
ttagcagata aattagcagg aaataaagaa ggataaggag aaagaactca agtaattatc   8700
cttcgttctc ttaattgaat tgcaattaaa ctcggcccaa tcttttacta aaaggattga   8760
gccgaatacc gctacaacag ctccctggaa caccaggaga acacacttat ctcgcgtctt   8820
gaggtgatac cacgcctgac acgtgagggc agtacggtta attcggttta gccggacatc   8880
agcgctcctc attgagcgct gggcccttca catgaagatc gcactgagga ttggtcctag   8940
ccaggcttct cagtactgat acagtacgcg tcgcttctcg tattgtttga gtcttggaat   9000
tagtttgtat ccttccgccg ctgccctaag aattctaatt gagctcgaac agtcgaccgc   9060
cggatcctgc tcgagtgcct ctaga                                         9085
```

<210> SEQ ID NO 56
<211> LENGTH: 9165
<212> TYPE: DNA
<213> ORGANISM: Artificial Sequence
<220> FEATURE:
<223> OTHER INFORMATION: An example of an episomal DNA vector

<400> SEQUENCE: 56

```
tgccgggcct agtcactgcg accccctttg tgaggaggca cccccttctcc cgaagttacg     60
gggctatttt gccgagttcc ttagagagag ttgtctcgcg cccctaggta ttctctacct    120
acccacctgt gtcggtttcc ggtacaggta ccctcttgtt gtaggtcgtt cgaacttttc    180
ctgggagtat ggcatcaatt actttagcgc cagagtgcgc gcctcgtact cgtactcgaa    240
ttttggctcg agggcatttt ctctacccct tacttaccct gaaaaaaaca gggagtcacc    300
ttatgttctt gaaccgataa ccatctttcg gctaacctag cctcctccgt ccctcgggac    360
caacaagggg cagtacagga atattaacct gttgtccatc gactacgcct ttcggcctga    420
tcttaggtcc tgacttaccc tccgtggacg aaccttgcgg aggaatcctt aggttttcgg    480
ggcattggat tctcaccaat gttttcgtta ctcaagccga cattctcgct tccgcttcgt    540
ccaaccctgc tcgcgcgggt acttctttct aaggcggaac gctcccctac cgattcattt    600
ttacatccca cagcttcggc aaatcgctta gccccgttca tcttcggcgc aagagcgctc    660
gatcagtgag ctattacgca ctctttgaag ggtggctgct tctaggcaaa cctcctggct    720
```

-continued

```
gtctctgcac tcctacctcc tttatcactg agcgatcatt taggggcctt agctggtgat    780
ctgggctgtt tccctctcga cagatgaagc ttatccccca tcgtctcact ggccgacctt    840
gacccgtcgg ggtcatatct agtattcaga gtttgcctcg atttggtacc gctctcgcgg    900
cccgcgccga aacagtgctt taccccctaga tgtccagtca actgctgcgc ctcaacgcat    960
ttcggggaga accagctagc tctgggttcg attggcattt caccgctaac cacaactcat   1020
ccgctgattt ttcaacatca gtcggttcgg acctccactt agtttcacct aaacttcatc   1080
ctggtcatgg atagatcacc caggttcggg tccataagca gtgacaatag ccctatgaag   1140
actcgctttc gctacggctc cggtggtttc ccttaaccaa gccactgcct atgagtcgcc   1200
ggctcattct tcaacaggca cgcggtcaga gccccagctc ctcccactgt tgggagctta   1260
cggtttcatg ttctatttca ctccccgcca ggggttcttt tcacctttcc ctcacggtac   1320
tacttcacta tcggtcaccc aggagtattt agccttgcaa ggtggtcctt gctgattcac   1380
acgggatttc acgtgcccca tgttactcgg gtcagagcat aagctagtga tgctttcggc   1440
tactggactt tcaccatcta gggtgcaaca ttcgactgct tcgcctagca gcacgacgct   1500
tgtattgctc tcccacaacc ccgttttcac ggtttaggct gctcccattt cgctcgccgc   1560
tactacggga atcgcttttg ctttcttttc ctctggctac taagatgttt cagttcgcca   1620
ggttgtctct tgcctgctcg tgaattcagc agcagttcga aaggttgacc tattcgggaa   1680
tcctcggatc tatgcttatt ttcaactccc cgaagcattt cgtcgcttac tacgcccttc   1740
ctcgtctctg ggtgcctagg tatccaccat aagcctttcc tcgtttgaac ctcgcccttc   1800
aactctatgc catcctaagg tgctgctaga tggaaggatc ttatcaacgt ccataaataa   1860
taaatcataa catagctaaa acaaaaaaat gaacgagttg gagataagcg gactcgaacc   1920
gctgacatcc gccacagggt aaatcaccgc ctctcaagcc ccaactgatt ctaccataga   1980
ggccaacgat agacaataac cctccgaaca cagcttacaa ctttcatcgt actgtgctct   2040
ccaaagagca actcttctca aaatatcaaa gggtgctgag ttggaatccc attcaaacaa   2100
ggattcttgt ggttgcggaa gatccagcta caggccgaga acgaaaagct tctccccccc   2160
tttatccgcc cgactctttg ctcttaagaa tgtaggtttg aagttaagaa tgagtaattg   2220
cacttctccg acccttaact gttcaaccta agatacggag aactaaggcg ttttcaggtt   2280
gaacagggtt ctatggtcgg tccgcgaccc ctggatgcca aagggtcctt ggggtgatct   2340
cgtagttcct acggggtgga gacgatgggg tcggtccatg gattttcttt ccttttgttt   2400
tcccgcattt cgctcaaagg gttgaaggga gatagtgcat caagctgttc gcaagggcca   2460
gcttgatcct cttccccagg atttcagatg aggaaaccct aggagagcca ccgactctaa   2520
ctaccgtcca tgtatgatcc atactagatc tgaccaactt cccatcctac ctcctctacg   2580
gacagcccat ccttgtctca gtagagtctt tcagtggcat gtttcggtcc tctttcccat   2640
tacttagaaa aagtgagcca ccggttcagg tacaagatac tatcattacc gcctggacaa   2700
ttagacatcc aacccgtaat cgcaacgacc caattgcaag agcggagctc taccaactga   2760
gctatatccc cccgagccaa gttggagcat gcatgaagga gtcaaatccg tcttttagtc   2820
ttttccttgg cgcagctggg ccatcctgga cttgaaccag agtcctcgcc cgtgaagtaa   2880
atcatcgcac ctacggtcca tccaattggg agagaatcaa tagattcctt ttcgggagcg   2940
attcatcctt cccgaacgca gcatacaact atccattgta ctgcgctctc caagtgtgct   3000
tgtttcccct tctttcttat catgacaagt ctttgtggaa taactctgat gagaagaaaa   3060
aagaaaacgt taagggacac tctaagatcc tttttcaaac ctgctcccat ttcgagtcaa   3120
```

gagaatggta cgatcccgcc gtcacctcag aataaaaggg gtgatctcgt agttcttggt 3180
ctgtgaagat acgttgttag gtgctccgtt tttctttttc cattgaggcc aaacctaaac 3240
ctgtgctcga gagatagtta tccatatact gataagggat gtatgaattc tcgagaggag 3300
aggagccatg atggtccccc ctggaccgcc cggatcccac gagtgaatag aaagttggat 3360
ctacattgga tctcacctga atcgccccat ctatcttcct gaggaggagt ttggtttcaa 3420
accccggttc aaacaggaga agtacgccat gctaatgtgc cttggatggt ccacatctca 3480
gggtcaggcg ctgatgaaca cattgaacta tctatgtggc tgatagccct cacagtccag 3540
gcacaacgac gcaattatca ggggcgcgct ctaccactga gctaatagcc cgttgtgtgg 3600
gcccccccgaa ggggcccact atgtcaaaag tgagagaaac cccatctctc tctttcccct 3660
ttgtttgcct catgtcgccc acggggcgac atgggtcaaa aaagaggagc tcctatcaag 3720
ttgttccgac ctaggataat aagctcatga gattagtgtc actgacattc tcatcaccca 3780
caggaaacga aaggagactt ccacctacta actttgcctc gataacccct tcgcttcagc 3840
ggtgtgaaac agtgtaaaac ccaatcaccc aaaaagcgtt ctctgttctc cctgaatagg 3900
ttaataagct agctcctgag ctaggtgtga cttcaccgtc gagaaacgaa acataacgga 3960
aatctaccta ctagtgcgat gtagcttttc tttactttaa cggggtgtga gtgacgcagt 4020
gtaaaaccta attacacaaa aagcattagt tctccctgaa aaggaggtga tccagtcgca 4080
ccttccagta cggctacctt gttacgactt cactccagtc actagccctg ccttcggcat 4140
ccccctcctt gcggttaagg taatgacttc gggcatggcc agctcccata gtgtgacggg 4200
cggtgtgtac aaggcccggg agcgcacgcg caaggtcgca actacccgag aatcgatgtg 4260
gcggaatggg ttacgtgagc tattatccgg cgggccctca atttaaatcg ttacagttgc 4320
tcgtaacggc aaccggctcg gtcctttttc cctagaacag tatcttatac ttgctgctct 4380
cgttacttcg gcgatcctgg tgcagtcggt ccgtaaatcg gcgcacactt ttacgtcgta 4440
ccagacaggc tcgcataagc cagccccgac acccgccaac acccgctgac gcgccctgac 4500
gggcttgtct gctcccggca tccgcttaca gacaagctgt gacctccggg agctgcatgt 4560
gtcagaggtt ttcaccgtca tcaccgaaac gcgcacgaaa gggcctcgtg atacgcctat 4620
ttttataggt taatgtcatg ataataatgg tttcttagac gtcaggtggc acttttcggg 4680
gaaatgtgcg cggaacccct atttgtttat ttttctaaat acattcaaat atgtatccgc 4740
tcatgagaca ataaccctga taaatgcttc aataatattg aaaaaggaag agtatgagta 4800
ttcaacattt ccgtgtcgcc cttattccct tttttgcggc attttgcctt cctgtttttg 4860
ctcacccaga aacgctggtg aaagtaaaag atgctgaaga tcagttgggt gcacgagtgg 4920
gttacatcga actggatctc aacagcggta agatccttga gagttttcgc cccgaagaac 4980
gttttccaat gatgagcact tttaaagttc tgctatgtgg cgcggtatta tcccgtattg 5040
acgccgggca agagcaactc ggtcgccgca tacactattc tcagaatgac ttggttgagt 5100
actcaccagt cacagaaaag catcttacgg atggcatgac agtaagagaa ttatgcagtg 5160
ctgccataac catgagtgat aacactgcgg ccaacttact tctgacaacg atcggaggac 5220
cgaaggagct aaccgctttt ttgcacaaca tgggggatca tgtaactcgc cttgatcgtt 5280
gggaaccgga gctgaatgaa gccataccaa acgacgagcg tgacaccacg atgcctgtag 5340
caatggcaac aacgttgcgc aaactattaa ctggcgaact acttactcta gcttcccggc 5400
aacaattaat agactggatg gaggcggata aagttgcagg accacttctg cgctcggccc 5460

-continued

```
ttccggctgg ctggtttatt gctgataaat ctggagccgg tgagcgtggc tcacgcggta   5520
tcattgcagc actggggcca gatggtaagc cctcccgtat cgtagttatc tacacgacgg   5580
ggagtcaggc aactatggat gaacgaaata gacagatcgc tgagataggt gcctcactga   5640
ttaagcattg gtaactgtca gaccaagttt actcatatat actttagatt gatttaaaac   5700
ttcattttta atttaaaagg atctaggtga agatcctttt tgataatctc atgaccaaaa   5760
tcccttaacg tgagttttcg ttccactgag cgtcagaccc cgtagaaaag atcaaaggat   5820
cttcttgaga tccttttttt ctgcgcgtaa tctgctgctt gcaaacaaaa aaaccaccgc   5880
taccagcggt ggtttgtttg ccggatcaag agctaccaac tctttttccg aaggtaactg   5940
gcttcagcag agcgcagata ccaaatactg ttcttctagt gtagccgtag ttaggccacc   6000
acttcaagaa ctctgtagca ccgcctacat acctcgctct gctaatcctg ttaccagtgg   6060
ctgctgccag tggcgataag tcgtgtctta ccgggttgga ctcaagacga tagttaccgg   6120
ataaggcgca gcggtcgggc tgaacggggg gttcgtgcac acagcccagc ttggagcgaa   6180
cgacctacac cgaactgaga tacctacagc gtgagctatg agaaagcgcc acgcttcccg   6240
aagggagaaa ggcggacagg tatccggtaa gcggcagggt cggaacagga gagcgcacga   6300
gggagcttcc agggggaaac gcctggtatc tttatagtcc tgtcgggttt cgccacctct   6360
gacttgagcg tcgatttttg tgatgctcgt caggggggcg gagcctatgg aaaaacgcca   6420
gcaacgcggc ctttttacgg ttcctggcct tttgctggcc ttttgctcac atgttctttc   6480
ctgcgttatc ccctgattct gtggataacc gtattaccgc ctttgagtga gctgataccg   6540
ctcgccgcag ccgaacgacc gagcgcagcg agtcagtgag cgaggaagcg gaagaacgcg   6600
gacacccagc gtaacaatct aatattgttt ctcaaatcgg gctgttatcg catggtgctc   6660
atgatgaggt tactgaccaa attcgccacg catcggtgct ggtagaatgt tcacttcgag   6720
gtgggtagac ggcgtcacgt gcaatgcctt gtcttcccct atctgcggcc ccgactgcct   6780
cgcgaagaca agggatcgga cgtcgaacgt attctgtttg ctaccggcac gggagtagga   6840
tcgttgatat acaccatgcg cgttaactct gacccccttc ctcttaaatg agaatggata   6900
agaggctcgt gggattgacg tgagggggca gggatggcta tatttctggg agcgaactcc   6960
gggcgaatta ctaataaaaa gccttccatt ttctattttg atttgtagaa aactagtgtg   7020
cttgggagtc cctgatgatt aaataaacca agattttacc aatgggggct agcgaagcgg   7080
tgatcgccga agtatcgact caactatcag aggtagttgg cgtcatcgag cgccatctcg   7140
aaccgacgtt gctggccgta catttgtacg gctccgcagt ggatggcggc ctgaagccac   7200
acagtgatat tgatttgctg gttacggtga ccgtaaggct tgatgaaaca acgcggcgag   7260
ctttgatcaa cgaccttttg gaaacttcgg cttcccctgg agagagcgag attctccgcg   7320
ctgtagaagt caccattgtt gtgcacgacg acatcattcc gtggcgttat ccagctaagc   7380
gcgaactgca atttggagaa tggcagcgca atgacattct tgcaggtatc ttcgagccag   7440
ccacgatcga cattgatctg gctatcttgc tgacaaaagc aagagaacat agcgttgcct   7500
tggtaggtcc agcggcggag gaactctttg atccggttcc tgaacaggat ctatttgagg   7560
cgctaaatga aaccttaacg ctatggaact cgccgcccga ctgggctggc gatgagcgaa   7620
atgtagtgct tacgttgtcc cgcatttggt acagcgcagt aaccggcaaa atcgcgccga   7680
aggatgtcgc tgccgactgg gcaatggagc gcctgccggc ccagtatcag cccgtcatac   7740
ttgaagctag acaggcttat cttggacaag aagaagatcg cttggcctcg cgcgcagatc   7800
agttggaaga atttgtccac tacgtgaaag gcgagatcac caaggtagtg ggcaaagaac   7860
```

ttgttgaagg aaaattggag ctagtagaag gtcttaaagt cgccatggct agtaaaggag 7920
aagaactttt cactggagtt gtcccaattc ttgttgaatt agatggtgat gttaatgggc 7980
acaaattttc tgtcagtgga gagggtgaag gtgatgcaac atacggaaaa cttaccctta 8040
aatttatttg cactactgga aaactacctg ttccttggcc aacacttgtc actactttct 8100
cttatggtgt tcaatgcttt tcaagatacc cagatcatat gaagcggcac gacttcttca 8160
agagcgccat gcctgaggga tacgtgcagg agaggaccat ctctttcaag gacgacggga 8220
actacaagac acgtgctgaa gtcaagtttg agggagacac cctcgtcaac aggatcgagc 8280
ttaagggaat cgatttcaag gaggacggaa acatcctcgg ccacaagttg gaatacaact 8340
acaactccca caacgtatac atcacggcag acaaacaaaa gaatggaatc aaagctaact 8400
tcaaaattag acacaacatt gaagatggaa gcgttcaact agcagaccat tatcaacaaa 8460
atactccaat tggcgatggc cctgtccttt taccagacaa ccattacctg tccacacaat 8520
ctgccctttc gaaagatccc aacgaaaaga gagatcacat ggtccttctt gagtttgtaa 8580
cagctgctgg gattacacat ggcatggatg aactatacaa ataagcttaa acagtagaca 8640
ttagcagata aattagcagg aaataaagaa ggataaggag aaagaactca agtaattatc 8700
cttcgttctc ttaattgaat tgcaattaaa ctcggcccaa tcttttacta aaaggattga 8760
gccgaatacc gctccaggca tcaaataaaa cgaaaggctc agtcgaaaga ctgggccttt 8820
cgttttatct gttgtttgtc ggtgaacgct ctcacaacag ctccctggaa caccaggaga 8880
acacacttat ctcgcgtctt gaggtgatac cacgcctgac acgtgagggc agtacggtta 8940
attcggttta gccggacatc agcgctcctc attgagcgct gggcccttca catgaagatc 9000
gcactgagga ttggtcctag ccaggcttct cagtactgat acagtacgcg tcgcttctcg 9060
tattgtttga gtcttggaat tagtttgtat ccttccgccg ctgccctaag aattctaatt 9120
gagctcgaac agtcgaccgc cggatcctgc tcgagtgcct ctaga 9165

<210> SEQ ID NO 57
<211> LENGTH: 5990
<212> TYPE: DNA
<213> ORGANISM: Artificial Sequence
<220> FEATURE:
<223> OTHER INFORMATION: An example of an episomal DNA vector

<400> SEQUENCE: 57
tgccagatcc aatgtagatc caactttcga ttcactcgtg ggatccgggc ggtccggggg 60
ggaccaccac ggctcctctc ttctcgtcac atcgacaatt caataaggta tccgacatta 120
acaatgattt aaattgtgtt cattgtgttt tttatggtac ataaccttca tagatttata 180
gattataaac tgaaagaagc ctcaaaaaca gaagaaaggg tggaaagtga ggaagaaaga 240
gatgtagaaa tagaaactgc ttccgaaatg aaggggacta aacaggaaca agagggatcc 300
actgaagaag atccttatcc ttctccttcc ctttttttcgg aagaagggtg ggatccggac 360
aaaatcgatg aaacggaaga aatccgagtg aatggaaagg acaaaataaa ggataaattc 420
cactctcact tcctatatga ggaagtatcc ttccccgcag tcaagaccaa ggttagtatt 480
ctctgctagg aagtttactt aggttactct agcatgtgcc tggataaccc tctaggcaaa 540
ggtggattga ctttgtactg tcctcagatc gacgttggat gaactgtcgc gccacgaggg 600
gctgtggagc gcattgcgac acattggtgc gctgctaacc catcctttcc agtacggcta 660
ctgatgtcca cgctcccagc ctgctacgct ccgcccggtg agagtggaat ttatccttta 720

-continued ttttgtcctt tccattcact cggatttctt ccgtttcatc gattttgtcc ggatcccacc 780
cttcttccga aaaaagggaa ggagaaggat aaggatcttc ttcagtggat ccctcttgtt 840
cctgtttagt ccccttcatt tcggaagcag tttctatttc tacatctctt tcttcctcac 900
tttccaccct ttcttctgtt tttgaggctt ctttcagttt tgctagaaag ttattctttt 960
cgtcttaatg attatatgta aatcgccctc tatatattaa ctctacttat atggaaaaac 1020
tatgattaag tagttacagt cgagaagaga ggagccgtgg tggtcccccc cggaccgccc 1080
ggatcccacg agtgaatcga aagttggatc tacattggat ctgggagcgc acgcgcaagg 1140
tcgcaactac ccgagaatcg atgtggcgga atgggttacg tgagctatta tccggcgggc 1200
cctcaattta aatcgttaca gttgctcgta acggcaaccg gctcggtcct ttttccctag 1260
aacagtatct tatacttgct gctctcgtta cttcggcgat cctggtgcag tcggtccgta 1320
aatcggcgca cacttttacg tcgtaccaga caggctcgca taagccagcc ccgacacccg 1380
ccaacacccg ctgacgcgcc ctgacgggct tgtctgctcc cggcatccgc ttacagacaa 1440
gctgtgacct ccgggagctg catgtgtcag aggttttcac cgtcatcacc gaaacgcgca 1500
cgaaagggcc tcgtgatacg cctattttta taggttaatg tcatgataat aatggtttct 1560
tagacgtcag gtggcacttt tcggggaaat gtgcgcggaa cccctatttg tttatttttc 1620
taaatacatt caaatatgta tccgctcatg agacaataac cctgataaat gcttcaataa 1680
tattgaaaaa ggaagagtat gagtattcaa catttccgtg tcgcccttat tccctttttt 1740
gcggcatttt gccttcctgt ttttgctcac ccagaaacgc tggtgaaagt aaaagatgct 1800
gaagatcagt tgggtgcacg agtgggttac atcgaactgg atctcaacag cggtaagatc 1860
cttgagagtt ttcgccccga agaacgtttt ccaatgatga gcacttttaa agttctgcta 1920
tgtggcgcgg tattatcccg tattgacgcc gggcaagagc aactcggtcg ccgcatacac 1980
tattctcaga atgacttggt tgagtactca ccagtcacag aaaagcatct tacggatggc 2040
atgacagtaa gagaattatg cagtgctgcc ataaccatga gtgataacac tgcggccaac 2100
ttacttctga caacgatcgg aggaccgaag gagctaaccg cttttttgca caacatgggg 2160
gatcatgtaa ctcgccttga tcgttgggaa ccggagctga atgaagccat accaaacgac 2220
gagcgtgaca ccacgatgcc tgtagcaatg gcaacaacgt tgcgcaaact attaactggc 2280
gaactactta ctctagcttc ccggcaacaa ttaatagact ggatggaggc ggataaagtt 2340
gcaggaccac ttctgcgctc ggcccttccg gctggctggt ttattgctga taaatctgga 2400
gccggtgagc gtggctcacg cggtatcatt gcagcactgg ggccagatgg taagccctcc 2460
cgtatcgtag ttatctacac gacggggagt caggcaacta tggatgaacg aaatagacag 2520
atcgctgaga taggtgcctc actgattaag cattggtaac tgtcagacca agtttactca 2580
tatatacttt agattgattt aaaacttcat ttttaattta aaaggatcta ggtgaagatc 2640
ctttttgata atctcatgac caaaatccct taacgtgagt tttcgttcca ctgagcgtca 2700
gaccccgtag aaaagatcaa aggatcttct tgagatcctt tttttctgcg cgtaatctgc 2760
tgcttgcaaa caaaaaaacc accgctacca gcggtggttt gtttgccgga tcaagagcta 2820
ccaactcttt ttccgaaggt aactggcttc agcagagcgc agataccaaa tactgttctt 2880
ctagtgtagc cgtagttagg ccaccacttc aagaactctg tagcaccgcc tacatacctc 2940
gctctgctaa tcctgttacc agtggctgct gccagtggcg ataagtcgtg tcttaccggg 3000
ttggactcaa gacgatagtt accggataag gcgcagcggt cgggctgaac ggggggttcg 3060
tgcacacagc ccagcttgga gcgaacgacc tacaccgaac tgagatacct acagcgtgag 3120

```
ctatgagaaa gcgccacgct tcccgaaggg agaaaggcgg acaggtatcc ggtaagcggc   3180
agggtcggaa caggagagcg cacgagggag cttccagggg gaaacgcctg gtatctttat   3240
agtcctgtcg ggtttcgcca cctctgactt gagcgtcgat ttttgtgatg ctcgtcaggg   3300
gggcggagcc tatggaaaaa cgccagcaac gcggcctttt tacggttcct ggccttttgc   3360
tggccttttg ctcacatgtt ctttcctgcg ttatcccctg attctgtgga taaccgtatt   3420
accgcctttg agtgagctga taccgctcgc cgcagccgaa cgaccgagcg cagcgagtca   3480
gtgagcgagg aagcggaaga acgcggacac ccagcgtaac aatctaatat tgtttctcaa   3540
atcgggctgt tatcgcatgg tgctcatgat gaggttactg accaaattcg ccacgcatcg   3600
gtgctggtag aatgttcact tcgaggtggg tagacggcgt cacgtgcaat gccttgtctt   3660
cccctatctg cggccccgac tgcctcgcga agacaaggga tcggacgtcg aacgtattct   3720
gtttgctacc ggcacgggag taggatcgtt gatatacacc atgcgcgtta actctgaccc   3780
ccttcctctt aaatgagaat ggataagagg ctcgtgggat tgacgtgagg gggcagggat   3840
ggctatattt ctgggagcga actccgggcg aattactaat aaaaagcctt ccatttctca   3900
ttttgatttg tagaaaacta gtgtgcttgg gagtccctga tgattaaata aaccaagatt   3960
ttaccaatgg gggctagcga agcggtgatc gccgaagtat cgactcaact atcagaggta   4020
gttggcgtca tcgagcgcca tctcgaaccg acgttgctgg ccgtacattt gtacggctcc   4080
gcagtggatg gcggcctgaa gccacacagt gatattgatt tgctggttac ggtgaccgta   4140
aggcttgatg aaacaacgcg gcgagctttg atcaacgacc ttttggaaac ttcggcttcc   4200
cctggagaga gcgagattct ccgcgctgta gaagtcacca ttgttgtgca cgacgacatc   4260
attccgtggc gttatccagc taagcgcgaa ctgcaatttg gagaatggca gcgcaatgac   4320
attcttgcag gtatcttcga gccagccacg atcgacattg atctggctat cttgctgaca   4380
aaagcaagag aacatagcgt tgccttggta ggtccagcgg cggaggaact ctttgatccg   4440
gttcctgaac aggatctatt tgaggcgcta aatgaaacct taacgctatg gaactcgccg   4500
cccgactggg ctggcgatga gcgaaatgta gtgcttacgt tgtcccgcat ttggtacagc   4560
gcagtaaccg gcaaaatcgc gccgaaggat gtcgctgccg actgggcaat ggagcgcctg   4620
ccggcccagt atcagcccgt catacttgaa gctagacagg cttatcttgg acaagaagaa   4680
gatcgcttgg cctcgcgcgc agatcagttg gaagaatttg tccactacgt gaaaggcgag   4740
atcaccaagg tagtgggcaa agaacttgtt gaaggaaaat tggagctagt agaaggtctt   4800
aaagtcgcca tggctagtaa aggagaagaa cttttcactg gagttgtccc aattcttgtt   4860
gaattagatg gtgatgttaa tgggcacaaa ttttctgtca gtggagaggg tgaaggtgat   4920
gcaacatacg gaaaacttac ccttaaattt atttgcacta ctggaaaact acctgttcct   4980
tggccaacac ttgtcactac tttctcttat ggtgttcaat gcttttcaag atacccagat   5040
catatgaagc ggcacgactt cttcaagagc gccatgcctg agggatacgt gcaggagagg   5100
accatctctt tcaaggacga cgggaactac aagacacgtg ctgaagtcaa gtttgaggga   5160
gacaccctcg tcaacaggat cgagcttaag ggaatcgatt tcaaggagga cggaaacatc   5220
ctcggccaca agttggaata caactacaac tcccacaacg tatacatcac ggcagacaaa   5280
caaaagaatg gaatcaaagc taacttcaaa attagacaca acattgaaga tggaagcgtt   5340
caactagcag accattatca acaaaatact ccaattggcg atggccctgt ccttttacca   5400
gacaaccatt acctgtccac acaatctgcc ctttcgaaag atcccaacga aaagagagat   5460
```

cacatggtcc ttcttgagtt tgtaacagct gctgggatta cacatggcat ggatgaacta 5520
tacaaataag cttaaacagt agacattagc agataaatta gcaggaaata aagaaggata 5580
aggagaaaga actcaagtaa ttatccttcg ttctcttaat tgaattgcaa ttaaactcgg 5640
cccaatcttt tactaaaagg attgagccga ataccgctac aacagctccc tggaacacca 5700
ggagaacaca cttatctcgc gtcttgaggt gataccacgc ctgacacgtg agggcagtac 5760
ggttaattcg gtttagccgg acatcagcgc tcctcattga gcgctgggcc cttcacatga 5820
agatcgcact gaggattggt cctagccagg cttctcagta ctgatacagt acgcgtcgct 5880
tctcgtattg tttgagtctt ggaattagtt tgtatccttc cgccgctgcc ctaagaattc 5940
taattgagct cgaacagtcg accgccggat cctgctcgag tgcctctaga 5990

<210> SEQ ID NO 58
<211> LENGTH: 6070
<212> TYPE: DNA
<213> ORGANISM: Artificial Sequence
<220> FEATURE:
<223> OTHER INFORMATION: An example of an episomal DNA vector

<400> SEQUENCE: 58
tgccagatcc aatgtagatc caactttcga ttcactcgtg ggatccgggc ggtccggggg 60
ggaccaccac ggctcctctc ttctcgtcac atcgacaatt caataaggta tccgacatta 120
acaatgattt aaattgtgtt cattgtgttt tttatggtac ataaccttca tagatttata 180
gattataaac tgaaagaagc ctcaaaaaca gaagaaaggg tggaaagtga ggaagaaaga 240
gatgtagaaa tagaaactgc ttccgaaatg aaggggacta aacaggaaca agagggatcc 300
actgaagaag atccttatcc ttctccttcc ctttttttcgg aagaagggtg ggatccggac 360
aaaatcgatg aaacggaaga aatccgagtg aatggaaagg acaaaataaa ggataaattc 420
cactctcact tcctatatga ggaagtatcc ttccccgcag tcaagaccaa ggttagtatt 480
ctctgctagg aagtttactt aggttactct agcatgtgcc tggataaccc tctaggcaaa 540
ggtggattga ctttgtactg tcctcagatc gacgttggat gaactgtcgc gccacgaggg 600
gctgtggagc gcattgcgac acattggtgc gctgctaacc catcctttcc agtacggcta 660
ctgatgtcca cgctcccagc ctgctacgct ccgcccggtg agagtggaat ttatccttta 720
ttttgtcctt tccattcact cggatttctt ccgtttcatc gattttgtcc ggatcccacc 780
cttcttccga aaaaagggaa ggagaaggat aaggatcttc ttcagtggat ccctcttgtt 840
cctgtttagt ccccttcatt tcggaagcag tttctatttc tacatctctt tcttcctcac 900
tttccaccct ttcttctgtt tttgaggctt ctttcagttt tgctagaaag ttattctttt 960
cgtcttaatg attatatgta aatcgccctc tatatattaa ctctacttat atggaaaaac 1020
tatgattaag tagttacagt cgagaagaga ggagccgtgg tggtcccccc cggaccgccc 1080
ggatcccacg agtgaatcga aagttggatc tacattggat ctgggagcgc acgcgcaagg 1140
tcgcaactac ccgagaatcg atgtggcgga atgggttacg tgagctatta tccggcgggc 1200
cctcaattta aatcgttaca gttgctcgta acggcaaccg gctcggtcct ttttccctag 1260
aacagtatct tatacttgct gctctcgtta cttcggcgat cctggtgcag tcggtccgta 1320
aatcggcgca cacttttacg tcgtaccaga caggctcgca taagccagcc ccgacacccg 1380
ccaacacccg ctgacgcgcc ctgacgggct tgtctgctcc cggcatccgc ttacagacaa 1440
gctgtgacct ccgggagctg catgtgtcag aggttttcac cgtcatcacc gaaacgcgca 1500
cgaaagggcc tcgtgatacg cctattttta taggttaatg tcatgataat aatggtttct 1560

```
tagacgtcag gtggcacttt tcggggaaat gtgcgcggaa cccctatttg tttatttttc   1620
taaatacatt caaatatgta tccgctcatg agacaataac cctgataaat gcttcaataa   1680
tattgaaaaa ggaagagtat gagtattcaa catttccgtg tcgcccttat tccctttttt   1740
gcggcatttt gccttcctgt ttttgctcac ccagaaacgc tggtgaaagt aaaagatgct   1800
gaagatcagt tgggtgcacg agtgggttac atcgaactgg atctcaacag cggtaagatc   1860
cttgagagtt ttcgccccga agaacgtttt ccaatgatga gcacttttaa agttctgcta   1920
tgtggcgcgg tattatcccg tattgacgcc gggcaagagc aactcggtcg ccgcatacac   1980
tattctcaga atgacttggt tgagtactca ccagtcacag aaaagcatct tacggatggc   2040
atgacagtaa gagaattatg cagtgctgcc ataaccatga gtgataacac tgcggccaac   2100
ttacttctga caacgatcgg aggaccgaag gagctaaccg cttttttgca caacatgggg   2160
gatcatgtaa ctcgccttga tcgttgggaa ccggagctga atgaagccat accaaacgac   2220
gagcgtgaca ccacgatgcc tgtagcaatg gcaacaacgt tgcgcaaact attaactggc   2280
gaactactta ctctagcttc ccggcaacaa ttaatagact ggatggaggc ggataaagtt   2340
gcaggaccac ttctgcgctc ggcccttccg gctggctggt ttattgctga taaatctgga   2400
gccggtgagc gtggctcacg cggtatcatt gcagcactgg ggccagatgg taagccctcc   2460
cgtatcgtag ttatctacac gacggggagt caggcaacta tggatgaacg aaatagacag   2520
atcgctgaga taggtgcctc actgattaag cattggtaac tgtcagacca agtttactca   2580
tatatacttt agattgattt aaaacttcat ttttaattta aaaggatcta ggtgaagatc   2640
ctttttgata atctcatgac caaaatccct taacgtgagt tttcgttcca ctgagcgtca   2700
gaccccgtag aaaagatcaa aggatcttct tgagatcctt tttttctgcg cgtaatctgc   2760
tgcttgcaaa caaaaaaacc accgctacca gcggtggttt gtttgccgga tcaagagcta   2820
ccaactcttt ttccgaaggt aactggcttc agcagagcgc agataccaaa tactgttctt   2880
ctagtgtagc cgtagttagg ccaccacttc aagaactctg tagcaccgcc tacatacctc   2940
gctctgctaa tcctgttacc agtggctgct gccagtggcg ataagtcgtg tcttaccggg   3000
ttggactcaa gacgatagtt accggataag gcgcagcggt cgggctgaac ggggggttcg   3060
tgcacacagc ccagcttgga gcgaacgacc tacaccgaac tgagatacct acagcgtgag   3120
ctatgagaaa gcgccacgct tcccgaaggg agaaaggcgg acaggtatcc ggtaagcggc   3180
agggtcggaa caggagagcg cacgagggag cttccagggg gaaacgcctg gtatctttat   3240
agtcctgtcg ggtttcgcca cctctgactt gagcgtcgat ttttgtgatg ctcgtcaggg   3300
gggcggagcc tatggaaaaa cgccagcaac gcggcctttt tacggttcct ggccttttgc   3360
tggccttttg ctcacatgtt ctttcctgcg ttatcccctg attctgtgga taaccgtatt   3420
accgcctttg agtgagctga taccgctcgc cgcagccgaa cgaccgagcg cagcgagtca   3480
gtgagcgagg aagcggaaga acgcggacac ccagcgtaac aatctaatat tgtttctcaa   3540
atcgggctgt tatcgcatgg tgctcatgat gaggttactg accaaattcg ccacgcatcg   3600
gtgctggtag aatgttcact tcgaggtggg tagacggcgt cacgtgcaat gccttgtctt   3660
cccctatctg cggccccgac tgcctcgcga agacaaggga tcggacgtcg aacgtattct   3720
gtttgctacc ggcacgggag taggatcgtt gatatacacc atgcgcgtta actctgaccc   3780
ccttcctctt aaatgagaat ggataagagg ctcgtgggat tgacgtgagg gggcagggat   3840
ggctatattt ctgggagcga actccgggcg aattactaat aaaaagcctt ccatttcta    3900
```

```
ttttgatttg tagaaaacta gtgtgcttgg gagtccctga tgattaaata aaccaagatt   3960
ttaccaatgg gggctagcga agcggtgatc gccgaagtat cgactcaact atcagaggta   4020
gttggcgtca tcgagcgcca tctcgaaccg acgttgctgg ccgtacattt gtacggctcc   4080
gcagtggatg gcggcctgaa gccacacagt gatattgatt tgctggttac ggtgaccgta   4140
aggcttgatg aaacaacgcg gcgagctttg atcaacgacc ttttggaaac ttcggcttcc   4200
cctggagaga gcgagattct ccgcgctgta gaagtcacca ttgttgtgca cgacgacatc   4260
attccgtggc gttatccagc taagcgcgaa ctgcaatttg gagaatggca gcgcaatgac   4320
attcttgcag gtatcttcga gccagccacg atcgacattg atctggctat cttgctgaca   4380
aaagcaagag aacatagcgt tgccttggta ggtccagcgg cggaggaact ctttgatccg   4440
gttcctgaac aggatctatt tgaggcgcta aatgaaacct taacgctatg gaactcgccg   4500
cccgactggg ctggcgatga gcgaaatgta gtgcttacgt tgtcccgcat ttggtacagc   4560
gcagtaaccg gcaaaatcgc gccgaaggat gtcgctgccg actgggcaat ggagcgcctg   4620
ccggcccagt atcagcccgt catacttgaa gctagacagg cttatcttgg acaagaagaa   4680
gatcgcttgg cctcgcgcgc agatcagttg gaagaatttg tccactacgt gaaaggcgag   4740
atcaccaagg tagtgggcaa agaacttgtt gaaggaaaat tggagctagt agaaggtctt   4800
aaagtcgcca tggctagtaa aggagaagaa cttttcactg gagttgtccc aattcttgtt   4860
gaattagatg gtgatgttaa tgggcacaaa ttttctgtca gtggagaggg tgaaggtgat   4920
gcaacatacg gaaaacttac ccttaaattt atttgcacta ctggaaaact acctgttcct   4980
tggccaacac ttgtcactac tttctcttat ggtgttcaat gcttttcaag atacccagat   5040
catatgaagc ggcacgactt cttcaagagc gccatgcctg agggatacgt gcaggagagg   5100
accatctctt tcaaggacga cgggaactac aagacacgtg ctgaagtcaa gtttgaggga   5160
gacaccctcg tcaacaggat cgagcttaag ggaatcgatt tcaaggagga cggaaacatc   5220
ctcggccaca agttggaata caactacaac tcccacaacg tatacatcac ggcagacaaa   5280
caaaagaatg gaatcaaagc taacttcaaa attagacaca acattgaaga tggaagcgtt   5340
caactagcag accattatca acaaaatact ccaattggcg atggccctgt ccttttacca   5400
gacaaccatt acctgtccac acaatctgcc ctttcgaaag atcccaacga aaagagagat   5460
cacatggtcc ttcttgagtt tgtaacagct gctgggatta cacatggcat ggatgaacta   5520
tacaaataag cttaaacagt agacattagc agataaatta gcaggaaata aagaaggata   5580
aggagaaaga actcaagtaa ttatccttcg ttctcttaat tgaattgcaa ttaaactcgg   5640
cccaatcttt tactaaaagg attgagccga ataccgctcc aggcatcaaa taaaacgaaa   5700
ggctcagtcg aaagactggg cctttcgttt tatctgttgt ttgtcggtga acgctctcac   5760
aacagctccc tggaacacca ggagaacaca cttatctcgc gtcttgaggt gataccacgc   5820
ctgacacgtg agggcagtac ggttaattcg gtttagccgg acatcagcgc tcctcattga   5880
gcgctgggcc cttcacatga agatcgcact gaggattggt cctagccagg cttctcagta   5940
ctgatacagt acgcgtcgct tctcgtattg tttgagtctt ggaattagtt tgtatccttc   6000
cgccgctgcc ctaagaattc taattgagct cgaacagtcg accgccggat cctgctcgag   6060
tgcctctaga                                                          6070
```

<210> SEQ ID NO 59
<211> LENGTH: 5729
<212> TYPE: DNA
<213> ORGANISM: Artificial Sequence
<220> FEATURE:
<223> OTHER INFORMATION: An example of an episomal DNA vector

<400> SEQUENCE: 59
tgcctcaggg agagctaatg cttgttgggt attttggtct gactcttcct tttcacccaa 60
aacgaggcca gctacatctg agtgaaactt ggagatggta gtcttctttc gtttctcgac 120
ggtgaagtaa gaccaagctc atgagcttat tatcctaggt cggaacaagt cggtaggatc 180
cccttttgga cgtccccatg ccctttccgc gcggggtagc atgtccccgc gccctttccg 240
cgctgggggg catgggggcg aaaaaaggaa ggaggggggat ggggtttctc tcgcttttga 300
catagcagcg ggcccccggtg ggaggcccgc acgacgacga cgattagctc attggtagga 360
tccccttttg gacgtcccca tgccctttcc gcgcggggta gcatgggggc gaaaaaagga 420
agtaaaataa ggaggctttg acatagcagc gggccccggt gggaggcccg cacgacacga 480
cgattagatt agctcattgg taggacgacg attagctcat tggtaggacg acgattagct 540
cattggtagg acgacgatta gctcgttggt attggtagga tccccttttg gacgttgaca 600
taggagcgga tgacatagga gcgggcccca gcgggagtcc cgcacgacga cgacacgacg 660
acgacgatta gctcgttggt attggtagga tccccttttg gacgttggga gcggatgaca 720
taggagcggg ccccagcggg agtcccgcac gacgacgaca cgacgacgac gattagctca 780
ttggtaggac gacgattagc tcattggtag gattagctca gtgttagagt tagagcgggc 840
cccagtggga ggcccgcaca agggagcgca cgcgcaaggt cgcaactacc cgagaatcga 900
tgtggcggaa tgggttacgt gagctattat ccggcgggcc ctcaatttaa atcgttacag 960
ttgctcgtaa cggcaaccgg ctcggtcctt tttccctaga acagtatctt atacttgctg 1020
ctctcgttac ttcggcgatc ctggtgcagt cggtccgtaa atcggcgcac acttttacgt 1080
cgtaccagac aggctcgcat aagccagccc cgacacccgc caacacccgc tgacgcgccc 1140
tgacgggctt gtctgctccc ggcatccgct tacagacaag ctgtgacctc cgggagctgc 1200
atgtgtcaga ggttttcacc gtcatcaccg aaacgcgcac gaaagggcct cgtgatacgc 1260
ctatttttat aggttaatgt catgataata atggtttctt agacgtcagg tggcactttt 1320
cggggaaatg tgcgcggaac ccctatttgt ttatttttct aaatacattc aaatatgtat 1380
ccgctcatga gacaataacc ctgataaatg cttcaataat attgaaaaag gaagagtatg 1440
agtattcaac atttccgtgt cgcccttatt cccttttttg cggcattttg ccttcctgtt 1500
tttgctcacc cagaaacgct ggtgaaagta aaagatgctg aagatcagtt gggtgcacga 1560
gtgggttaca tcgaactgga tctcaacagc ggtaagatcc ttgagagttt tcgccccgaa 1620
gaacgttttc caatgatgag cacttttaaa gttctgctat gtggcgcggt attatcccgt 1680
attgacgccg ggcaagagca actcggtcgc cgcatacact attctcagaa tgacttggtt 1740
gagtactcac cagtcacaga aaagcatctt acggatggca tgacagtaag agaattatgc 1800
agtgctgcca taaccatgag tgataacact gcggccaact tacttctgac aacgatcgga 1860
ggaccgaagg agctaaccgc ttttttgcac aacatggggg atcatgtaac tcgccttgat 1920
cgttgggaac cggagctgaa tgaagccata ccaaacgacg agcgtgacac cacgatgcct 1980
gtagcaatgg caacaacgtt gcgcaaacta ttaactggcg aactacttac tctagcttcc 2040
cggcaacaat taatagactg gatggaggcg gataaagttg caggaccact tctgcgctcg 2100
gcccttccgg ctggctggtt tattgctgat aaatctggag ccggtgagcg tggctcacgc 2160
ggtatcattg cagcactggg gccagatggt aagccctccc gtatcgtagt tatctacacg 2220

-continued

```
acggggagtc aggcaactat ggatgaacga aatagacaga tcgctgagat aggtgcctca   2280
ctgattaagc attggtaact gtcagaccaa gtttactcat atatacttta gattgattta   2340
aaacttcatt tttaatttaa aaggatctag gtgaagatcc tttttgataa tctcatgacc   2400
aaaatccctt aacgtgagtt ttcgttccac tgagcgtcag accccgtaga aaagatcaaa   2460
ggatcttctt gagatccttt ttttctgcgc gtaatctgct gcttgcaaac aaaaaaacca   2520
ccgctaccag cggtggtttg tttgccggat caagagctac caactctttt tccgaaggta   2580
actggcttca gcagagcgca gataccaaat actgttcttc tagtgtagcc gtagttaggc   2640
caccacttca agaactctgt agcaccgcct acatacctcg ctctgctaat cctgttacca   2700
gtggctgctg ccagtggcga taagtcgtgt cttaccgggt tggactcaag acgatagtta   2760
ccggataagg cgcagcggtc gggctgaacg gggggttcgt gcacacagcc cagcttggag   2820
cgaacgacct acaccgaact gagataccta cagcgtgagc tatgagaaag cgccacgctt   2880
cccgaaggga gaaaggcgga caggtatccg gtaagcggca gggtcggaac aggagagcgc   2940
acgagggagc ttccaggggg aaacgcctgg tatctttata gtcctgtcgg gtttcgccac   3000
ctctgacttg agcgtcgatt tttgtgatgc tcgtcagggg ggcggagcct atggaaaaac   3060
gccagcaacg cggccttttt acggttcctg gccttttgct ggccttttgc tcacatgttc   3120
tttcctgcgt tatcccctga ttctgtggat aaccgtatta ccgcctttga gtgagctgat   3180
accgctcgcc gcagccgaac gaccgagcgc agcgagtcag tgagcgagga agcggaagaa   3240
cgcggacacc cagcgtaaca atctaatatt gtttctcaaa tcgggctgtt atcgcatggt   3300
gctcatgatg aggttactga ccaaattcgc cacgcatcgg tgctggtaga atgttcactt   3360
cgaggtgggt agacggcgtc acgtgcaatg ccttgtcttc ccctatctgc ggccccgact   3420
gcctcgcgaa gacaagggat cggacgtcga acgtattctg tttgctaccg gcacgggagt   3480
aggatcgttg atatacacca tgcgcgttaa ctctgacccc cttcctctta aatgagaatg   3540
gataagaggc tcgtgggatt gacgtgaggg ggcagggatg gctatatttc tgggagcgaa   3600
ctccgggcga attactaata aaaagccttc cattttctat tttgatttgt agaaaactag   3660
tgtgcttggg agtccctgat gattaaataa accaagattt taccaatggg ggctagcgaa   3720
gcggtgatcg ccgaagtatc gactcaacta tcagaggtag ttggcgtcat cgagcgccat   3780
ctcgaaccga cgttgctggc cgtacatttg tacggctccg cagtggatgg cggcctgaag   3840
ccacacagtg atattgattt gctggttacg gtgaccgtaa ggcttgatga aacaacgcgg   3900
cgagctttga tcaacgacct tttggaaact tcggcttccc ctggagagag cgagattctc   3960
cgcgctgtag aagtcaccat tgttgtgcac gacgacatca ttccgtggcg ttatccagct   4020
aagcgcgaac tgcaatttgg agaatggcag cgcaatgaca ttcttgcagg tatcttcgag   4080
ccagccacga tcgacattga tctggctatc ttgctgacaa aagcaagaga acatagcgtt   4140
gccttggtag gtccagcggc ggaggaactc tttgatccgg ttcctgaaca ggatctattt   4200
gaggcgctaa atgaaacctt aacgctatgg aactcgccgc ccgactgggc tggcgatgag   4260
cgaaatgtag tgcttacgtt gtcccgcatt tggtacagcg cagtaaccgg caaaatcgcg   4320
ccgaaggatg tcgctgccga ctgggcaatg gagcgcctgc cggcccagta tcagcccgtc   4380
atacttgaag ctagacaggc ttatcttgga caagaagaag atcgcttggc ctcgcgcgca   4440
gatcagttgg aagaatttgt ccactacgtg aaaggcgaga tcaccaaggt agtgggcaaa   4500
gaacttgttg aaggaaaatt ggagctagta gaaggtctta aagtcgccat ggctagtaaa   4560
ggagaagaac ttttcactgg agttgtccca attcttgttg aattagatgg tgatgttaat   4620
```

gggcacaaat tttctgtcag tggagagggt gaaggtgatg caacatacgg aaaacttacc 4680
cttaaattta tttgcactac tggaaaacta cctgttcctt ggccaacact tgtcactact 4740
ttctcttatg gtgttcaatg cttttcaaga tacccagatc atatgaagcg gcacgacttc 4800
ttcaagagcg ccatgcctga gggatacgtg caggagagga ccatctcttt caaggacgac 4860
gggaactaca agacacgtgc tgaagtcaag tttgagggag acaccctcgt caacaggatc 4920
gagcttaagg gaatcgattt caaggaggac ggaaacatcc tcggccacaa gttggaatac 4980
aactacaact cccacaacgt atacatcacg gcagacaaac aaaagaatgg aatcaaagct 5040
aacttcaaaa ttagacacaa cattgaagat ggaagcgttc aactagcaga ccattatcaa 5100
caaaatactc caattggcga tggccctgtc cttttaccag acaaccatta cctgtccaca 5160
caatctgccc tttcgaaaga tcccaacgaa aagagagatc acatggtcct tcttgagttt 5220
gtaacagctg ctgggattac acatggcatg gatgaactat acaaataagc ttaaacagta 5280
gacattagca gataaattag caggaaataa agaaggataa ggagaaagaa ctcaagtaat 5340
tatccttcgt tctcttaatt gaattgcaat taaactcggc ccaatctttt actaaaagga 5400
ttgagccgaa taccgctaca acagctccct ggaacaccag gagaacacac ttatctcgcg 5460
tcttgaggtg ataccacgcc tgacacgtga gggcagtacg gttaattcgg tttagccgga 5520
catcagcgct cctcattgag cgctgggccc ttcacatgaa gatcgcactg aggattggtc 5580
ctagccaggc ttctcagtac tgatacagta cgcgtcgctt ctcgtattgt ttgagtcttg 5640
gaattagttt gtatccttcc gccgctgccc taagaattct aattgagctc gaacagtcga 5700
ccgccggatc ctgctcgagt gcctctaga 5729

<210> SEQ ID NO 60
<211> LENGTH: 5809
<212> TYPE: DNA
<213> ORGANISM: Artificial Sequence
<220> FEATURE:
<223> OTHER INFORMATION: An example of an episomal DNA vector

<400> SEQUENCE: 60
tgcctcaggg agagctaatg cttgttgggt attttggtct gactcttcct tttcacccaa 60
aacgaggcca gctacatctg agtgaaactt ggagatggta gtcttctttc gtttctcgac 120
ggtgaagtaa gaccaagctc atgagcttat tatcctaggt cggaacaagt cggtaggatc 180 ccccttttgga cgtccccatg ccctttccgc gcggggtagc atgtccccgc gccctttccg 240
cgctgggggg catgggggcg aaaaaaggaa ggagggggat ggggtttctc tcgcttttga 300
catagcagcg ggccccggtg ggaggcccgc acgacgacga cgattagctc attggtagga 360
tccccttttg gacgtcccca tgccctttcc gcgcggggta gcatgggggc gaaaaaagga 420
agtaaaataa ggaggctttg acatagcagc gggccccggt gggaggcccg cacgacacga 480
cgattagatt agctcattgg taggacgacg attagctcat tggtaggacg acgattagct 540
cattggtagg acgacgatta gctcgttggt attggtagga tccccttttg gacgttgaca 600
taggagcgga tgacatagga gcgggcccca gcgggagtcc cgcacgacga cgacacgacg 660
acgacgatta gctcgttggt attggtagga tccccttttg gacgttggga gcggatgaca 720
taggagcggg ccccagcggg agtcccgcac gacgacgaca cgacgacgac gattagctca 780
ttggtaggac gacgattagc tcattggtag gattagctca gtgttagagt tagagcgggc 840
cccagtggga ggcccgcaca agggagcgca cgcgcaaggt cgcaactacc cgagaatcga 900

-continued

```
tgtggcggaa tgggttacgt gagctattat ccggcgggcc ctcaatttaa atcgttacag    960
ttgctcgtaa cggcaaccgg ctcggtcctt tttccctaga acagtatctt atacttgctg   1020
ctctcgttac ttcggcgatc ctggtgcagt cggtccgtaa atcggcgcac acttttacgt   1080
cgtaccagac aggctcgcat aagccagccc cgacacccgc caacacccgc tgacgcgccc   1140
tgacgggctt gtctgctccc ggcatccgct tacagacaag ctgtgacctc cgggagctgc   1200
atgtgtcaga ggttttcacc gtcatcaccg aaacgcgcac gaaagggcct cgtgatacgc   1260
ctatttttat aggttaatgt catgataata atggtttctt agacgtcagg tggcactttt   1320
cggggaaatg tgcgcggaac ccctatttgt ttatttttct aaatacattc aaatatgtat   1380
ccgctcatga gacaataacc ctgataaatg cttcaataat attgaaaaag gaagagtatg   1440
agtattcaac atttccgtgt cgcccttatt cccttttttg cggcattttg ccttcctgtt   1500
tttgctcacc cagaaacgct ggtgaaagta aaagatgctg aagatcagtt gggtgcacga   1560
gtgggttaca tcgaactgga tctcaacagc ggtaagatcc ttgagagttt tcgccccgaa   1620
gaacgttttc caatgatgag cacttttaaa gttctgctat gtggcgcggt attatcccgt   1680
attgacgccg ggcaagagca actcggtcgc cgcatacact attctcagaa tgacttggtt   1740
gagtactcac cagtcacaga aaagcatctt acggatggca tgacagtaag agaattatgc   1800
agtgctgcca taaccatgag tgataacact gcggccaact tacttctgac aacgatcgga   1860
ggaccgaagg agctaaccgc ttttttgcac aacatggggg atcatgtaac tcgccttgat   1920
cgttgggaac cggagctgaa tgaagccata ccaaacgacg agcgtgacac cacgatgcct   1980
gtagcaatgg caacaacgtt gcgcaaacta ttaactggcg aactacttac tctagcttcc   2040
cggcaacaat taatagactg gatggaggcg gataaagttg caggaccact tctgcgctcg   2100
gcccttccgg ctggctggtt tattgctgat aaatctggag ccggtgagcg tggctcacgc   2160
ggtatcattg cagcactggg gccagatggt aagccctccc gtatcgtagt tatctacacg   2220
acggggagtc aggcaactat ggatgaacga aatagacaga tcgctgagat aggtgcctca   2280
ctgattaagc attggtaact gtcagaccaa gtttactcat atatacttta gattgattta   2340
aaacttcatt tttaatttaa aaggatctag gtgaagatcc tttttgataa tctcatgacc   2400
aaaatccctt aacgtgagtt ttcgttccac tgagcgtcag accccgtaga aaagatcaaa   2460
ggatcttctt gagatccttt ttttctgcgc gtaatctgct gcttgcaaac aaaaaaacca   2520
ccgctaccag cggtggtttg tttgccggat caagagctac caactctttt tccgaaggta   2580
actggcttca gcagagcgca gataccaaat actgttcttc tagtgtagcc gtagttaggc   2640
caccacttca agaactctgt agcaccgcct acatacctcg ctctgctaat cctgttacca   2700
gtggctgctg ccagtggcga taagtcgtgt cttaccgggt tggactcaag acgatagtta   2760
ccggataagg cgcagcggtc gggctgaacg gggggttcgt gcacacagcc cagcttggag   2820
cgaacgacct acaccgaact gagataccta cagcgtgagc tatgagaaag cgccacgctt   2880
cccgaaggga gaaaggcgga caggtatccg gtaagcggca gggtcggaac aggagagcgc   2940
acgagggagc ttccaggggg aaacgcctgg tatctttata gtcctgtcgg gtttcgccac   3000
ctctgacttg agcgtcgatt tttgtgatgc tcgtcagggg ggcggagcct atggaaaaac   3060
gccagcaacg cggccttttt acggttcctg gccttttgct ggccttttgc tcacatgttc   3120
tttcctgcgt tatcccctga ttctgtggat aaccgtatta ccgcctttga gtgagctgat   3180
accgctcgcc gcagccgaac gaccgagcgc agcgagtcag tgagcgagga agcggaagaa   3240
cgcggacacc cagcgtaaca atctaatatt gtttctcaaa tcgggctgtt atcgcatggt   3300
```

-continued

```
gctcatgatg aggttactga ccaaattcgc cacgcatcgg tgctggtaga atgttcactt   3360

cgaggtgggt agacggcgtc acgtgcaatg ccttgtcttc ccctatctgc ggccccgact   3420

gcctcgcgaa gacaagggat cggacgtcga acgtattctg tttgctaccg gcacgggagt   3480

aggatcgttg atatacacca tgcgcgttaa ctctgacccc cttcctctta aatgagaatg   3540

gataagaggc tcgtgggatt gacgtgaggg ggcagggatg gctatatttc tgggagcgaa   3600

ctccgggcga attactaata aaaagccttc cattttctat tttgatttgt agaaaactag   3660

tgtgcttggg agtccctgat gattaaataa accaagattt taccaatggg ggctagcgaa   3720

gcggtgatcg ccgaagtatc gactcaacta tcagaggtag ttggcgtcat cgagcgccat   3780

ctcgaaccga cgttgctggc cgtacatttg tacggctccg cagtggatgg cggcctgaag   3840

ccacacagtg atattgattt gctggttacg gtgaccgtaa ggcttgatga aacaacgcgg   3900

cgagctttga tcaacgacct tttggaaact tcggcttccc ctggagagag cgagattctc   3960

cgcgctgtag aagtcaccat tgttgtgcac gacgacatca ttccgtggcg ttatccagct   4020

aagcgcgaac tgcaatttgg agaatggcag cgcaatgaca ttcttgcagg tatcttcgag   4080

ccagccacga tcgacattga tctggctatc ttgctgacaa aagcaagaga acatagcgtt   4140

gccttggtag gtccagcggc ggaggaactc tttgatccgg ttcctgaaca ggatctattt   4200

gaggcgctaa atgaaacctt aacgctatgg aactcgccgc ccgactgggc tggcgatgag   4260

cgaaatgtag tgcttacgtt gtcccgcatt tggtacagcg cagtaaccgg caaaatcgcg   4320

ccgaaggatg tcgctgccga ctgggcaatg gagcgcctgc cggcccagta tcagcccgtc   4380

atacttgaag ctagacaggc ttatcttgga caagaagaag atcgcttggc ctcgcgcgca   4440

gatcagttgg aagaatttgt ccactacgtg aaaggcgaga tcaccaaggt agtgggcaaa   4500

gaacttgttg aaggaaaatt ggagctagta gaaggtctta aagtcgccat ggctagtaaa   4560

ggagaagaac ttttcactgg agttgtccca attcttgttg aattagatgg tgatgttaat   4620

gggcacaaat tttctgtcag tggagagggt gaaggtgatg caacatacgg aaaacttacc   4680

cttaaattta tttgcactac tggaaaacta cctgttcctt ggccaacact tgtcactact   4740

ttctcttatg gtgttcaatg cttttcaaga tacccagatc atatgaagcg gcacgacttc   4800

ttcaagagcg ccatgcctga gggatacgtg caggagagga ccatctcttt caaggacgac   4860

gggaactaca agacacgtgc tgaagtcaag tttgagggag acaccctcgt caacaggatc   4920

gagcttaagg gaatcgattt caaggaggac ggaaacatcc tcggccacaa gttggaatac   4980

aactacaact cccacaacgt atacatcacg gcagacaaac aaaagaatgg aatcaaagct   5040

aacttcaaaa ttagacacaa cattgaagat ggaagcgttc aactagcaga ccattatcaa   5100

caaaatactc caattggcga tggccctgtc cttttaccag acaaccatta cctgtccaca   5160

caatctgccc tttcgaaaga tcccaacgaa aagagagatc acatggtcct tcttgagttt   5220

gtaacagctg ctgggattac acatggcatg gatgaactat acaaataagc ttaaacagta   5280

gacattagca gataaattag caggaaataa agaaggataa ggagaaagaa ctcaagtaat   5340

tatccttcgt tctcttaatt gaattgcaat taaactcggc ccaatctttt actaaaagga   5400

ttgagccgaa taccgctcca ggcatcaaat aaaacgaaag gctcagtcga aagactgggc   5460

ctttcgtttt atctgttgtt tgtcggtgaa cgctctcaca acagctccct ggaacaccag   5520

gagaacacac ttatctcgcg tcttgaggtg ataccacgcc tgacacgtga gggcagtacg   5580

gttaattcgg tttagccgga catcagcgct cctcattgag cgctgggccc ttcacatgaa   5640
```

gatcgcactg aggattggtc ctagccaggc ttctcagtac tgatacagta cgcgtcgctt 5700
ctcgtattgt ttgagtcttg gaattagttt gtatccttcc gccgctgccc taagaattct 5760
aattgagctc gaacagtcga ccgccggatc ctgctcgagt gcctctaga 5809

<210> SEQ ID NO 61
<211> LENGTH: 7731
<212> TYPE: DNA
<213> ORGANISM: Artificial Sequence
<220> FEATURE:
<223> OTHER INFORMATION: An example of an episomal DNA vector

<400> SEQUENCE: 61
tgccagaaca tgctgagcca aatcttcttc atggaaaacc tgcttgattt agatcgggag 60
aatcgtacgg ttttatgaaa ccatgtgcta tggctcgaat ccgtattcaa tcctatttcc 120
gataggagca gttgacaatg gaatccaatt tttccattat tttcgtatcc gtaatagtgc 180
gaaacgaagg cccgtctcca agttgttcaa gaataaatag tggcgttgag tttcttgacc 240
ctttgtctta ggattagtca gttccatttc ttgatgggag cagggaaggg atataactca 300
gcggtagagt gtcaccttga cgtggtggaa gtcatcagtt cgagcctgat tatccctaaa 360
accaatgcga gtttttctat tttgacttac tcccccgccg tgatcgaatg aaaatggata 420
agaggctcgt gggattgacg tgaggggata ggtatgccta ttccgaatcc gctttgtcta 480
cgaacaagga agctataagt aatgcaacta tgaatctcat ggagagttcg atcctggctc 540
aggatgaacg ctggcggcat gcttaacaca tgcgagtcgg acgggaagtg gtgtttccag 600
tggcggacgg gtgagtaacg cgtaagaacc tgcccttggg aggggaacaa cagctggaaa 660
cggctgctaa taccccgtag gctgaggagc aaaaggagga atccgcccga ggaggggctc 720
gcgtctgatt agctagttgg tgaggcaata gcttaccaag gcgatgatca gtagctggtc 780
cgagaggatg atcagccaca ctgggactga gacacggccc agactcctac gggaggcagc 840
agtggggaat tttccgcaat gggcgaaagc ctgacggagc aatgccgcgt ggaggtagaa 900
ggcccacggg tcgtgaactt cttttcccgg agaagaagca atgacggtat ccggggaata 960
agcatcggct aactctgtgc cagcagccgc ggtaagacag aggatgcaag cgttatccgg 1020
aatgattggg cgtaaagcgt ctgtaggtgg ctttttaagt ccgccgtcaa atcccagggc 1080
tcaaccctgg acaggcggtg gaaactacca agctggagta cggtaggggc agagggaatt 1140
tccggtggag cgatgaaatg cgttgagatc ggaaagaaca ccaacggcga aagcactctg 1200
ctgggccgac actgacactg agagacgaaa gctaggggag cgaatgggat tagtgacccc 1260
agtagtccta gccgtaaacg atggatacta ggcgctgtgc gtatcgaccc gtgcagtgct 1320
gtagctaacg cgttaagtat cccgcctggg gagtacgttc gcaagaatga aactcaaagg 1380
aattgacggg ggcccgcaca agcggtggag catgtggttt aattcgatgc aaagcgaaga 1440
accttaccag ggcttgacat gccgcgaacc cttttgaaag agaggtgtgc cttcgggaac 1500
gcggacacag gtggtgcatg gctgtcgtca gctcgtgccg taaggtgttg ggttaagtcc 1560
cgcaacgagc gcaaccctcg tgtttagttg ccaatgttga gtttggaacc ctgaacagac 1620
tgccggtgct aagccggagg aaggcgagga tgacgtcaag tcatcatgcc ccttacgccc 1680
tgggcgacac acgtgctaca atggccggga caaagggtcg cgatcccgcg agggtgagct 1740
aactccaaaa acccgtcctc agttcggatt gcaggctgca actcgcctgc atgaagtagg 1800
aatcgctagt aatcgccggt cagccatacg gcggtgaatt cgttcccggg ccttgtacac 1860
accgcccgtc acactatggg agctggccat gcctgaagtc gttaccttaa ccacaaggag 1920
ggggatgccg aaggcaaggc ttggtgactg gagtgaagtc gtaacaaggt agccgtactg 1980
gaaggtgcgg ctggatcacc tccttttcag ggagagctaa tgcttgttgg gtattttggt 2040
ctgactcttc cttttcaccc aaaacgaggc cagctacatc tgagtgaaac ttggagatgg 2100
tagtcttctt tcgtttctcg acggtgaagt aagaccaagc tcatgagctt attatcctag 2160
gtcggaacaa gtcggtagga tccccttttg gacgtcccca tgccctttcc gcgcggggta 2220
gcatgtcccc gcgccctttc cgcgctgggg ggcatggggg cgaaaaaagg aaggaggggg 2280
atggggtttc tctcgctttt gacatagcag cgggccccgg tgggaggccc gcacgacgac 2340
gacgattagc tcattggtag gatccccttt tggacgtccc catgcccttt ccgcgcgggg 2400
tagcatgggg gcgaaaaaag gaagtaaaat aaggaggctt tgacatagca gcgggccccg 2460
gtgggaggcc cgcacgacac gacgattaga ttagctcatt ggtaggacga cgattagctc 2520
attggtagga cgacgattag ctcattggta ggacgacgat tagctcgttg gtattggtag 2580
gatccccttt tggacgttga cataggagcg gatgacatag gagcgggccc cagcgggagt 2640
cccgcacgac gacgacacga cgacgacgat tagctcgttg gtattggtag gatccccttt 2700
tggacgttgg gagcggatga cataggagcg ggccccagcg ggagtcccgc acgacgacga 2760
cacgacgacg acgattagct cattggtagg acgacgatta gctcattggt aggattagct 2820
cagtgttaga gttagagcgg gccccagtgg gaggcccgca caagggagcg cacgcgcaag 2880
gtcgcaacta cccgagaatc gatgtggcgg aatgggttac gtgagctatt atccggcggg 2940
ccctcaattt aaatcgttac agttgctcgt aacggcaacc ggctcggtcc tttttcccta 3000
gaacagtatc ttatacttgc tgctctcgtt acttcggcga tcctggtgca gtcggtccgt 3060
aaatcggcgc acacttttac gtcgtaccag acaggctcgc ataagccagc cccgacaccc 3120
gccaacaccc gctgacgcgc cctgacgggc ttgtctgctc ccggcatccg cttacagaca 3180
agctgtgacc tccgggagct gcatgtgtca gaggttttca ccgtcatcac cgaaacgcgc 3240
acgaaagggc ctcgtgatac gcctattttt ataggttaat gtcatgataa taatggtttc 3300
ttagacgtca ggtggcactt ttcggggaaa tgtgcgcgga acccctattt gtttattttt 3360
ctaaatacat tcaaatatgt atccgctcat gagacaataa ccctgataaa tgcttcaata 3420
atattgaaaa aggaagagta tgagtattca acatttccgt gtcgccctta ttcccttttt 3480
tgcggcattt tgccttcctg tttttgctca cccagaaacg ctggtgaaag taaaagatgc 3540
tgaagatcag ttgggtgcac gagtgggtta catcgaactg gatctcaaca gcggtaagat 3600
ccttgagagt tttcgccccg aagaacgttt tccaatgatg agcactttta aagttctgct 3660
atgtggcgcg gtattatccc gtattgacgc cgggcaagag caactcggtc gccgcataca 3720
ctattctcag aatgacttgg ttgagtactc accagtcaca gaaaagcatc ttacggatgg 3780
catgacagta agagaattat gcagtgctgc cataaccatg agtgataaca ctgcggccaa 3840
cttacttctg acaacgatcg gaggaccgaa ggagctaacc gcttttttgc acaacatggg 3900
ggatcatgta actcgccttg atcgttggga accggagctg aatgaagcca taccaaacga 3960
cgagcgtgac accacgatgc ctgtagcaat ggcaacaacg ttgcgcaaac tattaactgg 4020
cgaactactt actctagctt cccggcaaca attaatagac tggatggagg cggataaagt 4080
tgcaggacca cttctgcgct cggcccttcc ggctggctgg tttattgctg ataaatctgg 4140
agccggtgag cgtggctcac gcggtatcat tgcagcactg gggccagatg gtaagccctc 4200
ccgtatcgta gttatctaca cgacggggag tcaggcaact atggatgaac gaaatagaca 4260

-continued

```
gatcgctgag ataggtgcct cactgattaa gcattggtaa ctgtcagacc aagtttactc   4320
atatatactt tagattgatt taaaacttca tttttaattt aaaaggatct aggtgaagat   4380
cctttttgat aatctcatga ccaaaatccc ttaacgtgag ttttcgttcc actgagcgtc   4440
agaccccgta gaaaagatca aaggatcttc ttgagatcct ttttttctgc gcgtaatctg   4500
ctgcttgcaa acaaaaaaac caccgctacc agcggtggtt tgtttgccgg atcaagagct   4560
accaactctt tttccgaagg taactggctt cagcagagcg cagataccaa atactgttct   4620
tctagtgtag ccgtagttag gccaccactt caagaactct gtagcaccgc ctacatacct   4680
cgctctgcta atcctgttac cagtggctgc tgccagtggc gataagtcgt gtcttaccgg   4740
gttggactca agacgatagt taccggataa ggcgcagcgg tcgggctgaa cggggggttc   4800
gtgcacacag cccagcttgg agcgaacgac ctacaccgaa ctgagatacc tacagcgtga   4860
gctatgagaa agcgccacgc ttcccgaagg gagaaaggcg gacaggtatc cggtaagcgg   4920
cagggtcgga acaggagagc gcacgaggga gcttccaggg ggaaacgcct ggtatcttta   4980
tagtcctgtc gggtttcgcc acctctgact tgagcgtcga tttttgtgat gctcgtcagg   5040
ggggcggagc ctatggaaaa acgccagcaa cgcggccttt ttacggttcc tggccttttg   5100
ctggcctttt gctcacatgt tctttcctgc gttatcccct gattctgtgg ataaccgtat   5160
taccgccttt gagtgagctg ataccgctcg ccgcagccga acgaccgagc gcagcgagtc   5220
agtgagcgag gaagcggaag aacgcggaca cccagcgtaa caatctaata ttgtttctca   5280
aatcgggctg ttatcgcatg gtgctcatga tgaggttact gaccaaattc gccacgcatc   5340
ggtgctggta gaatgttcac ttcgaggtgg gtagacggcg tcacgtgcaa tgccttgtct   5400
tcccctatct gcggccccga ctgcctcgcg aagacaaggg atcggacgtc gaacgtattc   5460
tgtttgctac cggcacggga gtaggatcgt tgatatacac catgcgcgtt aactctgacc   5520
cccttcctct taaatgagaa tggataagag gctcgtggga ttgacgtgag gggcaggga   5580
tggctatatt tctgggagcg aactccgggc gaattactaa taaaaagcct tccattttct   5640
attttgattt gtagaaaact agtgtgcttg ggagtccctg atgattaaat aaaccaagat   5700
tttaccaatg gggctagcg aagcggtgat cgccgaagta tcgactcaac tatcagaggt   5760
agttggcgtc atcgagcgcc atctcgaacc gacgttgctg gccgtacatt tgtacggctc   5820
cgcagtggat ggcggcctga agccacacag tgatattgat ttgctggtta cggtgaccgt   5880
aaggcttgat gaaacaacgc ggcgagcttt gatcaacgac cttttggaaa cttcggcttc   5940
ccctggagag agcgagattc tccgcgctgt agaagtcacc attgttgtgc acgacgacat   6000
cattccgtgg cgttatccag ctaagcgcga actgcaattt ggagaatggc agcgcaatga   6060
cattcttgca ggtatcttcg agccagccac gatcgacatt gatctggcta tcttgctgac   6120
aaaagcaaga gaacatagcg ttgccttggt aggtccagcg gcggaggaac tctttgatcc   6180
ggttcctgaa caggatctat ttgaggcgct aaatgaaacc ttaacgctat ggaactcgcc   6240
gcccgactgg gctggcgatg agcgaaatgt agtgcttacg ttgtcccgca tttggtacag   6300
cgcagtaacc ggcaaaatcg cgccgaagga tgtcgctgcc gactgggcaa tggagcgcct   6360
gccggcccag tatcagcccg tcatacttga agctagacag gcttatcttg gacaagaaga   6420
agatcgcttg gcctcgcgcg cagatcagtt ggaagaattt gtccactacg tgaaaggcga   6480
gatcaccaag gtagtgggca aagaacttgt tgaaggaaaa ttggagctag tagaaggtct   6540
taaagtcgcc atggctagta aaggagaaga acttttcact ggagttgtcc caattcttgt   6600
tgaattagat ggtgatgtta atgggcacaa attttctgtc agtggagagg gtgaaggtga   6660
```

```
tgcaacatac ggaaaactta cccttaaatt tatttgcact actggaaaac tacctgttcc   6720
ttggccaaca cttgtcacta ctttctctta tggtgttcaa tgcttttcaa gatacccaga   6780
tcatatgaag cggcacgact tcttcaagag cgccatgcct gagggatacg tgcaggagag   6840
gaccatctct ttcaaggacg acgggaacta caagacacgt gctgaagtca agtttgaggg   6900
agacaccctc gtcaacagga tcgagcttaa gggaatcgat ttcaaggagg acggaaacat   6960
cctcggccac aagttggaat acaactacaa ctcccacaac gtatacatca cggcagacaa   7020
acaaaagaat ggaatcaaag ctaacttcaa aattagacac aacattgaag atggaagcgt   7080
tcaactagca gaccattatc aacaaaatac tccaattggc gatggccctg tccttttacc   7140
agacaaccat tacctgtcca cacaatctgc cctttcgaaa gatcccaacg aaaagagaga   7200
tcacatggtc cttcttgagt ttgtaacagc tgctgggatt acacatggca tggatgaact   7260
atacaaataa gcttaaacag tagacattag cagataaatt agcaggaaat aaagaaggat   7320
aaggagaaag aactcaagta attatccttc gttctcttaa ttgaattgca attaaactcg   7380
gcccaatctt ttactaaaag gattgagccg aataccgcta caacagctcc ctggaacacc   7440
aggagaacac acttatctcg cgtcttgagg tgataccacg cctgacacgt gagggcagta   7500
cggttaattc ggtttagccg gacatcagcg ctcctcattg agcgctgggc ccttcacatg   7560
aagatcgcac tgaggattgg tcctagccag gcttctcagt actgatacag tacgcgtcgc   7620
ttctcgtatt gtttgagtct tggaattagt ttgtatcctt ccgccgctgc cctaagaatt   7680
ctaattgagc tcgaacagtc gaccgccgga tcctgctcga gtgcctctag a            7731
```

<210> SEQ ID NO 62
<211> LENGTH: 7811
<212> TYPE: DNA
<213> ORGANISM: Artificial Sequence
<220> FEATURE:
<223> OTHER INFORMATION: An example of an episomal DNA vector

<400> SEQUENCE: 62

```
tgccagaaca tgctgagcca aatcttcttc atggaaaacc tgcttgattt agatcgggag     60
aatcgtacgg ttttatgaaa ccatgtgcta tggctcgaat ccgtattcaa tcctatttcc    120
gataggagca gttgacaatg gaatccaatt tttccattat tttcgtatcc gtaatagtgc    180
gaaacgaagg cccgtctcca agttgttcaa gaataaatag tggcgttgag tttcttgacc    240
ctttgtctta ggattagtca gttccatttc ttgatgggag cagggaaggg atataactca    300
gcggtagagt gtcaccttga cgtggtggaa gtcatcagtt cgagcctgat tatccctaaa    360
accaatgcga gtttttctat tttgacttac tcccccgccg tgatcgaatg aaaatggata    420
agaggctcgt gggattgacg tgaggggata ggtatgccta ttccgaatcc gctttgtcta    480
cgaacaagga agctataagt aatgcaacta tgaatctcat ggagagttcg atcctggctc    540
aggatgaacg ctggcggcat gcttaacaca tgcgagtcgg acgggaagtg gtgtttccag    600
tggcggacgg gtgagtaacg cgtaagaacc tgcccttggg aggggaacaa cagctggaaa    660
cggctgctaa taccccgtag gctgaggagc aaaaggagga atccgcccga ggaggggctc    720
gcgtctgatt agctagttgg tgaggcaata gcttaccaag gcgatgatca gtagctggtc    780
cgagaggatg atcagccaca ctgggactga gacacggccc agactcctac gggaggcagc    840
agtggggaat tttccgcaat gggcgaaagc ctgacggagc aatgccgcgt ggaggtagaa    900
ggcccacggg tcgtgaactt cttttcccgg agaagaagca atgacggtat ccggggaata    960
```

-continued

```
agcatcggct aactctgtgc cagcagccgc ggtaagacag aggatgcaag cgttatccgg   1020
aatgattggg cgtaaagcgt ctgtaggtgg ctttttaagt ccgccgtcaa atcccagggc   1080
tcaaccctgg acaggcggtg gaaactacca agctggagta cggtaggggc agagggaatt   1140
tccggtggag cgatgaaatg cgttgagatc ggaaagaaca ccaacggcga aagcactctg   1200
ctgggccgac actgacactg agagacgaaa gctaggggag cgaatgggat tagtgacccc   1260
agtagtccta gccgtaaacg atggatacta ggcgctgtgc gtatcgaccc gtgcagtgct   1320
gtagctaacg cgttaagtat cccgcctggg gagtacgttc gcaagaatga aactcaaagg   1380
aattgacggg ggcccgcaca agcggtggag catgtggttt aattcgatgc aaagcgaaga   1440
accttaccag ggcttgacat gccgcgaacc cttttgaaag agaggtgtgc cttcgggaac   1500
gcggacacag gtggtgcatg gctgtcgtca gctcgtgccg taaggtgttg ggttaagtcc   1560
cgcaacgagc gcaaccctcg tgtttagttg ccaatgttga gtttggaacc ctgaacagac   1620
tgccggtgct aagccggagg aaggcgagga tgacgtcaag tcatcatgcc ccttacgccc   1680
tgggcgacac acgtgctaca atggccggga caaagggtcg cgatcccgcg agggtgagct   1740
aactccaaaa acccgtcctc agttcggatt gcaggctgca actcgcctgc atgaagtagg   1800
aatcgctagt aatcgccggt cagccatacg gcggtgaatt cgttcccggg ccttgtacac   1860
accgcccgtc acactatggg agctggccat gcctgaagtc gttaccttaa ccacaaggag   1920
ggggatgccg aaggcaaggc ttggtgactg gagtgaagtc gtaacaaggt agccgtactg   1980
gaaggtgcgg ctggatcacc tccttttcag ggagagctaa tgcttgttgg gtattttggt   2040
ctgactcttc cttttcaccc aaaacgaggc cagctacatc tgagtgaaac ttggagatgg   2100
tagtcttctt tcgtttctcg acggtgaagt aagaccaagc tcatgagctt attatcctag   2160
gtcggaacaa gtcggtagga tccccttttg gacgtcccca tgccctttcc gcgcggggta   2220
gcatgtcccc gcgccctttc cgcgctgggg ggcatggggg cgaaaaaagg aaggaggggg   2280
atggggtttc tctcgctttt gacatagcag cgggccccgg tgggaggccc gcacgacgac   2340
gacgattagc tcattggtag gatccccttt tggacgtccc catgcccttt ccgcgcgggg   2400
tagcatgggg gcgaaaaaag gaagtaaaat aaggaggctt tgacatagca gcgggccccg   2460
gtgggaggcc cgcacgacac gacgattaga ttagctcatt ggtaggacga cgattagctc   2520
attggtagga cgacgattag ctcattggta ggacgacgat tagctcgttg gtattggtag   2580
gatccccttt tggacgttga cataggagcg gatgacatag gagcgggccc cagcgggagt   2640
cccgcacgac gacgacacga cgacgacgat tagctcgttg gtattggtag gatccccttt   2700
tggacgttgg gagcggatga cataggagcg ggccccagcg ggagtcccgc acgacgacga   2760
cacgacgacg acgattagct cattggtagg acgacgatta gctcattggt aggattagct   2820
cagtgttaga gttagagcgg gccccagtgg gaggcccgca caagggagcg cacgcgcaag   2880
gtcgcaacta cccgagaatc gatgtggcgg aatgggttac gtgagctatt atccggcggg   2940
ccctcaattt aaatcgttac agttgctcgt aacggcaacc ggctcggtcc tttttcccta   3000
gaacagtatc ttatacttgc tgctctcgtt acttcggcga tcctggtgca gtcggtccgt   3060
aaatcggcgc acacttttac gtcgtaccag acaggctcgc ataagccagc cccgacaccc   3120
gccaacaccc gctgacgcgc cctgacgggc ttgtctgctc ccggcatccg cttacagaca   3180
agctgtgacc tccgggagct gcatgtgtca gaggttttca ccgtcatcac cgaaacgcgc   3240
acgaaagggc ctcgtgatac gcctattttt ataggttaat gtcatgataa taatggtttc   3300
ttagacgtca ggtggcactt ttcggggaaa tgtgcgcgga acccctattt gtttattttt   3360
```

```
ctaaatacat tcaaatatgt atccgctcat gagacaataa ccctgataaa tgcttcaata   3420
atattgaaaa aggaagagta tgagtattca acatttccgt gtcgccctta ttcccttttt   3480
tgcggcattt tgccttcctg tttttgctca cccagaaacg ctggtgaaag taaaagatgc   3540
tgaagatcag ttgggtgcac gagtgggtta catcgaactg gatctcaaca gcggtaagat   3600
ccttgagagt tttcgccccg aagaacgttt tccaatgatg agcactttta aagttctgct   3660
atgtggcgcg gtattatccc gtattgacgc cgggcaagag caactcggtc gccgcataca   3720
ctattctcag aatgacttgg ttgagtactc accagtcaca gaaaagcatc ttacggatgg   3780
catgacagta agagaattat gcagtgctgc cataaccatg agtgataaca ctgcggccaa   3840
cttacttctg acaacgatcg gaggaccgaa ggagctaacc gcttttttgc acaacatggg   3900
ggatcatgta actcgccttg atcgttggga accggagctg aatgaagcca taccaaacga   3960
cgagcgtgac accacgatgc ctgtagcaat ggcaacaacg ttgcgcaaac tattaactgg   4020
cgaactactt actctagctt cccggcaaca attaatagac tggatggagg cggataaagt   4080
tgcaggacca cttctgcgct cggcccttcc ggctggctgg tttattgctg ataaatctgg   4140
agccggtgag cgtggctcac gcggtatcat tgcagcactg gggccagatg gtaagccctc   4200
ccgtatcgta gttatctaca cgacggggag tcaggcaact atggatgaac gaaatagaca   4260
gatcgctgag ataggtgcct cactgattaa gcattggtaa ctgtcagacc aagtttactc   4320
atatatactt tagattgatt taaaacttca tttttaattt aaaaggatct aggtgaagat   4380
cctttttgat aatctcatga ccaaaatccc ttaacgtgag ttttcgttcc actgagcgtc   4440
agaccccgta gaaaagatca aaggatcttc ttgagatcct ttttttctgc gcgtaatctg   4500
ctgcttgcaa acaaaaaaac caccgctacc agcggtggtt tgtttgccgg atcaagagct   4560
accaactctt tttccgaagg taactggctt cagcagagcg cagataccaa atactgttct   4620
tctagtgtag ccgtagttag gccaccactt caagaactct gtagcaccgc ctacatacct   4680
cgctctgcta atcctgttac cagtggctgc tgccagtggc gataagtcgt gtcttaccgg   4740
gttggactca agacgatagt taccggataa ggcgcagcgg tcgggctgaa cggggggttc   4800
gtgcacacag cccagcttgg agcgaacgac ctacaccgaa ctgagatacc tacagcgtga   4860
gctatgagaa agcgccacgc ttcccgaagg gagaaaggcg gacaggtatc cggtaagcgg   4920
cagggtcgga acaggagagc gcacgaggga gcttccaggg ggaaacgcct ggtatcttta   4980
tagtcctgtc gggtttcgcc acctctgact tgagcgtcga tttttgtgat gctcgtcagg   5040
ggggcggagc ctatggaaaa acgccagcaa cgcggccttt ttacggttcc tggccttttg   5100
ctggcctttt gctcacatgt tctttcctgc gttatcccct gattctgtgg ataaccgtat   5160
taccgccttt gagtgagctg ataccgctcg ccgcagccga acgaccgagc gcagcgagtc   5220
agtgagcgag gaagcggaag aacgcggaca cccagcgtaa caatctaata ttgtttctca   5280
aatcgggctg ttatcgcatg gtgctcatga tgaggttact gaccaaattc gccacgcatc   5340
ggtgctggta gaatgttcac ttcgaggtgg gtagacggcg tcacgtgcaa tgccttgtct   5400
tcccctatct gcggccccga ctgcctcgcg aagacaaggg atcggacgtc gaacgtattc   5460
tgtttgctac cggcacggga gtaggatcgt tgatatacac catgcgcgtt aactctgacc   5520
cccttcctct taaatgagaa tggataagag gctcgtggga ttgacgtgag gggcaggga   5580
tggctatatt tctgggagcg aactccgggc gaattactaa taaaaagcct tccattttct   5640
attttgattt gtagaaaact agtgtgcttg ggagtccctg atgattaaat aaaccaagat   5700
```

```
tttaccaatg ggggctagcg aagcggtgat cgccgaagta tcgactcaac tatcagaggt   5760
agttggcgtc atcgagcgcc atctcgaacc gacgttgctg gccgtacatt tgtacggctc   5820
cgcagtggat ggcggcctga agccacacag tgatattgat ttgctggtta cggtgaccgt   5880
aaggcttgat gaaacaacgc ggcgagcttt gatcaacgac cttttggaaa cttcggcttc   5940
ccctggagag agcgagattc tccgcgctgt agaagtcacc attgttgtgc acgacgacat   6000
cattccgtgg cgttatccag ctaagcgcga actgcaattt ggagaatggc agcgcaatga   6060
cattcttgca ggtatcttcg agccagccac gatcgacatt gatctggcta tcttgctgac   6120
aaaagcaaga gaacatagcg ttgccttggt aggtccagcg gcggaggaac tctttgatcc   6180
ggttcctgaa caggatctat ttgaggcgct aaatgaaacc ttaacgctat ggaactcgcc   6240
gcccgactgg gctggcgatg agcgaaatgt agtgcttacg ttgtcccgca tttggtacag   6300
cgcagtaacc ggcaaaatcg cgccgaagga tgtcgctgcc gactgggcaa tggagcgcct   6360
gccggcccag tatcagcccg tcatacttga agctagacag gcttatcttg gacaagaaga   6420
agatcgcttg gcctcgcgcg cagatcagtt ggaagaattt gtccactacg tgaaaggcga   6480
gatcaccaag gtagtgggca aagaacttgt tgaaggaaaa ttggagctag tagaaggtct   6540
taaagtcgcc atggctagta aaggagaaga acttttcact ggagttgtcc caattcttgt   6600
tgaattagat ggtgatgtta atgggcacaa attttctgtc agtggagagg gtgaaggtga   6660
tgcaacatac ggaaaactta cccttaaatt tatttgcact actggaaaac tacctgttcc   6720
ttggccaaca cttgtcacta ctttctctta tggtgttcaa tgcttttcaa gatacccaga   6780
tcatatgaag cggcacgact tcttcaagag cgccatgcct gagggatacg tgcaggagag   6840
gaccatctct ttcaaggacg acgggaacta caagacacgt gctgaagtca agtttgaggg   6900
agacaccctc gtcaacagga tcgagcttaa gggaatcgat ttcaaggagg acggaaacat   6960
cctcggccac aagttggaat acaactacaa ctcccacaac gtatacatca cggcagacaa   7020
acaaaagaat ggaatcaaag ctaacttcaa aattagacac aacattgaag atggaagcgt   7080
tcaactagca gaccattatc aacaaaatac tccaattggc gatggccctg tccttttacc   7140
agacaaccat tacctgtcca cacaatctgc cctttcgaaa gatcccaacg aaaagagaga   7200
tcacatggtc cttcttgagt ttgtaacagc tgctgggatt acacatggca tggatgaact   7260
atacaaataa gcttaaacag tagacattag cagataaatt agcaggaaat aaagaaggat   7320
aaggagaaag aactcaagta attatccttc gttctcttaa ttgaattgca attaaactcg   7380
gcccaatctt ttactaaaag gattgagccg aataccgctc caggcatcaa ataaaacgaa   7440
aggctcagtc gaaagactgg gcctttcgtt ttatctgttg tttgtcggtg aacgctctca   7500
caacagctcc ctggaacacc aggagaacac acttatctcg cgtcttgagg tgataccacg   7560
cctgacacgt gagggcagta cggttaattc ggtttagccg gacatcagcg ctcctcattg   7620
agcgctgggc ccttcacatg aagatcgcac tgaggattgg tcctagccag gcttctcagt   7680
actgatacag tacgcgtcgc ttctcgtatt gtttgagtct tggaattagt ttgtatcctt   7740
ccgccgctgc cctaagaatt ctaattgagc tcgaacagtc gaccgccgga tcctgctcga   7800
gtgcctctag a                                                        7811
```

<210> SEQ ID NO 63
<211> LENGTH: 6830
<212> TYPE: DNA
<213> ORGANISM: Artificial Sequence
<220> FEATURE:
<223> OTHER INFORMATION: An example of an episomal DNA vector

<400> SEQUENCE: 63
tgccagaaca tgctgagcca aatcttcttc atggaaaacc tgcttgattt agatcgggag 60
aatcgtacgg ttttatgaaa ccatgtgcta tggctcgaat ccgtattcaa tcctatttcc 120
gataggagca gttgacaatg gaatccaatt tttccattat tttcgtatcc gtaatagtgc 180
gaaacgaagg cccgtctcca agttgttcaa gaataaatag tggcgttgag tttcttgacc 240
ctttgtctta ggattagtca gttccatttc ttgatgggag cagggaaggg atataactca 300
gcggtagagt gtcaccttga cgtggtggaa gtcatcagtt cgagcctgat tatccctaaa 360
accaatgcga gtttttctat tttgacttac tcccccgccg tgatcgaatg aaaatggata 420
agaggctcgt gggattgacg tgaggggata ggtatgccta ttccgaatcc gctttgtcta 480
cgaacaagga agctataagt aatgcaacta tgaatctcat ggagagttcg atcctggctc 540
aggatgaacg ctggcggcat gcttaacaca tgcgagtcgg acgggaagtg gtgtttccag 600
tggcggacgg gtgagtaacg cgtaagaacc tgcccttggg aggggaacaa cagctggaaa 660
cggctgctaa taccccgtag gctgaggagc aaaaggagga atccgcccga ggaggggctc 720
gcgtctgatt agctagttgg tgaggcaata gcttaccaag gcgatgatca gtagctggtc 780
cgagaggatg atcagccaca ctgggactga gacacggccc agactcctac gggaggcagc 840
agtggggaat tttccgcaat gggcgaaagc ctgacggagc aatgccgcgt ggaggtagaa 900
ggcccacggg tcgtgaactt cttttcccgg agaagaagca atgacggtat ccggggaata 960
agcatcggct aactctgtgc cagcagccgc ggtaagacag aggattcaca tcgacaattc 1020
aataaggtat ccgacattaa caatgattta aattgtgttc attgtgtttt ttatggtaca 1080
taaccttcat agatttatag attattcagg gagagctaat gcttgttggg tattttggtc 1140
tgactcttcc ttttcaccca aaacgaggcc agctacatct gagtgaaact tggagatggt 1200
agtcttcttt cgtttctcga cggtgaagta agaccaagct catgagctta ttatcctagg 1260
tcggaacaag tcggtaggat ccccttttgg acgtccccat gccctttccg cgcggggtag 1320
catgtccccg cgccctttcc gcgctggggg gcatgggggc gaaaaaagga aggaggggga 1380
tggggtttct ctcgcttttg acatagcagc gggccccggt gggaggcccg cacgacgacg 1440
acgattagct cattggtagg atcccctttt ggacgtcccc atgccctttc cgcgcggggt 1500
agcatggggg cgaaaaaagg aagtaaaata aggaggcttt gacatagcag cgggccccgg 1560
tgggaggccc gcacgacacg acgattagat tagctcattg gtaggacgac gattagctca 1620
ttggtaggac gacgattagc tcattggtag gacgacgatt agctcgttgg tattggtagg 1680 atccccttt ggacgttgac ataggagcgg atgacatagg agcgggcccc agcgggagtc 1740
ccgcacgacg acgacacgac gacgacgatt agctcgttgg tattggtagg atccccttt 1800 ggacgttggg agcggatgac ataggagcgg gccccagcgg gagtcccgca cgacgacgac 1860
acgacgacga cgattagctc attggtagga cgacgattag ctcattggta ggattagctc 1920
agtgttagag ttagagcggg ccccagtggg aggcccgcac aagggagcgc acgcgcaagg 1980
tcgcaactac ccgagaatcg atgtggcgga atgggttacg tgagctatta tccggcgggc 2040
cctcaattta aatcgttaca gttgctcgta acggcaaccg gctcggtcct ttttccctag 2100
aacagtatct tatacttgct gctctcgtta cttcggcgat cctggtgcag tcggtccgta 2160
aatcggcgca cacttttacg tcgtaccaga caggctcgca taagccagcc ccgacacccg 2220
ccaacacccg ctgacgcgcc ctgacgggct tgtctgctcc cggcatccgc ttacagacaa 2280

-continued gctgtgacct ccgggagctg catgtgtcag aggttttcac cgtcatcacc gaaacgcgca 2340
cgaaagggcc tcgtgatacg cctattttta taggttaatg tcatgataat aatggtttct 2400
tagacgtcag gtggcacttt tcggggaaat gtgcgcggaa cccctatttg tttatttttc 2460
taaatacatt caaatatgta tccgctcatg agacaataac cctgataaat gcttcaataa 2520
tattgaaaaa ggaagagtat gagtattcaa catttccgtg tcgcccttat tccctttttt 2580
gcggcatttt gccttcctgt ttttgctcac ccagaaacgc tggtgaaagt aaaagatgct 2640
gaagatcagt tgggtgcacg agtgggttac atcgaactgg atctcaacag cggtaagatc 2700
cttgagagtt ttcgccccga agaacgtttt ccaatgatga gcacttttaa agttctgcta 2760
tgtggcgcgg tattatcccg tattgacgcc gggcaagagc aactcggtcg ccgcatacac 2820
tattctcaga atgacttggt tgagtactca ccagtcacag aaaagcatct tacggatggc 2880
atgacagtaa gagaattatg cagtgctgcc ataaccatga gtgataacac tgcggccaac 2940
ttacttctga caacgatcgg aggaccgaag gagctaaccg cttttttgca caacatgggg 3000
gatcatgtaa ctcgccttga tcgttgggaa ccggagctga atgaagccat accaaacgac 3060
gagcgtgaca ccacgatgcc tgtagcaatg gcaacaacgt tgcgcaaact attaactggc 3120
gaactactta ctctagcttc ccggcaacaa ttaatagact ggatggaggc ggataaagtt 3180
gcaggaccac ttctgcgctc ggcccttccg gctggctggt ttattgctga taaatctgga 3240
gccggtgagc gtggctcacg cggtatcatt gcagcactgg ggccagatgg taagccctcc 3300
cgtatcgtag ttatctacac gacggggagt caggcaacta tggatgaacg aaatagacag 3360
atcgctgaga taggtgcctc actgattaag cattggtaac tgtcagacca agtttactca 3420
tatatacttt agattgattt aaaacttcat ttttaattta aaaggatcta ggtgaagatc 3480
ctttttgata atctcatgac caaaatccct taacgtgagt tttcgttcca ctgagcgtca 3540
gaccccgtag aaaagatcaa aggatcttct tgagatcctt tttttctgcg cgtaatctgc 3600
tgcttgcaaa caaaaaaacc accgctacca gcggtggttt gtttgccgga tcaagagcta 3660
ccaactcttt ttccgaaggt aactggcttc agcagagcgc agataccaaa tactgttctt 3720
ctagtgtagc cgtagttagg ccaccacttc aagaactctg tagcaccgcc tacatacctc 3780
gctctgctaa tcctgttacc agtggctgct gccagtggcg ataagtcgtg tcttaccggg 3840
ttggactcaa gacgatagtt accggataag gcgcagcggt cgggctgaac ggggggttcg 3900
tgcacacagc ccagcttgga gcgaacgacc tacaccgaac tgagatacct acagcgtgag 3960
ctatgagaaa gcgccacgct tcccgaaggg agaaaggcgg acaggtatcc ggtaagcggc 4020
agggtcggaa caggagagcg cacgagggag cttccagggg gaaacgcctg gtatctttat 4080
agtcctgtcg ggtttcgcca cctctgactt gagcgtcgat ttttgtgatg ctcgtcaggg 4140
gggcggagcc tatggaaaaa cgccagcaac gcggcctttt tacggttcct ggccttttgc 4200
tggccttttg ctcacatgtt ctttcctgcg ttatcccctg attctgtgga taaccgtatt 4260
accgcctttg agtgagctga taccgctcgc cgcagccgaa cgaccgagcg cagcgagtca 4320
gtgagcgagg aagcggaaga acgcggacac ccagcgtaac aatctaatat tgtttctcaa 4380
atcgggctgt tatcgcatgg tgctcatgat gaggttactg accaaattcg ccacgcatcg 4440
gtgctggtag aatgttcact tcgaggtggg tagacggcgt cacgtgcaat gccttgtctt 4500
cccctatctg cggccccgac tgcctcgcga agacaaggga tcggacgtcg aacgtattct 4560
gtttgctacc ggcacgggag taggatcgtt gatatacacc atgcgcgtta actctgaccc 4620
ccttcctctt aaatgagaat ggataagagg ctcgtgggat tgacgtgagg gggcagggat 4680

```
ggctatattt ctgggagcga actccgggcg aattactaat aaaaagcctt ccattttcta   4740
ttttgatttg tagaaaacta gtgtgcttgg gagtccctga tgattaaata aaccaagatt   4800
ttaccaatgg gggctagcga agcggtgatc gccgaagtat cgactcaact atcagaggta   4860
gttggcgtca tcgagcgcca tctcgaaccg acgttgctgg ccgtacattt gtacggctcc   4920
gcagtggatg gcggcctgaa gccacacagt gatattgatt tgctggttac ggtgaccgta   4980
aggcttgatg aaacaacgcg gcgagctttg atcaacgacc ttttggaaac ttcggcttcc   5040
cctggagaga gcgagattct ccgcgctgta gaagtcacca ttgttgtgca cgacgacatc   5100
attccgtggc gttatccagc taagcgcgaa ctgcaatttg gagaatggca gcgcaatgac   5160
attcttgcag gtatcttcga gccagccacg atcgacattg atctggctat cttgctgaca   5220
aaagcaagag aacatagcgt tgccttggta ggtccagcgg cggaggaact ctttgatccg   5280
gttcctgaac aggatctatt tgaggcgcta aatgaaacct taacgctatg gaactcgccg   5340
cccgactggg ctggcgatga gcgaaatgta gtgcttacgt tgtcccgcat ttggtacagc   5400
gcagtaaccg gcaaaatcgc gccgaaggat gtcgctgccg actgggcaat ggagcgcctg   5460
ccggcccagt atcagcccgt catacttgaa gctagacagg cttatcttgg acaagaagaa   5520
gatcgcttgg cctcgcgcgc agatcagttg gaagaatttg tccactacgt gaaaggcgag   5580
atcaccaagg tagtgggcaa agaacttgtt gaaggaaaat tggagctagt agaaggtctt   5640
aaagtcgcca tggctagtaa aggagaagaa cttttcactg gagttgtccc aattcttgtt   5700
gaattagatg gtgatgttaa tgggcacaaa ttttctgtca gtggagaggg tgaaggtgat   5760
gcaacatacg gaaaacttac ccttaaattt atttgcacta ctggaaaact acctgttcct   5820
tggccaacac ttgtcactac tttctcttat ggtgttcaat gcttttcaag atacccagat   5880
catatgaagc ggcacgactt cttcaagagc gccatgcctg agggatacgt gcaggagagg   5940
accatctctt tcaaggacga cgggaactac aagacacgtg ctgaagtcaa gtttgaggga   6000
gacaccctcg tcaacaggat cgagcttaag ggaatcgatt tcaaggagga cggaaacatc   6060
ctcggccaca agttggaata caactacaac tcccacaacg tatacatcac ggcagacaaa   6120
caaaagaatg gaatcaaagc taacttcaaa attagacaca acattgaaga tggaagcgtt   6180
caactagcag accattatca acaaaatact ccaattggcg atggccctgt ccttttacca   6240
gacaaccatt acctgtccac acaatctgcc ctttcgaaag atcccaacga aaagagagat   6300
cacatggtcc ttcttgagtt tgtaacagct gctgggatta cacatggcat ggatgaacta   6360
tacaaataag cttaaacagt agacattagc agataaatta gcaggaaata aagaaggata   6420
aggagaaaga actcaagtaa ttatccttcg ttctcttaat tgaattgcaa ttaaactcgg   6480
cccaatcttt tactaaaagg attgagccga ataccgctac aacagctccc tggaacacca   6540
ggagaacaca cttatctcgc gtcttgaggt gataccacgc ctgacacgtg agggcagtac   6600
ggttaattcg gtttagccgg acatcagcgc tcctcattga gcgctgggcc cttcacatga   6660
agatcgcact gaggattggt cctagccagg cttctcagta ctgatacagt acgcgtcgct   6720
tctcgtattg tttgagtctt ggaattagtt tgtatccttc cgccgctgcc ctaagaattc   6780
taattgagct cgaacagtcg accgccggat cctgctcgag tgcctctaga              6830
```

<210> SEQ ID NO 64
<211> LENGTH: 6910
<212> TYPE: DNA
<213> ORGANISM: Artificial Sequence
<220> FEATURE:

-continued

<223> OTHER INFORMATION: An example of an episomal DNA vector

<400> SEQUENCE: 64
tgccagaaca tgctgagcca aatcttcttc atggaaaacc tgcttgattt agatcgggag 60
aatcgtacgg ttttatgaaa ccatgtgcta tggctcgaat ccgtattcaa tcctatttcc 120
gataggagca gttgacaatg gaatccaatt tttccattat tttcgtatcc gtaatagtgc 180
gaaacgaagg cccgtctcca agttgttcaa gaataaatag tggcgttgag tttcttgacc 240
ctttgtctta ggattagtca gttccatttc ttgatgggag cagggaaggg atataactca 300
gcggtagagt gtcaccttga cgtggtggaa gtcatcagtt cgagcctgat tatccctaaa 360
accaatgcga gtttttctat tttgacttac tcccccgccg tgatcgaatg aaaatggata 420
agaggctcgt gggattgacg tgaggggata ggtatgccta ttccgaatcc gctttgtcta 480
cgaacaagga agctataagt aatgcaacta tgaatctcat ggagagttcg atcctggctc 540
aggatgaacg ctggcggcat gcttaacaca tgcgagtcgg acgggaagtg gtgtttccag 600
tggcggacgg gtgagtaacg cgtaagaacc tgcccttggg aggggaacaa cagctggaaa 660
cggctgctaa taccccgtag gctgaggagc aaaaggagga atccgcccga ggaggggctc 720
gcgtctgatt agctagttgg tgaggcaata gcttaccaag gcgatgatca gtagctggtc 780
cgagaggatg atcagccaca ctgggactga gacacggccc agactcctac gggaggcagc 840
agtggggaat tttccgcaat gggcgaaagc ctgacggagc aatgccgcgt ggaggtagaa 900
ggcccacggg tcgtgaactt cttttcccgg agaagaagca atgacggtat ccggggaata 960
agcatcggct aactctgtgc cagcagccgc ggtaagacag aggattcaca tcgacaattc 1020
aataaggtat ccgacattaa caatgattta aattgtgttc attgtgtttt ttatggtaca 1080
taaccttcat agatttatag attattcagg gagagctaat gcttgttggg tattttggtc 1140
tgactcttcc ttttcaccca aaacgaggcc agctacatct gagtgaaact tggagatggt 1200
agtcttcttt cgtttctcga cggtgaagta agaccaagct catgagctta ttatcctagg 1260
tcggaacaag tcggtaggat ccccttttgg acgtccccat gccctttccg cgcggggtag 1320
catgtccccg cgccctttcc gcgctggggg gcatgggggc gaaaaaagga aggaggggga 1380
tggggtttct ctcgcttttg acatagcagc gggccccggt gggaggcccg cacgacgacg 1440
acgattagct cattggtagg atcccctttt ggacgtcccc atgccctttc cgcgcggggt 1500
agcatggggg cgaaaaaagg aagtaaaata aggaggcttt gacatagcag cgggccccgg 1560
tgggaggccc gcacgacacg acgattagat tagctcattg gtaggacgac gattagctca 1620
ttggtaggac gacgattagc tcattggtag gacgacgatt agctcgttgg tattggtagg 1680
atccccttttt ggacgttgac ataggagcgg atgacatagg agcgggcccc agcgggagtc 1740
ccgcacgacg acgacacgac gacgacgatt agctcgttgg tattggtagg atcccctttt 1800
ggacgttggg agcggatgac ataggagcgg gccccagcgg gagtcccgca cgacgacgac 1860
acgacgacga cgattagctc attggtagga cgacgattag ctcattggta ggattagctc 1920
agtgttagag ttagagcggg ccccagtggg aggcccgcac aagggagcgc acgcgcaagg 1980
tcgcaactac ccgagaatcg atgtggcgga atgggttacg tgagctatta tccggcgggc 2040
cctcaattta aatcgttaca gttgctcgta acggcaaccg gctcggtcct ttttccctag 2100
aacagtatct tatacttgct gctctcgtta cttcggcgat cctggtgcag tcggtccgta 2160
aatcggcgca cacttttacg tcgtaccaga caggctcgca taagccagcc ccgacacccg 2220
ccaacacccg ctgacgcgcc ctgacgggct tgtctgctcc cggcatccgc ttacagacaa 2280

-continued

```
gctgtgacct ccgggagctg catgtgtcag aggttttcac cgtcatcacc gaaacgcgca   2340
cgaaagggcc tcgtgatacg cctattttta taggttaatg tcatgataat aatggtttct   2400
tagacgtcag gtggcacttt tcggggaaat gtgcgcggaa cccctatttg tttatttttc   2460
taaatacatt caaatatgta tccgctcatg agacaataac cctgataaat gcttcaataa   2520
tattgaaaaa ggaagagtat gagtattcaa catttccgtg tcgcccttat tccctttttt   2580
gcggcatttt gccttcctgt ttttgctcac ccagaaacgc tggtgaaagt aaaagatgct   2640
gaagatcagt tgggtgcacg agtgggttac atcgaactgg atctcaacag cggtaagatc   2700
cttgagagtt ttcgccccga agaacgtttt ccaatgatga gcacttttaa agttctgcta   2760
tgtggcgcgg tattatcccg tattgacgcc gggcaagagc aactcggtcg ccgcatacac   2820
tattctcaga atgacttggt tgagtactca ccagtcacag aaaagcatct tacggatggc   2880
atgacagtaa gagaattatg cagtgctgcc ataaccatga gtgataacac tgcggccaac   2940
ttacttctga caacgatcgg aggaccgaag gagctaaccg cttttttgca caacatgggg   3000
gatcatgtaa ctcgccttga tcgttgggaa ccggagctga atgaagccat accaaacgac   3060
gagcgtgaca ccacgatgcc tgtagcaatg gcaacaacgt tgcgcaaact attaactggc   3120
gaactactta ctctagcttc ccggcaacaa ttaatagact ggatggaggc ggataaagtt   3180
gcaggaccac ttctgcgctc ggcccttccg gctggctggt ttattgctga taaatctgga   3240
gccggtgagc gtggctcacg cggtatcatt gcagcactgg ggccagatgg taagccctcc   3300
cgtatcgtag ttatctacac gacggggagt caggcaacta tggatgaacg aaatagacag   3360
atcgctgaga taggtgcctc actgattaag cattggtaac tgtcagacca agtttactca   3420
tatatacttt agattgattt aaaacttcat ttttaattta aaaggatcta ggtgaagatc   3480
ctttttgata atctcatgac caaaatccct taacgtgagt tttcgttcca ctgagcgtca   3540
gaccccgtag aaaagatcaa aggatcttct tgagatcctt tttttctgcg cgtaatctgc   3600
tgcttgcaaa caaaaaaacc accgctacca gcggtggttt gtttgccgga tcaagagcta   3660
ccaactcttt ttccgaaggt aactggcttc agcagagcgc agataccaaa tactgttctt   3720
ctagtgtagc cgtagttagg ccaccacttc aagaactctg tagcaccgcc tacatacctc   3780
gctctgctaa tcctgttacc agtggctgct gccagtggcg ataagtcgtg tcttaccggg   3840
ttggactcaa gacgatagtt accggataag gcgcagcggt cgggctgaac ggggggttcg   3900
tgcacacagc ccagcttgga gcgaacgacc tacaccgaac tgagatacct acagcgtgag   3960
ctatgagaaa gcgccacgct tcccgaaggg agaaaggcgg acaggtatcc ggtaagcggc   4020
agggtcggaa caggagagcg cacgagggag cttccagggg gaaacgcctg gtatctttat   4080
agtcctgtcg ggtttcgcca cctctgactt gagcgtcgat ttttgtgatg ctcgtcaggg   4140
gggcggagcc tatggaaaaa cgccagcaac gcggcctttt tacggttcct ggccttttgc   4200
tggccttttg ctcacatgtt ctttcctgcg ttatcccctg attctgtgga taaccgtatt   4260
accgcctttg agtgagctga taccgctcgc cgcagccgaa cgaccgagcg cagcgagtca   4320
gtgagcgagg aagcggaaga acgcggacac ccagcgtaac aatctaatat tgtttctcaa   4380
atcgggctgt tatcgcatgg tgctcatgat gaggttactg accaaattcg ccacgcatcg   4440
gtgctggtag aatgttcact tcgaggtggg tagacggcgt cacgtgcaat gccttgtctt   4500
cccctatctg cggccccgac tgcctcgcga agacaaggga tcggacgtcg aacgtattct   4560
gtttgctacc ggcacgggag taggatcgtt gatatacacc atgcgcgtta actctgaccc   4620
```

-continued

```
ccttcctctt aaatgagaat ggataagagg ctcgtgggat tgacgtgagg gggcagggat   4680
ggctatattt ctgggagcga actccgggcg aattactaat aaaaagcctt ccattttcta   4740
ttttgatttg tagaaaacta gtgtgcttgg gagtccctga tgattaaata aaccaagatt   4800
ttaccaatgg gggctagcga agcggtgatc gccgaagtat cgactcaact atcagaggta   4860
gttggcgtca tcgagcgcca tctcgaaccg acgttgctgg ccgtacattt gtacggctcc   4920
gcagtggatg gcggcctgaa gccacacagt gatattgatt tgctggttac ggtgaccgta   4980
aggcttgatg aaacaacgcg gcgagctttg atcaacgacc ttttggaaac ttcggcttcc   5040
cctggagaga gcgagattct ccgcgctgta gaagtcacca ttgttgtgca cgacgacatc   5100
attccgtggc gttatccagc taagcgcgaa ctgcaatttg gagaatggca gcgcaatgac   5160
attcttgcag gtatcttcga gccagccacg atcgacattg atctggctat cttgctgaca   5220
aaagcaagag aacatagcgt tgccttggta ggtccagcgg cggaggaact ctttgatccg   5280
gttcctgaac aggatctatt tgaggcgcta aatgaaacct taacgctatg gaactcgccg   5340
cccgactggg ctggcgatga gcgaaatgta gtgcttacgt tgtcccgcat ttggtacagc   5400
gcagtaaccg gcaaaatcgc gccgaaggat gtcgctgccg actgggcaat ggagcgcctg   5460
ccggcccagt atcagcccgt catacttgaa gctagacagg cttatcttgg acaagaagaa   5520
gatcgcttgg cctcgcgcgc agatcagttg gaagaatttg tccactacgt gaaaggcgag   5580
atcaccaagg tagtgggcaa agaacttgtt gaaggaaaat tggagctagt agaaggtctt   5640
aaagtcgcca tggctagtaa aggagaagaa cttttcactg gagttgtccc aattcttgtt   5700
gaattagatg gtgatgttaa tgggcacaaa ttttctgtca gtggagaggg tgaaggtgat   5760
gcaacatacg gaaaacttac ccttaaattt atttgcacta ctggaaaact acctgttcct   5820
tggccaacac ttgtcactac tttctcttat ggtgttcaat gcttttcaag atacccagat   5880
catatgaagc ggcacgactt cttcaagagc gccatgcctg agggatacgt gcaggagagg   5940
accatctctt tcaaggacga cgggaactac aagacacgtg ctgaagtcaa gtttgaggga   6000
gacaccctcg tcaacaggat cgagcttaag ggaatcgatt tcaaggagga cggaaacatc   6060
ctcggccaca agttggaata caactacaac tcccacaacg tatacatcac ggcagacaaa   6120
caaaagaatg gaatcaaagc taacttcaaa attagacaca acattgaaga tggaagcgtt   6180
caactagcag accattatca acaaaatact ccaattggcg atggccctgt ccttttacca   6240
gacaaccatt acctgtccac acaatctgcc ctttcgaaag atcccaacga aaagagagat   6300
cacatggtcc ttcttgagtt tgtaacagct gctgggatta cacatggcat ggatgaacta   6360
tacaaataag cttaaacagt agacattagc agataaatta gcaggaaata aagaaggata   6420
aggagaaaga actcaagtaa ttatccttcg ttctcttaat tgaattgcaa ttaaactcgg   6480
cccaatcttt tactaaaagg attgagccga ataccgctcc aggcatcaaa taaaacgaaa   6540
ggctcagtcg aaagactggg cctttcgttt tatctgttgt ttgtcggtga acgctctcac   6600
aacagctccc tggaacacca ggagaacaca cttatctcgc gtcttgaggt gataccacgc   6660
ctgacacgtg agggcagtac ggttaattcg gtttagccgg acatcagcgc tcctcattga   6720
gcgctgggcc cttcacatga agatcgcact gaggattggt cctagccagg cttctcagta   6780
ctgatacagt acgcgtcgct tctcgtattg tttgagtctt ggaattagtt tgtatccttc   6840
cgccgctgcc ctaagaattc taattgagct cgaacagtcg accgccggat cctgctcgag   6900
tgcctctaga                                                          6910
```

<210> SEQ ID NO 65
<211> LENGTH: 9664
<212> TYPE: DNA
<213> ORGANISM: Artificial Sequence
<220> FEATURE:
<223> OTHER INFORMATION: An example of an episomal DNA vector

<400> SEQUENCE: 65
tgccgagctc ggattctaac cttgtgtcag acccgcgggc caagggacag tctcaggtag 60
acagtttcta tggggcgtag gcctcccaaa aggtaacgga ggcgtgcaaa ggtttcctcg 120
ggccagacgg acattggtcc tcgagtgcaa aggcagaagg gagcttgact gcaagactca 180
cccgtcgagc agagacgaaa gtcggcctta gtgatccgac ggtgccgagt ggaagggccg 240
tcgctcaacg gataaaagtt actctaggga taacaggctg atcttcccca agagtccaca 300
tcgacgggaa ggtttggcac ctcgatgtcg gctcttcgcc acctggagct gtaggtggtt 360
ccaagggttg ggctgttcgc ccattaatgc ggtacgtgag ctgggttcag aacgtcgtga 420
gacagttcgg tccatatccg gtgtgggcgt tagagcattg agaggacctt tccctagtac 480
gagaggaccg ggaaggacgc acctctggtg taccagttat cgtgcctacg gtaaacgctg 540
ggtagccaag tgcggagagg ataactgctg aaagcatata agtagtaagc ccaccccaag 600
atgagtgctc tctcctccga cttccctaga gcctccggta gcacagccga gacagcgacg 660
ggttctccac ccatacgggg atggagcgac agaagcatgg aaataggata aggtagcggc 720
gagacgagcc gtttaaatag gtgtcaagtg gaagtgcagt gatgtatgca gctgaggcat 780
cctaacgaac gaacgatttg aaccttgttc ctacacgacc tgatcaaatc gatcaggcac 840
ttgccatcta tcttcattgt tcaactcttt gatgaaaaga tgaaaaaacc aaaaaaaagc 900
tctgcccttc catctcttgg atagatagag agggagggca gaggcctttg gtgtcccttc 960
cagtcaagaa ttggggcttc acaattacta gccaatattt ctctcatgcc tttcctcgtt 1020
catggttcga tattctggtg tcctaggcgt agaggaacca caccaatcca tcccgaattt 1080
ggtggttaaa ctctactgcg gtgacgatac tgtaggggag gtcctgcggc aaaatagctc 1140
gatgccagaa tgataaaaag cttaacacct cttatttgac tttttcacta ttttgaaata 1200
cgaaaaagat ccaaatccaa aatgcaaagg tcgtcttatt caaaacctca atcatcacat 1260
cccctctctc ccacttcaca cctcggaacg cactgttctt atagagagaa aggggctttc 1320
ccatcttctt aacccgaaat gaaatggctg aggagaggga ggttcctttt ggggggtacc 1380
cccgggaaga gatccagtgg agacggggtg ggcctgtagc tcagaggatt agagcacgtg 1440
gctacgaacc acggtgtcgg gggttcgaat ccctcctcgc ccacagcctt ccaaagggga 1500
agggccttta ctttcccct gagggtagga aaaccatgat cgggatagcg gacgtaaagc 1560
tattgaactt gggtatgctc tttccttttg tcgaagtgga atcgtagaac agaatgtgat 1620
acgatgagat aaaatgcaat agaaacaagg atagcgaacg ggttacctac tcctaagggt 1680
caaagcaagc cctttaattc aattctttat tcttacatta aagaatgaat caaatctccc 1740
caagtaggat tcgaacctac gaccagtcag ttaacagccg accgctctac cactgagcta 1800
ctgaggaaca agggggattc gacctcctag agttcaactc ccgctctcaa cccatgaaca 1860
atatgagtcc gaagcttctt tcgtaactcc cggaatttct tcgtagtggc tccgttccat 1920
gcctcatttc ataggtaagc ccagagtggc tctatttcat tctatttcac ttcctagcac 1980
ttcctatcat ttaatatcca tccctttggt cttattgaca taagagatgt catttatagt 2040
ctatctcttt ctatatatgg aaagtcaaga aattctcatc gaaacatcga gaaattgtgc 2100

-continued

```
atatagaaaa ctctaaagaa agaaaaaaag cacacccatg ccatgatttt caaatctttt   2160
ctacttagta gtctaagttt ctcgatgagg ataattaatt cggtcgttgc ggtcggactc   2220
tattatgggt ttctgaccac attctccatg ggtccctctt agatctttcc tatatgagga   2280
agtatccttc cccgcagtca agaccaaggt tagtattctc tgctaggaag tttacttagg   2340
ttactctagc atgtgcctgg ataaccctct aggcaaaggt ggattgactt tgtactgtcc   2400
tcagatcgac gttggatgaa ctgtcgcgcc acgaggggct gtggagcgca ttgcgacaca   2460
ttggtgcgct gctaacccat cctttccagt acggctactg atgtccacgc tcccagcctg   2520
ctacgctccg cccgagatct aagagggacc catggagaat gtggtcagaa acccataata   2580
gagtccgacc gcaacgaccg aattaattat cctcatcgag aaacttagac tactaagtag   2640
aaaagatttg aaaatcatgg catgggtgtg ctttttttct ttctttagag ttttctatat   2700
gcacaatttc tcgatgtttc gatgagaatt tcttgacttt ccatatatag aaagagatag   2760
actataaatg acatctctta tgtcaataag accaaaggga tggatattaa atgataggaa   2820
gtgctaggaa gtgaaataga atgaaataga gccactctgg gcttacctat gaaatgaggc   2880
atggaacgga gccactacga agaaattccg ggagttacga aagaagcttc ggactcatat   2940
tgttcatggg ttgagagcgg gagttgaact ctaggaggtc gaatccccct tgttcctcag   3000
tagctcagtg gtagagcggt cggctgttaa ctgactggtc gtaggttcga atcctacttg   3060
gggagatttg attcattctt taatgtaaga ataaagaatt gaattaaagg gcttgctttg   3120
acccttagga gtaggtaacc cgttcgctat ccttgtttct attgcatttt atctcatcgt   3180
atcacattct gttctacgat tccacttcga caaaaggaaa gagcataccc aagttcaata   3240
gctttacgtc cgctatcccg atcatggttt tcctaccctc agggggaaag taaaggccct   3300
tccccttttgg aaggctgtgg gcgaggaggg attcgaaccc ccgacaccgt ggttcgtagc   3360
cacgtgctct aatcctctga gctacaggcc caccccgtct ccactggatc tcttcccggg   3420
ggtaccccc aaaaggaacc tccctctcct cagccatttc atttcgggtt aagaagatgg   3480
gaaagcccct ttctctctat aagaacagtg cgttccgagg tgtgaagtgg gagagagggg   3540
atgtgatgat tgaggttttg aataagacga cctttgcatt ttggatttgg atctttttcg   3600
tatttcaaaa tagtgaaaaa gtcaaataag aggtgttaag ctttttatca ttctggcatc   3660
gagctatttt gccgcaggac ctcccctaca gtatcgtcac cgcagtagag tttaaccacc   3720
aaattcggga tggattggtg tggttcctct acgcctagga caccagaata tcgaaccatg   3780
aacgaggaaa ggcatgagag aaatattggc tagtaattgt gaagccccaa ttcttgactg   3840
gaagggacac caaaggcctc tgccctccct ctctatctat ccaagagatg gaagggcaga   3900
gctttttttt ggtttttca tcttttcatc aaagagttga acaatgaaga tagatggcaa   3960
gtgcctgatc gatttgatca ggtcgtgtag gaacaaggtt caaatcgttc gttcgttagg   4020
atgcctcagc tgcatacatc actgcacttc cacttgacac ctatttaaac ggctcgtctc   4080
gccgctacct tatcctattt ccatgcttct gtcgctccat ccccgtatgg gtggagaacc   4140
cgtcgctgtc tcggctgtgc taccggaggc tctagggaag tcggaggaga gagcactcat   4200
cttggggtgg gcttactact tatatgcttt cagcagttat cctctccgca cttggctacc   4260
cagcgtttac cgtaggcacg ataactggta caccagaggt gcgtccttcc cggtcctctc   4320
gtactaggga aaggtcctct caatgctcta acgcccacac cggatatgga ccgaactgtc   4380
tcacgacgtt ctgaacccag ctcacgtacc gcattaatgg gcgaacagcc caacccttgg   4440
aaccacctac agctccaggt ggcgaagagc cgacatcgag gtgccaaacc ttcccgtcga   4500
```

```
tgtggactct tggggaagat cagcctgtta tccctagagt aacttttatc cgttgagcga   4560
cggcccttcc actcggcacc gtcggatcac taaggccgac tttcgtctct gctcgacggg   4620
tgagtcttgc agtcaagctc ccttctgcct ttgcactcga ggaccaatgt ccgtctggcc   4680
cgaggaaacc tttgcacgcc tccgttacct tttgggaggc ctacgcccca tagaaactgt   4740
ctacctgaga ctgtcccttg gcccgcgggt ctgacacaag gttagaatcc gagctcggga   4800
gcgcacgcgc aaggtcgcaa ctacccgaga atcgatgtgg cggaatgggt tacgtgagct   4860
attatccggc gggccctcaa tttaaatcgt tacagttgct cgtaacggca accggctcgg   4920
tcctttttcc ctagaacagt atcttatact tgctgctctc gttacttcgg cgatcctggt   4980
gcagtcggtc cgtaaatcgg cgcacacttt tacgtcgtac cagacaggct cgcataagcc   5040
agccccgaca cccgccaaca cccgctgacg cgccctgacg ggcttgtctg ctcccggcat   5100
ccgcttacag acaagctgtg acctccggga gctgcatgtg tcagaggttt tcaccgtcat   5160
caccgaaacg cgcacgaaag ggcctcgtga tacgcctatt tttataggtt aatgtcatga   5220
taataatggt ttcttagacg tcaggtggca cttttcgggg aaatgtgcgc ggaaccccta   5280
tttgtttatt tttctaaata cattcaaata tgtatccgct catgagacaa taaccctgat   5340
aaatgcttca ataatattga aaaaggaaga gtatgagtat tcaacatttc cgtgtcgccc   5400
ttattccctt ttttgcggca ttttgccttc ctgtttttgc tcacccagaa acgctggtga   5460
aagtaaaaga tgctgaagat cagttgggtg cacgagtggg ttacatcgaa ctggatctca   5520
acagcggtaa gatccttgag agttttcgcc ccgaagaacg ttttccaatg atgagcactt   5580
ttaaagttct gctatgtggc gcggtattat cccgtattga cgccgggcaa gagcaactcg   5640
gtcgccgcat acactattct cagaatgact tggttgagta ctcaccagtc acagaaaagc   5700
atcttacgga tggcatgaca gtaagagaat tatgcagtgc tgccataacc atgagtgata   5760
acactgcggc caacttactt ctgacaacga tcggaggacc gaaggagcta accgcttttt   5820
tgcacaacat gggggatcat gtaactcgcc ttgatcgttg ggaaccggag ctgaatgaag   5880
ccataccaaa cgacgagcgt gacaccacga tgcctgtagc aatggcaaca acgttgcgca   5940
aactattaac tggcgaacta cttactctag cttcccggca acaattaata gactggatgg   6000
aggcggataa agttgcagga ccacttctgc gctcggccct tccggctggc tggtttattg   6060
ctgataaatc tggagccggt gagcgtggct cacgcggtat cattgcagca ctggggccag   6120
atggtaagcc ctcccgtatc gtagttatct acacgacggg gagtcaggca actatggatg   6180
aacgaaatag acagatcgct gagataggtg cctcactgat taagcattgg taactgtcag   6240
accaagttta ctcatatata ctttagattg atttaaaact tcatttttaa tttaaaagga   6300
tctaggtgaa gatccttttt gataatctca tgaccaaaat cccttaacgt gagttttcgt   6360
tccactgagc gtcagacccc gtagaaaaga tcaaaggatc ttcttgagat cctttttttc   6420
tgcgcgtaat ctgctgcttg caaacaaaaa aaccaccgct accagcggtg gtttgtttgc   6480
cggatcaaga gctaccaact ctttttccga aggtaactgg cttcagcaga gcgcagatac   6540
caaatactgt tcttctagtg tagccgtagt taggccacca cttcaagaac tctgtagcac   6600
cgcctacata cctcgctctg ctaatcctgt taccagtggc tgctgccagt ggcgataagt   6660
cgtgtcttac cgggttggac tcaagacgat agttaccgga taaggcgcag cggtcgggct   6720
gaacgggggg ttcgtgcaca cagcccagct tggagcgaac gacctacacc gaactgagat   6780
acctacagcg tgagctatga gaaagcgcca cgcttcccga agggagaaag gcggacaggt   6840
```

atccggtaag cggcagggtc ggaacaggag agcgcacgag ggagcttcca gggggaaacg 6900
cctggtatct ttatagtcct gtcgggtttc gccacctctg acttgagcgt cgatttttgt 6960
gatgctcgtc aggggggcgg agcctatgga aaaacgccag caacgcggcc tttttacggt 7020
tcctggcctt ttgctggcct tttgctcaca tgttctttcc tgcgttatcc cctgattctg 7080
tggataaccg tattaccgcc tttgagtgag ctgataccgc tcgccgcagc cgaacgaccg 7140
agcgcagcga gtcagtgagc gaggaagcgg aagaacgcgg acacccagcg taacaatcta 7200
atattgtttc tcaaatcggg ctgttatcgc atggtgctca tgatgaggtt actgaccaaa 7260
ttcgccacgc atcggtgctg gtagaatgtt cacttcgagg tgggtagacg gcgtcacgtg 7320
caatgccttg tcttccccta tctgcggccc cgactgcctc gcgaagacaa gggatcggac 7380
gtcgaacgta ttctgtttgc taccggcacg ggagtaggat cgttgatata caccatgcgc 7440
gttaactctg accccttcc tcttaaatga gaatggataa gaggctcgtg ggattgacgt 7500
gagggggcag ggatggctat atttctggga gcgaactccg ggcgaattac taataaaaag 7560
ccttccattt tctattttga tttgtagaaa actagtgtgc ttgggagtcc ctgatgatta 7620
aataaaccaa gattttacca atgggggcta gcgaagcggt gatcgccgaa gtatcgactc 7680
aactatcaga ggtagttggc gtcatcgagc gccatctcga accgacgttg ctggccgtac 7740
atttgtacgg ctccgcagtg gatggcggcc tgaagccaca cagtgatatt gatttgctgg 7800
ttacggtgac cgtaaggctt gatgaaacaa cgcggcgagc tttgatcaac gaccttttgg 7860
aaacttcggc ttcccctgga gagagcgaga ttctccgcgc tgtagaagtc accattgttg 7920
tgcacgacga catcattccg tggcgttatc cagctaagcg cgaactgcaa tttggagaat 7980
ggcagcgcaa tgacattctt gcaggtatct tcgagccagc cacgatcgac attgatctgg 8040
ctatcttgct gacaaaagca agagaacata gcgttgcctt ggtaggtcca gcggcggagg 8100
aactctttga tccggttcct gaacaggatc tatttgaggc gctaaatgaa accttaacgc 8160
tatggaactc gccgcccgac tgggctggcg atgagcgaaa tgtagtgctt acgttgtccc 8220
gcatttggta cagcgcagta accggcaaaa tcgcgccgaa ggatgtcgct gccgactggg 8280
caatggagcg cctgccggcc cagtatcagc ccgtcatact tgaagctaga caggcttatc 8340
ttggacaaga agaagatcgc ttggcctcgc gcgcagatca gttggaagaa tttgtccact 8400
acgtgaaagg cgagatcacc aaggtagtgg gcaaagaact tgttgaagga aaattggagc 8460
tagtagaagg tcttaaagtc gccatggcta gtaaaggaga agaacttttc actggagttg 8520
tcccaattct tgttgaatta gatggtgatg ttaatgggca caaattttct gtcagtggag 8580
agggtgaagg tgatgcaaca tacggaaaac ttacccttaa atttatttgc actactggaa 8640
aactacctgt tccttggcca acacttgtca ctactttctc ttatggtgtt caatgctttt 8700
caagataccc agatcatatg aagcggcacg acttcttcaa gagcgccatg cctgagggat 8760
acgtgcagga gaggaccatc tctttcaagg acgacgggaa ctacaagaca cgtgctgaag 8820
tcaagtttga gggagacacc ctcgtcaaca ggatcgagct taagggaatc gatttcaagg 8880
aggacggaaa catcctcggc cacaagttgg aatacaacta caactcccac aacgtataca 8940
tcacggcaga caaacaaaag aatggaatca aagctaactt caaaattaga cacaacattg 9000
aagatggaag cgttcaacta gcagaccatt atcaacaaaa tactccaatt ggcgatggcc 9060
ctgtcctttt accagacaac cattacctgt ccacacaatc tgccctttcg aaagatccca 9120
acgaaaagag agatcacatg gtccttcttg agtttgtaac agctgctggg attacacatg 9180
gcatggatga actatacaaa taagcttaaa cagtagacat tagcagataa attagcagga 9240
aataaagaag gataaggaga aagaactcaa gtaattatcc ttcgttctct taattgaatt 9300
gcaattaaac tcggcccaat cttttactaa aaggattgag ccgaataccg ctacaacagc 9360
tccctggaac accaggagaa cacacttatc tcgcgtcttg aggtgatacc acgcctgaca 9420
cgtgagggca gtacggttaa ttcggtttag ccggacatca gcgctcctca ttgagcgctg 9480
ggcccttcac atgaagatcg cactgaggat tggtcctagc caggcttctc agtactgata 9540
cagtacgcgt cgcttctcgt attgtttgag tcttggaatt agtttgtatc cttccgccgc 9600
tgccctaaga attctaattg agctcgaaca gtcgaccgcc ggatcctgct cgagtgcctc 9660
taga 9664

<210> SEQ ID NO 66
<211> LENGTH: 9744
<212> TYPE: DNA
<213> ORGANISM: Artificial Sequence
<220> FEATURE:
<223> OTHER INFORMATION: An example of an episomal DNA vector

<400> SEQUENCE: 66
tgccgagctc ggattctaac cttgtgtcag acccgcgggc caagggacag tctcaggtag 60
acagtttcta tggggcgtag gcctcccaaa aggtaacgga ggcgtgcaaa ggtttcctcg 120
ggccagacgg acattggtcc tcgagtgcaa aggcagaagg gagcttgact gcaagactca 180
cccgtcgagc agagacgaaa gtcggcctta gtgatccgac ggtgccgagt ggaagggccg 240
tcgctcaacg gataaaagtt actctaggga taacaggctg atcttcccca agagtccaca 300
tcgacgggaa ggtttggcac ctcgatgtcg gctcttcgcc acctggagct gtaggtggtt 360
ccaagggttg ggctgttcgc ccattaatgc ggtacgtgag ctgggttcag aacgtcgtga 420
gacagttcgg tccatatccg gtgtgggcgt tagagcattg agaggacctt tccctagtac 480
gagaggaccg ggaaggacgc acctctggtg taccagttat cgtgcctacg gtaaacgctg 540
ggtagccaag tgcggagagg ataactgctg aaagcatata agtagtaagc ccaccccaag 600
atgagtgctc tctcctccga cttccctaga gcctccggta gcacagccga gacagcgacg 660
ggttctccac ccatacgggg atggagcgac agaagcatgg aaataggata aggtagcggc 720
gagacgagcc gtttaaatag gtgtcaagtg gaagtgcagt gatgtatgca gctgaggcat 780
cctaacgaac gaacgatttg aaccttgttc ctacacgacc tgatcaaatc gatcaggcac 840
ttgccatcta tcttcattgt tcaactcttt gatgaaaaga tgaaaaaacc aaaaaaaagc 900
tctgcccttc catctcttgg atagatagag agggagggca gaggcctttg gtgtcccttc 960
cagtcaagaa ttggggcttc acaattacta gccaatattt ctctcatgcc tttcctcgtt 1020
catggttcga tattctggtg tcctaggcgt agaggaacca caccaatcca tcccgaattt 1080
ggtggttaaa ctctactgcg gtgacgatac tgtaggggag gtcctgcggc aaaatagctc 1140
gatgccagaa tgataaaaag cttaacacct cttatttgac tttttcacta ttttgaaata 1200 cgaaaaaagat ccaaatccaa aatgcaaagg tcgtcttatt caaaacctca atcatcacat 1260
cccctctctc ccacttcaca cctcggaacg cactgttctt atagagagaa aggggctttc 1320
ccatcttctt aacccgaaat gaaatggctg aggagaggga ggttcctttt ggggggtacc 1380
cccgggaaga gatccagtgg agacggggtg ggcctgtagc tcagaggatt agagcacgtg 1440
gctacgaacc acggtgtcgg gggttcgaat ccctcctcgc ccacagcctt ccaaagggga 1500
agggccttta ctttccccct gagggtagga aaaccatgat cgggatagcg gacgtaaagc 1560

-continued

```
tattgaactt gggtatgctc tttccttttg tcgaagtgga atcgtagaac agaatgtgat   1620
acgatgagat aaaatgcaat agaaacaagg atagcgaacg ggttacctac tcctaagggt   1680
caaagcaagc cctttaattc aattctttat tcttacatta aagaatgaat caaatctccc   1740
caagtaggat tcgaacctac gaccagtcag ttaacagccg accgctctac cactgagcta   1800
ctgaggaaca agggggattc gacctcctag agttcaactc ccgctctcaa cccatgaaca   1860
atatgagtcc gaagcttctt tcgtaactcc cggaatttct tcgtagtggc tccgttccat   1920
gcctcatttc ataggtaagc ccagagtggc tctatttcat tctatttcac ttcctagcac   1980
ttcctatcat ttaatatcca tccctttggt cttattgaca taagagatgt catttatagt   2040
ctatctcttt ctatatatgg aaagtcaaga aattctcatc gaaacatcga gaaattgtgc   2100
atatagaaaa ctctaaagaa agaaaaaaag cacacccatg ccatgatttt caaatctttt   2160
ctacttagta gtctaagttt ctcgatgagg ataattaatt cggtcgttgc ggtcggactc   2220
tattatgggt ttctgaccac attctccatg ggtccctctt agatctttcc tatatgagga   2280
agtatccttc cccgcagtca agaccaaggt tagtattctc tgctaggaag tttacttagg   2340
ttactctagc atgtgcctgg ataaccctct aggcaaaggt ggattgactt tgtactgtcc   2400
tcagatcgac gttggatgaa ctgtcgcgcc acgaggggct gtggagcgca ttgcgacaca   2460
ttggtgcgct gctaacccat cctttccagt acggctactg atgtccacgc tcccagcctg   2520
ctacgctccg cccgagatct aagagggacc catggagaat gtggtcagaa acccataata   2580
gagtccgacc gcaacgaccg aattaattat cctcatcgag aaacttagac tactaagtag   2640
aaaagatttg aaaatcatgg catgggtgtg cttttttttct ttctttagag ttttctatat   2700
gcacaatttc tcgatgtttc gatgagaatt tcttgacttt ccatatatag aaagagatag   2760
actataaatg acatctctta tgtcaataag accaaaggga tggatattaa atgataggaa   2820
gtgctaggaa gtgaaataga atgaaataga gccactctgg gcttacctat gaaatgaggc   2880
atggaacgga gccactacga agaaattccg ggagttacga aagaagcttc ggactcatat   2940
tgttcatggg ttgagagcgg gagttgaact ctaggaggtc gaatccccct tgttcctcag   3000
tagctcagtg gtagagcggt cggctgttaa ctgactggtc gtaggttcga atcctacttg   3060
gggagatttg attcattctt taatgtaaga ataaagaatt gaattaaagg gcttgctttg   3120
acccttagga gtaggtaacc cgttcgctat ccttgtttct attgcatttt atctcatcgt   3180
atcacattct gttctacgat tccacttcga caaaaggaaa gagcataccc aagttcaata   3240
gctttacgtc cgctatcccg atcatggttt tcctaccctc agggggaaag taaaggccct   3300
tcccctttgg aaggctgtgg gcgaggaggg attcgaaccc ccgacaccgt ggttcgtagc   3360
cacgtgctct aatcctctga gctacaggcc caccccgtct ccactggatc tcttcccggg   3420
ggtacccccc aaaaggaacc tccctctcct cagccatttc atttcgggtt aagaagatgg   3480
gaaagcccct ttctctctat aagaacagtg cgttccgagg tgtgaagtgg gagagagggg   3540
atgtgatgat tgaggttttg aataagacga cctttgcatt ttggatttgg atctttttcg   3600
tatttcaaaa tagtgaaaaa gtcaaataag aggtgttaag ctttttatca ttctggcatc   3660
gagctatttt gccgcaggac ctcccctaca gtatcgtcac cgcagtagag tttaaccacc   3720
aaattcggga tggattggtg tggttcctct acgcctagga caccagaata tcgaaccatg   3780
aacgaggaaa ggcatgagag aaatattggc tagtaattgt gaagccccaa ttcttgactg   3840
gaagggacac caaaggcctc tgccctccct ctctatctat ccaagagatg gaagggcaga   3900
gctttttttt ggtttttca tcttttcatc aaagagttga acaatgaaga tagatggcaa   3960
```

gtgcctgatc gatttgatca ggtcgtgtag gaacaaggtt caaatcgttc gttcgttagg 4020
atgcctcagc tgcatacatc actgcacttc cacttgacac ctatttaaac ggctcgtctc 4080
gccgctacct tatcctattt ccatgcttct gtcgctccat ccccgtatgg gtggagaacc 4140
cgtcgctgtc tcggctgtgc taccggaggc tctagggaag tcggaggaga gagcactcat 4200
cttggggtgg gcttactact tatatgcttt cagcagttat cctctccgca cttggctacc 4260
cagcgtttac cgtaggcacg ataactggta caccagaggt gcgtccttcc cggtcctctc 4320
gtactaggga aaggtcctct caatgctcta acgcccacac cggatatgga ccgaactgtc 4380
tcacgacgtt ctgaacccag ctcacgtacc gcattaatgg gcgaacagcc caacccttgg 4440
aaccacctac agctccaggt ggcgaagagc cgacatcgag gtgccaaacc ttcccgtcga 4500
tgtggactct tggggaagat cagcctgtta tccctagagt aacttttatc cgttgagcga 4560
cggcccttcc actcggcacc gtcggatcac taaggccgac tttcgtctct gctcgacggg 4620
tgagtcttgc agtcaagctc ccttctgcct ttgcactcga ggaccaatgt ccgtctggcc 4680
cgaggaaacc tttgcacgcc tccgttacct tttgggaggc ctacgcccca tagaaactgt 4740
ctacctgaga ctgtcccttg gcccgcgggt ctgacacaag gttagaatcc gagctcggga 4800
gcgcacgcgc aaggtcgcaa ctacccgaga atcgatgtgg cggaatgggt tacgtgagct 4860
attatccggc gggccctcaa tttaaatcgt tacagttgct cgtaacggca accggctcgg 4920
tcctttttcc ctagaacagt atcttatact tgctgctctc gttacttcgg cgatcctggt 4980
gcagtcggtc cgtaaatcgg cgcacacttt tacgtcgtac cagacaggct cgcataagcc 5040
agccccgaca cccgccaaca cccgctgacg cgccctgacg ggcttgtctg ctcccggcat 5100
ccgcttacag acaagctgtg acctccggga gctgcatgtg tcagaggttt tcaccgtcat 5160
caccgaaacg cgcacgaaag ggcctcgtga tacgcctatt tttataggtt aatgtcatga 5220
taataatggt ttcttagacg tcaggtggca cttttcgggg aaatgtgcgc ggaaccccta 5280
tttgtttatt tttctaaata cattcaaata tgtatccgct catgagacaa taaccctgat 5340
aaatgcttca ataatattga aaaaggaaga gtatgagtat tcaacatttc cgtgtcgccc 5400
ttattccctt ttttgcggca ttttgccttc ctgtttttgc tcacccagaa acgctggtga 5460
aagtaaaaga tgctgaagat cagttgggtg cacgagtggg ttacatcgaa ctggatctca 5520
acagcggtaa gatccttgag agttttcgcc ccgaagaacg ttttccaatg atgagcactt 5580
ttaaagttct gctatgtggc gcggtattat cccgtattga cgccgggcaa gagcaactcg 5640
gtcgccgcat acactattct cagaatgact tggttgagta ctcaccagtc acagaaaagc 5700
atcttacgga tggcatgaca gtaagagaat tatgcagtgc tgccataacc atgagtgata 5760
acactgcggc caacttactt ctgacaacga tcggaggacc gaaggagcta accgcttttt 5820
tgcacaacat gggggatcat gtaactcgcc ttgatcgttg ggaaccggag ctgaatgaag 5880
ccataccaaa cgacgagcgt gacaccacga tgcctgtagc aatggcaaca acgttgcgca 5940
aactattaac tggcgaacta cttactctag cttcccggca acaattaata gactggatgg 6000
aggcggataa agttgcagga ccacttctgc gctcggccct tccggctggc tggtttattg 6060
ctgataaatc tggagccggt gagcgtggct cacgcggtat cattgcagca ctggggccag 6120
atggtaagcc ctcccgtatc gtagttatct acacgacggg gagtcaggca actatggatg 6180
aacgaaatag acagatcgct gagataggtg cctcactgat taagcattgg taactgtcag 6240
accaagttta ctcatatata ctttagattg atttaaaact tcatttttaa tttaaaagga 6300

```
tctaggtgaa gatccttttt gataatctca tgaccaaaat cccttaacgt gagttttcgt   6360
tccactgagc gtcagacccc gtagaaaaga tcaaaggatc ttcttgagat cctttttttc   6420
tgcgcgtaat ctgctgcttg caaacaaaaa aaccaccgct accagcggtg gtttgtttgc   6480
cggatcaaga gctaccaact ctttttccga aggtaactgg cttcagcaga gcgcagatac   6540
caaatactgt tcttctagtg tagccgtagt taggccacca cttcaagaac tctgtagcac   6600
cgcctacata cctcgctctg ctaatcctgt taccagtggc tgctgccagt ggcgataagt   6660
cgtgtcttac cgggttggac tcaagacgat agttaccgga taaggcgcag cggtcgggct   6720
gaacgggggg ttcgtgcaca cagcccagct tggagcgaac gacctacacc gaactgagat   6780
acctacagcg tgagctatga gaaagcgcca cgcttcccga agggagaaag gcggacaggt   6840
atccggtaag cggcagggtc ggaacaggag agcgcacgag ggagcttcca gggggaaacg   6900
cctggtatct ttatagtcct gtcgggtttc gccacctctg acttgagcgt cgatttttgt   6960
gatgctcgtc aggggggcgg agcctatgga aaaacgccag caacgcggcc tttttacggt   7020
tcctggcctt ttgctggcct tttgctcaca tgttctttcc tgcgttatcc cctgattctg   7080
tggataaccg tattaccgcc tttgagtgag ctgataccgc tcgccgcagc cgaacgaccg   7140
agcgcagcga gtcagtgagc gaggaagcgg aagaacgcgg acacccagcg taacaatcta   7200
atattgtttc tcaaatcggg ctgttatcgc atggtgctca tgatgaggtt actgaccaaa   7260
ttcgccacgc atcggtgctg gtagaatgtt cacttcgagg tgggtagacg gcgtcacgtg   7320
caatgccttg tcttccccta tctgcggccc cgactgcctc gcgaagacaa gggatcggac   7380
gtcgaacgta ttctgtttgc taccggcacg ggagtaggat cgttgatata caccatgcgc   7440
gttaactctg accccttcc tcttaaatga gaatggataa gaggctcgtg ggattgacgt   7500
gagggggcag ggatggctat atttctggga gcgaactccg ggcgaattac taataaaaag   7560
ccttccattt tctattttga tttgtagaaa actagtgtgc ttgggagtcc ctgatgatta   7620
aataaaccaa gattttacca atgggggcta gcgaagcggt gatcgccgaa gtatcgactc   7680
aactatcaga ggtagttggc gtcatcgagc gccatctcga accgacgttg ctggccgtac   7740
atttgtacgg ctccgcagtg gatggcggcc tgaagccaca cagtgatatt gatttgctgg   7800
ttacggtgac cgtaaggctt gatgaaacaa cgcggcgagc tttgatcaac gaccttttgg   7860
aaacttcggc ttcccctgga gagagcgaga ttctccgcgc tgtagaagtc accattgttg   7920
tgcacgacga catcattccg tggcgttatc cagctaagcg cgaactgcaa tttggagaat   7980
ggcagcgcaa tgacattctt gcaggtatct tcgagccagc cacgatcgac attgatctgg   8040
ctatcttgct gacaaaagca agagaacata gcgttgcctt ggtaggtcca gcggcggagg   8100
aactctttga tccggttcct gaacaggatc tatttgaggc gctaaatgaa accttaacgc   8160
tatggaactc gccgcccgac tgggctggcg atgagcgaaa tgtagtgctt acgttgtccc   8220
gcatttggta cagcgcagta accggcaaaa tcgcgccgaa ggatgtcgct gccgactggg   8280
caatggagcg cctgccggcc cagtatcagc ccgtcatact tgaagctaga caggcttatc   8340
ttggacaaga agaagatcgc ttggcctcgc gcgcagatca gttggaagaa tttgtccact   8400
acgtgaaagg cgagatcacc aaggtagtgg gcaaagaact tgttgaagga aaattggagc   8460
tagtagaagg tcttaaagtc gccatggcta gtaaaggaga agaacttttc actggagttg   8520
tcccaattct tgttgaatta gatggtgatg ttaatgggca caaattttct gtcagtggag   8580
agggtgaagg tgatgcaaca tacggaaaac ttacccttaa atttatttgc actactggaa   8640
aactacctgt tccttggcca acacttgtca ctactttctc ttatggtgtt caatgctttt   8700
```

caagataccc agatcatatg aagcggcacg acttcttcaa gagcgccatg cctgagggat 8760
acgtgcagga gaggaccatc tctttcaagg acgacgggaa ctacaagaca cgtgctgaag 8820
tcaagtttga gggagacacc ctcgtcaaca ggatcgagct taagggaatc gatttcaagg 8880
aggacggaaa catcctcggc cacaagttgg aatacaacta caactcccac aacgtataca 8940
tcacggcaga caaacaaaag aatggaatca aagctaactt caaaattaga cacaacattg 9000
aagatggaag cgttcaacta gcagaccatt atcaacaaaa tactccaatt ggcgatggcc 9060
ctgtcctttt accagacaac cattacctgt ccacacaatc tgccctttcg aaagatccca 9120
acgaaaagag agatcacatg gtccttcttg agtttgtaac agctgctggg attacacatg 9180
gcatggatga actatacaaa taagcttaaa cagtagacat tagcagataa attagcagga 9240
aataaagaag gataaggaga aagaactcaa gtaattatcc ttcgttctct taattgaatt 9300
gcaattaaac tcggcccaat cttttactaa aaggattgag ccgaataccg ctccaggcat 9360
caaataaaac gaaaggctca gtcgaaagac tgggcctttc gttttatctg ttgtttgtcg 9420
gtgaacgctc tcacaacagc tccctggaac accaggagaa cacacttatc tcgcgtcttg 9480
aggtgatacc acgcctgaca cgtgagggca gtacggttaa ttcggtttag ccggacatca 9540
gcgctcctca ttgagcgctg ggcccttcac atgaagatcg cactgaggat tggtcctagc 9600
caggcttctc agtactgata cagtacgcgt cgcttctcgt attgtttgag tcttggaatt 9660
agtttgtatc cttccgccgc tgccctaaga attctaattg agctcgaaca gtcgaccgcc 9720
ggatcctgct cgagtgcctc taga 9744

<210> SEQ ID NO 67
<211> LENGTH: 7134
<212> TYPE: DNA
<213> ORGANISM: Artificial Sequence
<220> FEATURE:
<223> OTHER INFORMATION: An example of an episomal DNA vector

<400> SEQUENCE: 67
tgccgagctc ggattctaac cttgtgtcag acccgcgggc caagggacag tctcaggtag 60
acagtttcta tggggcgtag gcctcccaaa aggtaacgga ggcgtgcaaa ggtttcctcg 120
ggccagacgg acattggtcc tcgagtgcaa aggcagaagg gagcttgact gcaagactca 180
cccgtcgagc agagacgaaa gtcggcctta gtgatccgac ggtgccgagt ggaagggccg 240
tcgctcaacg gataaaagtt actctaggga taacaggctg atcttcccca agagtccaca 300
tcgacgggaa ggtttggcac ctcgatgtcg gctcttcgcc acctggagct gtaggtggtt 360
ccaagggttg ggctgttcgc ccattaatgc ggtacgtgag ctgggttcag aacgtcgtga 420
gacagttcgg tccatatccg gtgtgggcgt tagagcattg agaggacctt tccctagtac 480
gagaggaccg ggaaggacgc acctctggtg taccagttat cgtgcctacg gtaaacgctg 540
ggtagccaag tgcggagagg ataactgctg aaagcatata agtagtaagc ccaccccaag 600
atgagtgctc tctcctccga cttccctaga gcctccggta gcacagccga gacagcgacg 660
ggttctccac ccatacgggg atggagcgac agaagcatgg aaataggata aggtagcggc 720
gagacgagcc gtttaaatag gtgtcaagtg gaagtgcagt gatgtatgca gctgaggcat 780
cctaacgaac gaacgatttg aaccttgttc ctacacgacc tgatcaaatc gatcaggcac 840
ttgccatcta tcttcattgt tcaactcttt gatgaaaaga tgaaaaaacc aaaaaaaagc 900
tctgcccttc catctcttgg atagatagag agggagggca gaggcctttg gtgtcccttc 960

-continued

```
cagtcaagaa ttggggcttc acaattacta gccaatattt ctctcatgcc tttcctcgtt   1020
catggttcga tattctggtg tcctaggcgt agaggaacca caccaatcca tcccgaattt   1080
ggtggttaaa ctctactgcg gtgacgatac tgtaggggag gtcctgcggc aaaatagctc   1140
gatgccagaa tgataaaaag cttaacacct cttatttgac tttttcacta ttttgaaata   1200
cgaaaaagat ccaaatccaa aatgcaaagg tcgtcttatt caaaacctca atcatcacat   1260
cccctctctc ccacttcaca cctcggaacg cactgttctt atagagagaa aggggctttc   1320
ccatcttctt aacccgaaat gaaatggctg aggagaggga ggttcctttt ggggggtacc   1380
cccgggaaga gatccagtgg agacggggtg ggcctgtagc tcagaggatt agagcacgtg   1440
gctacgaacc acggtgtcgg gggttcgaat ccctcctcgc ccacagcctt ccaaagggga   1500
agggccttta ctttcccccct gagggtagga aaaccatgat cgggatagcg gacgtaaagc   1560
tattgaactt gggtatgctc tttccttttg tcgaagtgga atcgtagaac agaatgtgat   1620
acgatgagat aaaatgcaat agaaacaagg atagcgaacg ggttacctac tcctaagggt   1680
caaagcaagc cctttaattc aattctttat tcttacatta aagaatgaat caaatctccc   1740
caagtaggat tcgaacctac gaccagtcag ttaacagccg accgctctac cactgagcta   1800
ctgaggaaca agggggattc gacctcctag agttcaactc ccgctctcaa cccatgaaca   1860
atatgagtcc gaagcttctt tcgtaactcc cggaatttct tcgtagtggc tccgttccat   1920
gcctcatttc ataggtaagc ccagagtggc tctatttcat tctatttcac ttcctagcac   1980
ttcctatcat ttaatatcca tccctttggt cttattgaca taagagatgt catttatagt   2040
ctatctcttt ctatatatgg aaagtcaaga aattctcatc gaaacatcga gaaattgtgc   2100
atatagaaaa ctctaaagaa agaaaaaaag cacacccatg ccatgatttt caaatctttt   2160
ctacttagta gtctaagttt ctcgatgagg ataattaatt cggtcgttgc ggtcggactc   2220
tattatgggt ttctgaccac attctccatg ggtccctctt agatctggga gcgcacgcgc   2280
aaggtcgcaa ctacccgaga atcgatgtgg cggaatgggt tacgtgagct attatccggc   2340
gggccctcaa tttaaatcgt tacagttgct cgtaacggca accggctcgg tcctttttcc   2400
ctagaacagt atcttatact tgctgctctc gttacttcgg cgatcctggt gcagtcggtc   2460
cgtaaatcgg cgcacacttt tacgtcgtac cagacaggct cgcataagcc agccccgaca   2520
cccgccaaca cccgctgacg cgccctgacg ggcttgtctg ctcccggcat ccgcttacag   2580
acaagctgtg acctccggga gctgcatgtg tcagaggttt tcaccgtcat caccgaaacg   2640
cgcacgaaag ggcctcgtga tacgcctatt tttataggtt aatgtcatga taataatggt   2700
ttcttagacg tcaggtggca cttttcgggg aaatgtgcgc ggaaccccta tttgtttatt   2760
tttctaaata cattcaaata tgtatccgct catgagacaa taaccctgat aaatgcttca   2820
ataatattga aaaaggaaga gtatgagtat tcaacatttc cgtgtcgccc ttattccctt   2880
ttttgcggca ttttgccttc ctgtttttgc tcacccagaa acgctggtga aagtaaaaga   2940
tgctgaagat cagttgggtg cacgagtggg ttacatcgaa ctggatctca acagcggtaa   3000
gatccttgag agttttcgcc ccgaagaacg ttttccaatg atgagcactt ttaaagttct   3060
gctatgtggc gcggtattat cccgtattga cgccgggcaa gagcaactcg gtcgccgcat   3120
acactattct cagaatgact tggttgagta ctcaccagtc acagaaaagc atcttacgga   3180
tggcatgaca gtaagagaat tatgcagtgc tgccataacc atgagtgata acactgcggc   3240
caacttactt ctgacaacga tcggaggacc gaaggagcta accgcttttt tgcacaacat   3300
gggggatcat gtaactcgcc ttgatcgttg ggaaccggag ctgaatgaag ccataccaaa   3360
```

```
cgacgagcgt gacaccacga tgcctgtagc aatggcaaca acgttgcgca aactattaac   3420
tggcgaacta cttactctag cttcccggca acaattaata gactggatgg aggcggataa   3480
agttgcagga ccacttctgc gctcggccct tccggctggc tggtttattg ctgataaatc   3540
tggagccggt gagcgtggct cacgcggtat cattgcagca ctggggccag atggtaagcc   3600
ctcccgtatc gtagttatct acacgacggg gagtcaggca actatggatg aacgaaatag   3660
acagatcgct gagataggtg cctcactgat taagcattgg taactgtcag accaagttta   3720
ctcatatata ctttagattg atttaaaact tcatttttaa tttaaaagga tctaggtgaa   3780
gatccttttt gataatctca tgaccaaaat cccttaacgt gagttttcgt tccactgagc   3840
gtcagacccc gtagaaaaga tcaaaggatc ttcttgagat cctttttttc tgcgcgtaat   3900
ctgctgcttg caaacaaaaa aaccaccgct accagcggtg gtttgtttgc cggatcaaga   3960
gctaccaact ctttttccga aggtaactgg cttcagcaga gcgcagatac caaatactgt   4020
tcttctagtg tagccgtagt taggccacca cttcaagaac tctgtagcac cgcctacata   4080
cctcgctctg ctaatcctgt taccagtggc tgctgccagt ggcgataagt cgtgtcttac   4140
cgggttggac tcaagacgat agttaccgga taaggcgcag cggtcgggct gaacgggggg   4200
ttcgtgcaca cagcccagct tggagcgaac gacctacacc gaactgagat acctacagcg   4260
tgagctatga gaaagcgcca cgcttcccga agggagaaag gcggacaggt atccggtaag   4320
cggcagggtc ggaacaggag agcgcacgag ggagcttcca gggggaaacg cctggtatct   4380
ttatagtcct gtcgggtttc gccacctctg acttgagcgt cgatttttgt gatgctcgtc   4440
aggggggcgg agcctatgga aaaacgccag caacgcggcc tttttacggt tcctggcctt   4500
ttgctggcct tttgctcaca tgttctttcc tgcgttatcc cctgattctg tggataaccg   4560
tattaccgcc tttgagtgag ctgataccgc tcgccgcagc cgaacgaccg agcgcagcga   4620
gtcagtgagc gaggaagcgg aagaacgcgg acacccagcg taacaatcta atattgtttc   4680
tcaaatcggg ctgttatcgc atggtgctca tgatgaggtt actgaccaaa ttcgccacgc   4740
atcggtgctg gtagaatgtt cacttcgagg tgggtagacg gcgtcacgtg caatgccttg   4800
tcttccccta tctgcggccc cgactgcctc gcgaagacaa gggatcggac gtcgaacgta   4860
ttctgtttgc taccggcacg ggagtaggat cgttgatata caccatgcgc gttaactctg   4920
acccccttcc tcttaaatga gaatggataa gaggctcgtg ggattgacgt gagggggcag   4980
ggatggctat atttctggga gcgaactccg ggcgaattac taataaaaag ccttccattt   5040
tctattttga tttgtagaaa actagtgtgc ttgggagtcc ctgatgatta aataaaccaa   5100
gattttacca atgggggcta gcgaagcggt gatcgccgaa gtatcgactc aactatcaga   5160
ggtagttggc gtcatcgagc gccatctcga accgacgttg ctggccgtac atttgtacgg   5220
ctccgcagtg gatggcggcc tgaagccaca cagtgatatt gatttgctgg ttacggtgac   5280
cgtaaggctt gatgaaacaa cgcggcgagc tttgatcaac gaccttttgg aaacttcggc   5340
ttcccctgga gagagcgaga ttctccgcgc tgtagaagtc accattgttg tgcacgacga   5400
catcattccg tggcgttatc cagctaagcg cgaactgcaa tttggagaat ggcagcgcaa   5460
tgacattctt gcaggtatct tcgagccagc cacgatcgac attgatctgg ctatcttgct   5520
gacaaaagca agagaacata gcgttgcctt ggtaggtcca gcggcggagg aactctttga   5580
tccggttcct gaacaggatc tatttgaggc gctaaatgaa accttaacgc tatggaactc   5640
gccgcccgac tgggctggcg atgagcgaaa tgtagtgctt acgttgtccc gcatttggta   5700
```

```
cagcgcagta accggcaaaa tcgcgccgaa ggatgtcgct gccgactggg caatggagcg   5760
cctgccggcc cagtatcagc ccgtcatact tgaagctaga caggcttatc ttggacaaga   5820
agaagatcgc ttggcctcgc gcgcagatca gttggaagaa tttgtccact acgtgaaagg   5880
cgagatcacc aaggtagtgg gcaaagaact tgttgaagga aaattggagc tagtagaagg   5940
tcttaaagtc gccatggcta gtaaaggaga agaacttttc actggagttg tcccaattct   6000
tgttgaatta gatggtgatg ttaatgggca caaattttct gtcagtggag agggtgaagg   6060
tgatgcaaca tacggaaaac ttacccttaa atttatttgc actactggaa aactacctgt   6120
tccttggcca acacttgtca ctactttctc ttatggtgtt caatgctttt caagataccc   6180
agatcatatg aagcggcacg acttcttcaa gagcgccatg cctgagggat acgtgcagga   6240
gaggaccatc tctttcaagg acgacgggaa ctacaagaca cgtgctgaag tcaagtttga   6300
gggagacacc ctcgtcaaca ggatcgagct taagggaatc gatttcaagg aggacggaaa   6360
catcctcggc cacaagttgg aatacaacta caactcccac aacgtataca tcacggcaga   6420
caaacaaaag aatggaatca aagctaactt caaaattaga cacaacattg aagatggaag   6480
cgttcaacta gcagaccatt atcaacaaaa tactccaatt ggcgatggcc ctgtcctttt   6540
accagacaac cattacctgt ccacacaatc tgccctttcg aaagatccca acgaaaagag   6600
agatcacatg gtccttcttg agtttgtaac agctgctggg attacacatg gcatggatga   6660
actatacaaa taagcttaaa cagtagacat tagcagataa attagcagga aataaagaag   6720
gataaggaga aagaactcaa gtaattatcc ttcgttctct taattgaatt gcaattaaac   6780
tcggcccaat cttttactaa aaggattgag ccgaataccg ctacaacagc tccctggaac   6840
accaggagaa cacacttatc tcgcgtcttg aggtgatacc acgcctgaca cgtgagggca   6900
gtacggttaa ttcggtttag ccggacatca gcgctcctca ttgagcgctg ggcccttcac   6960
atgaagatcg cactgaggat tggtcctagc caggcttctc agtactgata cagtacgcgt   7020
cgcttctcgt attgtttgag tcttggaatt agtttgtatc cttccgccgc tgccctaaga   7080
attctaattg agctcgaaca gtcgaccgcc ggatcctgct cgagtgcctc taga         7134
```

```
<210> SEQ ID NO 68
<211> LENGTH: 7214
<212> TYPE: DNA
<213> ORGANISM: Artificial Sequence
<220> FEATURE:
<223> OTHER INFORMATION: An example of an episomal DNA vector

<400> SEQUENCE: 68

tgccgagctc ggattctaac cttgtgtcag acccgcgggc caagggacag tctcaggtag     60
acagtttcta tggggcgtag gcctcccaaa aggtaacgga ggcgtgcaaa ggtttcctcg    120
ggccagacgg acattggtcc tcgagtgcaa aggcagaagg gagcttgact gcaagactca    180
cccgtcgagc agagacgaaa gtcggcctta gtgatccgac ggtgccgagt ggaagggccg    240
tcgctcaacg gataaaagtt actctaggga taacaggctg atcttcccca agagtccaca    300
tcgacgggaa ggtttggcac ctcgatgtcg gctcttcgcc acctggagct gtaggtggtt    360
ccaagggttg ggctgttcgc ccattaatgc ggtacgtgag ctgggttcag aacgtcgtga    420
gacagttcgg tccatatccg gtgtgggcgt tagagcattg agaggacctt tccctagtac    480
gagaggaccg ggaaggacgc acctctggtg taccagttat cgtgcctacg gtaaacgctg    540
ggtagccaag tgcggagagg ataactgctg aaagcatata agtagtaagc ccaccccaag    600
atgagtgctc tctcctccga cttccctaga gcctccggta gcacagccga gacagcgacg    660
```

```
ggttctccac ccatacgggg atggagcgac agaagcatgg aaataggata aggtagcggc    720
gagacgagcc gtttaaatag gtgtcaagtg gaagtgcagt gatgtatgca gctgaggcat    780
cctaacgaac gaacgatttg aaccttgttc ctacacgacc tgatcaaatc gatcaggcac    840
ttgccatcta tcttcattgt tcaactcttt gatgaaaaga tgaaaaaacc aaaaaaaagc    900
tctgcccttc catctcttgg atagatagag agggagggca gaggcctttg gtgtcccttc    960
cagtcaagaa ttggggcttc acaattacta gccaatattt ctctcatgcc tttcctcgtt   1020
catggttcga tattctggtg tcctaggcgt agaggaacca caccaatcca tcccgaattt   1080
ggtggttaaa ctctactgcg gtgacgatac tgtaggggag gtcctgcggc aaaatagctc   1140
gatgccagaa tgataaaaag cttaacacct cttatttgac tttttcacta ttttgaaata   1200
cgaaaaagat ccaaatccaa aatgcaaagg tcgtcttatt caaaacctca atcatcacat   1260
cccctctctc ccacttcaca cctcggaacg cactgttctt atagagagaa aggggctttc   1320
ccatcttctt aacccgaaat gaaatggctg aggagaggga ggttcctttt ggggggtacc   1380
cccgggaaga gatccagtgg agacggggtg ggcctgtagc tcagaggatt agagcacgtg   1440
gctacgaacc acggtgtcgg gggttcgaat ccctcctcgc ccacagcctt ccaaagggga   1500
agggccttta ctttccccct gagggtagga aaaccatgat cgggatagcg gacgtaaagc   1560
tattgaactt gggtatgctc tttccttttg tcgaagtgga atcgtagaac agaatgtgat   1620
acgatgagat aaaatgcaat agaaacaagg atagcgaacg ggttacctac tcctaagggt   1680
caaagcaagc cctttaattc aattctttat tcttacatta aagaatgaat caaatctccc   1740
caagtaggat tcgaacctac gaccagtcag ttaacagccg accgctctac cactgagcta   1800
ctgaggaaca agggggattc gacctcctag agttcaactc ccgctctcaa cccatgaaca   1860
atatgagtcc gaagcttctt tcgtaactcc cggaatttct tcgtagtggc tccgttccat   1920
gcctcatttc ataggtaagc ccagagtggc tctatttcat tctatttcac ttcctagcac   1980
ttcctatcat ttaatatcca tccctttggt cttattgaca taagagatgt catttatagt   2040
ctatctcttt ctatatatgg aaagtcaaga aattctcatc gaaacatcga gaaattgtgc   2100
atatagaaaa ctctaaagaa agaaaaaaag cacacccatg ccatgatttt caaatctttt   2160
ctacttagta gtctaagttt ctcgatgagg ataattaatt cggtcgttgc ggtcggactc   2220
tattatgggt ttctgaccac attctccatg ggtccctctt agatctggga gcgcacgcgc   2280
aaggtcgcaa ctacccgaga atcgatgtgg cggaatgggt tacgtgagct attatccggc   2340
gggccctcaa tttaaatcgt tacagttgct cgtaacggca accggctcgg tccttttttcc   2400
ctagaacagt atcttatact tgctgctctc gttacttcgg cgatcctggt gcagtcggtc   2460
cgtaaatcgg cgcacacttt tacgtcgtac cagacaggct cgcataagcc agccccgaca   2520
cccgccaaca cccgctgacg cgccctgacg ggcttgtctg ctcccggcat ccgcttacag   2580
acaagctgtg acctccggga gctgcatgtg tcagaggttt tcaccgtcat caccgaaacg   2640
cgcacgaaag ggcctcgtga tacgcctatt tttataggtt aatgtcatga taataatggt   2700
ttcttagacg tcaggtggca cttttcgggg aaatgtgcgc ggaaccccta tttgtttatt   2760
tttctaaata cattcaaata tgtatccgct catgagacaa taaccctgat aaatgcttca   2820
ataatattga aaaaggaaga gtatgagtat tcaacatttc cgtgtcgccc ttattccctt   2880
ttttgcggca ttttgccttc ctgtttttgc tcacccagaa acgctggtga aagtaaaaga   2940
tgctgaagat cagttgggtg cacgagtggg ttacatcgaa ctggatctca acagcggtaa   3000
```

-continued

```
gatccttgag agttttcgcc ccgaagaacg ttttccaatg atgagcactt ttaaagttct   3060
gctatgtggc gcggtattat cccgtattga cgccgggcaa gagcaactcg gtcgccgcat   3120
acactattct cagaatgact tggttgagta ctcaccagtc acagaaaagc atcttacgga   3180
tggcatgaca gtaagagaat tatgcagtgc tgccataacc atgagtgata acactgcggc   3240
caacttactt ctgacaacga tcggaggacc gaaggagcta accgcttttt tgcacaacat   3300
gggggatcat gtaactcgcc ttgatcgttg ggaaccggag ctgaatgaag ccataccaaa   3360
cgacgagcgt gacaccacga tgcctgtagc aatggcaaca acgttgcgca aactattaac   3420
tggcgaacta cttactctag cttcccggca acaattaata gactggatgg aggcggataa   3480
agttgcagga ccacttctgc gctcggccct tccggctggc tggtttattg ctgataaatc   3540
tggagccggt gagcgtggct cacgcggtat cattgcagca ctggggccag atggtaagcc   3600
ctcccgtatc gtagttatct acacgacggg gagtcaggca actatggatg aacgaaatag   3660
acagatcgct gagataggtg cctcactgat taagcattgg taactgtcag accaagttta   3720
ctcatatata ctttagattg atttaaaact tcatttttaa tttaaaagga tctaggtgaa   3780
gatccttttt gataatctca tgaccaaaat cccttaacgt gagttttcgt tccactgagc   3840
gtcagacccc gtagaaaaga tcaaaggatc ttcttgagat cctttttttc tgcgcgtaat   3900
ctgctgcttg caaacaaaaa aaccaccgct accagcggtg gtttgtttgc cggatcaaga   3960
gctaccaact ctttttccga aggtaactgg cttcagcaga gcgcagatac caaatactgt   4020
tcttctagtg tagccgtagt taggccacca cttcaagaac tctgtagcac cgcctacata   4080
cctcgctctg ctaatcctgt taccagtggc tgctgccagt ggcgataagt cgtgtcttac   4140
cgggttggac tcaagacgat agttaccgga taaggcgcag cggtcgggct gaacgggggg   4200
ttcgtgcaca cagcccagct tggagcgaac gacctacacc gaactgagat acctacagcg   4260
tgagctatga gaaagcgcca cgcttcccga agggagaaag gcggacaggt atccggtaag   4320
cggcagggtc ggaacaggag agcgcacgag ggagcttcca gggggaaacg cctggtatct   4380
ttatagtcct gtcgggtttc gccacctctg acttgagcgt cgatttttgt gatgctcgtc   4440
aggggggcgg agcctatgga aaaacgccag caacgcggcc tttttacggt tcctggcctt   4500
ttgctggcct tttgctcaca tgttctttcc tgcgttatcc cctgattctg tggataaccg   4560
tattaccgcc tttgagtgag ctgataccgc tcgccgcagc cgaacgaccg agcgcagcga   4620
gtcagtgagc gaggaagcgg aagaacgcgg acacccagcg taacaatcta atattgtttc   4680
tcaaatcggg ctgttatcgc atggtgctca tgatgaggtt actgaccaaa ttcgccacgc   4740
atcggtgctg gtagaatgtt cacttcgagg tgggtagacg gcgtcacgtg caatgccttg   4800
tcttccccta tctgcggccc cgactgcctc gcgaagacaa gggatcggac gtcgaacgta   4860
ttctgtttgc taccggcacg ggagtaggat cgttgatata caccatgcgc gttaactctg   4920
accccccttcc tcttaaatga gaatggataa gaggctcgtg ggattgacgt gagggggcag   4980
ggatggctat atttctggga gcgaactccg ggcgaattac taataaaaag ccttccattt   5040
tctattttga tttgtagaaa actagtgtgc ttgggagtcc ctgatgatta aataaaccaa   5100
gattttacca atgggggcta gcgaagcggt gatcgccgaa gtatcgactc aactatcaga   5160
ggtagttggc gtcatcgagc gccatctcga accgacgttg ctggccgtac atttgtacgg   5220
ctccgcagtg gatggcggcc tgaagccaca cagtgatatt gatttgctgg ttacggtgac   5280
cgtaaggctt gatgaaacaa cgcggcgagc tttgatcaac gaccttttgg aaacttcggc   5340
ttcccctgga gagagcgaga ttctccgcgc tgtagaagtc accattgttg tgcacgacga   5400
```

catcattccg tggcgttatc cagctaagcg cgaactgcaa tttggagaat ggcagcgcaa 5460
tgacattctt gcaggtatct tcgagccagc cacgatcgac attgatctgg ctatcttgct 5520
gacaaaagca agagaacata gcgttgcctt ggtaggtcca gcggcggagg aactctttga 5580
tccggttcct gaacaggatc tatttgaggc gctaaatgaa accttaacgc tatggaactc 5640
gccgcccgac tgggctggcg atgagcgaaa tgtagtgctt acgttgtccc gcatttggta 5700
cagcgcagta accggcaaaa tcgcgccgaa ggatgtcgct gccgactggg caatggagcg 5760
cctgccggcc cagtatcagc ccgtcatact tgaagctaga caggcttatc ttggacaaga 5820
agaagatcgc ttggcctcgc gcgcagatca gttggaagaa tttgtccact acgtgaaagg 5880
cgagatcacc aaggtagtgg gcaaagaact tgttgaagga aaattggagc tagtagaagg 5940
tcttaaagtc gccatggcta gtaaaggaga agaacttttc actggagttg tcccaattct 6000
tgttgaatta gatggtgatg ttaatgggca caaattttct gtcagtggag agggtgaagg 6060
tgatgcaaca tacggaaaac ttacccttaa atttatttgc actactggaa aactacctgt 6120
tccttggcca acacttgtca ctactttctc ttatggtgtt caatgctttt caagataccc 6180
agatcatatg aagcggcacg acttcttcaa gagcgccatg cctgagggat acgtgcagga 6240
gaggaccatc tctttcaagg acgacgggaa ctacaagaca cgtgctgaag tcaagtttga 6300
gggagacacc ctcgtcaaca ggatcgagct taagggaatc gatttcaagg aggacggaaa 6360
catcctcggc cacaagttgg aatacaacta caactcccac aacgtataca tcacggcaga 6420
caaacaaaag aatggaatca aagctaactt caaaattaga cacaacattg aagatggaag 6480
cgttcaacta gcagaccatt atcaacaaaa tactccaatt ggcgatggcc ctgtcctttt 6540
accagacaac cattacctgt ccacacaatc tgccctttcg aaagatccca acgaaaagag 6600
agatcacatg gtccttcttg agtttgtaac agctgctggg attacacatg gcatggatga 6660
actatacaaa taagcttaaa cagtagacat tagcagataa attagcagga aataaagaag 6720
gataaggaga aagaactcaa gtaattatcc ttcgttctct taattgaatt gcaattaaac 6780
tcggcccaat cttttactaa aaggattgag ccgaataccg ctccaggcat caaataaaac 6840
gaaaggctca gtcgaaagac tgggcctttc gttttatctg ttgtttgtcg gtgaacgctc 6900
tcacaacagc tccctggaac accaggagaa cacacttatc tcgcgtcttg aggtgatacc 6960
acgcctgaca cgtgagggca gtacggttaa ttcggtttag ccggacatca gcgctcctca 7020
ttgagcgctg ggcccttcac atgaagatcg cactgaggat tggtcctagc caggcttctc 7080
agtactgata cagtacgcgt cgcttctcgt attgtttgag tcttggaatt agtttgtatc 7140
cttccgccgc tgccctaaga attctaattg agctcgaaca gtcgaccgcc ggatcctgct 7200
cgagtgcctc taga 7214

<210> SEQ ID NO 69
<211> LENGTH: 5990
<212> TYPE: DNA
<213> ORGANISM: Artificial Sequence
<220> FEATURE:
<223> OTHER INFORMATION: An example of an episomal DNA vector

<400> SEQUENCE: 69
tgcccgagaa gagaggagcc gtggtggtcc cccccggacc gcccggatcc cacgagtgaa 60
tcgaaagttg gatctacatt ggatcttcac atcgacaatt caataaggta tccgacatta 120
acaatgattt aaattgtgtt cattgtgttt tttatggtac ataaccttca tagatttata 180

```
gattatcctg tctctgtaag gtgagagtgg aatttatcct ttattttgtc ctttccattc    240
actcggattt cttccgtttc atcgattttg tccggatccc acctttcttc cgaaaaaagg    300
gaaggagaag gataaggatc ttcttcagtg gatccctctt gttcctgttt agtccccttc    360
atttcggaag ctgtttctat ttctacatct ctttcttcct cactttccac cctttcttct    420
gtttttgagt tcctatatga ggaagtatcc ttccccgcag tcaagaccaa ggttagtatt    480
ctctgctagg aagtttactt aggttactct agcatgtgcc tggataaccc tctaggcaaa    540
ggtggattga ctttgtactg tcctcagatc gacgttggat gaactgtcgc gccacgaggg    600
gctgtggagc gcattgcgac acattggtgc gctgctaacc catcctttcc agtacggcta    660
ctgatgtcca cgctcccagc ctgctacgct ccgcccgctc aaaaacagaa gaaagggtgg    720
aaagtgagga agaaagagat gtagaaatag aaacagcttc cgaaatgaag ggactaaac     780
aggaacaaga gggatccact gaagaagatc cttatccttc tccttccctt ttttcggaag    840
aaaggtggga tccggacaaa atcgatgaaa cggaagaaat ccgagtgaat ggaaaggaca    900
aaataaagga taaattccac tctcacctta cagagacagg tgctagaaag ttattctttt    960
cgtcttaatg attatatgta aatcgccctc tatatattaa ctctacttat atggaaaaac   1020
tatgattaag tagttacagt agatccaatg tagatccaac tttcgattca ctcgtgggat   1080
ccgggcggtc cggggggac caccacggct cctctcttct cggggagcgc acgcgcaagg    1140
tcgcaactac ccgagaatcg atgtggcgga atgggttacg tgagctatta tccggcgggc   1200
cctcaattta aatcgttaca gttgctcgta acggcaaccg gctcggtcct ttttccctag   1260
aacagtatct tatacttgct gctctcgtta cttcggcgat cctggtgcag tcggtccgta   1320
aatcggcgca cacttttacg tcgtaccaga caggctcgca taagccagcc ccgacacccg   1380
ccaacacccg ctgacgcgcc ctgacgggct tgtctgctcc cggcatccgc ttacagacaa   1440
gctgtgacct ccgggagctg catgtgtcag aggttttcac cgtcatcacc gaaacgcgca   1500
cgaaagggcc tcgtgatacg cctattttta taggttaatg tcatgataat aatggtttct   1560
tagacgtcag gtggcacttt tcggggaaat gtgcgcggaa cccctatttg tttatttttc   1620
taaatacatt caaatatgta tccgctcatg agacaataac cctgataaat gcttcaataa   1680
tattgaaaaa ggaagagtat gagtattcaa catttccgtg tcgcccttat tccctttttt   1740
gcggcatttt gccttcctgt ttttgctcac ccagaaacgc tggtgaaagt aaaagatgct   1800
gaagatcagt tgggtgcacg agtgggttac atcgaactgg atctcaacag cggtaagatc   1860
cttgagagtt ttcgccccga agaacgtttt ccaatgatga gcacttttaa agttctgcta   1920
tgtggcgcgg tattatcccg tattgacgcc gggcaagagc aactcggtcg ccgcatacac   1980
tattctcaga atgacttggt tgagtactca ccagtcacag aaaagcatct tacggatggc   2040
atgacagtaa gagaattatg cagtgctgcc ataaccatga gtgataacac tgcggccaac   2100
ttacttctga caacgatcgg aggaccgaag gagctaaccg cttttttgca caacatgggg   2160
gatcatgtaa ctcgccttga tcgttgggaa ccggagctga atgaagccat accaaacgac   2220
gagcgtgaca ccacgatgcc tgtagcaatg gcaacaacgt tgcgcaaact attaactggc   2280
gaactactta ctctagcttc ccggcaacaa ttaatagact ggatggaggc ggataaagtt   2340
gcaggaccac ttctgcgctc ggcccttccg gctggctggt ttattgctga taaatctgga   2400
gccggtgagc gtggctcacg cggtatcatt gcagcactgg ggccagatgg taagccctcc   2460
cgtatcgtag ttatctacac gacggggagt caggcaacta tggatgaacg aaatagacag   2520
atcgctgaga taggtgcctc actgattaag cattggtaac tgtcagacca agtttactca   2580
```

```
tatatacttt agattgattt aaaacttcat ttttaattta aaaggatcta ggtgaagatc   2640
ctttttgata atctcatgac caaaatccct taacgtgagt tttcgttcca ctgagcgtca   2700
gaccccgtag aaaagatcaa aggatcttct tgagatcctt tttttctgcg cgtaatctgc   2760
tgcttgcaaa caaaaaaacc accgctacca gcggtggttt gtttgccgga tcaagagcta   2820
ccaactcttt ttccgaaggt aactggcttc agcagagcgc agataccaaa tactgttctt   2880
ctagtgtagc cgtagttagg ccaccacttc aagaactctg tagcaccgcc tacatacctc   2940
gctctgctaa tcctgttacc agtggctgct gccagtggcg ataagtcgtg tcttaccggg   3000
ttggactcaa gacgatagtt accggataag gcgcagcggt cgggctgaac ggggggttcg   3060
tgcacacagc ccagcttgga gcgaacgacc tacaccgaac tgagatacct acagcgtgag   3120
ctatgagaaa gcgccacgct tcccgaaggg agaaaggcgg acaggtatcc ggtaagcggc   3180
agggtcggaa caggagagcg cacgagggag cttccagggg gaaacgcctg gtatctttat   3240
agtcctgtcg ggtttcgcca cctctgactt gagcgtcgat ttttgtgatg ctcgtcaggg   3300
gggcggagcc tatggaaaaa cgccagcaac gcggcctttt tacggttcct ggccttttgc   3360
tggccttttg ctcacatgtt ctttcctgcg ttatcccctg attctgtgga taaccgtatt   3420
accgcctttg agtgagctga taccgctcgc cgcagccgaa cgaccgagcg cagcgagtca   3480
gtgagcgagg aagcggaaga acgcggacac ccagcgtaac aatctaatat tgtttctcaa   3540
atcgggctgt tatcgcatgg tgctcatgat gaggttactg accaaattcg ccacgcatcg   3600
gtgctggtag aatgttcact tcgaggtggg tagacggcgt cacgtgcaat gccttgtctt   3660
cccctatctg cggccccgac tgcctcgcga agacaaggga tcggacgtcg aacgtattct   3720
gtttgctacc ggcacgggag taggatcgtt gatatacacc atgcgcgtta actctgaccc   3780
ccttcctctt aaatgagaat ggataagagg ctcgtgggat tgacgtgagg gggcagggat   3840
ggctatattt ctgggagcga actccgggcg aattactaat aaaaagcctt ccattttcta   3900
ttttgatttg tagaaaacta gtgtgcttgg gagtccctga tgattaaata aaccaagatt   3960
ttaccaatgg gggctagcga agcggtgatc gccgaagtat cgactcaact atcagaggta   4020
gttggcgtca tcgagcgcca tctcgaaccg acgttgctgg ccgtacattt gtacggctcc   4080
gcagtggatg gcggcctgaa gccacacagt gatattgatt tgctggttac ggtgaccgta   4140
aggcttgatg aaacaacgcg gcgagctttg atcaacgacc ttttggaaac ttcggcttcc   4200
cctggagaga gcgagattct ccgcgctgta gaagtcacca ttgttgtgca cgacgacatc   4260
attccgtggc gttatccagc taagcgcgaa ctgcaatttg gagaatggca gcgcaatgac   4320
attcttgcag gtatcttcga gccagccacg atcgacattg atctggctat cttgctgaca   4380
aaagcaagag aacatagcgt tgccttggta ggtccagcgg cggaggaact ctttgatccg   4440
gttcctgaac aggatctatt tgaggcgcta aatgaaacct taacgctatg gaactcgccg   4500
cccgactggg ctggcgatga gcgaaatgta gtgcttacgt tgtcccgcat ttggtacagc   4560
gcagtaaccg gcaaaatcgc gccgaaggat gtcgctgccg actgggcaat ggagcgcctg   4620
ccggcccagt atcagcccgt catacttgaa gctagacagg cttatcttgg acaagaagaa   4680
gatcgcttgg cctcgcgcgc agatcagttg gaagaatttg tccactacgt gaaaggcgag   4740
atcaccaagg tagtgggcaa agaacttgtt gaaggaaaat tggagctagt agaaggtctt   4800
aaagtcgcca tggctagtaa aggagaagaa cttttcactg gagttgtccc aattcttgtt   4860
gaattagatg gtgatgttaa tgggcacaaa ttttctgtca gtggagaggg tgaaggtgat   4920
```

gcaacatacg gaaaacttac ccttaaattt atttgcacta ctggaaaact acctgttcct 4980
tggccaacac ttgtcactac tttctcttat ggtgttcaat gcttttcaag atacccagat 5040
catatgaagc ggcacgactt cttcaagagc gccatgcctg agggatacgt gcaggagagg 5100
accatctctt tcaaggacga cgggaactac aagacacgtg ctgaagtcaa gtttgaggga 5160
gacaccctcg tcaacaggat cgagcttaag ggaatcgatt tcaaggagga cggaaacatc 5220
ctcggccaca agttggaata caactacaac tcccacaacg tatacatcac ggcagacaaa 5280
caaaagaatg gaatcaaagc taacttcaaa attagacaca acattgaaga tggaagcgtt 5340
caactagcag accattatca acaaaatact ccaattggcg atggccctgt ccttttacca 5400
gacaaccatt acctgtccac acaatctgcc ctttcgaaag atcccaacga aaagagagat 5460
cacatggtcc ttcttgagtt tgtaacagct gctgggatta cacatggcat ggatgaacta 5520
tacaaataag cttaaacagt agacattagc agataaatta gcaggaaata aagaaggata 5580
aggagaaaga actcaagtaa ttatccttcg ttctcttaat tgaattgcaa ttaaactcgg 5640
cccaatcttt tactaaaagg attgagccga ataccgctac aacagctccc tggaacacca 5700
ggagaacaca cttatctcgc gtcttgaggt gataccacgc ctgacacgtg agggcagtac 5760
ggttaattcg gtttagccgg acatcagcgc tcctcattga gcgctgggcc cttcacatga 5820
agatcgcact gaggattggt cctagccagg cttctcagta ctgatacagt acgcgtcgct 5880
tctcgtattg tttgagtctt ggaattagtt tgtatccttc cgccgctgcc ctaagaattc 5940
taattgagct cgaacagtcg accgccggat cctgctcgag tgcctctaga 5990

<210> SEQ ID NO 70
<211> LENGTH: 6070
<212> TYPE: DNA
<213> ORGANISM: Artificial Sequence
<220> FEATURE:
<223> OTHER INFORMATION: An example of an episomal DNA vector

<400> SEQUENCE: 70
tgcccgagaa gagaggagcc gtggtggtcc cccccggacc gcccggatcc cacgagtgaa 60
tcgaaagttg gatctacatt ggatcttcac atcgacaatt caataaggta tccgacatta 120
acaatgattt aaattgtgtt cattgtgttt tttatggtac ataaccttca tagatttata 180
gattatcctg tctctgtaag gtgagagtgg aatttatcct ttattttgtc ctttccattc 240
actcggattt cttccgtttc atcgattttg tccggatccc acctttcttc cgaaaaaagg 300
gaaggagaag gataaggatc ttcttcagtg gatccctctt gttcctgttt agtccccttc 360
atttcggaag ctgtttctat ttctacatct ctttcttcct cactttccac cctttcttct 420
gtttttgagt tcctatatga ggaagtatcc ttccccgcag tcaagaccaa ggttagtatt 480
ctctgctagg aagtttactt aggttactct agcatgtgcc tggataaccc tctaggcaaa 540
ggtggattga ctttgtactg tcctcagatc gacgttggat gaactgtcgc gccacgaggg 600
gctgtggagc gcattgcgac acattggtgc gctgctaacc catcctttcc agtacggcta 660
ctgatgtcca cgctcccagc ctgctacgct ccgcccgctc aaaaacagaa gaaagggtgg 720
aaagtgagga agaaagagat gtagaaatag aaacagcttc cgaaatgaag gggactaaac 780
aggaacaaga gggatccact gaagaagatc cttatccttc tccttccctt ttttcggaag 840
aaaggtggga tccggacaaa atcgatgaaa cggaagaaat ccgagtgaat ggaaaggaca 900
aaataaagga taaattccac tctcacctta cagagacagg tgctagaaag ttattctttt 960
cgtcttaatg attatatgta aatcgccctc tatatattaa ctctacttat atggaaaaac 1020

-continued

```
tatgattaag tagttacagt agatccaatg tagatccaac tttcgattca ctcgtgggat   1080
ccgggcggtc cgggggggac caccacggct cctctcttct cggggagcgc acgcgcaagg   1140
tcgcaactac ccgagaatcg atgtggcgga atgggttacg tgagctatta tccggcgggc   1200
cctcaattta aatcgttaca gttgctcgta acggcaaccg gctcggtcct ttttccctag   1260
aacagtatct tatacttgct gctctcgtta cttcggcgat cctggtgcag tcggtccgta   1320
aatcggcgca cacttttacg tcgtaccaga caggctcgca taagccagcc ccgacacccg   1380
ccaacacccg ctgacgcgcc ctgacgggct tgtctgctcc cggcatccgc ttacagacaa   1440
gctgtgacct ccgggagctg catgtgtcag aggttttcac cgtcatcacc gaaacgcgca   1500
cgaaagggcc tcgtgatacg cctattttta taggttaatg tcatgataat aatggtttct   1560
tagacgtcag gtggcacttt tcggggaaat gtgcgcggaa cccctatttg tttatttttc   1620
taaatacatt caaatatgta tccgctcatg agacaataac cctgataaat gcttcaataa   1680
tattgaaaaa ggaagagtat gagtattcaa catttccgtg tcgcccttat tccctttttt   1740
gcggcatttt gccttcctgt ttttgctcac ccagaaacgc tggtgaaagt aaaagatgct   1800
gaagatcagt tgggtgcacg agtgggttac atcgaactgg atctcaacag cggtaagatc   1860
cttgagagtt ttcgccccga agaacgtttt ccaatgatga gcacttttaa agttctgcta   1920
tgtggcgcgg tattatcccg tattgacgcc gggcaagagc aactcggtcg ccgcatacac   1980
tattctcaga atgacttggt tgagtactca ccagtcacag aaaagcatct tacggatggc   2040
atgacagtaa gagaattatg cagtgctgcc ataaccatga gtgataacac tgcggccaac   2100
ttacttctga caacgatcgg aggaccgaag gagctaaccg cttttttgca caacatgggg   2160
gatcatgtaa ctcgccttga tcgttgggaa ccggagctga atgaagccat accaaacgac   2220
gagcgtgaca ccacgatgcc tgtagcaatg gcaacaacgt tgcgcaaact attaactggc   2280
gaactactta ctctagcttc ccggcaacaa ttaatagact ggatggaggc ggataaagtt   2340
gcaggaccac ttctgcgctc ggcccttccg gctggctggt ttattgctga taaatctgga   2400
gccggtgagc gtggctcacg cggtatcatt gcagcactgg ggccagatgg taagccctcc   2460
cgtatcgtag ttatctacac gacggggagt caggcaacta tggatgaacg aaatagacag   2520
atcgctgaga taggtgcctc actgattaag cattggtaac tgtcagacca agtttactca   2580
tatatacttt agattgattt aaaacttcat ttttaattta aaaggatcta ggtgaagatc   2640
ctttttgata atctcatgac caaaatccct taacgtgagt tttcgttcca ctgagcgtca   2700
gaccccgtag aaaagatcaa aggatcttct tgagatcctt tttttctgcg cgtaatctgc   2760
tgcttgcaaa caaaaaaacc accgctacca gcggtggttt gtttgccgga tcaagagcta   2820
ccaactcttt ttccgaaggt aactggcttc agcagagcgc agataccaaa tactgttctt   2880
ctagtgtagc cgtagttagg ccaccacttc aagaactctg tagcaccgcc tacatacctc   2940
gctctgctaa tcctgttacc agtggctgct gccagtggcg ataagtcgtg tcttaccggg   3000
ttggactcaa gacgatagtt accggataag gcgcagcggt cgggctgaac ggggggttcg   3060
tgcacacagc ccagcttgga gcgaacgacc tacaccgaac tgagatacct acagcgtgag   3120
ctatgagaaa gcgccacgct tcccgaaggg agaaaggcgg acaggtatcc ggtaagcggc   3180
agggtcggaa caggagagcg cacgagggag cttccagggg gaaacgcctg gtatctttat   3240
agtcctgtcg ggtttcgcca cctctgactt gagcgtcgat ttttgtgatg ctcgtcaggg   3300
gggcggagcc tatggaaaaa cgccagcaac gcggcctttt tacggttcct ggccttttgc   3360
```

-continued tggcctttttg ctcacatgtt ctttcctgcg ttatcccctg attctgtgga taaccgtatt 3420
accgcctttg agtgagctga taccgctcgc cgcagccgaa cgaccgagcg cagcgagtca 3480
gtgagcgagg aagcggaaga acgcggacac ccagcgtaac aatctaatat tgtttctcaa 3540
atcgggctgt tatcgcatgg tgctcatgat gaggttactg accaaattcg ccacgcatcg 3600
gtgctggtag aatgttcact tcgaggtggg tagacggcgt cacgtgcaat gccttgtctt 3660
cccctatctg cggccccgac tgcctcgcga agacaaggga tcggacgtcg aacgtattct 3720
gtttgctacc ggcacgggag taggatcgtt gatatacacc atgcgcgtta actctgaccc 3780
ccttcctctt aaatgagaat ggataagagg ctcgtgggat tgacgtgagg gggcagggat 3840
ggctatattt ctgggagcga actccgggcg aattactaat aaaaagcctt ccattttcta 3900
ttttgatttg tagaaaacta gtgtgcttgg gagtccctga tgattaaata aaccaagatt 3960
ttaccaatgg gggctagcga agcggtgatc gccgaagtat cgactcaact atcagaggta 4020
gttggcgtca tcgagcgcca tctcgaaccg acgttgctgg ccgtacattt gtacggctcc 4080
gcagtggatg gcggcctgaa gccacacagt gatattgatt tgctggttac ggtgaccgta 4140
aggcttgatg aaacaacgcg gcgagctttg atcaacgacc ttttggaaac ttcggcttcc 4200
cctggagaga gcgagattct ccgcgctgta gaagtcacca ttgttgtgca cgacgacatc 4260
attccgtggc gttatccagc taagcgcgaa ctgcaatttg gagaatggca gcgcaatgac 4320
attcttgcag gtatcttcga gccagccacg atcgacattg atctggctat cttgctgaca 4380
aaagcaagag aacatagcgt tgccttggta ggtccagcgg cggaggaact ctttgatccg 4440
gttcctgaac aggatctatt tgaggcgcta aatgaaacct taacgctatg gaactcgccg 4500
cccgactggg ctggcgatga gcgaaatgta gtgcttacgt tgtcccgcat ttggtacagc 4560
gcagtaaccg gcaaaatcgc gccgaaggat gtcgctgccg actgggcaat ggagcgcctg 4620
ccggcccagt atcagcccgt catacttgaa gctagacagg cttatcttgg acaagaagaa 4680
gatcgcttgg cctcgcgcgc agatcagttg gaagaatttg tccactacgt gaaaggcgag 4740
atcaccaagg tagtgggcaa agaacttgtt gaaggaaaat tggagctagt agaaggtctt 4800
aaagtcgcca tggctagtaa aggagaagaa cttttcactg gagttgtccc aattcttgtt 4860
gaattagatg gtgatgttaa tgggcacaaa ttttctgtca gtggagaggg tgaaggtgat 4920
gcaacatacg gaaaacttac ccttaaattt atttgcacta ctggaaaact acctgttcct 4980
tggccaacac ttgtcactac tttctcttat ggtgttcaat gcttttcaag atacccagat 5040
catatgaagc ggcacgactt cttcaagagc gccatgcctg agggatacgt gcaggagagg 5100
accatctctt tcaaggacga cgggaactac aagacacgtg ctgaagtcaa gtttgaggga 5160
gacaccctcg tcaacaggat cgagcttaag ggaatcgatt tcaaggagga cggaaacatc 5220
ctcggccaca agttggaata caactacaac tcccacaacg tatacatcac ggcagacaaa 5280
caaaagaatg gaatcaaagc taacttcaaa attagacaca acattgaaga tggaagcgtt 5340
caactagcag accattatca acaaaatact ccaattggcg atggccctgt ccttttacca 5400
gacaaccatt acctgtccac acaatctgcc ctttcgaaag atcccaacga aaagagagat 5460
cacatggtcc ttcttgagtt tgtaacagct gctgggatta cacatggcat ggatgaacta 5520
tacaaataag cttaaacagt agacattagc agataaatta gcaggaaata aagaaggata 5580
aggagaaaga actcaagtaa ttatccttcg ttctcttaat tgaattgcaa ttaaactcgg 5640
cccaatcttt tactaaaagg attgagccga ataccgctcc aggcatcaaa taaaacgaaa 5700
ggctcagtcg aaagactggg cctttcgttt tatctgttgt ttgtcggtga acgctctcac 5760

```
aacagctccc tggaacacca ggagaacaca cttatctcgc gtcttgaggt gataccacgc   5820

ctgacacgtg agggcagtac ggttaattcg gtttagccgg acatcagcgc tcctcattga   5880

gcgctgggcc cttcacatga agatcgcact gaggattggt cctagccagg cttctcagta   5940

ctgatacagt acgcgtcgct tctcgtattg tttgagtctt ggaattagtt tgtatccttc   6000

cgccgctgcc ctaagaattc taattgagct cgaacagtcg accgccggat cctgctcgag   6060

tgcctctaga                                                          6070
```

<210> SEQ ID NO 71
<211> LENGTH: 5697
<212> TYPE: DNA
<213> ORGANISM: Artificial Sequence
<220> FEATURE:
<223> OTHER INFORMATION: An example of an episomal DNA vector

<400> SEQUENCE: 71

```
tgcccctaag gtgctgctaa atggatggat cttatcaacg tccatgaatg ataaatcata     60

gatcgaaccg ccgaatcgga aaaattgggt gctatcataa agctttgtat cggctaagtt    120

cacgagttgg agataagcgg actcgaaccg ctgacatccg ccgcagggta aaccaccgcc    180

tctcaggtcc cccgactgat tctaccatag aggccaacga tagacaataa ctcccccccg    240

aacacagctt acaactttca tcgtactgtg ctctccaaag agcaactctt ctcaaaatct    300

cactcaaaag gtgctgagtt ggaatcccat tctaactaag aatgagtcat tgcccttctc    360

cgaccctgac tgcccaacct gagagcggac agctaatgcg ttccacttat tgaacagggt    420

tctatggtcg gtccgtgacc cctggatgcc gaaggcgtcc ttggggtgat ctcgtagttc    480

ctacggggtg gagatgatgg ggtcggtcca tggattttcc ttccttttct tttgccgcat    540

ttcgctcaaa gggttgaagg gagatagtgc atcaagctgt tcgcaagggc caacttgatc    600

ctcttcccca gagatctcag atgagggaac cctgggagag ccgccgactc caactaccgt    660

ccatgtacga tccatactag atctgaccaa ctgcccatcc tacctcctct acgttcttga    720

cagcccatct ttgtctcagt agagtctttc agtggcacgt ttcggtcctc ttccccatta    780

cttagaaaaa gtgagccacc ggttcaggta caagatacta tcattaccgg ggagcgcacg    840

cgcaaggtcg caactacccg agaatcgatg tggcggaatg ggttacgtga gctattatcc    900

ggcgggccct caatttaaat cgttacagtt gctcgtaacg gcaaccggct cggtcctttt    960

tccctagaac agtatcttat acttgctgct ctcgttactt cggcgatcct ggtgcagtcg   1020

gtccgtaaat cggcgcacac ttttacgtcg taccagacag gctcgcataa gccagccccg   1080

acacccgcca acacccgctg acgcgccctg acgggcttgt ctgctcccgg catccgctta   1140

cagacaagct gtgacctccg ggagctgcat gtgtcagagg ttttcaccgt catcaccgaa   1200

acgcgcacga aagggcctcg tgatacgcct atttttatag gttaatgtca tgataataat   1260

ggtttcttag acgtcaggtg gcacttttcg gggaaatgtg cgcggaaccc ctatttgttt   1320

atttttctaa atacattcaa atatgtatcc gctcatgaga caataaccct gataaatgct   1380

tcaataatat tgaaaaagga agagtatgag tattcaacat ttccgtgtcg cccttattcc   1440

cttttttgcg gcattttgcc ttcctgtttt tgctcaccca gaaacgctgg tgaaagtaaa   1500

agatgctgaa gatcagttgg gtgcacgagt gggttacatc gaactggatc tcaacagcgg   1560

taagatcctt gagagttttc gccccgaaga acgttttcca atgatgagca cttttaaagt   1620

tctgctatgt ggcgcggtat tatcccgtat tgacgccggg caagagcaac tcggtcgccg   1680
```

```
catacactat tctcagaatg acttggttga gtactcacca gtcacagaaa agcatcttac   1740
ggatggcatg acagtaagag aattatgcag tgctgccata accatgagtg ataacactgc   1800
ggccaactta cttctgacaa cgatcggagg accgaaggag ctaaccgctt ttttgcacaa   1860
catgggggat catgtaactc gccttgatcg ttgggaaccg gagctgaatg aagccatacc   1920
aaacgacgag cgtgacacca cgatgcctgt agcaatggca acaacgttgc gcaaactatt   1980
aactggcgaa ctacttactc tagcttcccg gcaacaatta atagactgga tggaggcgga   2040
taaagttgca ggaccacttc tgcgctcggc ccttccggct ggctggttta ttgctgataa   2100
atctggagcc ggtgagcgtg gctcacgcgg tatcattgca gcactggggc cagatggtaa   2160
gccctcccgt atcgtagtta tctacacgac ggggagtcag gcaactatgg atgaacgaaa   2220
tagacagatc gctgagatag gtgcctcact gattaagcat tggtaactgt cagaccaagt   2280
ttactcatat atactttaga ttgatttaaa acttcatttt taatttaaaa ggatctaggt   2340
gaagatcctt tttgataatc tcatgaccaa aatcccttaa cgtgagtttt cgttccactg   2400
agcgtcagac cccgtagaaa agatcaaagg atcttcttga gatccttttt ttctgcgcgt   2460
aatctgctgc ttgcaaacaa aaaaaccacc gctaccagcg gtggtttgtt tgccggatca   2520
agagctacca actctttttc cgaaggtaac tggcttcagc agagcgcaga taccaaatac   2580
tgttcttcta gtgtagccgt agttaggcca ccacttcaag aactctgtag caccgcctac   2640
atacctcgct ctgctaatcc tgttaccagt ggctgctgcc agtggcgata agtcgtgtct   2700
taccgggttg gactcaagac gatagttacc ggataaggcg cagcggtcgg gctgaacggg   2760
gggttcgtgc acacagccca gcttggagcg aacgacctac accgaactga gatacctaca   2820
gcgtgagcta tgagaaagcg ccacgcttcc cgaagggaga aaggcggaca ggtatccggt   2880
aagcggcagg gtcggaacag gagagcgcac gagggagctt ccagggggaa acgcctggta   2940
tctttatagt cctgtcgggt ttcgccacct ctgacttgag cgtcgatttt tgtgatgctc   3000
gtcagggggg cggagcctat ggaaaaacgc cagcaacgcg gcctttttac ggttcctggc   3060
cttttgctgg ccttttgctc acatgttctt tcctgcgtta tcccctgatt ctgtggataa   3120
ccgtattacc gcctttgagt gagctgatac cgctcgccgc agccgaacga ccgagcgcag   3180
cgagtcagtg agcgaggaag cggaagaacg cggacaccca gcgtaacaat ctaatattgt   3240
ttctcaaatc gggctgttat cgcatggtgc tcatgatgag gttactgacc aaattcgcca   3300
cgcatcggtg ctggtagaat gttcacttcg aggtgggtag acggcgtcac gtgcaatgcc   3360
ttgtcttccc ctatctgcgg ccccgactgc ctcgcgaaga caagggatcg gacgtcgaac   3420
gtattctgtt tgctaccggc acgggagtag gatcgttgat atacaccatg cgcgttaact   3480
ctgacccccct tcctcttaaa tgagaatgga taagaggctc gtgggattga cgtgaggggg   3540
cagggatggc tatatttctg ggagcgaact ccgggcgaat tactaataaa aagccttcca   3600
ttttctattt tgatttgtag aaaactagtg tgcttgggag tccctgatga ttaaataaac   3660
caagatttta ccaatggggg ctagcgaagc ggtgatcgcc gaagtatcga ctcaactatc   3720
agaggtagtt ggcgtcatcg agcgccatct cgaaccgacg ttgctggccg tacatttgta   3780
cggctccgca gtggatggcg gcctgaagcc acacagtgat attgatttgc tggttacggt   3840
gaccgtaagg cttgatgaaa caacgcggcg agctttgatc aacgaccttt tggaaacttc   3900
ggcttcccct ggagagagcg agattctccg cgctgtagaa gtcaccattg ttgtgcacga   3960
cgacatcatt ccgtggcgtt atccagctaa gcgcgaactg caatttggag aatggcagcg   4020
caatgacatt cttgcaggta tcttcgagcc agccacgatc gacattgatc tggctatctt   4080
```

gctgacaaaa gcaagagaac atagcgttgc cttggtaggt ccagcggcgg aggaactctt 4140
tgatccggtt cctgaacagg atctatttga ggcgctaaat gaaaccttaa cgctatggaa 4200
ctcgccgccc gactgggctg gcgatgagcg aaatgtagtg cttacgttgt cccgcatttg 4260
gtacagcgca gtaaccggca aaatcgcgcc gaaggatgtc gctgccgact gggcaatgga 4320
gcgcctgccg gcccagtatc agcccgtcat acttgaagct agacaggctt atcttggaca 4380
agaagaagat cgcttggcct cgcgcgcaga tcagttggaa gaatttgtcc actacgtgaa 4440
aggcgagatc accaaggtag tgggcaaaga acttgttgaa ggaaaattgg agctagtaga 4500
aggtcttaaa gtcgccatgg ctagtaaagg agaagaactt ttcactggag ttgtcccaat 4560
tcttgttgaa ttagatggtg atgttaatgg gcacaaattt tctgtcagtg gagagggtga 4620
aggtgatgca acatacggaa aacttaccct taaatttatt tgcactactg gaaaactacc 4680
tgttccttgg ccaacacttg tcactacttt ctcttatggt gttcaatgct tttcaagata 4740
cccagatcat atgaagcggc acgacttctt caagagcgcc atgcctgagg gatacgtgca 4800
ggagaggacc atctctttca aggacgacgg gaactacaag acacgtgctg aagtcaagtt 4860
tgagggagac accctcgtca acaggatcga gcttaaggga atcgatttca aggaggacgg 4920
aaacatcctc ggccacaagt tggaatacaa ctacaactcc cacaacgtat acatcacggc 4980
agacaaacaa aagaatggaa tcaaagctaa cttcaaaatt agacacaaca ttgaagatgg 5040
aagcgttcaa ctagcagacc attatcaaca aaatactcca attggcgatg gccctgtcct 5100
tttaccagac aaccattacc tgtccacaca atctgccctt tcgaaagatc ccaacgaaaa 5160
gagagatcac atggtccttc ttgagtttgt aacagctgct gggattacac atggcatgga 5220
tgaactatac aaataagctt aaacagtaga cattagcaga taaattagca ggaaataaag 5280
aaggataagg agaaagaact caagtaatta tccttcgttc tcttaattga attgcaatta 5340
aactcggccc aatcttttac taaaaggatt gagccgaata ccgctacaac agctccctgg 5400
aacaccagga gaacacactt atctcgcgtc ttgaggtgat accacgcctg acacgtgagg 5460
gcagtacggt taattcggtt tagccggaca tcagcgctcc tcattgagcg ctgggccctt 5520
cacatgaaga tcgcactgag gattggtcct agccaggctt ctcagtactg atacagtacg 5580
cgtcgcttct cgtattgttt gagtcttgga attagtttgt atccttccgc cgctgcccta 5640
agaattctaa ttgagctcga acagtcgacc gccggatcct gctcgagtgc ctctaga 5697

<210> SEQ ID NO 72
<211> LENGTH: 5777
<212> TYPE: DNA
<213> ORGANISM: Artificial Sequence
<220> FEATURE:
<223> OTHER INFORMATION: An example of an episomal DNA vector

<400> SEQUENCE: 72
tgcccctaag gtgctgctaa atggatggat cttatcaacg tccatgaatg ataaatcata 60
gatcgaaccg ccgaatcgga aaaattgggt gctatcataa agctttgtat cggctaagtt 120
cacgagttgg agataagcgg actcgaaccg ctgacatccg ccgcagggta aaccaccgcc 180
tctcaggtcc cccgactgat tctaccatag aggccaacga tagacaataa ctcccccccg 240
aacacagctt acaactttca tcgtactgtg ctctccaaag agcaactctt ctcaaaatct 300
cactcaaaag gtgctgagtt ggaatcccat tctaactaag aatgagtcat tgcccttctc 360
cgaccctgac tgcccaacct gagagcggac agctaatgcg ttccacttat tgaacagggt 420

```
tctatggtcg gtccgtgacc cctggatgcc gaaggcgtcc ttggggtgat ctcgtagttc    480
ctacggggtg gagatgatgg ggtcggtcca tggattttcc ttccttttct tttgccgcat    540
ttcgctcaaa gggttgaagg gagatagtgc atcaagctgt tcgcaagggc caacttgatc    600
ctcttcccca gagatctcag atgagggaac cctgggagag ccgccgactc caactaccgt    660
ccatgtacga tccatactag atctgaccaa ctgcccatcc tacctcctct acgttcttga    720
cagcccatct ttgtctcagt agagtctttc agtggcacgt ttcggtcctc ttccccatta    780
cttagaaaaa gtgagccacc ggttcaggta caagatacta tcattaccgg ggagcgcacg    840
cgcaaggtcg caactacccg agaatcgatg tggcggaatg ggttacgtga gctattatcc    900
ggcgggccct caatttaaat cgttacagtt gctcgtaacg gcaaccggct cggtcctttt    960
tccctagaac agtatcttat acttgctgct ctcgttactt cggcgatcct ggtgcagtcg   1020
gtccgtaaat cggcgcacac ttttacgtcg taccagacag gctcgcataa gccagccccg   1080
acacccgcca acacccgctg acgcgccctg acgggcttgt ctgctcccgg catccgctta   1140
cagacaagct gtgacctccg ggagctgcat gtgtcagagg ttttcaccgt catcaccgaa   1200
acgcgcacga aagggcctcg tgatacgcct atttttatag gttaatgtca tgataataat   1260
ggtttcttag acgtcaggtg gcacttttcg gggaaatgtg cgcggaaccc ctatttgttt   1320
atttttctaa atacattcaa atatgtatcc gctcatgaga caataaccct gataaatgct   1380
tcaataatat tgaaaaagga agagtatgag tattcaacat ttccgtgtcg cccttattcc   1440
cttttttgcg gcattttgcc ttcctgtttt tgctcaccca gaaacgctgg tgaaagtaaa   1500
agatgctgaa gatcagttgg gtgcacgagt gggttacatc gaactggatc tcaacagcgg   1560
taagatcctt gagagttttc gccccgaaga acgttttcca atgatgagca cttttaaagt   1620
tctgctatgt ggcgcggtat tatcccgtat tgacgccggg caagagcaac tcggtcgccg   1680
catacactat tctcagaatg acttggttga gtactcacca gtcacagaaa agcatcttac   1740
ggatggcatg acagtaagag aattatgcag tgctgccata accatgagtg ataacactgc   1800
ggccaactta cttctgacaa cgatcggagg accgaaggag ctaaccgctt ttttgcacaa   1860
catgggggat catgtaactc gccttgatcg ttgggaaccg gagctgaatg aagccatacc   1920
aaacgacgag cgtgacacca cgatgcctgt agcaatggca acaacgttgc gcaaactatt   1980
aactggcgaa ctacttactc tagcttcccg gcaacaatta atagactgga tggaggcgga   2040
taaagttgca ggaccacttc tgcgctcggc ccttccggct ggctggttta ttgctgataa   2100
atctggagcc ggtgagcgtg gctcacgcgg tatcattgca gcactggggc cagatggtaa   2160
gccctcccgt atcgtagtta tctacacgac ggggagtcag gcaactatgg atgaacgaaa   2220
tagacagatc gctgagatag gtgcctcact gattaagcat tggtaactgt cagaccaagt   2280
ttactcatat atactttaga ttgatttaaa acttcatttt taatttaaaa ggatctaggt   2340
gaagatcctt tttgataatc tcatgaccaa aatcccttaa cgtgagtttt cgttccactg   2400
agcgtcagac cccgtagaaa agatcaaagg atcttcttga gatccttttt ttctgcgcgt   2460
aatctgctgc ttgcaaacaa aaaaaccacc gctaccagcg gtggtttgtt tgccggatca   2520
agagctacca actctttttc cgaaggtaac tggcttcagc agagcgcaga taccaaatac   2580
tgttcttcta gtgtagccgt agttaggcca ccacttcaag aactctgtag caccgcctac   2640
atacctcgct ctgctaatcc tgttaccagt ggctgctgcc agtggcgata agtcgtgtct   2700
taccgggttg gactcaagac gatagttacc ggataaggcg cagcggtcgg gctgaacggg   2760
gggttcgtgc acacagccca gcttggagcg aacgacctac accgaactga gatacctaca   2820
```

-continued gcgtgagcta tgagaaagcg ccacgcttcc cgaagggaga aaggcggaca ggtatccggt 2880
aagcggcagg gtcggaacag gagagcgcac gagggagctt ccagggggaa acgcctggta 2940
tctttatagt cctgtcgggt ttcgccacct ctgacttgag cgtcgatttt tgtgatgctc 3000
gtcagggggg cggagcctat ggaaaaacgc cagcaacgcg gcctttttac ggttcctggc 3060
cttttgctgg ccttttgctc acatgttctt tcctgcgtta tcccctgatt ctgtggataa 3120
ccgtattacc gcctttgagt gagctgatac cgctcgccgc agccgaacga ccgagcgcag 3180
cgagtcagtg agcgaggaag cggaagaacg cggacaccca gcgtaacaat ctaatattgt 3240
ttctcaaatc gggctgttat cgcatggtgc tcatgatgag gttactgacc aaattcgcca 3300
cgcatcggtg ctggtagaat gttcacttcg aggtgggtag acggcgtcac gtgcaatgcc 3360
ttgtcttccc ctatctgcgg ccccgactgc ctcgcgaaga caagggatcg gacgtcgaac 3420
gtattctgtt tgctaccggc acgggagtag gatcgttgat atacaccatg cgcgttaact 3480 ctgacccccct tcctcttaaa tgagaatgga taagaggctc gtgggattga cgtgaggggg 3540
cagggatggc tatatttctg ggagcgaact ccgggcgaat tactaataaa aagccttcca 3600
ttttctattt tgatttgtag aaaactagtg tgcttgggag tccctgatga ttaaataaac 3660
caagatttta ccaatggggg ctagcgaagc ggtgatcgcc gaagtatcga ctcaactatc 3720
agaggtagtt ggcgtcatcg agcgccatct cgaaccgacg ttgctggccg tacatttgta 3780
cggctccgca gtggatggcg gcctgaagcc acacagtgat attgatttgc tggttacggt 3840
gaccgtaagg cttgatgaaa caacgcggcg agctttgatc aacgaccttt tggaaacttc 3900
ggcttcccct ggagagagcg agattctccg cgctgtagaa gtcaccattg ttgtgcacga 3960
cgacatcatt ccgtggcgtt atccagctaa gcgcgaactg caatttggag aatggcagcg 4020
caatgacatt cttgcaggta tcttcgagcc agccacgatc gacattgatc tggctatctt 4080
gctgacaaaa gcaagagaac atagcgttgc cttggtaggt ccagcggcgg aggaactctt 4140
tgatccggtt cctgaacagg atctatttga ggcgctaaat gaaaccttaa cgctatggaa 4200
ctcgccgccc gactgggctg gcgatgagcg aaatgtagtg cttacgttgt cccgcatttg 4260
gtacagcgca gtaaccggca aaatcgcgcc gaaggatgtc gctgccgact gggcaatgga 4320
gcgcctgccg gcccagtatc agcccgtcat acttgaagct agacaggctt atcttggaca 4380
agaagaagat cgcttggcct cgcgcgcaga tcagttggaa gaatttgtcc actacgtgaa 4440
aggcgagatc accaaggtag tgggcaaaga acttgttgaa ggaaaattgg agctagtaga 4500
aggtcttaaa gtcgccatgg ctagtaaagg agaagaactt ttcactggag ttgtcccaat 4560
tcttgttgaa ttagatggtg atgttaatgg gcacaaattt tctgtcagtg gagagggtga 4620
aggtgatgca acatacggaa aacttaccct taaatttatt tgcactactg gaaaactacc 4680
tgttccttgg ccaacacttg tcactacttt ctcttatggt gttcaatgct tttcaagata 4740
cccagatcat atgaagcggc acgacttctt caagagcgcc atgcctgagg gatacgtgca 4800
ggagaggacc atctctttca aggacgacgg gaactacaag acacgtgctg aagtcaagtt 4860
tgagggagac accctcgtca acaggatcga gcttaaggga atcgatttca aggaggacgg 4920
aaacatcctc ggccacaagt tggaatacaa ctacaactcc cacaacgtat acatcacggc 4980
agacaaacaa aagaatggaa tcaaagctaa cttcaaaatt agacacaaca ttgaagatgg 5040
aagcgttcaa ctagcagacc attatcaaca aaatactcca attggcgatg gccctgtcct 5100
tttaccagac aaccattacc tgtccacaca atctgccctt tcgaaagatc ccaacgaaaa 5160

-continued gagagatcac atggtccttc ttgagtttgt aacagctgct gggattacac atggcatgga 5220
tgaactatac aaataagctt aaacagtaga cattagcaga taaattagca ggaaataaag 5280
aaggataagg agaaagaact caagtaatta tccttcgttc tcttaattga attgcaatta 5340
aactcggccc aatcttttac taaaaggatt gagccgaata ccgctccagg catcaaataa 5400
aacgaaaggc tcagtcgaaa gactgggcct ttcgttttat ctgttgtttg tcggtgaacg 5460
ctctcacaac agctccctgg aacaccagga gaacacactt atctcgcgtc ttgaggtgat 5520
accacgcctg acacgtgagg gcagtacggt taattcggtt tagccggaca tcagcgctcc 5580
tcattgagcg ctgggccctt cacatgaaga tcgcactgag gattggtcct agccaggctt 5640
ctcagtactg atacagtacg cgtcgcttct cgtattgttt gagtcttgga attagtttgt 5700
atccttccgc cgctgcccta agaattctaa ttgagctcga acagtcgacc gccggatcct 5760
gctcgagtgc ctctaga 5777

<210> SEQ ID NO 73
<211> LENGTH: 5990
<212> TYPE: DNA
<213> ORGANISM: Artificial Sequence
<220> FEATURE:
<223> OTHER INFORMATION: An example of an episomal DNA vector

<400> SEQUENCE: 73
tgcccgagaa gagaggagcc gtggtggtcc cccccggacc gcccggatcc cacgagtgaa 60
tcgaaagttg gatctacatt ggatcttcac atcgacaatt caataaggta tccgacatta 120
acaatgattt aaattgtgtt cattgtgttt tttatggtac ataaccttca tagatttata 180
gattatctca aaaacagaag aaagggtgga aagtgaggaa gaaagagatg tagaaataga 240
aacagcttcc gaaatgaagg ggactaaaca ggaacaagag ggatccactg aagaagatcc 300
ttatccttct ccttcccttt tttcggaaga aaggtgggat ccggacaaaa tcgatgaaac 360
ggaagaaatc cgagtgaatg gaaaggacaa aataaaggat aaattccact ctcaccttac 420
agagacaggt tcctatatga ggaagtatcc ttccccgcag tcaagaccaa ggttagtatt 480
ctctgctagg aagtttactt aggttactct agcatgtgcc tggataaccc tctaggcaaa 540
ggtggattga ctttgtactg tcctcagatc gacgttggat gaactgtcgc gccacgaggg 600
gctgtggagc gcattgcgac acattggtgc gctgctaacc catcctttcc agtacggcta 660
ctgatgtcca cgctcccagc ctgctacgct ccgcccgcct gtctctgtaa ggtgagagtg 720
gaatttatcc tttattttgt cctttccatt cactcggatt tcttccgttt catcgatttt 780
gtccggatcc cacctttctt ccgaaaaaag ggaaggagaa ggataaggat cttcttcagt 840
ggatccctct tgttcctgtt tagtcccctt catttcggaa gctgtttcta tttctacatc 900
tctttcttcc tcactttcca ccctttcttc tgtttttgag tgctagaaag ttattctttt 960
cgtcttaatg attatatgta aatcgccctc tatatattaa ctctacttat atggaaaaac 1020
tatgattaag tagttacagt agatccaatg tagatccaac tttcgattca ctcgtgggat 1080
ccgggcggtc cggggggga caccacggct cctctcttct cggggagcgc acgcgcaagg 1140
tcgcaactac ccgagaatcg atgtggcgga atgggttacg tgagctatta tccggcgggc 1200
cctcaattta aatcgttaca gttgctcgta acggcaaccg gctcggtcct ttttccctag 1260
aacagtatct tatacttgct gctctcgtta cttcggcgat cctggtgcag tcggtccgta 1320
aatcggcgca cacttttacg tcgtaccaga caggctcgca taagccagcc ccgacacccg 1380
ccaacacccg ctgacgcgcc ctgacgggct tgtctgctcc cggcatccgc ttacagacaa 1440

```
gctgtgacct ccgggagctg catgtgtcag aggttttcac cgtcatcacc gaaacgcgca   1500
cgaaagggcc tcgtgatacg cctattttta taggttaatg tcatgataat aatggtttct   1560
tagacgtcag gtggcacttt tcggggaaat gtgcgcggaa cccctatttg tttatttttc   1620
taaatacatt caaatatgta tccgctcatg agacaataac cctgataaat gcttcaataa   1680
tattgaaaaa ggaagagtat gagtattcaa catttccgtg tcgcccttat tccctttttt   1740
gcggcatttt gccttcctgt ttttgctcac ccagaaacgc tggtgaaagt aaaagatgct   1800
gaagatcagt tgggtgcacg agtgggttac atcgaactgg atctcaacag cggtaagatc   1860
cttgagagtt ttcgccccga agaacgtttt ccaatgatga gcacttttaa agttctgcta   1920
tgtggcgcgg tattatcccg tattgacgcc gggcaagagc aactcggtcg ccgcatacac   1980
tattctcaga atgacttggt tgagtactca ccagtcacag aaaagcatct tacggatggc   2040
atgacagtaa gagaattatg cagtgctgcc ataaccatga gtgataacac tgcggccaac   2100
ttacttctga caacgatcgg aggaccgaag gagctaaccg cttttttgca caacatgggg   2160
gatcatgtaa ctcgccttga tcgttgggaa ccggagctga atgaagccat accaaacgac   2220
gagcgtgaca ccacgatgcc tgtagcaatg gcaacaacgt tgcgcaaact attaactggc   2280
gaactactta ctctagcttc ccggcaacaa ttaatagact ggatggaggc ggataaagtt   2340
gcaggaccac ttctgcgctc ggcccttccg gctggctggt ttattgctga taaatctgga   2400
gccggtgagc gtggctcacg cggtatcatt gcagcactgg ggccagatgg taagccctcc   2460
cgtatcgtag ttatctacac gacggggagt caggcaacta tggatgaacg aaatagacag   2520
atcgctgaga taggtgcctc actgattaag cattggtaac tgtcagacca agtttactca   2580
tatatacttt agattgattt aaaacttcat ttttaattta aaaggatcta ggtgaagatc   2640
ctttttgata atctcatgac caaaatccct taacgtgagt tttcgttcca ctgagcgtca   2700
gaccccgtag aaaagatcaa aggatcttct tgagatcctt tttttctgcg cgtaatctgc   2760
tgcttgcaaa caaaaaaacc accgctacca gcggtggttt gtttgccgga tcaagagcta   2820
ccaactcttt ttccgaaggt aactggcttc agcagagcgc agataccaaa tactgttctt   2880
ctagtgtagc cgtagttagg ccaccacttc aagaactctg tagcaccgcc tacatacctc   2940
gctctgctaa tcctgttacc agtggctgct gccagtggcg ataagtcgtg tcttaccggg   3000
ttggactcaa gacgatagtt accggataag gcgcagcggt cgggctgaac ggggggttcg   3060
tgcacacagc ccagcttgga gcgaacgacc tacaccgaac tgagatacct acagcgtgag   3120
ctatgagaaa gcgccacgct tcccgaaggg agaaaggcgg acaggtatcc ggtaagcggc   3180
agggtcggaa caggagagcg cacgagggag cttccagggg gaaacgcctg gtatctttat   3240
agtcctgtcg ggtttcgcca cctctgactt gagcgtcgat ttttgtgatg ctcgtcaggg   3300
gggcggagcc tatggaaaaa cgccagcaac gcggcctttt tacggttcct ggccttttgc   3360
tggccttttg ctcacatgtt ctttcctgcg ttatcccctg attctgtgga taaccgtatt   3420
accgcctttg agtgagctga taccgctcgc cgcagccgaa cgaccgagcg cagcgagtca   3480
gtgagcgagg aagcggaaga acgcggacac ccagcgtaac aatctaatat tgtttctcaa   3540
atcgggctgt tatcgcatgg tgctcatgat gaggttactg accaaattcg ccacgcatcg   3600
gtgctggtag aatgttcact tcgaggtggg tagacggcgt cacgtgcaat gccttgtctt   3660
cccctatctg cggccccgac tgcctcgcga agacaaggga tcggacgtcg aacgtattct   3720
gtttgctacc ggcacgggag taggatcgtt gatatacacc atgcgcgtta actctgaccc   3780
```

```
ccttcctctt aaatgagaat ggataagagg ctcgtgggat tgacgtgagg gggcagggat   3840

ggctatattt ctgggagcga actccgggcg aattactaat aaaaagcctt ccattttcta   3900

ttttgatttg tagaaaacta gtgtgcttgg gagtccctga tgattaaata aaccaagatt   3960

ttaccaatgg gggctagcga agcggtgatc gccgaagtat cgactcaact atcagaggta   4020

gttggcgtca tcgagcgcca tctcgaaccg acgttgctgg ccgtacattt gtacggctcc   4080

gcagtggatg gcggcctgaa gccacacagt gatattgatt tgctggttac ggtgaccgta   4140

aggcttgatg aaacaacgcg gcgagctttg atcaacgacc ttttggaaac ttcggcttcc   4200

cctggagaga gcgagattct ccgcgctgta gaagtcacca ttgttgtgca cgacgacatc   4260

attccgtggc gttatccagc taagcgcgaa ctgcaatttg gagaatggca gcgcaatgac   4320

attcttgcag gtatcttcga gccagccacg atcgacattg atctggctat cttgctgaca   4380

aaagcaagag aacatagcgt tgccttggta ggtccagcgg cggaggaact ctttgatccg   4440

gttcctgaac aggatctatt tgaggcgcta aatgaaacct taacgctatg gaactcgccg   4500

cccgactggg ctggcgatga gcgaaatgta gtgcttacgt tgtcccgcat ttggtacagc   4560

gcagtaaccg gcaaaatcgc gccgaaggat gtcgctgccg actgggcaat ggagcgcctg   4620

ccggcccagt atcagcccgt catacttgaa gctagacagg cttatcttgg acaagaagaa   4680

gatcgcttgg cctcgcgcgc agatcagttg gaagaatttg tccactacgt gaaaggcgag   4740

atcaccaagg tagtgggcaa agaacttgtt gaaggaaaat tggagctagt agaaggtctt   4800

aaagtcgcca tggctagtaa aggagaagaa cttttcactg gagttgtccc aattcttgtt   4860

gaattagatg gtgatgttaa tgggcacaaa ttttctgtca gtggagaggg tgaaggtgat   4920

gcaacatacg gaaaacttac ccttaaattt atttgcacta ctggaaaact acctgttcct   4980

tggccaacac ttgtcactac tttctcttat ggtgttcaat gcttttcaag atacccagat   5040

catatgaagc ggcacgactt cttcaagagc gccatgcctg agggatacgt gcaggagagg   5100

accatctctt tcaaggacga cgggaactac aagacacgtg ctgaagtcaa gtttgaggga   5160

gacaccctcg tcaacaggat cgagcttaag ggaatcgatt tcaaggagga cggaaacatc   5220

ctcggccaca agttggaata caactacaac tcccacaacg tatacatcac ggcagacaaa   5280

caaaagaatg gaatcaaagc taacttcaaa attagacaca acattgaaga tggaagcgtt   5340

caactagcag accattatca acaaaatact ccaattggcg atggccctgt ccttttacca   5400

gacaaccatt acctgtccac acaatctgcc ctttcgaaag atcccaacga aaagagagat   5460

cacatggtcc ttcttgagtt tgtaacagct gctgggatta cacatggcat ggatgaacta   5520

tacaaataag cttaaacagt agacattagc agataaatta gcaggaaata aagaaggata   5580

aggagaaaga actcaagtaa ttatccttcg ttctcttaat tgaattgcaa ttaaactcgg   5640

cccaatcttt tactaaaagg attgagccga ataccgctac aacagctccc tggaacacca   5700

ggagaacaca cttatctcgc gtcttgaggt gataccacgc ctgacacgtg agggcagtac   5760

ggttaattcg gtttagccgg acatcagcgc tcctcattga gcgctgggcc cttcacatga   5820

agatcgcact gaggattggt cctagccagg cttctcagta ctgatacagt acgcgtcgct   5880

tctcgtattg tttgagtctt ggaattagtt tgtatccttc cgccgctgcc ctaagaattc   5940

taattgagct cgaacagtcg accgccggat cctgctcgag tgcctctaga              5990
```

<210> SEQ ID NO 74
<211> LENGTH: 6070
<212> TYPE: DNA
<213> ORGANISM: Artificial Sequence
<220> FEATURE:
<223> OTHER INFORMATION: An example of an episomal DNA vector

<400> SEQUENCE: 74

```
tgcccgagaa gagaggagcc gtggtggtcc cccccggacc gcccggatcc cacgagtgaa     60
tcgaaagttg gatctacatt ggatcttcac atcgacaatt caataaggta tccgacatta    120
acaatgattt aaattgtgtt cattgtgttt tttatggtac ataaccttca tagatttata    180
gattatctca aaaacagaag aaagggtgga aagtgaggaa gaaagagatg tagaaataga    240
aacagcttcc gaaatgaagg ggactaaaca ggaacaagag ggatccactg aagaagatcc    300
ttatccttct ccttcccttt tttcggaaga aaggtgggat ccggacaaaa tcgatgaaac    360
ggaagaaatc cgagtgaatg gaaaggacaa aataaaggat aaattccact ctcaccttac    420
agagacaggt tcctatatga ggaagtatcc ttccccgcag tcaagaccaa ggttagtatt    480
ctctgctagg aagtttactt aggttactct agcatgtgcc tggataaccc tctaggcaaa    540
ggtggattga ctttgtactg tcctcagatc gacgttggat gaactgtcgc gccacgaggg    600
gctgtggagc gcattgcgac acattggtgc gctgctaacc catcctttcc agtacggcta    660
ctgatgtcca cgctcccagc ctgctacgct ccgcccgcct gtctctgtaa ggtgagagtg    720
gaatttatcc tttattttgt cctttccatt cactcggatt tcttccgttt catcgatttt    780
gtccggatcc cacctttctt ccgaaaaaag ggaaggagaa ggataaggat cttcttcagt    840
ggatccctct tgttcctgtt tagtcccctt catttcggaa gctgtttcta tttctacatc    900
tctttcttcc tcactttcca ccctttcttc tgtttttgag tgctagaaag ttattctttt    960
cgtcttaatg attatatgta aatcgccctc tatatattaa ctctacttat atggaaaaac   1020
tatgattaag tagttacagt agatccaatg tagatccaac tttcgattca ctcgtgggat   1080
ccgggcggtc cggggggggac caccacggct cctctcttct cggggagcgc acgcgcaagg   1140
tcgcaactac ccgagaatcg atgtggcgga atgggttacg tgagctatta tccggcgggc   1200
cctcaattta aatcgttaca gttgctcgta acggcaaccg gctcggtcct ttttccctag   1260
aacagtatct tatacttgct gctctcgtta cttcggcgat cctggtgcag tcggtccgta   1320
aatcggcgca cacttttacg tcgtaccaga caggctcgca taagccagcc ccgacacccg   1380
ccaacacccg ctgacgcgcc ctgacgggct tgtctgctcc cggcatccgc ttacagacaa   1440
gctgtgacct ccgggagctg catgtgtcag aggttttcac cgtcatcacc gaaacgcgca   1500
cgaaagggcc tcgtgatacg cctattttta taggttaatg tcatgataat aatggtttct   1560
tagacgtcag gtggcacttt tcggggaaat gtgcgcggaa cccctatttg tttatttttc   1620
taaatacatt caaatatgta tccgctcatg agacaataac cctgataaat gcttcaataa   1680
tattgaaaaa ggaagagtat gagtattcaa catttccgtg tcgcccttat tccctttttt   1740
gcggcatttt gccttcctgt ttttgctcac ccagaaacgc tggtgaaagt aaaagatgct   1800
gaagatcagt tgggtgcacg agtgggttac atcgaactgg atctcaacag cggtaagatc   1860
cttgagagtt ttcgccccga agaacgtttt ccaatgatga gcacttttaa agttctgcta   1920
tgtggcgcgg tattatcccg tattgacgcc gggcaagagc aactcggtcg ccgcatacac   1980
tattctcaga atgacttggt tgagtactca ccagtcacag aaaagcatct tacggatggc   2040
atgacagtaa gagaattatg cagtgctgcc ataaccatga gtgataacac tgcggccaac   2100
ttacttctga caacgatcgg aggaccgaag gagctaaccg cttttttgca caacatgggg   2160
gatcatgtaa ctcgccttga tcgttgggaa ccggagctga atgaagccat accaaacgac   2220
```

gagcgtgaca ccacgatgcc tgtagcaatg gcaacaacgt tgcgcaaact attaactggc 2280
gaactactta ctctagcttc ccggcaacaa ttaatagact ggatggaggc ggataaagtt 2340
gcaggaccac ttctgcgctc ggcccttccg gctggctggt ttattgctga taaatctgga 2400
gccggtgagc gtggctcacg cggtatcatt gcagcactgg ggccagatgg taagccctcc 2460
cgtatcgtag ttatctacac gacggggagt caggcaacta tggatgaacg aaatagacag 2520
atcgctgaga taggtgcctc actgattaag cattggtaac tgtcagacca agtttactca 2580
tatatacttt agattgattt aaaacttcat ttttaattta aaaggatcta ggtgaagatc 2640
ctttttgata atctcatgac caaaatccct taacgtgagt tttcgttcca ctgagcgtca 2700
gaccccgtag aaaagatcaa aggatcttct tgagatcctt tttttctgcg cgtaatctgc 2760
tgcttgcaaa caaaaaaacc accgctacca gcggtggttt gtttgccgga tcaagagcta 2820
ccaactcttt ttccgaaggt aactggcttc agcagagcgc agataccaaa tactgttctt 2880
ctagtgtagc cgtagttagg ccaccacttc aagaactctg tagcaccgcc tacatacctc 2940
gctctgctaa tcctgttacc agtggctgct gccagtggcg ataagtcgtg tcttaccggg 3000
ttggactcaa gacgatagtt accggataag gcgcagcggt cgggctgaac ggggggttcg 3060
tgcacacagc ccagcttgga gcgaacgacc tacaccgaac tgagatacct acagcgtgag 3120
ctatgagaaa gcgccacgct tcccgaaggg agaaaggcgg acaggtatcc ggtaagcggc 3180
agggtcggaa caggagagcg cacgagggag cttccagggg gaaacgcctg gtatctttat 3240
agtcctgtcg ggtttcgcca cctctgactt gagcgtcgat ttttgtgatg ctcgtcaggg 3300
gggcggagcc tatggaaaaa cgccagcaac gcggcctttt tacggttcct ggccttttgc 3360
tggccttttg ctcacatgtt ctttcctgcg ttatcccctg attctgtgga taaccgtatt 3420
accgcctttg agtgagctga taccgctcgc cgcagccgaa cgaccgagcg cagcgagtca 3480
gtgagcgagg aagcggaaga acgcggacac ccagcgtaac aatctaatat tgtttctcaa 3540
atcgggctgt tatcgcatgg tgctcatgat gaggttactg accaaattcg ccacgcatcg 3600
gtgctggtag aatgttcact tcgaggtggg tagacggcgt cacgtgcaat gccttgtctt 3660
cccctatctg cggccccgac tgcctcgcga agacaaggga tcggacgtcg aacgtattct 3720
gtttgctacc ggcacgggag taggatcgtt gatatacacc atgcgcgtta actctgaccc 3780
ccttcctctt aaatgagaat ggataagagg ctcgtgggat tgacgtgagg gggcagggat 3840
ggctatattt ctgggagcga actccgggcg aattactaat aaaaagcctt ccattttcta 3900
ttttgatttg tagaaaacta gtgtgcttgg gagtccctga tgattaaata aaccaagatt 3960
ttaccaatgg gggctagcga agcggtgatc gccgaagtat cgactcaact atcagaggta 4020
gttggcgtca tcgagcgcca tctcgaaccg acgttgctgg ccgtacattt gtacggctcc 4080
gcagtggatg gcggcctgaa gccacacagt gatattgatt tgctggttac ggtgaccgta 4140
aggcttgatg aaacaacgcg gcgagctttg atcaacgacc ttttggaaac ttcggcttcc 4200
cctggagaga gcgagattct ccgcgctgta gaagtcacca ttgttgtgca cgacgacatc 4260
attccgtggc gttatccagc taagcgcgaa ctgcaatttg gagaatggca gcgcaatgac 4320
attcttgcag gtatcttcga gccagccacg atcgacattg atctggctat cttgctgaca 4380
aaagcaagag aacatagcgt tgccttggta ggtccagcgg cggaggaact ctttgatccg 4440
gttcctgaac aggatctatt tgaggcgcta aatgaaacct taacgctatg gaactcgccg 4500
cccgactggg ctggcgatga gcgaaatgta gtgcttacgt tgtcccgcat ttggtacagc 4560
gcagtaaccg gcaaaatcgc gccgaaggat gtcgctgccg actgggcaat ggagcgcctg 4620
ccggcccagt atcagcccgt catacttgaa gctagacagg cttatcttgg acaagaagaa 4680
gatcgcttgg cctcgcgcgc agatcagttg gaagaatttg tccactacgt gaaaggcgag 4740
atcaccaagg tagtgggcaa agaacttgtt gaaggaaaat tggagctagt agaaggtctt 4800
aaagtcgcca tggctagtaa aggagaagaa cttttcactg gagttgtccc aattcttgtt 4860
gaattagatg gtgatgttaa tgggcacaaa ttttctgtca gtggagaggg tgaaggtgat 4920
gcaacatacg gaaaacttac ccttaaattt atttgcacta ctggaaaact acctgttcct 4980
tggccaacac ttgtcactac tttctcttat ggtgttcaat gcttttcaag atacccagat 5040
catatgaagc ggcacgactt cttcaagagc gccatgcctg agggatacgt gcaggagagg 5100
accatctctt tcaaggacga cgggaactac aagacacgtg ctgaagtcaa gtttgaggga 5160
gacaccctcg tcaacaggat cgagcttaag ggaatcgatt tcaaggagga cggaaacatc 5220
ctcggccaca agttggaata caactacaac tcccacaacg tatacatcac ggcagacaaa 5280
caaaagaatg gaatcaaagc taacttcaaa attagacaca acattgaaga tggaagcgtt 5340
caactagcag accattatca acaaaatact ccaattggcg atggccctgt ccttttacca 5400
gacaaccatt acctgtccac acaatctgcc ctttcgaaag atcccaacga aaagagagat 5460
cacatggtcc ttcttgagtt tgtaacagct gctgggatta cacatggcat ggatgaacta 5520
tacaaataag cttaaacagt agacattagc agataaatta gcaggaaata aagaaggata 5580
aggagaaaga actcaagtaa ttatccttcg ttctcttaat tgaattgcaa ttaaactcgg 5640
cccaatcttt tactaaaagg attgagccga ataccgctcc aggcatcaaa taaaacgaaa 5700
ggctcagtcg aaagactggg cctttcgttt tatctgttgt ttgtcggtga acgctctcac 5760
aacagctccc tggaacacca ggagaacaca cttatctcgc gtcttgaggt gataccacgc 5820
ctgacacgtg agggcagtac ggttaattcg gtttagccgg acatcagcgc tcctcattga 5880
gcgctgggcc cttcacatga agatcgcact gaggattggt cctagccagg cttctcagta 5940
ctgatacagt acgcgtcgct tctcgtattg tttgagtctt ggaattagtt tgtatccttc 6000
cgccgctgcc ctaagaattc taattgagct cgaacagtcg accgccggat cctgctcgag 6060
tgcctctaga 6070

<210> SEQ ID NO 75
<211> LENGTH: 5990
<212> TYPE: DNA
<213> ORGANISM: Artificial Sequence
<220> FEATURE:
<223> OTHER INFORMATION: An example of an episomal DNA vector

<400> SEQUENCE: 75
tgcccaccat agcgcgccgg ttgcctgcgg ttactggacc aagctcgtca actcggagca 60
ggctttatgg gcctcgcttc cttaagtcac atcgacaatt caataaggta tccgacatta 120
acaatgattt aaattgtgtt cattgtgttt tttatggtac ataaccttca tagatttata 180
gattatctca aaaacagaag aaagggtgga aagtgaggaa gaaagagatg tagaaataga 240
aacagcttcc gaaatgaagg ggactaaaca ggaacaagag ggatccactg aagaagatcc 300
ttatccttct ccttcccttt tttcggaaga aaggtgggat ccggacaaaa tcgatgaaac 360
ggaagaaatc cgagtgaatg gaaaggacaa aataaaggat aaattccact ctcaccttac 420
agagacaggt tcctatatga ggaagtatcc ttccccgcag tcaagaccaa ggttagtatt 480
ctctgctagg aagtttactt aggttactct agcatgtgcc tggataaccc tctaggcaaa 540

-continued

```
ggtggattga ctttgtactg tcctcagatc gacgttggat gaactgtcgc gccacgaggg    600
gctgtggagc gcattgcgac acattggtgc gctgctaacc catcctttcc agtacggcta    660
ctgatgtcca cgctcccagc ctgctacgct ccgcccggcg tggtctgctg tcctacttcc    720
ctgtgttccc gtcgaatctt tttttgcttt gccttctccc cattccaatc tttgcgactg    780
aaacgtacgt acactgtgct ttgcattatt agtttttgaa attgtggcct attttttgtc    840
cttaaaccgc tcatctttac accatcgttc tttgtggaca ttctttttcct tgctaattgg    900
tattctacaa actggcacta gctgtagtca atctgactgt tgctagaaag ttattctttt    960
cgtcttaatg attatatgta aatcgccctc tatatattaa ctctacttat atggaaaaac   1020
tatgattaag tagttacagt cgacgcgcgg gtgacacccc tacgccgact cgataaacag   1080
gatgggtcat gggcctggca cgtgttattc aaaggtacag cggggagcgc acgcgcaagg   1140
tcgcaactac ccgagaatcg atgtggcgga atgggttacg tgagctatta tccggcgggc   1200
cctcaattta aatcgttaca gttgctcgta acggcaaccg gctcggtcct tttccctag    1260
aacagtatct tatacttgct gctctcgtta cttcggcgat cctggtgcag tcggtccgta   1320
aatcggcgca cacttttacg tcgtaccaga caggctcgca taagccagcc ccgacacccg   1380
ccaacacccg ctgacgcgcc ctgacgggct tgtctgctcc cggcatccgc ttacagacaa   1440
gctgtgacct ccgggagctg catgtgtcag aggttttcac cgtcatcacc gaaacgcgca   1500
cgaaagggcc tcgtgatacg cctattttta taggttaatg tcatgataat aatggtttct   1560
tagacgtcag gtggcacttt tcggggaaat gtgcgcggaa cccctatttg tttatttttc   1620
taaatacatt caaatatgta tccgctcatg agacaataac cctgataaat gcttcaataa   1680
tattgaaaaa ggaagagtat gagtattcaa catttccgtg tcgcccttat tccctttttt   1740
gcggcatttt gccttcctgt ttttgctcac ccagaaacgc tggtgaaagt aaaagatgct   1800
gaagatcagt tgggtgcacg agtgggttac atcgaactgg atctcaacag cggtaagatc   1860
cttgagagtt ttcgccccga agaacgtttt ccaatgatga gcacttttaa agttctgcta   1920
tgtggcgcgg tattatcccg tattgacgcc gggcaagagc aactcggtcg ccgcatacac   1980
tattctcaga atgacttggt tgagtactca ccagtcacag aaaagcatct tacggatggc   2040
atgacagtaa gagaattatg cagtgctgcc ataaccatga gtgataacac tgcggccaac   2100
ttacttctga caacgatcgg aggaccgaag gagctaaccg cttttttgca caacatgggg   2160
gatcatgtaa ctcgccttga tcgttgggaa ccggagctga atgaagccat accaaacgac   2220
gagcgtgaca ccacgatgcc tgtagcaatg gcaacaacgt tgcgcaaact attaactggc   2280
gaactactta ctctagcttc ccggcaacaa ttaatagact ggatggaggc ggataaagtt   2340
gcaggaccac ttctgcgctc ggcccttccg gctggctggt ttattgctga taaatctgga   2400
gccggtgagc gtggctcacg cggtatcatt gcagcactgg ggccagatgg taagccctcc   2460
cgtatcgtag ttatctacac gacggggagt caggcaacta tggatgaacg aaatagacag   2520
atcgctgaga taggtgcctc actgattaag cattggtaac tgtcagacca agtttactca   2580
tatatacttt agattgattt aaaacttcat ttttaattta aaaggatcta ggtgaagatc   2640
ctttttgata atctcatgac caaaatccct taacgtgagt tttcgttcca ctgagcgtca   2700
gaccccgtag aaaagatcaa aggatcttct tgagatcctt tttttctgcg cgtaatctgc   2760
tgcttgcaaa caaaaaaacc accgctacca gcggtggttt gtttgccgga tcaagagcta   2820
ccaactcttt ttccgaaggt aactggcttc agcagagcgc agataccaaa tactgttctt   2880
ctagtgtagc cgtagttagg ccaccacttc aagaactctg tagcaccgcc tacatacctc   2940
```

```
gctctgctaa tcctgttacc agtggctgct gccagtggcg ataagtcgtg tcttaccggg   3000
ttggactcaa gacgatagtt accggataag gcgcagcggt cgggctgaac ggggggttcg   3060
tgcacacagc ccagcttgga gcgaacgacc tacaccgaac tgagatacct acagcgtgag   3120
ctatgagaaa gcgccacgct tcccgaaggg agaaaggcgg acaggtatcc ggtaagcggc   3180
agggtcggaa caggagagcg cacgagggag cttccagggg gaaacgcctg gtatctttat   3240
agtcctgtcg ggtttcgcca cctctgactt gagcgtcgat ttttgtgatg ctcgtcaggg   3300
gggcggagcc tatggaaaaa cgccagcaac gcggcctttt tacggttcct ggccttttgc   3360
tggccttttg ctcacatgtt ctttcctgcg ttatcccctg attctgtgga taaccgtatt   3420
accgcctttg agtgagctga taccgctcgc cgcagccgaa cgaccgagcg cagcgagtca   3480
gtgagcgagg aagcggaaga acgcggacac ccagcgtaac aatctaatat tgtttctcaa   3540
atcgggctgt tatcgcatgg tgctcatgat gaggttactg accaaattcg ccacgcatcg   3600
gtgctggtag aatgttcact tcgaggtggg tagacggcgt cacgtgcaat gccttgtctt   3660
cccctatctg cggccccgac tgcctcgcga agacaaggga tcggacgtcg aacgtattct   3720
gtttgctacc ggcacgggag taggatcgtt gatatacacc atgcgcgtta actctgaccc   3780
ccttcctctt aaatgagaat ggataagagg ctcgtgggat tgacgtgagg gggcagggat   3840
ggctatattt ctgggagcga actccgggcg aattactaat aaaaagcctt ccattttcta   3900
ttttgatttg tagaaaacta gtgtgcttgg gagtccctga tgattaaata aaccaagatt   3960
ttaccaatgg gggctagcga agcggtgatc gccgaagtat cgactcaact atcagaggta   4020
gttggcgtca tcgagcgcca tctcgaaccg acgttgctgg ccgtacattt gtacggctcc   4080
gcagtggatg gcggcctgaa gccacacagt gatattgatt tgctggttac ggtgaccgta   4140
aggcttgatg aaacaacgcg gcgagctttg atcaacgacc ttttggaaac ttcggcttcc   4200
cctggagaga gcgagattct ccgcgctgta gaagtcacca ttgttgtgca cgacgacatc   4260
attccgtggc gttatccagc taagcgcgaa ctgcaatttg gagaatggca gcgcaatgac   4320
attcttgcag gtatcttcga gccagccacg atcgacattg atctggctat cttgctgaca   4380
aaagcaagag aacatagcgt tgccttggta ggtccagcgg cggaggaact ctttgatccg   4440
gttcctgaac aggatctatt tgaggcgcta aatgaaacct taacgctatg gaactcgccg   4500
cccgactggg ctggcgatga gcgaaatgta gtgcttacgt tgtcccgcat ttggtacagc   4560
gcagtaaccg gcaaaatcgc gccgaaggat gtcgctgccg actgggcaat ggagcgcctg   4620
ccggcccagt atcagcccgt catacttgaa gctagacagg cttatcttgg acaagaagaa   4680
gatcgcttgg cctcgcgcgc agatcagttg gaagaatttg tccactacgt gaaaggcgag   4740
atcaccaagg tagtgggcaa agaacttgtt gaaggaaaat tggagctagt agaaggtctt   4800
aaagtcgcca tggctagtaa aggagaagaa cttttcactg gagttgtccc aattcttgtt   4860
gaattagatg gtgatgttaa tgggcacaaa ttttctgtca gtggagaggg tgaaggtgat   4920
gcaacatacg gaaaacttac ccttaaattt atttgcacta ctggaaaact acctgttcct   4980
tggccaacac ttgtcactac tttctcttat ggtgttcaat gcttttcaag atacccagat   5040
catatgaagc ggcacgactt cttcaagagc gccatgcctg agggatacgt gcaggagagg   5100
accatctctt tcaaggacga cgggaactac aagacacgtg ctgaagtcaa gtttgaggga   5160
gacaccctcg tcaacaggat cgagcttaag ggaatcgatt tcaaggagga cggaaacatc   5220
ctcggccaca agttggaata caactacaac tcccacaacg tatacatcac ggcagacaaa   5280
```

caaaagaatg gaatcaaagc taacttcaaa attagacaca acattgaaga tggaagcgtt 5340
caactagcag accattatca acaaaatact ccaattggcg atggccctgt ccttttacca 5400
gacaaccatt acctgtccac acaatctgcc ctttcgaaag atcccaacga aaagagagat 5460
cacatggtcc ttcttgagtt tgtaacagct gctgggatta cacatggcat ggatgaacta 5520
tacaaataag cttaaacagt agacattagc agataaatta gcaggaaata aagaaggata 5580
aggagaaaga actcaagtaa ttatccttcg ttctcttaat tgaattgcaa ttaaactcgg 5640
cccaatcttt tactaaaagg attgagccga ataccgctac aacagctccc tggaacacca 5700
ggagaacaca cttatctcgc gtcttgaggt gataccacgc ctgacacgtg agggcagtac 5760
ggttaattcg gtttagccgg acatcagcgc tcctcattga gcgctgggcc cttcacatga 5820
agatcgcact gaggattggt cctagccagg cttctcagta ctgatacagt acgcgtcgct 5880
tctcgtattg tttgagtctt ggaattagtt tgtatccttc cgccgctgcc ctaagaattc 5940
taattgagct cgaacagtcg accgccggat cctgctcgag tgcctctaga 5990

<210> SEQ ID NO 76
<211> LENGTH: 6070
<212> TYPE: DNA
<213> ORGANISM: Artificial Sequence
<220> FEATURE:
<223> OTHER INFORMATION: An example of an episomal DNA vector

<400> SEQUENCE: 76
tgcccaccat agcgcgccgg ttgcctgcgg ttactggacc aagctcgtca actcggagca 60
ggctttatgg gcctcgcttc cttaagtcac atcgacaatt caataaggta tccgacatta 120
acaatgattt aaattgtgtt cattgtgttt tttatggtac ataaccttca tagatttata 180
gattatctca aaaacagaag aaagggtgga aagtgaggaa gaaagagatg tagaaataga 240
aacagcttcc gaaatgaagg ggactaaaca ggaacaagag ggatccactg aagaagatcc 300
ttatccttct ccttcccttt tttcggaaga aaggtgggat ccggacaaaa tcgatgaaac 360
ggaagaaatc cgagtgaatg gaaaggacaa aataaaggat aaattccact ctcaccttac 420
agagacaggt tcctatatga ggaagtatcc ttccccgcag tcaagaccaa ggttagtatt 480
ctctgctagg aagtttactt aggttactct agcatgtgcc tggataaccc tctaggcaaa 540
ggtggattga ctttgtactg tcctcagatc gacgttggat gaactgtcgc gccacgaggg 600
gctgtggagc gcattgcgac acattggtgc gctgctaacc catcctttcc agtacggcta 660
ctgatgtcca cgctcccagc ctgctacgct ccgcccggcg tggtctgctg tcctacttcc 720
ctgtgttccc gtcgaatctt tttttgcttt gccttctccc cattccaatc tttgcgactg 780
aaacgtacgt acactgtgct ttgcattatt agtttttgaa attgtggcct attttttgtc 840
cttaaaccgc tcatctttac accatcgttc tttgtggaca ttcttttcct tgctaattgg 900
tattctacaa actggcacta gctgtagtca atctgactgt tgctagaaag ttattctttt 960
cgtcttaatg attatatgta aatcgccctc tatatattaa ctctacttat atggaaaaac 1020
tatgattaag tagttacagt cgacgcgcgg gtgacacccc tacgccgact cgataaacag 1080
gatgggtcat gggcctggca cgtgttattc aaaggtacag cggggagcgc acgcgcaagg 1140
tcgcaactac ccgagaatcg atgtggcgga atgggttacg tgagctatta tccggcgggc 1200
cctcaattta aatcgttaca gttgctcgta acggcaaccg gctcggtcct ttttccctag 1260
aacagtatct tatacttgct gctctcgtta cttcggcgat cctggtgcag tcggtccgta 1320
aatcggcgca cacttttacg tcgtaccaga caggctcgca taagccagcc ccgacacccg 1380
ccaacacccg ctgacgcgcc ctgacgggct tgtctgctcc cggcatccgc ttacagacaa 1440
gctgtgacct ccgggagctg catgtgtcag aggttttcac cgtcatcacc gaaacgcgca 1500
cgaaagggcc tcgtgatacg cctattttta taggttaatg tcatgataat aatggtttct 1560
tagacgtcag gtggcacttt tcggggaaat gtgcgcggaa cccctatttg tttatttttc 1620
taaatacatt caaatatgta tccgctcatg agacaataac cctgataaat gcttcaataa 1680
tattgaaaaa ggaagagtat gagtattcaa catttccgtg tcgcccttat tccctttttt 1740
gcggcatttt gccttcctgt ttttgctcac ccagaaacgc tggtgaaagt aaaagatgct 1800
gaagatcagt tgggtgcacg agtgggttac atcgaactgg atctcaacag cggtaagatc 1860
cttgagagtt ttcgccccga agaacgtttt ccaatgatga gcacttttaa agttctgcta 1920
tgtggcgcgg tattatcccg tattgacgcc gggcaagagc aactcggtcg ccgcatacac 1980
tattctcaga atgacttggt tgagtactca ccagtcacag aaaagcatct tacggatggc 2040
atgacagtaa gagaattatg cagtgctgcc ataaccatga gtgataacac tgcggccaac 2100
ttacttctga caacgatcgg aggaccgaag gagctaaccg cttttttgca caacatgggg 2160
gatcatgtaa ctcgccttga tcgttgggaa ccggagctga atgaagccat accaaacgac 2220
gagcgtgaca ccacgatgcc tgtagcaatg gcaacaacgt tgcgcaaact attaactggc 2280
gaactactta ctctagcttc ccggcaacaa ttaatagact ggatggaggc ggataaagtt 2340
gcaggaccac ttctgcgctc ggcccttccg gctggctggt ttattgctga taaatctgga 2400
gccggtgagc gtggctcacg cggtatcatt gcagcactgg ggccagatgg taagccctcc 2460
cgtatcgtag ttatctacac gacggggagt caggcaacta tggatgaacg aaatagacag 2520
atcgctgaga taggtgcctc actgattaag cattggtaac tgtcagacca agtttactca 2580
tatatacttt agattgattt aaaacttcat ttttaattta aaaggatcta ggtgaagatc 2640
ctttttgata atctcatgac caaaatccct taacgtgagt tttcgttcca ctgagcgtca 2700
gaccccgtag aaaagatcaa aggatcttct tgagatcctt tttttctgcg cgtaatctgc 2760
tgcttgcaaa caaaaaaacc accgctacca gcggtggttt gtttgccgga tcaagagcta 2820
ccaactcttt ttccgaaggt aactggcttc agcagagcgc agataccaaa tactgttctt 2880
ctagtgtagc cgtagttagg ccaccacttc aagaactctg tagcaccgcc tacatacctc 2940
gctctgctaa tcctgttacc agtggctgct gccagtggcg ataagtcgtg tcttaccggg 3000
ttggactcaa gacgatagtt accggataag gcgcagcggt cgggctgaac ggggggttcg 3060
tgcacacagc ccagcttgga gcgaacgacc tacaccgaac tgagatacct acagcgtgag 3120
ctatgagaaa gcgccacgct tcccgaaggg agaaaggcgg acaggtatcc ggtaagcggc 3180
agggtcggaa caggagagcg cacgagggag cttccagggg gaaacgcctg gtatctttat 3240
agtcctgtcg ggtttcgcca cctctgactt gagcgtcgat ttttgtgatg ctcgtcaggg 3300
gggcggagcc tatggaaaaa cgccagcaac gcggcctttt tacggttcct ggccttttgc 3360
tggccttttg ctcacatgtt ctttcctgcg ttatcccctg attctgtgga taaccgtatt 3420
accgcctttg agtgagctga taccgctcgc cgcagccgaa cgaccgagcg cagcgagtca 3480
gtgagcgagg aagcggaaga acgcggacac ccagcgtaac aatctaatat tgtttctcaa 3540
atcgggctgt tatcgcatgg tgctcatgat gaggttactg accaaattcg ccacgcatcg 3600
gtgctggtag aatgttcact tcgaggtggg tagacggcgt cacgtgcaat gccttgtctt 3660
cccctatctg cggccccgac tgcctcgcga agacaaggga tcggacgtcg aacgtattct 3720

-continued

```
gtttgctacc ggcacgggag taggatcgtt gatatacacc atgcgcgtta actctgaccc   3780
ccttcctctt aaatgagaat ggataagagg ctcgtgggat tgacgtgagg gggcagggat   3840
ggctatattt ctgggagcga actccgggcg aattactaat aaaaagcctt ccattttcta   3900
ttttgatttg tagaaaacta gtgtgcttgg gagtccctga tgattaaata aaccaagatt   3960
ttaccaatgg gggctagcga agcggtgatc gccgaagtat cgactcaact atcagaggta   4020
gttggcgtca tcgagcgcca tctcgaaccg acgttgctgg ccgtacattt gtacggctcc   4080
gcagtggatg gcggcctgaa gccacacagt gatattgatt tgctggttac ggtgaccgta   4140
aggcttgatg aaacaacgcg gcgagctttg atcaacgacc ttttggaaac ttcggcttcc   4200
cctggagaga gcgagattct ccgcgctgta gaagtcacca ttgttgtgca cgacgacatc   4260
attccgtggc gttatccagc taagcgcgaa ctgcaatttg gagaatggca gcgcaatgac   4320
attcttgcag gtatcttcga gccagccacg atcgacattg atctggctat cttgctgaca   4380
aaagcaagag aacatagcgt tgccttggta ggtccagcgg cggaggaact ctttgatccg   4440
gttcctgaac aggatctatt tgaggcgcta aatgaaacct taacgctatg gaactcgccg   4500
cccgactggg ctggcgatga gcgaaatgta gtgcttacgt tgtcccgcat ttggtacagc   4560
gcagtaaccg gcaaaatcgc gccgaaggat gtcgctgccg actgggcaat ggagcgcctg   4620
ccggcccagt atcagcccgt catacttgaa gctagacagg cttatcttgg acaagaagaa   4680
gatcgcttgg cctcgcgcgc agatcagttg gaagaatttg tccactacgt gaaaggcgag   4740
atcaccaagg tagtgggcaa agaacttgtt gaaggaaaat tggagctagt agaaggtctt   4800
aaagtcgcca tggctagtaa aggagaagaa cttttcactg gagttgtccc aattcttgtt   4860
gaattagatg gtgatgttaa tgggcacaaa ttttctgtca gtggagaggg tgaaggtgat   4920
gcaacatacg gaaaacttac ccttaaattt atttgcacta ctggaaaact acctgttcct   4980
tggccaacac ttgtcactac tttctcttat ggtgttcaat gcttttcaag atacccagat   5040
catatgaagc ggcacgactt cttcaagagc gccatgcctg agggatacgt gcaggagagg   5100
accatctctt tcaaggacga cgggaactac aagacacgtg ctgaagtcaa gtttgaggga   5160
gacaccctcg tcaacaggat cgagcttaag ggaatcgatt tcaaggagga cggaaacatc   5220
ctcggccaca agttggaata caactacaac tcccacaacg tatacatcac ggcagacaaa   5280
caaaagaatg gaatcaaagc taacttcaaa attagacaca acattgaaga tggaagcgtt   5340
caactagcag accattatca acaaaatact ccaattggcg atggccctgt ccttttacca   5400
gacaaccatt acctgtccac acaatctgcc ctttcgaaag atcccaacga aaagagagat   5460
cacatggtcc ttcttgagtt tgtaacagct gctgggatta cacatggcat ggatgaacta   5520
tacaaataag cttaaacagt agacattagc agataaatta gcaggaaata aagaaggata   5580
aggagaaaga actcaagtaa ttatccttcg ttctcttaat tgaattgcaa ttaaactcgg   5640
cccaatcttt tactaaaagg attgagccga ataccgctcc aggcatcaaa taaaacgaaa   5700
ggctcagtcg aaagactggg cctttcgttt tatctgttgt ttgtcggtga acgctctcac   5760
aacagctccc tggaacacca ggagaacaca cttatctcgc gtcttgaggt gataccacgc   5820
ctgacacgtg agggcagtac ggttaattcg gtttagccgg acatcagcgc tcctcattga   5880
gcgctgggcc cttcacatga agatcgcact gaggattggt cctagccagg cttctcagta   5940
ctgatacagt acgcgtcgct tctcgtattg tttgagtctt ggaattagtt tgtatccttc   6000
cgccgctgcc ctaagaattc taattgagct cgaacagtcg accgccggat cctgctcgag   6060
tgcctctaga                                                          6070
```

<210> SEQ ID NO 77
<211> LENGTH: 5990
<212> TYPE: DNA
<213> ORGANISM: Artificial Sequence
<220> FEATURE:
<223> OTHER INFORMATION: An example of an episomal DNA vector

<400> SEQUENCE: 77
tgcccaccat agcgcgccgg ttgcctgcgg ttactggacc aagctcgtca actcggagca 60
ggctttatgg gcctcgcttc cttaagtcac atcgacaatt caataaggta tccgacatta 120
acaatgattt aaattgtgtt cattgtgttt tttatggtac ataaccttca tagatttata 180
gattatctca aaaacagaag aaagggtgga aagtgaggaa gaaagagatg tagaaataga 240
aacagcttcc gaaatgaagg ggactaaaca ggaacaagag ggatccactg aagaagatcc 300
ttatccttct ccttcccttt tttcggaaga aaggtgggat ccggacaaaa tcgatgaaac 360
ggaagaaatc cgagtgaatg gaaaggacaa aataaaggat aaattccact ctcaccttac 420
agagacaggt tcctatatga ggaagtatcc ttccccgcag tcaagaccaa ggttagtatt 480
ctctgctagg aagtttactt aggttactct agcatgtgcc tggataaccc tctaggcaaa 540
ggtggattga ctttgtactg tcctcagatc gacgttggat gaactgtcgc gccacgaggg 600
gctgtggagc gcattgcgac acattggtgc gctgctaacc catcctttcc agtacggcta 660
ctgatgtcca cgctcccagc ctgctacgct ccgcccgcct gtctctgtaa ggtgagagtg 720
gaatttatcc tttattttgt cctttccatt cactcggatt tcttccgttt catcgatttt 780
gtccggatcc cacctttctt ccgaaaaaag ggaaggagaa ggataaggat cttcttcagt 840
ggatccctct tgttcctgtt tagtcccctt catttcggaa gctgtttcta tttctacatc 900
tctttcttcc tcactttcca ccctttcttc tgtttttgag tgctagaaag ttattctttt 960
cgtcttaatg attatatgta aatcgccctc tatatattaa ctctacttat atggaaaaac 1020
tatgattaag tagttacagt cgagaagaga ggagccgtgg tggtccccc cggaccgccc 1080
ggatcccacg agtgaatcga aagttggatc tacattggat ctgggagcgc acgcgcaagg 1140
tcgcaactac ccgagaatcg atgtggcgga atgggttacg tgagctatta tccggcgggc 1200
cctcaattta aatcgttaca gttgctcgta acggcaaccg gctcggtcct ttttccctag 1260
aacagtatct tatacttgct gctctcgtta cttcggcgat cctggtgcag tcggtccgta 1320
aatcggcgca cacttttacg tcgtaccaga caggctcgca taagccagcc ccgacacccg 1380
ccaacacccg ctgacgcgcc ctgacgggct tgtctgctcc cggcatccgc ttacagacaa 1440
gctgtgacct ccgggagctg catgtgtcag aggttttcac cgtcatcacc gaaacgcgca 1500
cgaaagggcc tcgtgatacg cctattttta taggttaatg tcatgataat aatggtttct 1560
tagacgtcag gtggcacttt tcggggaaat gtgcgcggaa cccctatttg tttatttttc 1620
taaatacatt caaatatgta tccgctcatg agacaataac cctgataaat gcttcaataa 1680
tattgaaaaa ggaagagtat gagtattcaa catttccgtg tcgcccttat tccctttttt 1740
gcggcatttt gccttcctgt ttttgctcac ccagaaacgc tggtgaaagt aaaagatgct 1800
gaagatcagt tgggtgcacg agtgggttac atcgaactgg atctcaacag cggtaagatc 1860
cttgagagtt ttcgccccga agaacgtttt ccaatgatga gcacttttaa agttctgcta 1920
tgtggcgcgg tattatcccg tattgacgcc gggcaagagc aactcggtcg ccgcatacac 1980
tattctcaga atgacttggt tgagtactca ccagtcacag aaaagcatct tacggatggc 2040

-continued

```
atgacagtaa gagaattatg cagtgctgcc ataaccatga gtgataacac tgcggccaac   2100
ttacttctga caacgatcgg aggaccgaag gagctaaccg cttttttgca caacatgggg   2160
gatcatgtaa ctcgccttga tcgttgggaa ccggagctga atgaagccat accaaacgac   2220
gagcgtgaca ccacgatgcc tgtagcaatg gcaacaacgt tgcgcaaact attaactggc   2280
gaactactta ctctagcttc ccggcaacaa ttaatagact ggatggaggc ggataaagtt   2340
gcaggaccac ttctgcgctc ggcccttccg gctggctggt ttattgctga taaatctgga   2400
gccggtgagc gtggctcacg cggtatcatt gcagcactgg ggccagatgg taagccctcc   2460
cgtatcgtag ttatctacac gacggggagt caggcaacta tggatgaacg aaatagacag   2520
atcgctgaga taggtgcctc actgattaag cattggtaac tgtcagacca agtttactca   2580
tatatacttt agattgattt aaaacttcat ttttaattta aaaggatcta ggtgaagatc   2640
ctttttgata atctcatgac caaaatccct taacgtgagt tttcgttcca ctgagcgtca   2700
gaccccgtag aaaagatcaa aggatcttct tgagatcctt tttttctgcg cgtaatctgc   2760
tgcttgcaaa caaaaaaacc accgctacca gcggtggttt gtttgccgga tcaagagcta   2820
ccaactcttt ttccgaaggt aactggcttc agcagagcgc agataccaaa tactgttctt   2880
ctagtgtagc cgtagttagg ccaccacttc aagaactctg tagcaccgcc tacatacctc   2940
gctctgctaa tcctgttacc agtggctgct gccagtggcg ataagtcgtg tcttaccggg   3000
ttggactcaa gacgatagtt accggataag gcgcagcggt cgggctgaac ggggggttcg   3060
tgcacacagc ccagcttgga gcgaacgacc tacaccgaac tgagatacct acagcgtgag   3120
ctatgagaaa gcgccacgct tcccgaaggg agaaaggcgg acaggtatcc ggtaagcggc   3180
agggtcggaa caggagagcg cacgagggag cttccagggg gaaacgcctg gtatctttat   3240
agtcctgtcg ggtttcgcca cctctgactt gagcgtcgat ttttgtgatg ctcgtcaggg   3300
gggcggagcc tatggaaaaa cgccagcaac gcggcctttt tacggttcct ggccttttgc   3360
tggccttttg ctcacatgtt ctttcctgcg ttatcccctg attctgtgga taaccgtatt   3420
accgcctttg agtgagctga taccgctcgc cgcagccgaa cgaccgagcg cagcgagtca   3480
gtgagcgagg aagcggaaga acgcggacac ccagcgtaac aatctaatat tgtttctcaa   3540
atcgggctgt tatcgcatgg tgctcatgat gaggttactg accaaattcg ccacgcatcg   3600
gtgctggtag aatgttcact tcgaggtggg tagacggcgt cacgtgcaat gccttgtctt   3660
cccctatctg cggccccgac tgcctcgcga agacaaggga tcggacgtcg aacgtattct   3720
gtttgctacc ggcacgggag taggatcgtt gatatacacc atgcgcgtta actctgaccc   3780
ccttcctctt aaatgagaat ggataagagg ctcgtgggat tgacgtgagg gggcagggat   3840
ggctatattt ctgggagcga actccgggcg aattactaat aaaaagcctt ccatttttcta   3900
ttttgatttg tagaaaacta gtgtgcttgg gagtccctga tgattaaata aaccaagatt   3960
ttaccaatgg gggctagcga agcggtgatc gccgaagtat cgactcaact atcagaggta   4020
gttggcgtca tcgagcgcca tctcgaaccg acgttgctgg ccgtacattt gtacggctcc   4080
gcagtggatg gcggcctgaa gccacacagt gatattgatt tgctggttac ggtgaccgta   4140
aggcttgatg aaacaacgcg gcgagctttg atcaacgacc ttttggaaac ttcggcttcc   4200
cctggagaga gcgagattct ccgcgctgta gaagtcacca ttgttgtgca cgacgacatc   4260
attccgtggc gttatccagc taagcgcgaa ctgcaatttg gagaatggca gcgcaatgac   4320
attcttgcag gtatcttcga gccagccacg atcgacattg atctggctat cttgctgaca   4380
aaagcaagag aacatagcgt tgccttggta ggtccagcgg cggaggaact ctttgatccg   4440
```

gttcctgaac aggatctatt tgaggcgcta aatgaaacct taacgctatg gaactcgccg 4500
cccgactggg ctggcgatga gcgaaatgta gtgcttacgt tgtcccgcat ttggtacagc 4560
gcagtaaccg gcaaaatcgc gccgaaggat gtcgctgccg actgggcaat ggagcgcctg 4620
ccggcccagt atcagcccgt catacttgaa gctagacagg cttatcttgg acaagaagaa 4680
gatcgcttgg cctcgcgcgc agatcagttg gaagaatttg tccactacgt gaaaggcgag 4740
atcaccaagg tagtgggcaa agaacttgtt gaaggaaaat tggagctagt agaaggtctt 4800
aaagtcgcca tggctagtaa aggagaagaa cttttcactg gagttgtccc aattcttgtt 4860
gaattagatg gtgatgttaa tgggcacaaa ttttctgtca gtggagaggg tgaaggtgat 4920
gcaacatacg gaaaacttac ccttaaattt atttgcacta ctggaaaact acctgttcct 4980
tggccaacac ttgtcactac tttctcttat ggtgttcaat gcttttcaag atacccagat 5040
catatgaagc ggcacgactt cttcaagagc gccatgcctg agggatacgt gcaggagagg 5100
accatctctt tcaaggacga cgggaactac aagacacgtg ctgaagtcaa gtttgaggga 5160
gacaccctcg tcaacaggat cgagcttaag ggaatcgatt tcaaggagga cggaaacatc 5220
ctcggccaca agttggaata caactacaac tcccacaacg tatacatcac ggcagacaaa 5280
caaaagaatg gaatcaaagc taacttcaaa attagacaca acattgaaga tggaagcgtt 5340
caactagcag accattatca acaaaatact ccaattggcg atggccctgt ccttttacca 5400
gacaaccatt acctgtccac acaatctgcc ctttcgaaag atcccaacga aaagagagat 5460
cacatggtcc ttcttgagtt tgtaacagct gctgggatta cacatggcat ggatgaacta 5520
tacaaataag cttaaacagt agacattagc agataaatta gcaggaaata aagaaggata 5580
aggagaaaga actcaagtaa ttatccttcg ttctcttaat tgaattgcaa ttaaactcgg 5640
cccaatcttt tactaaaagg attgagccga ataccgctac aacagctccc tggaacacca 5700
ggagaacaca cttatctcgc gtcttgaggt gataccacgc ctgacacgtg agggcagtac 5760
ggttaattcg gtttagccgg acatcagcgc tcctcattga gcgctgggcc cttcacatga 5820
agatcgcact gaggattggt cctagccagg cttctcagta ctgatacagt acgcgtcgct 5880
tctcgtattg tttgagtctt ggaattagtt tgtatccttc cgccgctgcc ctaagaattc 5940
taattgagct cgaacagtcg accgccggat cctgctcgag tgcctctaga 5990

<210> SEQ ID NO 78
<211> LENGTH: 6070
<212> TYPE: DNA
<213> ORGANISM: Artificial Sequence
<220> FEATURE:
<223> OTHER INFORMATION: An example of an episomal DNA vector

<400> SEQUENCE: 78
tgcccaccat agcgcgccgg ttgcctgcgg ttactggacc aagctcgtca actcggagca 60
ggctttatgg gcctcgcttc cttaagtcac atcgacaatt caataaggta tccgacatta 120
acaatgattt aaattgtgtt cattgtgttt tttatggtac ataaccttca tagatttata 180
gattatctca aaaacagaag aaagggtgga aagtgaggaa gaaagagatg tagaaataga 240
aacagcttcc gaaatgaagg ggactaaaca ggaacaagag ggatccactg aagaagatcc 300
ttatccttct ccttcccttt tttcggaaga aaggtgggat ccggacaaaa tcgatgaaac 360
ggaagaaatc cgagtgaatg gaaaggacaa aataaaggat aaattccact ctcaccttac 420
agagacaggt tcctatatga ggaagtatcc ttccccgcag tcaagaccaa ggttagtatt 480

-continued

```
ctctgctagg aagtttactt aggttactct agcatgtgcc tggataaccc tctaggcaaa    540
ggtggattga ctttgtactg tcctcagatc gacgttggat gaactgtcgc gccacgaggg    600
gctgtggagc gcattgcgac acattggtgc gctgctaacc catcctttcc agtacggcta    660
ctgatgtcca cgctcccagc ctgctacgct ccgcccgcct gtctctgtaa ggtgagagtg    720
gaatttatcc tttattttgt cctttccatt cactcggatt tcttccgttt catcgatttt    780
gtccggatcc cacctttctt ccgaaaaaag ggaaggagaa ggataaggat cttcttcagt    840
ggatccctct tgttcctgtt tagtcccctt catttcggaa gctgtttcta tttctacatc    900
tctttcttcc tcactttcca ccctttcttc tgtttttgag tgctagaaag ttattctttt    960
cgtcttaatg attatatgta aatcgccctc tatatattaa ctctacttat atggaaaaac   1020
tatgattaag tagttacagt cgagaagaga ggagccgtgg tggtcccccc cggaccgccc   1080
ggatcccacg agtgaatcga aagttggatc tacattggat ctgggagcgc acgcgcaagg   1140
tcgcaactac ccgagaatcg atgtggcgga atgggttacg tgagctatta tccggcgggc   1200
cctcaattta aatcgttaca gttgctcgta acggcaaccg gctcggtcct ttttccctag   1260
aacagtatct tatacttgct gctctcgtta cttcggcgat cctggtgcag tcggtccgta   1320
aatcggcgca cacttttacg tcgtaccaga caggctcgca taagccagcc ccgacacccg   1380
ccaacacccg ctgacgcgcc ctgacgggct tgtctgctcc cggcatccgc ttacagacaa   1440
gctgtgacct ccgggagctg catgtgtcag aggttttcac cgtcatcacc gaaacgcgca   1500
cgaaagggcc tcgtgatacg cctattttta taggttaatg tcatgataat aatggtttct   1560
tagacgtcag gtggcacttt tcggggaaat gtgcgcggaa cccctatttg tttatttttc   1620
taaatacatt caaatatgta tccgctcatg agacaataac cctgataaat gcttcaataa   1680
tattgaaaaa ggaagagtat gagtattcaa catttccgtg tcgcccttat tccctttttt   1740
gcggcatttt gccttcctgt ttttgctcac ccagaaacgc tggtgaaagt aaaagatgct   1800
gaagatcagt tgggtgcacg agtgggttac atcgaactgg atctcaacag cggtaagatc   1860
cttgagagtt ttcgccccga agaacgtttt ccaatgatga gcacttttaa agttctgcta   1920
tgtggcgcgg tattatcccg tattgacgcc gggcaagagc aactcggtcg ccgcatacac   1980
tattctcaga atgacttggt tgagtactca ccagtcacag aaaagcatct tacggatggc   2040
atgacagtaa gagaattatg cagtgctgcc ataaccatga gtgataacac tgcggccaac   2100
ttacttctga caacgatcgg aggaccgaag gagctaaccg cttttttgca caacatgggg   2160
gatcatgtaa ctcgccttga tcgttgggaa ccggagctga atgaagccat accaaacgac   2220
gagcgtgaca ccacgatgcc tgtagcaatg gcaacaacgt tgcgcaaact attaactggc   2280
gaactactta ctctagcttc ccggcaacaa ttaatagact ggatggaggc ggataaagtt   2340
gcaggaccac ttctgcgctc ggcccttccg gctggctggt ttattgctga taaatctgga   2400
gccggtgagc gtggctcacg cggtatcatt gcagcactgg ggccagatgg taagccctcc   2460
cgtatcgtag ttatctacac gacggggagt caggcaacta tggatgaacg aaatagacag   2520
atcgctgaga taggtgcctc actgattaag cattggtaac tgtcagacca agtttactca   2580
tatatacttt agattgattt aaaacttcat ttttaattta aaaggatcta ggtgaagatc   2640
ctttttgata atctcatgac caaaatccct taacgtgagt tttcgttcca ctgagcgtca   2700
gaccccgtag aaaagatcaa aggatcttct tgagatcctt tttttctgcg cgtaatctgc   2760
tgcttgcaaa caaaaaaacc accgctacca gcggtggttt gtttgccgga tcaagagcta   2820
ccaactcttt ttccgaaggt aactggcttc agcagagcgc agataccaaa tactgttctt   2880
```

```
ctagtgtagc cgtagttagg ccaccacttc aagaactctg tagcaccgcc tacatacctc   2940
gctctgctaa tcctgttacc agtggctgct gccagtggcg ataagtcgtg tcttaccggg   3000
ttggactcaa gacgatagtt accggataag gcgcagcggt cgggctgaac ggggggttcg   3060
tgcacacagc ccagcttgga gcgaacgacc tacaccgaac tgagatacct acagcgtgag   3120
ctatgagaaa gcgccacgct tcccgaaggg agaaaggcgg acaggtatcc ggtaagcggc   3180
agggtcggaa caggagagcg cacgagggag cttccagggg gaaacgcctg gtatctttat   3240
agtcctgtcg ggtttcgcca cctctgactt gagcgtcgat ttttgtgatg ctcgtcaggg   3300
gggcggagcc tatggaaaaa cgccagcaac gcggcctttt tacggttcct ggccttttgc   3360
tggccttttg ctcacatgtt ctttcctgcg ttatcccctg attctgtgga taaccgtatt   3420
accgcctttg agtgagctga taccgctcgc cgcagccgaa cgaccgagcg cagcgagtca   3480
gtgagcgagg aagcggaaga acgcggacac ccagcgtaac aatctaatat tgtttctcaa   3540
atcgggctgt tatcgcatgg tgctcatgat gaggttactg accaaattcg ccacgcatcg   3600
gtgctggtag aatgttcact tcgaggtggg tagacggcgt cacgtgcaat gccttgtctt   3660
cccctatctg cggccccgac tgcctcgcga agacaaggga tcggacgtcg aacgtattct   3720
gtttgctacc ggcacgggag taggatcgtt gatatacacc atgcgcgtta actctgaccc   3780
ccttcctctt aaatgagaat ggataagagg ctcgtgggat tgacgtgagg gggcagggat   3840
ggctatattt ctgggagcga actccgggcg aattactaat aaaaagcctt ccatttcta    3900
ttttgatttg tagaaaacta gtgtgcttgg gagtccctga tgattaaata aaccaagatt   3960
ttaccaatgg gggctagcga agcggtgatc gccgaagtat cgactcaact atcagaggta   4020
gttggcgtca tcgagcgcca tctcgaaccg acgttgctgg ccgtacattt gtacggctcc   4080
gcagtggatg gcggcctgaa gccacacagt gatattgatt tgctggttac ggtgaccgta   4140
aggcttgatg aaacaacgcg gcgagctttg atcaacgacc ttttggaaac ttcggcttcc   4200
cctggagaga gcgagattct ccgcgctgta gaagtcacca ttgttgtgca cgacgacatc   4260
attccgtggc gttatccagc taagcgcgaa ctgcaatttg gagaatggca gcgcaatgac   4320
attcttgcag gtatcttcga gccagccacg atcgacattg atctggctat cttgctgaca   4380
aaagcaagag aacatagcgt tgccttggta ggtccagcgg cggaggaact ctttgatccg   4440
gttcctgaac aggatctatt tgaggcgcta aatgaaacct taacgctatg gaactcgccg   4500
cccgactggg ctggcgatga gcgaaatgta gtgcttacgt tgtcccgcat ttggtacagc   4560
gcagtaaccg gcaaaatcgc gccgaaggat gtcgctgccg actgggcaat ggagcgcctg   4620
ccggcccagt atcagcccgt catacttgaa gctagacagg cttatcttgg acaagaagaa   4680
gatcgcttgg cctcgcgcgc agatcagttg gaagaatttg tccactacgt gaaaggcgag   4740
atcaccaagg tagtgggcaa agaacttgtt gaaggaaaat tggagctagt agaaggtctt   4800
aaagtcgcca tggctagtaa aggagaagaa cttttcactg gagttgtccc aattcttgtt   4860
gaattagatg gtgatgttaa tgggcacaaa ttttctgtca gtggagaggg tgaaggtgat   4920
gcaacatacg gaaaacttac ccttaaattt atttgcacta ctggaaaact acctgttcct   4980
tggccaacac ttgtcactac tttctcttat ggtgttcaat gcttttcaag atacccagat   5040
catatgaagc ggcacgactt cttcaagagc gccatgcctg agggatacgt gcaggagagg   5100
accatctctt tcaaggacga cgggaactac aagacacgtg ctgaagtcaa gtttgaggga   5160
gacaccctcg tcaacaggat cgagcttaag ggaatcgatt tcaaggagga cggaaacatc   5220
```

```
ctcggccaca agttggaata caactacaac tcccacaacg tatacatcac ggcagacaaa   5280

caaaagaatg gaatcaaagc taacttcaaa attagacaca acattgaaga tggaagcgtt   5340

caactagcag accattatca acaaaatact ccaattggcg atggccctgt ccttttacca   5400

gacaaccatt acctgtccac acaatctgcc ctttcgaaag atcccaacga aaagagagat   5460

cacatggtcc ttcttgagtt tgtaacagct gctgggatta cacatggcat ggatgaacta   5520

tacaaataag cttaaacagt agacattagc agataaatta gcaggaaata aagaaggata   5580

aggagaaaga actcaagtaa ttatccttcg ttctcttaat tgaattgcaa ttaaactcgg   5640

cccaatcttt tactaaaagg attgagccga ataccgctcc aggcatcaaa taaaacgaaa   5700

ggctcagtcg aaagactggg cctttcgttt tatctgttgt ttgtcggtga acgctctcac   5760

aacagctccc tggaacacca ggagaacaca cttatctcgc gtcttgaggt gataccacgc   5820

ctgacacgtg agggcagtac ggttaattcg gtttagccgg acatcagcgc tcctcattga   5880

gcgctgggcc cttcacatga agatcgcact gaggattggt cctagccagg cttctcagta   5940

ctgatacagt acgcgtcgct tctcgtattg tttgagtctt ggaattagtt tgtatccttc   6000

cgccgctgcc ctaagaattc taattgagct cgaacagtcg accgccggat cctgctcgag   6060

tgcctctaga                                                          6070
```

<210> SEQ ID NO 79
<211> LENGTH: 5990
<212> TYPE: DNA
<213> ORGANISM: Artificial Sequence
<220> FEATURE:
<223> OTHER INFORMATION: An example of an episomal DNA vector

<400> SEQUENCE: 79

```
tgcccaccat agcgcgccgg ttgcctgcgg ttactggacc aagctcgtca actcggagca     60

ggctttatgg gcctcgcttc cttaagtcac atcgacaatt caataaggta tccgacatta    120

acaatgattt aaattgtgtt cattgtgttt tttatggtac ataaccttca tagatttata    180

gattatctca aaaacagaag aaagggtgga aagtgaggaa gaaagagatg tagaaataga    240

aacagcttcc gaaatgaagg ggactaaaca ggaacaagag ggatccactg aagaagatcc    300

ttatccttct ccttcccttt tttcggaaga aaggtgggat ccggacaaaa tcgatgaaac    360

ggaagaaatc cgagtgaatg gaaaggacaa aataaaggat aaattccact ctcaccttac    420

agagacaggt tcctatatga ggaagtatcc ttccccgcag tcaagaccaa ggttagtatt    480

ctctgctagg aagtttactt aggttactct agcatgtgcc tggataaccc tctaggcaaa    540

ggtggattga ctttgtactg tcctcagatc gacgttggat gaactgtcgc gccacgaggg    600

gctgtggagc gcattgcgac acattggtgc gctgctaacc catcctttcc agtacggcta    660

ctgatgtcca cgctcccagc ctgctacgct ccgcccgcct gtctctgtaa ggtgagagtg    720

gaatttatcc tttattttgt cctttccatt cactcggatt tcttccgttt catcgatttt    780

gtccggatcc cacctttctt ccgaaaaaag ggaaggagaa ggataaggat cttcttcagt    840

ggatccctct tgttcctgtt tagtcccctt catttcggaa gctgtttcta tttctacatc    900

tctttcttcc tcactttcca ccctttcttc tgtttttgag tgctagaaag ttattctttt    960

cgtcttaatg attatatgta aatcgccctc tatatattaa ctctacttat atggaaaaac   1020

tatgattaag tagttacagt cgacgcgcgg gtgacacccc tacgccgact cgataaacag   1080

gatgggtcat gggcctggca cgtgttattc aaaggtacag cggggagcgc acgcgcaagg   1140

tcgcaactac ccgagaatcg atgtggcgga atgggttacg tgagctatta tccggcgggc   1200
```

-continued

```
cctcaattta aatcgttaca gttgctcgta acggcaaccg gctcggtcct ttttccctag   1260
aacagtatct tatacttgct gctctcgtta cttcggcgat cctggtgcag tcggtccgta   1320
aatcggcgca cacttttacg tcgtaccaga caggctcgca taagccagcc ccgacacccg   1380
ccaacacccg ctgacgcgcc ctgacgggct tgtctgctcc cggcatccgc ttacagacaa   1440
gctgtgacct ccgggagctg catgtgtcag aggttttcac cgtcatcacc gaaacgcgca   1500
cgaaagggcc tcgtgatacg cctattttta taggttaatg tcatgataat aatggtttct   1560
tagacgtcag gtggcacttt tcggggaaat gtgcgcggaa cccctatttg tttatttttc   1620
taaatacatt caaatatgta tccgctcatg agacaataac cctgataaat gcttcaataa   1680
tattgaaaaa ggaagagtat gagtattcaa catttccgtg tcgcccttat tccctttttt   1740
gcggcatttt gccttcctgt ttttgctcac ccagaaacgc tggtgaaagt aaaagatgct   1800
gaagatcagt tgggtgcacg agtgggttac atcgaactgg atctcaacag cggtaagatc   1860
cttgagagtt ttcgccccga agaacgtttt ccaatgatga gcacttttaa agttctgcta   1920
tgtggcgcgg tattatcccg tattgacgcc gggcaagagc aactcggtcg ccgcatacac   1980
tattctcaga atgacttggt tgagtactca ccagtcacag aaaagcatct tacggatggc   2040
atgacagtaa gagaattatg cagtgctgcc ataaccatga gtgataacac tgcggccaac   2100
ttacttctga caacgatcgg aggaccgaag gagctaaccg cttttttgca caacatgggg   2160
gatcatgtaa ctcgccttga tcgttgggaa ccggagctga atgaagccat accaaacgac   2220
gagcgtgaca ccacgatgcc tgtagcaatg gcaacaacgt tgcgcaaact attaactggc   2280
gaactactta ctctagcttc ccggcaacaa ttaatagact ggatggaggc ggataaagtt   2340
gcaggaccac ttctgcgctc ggcccttccg gctggctggt ttattgctga taaatctgga   2400
gccggtgagc gtggctcacg cggtatcatt gcagcactgg ggccagatgg taagccctcc   2460
cgtatcgtag ttatctacac gacggggagt caggcaacta tggatgaacg aaatagacag   2520
atcgctgaga taggtgcctc actgattaag cattggtaac tgtcagacca agtttactca   2580
tatatacttt agattgattt aaaacttcat ttttaattta aaaggatcta ggtgaagatc   2640
ctttttgata atctcatgac caaaatccct taacgtgagt tttcgttcca ctgagcgtca   2700
gaccccgtag aaaagatcaa aggatcttct tgagatcctt tttttctgcg cgtaatctgc   2760
tgcttgcaaa caaaaaaacc accgctacca gcggtggttt gtttgccgga tcaagagcta   2820
ccaactcttt ttccgaaggt aactggcttc agcagagcgc agataccaaa tactgttctt   2880
ctagtgtagc cgtagttagg ccaccacttc aagaactctg tagcaccgcc tacatacctc   2940
gctctgctaa tcctgttacc agtggctgct gccagtggcg ataagtcgtg tcttaccggg   3000
ttggactcaa gacgatagtt accggataag gcgcagcggt cgggctgaac ggggggttcg   3060
tgcacacagc ccagcttgga gcgaacgacc tacaccgaac tgagatacct acagcgtgag   3120
ctatgagaaa gcgccacgct tcccgaaggg agaaaggcgg acaggtatcc ggtaagcggc   3180
agggtcggaa caggagagcg cacgagggag cttccagggg gaaacgcctg gtatctttat   3240
agtcctgtcg ggtttcgcca cctctgactt gagcgtcgat ttttgtgatg ctcgtcaggg   3300
gggcggagcc tatggaaaaa cgccagcaac gcggcctttt tacggttcct ggccttttgc   3360
tggccttttg ctcacatgtt ctttcctgcg ttatcccctg attctgtgga taaccgtatt   3420
accgcctttg agtgagctga taccgctcgc cgcagccgaa cgaccgagcg cagcgagtca   3480
gtgagcgagg aagcggaaga acgcggacac ccagcgtaac aatctaatat tgtttctcaa   3540
```

-continued

```
atcgggctgt tatcgcatgg tgctcatgat gaggttactg accaaattcg ccacgcatcg   3600
gtgctggtag aatgttcact tcgaggtggg tagacggcgt cacgtgcaat gccttgtctt   3660
cccctatctg cggccccgac tgcctcgcga agacaaggga tcggacgtcg aacgtattct   3720
gtttgctacc ggcacgggag taggatcgtt gatatacacc atgcgcgtta actctgaccc   3780
ccttcctctt aaatgagaat ggataagagg ctcgtgggat tgacgtgagg gggcagggat   3840
ggctatattt ctgggagcga actccgggcg aattactaat aaaaagcctt ccatttteta   3900
ttttgatttg tagaaaacta gtgtgcttgg gagtccctga tgattaaata aaccaagatt   3960
ttaccaatgg gggctagcga agcggtgatc gccgaagtat cgactcaact atcagaggta   4020
gttggcgtca tcgagcgcca tctcgaaccg acgttgctgg ccgtacattt gtacggctcc   4080
gcagtggatg gcggcctgaa gccacacagt gatattgatt tgctggttac ggtgaccgta   4140
aggcttgatg aaacaacgcg gcgagctttg atcaacgacc ttttggaaac ttcggcttcc   4200
cctggagaga gcgagattct ccgcgctgta gaagtcacca ttgttgtgca cgacgacatc   4260
attccgtggc gttatccagc taagcgcgaa ctgcaatttg gagaatggca gcgcaatgac   4320
attcttgcag gtatcttcga gccagccacg atcgacattg atctggctat cttgctgaca   4380
aaagcaagag aacatagcgt tgccttggta ggtccagcgg cggaggaact ctttgatccg   4440
gttcctgaac aggatctatt tgaggcgcta aatgaaacct taacgctatg gaactcgccg   4500
cccgactggg ctggcgatga gcgaaatgta gtgcttacgt tgtcccgcat ttggtacagc   4560
gcagtaaccg gcaaaatcgc gccgaaggat gtcgctgccg actgggcaat ggagcgcctg   4620
ccggcccagt atcagcccgt catacttgaa gctagacagg cttatcttgg acaagaagaa   4680
gatcgcttgg cctcgcgcgc agatcagttg gaagaatttg tccactacgt gaaaggcgag   4740
atcaccaagg tagtgggcaa agaacttgtt gaaggaaaat tggagctagt agaaggtctt   4800
aaagtcgcca tggctagtaa aggagaagaa cttttcactg gagttgtccc aattcttgtt   4860
gaattagatg gtgatgttaa tgggcacaaa ttttctgtca gtggagaggg tgaaggtgat   4920
gcaacatacg gaaaacttac ccttaaattt atttgcacta ctggaaaact acctgttcct   4980
tggccaacac ttgtcactac tttctcttat ggtgttcaat gcttttcaag atacccagat   5040
catatgaagc ggcacgactt cttcaagagc gccatgcctg agggatacgt gcaggagagg   5100
accatctctt tcaaggacga cgggaactac aagacacgtg ctgaagtcaa gtttgaggga   5160
gacaccctcg tcaacaggat cgagcttaag ggaatcgatt tcaaggagga cggaaacatc   5220
ctcggccaca agttggaata caactacaac tcccacaacg tatacatcac ggcagacaaa   5280
caaaagaatg gaatcaaagc taacttcaaa attagacaca acattgaaga tggaagcgtt   5340
caactagcag accattatca acaaaatact ccaattggcg atggccctgt ccttttacca   5400
gacaaccatt acctgtccac acaatctgcc ctttcgaaag atcccaacga aaagagagat   5460
cacatggtcc ttcttgagtt tgtaacagct gctgggatta cacatggcat ggatgaacta   5520
tacaaataag cttaaacagt agacattagc agataaatta gcaggaaata aagaaggata   5580
aggagaaaga actcaagtaa ttatccttcg ttctcttaat tgaattgcaa ttaaactcgg   5640
cccaatcttt tactaaaagg attgagccga ataccgctac aacagctccc tggaacacca   5700
ggagaacaca cttatctcgc gtcttgaggt gataccacgc ctgacacgtg agggcagtac   5760
ggttaattcg gtttagccgg acatcagcgc tcctcattga gcgctgggcc cttcacatga   5820
agatcgcact gaggattggt cctagccagg cttctcagta ctgatacagt acgcgtcgct   5880
tctcgtattg tttgagtctt ggaattagtt tgtatccttc cgccgctgcc ctaagaattc   5940
```

taattgagct cgaacagtcg accgccggat cctgctcgag tgcctctaga 5990

<210> SEQ ID NO 80
<211> LENGTH: 6070
<212> TYPE: DNA
<213> ORGANISM: Artificial Sequence
<220> FEATURE:
<223> OTHER INFORMATION: An example of an episomal DNA vector

<400> SEQUENCE: 80
tgcccaccat agcgcgccgg ttgcctgcgg ttactggacc aagctcgtca actcggagca 60
ggctttatgg gcctcgcttc cttaagtcac atcgacaatt caataaggta tccgacatta 120
acaatgattt aaattgtgtt cattgtgttt tttatggtac ataaccttca tagatttata 180
gattatctca aaaacagaag aaagggtgga aagtgaggaa gaaagagatg tagaaataga 240
aacagcttcc gaaatgaagg ggactaaaca ggaacaagag ggatccactg aagaagatcc 300
ttatccttct ccttcccttt tttcggaaga aaggtgggat ccggacaaaa tcgatgaaac 360
ggaagaaatc cgagtgaatg gaaaggacaa aataaaggat aaattccact ctcaccttac 420
agagacaggt tcctatatga ggaagtatcc ttccccgcag tcaagaccaa ggttagtatt 480
ctctgctagg aagtttactt aggttactct agcatgtgcc tggataaccc tctaggcaaa 540
ggtggattga ctttgtactg tcctcagatc gacgttggat gaactgtcgc gccacgaggg 600
gctgtggagc gcattgcgac acattggtgc gctgctaacc catcctttcc agtacggcta 660
ctgatgtcca cgctcccagc ctgctacgct ccgcccgcct gtctctgtaa ggtgagagtg 720
gaatttatcc tttattttgt cctttccatt cactcggatt tcttccgttt catcgatttt 780
gtccggatcc cacctttctt ccgaaaaaag ggaaggagaa ggataaggat cttcttcagt 840
ggatccctct tgttcctgtt tagtcccctt catttcggaa gctgtttcta tttctacatc 900
tctttcttcc tcactttcca ccctttcttc tgtttttgag tgctagaaag ttattctttt 960
cgtcttaatg attatatgta aatcgccctc tatatattaa ctctacttat atggaaaaac 1020
tatgattaag tagttacagt cgacgcgcgg gtgacacccc tacgccgact cgataaacag 1080
gatgggtcat gggcctggca cgtgttattc aaaggtacag cggggagcgc acgcgcaagg 1140
tcgcaactac ccgagaatcg atgtggcgga atgggttacg tgagctatta tccggcgggc 1200
cctcaattta aatcgttaca gttgctcgta acggcaaccg gctcggtcct ttttccctag 1260
aacagtatct tatacttgct gctctcgtta cttcggcgat cctggtgcag tcggtccgta 1320
aatcggcgca cacttttacg tcgtaccaga caggctcgca taagccagcc ccgacacccg 1380
ccaacacccg ctgacgcgcc ctgacgggct tgtctgctcc cggcatccgc ttacagacaa 1440
gctgtgacct ccgggagctg catgtgtcag aggttttcac cgtcatcacc gaaacgcgca 1500
cgaaagggcc tcgtgatacg cctattttta taggttaatg tcatgataat aatggtttct 1560
tagacgtcag gtggcacttt tcggggaaat gtgcgcggaa cccctatttg tttatttttc 1620
taaatacatt caaatatgta tccgctcatg agacaataac cctgataaat gcttcaataa 1680
tattgaaaaa ggaagagtat gagtattcaa catttccgtg tcgcccttat tccctttttt 1740
gcggcatttt gccttcctgt ttttgctcac ccagaaacgc tggtgaaagt aaaagatgct 1800
gaagatcagt tgggtgcacg agtgggttac atcgaactgg atctcaacag cggtaagatc 1860
cttgagagtt ttcgccccga agaacgtttt ccaatgatga gcacttttaa agttctgcta 1920
tgtggcgcgg tattatcccg tattgacgcc gggcaagagc aactcggtcg ccgcatacac 1980

-continued tattctcaga atgacttggt tgagtactca ccagtcacag aaaagcatct tacggatggc 2040
atgacagtaa gagaattatg cagtgctgcc ataaccatga gtgataacac tgcggccaac 2100
ttacttctga caacgatcgg aggaccgaag gagctaaccg cttttttgca caacatgggg 2160
gatcatgtaa ctcgccttga tcgttgggaa ccggagctga atgaagccat accaaacgac 2220
gagcgtgaca ccacgatgcc tgtagcaatg gcaacaacgt tgcgcaaact attaactggc 2280
gaactactta ctctagcttc ccggcaacaa ttaatagact ggatggaggc ggataaagtt 2340
gcaggaccac ttctgcgctc ggcccttccg gctggctggt ttattgctga taaatctgga 2400
gccggtgagc gtggctcacg cggtatcatt gcagcactgg ggccagatgg taagccctcc 2460
cgtatcgtag ttatctacac gacggggagt caggcaacta tggatgaacg aaatagacag 2520
atcgctgaga taggtgcctc actgattaag cattggtaac tgtcagacca agtttactca 2580
tatatacttt agattgattt aaaacttcat ttttaattta aaaggatcta ggtgaagatc 2640
ctttttgata atctcatgac caaaatccct taacgtgagt tttcgttcca ctgagcgtca 2700
gaccccgtag aaaagatcaa aggatcttct tgagatcctt tttttctgcg cgtaatctgc 2760
tgcttgcaaa caaaaaaacc accgctacca gcggtggttt gtttgccgga tcaagagcta 2820
ccaactcttt ttccgaaggt aactggcttc agcagagcgc agataccaaa tactgttctt 2880
ctagtgtagc cgtagttagg ccaccacttc aagaactctg tagcaccgcc tacatacctc 2940
gctctgctaa tcctgttacc agtggctgct gccagtggcg ataagtcgtg tcttaccggg 3000
ttggactcaa gacgatagtt accggataag gcgcagcggt cgggctgaac ggggggttcg 3060
tgcacacagc ccagcttgga gcgaacgacc tacaccgaac tgagatacct acagcgtgag 3120
ctatgagaaa gcgccacgct tcccgaaggg agaaaggcgg acaggtatcc ggtaagcggc 3180
agggtcggaa caggagagcg cacgagggag cttccagggg gaaacgcctg gtatctttat 3240
agtcctgtcg ggtttcgcca cctctgactt gagcgtcgat ttttgtgatg ctcgtcaggg 3300
gggcggagcc tatggaaaaa cgccagcaac gcggcctttt tacggttcct ggccttttgc 3360
tggccttttg ctcacatgtt ctttcctgcg ttatcccctg attctgtgga taaccgtatt 3420
accgcctttg agtgagctga taccgctcgc cgcagccgaa cgaccgagcg cagcgagtca 3480
gtgagcgagg aagcggaaga acgcggacac ccagcgtaac aatctaatat tgtttctcaa 3540
atcgggctgt tatcgcatgg tgctcatgat gaggttactg accaaattcg ccacgcatcg 3600
gtgctggtag aatgttcact tcgaggtggg tagacggcgt cacgtgcaat gccttgtctt 3660
cccctatctg cggccccgac tgcctcgcga agacaaggga tcggacgtcg aacgtattct 3720
gtttgctacc ggcacgggag taggatcgtt gatatacacc atgcgcgtta actctgaccc 3780
ccttcctctt aaatgagaat ggataagagg ctcgtgggat tgacgtgagg gggcagggat 3840
ggctatattt ctgggagcga actccgggcg aattactaat aaaaagcctt ccattttcta 3900
ttttgatttg tagaaaacta gtgtgcttgg gagtccctga tgattaaata aaccaagatt 3960
ttaccaatgg gggctagcga agcggtgatc gccgaagtat cgactcaact atcagaggta 4020
gttggcgtca tcgagcgcca tctcgaaccg acgttgctgg ccgtacattt gtacggctcc 4080
gcagtggatg gcggcctgaa gccacacagt gatattgatt tgctggttac ggtgaccgta 4140
aggcttgatg aaacaacgcg gcgagctttg atcaacgacc ttttggaaac ttcggcttcc 4200
cctggagaga gcgagattct ccgcgctgta gaagtcacca ttgttgtgca cgacgacatc 4260
attccgtggc gttatccagc taagcgcgaa ctgcaatttg gagaatggca gcgcaatgac 4320
attcttgcag gtatcttcga gccagccacg atcgacattg atctggctat cttgctgaca 4380
aaagcaagag aacatagcgt tgccttggta ggtccagcgg cggaggaact ctttgatccg 4440
gttcctgaac aggatctatt tgaggcgcta aatgaaacct taacgctatg gaactcgccg 4500
cccgactggg ctggcgatga gcgaaatgta gtgcttacgt tgtcccgcat ttggtacagc 4560
gcagtaaccg gcaaaatcgc gccgaaggat gtcgctgccg actgggcaat ggagcgcctg 4620
ccggcccagt atcagcccgt catacttgaa gctagacagg cttatcttgg acaagaagaa 4680
gatcgcttgg cctcgcgcgc agatcagttg gaagaatttg tccactacgt gaaaggcgag 4740
atcaccaagg tagtgggcaa agaacttgtt gaaggaaaat tggagctagt agaaggtctt 4800
aaagtcgcca tggctagtaa aggagaagaa cttttcactg gagttgtccc aattcttgtt 4860
gaattagatg gtgatgttaa tgggcacaaa ttttctgtca gtggagaggg tgaaggtgat 4920
gcaacatacg gaaaacttac ccttaaattt atttgcacta ctggaaaact acctgttcct 4980
tggccaacac ttgtcactac tttctcttat ggtgttcaat gcttttcaag atacccagat 5040
catatgaagc ggcacgactt cttcaagagc gccatgcctg agggatacgt gcaggagagg 5100
accatctctt tcaaggacga cgggaactac aagacacgtg ctgaagtcaa gtttgaggga 5160
gacaccctcg tcaacaggat cgagcttaag ggaatcgatt tcaaggagga cggaaacatc 5220
ctcggccaca agttggaata caactacaac tcccacaacg tatacatcac ggcagacaaa 5280
caaaagaatg gaatcaaagc taacttcaaa attagacaca acattgaaga tggaagcgtt 5340
caactagcag accattatca acaaaatact ccaattggcg atggccctgt ccttttacca 5400
gacaaccatt acctgtccac acaatctgcc ctttcgaaag atcccaacga aaagagagat 5460
cacatggtcc ttcttgagtt tgtaacagct gctgggatta cacatggcat ggatgaacta 5520
tacaaataag cttaaacagt agacattagc agataaatta gcaggaaata aagaaggata 5580
aggagaaaga actcaagtaa ttatccttcg ttctcttaat tgaattgcaa ttaaactcgg 5640
cccaatcttt tactaaaagg attgagccga ataccgctcc aggcatcaaa taaaacgaaa 5700
ggctcagtcg aaagactggg cctttcgttt tatctgttgt ttgtcggtga acgctctcac 5760
aacagctccc tggaacacca ggagaacaca cttatctcgc gtcttgaggt gataccacgc 5820
ctgacacgtg agggcagtac ggttaattcg gtttagccgg acatcagcgc tcctcattga 5880
gcgctgggcc cttcacatga agatcgcact gaggattggt cctagccagg cttctcagta 5940
ctgatacagt acgcgtcgct tctcgtattg tttgagtctt ggaattagtt tgtatccttc 6000
cgccgctgcc ctaagaattc taattgagct cgaacagtcg accgccggat cctgctcgag 6060
tgcctctaga 6070

<210> SEQ ID NO 81
<211> LENGTH: 5990
<212> TYPE: DNA
<213> ORGANISM: Artificial Sequence
<220> FEATURE:
<223> OTHER INFORMATION: An example of an episomal DNA vector

<400> SEQUENCE: 81
tgccagatcc aatgtagatc caactttcga ttcactcgtg ggatccgggc ggtccggggg 60
ggaccaccac ggctcctctc ttctcgtcac atcgacaatt caataaggta tccgacatta 120
acaatgattt aaattgtgtt cattgtgttt tttatggtac ataaccttca tagatttata 180
gattatctca aaaacagaag aaagggtgga aagtgaggaa gaaagagatg tagaaataga 240
aacagcttcc gaaatgaagg ggactaaaca ggaacaagag ggatccactg aagaagatcc 300

-continued

```
ttatccttct ccttcccttt tttcggaaga aaggtgggat ccggacaaaa tcgatgaaac    360
ggaagaaatc cgagtgaatg gaaaggacaa aataaaggat aaattccact ctcaccttac    420
agagacaggt tcctatatga ggaagtatcc ttccccgcag tcaagaccaa ggttagtatt    480
ctctgctagg aagtttactt aggttactct agcatgtgcc tggataaccc tctaggcaaa    540
ggtggattga ctttgtactg tcctcagatc gacgttggat gaactgtcgc gccacgaggg    600
gctgtggagc gcattgcgac acattggtgc gctgctaacc catcctttcc agtacggcta    660
ctgatgtcca cgctcccagc ctgctacgct ccgcccgctc aaaaacagaa gaaagggtgg    720
aaagtgagga agaaagagat gtagaaatag aaacagcttc cgaaatgaag ggactaaac     780
aggaacaaga gggatccact gaagaagatc cttatccttc tccttccctt ttttcggaag    840
aaaggtggga tccggacaaa atcgatgaaa cggaagaaat ccgagtgaat ggaaaggaca    900
aaataaagga taaattccac tctcacctta cagagacagg tgctagaaag ttattctttt    960
cgtcttaatg attatatgta aatcgccctc tatatattaa ctctacttat atggaaaaac   1020
tatgattaag tagttacagt agatccaatg tagatccaac tttcgattca ctcgtgggat   1080
ccgggcggtc cggggggac caccacggct cctctcttct cggggagcgc acgcgcaagg   1140
tcgcaactac ccgagaatcg atgtggcgga atgggttacg tgagctatta tccggcgggc   1200
cctcaattta aatcgttaca gttgctcgta acggcaaccg gctcggtcct ttttccctag   1260
aacagtatct tatacttgct gctctcgtta cttcggcgat cctggtgcag tcggtccgta   1320
aatcggcgca cacttttacg tcgtaccaga caggctcgca taagccagcc ccgacacccg   1380
ccaacacccg ctgacgcgcc ctgacgggct tgtctgctcc cggcatccgc ttacagacaa   1440
gctgtgacct ccgggagctg catgtgtcag aggttttcac cgtcatcacc gaaacgcgca   1500
cgaaagggcc tcgtgatacg cctattttta taggttaatg tcatgataat aatggtttct   1560
tagacgtcag gtggcacttt tcggggaaat gtgcgcggaa cccctatttg tttatttttc   1620
taaatacatt caaatatgta tccgctcatg agacaataac cctgataaat gcttcaataa   1680
tattgaaaaa ggaagagtat gagtattcaa catttccgtg tcgcccttat tccctttttt   1740
gcggcatttt gccttcctgt ttttgctcac ccagaaacgc tggtgaaagt aaaagatgct   1800
gaagatcagt tgggtgcacg agtgggttac atcgaactgg atctcaacag cggtaagatc   1860
cttgagagtt ttcgccccga agaacgtttt ccaatgatga gcacttttaa agttctgcta   1920
tgtggcgcgg tattatcccg tattgacgcc gggcaagagc aactcggtcg ccgcatacac   1980
tattctcaga atgacttggt tgagtactca ccagtcacag aaaagcatct tacggatggc   2040
atgacagtaa gagaattatg cagtgctgcc ataaccatga gtgataacac tgcggccaac   2100
ttacttctga caacgatcgg aggaccgaag gagctaaccg cttttttgca caacatgggg   2160
gatcatgtaa ctcgccttga tcgttgggaa ccggagctga atgaagccat accaaacgac   2220
gagcgtgaca ccacgatgcc tgtagcaatg gcaacaacgt tgcgcaaact attaactggc   2280
gaactactta ctctagcttc ccggcaacaa ttaatagact ggatggaggc ggataaagtt   2340
gcaggaccac ttctgcgctc ggcccttccg gctggctggt ttattgctga taaatctgga   2400
gccggtgagc gtggctcacg cggtatcatt gcagcactgg ggccagatgg taagccctcc   2460
cgtatcgtag ttatctacac gacggggagt caggcaacta tggatgaacg aaatagacag   2520
atcgctgaga taggtgcctc actgattaag cattggtaac tgtcagacca agtttactca   2580
tatatacttt agattgattt aaaacttcat ttttaattta aaaggatcta ggtgaagatc   2640
ctttttgata atctcatgac caaaatccct taacgtgagt tttcgttcca ctgagcgtca   2700
```

gaccccgtag aaaagatcaa aggatcttct tgagatcctt tttttctgcg cgtaatctgc 2760
tgcttgcaaa caaaaaaacc accgctacca gcggtggttt gtttgccgga tcaagagcta 2820
ccaactcttt ttccgaaggt aactggcttc agcagagcgc agataccaaa tactgttctt 2880
ctagtgtagc cgtagttagg ccaccacttc aagaactctg tagcaccgcc tacatacctc 2940
gctctgctaa tcctgttacc agtggctgct gccagtggcg ataagtcgtg tcttaccggg 3000
ttggactcaa gacgatagtt accggataag gcgcagcggt cgggctgaac ggggggttcg 3060
tgcacacagc ccagcttgga gcgaacgacc tacaccgaac tgagatacct acagcgtgag 3120
ctatgagaaa gcgccacgct tcccgaaggg agaaaggcgg acaggtatcc ggtaagcggc 3180
agggtcggaa caggagagcg cacgagggag cttccagggg gaaacgcctg gtatctttat 3240
agtcctgtcg ggtttcgcca cctctgactt gagcgtcgat ttttgtgatg ctcgtcaggg 3300
gggcggagcc tatggaaaaa cgccagcaac gcggcctttt tacggttcct ggccttttgc 3360
tggccttttg ctcacatgtt ctttcctgcg ttatcccctg attctgtgga taaccgtatt 3420
accgcctttg agtgagctga taccgctcgc cgcagccgaa cgaccgagcg cagcgagtca 3480
gtgagcgagg aagcggaaga acgcggacac ccagcgtaac aatctaatat tgtttctcaa 3540
atcgggctgt tatcgcatgg tgctcatgat gaggttactg accaaattcg ccacgcatcg 3600
gtgctggtag aatgttcact tcgaggtggg tagacggcgt cacgtgcaat gccttgtctt 3660
cccctatctg cggccccgac tgcctcgcga agacaaggga tcggacgtcg aacgtattct 3720
gtttgctacc ggcacgggag taggatcgtt gatatacacc atgcgcgtta actctgaccc 3780
ccttcctctt aaatgagaat ggataagagg ctcgtgggat tgacgtgagg gggcagggat 3840
ggctatattt ctgggagcga actccgggcg aattactaat aaaaagcctt ccattttcta 3900
ttttgatttg tagaaaacta gtgtgcttgg gagtccctga tgattaaata aaccaagatt 3960
ttaccaatgg gggctagcga agcggtgatc gccgaagtat cgactcaact atcagaggta 4020
gttggcgtca tcgagcgcca tctcgaaccg acgttgctgg ccgtacattt gtacggctcc 4080
gcagtggatg gcggcctgaa gccacacagt gatattgatt tgctggttac ggtgaccgta 4140
aggcttgatg aaacaacgcg gcgagctttg atcaacgacc ttttggaaac ttcggcttcc 4200
cctggagaga gcgagattct ccgcgctgta gaagtcacca ttgttgtgca cgacgacatc 4260
attccgtggc gttatccagc taagcgcgaa ctgcaatttg gagaatggca gcgcaatgac 4320
attcttgcag gtatcttcga gccagccacg atcgacattg atctggctat cttgctgaca 4380
aaagcaagag aacatagcgt tgccttggta ggtccagcgg cggaggaact ctttgatccg 4440
gttcctgaac aggatctatt tgaggcgcta aatgaaacct taacgctatg gaactcgccg 4500
cccgactggg ctggcgatga gcgaaatgta gtgcttacgt tgtcccgcat ttggtacagc 4560
gcagtaaccg gcaaaatcgc gccgaaggat gtcgctgccg actgggcaat ggagcgcctg 4620
ccggcccagt atcagcccgt catacttgaa gctagacagg cttatcttgg acaagaagaa 4680
gatcgcttgg cctcgcgcgc agatcagttg gaagaatttg tccactacgt gaaaggcgag 4740
atcaccaagg tagtgggcaa agaacttgtt gaaggaaaat tggagctagt agaaggtctt 4800
aaagtcgcca tggctagtaa aggagaagaa cttttcactg gagttgtccc aattcttgtt 4860
gaattagatg gtgatgttaa tgggcacaaa ttttctgtca gtggagaggg tgaaggtgat 4920
gcaacatacg gaaaacttac ccttaaattt atttgcacta ctggaaaact acctgttcct 4980
tggccaacac ttgtcactac tttctcttat ggtgttcaat gcttttcaag atacccagat 5040
catatgaagc ggcacgactt cttcaagagc gccatgcctg agggatacgt gcaggagagg 5100
accatctctt tcaaggacga cgggaactac aagacacgtg ctgaagtcaa gtttgaggga 5160
gacaccctcg tcaacaggat cgagcttaag ggaatcgatt tcaaggagga cggaaacatc 5220
ctcggccaca agttggaata caactacaac tcccacaacg tatacatcac ggcagacaaa 5280
caaaagaatg gaatcaaagc taacttcaaa attagacaca acattgaaga tggaagcgtt 5340
caactagcag accattatca acaaaatact ccaattggcg atggccctgt ccttttacca 5400
gacaaccatt acctgtccac acaatctgcc ctttcgaaag atcccaacga aaagagagat 5460
cacatggtcc ttcttgagtt tgtaacagct gctgggatta cacatggcat ggatgaacta 5520
tacaaataag cttaaacagt agacattagc agataaatta gcaggaaata aagaaggata 5580
aggagaaaga actcaagtaa ttatccttcg ttctcttaat tgaattgcaa ttaaactcgg 5640
cccaatcttt tactaaaagg attgagccga ataccgctac aacagctccc tggaacacca 5700
ggagaacaca cttatctcgc gtcttgaggt gataccacgc ctgacacgtg agggcagtac 5760
ggttaattcg gtttagccgg acatcagcgc tcctcattga gcgctgggcc cttcacatga 5820
agatcgcact gaggattggt cctagccagg cttctcagta ctgatacagt acgcgtcgct 5880
tctcgtattg tttgagtctt ggaattagtt tgtatccttc cgccgctgcc ctaagaattc 5940
taattgagct cgaacagtcg accgccggat cctgctcgag tgcctctaga 5990

<210> SEQ ID NO 82
<211> LENGTH: 6070
<212> TYPE: DNA
<213> ORGANISM: Artificial Sequence
<220> FEATURE:
<223> OTHER INFORMATION: An example of an episomal DNA vector

<400> SEQUENCE: 82
tgccagatcc aatgtagatc caactttcga ttcactcgtg ggatccgggc ggtccggggg 60
ggaccaccac ggctcctctc ttctcgtcac atcgacaatt caataaggta tccgacatta 120
acaatgattt aaattgtgtt cattgtgttt tttatggtac ataaccttca tagatttata 180
gattatctca aaaacagaag aaagggtgga aagtgaggaa gaaagagatg tagaaataga 240
aacagcttcc gaaatgaagg ggactaaaca ggaacaagag ggatccactg aagaagatcc 300
ttatccttct ccttcccttt tttcggaaga aaggtgggat ccggacaaaa tcgatgaaac 360
ggaagaaatc cgagtgaatg gaaaggacaa aataaaggat aaattccact ctcaccttac 420
agagacaggt tcctatatga ggaagtatcc ttccccgcag tcaagaccaa ggttagtatt 480
ctctgctagg aagtttactt aggttactct agcatgtgcc tggataaccc tctaggcaaa 540
ggtggattga ctttgtactg tcctcagatc gacgttggat gaactgtcgc gccacgaggg 600
gctgtggagc gcattgcgac acattggtgc gctgctaacc catcctttcc agtacggcta 660
ctgatgtcca cgctcccagc ctgctacgct ccgcccgctc aaaaacagaa gaaagggtgg 720
aaagtgagga agaaagagat gtagaaatag aaacagcttc cgaaatgaag gggactaaac 780
aggaacaaga gggatccact gaagaagatc cttatccttc tccttccctt ttttcggaag 840
aaaggtggga tccggacaaa atcgatgaaa cggaagaaat ccgagtgaat ggaaaggaca 900
aaataaagga taaattccac tctcacctta cagagacagg tgctagaaag ttattctttt 960
cgtcttaatg attatatgta aatcgccctc tatatattaa ctctacttat atggaaaaac 1020
tatgattaag tagttacagt agatccaatg tagatccaac tttcgattca ctcgtgggat 1080
ccgggcggtc cgggggggac caccacggct cctctcttct cggggagcgc acgcgcaagg 1140
tcgcaactac ccgagaatcg atgtggcgga atgggttacg tgagctatta tccggcgggc 1200
cctcaattta aatcgttaca gttgctcgta acggcaaccg gctcggtcct ttttccctag 1260
aacagtatct tatacttgct gctctcgtta cttcggcgat cctggtgcag tcggtccgta 1320
aatcggcgca cacttttacg tcgtaccaga caggctcgca taagccagcc ccgacacccg 1380
ccaacacccg ctgacgcgcc ctgacgggct tgtctgctcc cggcatccgc ttacagacaa 1440
gctgtgacct ccgggagctg catgtgtcag aggttttcac cgtcatcacc gaaacgcgca 1500
cgaaagggcc tcgtgatacg cctattttta taggttaatg tcatgataat aatggtttct 1560
tagacgtcag gtggcacttt tcggggaaat gtgcgcggaa cccctatttg tttatttttc 1620
taaatacatt caaatatgta tccgctcatg agacaataac cctgataaat gcttcaataa 1680
tattgaaaaa ggaagagtat gagtattcaa catttccgtg tcgcccttat tccctttttt 1740
gcggcatttt gccttcctgt ttttgctcac ccagaaacgc tggtgaaagt aaaagatgct 1800
gaagatcagt tgggtgcacg agtgggttac atcgaactgg atctcaacag cggtaagatc 1860
cttgagagtt ttcgccccga agaacgtttt ccaatgatga gcacttttaa agttctgcta 1920
tgtggcgcgg tattatcccg tattgacgcc gggcaagagc aactcggtcg ccgcatacac 1980
tattctcaga atgacttggt tgagtactca ccagtcacag aaaagcatct tacggatggc 2040
atgacagtaa gagaattatg cagtgctgcc ataaccatga gtgataacac tgcggccaac 2100
ttacttctga caacgatcgg aggaccgaag gagctaaccg cttttttgca caacatgggg 2160
gatcatgtaa ctcgccttga tcgttgggaa ccggagctga atgaagccat accaaacgac 2220
gagcgtgaca ccacgatgcc tgtagcaatg gcaacaacgt tgcgcaaact attaactggc 2280
gaactactta ctctagcttc ccggcaacaa ttaatagact ggatggaggc ggataaagtt 2340
gcaggaccac ttctgcgctc ggcccttccg gctggctggt ttattgctga taaatctgga 2400
gccggtgagc gtggctcacg cggtatcatt gcagcactgg ggccagatgg taagccctcc 2460
cgtatcgtag ttatctacac gacggggagt caggcaacta tggatgaacg aaatagacag 2520
atcgctgaga taggtgcctc actgattaag cattggtaac tgtcagacca agtttactca 2580
tatatacttt agattgattt aaaacttcat ttttaattta aaaggatcta ggtgaagatc 2640
ctttttgata atctcatgac caaaatccct taacgtgagt tttcgttcca ctgagcgtca 2700
gaccccgtag aaaagatcaa aggatcttct tgagatcctt tttttctgcg cgtaatctgc 2760
tgcttgcaaa caaaaaaacc accgctacca gcggtggttt gtttgccgga tcaagagcta 2820
ccaactcttt ttccgaaggt aactggcttc agcagagcgc agataccaaa tactgttctt 2880
ctagtgtagc cgtagttagg ccaccacttc aagaactctg tagcaccgcc tacatacctc 2940
gctctgctaa tcctgttacc agtggctgct gccagtggcg ataagtcgtg tcttaccggg 3000
ttggactcaa gacgatagtt accggataag gcgcagcggt cgggctgaac ggggggttcg 3060
tgcacacagc ccagcttgga gcgaacgacc tacaccgaac tgagatacct acagcgtgag 3120
ctatgagaaa gcgccacgct tcccgaaggg agaaaggcgg acaggtatcc ggtaagcggc 3180
agggtcggaa caggagagcg cacgagggag cttccagggg gaaacgcctg gtatctttat 3240
agtcctgtcg ggtttcgcca cctctgactt gagcgtcgat ttttgtgatg ctcgtcaggg 3300
gggcggagcc tatggaaaaa cgccagcaac gcggcctttt tacggttcct ggccttttgc 3360
tggccttttg ctcacatgtt ctttcctgcg ttatcccctg attctgtgga taaccgtatt 3420
accgcctttg agtgagctga taccgctcgc cgcagccgaa cgaccgagcg cagcgagtca 3480

```
gtgagcgagg aagcggaaga acgcggacac ccagcgtaac aatctaatat tgtttctcaa   3540
atcgggctgt tatcgcatgg tgctcatgat gaggttactg accaaattcg ccacgcatcg   3600
gtgctggtag aatgttcact tcgaggtggg tagacggcgt cacgtgcaat gccttgtctt   3660
cccctatctg cggccccgac tgcctcgcga agacaaggga tcggacgtcg aacgtattct   3720
gtttgctacc ggcacgggag taggatcgtt gatatacacc atgcgcgtta actctgaccc   3780
ccttcctctt aaatgagaat ggataagagg ctcgtgggat tgacgtgagg gggcagggat   3840
ggctatattt ctgggagcga actccgggcg aattactaat aaaaagcctt ccattttcta   3900
ttttgatttg tagaaaacta gtgtgcttgg gagtccctga tgattaaata aaccaagatt   3960
ttaccaatgg gggctagcga agcggtgatc gccgaagtat cgactcaact atcagaggta   4020
gttggcgtca tcgagcgcca tctcgaaccg acgttgctgg ccgtacattt gtacggctcc   4080
gcagtggatg gcggcctgaa gccacacagt gatattgatt tgctggttac ggtgaccgta   4140
aggcttgatg aaacaacgcg gcgagctttg atcaacgacc ttttggaaac ttcggcttcc   4200
cctggagaga gcgagattct ccgcgctgta gaagtcacca ttgttgtgca cgacgacatc   4260
attccgtggc gttatccagc taagcgcgaa ctgcaatttg gagaatggca gcgcaatgac   4320
attcttgcag gtatcttcga gccagccacg atcgacattg atctggctat cttgctgaca   4380
aaagcaagag aacatagcgt tgccttggta ggtccagcgg cggaggaact ctttgatccg   4440
gttcctgaac aggatctatt tgaggcgcta aatgaaacct taacgctatg gaactcgccg   4500
cccgactggg ctggcgatga gcgaaatgta gtgcttacgt tgtcccgcat ttggtacagc   4560
gcagtaaccg gcaaaatcgc gccgaaggat gtcgctgccg actgggcaat ggagcgcctg   4620
ccggcccagt atcagcccgt catacttgaa gctagacagg cttatcttgg acaagaagaa   4680
gatcgcttgg cctcgcgcgc agatcagttg gaagaatttg tccactacgt gaaaggcgag   4740
atcaccaagg tagtgggcaa agaacttgtt gaaggaaaat tggagctagt agaaggtctt   4800
aaagtcgcca tggctagtaa aggagaagaa cttttcactg gagttgtccc aattcttgtt   4860
gaattagatg gtgatgttaa tgggcacaaa ttttctgtca gtggagaggg tgaaggtgat   4920
gcaacatacg gaaaacttac ccttaaattt atttgcacta ctggaaaact acctgttcct   4980
tggccaacac ttgtcactac tttctcttat ggtgttcaat gcttttcaag atacccagat   5040
catatgaagc ggcacgactt cttcaagagc gccatgcctg agggatacgt gcaggagagg   5100
accatctctt tcaaggacga cgggaactac aagacacgtg ctgaagtcaa gtttgaggga   5160
gacaccctcg tcaacaggat cgagcttaag ggaatcgatt tcaaggagga cggaaacatc   5220
ctcggccaca agttggaata caactacaac tcccacaacg tatacatcac ggcagacaaa   5280
caaaagaatg gaatcaaagc taacttcaaa attagacaca acattgaaga tggaagcgtt   5340
caactagcag accattatca acaaaatact ccaattggcg atggccctgt ccttttacca   5400
gacaaccatt acctgtccac acaatctgcc ctttcgaaag atcccaacga aaagagagat   5460
cacatggtcc ttcttgagtt tgtaacagct gctgggatta cacatggcat ggatgaacta   5520
tacaaataag cttaaacagt agacattagc agataaatta gcaggaaata aagaaggata   5580
aggagaaaga actcaagtaa ttatccttcg ttctcttaat tgaattgcaa ttaaactcgg   5640
cccaatcttt tactaaaagg attgagccga ataccgctcc aggcatcaaa taaaacgaaa   5700
ggctcagtcg aaagactggg cctttcgttt tatctgttgt ttgtcggtga acgctctcac   5760
aacagctccc tggaacacca ggagaacaca cttatctcgc gtcttgaggt gataccacgc   5820
ctgacacgtg agggcagtac ggttaattcg gtttagccgg acatcagcgc tcctcattga   5880
```

gcgctgggcc cttcacatga agatcgcact gaggattggt cctagccagg cttctcagta 5940
ctgatacagt acgcgtcgct tctcgtattg tttgagtctt ggaattagtt tgtatccttc 6000
cgccgctgcc ctaagaattc taattgagct cgaacagtcg accgccggat cctgctcgag 6060
tgcctctaga 6070

<210> SEQ ID NO 83
<211> LENGTH: 5990
<212> TYPE: DNA
<213> ORGANISM: Artificial Sequence
<220> FEATURE:
<223> OTHER INFORMATION: An example of an episomal DNA vector

<400> SEQUENCE: 83
tgccagatcc aatgtagatc caactttcga ttcactcgtg ggatccgggc ggtccggggg 60
ggaccaccac ggctcctctc ttctcgtcac atcgacaatt caataaggta tccgacatta 120
acaatgattt aaattgtgtt cattgtgttt tttatggtac ataaccttca tagatttata 180
gattatctca aaaacagaag aaagggtgga aagtgaggaa gaaagagatg tagaaataga 240
aacagcttcc gaaatgaagg ggactaaaca ggaacaagag ggatccactg aagaagatcc 300
ttatccttct ccttcccttt tttcggaaga aaggtgggat ccggacaaaa tcgatgaaac 360
ggaagaaatc cgagtgaatg gaaaggacaa aataaaggat aaattccact ctcaccttac 420
agagacaggt tcctatatga ggaagtatcc ttccccgcag tcaagaccaa ggttagtatt 480
ctctgctagg aagtttactt aggttactct agcatgtgcc tggataaccc tctaggcaaa 540
ggtggattga ctttgtactg tcctcagatc gacgttggat gaactgtcgc gccacgaggg 600
gctgtggagc gcattgcgac acattggtgc gctgctaacc catcctttcc agtacggcta 660
ctgatgtcca cgctcccagc ctgctacgct ccgcccgcct gtctctgtaa ggtgagagtg 720
gaatttatcc tttattttgt cctttccatt cactcggatt tcttccgttt catcgatttt 780
gtccggatcc cacctttctt ccgaaaaaag ggaaggagaa ggataaggat cttcttcagt 840
ggatccctct tgttcctgtt tagtcccctt catttcggaa gctgtttcta tttctacatc 900
tctttcttcc tcactttcca ccctttcttc tgtttttgag tgctagaaag ttattctttt 960
cgtcttaatg attatatgta aatcgccctc tatatattaa ctctacttat atggaaaaac 1020
tatgattaag tagttacagt cgagaagaga ggagccgtgg tggtcccccc cggaccgccc 1080
ggatcccacg agtgaatcga aagttggatc tacattggat ctgggagcgc acgcgcaagg 1140
tcgcaactac ccgagaatcg atgtggcgga atgggttacg tgagctatta tccggcgggc 1200
cctcaattta aatcgttaca gttgctcgta acggcaaccg gctcggtcct ttttccctag 1260
aacagtatct tatacttgct gctctcgtta cttcggcgat cctggtgcag tcggtccgta 1320
aatcggcgca cacttttacg tcgtaccaga caggctcgca taagccagcc ccgacacccg 1380
ccaacacccg ctgacgcgcc ctgacgggct tgtctgctcc cggcatccgc ttacagacaa 1440
gctgtgacct ccgggagctg catgtgtcag aggttttcac cgtcatcacc gaaacgcgca 1500
cgaaagggcc tcgtgatacg cctattttta taggttaatg tcatgataat aatggtttct 1560
tagacgtcag gtggcacttt tcggggaaat gtgcgcggaa cccctatttg tttatttttc 1620
taaatacatt caaatatgta tccgctcatg agacaataac cctgataaat gcttcaataa 1680
tattgaaaaa ggaagagtat gagtattcaa catttccgtg tcgcccttat tccctttttt 1740
gcggcatttt gccttcctgt ttttgctcac ccagaaacgc tggtgaaagt aaaagatgct 1800

-continued

```
gaagatcagt tgggtgcacg agtgggttac atcgaactgg atctcaacag cggtaagatc   1860
cttgagagtt ttcgccccga agaacgtttt ccaatgatga gcacttttaa agttctgcta   1920
tgtggcgcgg tattatcccg tattgacgcc gggcaagagc aactcggtcg ccgcatacac   1980
tattctcaga atgacttggt tgagtactca ccagtcacag aaaagcatct tacggatggc   2040
atgacagtaa gagaattatg cagtgctgcc ataaccatga gtgataacac tgcggccaac   2100
ttacttctga caacgatcgg aggaccgaag gagctaaccg cttttttgca caacatgggg   2160
gatcatgtaa ctcgccttga tcgttgggaa ccggagctga atgaagccat accaaacgac   2220
gagcgtgaca ccacgatgcc tgtagcaatg gcaacaacgt tgcgcaaact attaactggc   2280
gaactactta ctctagcttc ccggcaacaa ttaatagact ggatggaggc ggataaagtt   2340
gcaggaccac ttctgcgctc ggcccttccg gctggctggt ttattgctga taaatctgga   2400
gccggtgagc gtggctcacg cggtatcatt gcagcactgg ggccagatgg taagccctcc   2460
cgtatcgtag ttatctacac gacggggagt caggcaacta tggatgaacg aaatagacag   2520
atcgctgaga taggtgcctc actgattaag cattggtaac tgtcagacca agtttactca   2580
tatatacttt agattgattt aaaacttcat ttttaattta aaaggatcta ggtgaagatc   2640
ctttttgata atctcatgac caaaatccct taacgtgagt tttcgttcca ctgagcgtca   2700
gaccccgtag aaaagatcaa aggatcttct tgagatcctt tttttctgcg cgtaatctgc   2760
tgcttgcaaa caaaaaaacc accgctacca gcggtggttt gtttgccgga tcaagagcta   2820
ccaactcttt ttccgaaggt aactggcttc agcagagcgc agataccaaa tactgttctt   2880
ctagtgtagc cgtagttagg ccaccacttc aagaactctg tagcaccgcc tacatacctc   2940
gctctgctaa tcctgttacc agtggctgct gccagtggcg ataagtcgtg tcttaccggg   3000
ttggactcaa gacgatagtt accggataag gcgcagcggt cgggctgaac ggggggttcg   3060
tgcacacagc ccagcttgga gcgaacgacc tacaccgaac tgagatacct acagcgtgag   3120
ctatgagaaa gcgccacgct tcccgaaggg agaaaggcgg acaggtatcc ggtaagcggc   3180
agggtcggaa caggagagcg cacgagggag cttccagggg gaaacgcctg gtatctttat   3240
agtcctgtcg ggtttcgcca cctctgactt gagcgtcgat ttttgtgatg ctcgtcaggg   3300
gggcggagcc tatggaaaaa cgccagcaac gcggcctttt tacggttcct ggccttttgc   3360
tggccttttg ctcacatgtt ctttcctgcg ttatcccctg attctgtgga taaccgtatt   3420
accgcctttg agtgagctga taccgctcgc cgcagccgaa cgaccgagcg cagcgagtca   3480
gtgagcgagg aagcggaaga acgcggacac ccagcgtaac aatctaatat tgtttctcaa   3540
atcgggctgt tatcgcatgg tgctcatgat gaggttactg accaaattcg ccacgcatcg   3600
gtgctggtag aatgttcact tcgaggtggg tagacggcgt cacgtgcaat gccttgtctt   3660
cccctatctg cggccccgac tgcctcgcga agacaaggga tcggacgtcg aacgtattct   3720
gtttgctacc ggcacgggag taggatcgtt gatatacacc atgcgcgtta actctgaccc   3780
ccttcctctt aaatgagaat ggataagagg ctcgtgggat tgacgtgagg gggcagggat   3840
ggctatattt ctgggagcga actccgggcg aattactaat aaaaagcctt ccattttcta   3900
ttttgatttg tagaaaacta gtgtgcttgg gagtccctga tgattaaata aaccaagatt   3960
ttaccaatgg gggctagcga agcggtgatc gccgaagtat cgactcaact atcagaggta   4020
gttggcgtca tcgagcgcca tctcgaaccg acgttgctgg ccgtacattt gtacggctcc   4080
gcagtggatg gcggcctgaa gccacacagt gatattgatt tgctggttac ggtgaccgta   4140
aggcttgatg aaacaacgcg gcgagctttg atcaacgacc ttttggaaac ttcggcttcc   4200
```

```
cctggagaga gcgagattct ccgcgctgta gaagtcacca ttgttgtgca cgacgacatc   4260

attccgtggc gttatccagc taagcgcgaa ctgcaatttg gagaatggca gcgcaatgac   4320

attcttgcag gtatcttcga gccagccacg atcgacattg atctggctat cttgctgaca   4380

aaagcaagag aacatagcgt tgccttggta ggtccagcgg cggaggaact ctttgatccg   4440

gttcctgaac aggatctatt tgaggcgcta aatgaaacct taacgctatg gaactcgccg   4500

cccgactggg ctggcgatga gcgaaatgta gtgcttacgt tgtcccgcat ttggtacagc   4560

gcagtaaccg gcaaaatcgc gccgaaggat gtcgctgccg actgggcaat ggagcgcctg   4620

ccggcccagt atcagcccgt catacttgaa gctagacagg cttatcttgg acaagaagaa   4680

gatcgcttgg cctcgcgcgc agatcagttg gaagaatttg tccactacgt gaaaggcgag   4740

atcaccaagg tagtgggcaa agaacttgtt gaaggaaaat tggagctagt agaaggtctt   4800

aaagtcgcca tggctagtaa aggagaagaa cttttcactg gagttgtccc aattcttgtt   4860

gaattagatg gtgatgttaa tgggcacaaa ttttctgtca gtggagaggg tgaaggtgat   4920

gcaacatacg gaaaacttac ccttaaattt atttgcacta ctggaaaact acctgttcct   4980

tggccaacac ttgtcactac tttctcttat ggtgttcaat gcttttcaag atacccagat   5040

catatgaagc ggcacgactt cttcaagagc gccatgcctg agggatacgt gcaggagagg   5100

accatctctt tcaaggacga cgggaactac aagacacgtg ctgaagtcaa gtttgaggga   5160

gacaccctcg tcaacaggat cgagcttaag ggaatcgatt tcaaggagga cggaaacatc   5220

ctcggccaca agttggaata caactacaac tcccacaacg tatacatcac ggcagacaaa   5280

caaaagaatg gaatcaaagc taacttcaaa attagacaca acattgaaga tggaagcgtt   5340

caactagcag accattatca acaaaatact ccaattggcg atggccctgt ccttttacca   5400

gacaaccatt acctgtccac acaatctgcc ctttcgaaag atcccaacga aaagagagat   5460

cacatggtcc ttcttgagtt tgtaacagct gctgggatta cacatggcat ggatgaacta   5520

tacaaataag cttaaacagt agacattagc agataaatta gcaggaaata aagaaggata   5580

aggagaaaga actcaagtaa ttatccttcg ttctcttaat tgaattgcaa ttaaactcgg   5640

cccaatcttt tactaaaagg attgagccga ataccgctac aacagctccc tggaacacca   5700

ggagaacaca cttatctcgc gtcttgaggt gataccacgc ctgacacgtg agggcagtac   5760

ggttaattcg gtttagccgg acatcagcgc tcctcattga gcgctgggcc cttcacatga   5820

agatcgcact gaggattggt cctagccagg cttctcagta ctgatacagt acgcgtcgct   5880

tctcgtattg tttgagtctt ggaattagtt tgtatccttc cgccgctgcc ctaagaattc   5940

taattgagct cgaacagtcg accgccggat cctgctcgag tgcctctaga              5990
```

<210> SEQ ID NO 84
<211> LENGTH: 6070
<212> TYPE: DNA
<213> ORGANISM: Artificial Sequence
<220> FEATURE:
<223> OTHER INFORMATION: An example of an episomal DNA vector

<400> SEQUENCE: 84

```
tgccagatcc aatgtagatc caactttcga ttcactcgtg ggatccgggc ggtccggggg     60

ggaccaccac ggctcctctc ttctcgtcac atcgacaatt caataaggta tccgacatta    120

acaatgattt aaattgtgtt cattgtgttt tttatggtac ataaccttca tagatttata    180

gattatctca aaaacagaag aaagggtgga aagtgaggaa gaaagagatg tagaaataga    240
```

-continued

```
aacagcttcc gaaatgaagg ggactaaaca ggaacaagag ggatccactg aagaagatcc    300
ttatccttct ccttcccttt tttcggaaga aaggtgggat ccggacaaaa tcgatgaaac    360
ggaagaaatc cgagtgaatg gaaaggacaa aataaaggat aaattccact ctcaccttac    420
agagacaggt tcctatatga ggaagtatcc ttccccgcag tcaagaccaa ggttagtatt    480
ctctgctagg aagtttactt aggttactct agcatgtgcc tggataaccc tctaggcaaa    540
ggtggattga ctttgtactg tcctcagatc gacgttggat gaactgtcgc gccacgaggg    600
gctgtggagc gcattgcgac acattggtgc gctgctaacc catcctttcc agtacggcta    660
ctgatgtcca cgctcccagc ctgctacgct ccgcccgcct gtctctgtaa ggtgagagtg    720
gaatttatcc tttattttgt cctttccatt cactcggatt tcttccgttt catcgatttt    780
gtccggatcc cacctttctt ccgaaaaaag ggaaggagaa ggataaggat cttcttcagt    840
ggatccctct tgttcctgtt tagtcccctt catttcggaa gctgtttcta tttctacatc    900
tctttcttcc tcactttcca ccctttcttc tgtttttgag tgctagaaag ttattctttt    960
cgtcttaatg attatatgta aatcgccctc tatatattaa ctctacttat atggaaaaac   1020
tatgattaag tagttacagt cgagaagaga ggagccgtgg tggtcccccc cggaccgccc   1080
ggatcccacg agtgaatcga aagttggatc tacattggat ctgggagcgc acgcgcaagg   1140
tcgcaactac ccgagaatcg atgtggcgga atgggttacg tgagctatta tccggcgggc   1200
cctcaattta aatcgttaca gttgctcgta acggcaaccg gctcggtcct tttccctag    1260
aacagtatct tatacttgct gctctcgtta cttcggcgat cctggtgcag tcggtccgta   1320
aatcggcgca cacttttacg tcgtaccaga caggctcgca taagccagcc ccgacacccg   1380
ccaacacccg ctgacgcgcc ctgacgggct tgtctgctcc cggcatccgc ttacagacaa   1440
gctgtgacct ccgggagctg catgtgtcag aggttttcac cgtcatcacc gaaacgcgca   1500
cgaaagggcc tcgtgatacg cctattttta taggttaatg tcatgataat aatggtttct   1560
tagacgtcag gtggcacttt tcggggaaat gtgcgcggaa cccctatttg tttatttttc   1620
taaatacatt caaatatgta tccgctcatg agacaataac cctgataaat gcttcaataa   1680
tattgaaaaa ggaagagtat gagtattcaa catttccgtg tcgcccttat tccctttttt   1740
gcggcatttt gccttcctgt ttttgctcac ccagaaacgc tggtgaaagt aaaagatgct   1800
gaagatcagt tgggtgcacg agtgggttac atcgaactgg atctcaacag cggtaagatc   1860
cttgagagtt ttcgccccga agaacgtttt ccaatgatga gcacttttaa agttctgcta   1920
tgtggcgcgg tattatcccg tattgacgcc gggcaagagc aactcggtcg ccgcatacac   1980
tattctcaga atgacttggt tgagtactca ccagtcacag aaaagcatct tacggatggc   2040
atgacagtaa gagaattatg cagtgctgcc ataaccatga gtgataacac tgcggccaac   2100
ttacttctga caacgatcgg aggaccgaag gagctaaccg cttttttgca caacatgggg   2160
gatcatgtaa ctcgccttga tcgttgggaa ccggagctga atgaagccat accaaacgac   2220
gagcgtgaca ccacgatgcc tgtagcaatg gcaacaacgt tgcgcaaact attaactggc   2280
gaactactta ctctagcttc ccggcaacaa ttaatagact ggatggaggc ggataaagtt   2340
gcaggaccac ttctgcgctc ggcccttccg gctggctggt ttattgctga taaatctgga   2400
gccggtgagc gtggctcacg cggtatcatt gcagcactgg ggccagatgg taagccctcc   2460
cgtatcgtag ttatctacac gacggggagt caggcaacta tggatgaacg aaatagacag   2520
atcgctgaga taggtgcctc actgattaag cattggtaac tgtcagacca agtttactca   2580
tatatacttt agattgattt aaaacttcat ttttaattta aaaggatcta ggtgaagatc   2640
```

-continued

```
cttttgata atctcatgac caaaatccct taacgtgagt tttcgttcca ctgagcgtca   2700
gaccccgtag aaaagatcaa aggatcttct tgagatcctt tttttctgcg cgtaatctgc   2760
tgcttgcaaa caaaaaaacc accgctacca gcggtggttt gtttgccgga tcaagagcta   2820
ccaactcttt ttccgaaggt aactggcttc agcagagcgc agataccaaa tactgttctt   2880
ctagtgtagc cgtagttagg ccaccacttc aagaactctg tagcaccgcc tacatacctc   2940
gctctgctaa tcctgttacc agtggctgct gccagtggcg ataagtcgtg tcttaccggg   3000
ttggactcaa gacgatagtt accggataag gcgcagcggt cgggctgaac ggggggttcg   3060
tgcacacagc ccagcttgga gcgaacgacc tacaccgaac tgagatacct acagcgtgag   3120
ctatgagaaa gcgccacgct tcccgaaggg agaaaggcgg acaggtatcc ggtaagcggc   3180
agggtcggaa caggagagcg cacgagggag cttccagggg gaaacgcctg gtatctttat   3240
agtcctgtcg ggtttcgcca cctctgactt gagcgtcgat ttttgtgatg ctcgtcaggg   3300
gggcggagcc tatggaaaaa cgccagcaac gcggcctttt tacggttcct ggccttttgc   3360
tggccttttg ctcacatgtt ctttcctgcg ttatcccctg attctgtgga taaccgtatt   3420
accgcctttg agtgagctga taccgctcgc cgcagccgaa cgaccgagcg cagcgagtca   3480
gtgagcgagg aagcggaaga acgcggacac ccagcgtaac aatctaatat tgtttctcaa   3540
atcgggctgt tatcgcatgg tgctcatgat gaggttactg accaaattcg ccacgcatcg   3600
gtgctggtag aatgttcact tcgaggtggg tagacggcgt cacgtgcaat gccttgtctt   3660
cccctatctg cggccccgac tgcctcgcga agacaaggga tcggacgtcg aacgtattct   3720
gtttgctacc ggcacgggag taggatcgtt gatatacacc atgcgcgtta actctgaccc   3780
ccttcctctt aaatgagaat ggataagagg ctcgtgggat tgacgtgagg gggcagggat   3840
ggctatattt ctgggagcga actccgggcg aattactaat aaaaagcctt ccatttteta   3900
ttttgatttg tagaaaacta gtgtgcttgg gagtccctga tgattaaata aaccaagatt   3960
ttaccaatgg gggctagcga agcggtgatc gccgaagtat cgactcaact atcagaggta   4020
gttggcgtca tcgagcgcca tctcgaaccg acgttgctgg ccgtacattt gtacggctcc   4080
gcagtggatg gcggcctgaa gccacacagt gatattgatt tgctggttac ggtgaccgta   4140
aggcttgatg aaacaacgcg gcgagctttg atcaacgacc ttttggaaac ttcggcttcc   4200
cctggagaga gcgagattct ccgcgctgta gaagtcacca ttgttgtgca cgacgacatc   4260
attccgtggc gttatccagc taagcgcgaa ctgcaatttg gagaatggca gcgcaatgac   4320
attcttgcag gtatcttcga gccagccacg atcgacattg atctggctat cttgctgaca   4380
aaagcaagag aacatagcgt tgccttggta ggtccagcgg cggaggaact ctttgatccg   4440
gttcctgaac aggatctatt tgaggcgcta aatgaaacct taacgctatg gaactcgccg   4500
cccgactggg ctggcgatga gcgaaatgta gtgcttacgt tgtcccgcat ttggtacagc   4560
gcagtaaccg gcaaaatcgc gccgaaggat gtcgctgccg actgggcaat ggagcgcctg   4620
ccggcccagt atcagcccgt catacttgaa gctagacagg cttatcttgg acaagaagaa   4680
gatcgcttgg cctcgcgcgc agatcagttg gaagaatttg tccactacgt gaaaggcgag   4740
atcaccaagg tagtgggcaa agaacttgtt gaaggaaaat tggagctagt agaaggtctt   4800
aaagtcgcca tggctagtaa aggagaagaa cttttcactg gagttgtccc aattcttgtt   4860
gaattagatg gtgatgttaa tgggcacaaa ttttctgtca gtggagaggg tgaaggtgat   4920
gcaacatacg gaaaacttac ccttaaattt atttgcacta ctggaaaact acctgttcct   4980
```

```
tggccaacac ttgtcactac tttctcttat ggtgttcaat gcttttcaag atacccagat   5040

catatgaagc ggcacgactt cttcaagagc gccatgcctg agggatacgt gcaggagagg   5100

accatctctt tcaaggacga cgggaactac aagacacgtg ctgaagtcaa gtttgaggga   5160

gacaccctcg tcaacaggat cgagcttaag ggaatcgatt tcaaggagga cggaaacatc   5220

ctcggccaca agttggaata caactacaac tcccacaacg tatacatcac ggcagacaaa   5280

caaaagaatg gaatcaaagc taacttcaaa attagacaca acattgaaga tggaagcgtt   5340

caactagcag accattatca acaaaatact ccaattggcg atggccctgt ccttttacca   5400

gacaaccatt acctgtccac acaatctgcc ctttcgaaag atcccaacga aaagagagat   5460

cacatggtcc ttcttgagtt tgtaacagct gctgggatta cacatggcat ggatgaacta   5520

tacaaataag cttaaacagt agacattagc agataaatta gcaggaaata aagaaggata   5580

aggagaaaga actcaagtaa ttatccttcg ttctcttaat tgaattgcaa ttaaactcgg   5640

cccaatcttt tactaaaagg attgagccga ataccgctcc aggcatcaaa taaaacgaaa   5700

ggctcagtcg aaagactggg cctttcgttt tatctgttgt ttgtcggtga acgctctcac   5760

aacagctccc tggaacacca ggagaacaca cttatctcgc gtcttgaggt gataccacgc   5820

ctgacacgtg agggcagtac ggttaattcg gtttagccgg acatcagcgc tcctcattga   5880

gcgctgggcc cttcacatga agatcgcact gaggattggt cctagccagg cttctcagta   5940

ctgatacagt acgcgtcgct tctcgtattg tttgagtctt ggaattagtt tgtatccttc   6000

cgccgctgcc ctaagaattc taattgagct cgaacagtcg accgccggat cctgctcgag   6060

tgcctctaga                                                           6070
```

<210> SEQ ID NO 85
<211> LENGTH: 9965
<212> TYPE: DNA
<213> ORGANISM: Artificial Sequence
<220> FEATURE:
<223> OTHER INFORMATION: An example of an episomal DNA vector

<400> SEQUENCE: 85

```
ggccattatg gccgttcgac acaattggga ttttttttgg aaattggaag cagttactaa     60

ttccaccccc tctccactgg atctgttccc gggagtaccc tcaaaaaaag gaacctttcc    120

tctccccagc catttcgggt taagaagatg tgaaggcgcg tttatctcta taagaagggt    180

gcgttccgag gtgtgaagtg ggagagaagg gatgtcacaa ttggggtttt gaataaaacg    240

acctttttgat ttttcatttt tttttttttc gttttcatat tgaaaaagta ataagaatga    300

gaggtgttaa gctttttatc atcctggcgt cgagctattt ttccgcagga cctcccctac    360

agtatcgtca ccgcagtaga gtttaaccac caagttcggg atggattggt gtggttcctc    420

tacgcctagg acaccagaat atcgaaccat gaacgaagaa aggcatgaga gaaaagcata    480

ttggctagtg attgtgaggc cccaattctt gactggaggg gacaccaaag gcctctgccc    540

ttccatccct tggatagata gagagggagg gcagagcttt tggttttttc atgttgtcaa    600

agagttgaac aatggttttt tcgtgttgtc aaagatttga acaatgaaaa tagatggcga    660

gtgcctgatc gaattgatca ggtcatgtag gaacaaggtt caagtctacc ggtctgttag    720

gatgcctcag ctgcatacat cactgcactt ccacttgaca cctatcgtaa tgataaacgg    780

ctcgtctcgc cgtgaccttc tcttgaattc tcaaaaaaac ttctgtcgct ccatccccgc    840

aggggcagag aacccgtcgc tgtctcggct gtgctaccgg aagctctggg gaagtcggaa    900

taggagagca ctcatcttgg ggtgggctta ctacttagat gctttcagca gttatccgct    960
```

-continued ccgcacttgg ctacccagcg tttaccgtgg gcacgataac tggtacacca gaggtgcgtc 1020
cttcccggtc ctctcgtact agggaaaggt cctctcaatg ctctaacgcc cacaccggat 1080
atggaccgaa ctgtctcacg acgttctgaa cccagctcac gtaccgcttt aatgggcgaa 1140
cagcccaacc cttggaacat actacagccc caggtggcga agagccgaca tcgaggtgcc 1200
aaaccttccc gtcgatgtga gctcttgggg aagatcagcc tgttatccct agagtaactt 1260
ttatccgttg agcgacggcc cttccactcg gcaccgtcgg atcactaagg ccgactttcg 1320
tccctgctcg acgggtgggt cttgcagtca agctcccttc tgcctttgca ctcgagggcc 1380
aatctccgtc cggcccgagg aaacctttgc acgcctccgt taccttttgg gaggcctacg 1440
ccccatagaa actgtctacc tgagactgtc ccttggcccg taggtcctga cacaaggtta 1500
gaattctagc ccttccagag tggtatctca ctgatggctc gggccccccc ggaaggaggc 1560
cttcttcgcc ttccacctaa gctgcgcagg aaaggcccaa agccaatccc agggaacagt 1620
gaagcttcat agggtctttc tgtccaggtg caggtagtcc gcatcttcac agacatgtct 1680
atttcaccga gcctctctcc gagacagtgc ccagatcgtt acgcctttcg tgcgggtcgg 1740
aacttacccg acaaggaatt tcgctacctt aggaccgtta tagttacggc cgccgttcac 1800
cggggcttcg gtcgccggct cccctgtcat caggtcacca acttccttga ccttccggca 1860
ctgggcaggc gtcagccccc atacatggtc ttacgacttt gcggagacct gtgtttttgg 1920
taaacagtcg cccgggcctg gtcactgcga cccccctttgt gaggaggcac cccttctccc 1980
gaagttacgg ggctattttg ccgagttcct tagagagagt tgtctcgcgc ccctaggtat 2040
tctctaccta cccacctgtg tcggtttcgg gtacaggtac cctcttgctt aacgtcgttc 2100
gagcttttcc tgggagtatg gcatgggtta cttcagcgcc gtagcgcctg gtattcgaac 2160
attggctcga ggcattttct ctaccccttc ttaccctgaa aaagcaggga caccttacgt 2220
tcttgaaccg ataaccatct ttcggctaac ctagcctcct ccgtccctcg ggactaacaa 2280
ggggtagtac aggaatattc acctgttgtc catcgactac gcctttcggc ctgatcttag 2340
gccctgactc accctccgtg gacgaacctt gcggaggaac ccttaggttt tcggggcatt 2400
ggattctcac caatgtttgc gttactcaag ccgacattct cgcttccgct tcgtccacca 2460
ccgctcgcgc ggaggcttct ctctaaggcg gaacgctccc ctaccgatgt atttttacat 2520
cccacagctt cggcagaccg cttagccccg ttcatcttcg gcgcaagagc gctcgatcag 2580
tgagctatta cgcactcttt caagggtggc tgcttctagg caaacctcct ggctgtctct 2640
gcacccctac ctcctttatc actgagcggt catttagggg ccttagctgg tgatccgggc 2700
tgtttccctc tcgacgatga agcttatccc ccatcgtctc actagccgac cttgacccct 2760
gttattttga ggtcatatct agtattcaga gtttgcctcg atttggtacc gctctcgcgg 2820
cccgcaccga aacagtgctt taccccctaga tgtccagtca actgctgcgc ctcaacgcat 2880
ttcggggaga accagctagc tctgggttcg agtggcattt caccccctaac cacaactcat 2940
ccgctgattc ttcaacatca gtcggttcgg acctccactt agtttcaccc aagcttcatc 3000
ctggtcatgg atagatcacc caggttcggg tccataagca gtgacaattg ccctatgaag 3060
actcgctttc gctacggctc cggtgggttc ccttaaccaa gccactgcct atgagtcgcc 3120
ggctcattct tcaacaggca cgcggtcaga gccctggctc ctcccactgc ttgggagctt 3180
acggtttcat gttctatttc actccccgat gggggttctt ttcacccttc cctcacggta 3240
ctacttcgct atcggtcacc caggagtatt tagccttgca aggtggtcct tgctgattca 3300
cacgggattc cacgtgcccc atgctactcg ggtcagagca taagctagtg atgctttcgg 3360
ctactggact ttcgccatct agggtgcagc attcgggctg cttcgcctag cagcacgacg 3420
cttgtattgc tctcccacaa ccccgttttc acggtttagg ctgctcccat ttcgctcgcc 3480
gctactacgg gaatcgcttt tgctttcttt tcctctggct actaagatgt ttcagttcgc 3540
caggttgtct cttgcctgcc catggattca gcagcagttc gaaaggttgc cctattcggg 3600
aatctccgga tctatgctta ttttcaactc cccgaagcat ttcgtcgatt actacgccct 3660
tcctagtctc tgggtgccta ggtatccacc gtaagccttt cctcgtttga acctcgccct 3720
tcacttttaa ggctatgcca tcctaaggtg ctgctaaatg gatggatctt atcaacgtcc 3780
atgaatgata aatcatagat cgaaccgccg aatcggaaaa attgggtgct atcataaagc 3840
tttgtatcgg ctaagttcac gagttggaga taagcggact cgaaccgctg acatccgccg 3900
cagggtaaac caccgcctct caggtccccc gactgattct accatagagg ccaacgatag 3960
acaataactc ccccccgaac acagcttaca actttcatcg tactgtgctc tccaaagagc 4020
aactcttctc aaaatctcac tcaaaaggtg ctgagttgga atcccattct aactaaggat 4080
tcttgtggtt ccggaggatc caactacagg agaaccagga acggagggct ttccccccct 4140
tccgcccgac tctttggtct taagaacgct ggttttaaga atgagtcatt gcccttctcc 4200
gaccctgact gcccaacctg agagcggaca gctaatgcgt tccacttatt gaacagggtt 4260
ctatggtcgg tccgtgaccc ctggatgccg aaggcgtcct tggggtgatc tcgtagttcc 4320
tacggggtgg agatgatggg gtcggtccat ggattttcct tccttttctt ttgccgcatt 4380
tcgctcaaag ggttgaaggg agatagtgca tcaagctgtt cgcaagggcc aacttgatcc 4440
tcttccccag agatctcaga tgagggaacc ctgggagagc cgccgactcc aactaccgtc 4500
catgtacgat ccatactaga tctgaccaac tgcccatcct acctcctcta cgttcttgac 4560
agcccatctt tgtctcagta gagtctttca gtggcacgtt tcggtcctct tccccattac 4620
ttagaaaaag tgagccaccg gttcaggtac aagatactat cattaccgcc tggacaatta 4680
gacatccaac ccgtaatcgc aacgacccaa ttgcaagagc ggagctctac caactgagct 4740
atatcccccc gagccaagtg gagcatgcat gaagtagtca gatgcttctt ctattctttt 4800
ccctggcgca gctgggccat cctggacttg aaccagagac ctcgcccgtg aagtaaatca 4860
tcgcacctac ggtccaacca attgggagag aatcaataga ttccttttcg ggagcgattc 4920
atccttcccg aacgcagcat acaactctcc gttgtactgc gctctccaag tgtgcttgtt 4980
ccccccttct tccttaccct ggcaagtctt tgtgaaataa ctccgatgag aagaaaaaag 5040
aaggcgttaa gagagcctcc tggcccaacc ctagacactc taagatcctt tttcaaacct 5100
gctcccattt cgatttcgag tcaagaaaaa aacggctcga atggtacgat ccctccgtca 5160
ccccagaatg aaaggggcga tctcgtagtt cttggtctgt gaagatgcgt tgttaggtgc 5220
tccattttat tttcccattg ctaaacctgt gctcgagaga tagctgtcca tacactgata 5280
agggatgtat ggattctcga gaagagagga gccgtggtgg tccccccccgg accgcccgga 5340 tcccacgagt gaatcgaaag ttggatctac attggatctc acccgaatcg ccccatctat 5400
cctcctgagg aggagtttgg tttcaaaccc cggttcgaac aggaggagta cgccatgcta 5460
atgtgccttg gatgatccac atctcagggt caggcgccga tgagcacatt gaactatcca 5520
tgtggctgag agccctcaca gcccaggcac aacgacgcaa ttatcagggg cgcgctctac 5580
cactgagcta atagcccgtc gtgcgagcct cccactgggg gcccgctatg ccaaaagcga 5640
gagaaacccc atccctctct ttcctttttt cgcccccatg tcgccacacg gggggaacat 5700

-continued

```
ggggacgtaa aaaagggggt cctatcaact tgttccgacc taggataata agctcatgag   5760
cttggtctta cttcaccgtc gagaaaggaa agatgacttc catctccaag tttaactcag   5820
acgtagctcc cttctttttt ttgggggtgt gaagcagtgt caaaccaaaa tacccaacaa   5880
gcattagctc tccctgaaaa ggaggtgatc cagccgcacc ttccagtacg gctaccttgt   5940
tacgacttca ctccagtcac tagccctgcc ttcggcatcc ccctccttgc ggttaaggta   6000
acgacttcgg gcatggccag ctcccatagt gtgacgggcg gtgtgtacaa ggcccgggaa   6060
cgaattcacc gccgtatggc tgaccggcga ttactagcga ttccggcttc atgcaggcga   6120
gttgcagcct gcaatccgaa ctgaggacgg gtttttgggg ttagctcacc ctcgcgggat   6180
cgcgaccctt tgtcccggcc attgtagcac gtgtgtcgcc cagggcataa ggggcatgat   6240
gacttgacgt catcctcacc ttcctccggc ttatcaccgg cagtctgttc agggttccaa   6300
actcaacgat ggcaactaaa cacgagggtt gcgctcgttg cgggacttaa cccaacacct   6360
tacggcacga gctgacgaca gccatgcacc acctgtgtcc gcgttcccga aggcacccct   6420
ctctttcaag aggattcgcg gcatgtcaag ccctggtaag gttcttcgct ttgcatcgaa   6480
ttaaaccaca tgctccaccg cttgtgcggg cccccgtcaa ttcctttgag tttcattctt   6540
gcgaacgtac tccccaggcg ggatacttaa cgcgttagct acagcactgc acgggtcgat   6600
acgcacagcg cctagtatcc atcgtttacg gctaggacta ctggggtatc taatcccatt   6660
cgctccccta gctttcgtgt ctcagtgtca gtgtcggccc agcagagtgc tttcgccgtt   6720
ggtgttcttt ccgatctcta cgcatttcac cgctccaccg gaaattccct ctgcccctac   6780
cgtactccag cttggtagtt tccaccgcct gtccagggtt gagccctggg atttgacggc   6840
ggacttaaaa agccacctac agacgcttta cgcccaatca ttccggataa cgcttgcatc   6900
ctctgtatta ccgcggctgc tggcacagag ttagccgatg cttattcccc agataccgtc   6960
attgcttctt ctccgggaaa agaagttcac gacccgtggg ccttctacct ccacgcggca   7020
ttgctccgtc aggctttcgc ccattgcgga aaattcccca ctgctgcctc ccgtaggagt   7080
ctgggccgtg tctcagtccc agtgtggctg atcatcctct cggaccagct actgatcatc   7140
gccttggtaa gctattgcct caccaactag ctaatcagac gcgagcccct cctcgggcgg   7200
attcctcctt ttgctcctca gcctacgggg tattagcagc cgtttccagc tgttgttccc   7260
ctcccaaggg caggttctta cgcgttactc acccgtccgc cactggaaac accgtttccc   7320
gtgtttcccg tccgacttgc atgtgttaag catgccgcca gcgttcatcc tgagccagga   7380
tcgaactctc catgagattc atagttgcat tacttatagc ttccttgttc gtagacaaag   7440
cggattcgga attgtctttc attccaaggc ataacttgta tccatgcgct tcatattcgc   7500
ccggagttcg ctcccagaaa tatagccatc cctgccccct cacgtcaatc ccacgagcct   7560
cttatccatt ctcattgaac gacggcgggg gagcaaatcc aactagaaaa actcacattg   7620
ggctgactct accacccagt caattctgtt ccacttaatc cctctttcat ggccggccat   7680
tatggccctg ggcctcatgg gccttccttt cactgcccgc tttccagtcg ggaaacctgt   7740
cgtgccagct gcattaacat ggtcatagct gtttccttgc gtattgggcg ctctccgctt   7800
cctcgctcac tgactcgctg cgctcggtcg ttcgggtaaa gcctggggtg cctaatgagc   7860
aaaaggccag caaaaggcca ggaaccgtaa aaaggccgcg ttgctggcgt ttttccatag   7920
gctccgcccc cctgacgagc atcacaaaaa tcgacgctca agtcagaggt ggcgaaaccc   7980
gacaggacta taaagatacc aggcgtttcc ccctggaagc tccctcgtgc gctctcctgt   8040
```

tccgaccctg ccgcttaccg gatacctgtc cgcctttctc ccttcgggaa gcgtggcgct 8100
ttctcatagc tcacgctgta ggtatctcag ttcggtgtag gtcgttcgct ccaagctggg 8160
ctgtgtgcac gaaccccccg ttcagcccga ccgctgcgcc ttatccggta actatcgtct 8220
tgagtccaac ccggtaagac acgacttatc gccactggca gcagccactg gtaacaggat 8280
tagcagagcg aggtatgtag gcggtgctac agagttcttg aagtggtggc ctaactacgg 8340
ctacactaga agaacagtat ttggtatctg cgctctgctg aagccagtta ccttcggaaa 8400
aagagttggt agctcttgat ccggcaaaca aaccaccgct ggtagcggtg gtttttttgt 8460
ttgcaagcag cagattacgc gcagaaaaaa aggatctcaa gaagatcctt tgatcttttc 8520
tacggggtct gacgctcagt ggaacgaaaa ctcacgttaa gggattttgg tcatgagatt 8580
atcaaaaagg atcttcacct agatcctttt aaattaaaaa tgaagtttta aatcaatcta 8640
aagtatatat gagtaaactt ggtctgacag ttattagaaa aattcatcca gcagacgata 8700
aaacgcaata cgctggctat ccggtgccgc aatgccatac agcaccagaa aacgatccgc 8760
ccattcgccg cccagttctt ccgcaatatc acgggtggcc agcgcaatat cctgataacg 8820
atccgccacg cccagacggc cgcaatcaat aaagccgcta aaacggccat tttccaccat 8880
aatgttcggc aggcacgcat caccatgggt caccaccaga tcttcgccat ccggcatgct 8940
cgctttcaga cgcgcaaaca gctctgccgg tgccaggccc tgatgttctt catccagatc 9000
atcctgatcc accaggcccg cttccatacg ggtacgcgca cgttcaatac gatgtttcgc 9060
ctgatgatca aacggacagg tcgccgggtc cagggtatgc agacgacgca tggcatccgc 9120
cataatgctc actttttctg ccggcgccag atggctagac agcagatcct gacccggcac 9180
ttcgcccagc agcagccaat cacggcccgc ttcggtcacc acatccagca ccgccgcaca 9240
cggaacaccg gtggtggcca gccagctcag acgcgccgct tcatcctgca gctcgttcag 9300
cgcaccgctc agatcggttt tcacaaacag caccggacga ccctgcgcgc tcagacgaaa 9360
caccgccgca tcagagcagc caatggtctg ctgcgcccaa tcatagccaa acagacgttc 9420
cacccacgct gccgggctac ccgcatgcag gccatcctgt tcaatcatac tcttcctttt 9480
tcaatattat tgaagcattt atcagggtta ttgtctcatg agcggataca tatttgaatg 9540
tatttagaaa aataaacaaa taggggttcc gcgcacattt ccccgaaaag tgccacctaa 9600
attgtaagcg ttaatatttt gttaaaattc gcgttaaatt tttgttaaat cagctcattt 9660
tttaaccaat aggccgaaat cggcaaaatc ccttataaat caaaagaata gaccgagata 9720
gggttgagtg gccgctacag ggcgctccca ttcgccattc aggctgcgca actgttggga 9780
agggcgtttc ggtgcgggcc tcttcgctat tacgccagct ggcgaaaggg ggatgtgctg 9840
caaggcgatt aagttgggta acgccagggt tttcccagtc acgacgttgt aaaacgacgg 9900
ccagtgagcg cgacgtaata cgactcacta tagggcgaat tgaaggaagg ccgtcaaggc 9960
cgcat 9965

<210> SEQ ID NO 86
<211> LENGTH: 9979
<212> TYPE: DNA
<213> ORGANISM: Artificial Sequence
<220> FEATURE:
<223> OTHER INFORMATION: An example of an episomal DNA vector

<400> SEQUENCE: 86
ggccattatg gccgttcgac acaattggga tttttttggg aaattggaag cagttactaa 60
ttccaccccc tctccactgg atctgttccg gggagtaccc tcaaaaaaag gaacctttcc 120

-continued

```
tctccccagc catttcgggt taagaagatg tgaaagcgcg tttatctcta taagtctata    180
agaagggtgc gttccgaggt gtgaagtggg agagaaggga tgtcacaatt ggggttttga    240
ataaaacgac ctttttattt ttcatttttt tttttcgttt tcatattgaa aaagtaataa    300
gaatgagagg tgttaagctt tttatcatcc tggcgtcgag ctatttttcc gcaggacctc    360
ccctacagta tcgtcaccgc agtagagttt aaccaccaag ttcgggatgg attggtgtgg    420
ttcctctacg cctaggacac cagaatatcg aaccatgaac gaagaaaggc atgagagaaa    480
agcatattgg ctagtgattg tgaggcccca attcttgact ggaggggaca ccaaaggcct    540
ctgcccttcc atcccttgga tagatagaga gggagggcag agcttttggt tttttcatgt    600
tgtcaaagag ttgaacaatg gtttttttcgt gttgtcaaag atttgaacaa tgaaaataga    660
tggcgagtgc ctgatcgaat tgatcaggtc atgtaggaac aaggttcaag tctaccggtc    720
tgttaggatg cctcagctgc atacatcact gcacttccac ttgacaccta tcgtaatgat    780
aaacggctcg tctcgccgtg accttctctt gaattctcaa aaaaacttct gtcgctccat    840
ccccgcaggg gcagagaacc cgtcgctgtc tcggctgtgc taccggaagc tctggggaag    900
tcggaatagg agagcactca tcttggggtg ggcttactac ttagatgctt tcagcagtta    960
tccgctccgc acttggctac ccagcgttta ccgtgggcac gataactggt acaccagagg   1020
tgcgtccttc ccggtcctct cgtactaggg aaaggtcctc tcaatgctct aacgcccaca   1080
ccggatatgg accgaactgt ctcacgacgt tctgaaccca gctcacgtac cgctttaatg   1140
ggcgaacagc ccaacccttg gaacatacta cagccccagg tggcgaagag ccgacatcga   1200
ggtgccaaac cttcccgtcg atgtgagctc ttggggaaga tcagcctgtt atccctagag   1260
taacttttat ccgttgagcg acggcccttc cactcggcac cgtcggatca ctaaggccga   1320
ctttcgtccc tgctcgacgg gtgggtcttg cagtcaagct cccttctgcc tttgcactcg   1380
agggccaatc tccgtccggc ccgaggaaac ctttgcacgc ctccgttacc ttttgggagg   1440
cctacgcccc atagaaactg tctacctgag actgtccctt ggcccgtagg tcctgacaca   1500
aggttagaat tctagccctt ccagagtggt atctcactga tggctcgggc ccccccggaa   1560
ggaggccttc ttcgccttcc acctaagctg cgcaggaaag gcccaaagcc aatcccaggg   1620
aacagtgaag cttcataggg tctttctgtc caggtgcagg tagtccgcat cttcacagac   1680
atgtctattt caccgagcct ctctccgaga cagtgcccag atcgttacgc ctttcgtgcg   1740
ggtcggaact tacccgacaa ggaatttcgc taccttagga ccgttatagt tacggccgcc   1800
gttcaccggg gcttcggtcg ccggctcccc tgtcatcagg tcaccaactt ccttgacctt   1860
ccggcactgg gcaggcgtca gcccccatac atggtcttac gactttgcgg agacctgtgt   1920
ttttggtaaa cagtcgcccg ggcctggtca ctgcgacccc ctttgtgagg aggcacccct   1980
tctcccgaag ttacggggct attttgccga gttccttaga gagagttgtc tcgcgcccct   2040
aggtattctc tacctaccca cctgtgtcgg tttcgggtac aggtaccctc ttgcttaacg   2100
tcgttcgagc ttttcctggg agtatggcat gggttacttc agcgccgtag cgcctggtat   2160
tcgaacattg gctcgaggca ttttctctac cccttcttac cctgaaaaag cagggacacc   2220
ttacgttctt gaaccgataa ccatctttcg gctaacctag cctcctccgt ccctcgggac   2280
taacaagggg tagtacagga atattcacct gttgtccatc gactacgcct ttcggcctga   2340
tcttaggccc tgactcaccc tccgtggacg aaccttgcgg aggaaccctt aggttttcgg   2400
ggcattggat tctcaccaat gtttgcgtta ctcaagccga cattctcgct tccgcttcgt   2460
```

-continued

```
ccaccaccgc tcgcgcggag gcttctctct aaggcggaac gctcccctac cgatgtattt   2520
ttacatccca cagcttcggc agaccgctta gccccgttca tcttcggcgc aagagcgctc   2580
gatcagtgag ctattacgca ctctttcaag ggtggctgct tctaggcaaa cctcctggct   2640
gtctctgcac ccctacctcc tttatcactg agcggtcatt taggggcctt agctggtgat   2700
ccgggctgtt tccctctcga cgatgaagct tatcccccat cgtctcacta gccgaccttg   2760
acccctgtta ttttgaggtc atatctagta ttcagagttt gcctcgattt ggtaccgctc   2820
tcgcggcccg caccgaaaca gtgctttacc cctagatgtc cagtcaactg ctgcgcctca   2880
acgcatttcg gggagaacca gctagctctg ggttcgagtg gcatttcacc cctaaccaca   2940
actcatccgc tgattcttca acatcagtcg gttcggacct ccacttagtt tcacccaagc   3000
ttcatcctgg tcatggatag atcacccagg ttcgggtcca taagcagtga caattgccct   3060
atgaagactc gctttcgcta cggctccggt gggttccctt aaccaagcca ctgcctatga   3120
gtcgccggct cattcttcaa caggcacgcg gtcagagccc tggctcctcc cactgcttgg   3180
gagcttacgg tttcatgttc tatttcactc cccgatgggg gttcttttca cccttccctc   3240
acggtactac ttcgctatcg gtcacccagg agtatttagc cttgcaaggt ggtccttgct   3300
gattcacacg ggattccacg tgccccatgc tactcgggtc agagcgtaag ctagtgatgc   3360
tttcggctac tggactttcg ccatctaggg tgcagcattc aggctgcttc gcctagcagc   3420
acgacgcttg tattgctctc ccacaacccc gttttcacgg tttaggctgc tcccatttcg   3480
ctcgccgcta ctacgggaat cgcttttgct ttcttttcct ctggctacta agatgtttca   3540
gttcgccagg ttgtctcttg cctgcccatg gattcagcag cagttcgaaa ggttgcccta   3600
ttcgggaatc tccggatcta tgcttatttt caactccccg aagcatttcg tcgattacta   3660
cgcccttcct cgtctctggg tgcctaggta tccaccgtaa gcctttcctc gtttgaacct   3720
cgcccttcac ttttaaggct atgccatcct aaggtgctgc taaatggatg gatcttatca   3780
acgtccatga atgataaatc atagatcgaa ccgccgaatc ggaaaaattg ggtgctatca   3840
taaagctttg tatcggctaa gttcacgagt tggagataag cggactcgaa ccgctgacat   3900
ccgccgcagg gtaaaccacc gcctctcagg tcccccgact gattctacca tagaggccaa   3960
cgatagacaa taactccccc ccgaacacag cttacaactt tcatcgtact gtgctctcca   4020
aagagcaact cttctcaaaa tctcactcaa aaggtgctga gttggaatcc cattctaact   4080
aaggattctt gtggttccgg aggatccaac tacaggagaa ccaggaacgg agggctttcc   4140
ccccttccg cccgactctt tggtcttaag aacgctggtt ttaagaatga gtcattgccc   4200
ttctccgacc ctgactgccc aacctgagag cggacagcta atgcgttcca cttattgaac   4260
agggttctat ggtcggtccg tgacccctgg atgccgaagg cgtccttggg gtgatctcgt   4320
agttcctacg gggtggagat gatggggtcg gtccatggat tttccttcct tttcttttgc   4380
cgcatttcgc tcaaagggtt gaagggagat agtgcatcaa gctgttcgca agggccaact   4440
tgatcctctt ccccagagat ctcagatgag ggaaccctgg gagagccgcc gactccaact   4500
accgtccatg tacgatccat actagatctg accaactgcc catcctacct cctctacgtt   4560
cttgacagcc catctttgtc tcagtagagt ctttcagtgg cacgtttcgg tcctcttccc   4620
cattacttag aaaaagtgag ccaccggttc aggtacaaga tactatcatt accgcctgga   4680
caattagaca tccaacccgt aatcgcaacg acccaattgc aagagcggag ctctaccaac   4740
tgagctatat ccccccgagc caagtggagc atgcatgaag tagtcagatg cttcttctat   4800
tcttttccct ggcgcagctg ggccatcctg gacttgaacc agagacctcg cccgtgaagt   4860
```

```
aaatcatcgc acctacggtc caaccaattg ggagagaatc aatagattcc ttttcgggag   4920
cgattcatcc ttcccgaacg cagcatacaa ctctccgttg tactgcgctc tccaagtgtg   4980
cttgttcccc ccttcttcct taccctggca agtctttgtg aaataactcc gatgagaaga   5040
aaaaagaagg cgttaagaga ccctcctggc ccaaccctag acactctaag atcctttttc   5100
aaacctgctc ccatttcgat ttcgagtcaa gaaaaaaacg gctcgaatgg tacgatccct   5160
ccgtcacccc agaatgaaag gggtgatctc gtagttcttg gtctgtgaag atgcgttgtt   5220
aggtgctcca ttttattttc ccattgaggc cgaacctaaa cctgtgctcg agagatagct   5280
gtccatacac tgataaggga tgtatggatt ctcgagaaga gaggagccgt ggtggtcccc   5340
cccggaccgc ccggatccca cgagtgaatc gaaagttgga tctacattgg atctcacccg   5400
aatcgcccca tctatcctcc tgaggaggag tttggtttca aaccccggtt cgaacaggag   5460
gagtacgcca tgctaatgtg ccttggatga tccacatctc agggtcaggc gccgatgagc   5520
acattgaact atccatgtgg ctgagagccc tcacagccca ggcacaacga cgcaattatc   5580
aggggcgcgc tctaccactg agctaatagc ccgtcgtgcg agcctcccac tgggggcccg   5640
ctatgccaaa agcgagagaa accccatccc tctctttcct tttttcgccc ccatgtcgcc   5700
acacggggga acatagggac gtaaaaaagg ggatcctatc aacttgttcc gacctaggat   5760
aataagctca tgagcttggt cttacttcac cgtcgagaaa ggaaagaaga cttccatctc   5820
caagtttaac tcagacgtag ctcccttctt ttttttgggg gtgtgaagca gtgtcaaacc   5880
aaaataccca acaagcatta gctctccctg aaaaggaggt gatccagccg caccttccag   5940
tacggctacc ttgttacgac ttcactccag tcactagccc tgccttcggc atccccctcc   6000
ttgcggttaa ggtaacgact tcgggcatgg ccagctccca tagtgtgacg ggcggtgtgt   6060
acaaggcccg ggaacgaatt caccgccgta tggctgaccg gcgattacta gcgattccgg   6120
cttcatgcag gcgagttgca gcctgcaatc cgaactgagg acgggttttt ggggttagct   6180
caccctcgcg ggatcgcgac cctttgtccc ggccattgta gcacgtgtgt cgcccagggc   6240
ataaggggca tgatgacttg acgtcatcct caccttcctc cggcttatca ccggcagtct   6300
gttcagggtt ccaaactcaa cgatggcaac taaacacgag ggttgcgctc gttgcgggac   6360
ttaacccaac accttacggc acgagctgac gacagccatg caccacctgt gtccgcgttc   6420
ccgaaggcac ccctctcttt caagaggatt cgcggcatgt caagccctgg taaggttctt   6480
cgctttgcat cgaattaaac cacatgctcc accgcttgtg cgggcccccg tcaattcctt   6540
tgagtttcat tcttgcgaac gtactcccca ggcgggatac ttaacgcgtt agctacagca   6600
ctgcacgggt cgatacgcac agcgcctagt atccatcgtt tacggctagg actactgggg   6660
tatctaatcc cattcgctcc cctagctttc gtctctcagt gtcagtgtcg gcccagcaga   6720
gtgctttcgc cgttggtgtt ctttccgatc tctacgcatt tcaccgctcc accggaaatt   6780
ccctctgccc ctaccgtact ccagcttggt agtttccacc gcctgtccag ggttgagccc   6840
tgggatttga cggcggactt aaaaagccac ctacagacgc tttacgccca atcattccgg   6900
ataacgcttg catcctctgt attaccgcgg ctgctggcac agagttagcc gatgcttatt   6960
ccccagatac cgtcattgct tcttctccgg gaaaagaagt tcacgacccg tgggccttct   7020
acctccacgc ggcattgctc cgtcaggctt tcgcccattg cggaaaattc cccactgctg   7080
cctcccgtag gagtctgggc cgtgtctcag tcccagtgtg gctgatcatc ctctcggacc   7140
agctactgat catcgccttg gtaagctatt gcctcaccaa ctagctaatc agacgcgagc   7200
```

-continued

```
ccctcctcgg gcggattcct ccttttgctc ctcagcctac ggggtattag cagccgtttc   7260
cagctgttgt tcccctccca agggcaggtt cttacgcgtt actcacccgt ccgccactgg   7320
aaacaccgtt tcccgtgttt cccgtccgac ttgcatgtgt taagcatgcc gccagcgttc   7380
atcctgagcc aggatcgaac tctccatgag attcatagtt gcattactta tagcttcctt   7440
gttcgtagac aaagcggatt cggaattgtc tttcattcca aggcataact tgtatccatg   7500
cgcttcatat tcgcccggag ttcgctccca gaaatatagt catccctgcc ccctcacgtc   7560
aatcccacga gcctcttatc cattctcatt gaacgacggc gggggagcaa atccaactag   7620
aaaaactcac attgggctga ctctaccacc cagtcaattc tgttccactt aatccctctt   7680
tcatggccgg ccattatggc cctgggcctc atgggccttc ctttcactgc ccgctttcca   7740
gtcgggaaac ctgtcgtgcc agctgcatta acatggtcat agctgtttcc ttgcgtattg   7800
ggcgctctcc gcttcctcgc tcactgactc gctgcgctcg gtcgttcggg taaagcctgg   7860
ggtgcctaat gagcaaaagg ccagcaaaag gccaggaacc gtaaaaaggc cgcgttgctg   7920
gcgtttttcc ataggctccg cccccctgac gagcatcaca aaaatcgacg ctcaagtcag   7980
aggtggcgaa acccgacagg actataaaga taccaggcgt ttccccctgg aagctccctc   8040
gtgcgctctc ctgttccgac cctgccgctt accggatacc tgtccgcctt tctcccttcg   8100
ggaagcgtgg cgctttctca tagctcacgc tgtaggtatc tcagttcggt gtaggtcgtt   8160
cgctccaagc tgggctgtgt gcacgaaccc cccgttcagc ccgaccgctg cgccttatcc   8220
ggtaactatc gtcttgagtc caacccggta agacacgact tatcgccact ggcagcagcc   8280
actggtaaca ggattagcag agcgaggtat gtaggcggtg ctacagagtt cttgaagtgg   8340
tggcctaact acggctacac tagaagaaca gtatttggta tctgcgctct gctgaagcca   8400
gttaccttcg gaaaaagagt tggtagctct tgatccggca aacaaaccac cgctggtagc   8460
ggtggttttt ttgtttgcaa gcagcagatt acgcgcagaa aaaaaggatc tcaagaagat   8520
cctttgatct tttctacggg gtctgacgct cagtggaacg aaaactcacg ttaagggatt   8580
ttggtcatga gattatcaaa aaggatcttc acctagatcc ttttaaatta aaaatgaagt   8640
tttaaatcaa tctaaagtat atatgagtaa acttggtctg acagttatta gaaaaattca   8700
tccagcagac gataaaacgc aatacgctgg ctatccggtg ccgcaatgcc atacagcacc   8760
agaaaacgat ccgcccattc gccgcccagt tcttccgcaa tatcacgggt ggccagcgca   8820
atatcctgat aacgatccgc cacgcccaga cggccgcaat caataaagcc gctaaaacgg   8880
ccattttcca ccataatgtt cggcaggcac gcatcaccat gggtcaccac cagatcttcg   8940
ccatccggca tgctcgcttt cagacgcgca aacagctctg ccggtgccag gccctgatgt   9000
tcttcatcca gatcatcctg atccaccagg cccgcttcca tacgggtacg cgcacgttca   9060
atacgatgtt tcgcctgatg atcaaacgga caggtcgccg ggtccagggt atgcagacga   9120
cgcatggcat ccgccataat gctcactttt tctgccggcg ccagatggct agacagcaga   9180
tcctgacccg gcacttcgcc cagcagcagc caatcacggc ccgcttcggt caccacatcc   9240
agcaccgccg cacacggaac accggtggtg gccagccagc tcagacgcgc cgcttcatcc   9300
tgcagctcgt tcagcgcacc gctcagatcg gttttcacaa acagcaccgg acgaccctgc   9360
gcgctcagac gaaacaccgc cgcatcagag cagccaatgg tctgctgcgc ccaatcatag   9420
ccaaacagac gttccaccca cgctgccggg ctacccgcat gcaggccatc ctgttcaatc   9480
atactcttcc tttttcaata ttattgaagc atttatcagg gttattgtct catgagcgga   9540
tacatatttg aatgtattta gaaaaataaa caaatagggg ttccgcgcac atttccccga   9600
```

aaagtgccac ctaaattgta agcgttaata ttttgttaaa attcgcgtta aatttttgtt 9660
aaatcagctc atttttaac caataggccg aaatcggcaa aatcccttat aaatcaaaag 9720
aatagaccga gatagggttg agtggccgct acagggcgct cccattcgcc attcaggctg 9780
cgcaactgtt gggaagggcg tttcggtgcg ggcctcttcg ctattacgcc agctggcgaa 9840
agggggatgt gctgcaaggc gattaagttg ggtaacgcca gggttttccc agtcacgacg 9900
ttgtaaaacg acggccagtg agcgcgacgt aatacgactc actatagggc gaattgaagg 9960
aaggccgtca aggccgcat 9979

<210> SEQ ID NO 87
<211> LENGTH: 12176
<212> TYPE: DNA
<213> ORGANISM: Artificial Sequence
<220> FEATURE:
<223> OTHER INFORMATION: An example of an episomal DNA vector

<400> SEQUENCE: 87
ggccattatg gccgttcgac acaattggga ttttttttgg aaattggaag cagttactaa 60
ttccaccccc tctccactgg atctgttccg ggagtaccc tcaaaaaaag gaacctttcc 120
tctccccagc catttcgggt taagaagatg tgaaagcgcg tttatctcta taagtctata 180
agaagggtgc gttccgaggt gtgaagtggg agagaaggga tgtcacaatt ggggttttga 240
ataaaacgac ctttttattt ttcatttttt tttttcgttt tcatattgaa aaagtaataa 300
gaatgagagg tgttaagctt tttatcatcc tggcgtcgag ctatttttcc gcaggacctc 360
ccctacagta tcgtcaccgc agtagagttt aaccaccaag ttcgggatgg attggtgtgg 420
ttcctctacg cctaggacac cagaatatcg aaccatgaac gaagaaaggc atgagagaaa 480
agcatattgg ctagtgattg tgaggcccca attcttgact ggaggggaca ccaaaggcct 540
ctgcccttcc atcccttgga tagatagaga gggagggcag agcttttggt tttttcatgt 600
tgtcaaagag ttgaacaatg gttttttcgt gttgtcaaag atttgaacaa tgaaaataga 660
tggcgagtgc ctgatcgaat tgatcaggtc atgtaggaac aaggttcaag tctaccggtc 720
tgttaggatg cctcagctgc atacatcact gcacttccac ttgacaccta tcgtaatgat 780
aaacggctcg tctcgccgtg accttctctt gaattctcaa aaaaacttct gtcgctccat 840
ccccgcaggg gcagagaacc cgtcgctgtc tcggctgtgc taccggaagc tctggggaag 900
tcggaatagg agagcactca tcttggggtg ggcttactac ttagatgctt tcagcagtta 960
tccgctccgc acttggctac ccagcgttta ccgtgggcac gataactggt acaccagagg 1020
tgcgtccttc ccggtcctct cgtactaggg aaaggtcctc tcaatgctct aacgcccaca 1080
ccggatatgg accgaactgt ctcacgacgt tctgaaccca gctcacgtac cgctttaatg 1140
ggcgaacagc ccaacccttg gaacatacta cagccccagg tggcgaagag ccgacatcga 1200
ggtgccaaac cttcccgtcg atgtgagctc ttggggaaga tcagcctgtt atccctagag 1260
taacttttat ccgttgagcg acggcccttc cactcggcac cgtcggatca ctaaggccga 1320
ctttcgtccc tgctcgacgg gtgggtcttg cagtcaagct cccttctgcc tttgcactcg 1380
agggccaatc tccgtccggc ccgaggaaac ctttgcacgc ctccgttacc ttttgggagg 1440
cctacgcccc atagaaactg tctacctgag actgtccctt ggcccgtagg tcctgacaca 1500
aggttagaat tctagccctt ccagagtggt atctcactga tggctcgggc ccccccggaa 1560
ggaggccttc ttcgccttcc acctaagctg cgcaggaaag gcccaaagcc aatcccaggg 1620
aacagtgaag cttcataggg tctttctgtc caggtgcagg tagtccgcat cttcacagac 1680
atgtctattt caccgagcct ctctccgaga cagtgcccag atcgttacgc ctttcgtgcg 1740
ggtcggaact tacccgacaa ggaatttcgc taccttagga ccgttatagt tacggccgcc 1800
gttcaccggg gcttcggtcg ccggctcccc tgtcatcagg tcaccaactt ccttgacctt 1860
ccggcactgg gcaggcgtca gcccccatac atggtcttac gactttgcgg agacctgtgt 1920
ttttggtaaa cagtcgcccg ggcctggtca ctgcgacccc ctttgtgagg aggcacccct 1980
tctcccgaag ttacggggct attttgccga gttccttaga gagagttgtc tcgcgcccct 2040
aggtattctc tacctaccca cctgtgtcgg tttcgggtac aggtaccctc ttgcttaacg 2100
tcgttcgagc ttttcctggg agtatggcat gggttacttc agcgccgtag cgcctggtat 2160
tcgaacattg gctcgaggca ttttctctac cccttcttac cctgaaaaag cagggacacc 2220
ttacgttctt gaaccgataa ccatctttcg gctaacctag cctcctccgt ccctcgggac 2280
taacaagggg tagtacagga atattcacct gttgtccatc gactacgcct ttcggcctga 2340
tcttaggccc tgactcaccc tccgtggacg aaccttgcgg aggaaccctt aggttttcgg 2400
ggcattggat tctcaccaat gtttgcgtta ctcaagccga cattctcgct tccgcttcgt 2460
ccaccaccgc tcgcgcggag gcttctctct aaggcggaac gctcccctac cgatgtattt 2520
ttacatccca cagcttcggc agaccgctta gccccgttca tcttcggcgc aagagcgctc 2580
gatcagtgag ctattacgca ctctttcaag ggtggctgct tctaggcaaa cctcctggct 2640
gtctctgcac ccctacctcc tttatcactg agcggtcatt taggggcctt agctggtgat 2700
ccgggctgtt tccctctcga cgatgaagct tatcccccat cgtctcacta gccgaccttg 2760
acccctgtta ttttgaggtc atatctagta ttcagagttt gcctcgattt ggtaccgctc 2820
tcgcggcccg caccgaaaca gtgctttacc cctagatgtc cagtcaactg ctgcgcctca 2880
acgcatttcg gggagaacca gctagctctg ggttcgagtg gcatttcacc cctaaccaca 2940
actcatccgc tgattcttca acatcagtcg gttcggacct ccacttagtt tcacccaagc 3000
ttcatcctgg tcatggatag atcacccagg ttcgggtcca taagcagtga caattgccct 3060
atgaagactc gctttcgcta cggctccggt gggttccctt aaccaagcca ctgcctatga 3120
gtcgccggct cattcttcaa caggcacgcg gtcagagccc tggctcctcc cactgcttgg 3180
gagcttacgg tttcatgttc tatttcactc cccgatgggg gttcttttca cccttccctc 3240
acggtactac ttcgctatcg gtcacccagg agtatttagc cttgcaaggt ggtccttgct 3300
gattcacacg ggattccacg tgccccatgc tactcgggtc agagcgtaag ctagtgatgc 3360
tttcggctac tggactttcg ccatctaggg tgcagcattc aggctgcttc gcctagcagc 3420
acgacgcttg tattgctctc ccacaacccc gttttcacgg tttaggctgc tcccatttcg 3480
ctcgccgcta ctacgggaat cgcttttgct ttcttttcct ctggctacta agatgtttca 3540
gttcgccagg ttgtctcttg cctgcccatg gattcagcag cagttcgaaa ggttgcccta 3600
ttcgggaatc tccggatcta tgcttatttt caactccccg aagcatttcg tcgattacta 3660
cgccccttcct cgtctctggg tgcctaggta tccaccgtaa gcctttcctc gtttgaacct 3720
cgcccttcac ttttaaggct atgccatcct aaggtgctgc taaatggatg gatcttatca 3780
acgtccatga atgataaatc atagatcgaa ccgccgaatc ggaaaaattg ggtgctatca 3840
taaagctttg tatcggctaa gttcacgagt tggagataag cggactcgaa ccgctgacat 3900
ccgccgcagg gtaaaccacc gcctctcagg tcccccgact gattctacca tagaggccaa 3960
cgatagacaa taactccccc ccgaacacag cttacaactt tcatcgtact gtgctctcca 4020

-continued

```
aagagcaact cttctcaaaa tctcactcaa aaggtgctga gttggaatcc cattctaact   4080
aaggattctt gtggttccgg aggatccaac tacaggagaa ccaggaacgg agggctttcc   4140
ccccttccg cccgactctt tggtcttaag aacgctggtt ttaagaatga gtcattgccc    4200
ttctccgacc ctgactgccc aacctgagag cggacagcta atgcgttcca cttattgaac   4260
agggttctat ggtcggtccg tgacccctgg atgccgaagg cgtccttggg gtgatctcgt   4320
agttcctacg gggtggagat gatggggtcg gtccatggat tttccttcct tttcttttgc   4380
cgcatttcgc tcaaagggtt gaagggagat agtgcatcaa gctgttcgca agggccaact   4440
tgatcctctt ccccagagat ctcagatgag ggaaccctgg gagagccgcc gactccaact   4500
accgtccatg tacgatccat actagatctg accaactgcc catcctacct cctctacgtt   4560
cttgacagcc catctttgtc tcagtagagt ctttcagtgg cacgtttcgg tcctcttccc   4620
cattacttag aaaaagtgag ccaccggttc aggtacaaga tactatcatt accgcctgga   4680
caattagaca tccaacccgt aatcgcaacg acccaattgc aagagcggag ctctaccaac   4740
tgagctatat ccccccgagc caagtggagc atgcatgaag tagtcagatg cttcttctat   4800
tcttttccct ggcgcagctg ggccatcctg gacttgaacc agagacctcg cccgtgaagt   4860
aaatcatcgc acctacggtc caaccaattg ggagagaatc aatagattcc ttttcgggag   4920
cgattcatcc ttcccgaacg cagcatacaa ctctccgttg tactgcgctc tccaagtgtg   4980
cttgttcccc ccttcttcct taccctggca agtctttgtg aaataactcc gatgagaaga   5040
aaaaagaagg cgttaagaga ccctcctggc ccaaccctag acactctaag atccttttc    5100
aaacctgctc ccatttcgat ttcgagtcaa gaaaaaaacg gctcgaatgg tacgatccct   5160
ccgtcacccc agaatgaaag gggtgatctc gtagttcttg gtctgtgaag atgcgttgtt   5220
aggtgctcca ttttatttc ccattgaggc cgaacctaaa cctgtgctcg agagatagct    5280
gtccatacac tgataaggga tgtatggatt ctcgagaaga gaggagccgt ggtggtcccc   5340
cccggaccgc ccggatccca cgagtgaatc gaaagttgga tctacattgg atctcacccg   5400
aatcgcccca tctatcctcc tgaggaggag tttggtttca aaccccggtt cgaacaggag   5460
gagtacgcca tgctaatgtg ccttggatga tccacatctc agggtcaggc gccgatgagc   5520
acattgaact atccatgtgg ctgagagccc tcacagccca ggcacaacga cgcaattatc   5580
aggggcgcgc tctaccactg agctaatagc ccgtcgtgcg agcctcccac tgggggcccg   5640
ctatgccaaa agcgagagaa accccatccc tctctttcct tttttcgccc ccatgtcgcc   5700
acacggggga acatagggac gtaaaaaagg ggatcctatc aacttgttcc gacctaggat   5760
aataagctca tgagcttggt cttacttcac cgtcgagaaa ggaaagaaga cttccatctc   5820
caagtttaac tcagacgtag ctcccttctt ttttttgggg gtgtgaagca gtgtcaaacc   5880
aaaataccca acaagcatta gctctccctg aaaaggaggt gatccagccg caccttccag   5940
tacggctacc ttgttacgac ttcactccag tcactagccc tgccttcggc atccccctcc   6000
ttgcggttaa ggtaacgact tcgggcatgg ccagctccca tagtgtgacg ggcggtgtgt   6060
acaaggcccg ggaacgaatt caccgccgta tggctgaccg gcgattacta gcgattccgg   6120
cttcatgcag gcgagttgca gcctgcaatc cgaactgagg acgggttttt ggggttagct   6180
caccctcgcg ggatcgcgac cctttgtccc ggccattgta gcacgtgtgt cgcccagggc   6240
ataaggggca tgatgacttg acgtcatcct caccttcctc cggcttatca ccggcagtct   6300
gttcagggtt ccaaactcaa cgatggcaac taaacacgag ggttgcgctc gttgcgggac   6360
```

```
ttaacccaac accttacggc acgagctgac gacagccatg caccacctgt gtccgcgttc   6420
ccgaaggcac ccctctcttt caagaggatt cgcggcatgt caagccctgg taaggttctt   6480
cgctttgcat cgaattaaac cacatgctcc accgcttgtg cgggcccccg tcaattcctt   6540
tgagtttcat tcttgcgaac gtactcccca ggcgggatac ttaacgcgtt agctacagca   6600
ctgcacgggt cgatacgcac agcgcctagt atccatcgtt tacggctagg actactgggg   6660
tatctaatcc cattcgctcc cctagctttc gtctctcagt gtcagtgtcg gcccagcaga   6720
gtgctttcgc cgttggtgtt ctttccgatc tctacgcatt tcaccgctcc accggaaatt   6780
ccctctgccc ctaccgtact ccagcttggt agtttccacc gcctgtccag ggttgagccc   6840
tgggatttga cggcggactt aaaaagccac ctacagacgc tttacgccca atcattccgg   6900
ataacgcttg catcctctgt attaccgcgg ctgctggcac agagttagcc gatgcttatt   6960
ccccagatac cgtcattgct tcttctccgg gaaaagaagt tcacgacccg tgggccttct   7020
acctccacgc ggcattgctc cgtcaggctt tcgcccattg cggaaaattc cccactgctg   7080
cctcccgtag gagtctgggc cgtgtctcag tcccagtgtg gctgatcatc ctctcggacc   7140
agctactgat catcgccttg gtaagctatt gcctcaccaa ctagctaatc agacgcgagc   7200
ccctcctcgg gcggattcct ccttttgctc ctcagcctac ggggtattag cagccgtttc   7260
cagctgttgt tcccctccca agggcaggtt cttacgcgtt actcacccgt ccgccactgg   7320
aaacaccgtt tcccgtgttt cccgtccgac ttgcatgtgt taagcatgcc gccagcgttc   7380
atcctgagcc aggatcgaac tctccatgag attcatagtt gcattactta tagcttcctt   7440
gttcgtagac aaagcggatt cggaattgtc tttcattcca aggcataact tgtatccatg   7500
cgcttcatat tcgcccggag ttcgctccca gaaatatagc catccctgcc ccctcacgtc   7560
aatcccacga gcctcttatc cattctcatt gaacgacggc gggggagcaa atccaactag   7620
aaaaactcac attgggctga ctctaccacc cagtcaattc tgttccactt aatccctctt   7680
tcatggccgg ccattatggc cctgggcctc atgggccttc ctttcactgc ccgctttcca   7740
gtcgggaaac ctgtcgtgcc agctgcatta acatggtcat agctgtttcc ttgcgtattg   7800
ggcgctctcc gcttcctcgc tcactgactc gctgcgctcg gtcgttcggg taaagcctgg   7860
ggtgcctaat gagcaaaagg ccagcaaaag gccaggaacc gtaaaaaggc cgcgttgctg   7920
gcgtttttcc ataggctccg cccccctgac gagcatcaca aaaatcgacg ctcaagtcag   7980
aggtggcgaa acccgacagg actataaaga taccaggcgt ttccccctgg aagctccctc   8040
gtgcgctctc ctgttccgac cctgccgctt accggatacc tgtccgcctt tctcccttcg   8100
ggaagcgtgg cgctttctca tagctcacgc tgtaggtatc tcagttcggt gtaggtcgtt   8160
cgctccaagc tgggctgtgt gcacgaaccc cccgttcagc ccgaccgctg cgccttatcc   8220
ggtaactatc gtcttgagtc caacccggta agacacgact tatcgccact ggcagcagcc   8280
actggtaaca ggattagcag agcgaggtat gtaggcggtg ctacagagtt cttgaagtgg   8340
tggcctaact acggctacac tagaagaaca gtatttggta tctgcgctct gctgaagcca   8400
gttaccttcg gaaaaagagt tggtagctct tgatccggca aacaaaccac cgctggtagc   8460
ggtggttttt ttgtttgcaa gcagcagatt acgcgcagaa aaaaaggatc tcaagaagat   8520
cctttgatct tttctacggg gtctgacgct cagtggaacg aaaactcacg ttaagggatt   8580
ttggtcatga gattatcaaa aaggatcttc acctagatcc ttttaaatta aaaatgaagt   8640
tttaaatcaa tctaaagtat atatgagtaa acttggtctg acagttatta gaaaaattca   8700
tccagcagac gataaaacgc aatacgctgg ctatccggtg ccgcaatgcc atacagcacc   8760
```

agaaaacgat ccgcccattc gccgcccagt tcttccgcaa tatcacgggt ggccagcgca 8820
atatcctgat aacgatccgc cacgcccaga cggccgcaat caataaagcc gctaaaacgg 8880
ccattttcca ccataatgtt cggcaggcac gcatcaccat gggtcaccac cagatcttcg 8940
ccatccggca tgctcgcttt cagacgcgca aacagctctg ccggtgccag gccctgatgt 9000
tcttcatcca gatcatcctg atccaccagg cccgcttcca tacgggtacg cgcacgttca 9060
atacgatgtt tcgcctgatg atcaaacgga caggtcgccg ggtccagggt atgcagacga 9120
cgcatggcat ccgccataat gctcactttt tctgccggcg ccagatggct agacagcaga 9180
tcctgacccg gcacttcgcc cagcagcagc caatcacggc ccgcttcggt caccacatcc 9240
agcaccgccg cacacggaac accggtggtg gccagccagc tcagacgcgc cgcttcatcc 9300
tgcagctcgt tcagcgcacc gctcagatcg gttttcacaa acagcaccgg acgaccctgc 9360
gcgctcagac gaaacaccgc cgcatcagag cagccaatgg tctgctgcgc ccaatcatag 9420
ccaaacagac gttccaccca cgctgccggg ctacccgcat gcaggccatc ctgttcaatc 9480
atactcttcc tttttcaata ttattgaagc atttatcagg gttattgtct catgagcgga 9540
tacatatttg aatgtattta gaaaaataaa caaatagggg ttccgcgcac atttccccga 9600
aaagtgccac ctaaattgta agcgttaata ttttgttaaa attcgcgtta aatttttgtt 9660
aaatcagctc attttttaac caataggccg aaatcggcaa aatcccttat aactgcagcc 9720
caaacaaata caaaatcaaa atagaatact caatcatgaa taaatgcaag aaaataacct 9780
ctccttcttt ttctataatg taaacaaaaa agtctatgta agtaaaatac tagtaaataa 9840
ataaaaagaa aaaaagaaag gagcaatagc accctcttga tagaacaaga aaatgattat 9900
tgctcctttc ttttcaaaac ctcctataga ctaggccagg atcgctctag attatttgta 9960
tagttcatcc atgccatgtg taatcccagc agctgttaca aactcaagaa ggaccatgtg 10020
gtctctcttt tcgttgggat ctttcgaaag ggcagattgt gtggacaggt aatggttgtc 10080
tggtaaaagg acagggccat cgccaattgg agtattttgt tgataatggt ctgctagttg 10140
aacgcttcca tcttcaatgt tgtgtctaat tttgaagtta gctttgattc cattcttttg 10200
tttgtctgcc gtgatgtata cgttgtggga gttgtagttg tattccaact tgtggccgag 10260
gatgtttccg tcctccttga aatcgattcc cttaagctcg atcctgttga cgagggtgtc 10320
tccctcaaac ttgacttcag cacgtgtctt gtagttcccg tcgtccttga aagagatggt 10380
cctctcctgc acgtatccct caggcatggc gctcttgaag aagtcgtgcc gcttcatatg 10440
atctgggtat cttgaaaagc attgaacacc ataagagaaa gtagtgacaa gtgttggcca 10500
tggaacaggt agttttccag tagtgcaaat aaatttaagg gtaagttttc cgtatgttgc 10560
atcaccttca ccctctccac tgacagaaaa tttgtgccca ttaacatcac catctaattc 10620
aacaagaatt gggacaactc cagtgaaaag ttcttctcct ttactcatat gctttttcca 10680
cttcatgcgg cggttttgga accagatctt gatgtgtctc attaaaatct tggtttattt 10740
aattatcagg gactcccaag cgcacgaatt ttcaaatgga aaactaaagg cttgttattt 10800
aacagtataa catgacttat atgcccgtgt caaccaatat ctatctggat ctagttcaat 10860
tttttgtaaa tcaaaagcgg tttgcaaaaa taaaaaaaaa aggatttcta tacactagtc 10920
gacgaagggc gaattcggct tagatttatt tgccgactac cttggtgatc tcgcctttca 10980
cgtagtggac aaattcttcc aactgatctg cgcgcgaggc caagcgatct tcttcttgtc 11040
caagataagc ctgtctagct tcaagtatga cgggctgata ctgggccggc aggcgctcca 11100
ttgcccagtc ggcagcgaca tccttcggcg cgattttgcc ggttactgcg ctgtaccaaa 11160
tgcgggacaa cgtaagcact acatttcgct catcgccagc ccagtcgggc ggcgagttcc 11220
atagcgttaa ggtttcattt agcgcctcaa atagatcctg ttcaggaacc ggatcaaaga 11280
gttcctccgc cgctggacct accaaggcaa cgctatgttc tcttgctttt gtcagcaaga 11340
tagccagatc aatgtcgatc gtggctggct cgaagatacc tgcaagaatg tcattgcgct 11400
gccattctcc aaattgcagt tcgcgcttag ctggataacg ccacggaatg atgtcgtcgt 11460
gcacaacaat ggtgacttct acagcgcgga gaatctcgct ctctccaggg gaagccgaag 11520
tttccaaaag gtcgttgatc aaagctcgcc gcgttgtttc atcaagcctt acggtcaccg 11580
taaccagcaa atcaatatca ctgtgtggct tcaggccgcc atccactgcg gagccgtaca 11640
aatgtacggc cagcaacgtc ggttcgagat ggcgctcgat gacgccaact acctctgata 11700
gttgagtcga tacttcggcg atcaccgctt ctgccatggt tccctcccta caactcactt 11760
gtatcgatgc gcttcatatt cgcccggagt tcgctcccag aaatatagcc atccctgccc 11820
cctcacgtca atcccacgag cctcttatcc attctcattg aacgacggcg ggggagcaaa 11880
tccaactaca aaaactcaca ttgttataaa tcaaaagaat agaccgagat agggttgagt 11940
ggccgctaca gggcgctccc attcgccatt caggctgcgc aactgttggg aagggcgttt 12000
cggtgcgggc ctcttcgcta ttacgccagc tggcgaaagg gggatgtgct gcaaggcgat 12060
taagttgggt aacgccaggg ttttcccagt cacgacgttg taaaacgacg gccagtgagc 12120
gcgacgtaat acgactcact atagggcgaa ttgaaggaag gccgtcaagg ccgcat 12176

<210> SEQ ID NO 88
<211> LENGTH: 4913
<212> TYPE: DNA
<213> ORGANISM: Artificial Sequence
<220> FEATURE:
<223> OTHER INFORMATION: An example of an episomal DNA vector

<400> SEQUENCE: 88
gaattctaat tgagctcgaa cagtcgaccg ccggatcctg ctcgagtgcc tctagatgcc 60
agagacccgc tatctgcaat cacgactgcc tcgcggtctc agggagcgca cgcgcaaggt 120
cgcaactacc cgagaatcga tgtggcggaa tgggttacgt gagctattat ccggcgggcc 180
ctcaatttaa atcgttacag ttgctcgtaa cggcaaccgg ctcggtcctt tttccctaga 240
acagtatctt atacttgctg ctctcgttac ttcggcgatc ctggtgcagt cggtccgtaa 300
atcggcgcac acttttacgt cgtaccagac aggctcgcat aagccagccc cgacacccgc 360
caacacccgc tgacgcgccc tgacgggctt gtctgctccc ggcatccgct tacagacaag 420
ctgtgacctc cgggagctgc atgtgtcaga ggttttcacc gtcatcaccg aaacgcgcac 480
gaaagggcct cgtgatacgc ctatttttat aggttaatgt catgataata atggtttctt 540
agacgtcagg tggcactttt cggggaaatg tgcgcggaac ccctatttgt ttatttttct 600
aaatacattc aaatatgtat ccgctcatga gacaataacc ctgataaatg cttcaataat 660
attgaaaaag gaagagtatg agtattcaac atttccgtgt cgcccttatt ccctttttg 720 cggcattttg ccttcctgtt tttgctcacc cagaaacgct ggtgaaagta aaagatgctg 780
aagatcagtt gggtgcacga gtgggttaca tcgaactgga tctcaacagc ggtaagatcc 840
ttgagagttt tcgccccgaa gaacgttttc caatgatgag cacttttaaa gttctgctat 900
gtggcgcggt attatcccgt attgacgccg ggcaagagca actcggtcgc cgcatacact 960
attctcagaa tgacttggtt gagtactcac cagtcacaga aaagcatctt acggatggca 1020

-continued

```
tgacagtaag agaattatgc agtgctgcca taaccatgag tgataacact gcggccaact   1080
tacttctgac aacgatcgga ggaccgaagg agctaaccgc ttttttgcac aacatggggg   1140
atcatgtaac tcgccttgat cgttgggaac cggagctgaa tgaagccata ccaaacgacg   1200
agcgtgacac cacgatgcct gtagcaatgg caacaacgtt gcgcaaacta ttaactggcg   1260
aactacttac tctagcttcc cggcaacaat taatagactg gatggaggcg gataaagttg   1320
caggaccact tctgcgctcg gcccttccgg ctggctggtt tattgctgat aaatctggag   1380
ccggtgagcg tggctcacgc ggtatcattg cagcactggg gccagatggt aagccctccc   1440
gtatcgtagt tatctacacg acggggagtc aggcaactat ggatgaacga aatagacaga   1500
tcgctgagat aggtgcctca ctgattaagc attggtaact gtcagaccaa gtttactcat   1560
atatacttta gattgattta aaacttcatt tttaatttaa aaggatctag gtgaagatcc   1620
tttttgataa tctcatgacc aaaatccctt aacgtgagtt ttcgttccac tgagcgtcag   1680
accccgtaga aaagatcaaa ggatcttctt gagatccttt ttttctgcgc gtaatctgct   1740
gcttgcaaac aaaaaaacca ccgctaccag cggtggtttg tttgccggat caagagctac   1800
caactctttt tccgaaggta actggcttca gcagagcgca gataccaaat actgttcttc   1860
tagtgtagcc gtagttaggc caccacttca agaactctgt agcaccgcct acatacctcg   1920
ctctgctaat cctgttacca gtggctgctg ccagtggcga taagtcgtgt cttaccgggt   1980
tggactcaag acgatagtta ccggataagg cgcagcggtc gggctgaacg gggggttcgt   2040
gcacacagcc cagcttggag cgaacgacct acaccgaact gagataccta cagcgtgagc   2100
tatgagaaag cgccacgctt cccgaaggga gaaaggcgga caggtatccg gtaagcggca   2160
gggtcggaac aggagagcgc acgagggagc ttccaggggg aaacgcctgg tatctttata   2220
gtcctgtcgg gtttcgccac ctctgacttg agcgtcgatt tttgtgatgc tcgtcagggg   2280
ggcggagcct atggaaaaac gccagcaacg cggccttttt acggttcctg gccttttgct   2340
ggccttttgc tcacatgttc tttcctgcgt tatcccctga ttctgtggat aaccgtatta   2400
ccgcctttga gtgagctgat accgctcgcc gcagccgaac gaccgagcgc agcgagtcag   2460
tgagcgagga agcggaagaa cgcggacacc cagcgtaaca atctaatatt gtttctcaaa   2520
tcgggctgtt atcgcatggt gctcatgatg aggttactga ccaaattcgc cacgcatcgg   2580
tgctggtaga atgttcactt cgaggtgggt agacggcgtc acgtgcaatg ccttgtcttc   2640
ccctatctgc ggccccgact gcctcgcgaa gacaagggat cggacgtcga acgtattctg   2700
tttgctaccg gcacgggagt aggatcgttg atatacacca tgcgcgttaa ctctgacccc   2760
cttcctctta aatgagaatg gataagaggc tcgtgggatt gacgtgaggg ggcagggatg   2820
gctatatttc tgggagcgaa ctccgggcga attactaata aaaagccttc catttctat    2880
tttgatttgt agaaaactag tgtgcttggg agtccctgat gattaaataa accaagattt   2940
taccaatggg ggctagcgaa gcggtgatcg ccgaagtatc gactcaacta tcagaggtag   3000
ttggcgtcat cgagcgccat ctcgaaccga cgttgctggc cgtacatttg tacggctccg   3060
cagtggatgg cggcctgaag ccacacagtg atattgattt gctggttacg gtgaccgtaa   3120
ggcttgatga aacaacgcgg cgagctttga tcaacgacct tttggaaact tcggcttccc   3180
ctggagagag cgagattctc cgcgctgtag aagtcaccat tgttgtgcac gacgacatca   3240
ttccgtggcg ttatccagct aagcgcgaac tgcaatttgg agaatggcag cgcaatgaca   3300
ttcttgcagg tatcttcgag ccagccacga tcgacattga tctggctatc ttgctgacaa   3360
```

```
aagcaagaga acatagcgtt gccttggtag gtccagcggc ggaggaactc tttgatccgg   3420

ttcctgaaca ggatctattt gaggcgctaa atgaaacctt aacgctatgg aactcgccgc   3480

ccgactgggc tggcgatgag cgaaatgtag tgcttacgtt gtcccgcatt tggtacagcg   3540

cagtaaccgg caaaatcgcg ccgaaggatg tcgctgccga ctgggcaatg gagcgcctgc   3600

cggcccagta tcagcccgtc atacttgaag ctagacaggc ttatcttgga caagaagaag   3660

atcgcttggc ctcgcgcgca gatcagttgg aagaatttgt ccactacgtg aaaggcgaga   3720

tcaccaaggt agtgggcaaa gaacttgttg aaggaaaatt ggagctagta gaaggtctta   3780

aagtcgccat ggctagtaaa ggagaagaac ttttcactgg agttgtccca attcttgttg   3840

aattagatgg tgatgttaat gggcacaaat tttctgtcag tggagagggt gaaggtgatg   3900

caacatacgg aaaacttacc cttaaattta tttgcactac tggaaaacta cctgttcctt   3960

ggccaacact tgtcactact ttctcttatg gtgttcaatg cttttcaaga tacccagatc   4020

atatgaagcg gcacgacttc ttcaagagcg ccatgcctga gggatacgtg caggagagga   4080

ccatctcttt caaggacgac gggaactaca agacacgtgc tgaagtcaag tttgagggag   4140

acaccctcgt caacaggatc gagcttaagg gaatcgattt caaggaggac ggaaacatcc   4200

tcggccacaa gttggaatac aactacaact cccacaacgt atacatcacg gcagacaaac   4260

aaaagaatgg aatcaaagct aacttcaaaa ttagacacaa cattgaagat ggaagcgttc   4320

aactagcaga ccattatcaa caaaatactc caattggcga tggccctgtc cttttaccag   4380

acaaccatta cctgtccaca caatctgccc tttcgaaaga tcccaacgaa aagagagatc   4440

acatggtcct tcttgagttt gtaacagctg ctgggattac acatggcatg gatgaactat   4500

acaaataagc ttaaacagta gacattagca gataaattag caggaaataa agaaggataa   4560

ggagaaagaa ctcaagtaat tatccttcgt tctcttaatt gaattgcaat taaactcggc   4620

ccaatctttt actaaaagga ttgagccgaa taccgctaca acagctccct ggaacaccag   4680

gagaacacac ttatctcgcg tcttgaggtg ataccacgcc tgacacgtga gggcagtacg   4740

gttaattcgg tttagccgga catcagcgct cctcattgag cgctgggccc ttcacatgaa   4800

gatcgcactg aggattggtc ctagccaggc ttctcagtac tgatacagta cgcgtcgctt   4860

ctcgtattgt ttgagtcttg gaattagttt gtatccttcc gccgctgccc taa          4913
```

<210> SEQ ID NO 89
<211> LENGTH: 4993
<212> TYPE: DNA
<213> ORGANISM: Artificial Sequence
<220> FEATURE:
<223> OTHER INFORMATION: An example of an episomal DNA vector

<400> SEQUENCE: 89

```
gaattctaat tgagctcgaa cagtcgaccg ccggatcctg ctcgagtgcc tctagatgcc     60

agagacccgc tatctgcaat cacgactgcc tcgcggtctc agggagcgca cgcgcaaggt    120

cgcaactacc cgagaatcga tgtggcggaa tgggttacgt gagctattat ccggcgggcc    180

ctcaatttaa atcgttacag ttgctcgtaa cggcaaccgg ctcggtcctt tttccctaga    240

acagtatctt atacttgctg ctctcgttac ttcggcgatc ctggtgcagt cggtccgtaa    300

atcggcgcac acttttacgt cgtaccagac aggctcgcat aagccagccc cgacacccgc    360

caacacccgc tgacgcgccc tgacgggctt gtctgctccc ggcatccgct tacagacaag    420

ctgtgacctc cgggagctgc atgtgtcaga ggttttcacc gtcatcaccg aaacgcgcac    480

gaaagggcct cgtgatacgc ctatttttat aggttaatgt catgataata atggtttctt    540
```

-continued agacgtcagg tggcactttt cggggaaatg tgcgcggaac ccctatttgt ttatttttct 600
aaatacattc aaatatgtat ccgctcatga gacaataacc ctgataaatg cttcaataat 660
attgaaaaag gaagagtatg agtattcaac atttccgtgt cgcccttatt ccctttttg 720
cggcattttg ccttcctgtt tttgctcacc cagaaacgct ggtgaaagta aaagatgctg 780
aagatcagtt gggtgcacga gtgggttaca tcgaactgga tctcaacagc ggtaagatcc 840
ttgagagttt tcgccccgaa gaacgttttc caatgatgag cacttttaaa gttctgctat 900
gtggcgcggt attatcccgt attgacgccg ggcaagagca actcggtcgc cgcatacact 960
attctcagaa tgacttggtt gagtactcac cagtcacaga aaagcatctt acggatggca 1020
tgacagtaag agaattatgc agtgctgcca taaccatgag tgataacact gcggccaact 1080
tacttctgac aacgatcgga ggaccgaagg agctaaccgc ttttttgcac aacatggggg 1140
atcatgtaac tcgccttgat cgttgggaac cggagctgaa tgaagccata ccaaacgacg 1200
agcgtgacac cacgatgcct gtagcaatgg caacaacgtt gcgcaaacta ttaactggcg 1260
aactacttac tctagcttcc cggcaacaat taatagactg gatggaggcg gataaagttg 1320
caggaccact tctgcgctcg gcccttccgg ctggctggtt tattgctgat aaatctggag 1380
ccggtgagcg tggctcacgc ggtatcattg cagcactggg gccagatggt aagccctccc 1440
gtatcgtagt tatctacacg acggggagtc aggcaactat ggatgaacga aatagacaga 1500
tcgctgagat aggtgcctca ctgattaagc attggtaact gtcagaccaa gtttactcat 1560
atatacttta gattgattta aaacttcatt tttaatttaa aaggatctag gtgaagatcc 1620
tttttgataa tctcatgacc aaaatccctt aacgtgagtt ttcgttccac tgagcgtcag 1680
accccgtaga aaagatcaaa ggatcttctt gagatccttt ttttctgcgc gtaatctgct 1740
gcttgcaaac aaaaaaacca ccgctaccag cggtggtttg tttgccggat caagagctac 1800
caactctttt tccgaaggta actggcttca gcagagcgca gataccaaat actgttcttc 1860
tagtgtagcc gtagttaggc caccacttca agaactctgt agcaccgcct acatacctcg 1920
ctctgctaat cctgttacca gtggctgctg ccagtggcga taagtcgtgt cttaccgggt 1980
tggactcaag acgatagtta ccggataagg cgcagcggtc gggctgaacg gggggttcgt 2040
gcacacagcc cagcttggag cgaacgacct acaccgaact gagataccta cagcgtgagc 2100
tatgagaaag cgccacgctt cccgaaggga gaaaggcgga caggtatccg gtaagcggca 2160
gggtcggaac aggagagcgc acgagggagc ttccaggggg aaacgcctgg tatctttata 2220
gtcctgtcgg gtttcgccac ctctgacttg agcgtcgatt tttgtgatgc tcgtcagggg 2280
ggcggagcct atggaaaaac gccagcaacg cggccttttt acggttcctg gccttttgct 2340
ggccttttgc tcacatgttc tttcctgcgt tatcccctga ttctgtggat aaccgtatta 2400
ccgcctttga gtgagctgat accgctcgcc gcagccgaac gaccgagcgc agcgagtcag 2460
tgagcgagga agcggaagaa cgcggacacc cagcgtaaca atctaatatt gtttctcaaa 2520
tcgggctgtt atcgcatggt gctcatgatg aggttactga ccaaattcgc cacgcatcgg 2580
tgctggtaga atgttcactt cgaggtgggt agacggcgtc acgtgcaatg ccttgtcttc 2640
ccctatctgc ggccccgact gcctcgcgaa gacaagggat cggacgtcga acgtattctg 2700
tttgctaccg gcacgggagt aggatcgttg atatacacca tgcgcgttaa ctctgacccc 2760
cttcctctta aatgagaatg gataagaggc tcgtgggatt gacgtgaggg ggcagggatg 2820
gctatatttc tgggagcgaa ctccgggcga attactaata aaaagccttc cattttctat 2880

-continued tttgatttgt agaaaactag tgtgcttggg agtccctgat gattaaataa accaagattt 2940
taccaatggg ggctagcgaa gcggtgatcg ccgaagtatc gactcaacta tcagaggtag 3000
ttggcgtcat cgagcgccat ctcgaaccga cgttgctggc cgtacatttg tacggctccg 3060
cagtggatgg cggcctgaag ccacacagtg atattgattt gctggttacg gtgaccgtaa 3120
ggcttgatga aacaacgcgg cgagctttga tcaacgacct tttggaaact tcggcttccc 3180
ctggagagag cgagattctc cgcgctgtag aagtcaccat tgttgtgcac gacgacatca 3240
ttccgtggcg ttatccagct aagcgcgaac tgcaatttgg agaatggcag cgcaatgaca 3300
ttcttgcagg tatcttcgag ccagccacga tcgacattga tctggctatc ttgctgacaa 3360
aagcaagaga acatagcgtt gccttggtag gtccagcggc ggaggaactc tttgatccgg 3420
ttcctgaaca ggatctattt gaggcgctaa atgaaacctt aacgctatgg aactcgccgc 3480
ccgactgggc tggcgatgag cgaaatgtag tgcttacgtt gtcccgcatt tggtacagcg 3540
cagtaaccgg caaaatcgcg ccgaaggatg tcgctgccga ctgggcaatg gagcgcctgc 3600
cggcccagta tcagcccgtc atacttgaag ctagacaggc ttatcttgga caagaagaag 3660
atcgcttggc ctcgcgcgca gatcagttgg aagaatttgt ccactacgtg aaaggcgaga 3720
tcaccaaggt agtgggcaaa gaacttgttg aaggaaaatt ggagctagta gaaggtctta 3780
aagtcgccat ggctagtaaa ggagaagaac ttttcactgg agttgtccca attcttgttg 3840
aattagatgg tgatgttaat gggcacaaat tttctgtcag tggagagggt gaaggtgatg 3900
caacatacgg aaaacttacc cttaaattta tttgcactac tggaaaacta cctgttcctt 3960
ggccaacact tgtcactact ttctcttatg gtgttcaatg cttttcaaga tacccagatc 4020
atatgaagcg gcacgacttc ttcaagagcg ccatgcctga gggatacgtg caggagagga 4080
ccatctcttt caaggacgac gggaactaca agacacgtgc tgaagtcaag tttgagggag 4140
acaccctcgt caacaggatc gagcttaagg gaatcgattt caaggaggac ggaaacatcc 4200
tcggccacaa gttggaatac aactacaact cccacaacgt atacatcacg gcagacaaac 4260
aaaagaatgg aatcaaagct aacttcaaaa ttagacacaa cattgaagat ggaagcgttc 4320
aactagcaga ccattatcaa caaaatactc caattggcga tggccctgtc cttttaccag 4380
acaaccatta cctgtccaca caatctgccc tttcgaaaga tcccaacgaa aagagagatc 4440
acatggtcct tcttgagttt gtaacagctg ctgggattac acatggcatg gatgaactat 4500
acaaataagc ttaaacagta gacattagca gataaattag caggaaataa agaaggataa 4560
ggagaaagaa ctcaagtaat tatccttcgt tctcttaatt gaattgcaat taaactcggc 4620
ccaatctttt actaaaagga ttgagccgaa taccgctcca ggcatcaaat aaaacgaaag 4680
gctcagtcga aagactgggc ctttcgtttt atctgttgtt tgtcggtgaa cgctctcaca 4740
acagctccct ggaacaccag gagaacacac ttatctcgcg tcttgaggtg ataccacgcc 4800
tgacacgtga gggcagtacg gttaattcgg tttagccgga catcagcgct cctcattgag 4860
cgctgggccc ttcacatgaa gatcgcactg aggattggtc ctagccaggc ttctcagtac 4920
tgatacagta cgcgtcgctt ctcgtattgt ttgagtcttg gaattagttt gtatccttcc 4980
gccgctgccc taa 4993

<210> SEQ ID NO 90
<211> LENGTH: 191
<212> TYPE: DNA
<213> ORGANISM: Artificial Sequence
<220> FEATURE:
<223> OTHER INFORMATION: Sequence of trnI used as a part of the promoter for driving the expression of the gene of interest

<400> SEQUENCE: 90
gccagggtaa ggaagaaggg gggaacaagc acacttggag agcgcagtac aacggagagt 60
tgtatgctgc gttcgggaag gatgaatcgc tcccgaaaag gaatctattg attctctccc 120
aattggttgg accgtaggtg cgatgattta cttcacgggc gaggtctctg gttcaagtcc 180
aggatggccc a 191

<210> SEQ ID NO 91
<211> LENGTH: 173
<212> TYPE: DNA
<213> ORGANISM: Artificial Sequence
<220> FEATURE:
<223> OTHER INFORMATION: Sequence of trnA used as a part of the promoter portion for driving the expression of the gene of interest

<400> SEQUENCE: 91
ggggatatag ctcagttggt agagctccgc tcttgcaatt gggtcgttgc gattacgggt 60
tggatgtcta attgtccagg cggtaatgat agtatcttgt acctgaaccg gtggctcact 120
ttttctaagt aatggggaag aggaccgaaa cgtgccactg aaagactcta ctg 173

<210> SEQ ID NO 92
<211> LENGTH: 31
<212> TYPE: DNA
<213> ORGANISM: Artificial Sequence
<220> FEATURE:
<223> OTHER INFORMATION: primer

<400> SEQUENCE: 92
caatgtgagt ttttgtagtt ggatttgctc c 31

<210> SEQ ID NO 93
<211> LENGTH: 25
<212> TYPE: DNA
<213> ORGANISM: Artificial Sequence
<220> FEATURE:
<223> OTHER INFORMATION: primer

<400> SEQUENCE: 93
cagtagagtc tttcagtggc acgtt 25

<210> SEQ ID NO 94
<211> LENGTH: 32
<212> TYPE: DNA
<213> ORGANISM: Artificial Sequence
<220> FEATURE:
<223> OTHER INFORMATION: primer

<400> SEQUENCE: 94
gactcattat aaaaactgcc gaattcggat cc 32

<210> SEQ ID NO 95
<211> LENGTH: 25
<212> TYPE: DNA
<213> ORGANISM: Artificial Sequence
<220> FEATURE:
<223> OTHER INFORMATION: primer

<400> SEQUENCE: 95
cagtagagtc tttcagtggc acgtt 25

<210> SEQ ID NO 96

<211> LENGTH: 23
<212> TYPE: DNA
<213> ORGANISM: Artificial Sequence
<220> FEATURE:
<223> OTHER INFORMATION: primer

<400> SEQUENCE: 96 cccccctaata taagacccga ccc 23

<210> SEQ ID NO 97
<211> LENGTH: 22
<212> TYPE: DNA
<213> ORGANISM: Artificial Sequence
<220> FEATURE:
<223> OTHER INFORMATION: primer

<400> SEQUENCE: 97
atgagtaaag gagaagaact tt 22

<210> SEQ ID NO 98
<211> LENGTH: 18
<212> TYPE: DNA
<213> ORGANISM: Artificial Sequence
<220> FEATURE:
<223> OTHER INFORMATION: primer

<400> SEQUENCE: 98
atggcagaag cggtgatc 18

<210> SEQ ID NO 99
<211> LENGTH: 21
<212> TYPE: DNA
<213> ORGANISM: Artificial Sequence
<220> FEATURE:
<223> OTHER INFORMATION: primer

<400> SEQUENCE: 99
atgattgaac aggatggcct g 21

<210> SEQ ID NO 100
<211> LENGTH: 19
<212> TYPE: DNA
<213> ORGANISM: Artificial Sequence
<220> FEATURE:
<223> OTHER INFORMATION: primer

<400> SEQUENCE: 100
atgcgtagcc gtaattgga 19

<210> SEQ ID NO 101
<211> LENGTH: 20
<212> TYPE: DNA
<213> ORGANISM: Artificial Sequence
<220> FEATURE:
<223> OTHER INFORMATION: primer

<400> SEQUENCE: 101
gctgccgaat cttctactgg 20

<210> SEQ ID NO 102
<211> LENGTH: 22
<212> TYPE: DNA
<213> ORGANISM: Artificial Sequence
<220> FEATURE:
<223> OTHER INFORMATION: primer

<400> SEQUENCE: 102
tctccactgg atctgttccc gg 22

<210> SEQ ID NO 103
<211> LENGTH: 21
<212> TYPE: DNA
<213> ORGANISM: Artificial Sequence
<220> FEATURE:
<223> OTHER INFORMATION: primer

<400> SEQUENCE: 103
caaacctgct cccatttcga g 21

<210> SEQ ID NO 104
<211> LENGTH: 20
<212> TYPE: DNA
<213> ORGANISM: Artificial Sequence
<220> FEATURE:
<223> OTHER INFORMATION: primer

<400> SEQUENCE: 104
gaaggcgtcc ttggggtgat 20

<210> SEQ ID NO 105
<211> LENGTH: 20
<212> TYPE: DNA
<213> ORGANISM: Artificial Sequence
<220> FEATURE:
<223> OTHER INFORMATION: primer

<400> SEQUENCE: 105
cggcagaaaa agtgagcatt 20

<210> SEQ ID NO 106
<211> LENGTH: 20
<212> TYPE: DNA
<213> ORGANISM: Artificial Sequence
<220> FEATURE:
<223> OTHER INFORMATION: primer

<400> SEQUENCE: 106
agatctgcga atccctgttg 20

<210> SEQ ID NO 107
<211> LENGTH: 33
<212> TYPE: DNA
<213> ORGANISM: Artificial Sequence
<220> FEATURE:
<223> OTHER INFORMATION: primer

<400> SEQUENCE: 107
ctgcagccca aacaaataca aaatcaaaat aga 33

<210> SEQ ID NO 108
<211> LENGTH: 21
<212> TYPE: DNA
<213> ORGANISM: Artificial Sequence
<220> FEATURE:
<223> OTHER INFORMATION: primer

<400> SEQUENCE: 108
gccagggtaa ggaagaaggg g 21

<210> SEQ ID NO 109
<211> LENGTH: 33
<212> TYPE: DNA

<213> ORGANISM: Artificial Sequence
<220> FEATURE:
<223> OTHER INFORMATION: primer

<400> SEQUENCE: 109
gactcattat aacatgtgca tcctctagta gcg 33

<210> SEQ ID NO 110
<211> LENGTH: 21
<212> TYPE: DNA
<213> ORGANISM: Artificial Sequence
<220> FEATURE:
<223> OTHER INFORMATION: primer

<400> SEQUENCE: 110
gccagggtaa ggaagaaggg g 21

<210> SEQ ID NO 111
<211> LENGTH: 24
<212> TYPE: DNA
<213> ORGANISM: Artificial Sequence
<220> FEATURE:
<223> OTHER INFORMATION: primer

<400> SEQUENCE: 111
ccgaattacg aaggcttagt tcgg 24

<210> SEQ ID NO 112
<211> LENGTH: 24
<212> TYPE: DNA
<213> ORGANISM: Artificial Sequence
<220> FEATURE:
<223> OTHER INFORMATION: primer

<400> SEQUENCE: 112
ttatttgtat agttcatcca tgcc 24

<210> SEQ ID NO 113
<211> LENGTH: 21
<212> TYPE: DNA
<213> ORGANISM: Artificial Sequence
<220> FEATURE:
<223> OTHER INFORMATION: primer

<400> SEQUENCE: 113
ttatttgccg actaccttgg t 21

<210> SEQ ID NO 114
<211> LENGTH: 23
<212> TYPE: DNA
<213> ORGANISM: Artificial Sequence
<220> FEATURE:
<223> OTHER INFORMATION: primer

<400> SEQUENCE: 114
ttagaaaaat tcatccagca gac 23

<210> SEQ ID NO 115
<211> LENGTH: 23
<212> TYPE: DNA
<213> ORGANISM: Artificial Sequence
<220> FEATURE:
<223> OTHER INFORMATION: primer

<400> SEQUENCE: 115
ttatttaccc accactttgg taa 23

-continued

```
<210> SEQ ID NO 116
<211> LENGTH: 20
<212> TYPE: DNA
<213> ORGANISM: Artificial Sequence
<220> FEATURE:
<223> OTHER INFORMATION: primer

<400> SEQUENCE: 116

cagggctttg aacccaaata                                                   20


<210> SEQ ID NO 117
<211> LENGTH: 21
<212> TYPE: DNA
<213> ORGANISM: Artificial Sequence
<220> FEATURE:
<223> OTHER INFORMATION: primer

<400> SEQUENCE: 117

catggacggt agttggagtc g                                                 21


<210> SEQ ID NO 118
<211> LENGTH: 24
<212> TYPE: DNA
<213> ORGANISM: Artificial Sequence
<220> FEATURE:
<223> OTHER INFORMATION: primer

<400> SEQUENCE: 118

gtggaacaga attgactggg tggt                                              24


<210> SEQ ID NO 119
<211> LENGTH: 22
<212> TYPE: DNA
<213> ORGANISM: Artificial Sequence
<220> FEATURE:
<223> OTHER INFORMATION: primer

<400> SEQUENCE: 119

tctctcgagc acaggtttag ca                                                22


<210> SEQ ID NO 120
<211> LENGTH: 20
<212> TYPE: DNA
<213> ORGANISM: Artificial Sequence
<220> FEATURE:
<223> OTHER INFORMATION: primer

<400> SEQUENCE: 120

cgcacgttca atacgatgtt                                                   20


<210> SEQ ID NO 121
<211> LENGTH: 20
<212> TYPE: DNA
<213> ORGANISM: Artificial Sequence
<220> FEATURE:
<223> OTHER INFORMATION: primer

<400> SEQUENCE: 121

caggggacga ccatacttgt                                                   20
```

UNITED STATES PATENT AND TRADEMARK OFFICE
CERTIFICATE OF CORRECTION

PATENT NO. : 11,549,121 B2
APPLICATION NO. : 16/595887
DATED : January 10, 2023
INVENTOR(S) : Scott C. Lenaghan et al.

It is certified that error appears in the above-identified patent and that said Letters Patent is hereby corrected as shown below:

In the Specification

Column 2,
Line 42, "5 'UTR: 5'" should read --5'UTR: 5'--.
Line 44, "3 'UTR: 3'" should read --3'UTR: 3'--.

Column 3,
Line 38, "5 'UTR: 5'" should read --5'UTR: 5'--.
Line 40, "3 'UTR: 3'" should read --3'UTR: 3'--.

Column 24,
Line 45, "Episomal DNA Vecors" should read --Episomal DNA Vectors--.

Signed and Sealed this
Fifteenth Day of August, 2023

Katherine Kelly Vidal
*Director of the United States Patent and Trademark Office*